United States Patent
Torrens-Spence et al.

(10) Patent No.: US 11,408,009 B2
(45) Date of Patent: Aug. 9, 2022

(54) HOST CELL EXPRESSION OF 4-HYDROXYPHENYLACETALDEHYDE SYNTHASE FOR PRODUCTION OF SALIDROSIDE, ICARISIDE D2, AND PRECURSORS

(71) Applicant: Whitehead Institute for Biomedical Research, Cambridge, MA (US)

(72) Inventors: Michael Torrens-Spence, Cambridge, MA (US); Jing-Ke Weng, Belmont, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 16/224,257

(22) Filed: Dec. 18, 2018

(65) Prior Publication Data

US 2019/0264221 A1    Aug. 29, 2019

Related U.S. Application Data

(60) Provisional application No. 62/607,271, filed on Dec. 18, 2017.

(51) Int. Cl.
| | | |
|---|---|---|
| *C12N 15/82* | (2006.01) | |
| *C12N 15/52* | (2006.01) | |
| *C12N 15/81* | (2006.01) | |
| *C12N 15/74* | (2006.01) | |

(Continued)

(52) U.S. Cl.
CPC ......... *C12N 15/8257* (2013.01); *C12N 15/52* (2013.01); *C12N 15/70* (2013.01); *C12N 15/743* (2013.01); *C12N 15/81* (2013.01); *C12N 15/8243* (2013.01); *C12N 15/8245* (2013.01); *C12P 17/06* (2013.01);

(Continued)

(58) Field of Classification Search
None
See application file for complete search history.

(56) References Cited

U.S. PATENT DOCUMENTS

| | | | |
|---|---|---|---|
| 10,415,052 B2 * | 9/2019 | Loque ................ | C12N 15/8255 |
| 2010/0297042 A1 * | 11/2010 | Goldstein ............... | A61P 17/16 |
| | | | 424/59 |

FOREIGN PATENT DOCUMENTS

| | | | | |
|---|---|---|---|---|
| CN | 101928308 A | * | 12/2010 | ............. C07H 15/18 |
| WO | 96/00787 A1 | | 1/1996 | |

OTHER PUBLICATIONS

English Translation of CN 101928308 A Specification. No publication date. Translation performed on Aug. 25, 2020; pp. 1-9.*

(Continued)

*Primary Examiner* — Cathy Kingdom Worley
(74) *Attorney, Agent, or Firm* — Hamilton, Brook, Smith & Reynolds, P.C.

(57) ABSTRACT

Transgenic host cells, vectors useful for making transgenic host cells, and kits useful for making transgenic host cells are described. Also described are transgenic plants. In some embodiments, transgenic host cells express a 4-hydroxyphenylacetaldehyde synthase (4HPAAS). In some embodiments, transgenic host cells express a tyrosol:UDP-glucose 8-O-glucosyltransferase (T8GT). The transgenic host cells are useful for biosynthesis of one or more of salidroside, icariside D2, tyrosol, and 4-hydroxypenylacetaldehyde.

20 Claims, 42 Drawing Sheets
(37 of 42 Drawing Sheet(s) Filed in Color)
Specification includes a Sequence Listing.

(51) Int. Cl.
  *C12P 17/06* (2006.01)
  *C12N 15/70* (2006.01)
(52) U.S. Cl.
  CPC . *C12Y 114/13068* (2013.01); *C12Y 204/0117* (2013.01); *C12Y 401/01* (2013.01)

(56) References Cited

OTHER PUBLICATIONS

English Translation of CN 101928308 A Claims. No publication date. Translation performed on Aug. 25, 2020; pp. 1-2.*
Lee et al. Rhodiola crenulata and its bioactive components, salidroside and tyrosol, reverse the hypoxia-induced reduction of plasma-membran-associated N,K-ATPase expression via inhibition of ROS-AMPK-PKC Pathway. (2013) Evidence-based Complementary and Alternative Medicine; vol. 2013; pp. 1-15 (Year: 2013).*
UniProtKB "Tyrosine decarboxylase" (2012) Accession I7B4Z2; pp. 1-4; printed from the world wide web at https://www.uniprot.org/uniprot/I7B4Z2 on Sep. 9, 2021. (Year: 2012).*
Lan et al. Engineering salidroside biosynthetic pathway in hairy root cultures of Rhodiola crenulata based on metabolic characterization of tyrosine decarboxylase. (2013) PLOS One; vol. 8; pp. 1-10 (Year: 2013).*
Bai, Y. et al., "Production of salidroside in metabolically engineered *Escherichia coli*," Scientific Reports, vol. 4; 8 pages (2014).
Chung, D. et al., "Production of three phenylethanoids, tyrosol, hydroxytyrosol. and salidroside, using plant genes expressing in *Escherichia coli*," Scientific Reports, vol. 7; 8 pages (2017).
Fan, B. et al., "Mining of efficient microbial UDP-glycosyltransferases by motif evolution cross plant kingdom for application in biosynthesis of salidroside," Scientific Reports, vol. 7; 9 pages (2017).
Lan, X. et al., "Engineering Salidroside Biosynthetic Pathway in Hairy Root Cultures of *Rhodiola crenulata* Based on Metabolic Characterization of Tyrosine Decarboxylase," PLOS one. vol. 8; c75459; 10 pages (2013).
Panossian, A. et al., "Mechanism of action in *Rhodiola*, salidroside, tyrosol and triandrin in isolated neuroglial cells: An interactive pathway analysis of the downstream effects using RNA microarray data," Phytomedicine, vol. 21; 1325-1348 (2014).
Torrens-Spence, M.P. et al., "Biochemical Evaluation of the Decarboxylation and Decarboxvlation-Deamination Activities of Plant Aromatic Amino Acid Decarboxylases," The Journal of Biological Chemistry, vol. 288; No. 4; 2376-2387 (2013).
Weng, J. et al., "Co-evolution of Hormone Metabolism and Signaling Networks Expands Plant Adaptive Plasticity," Cell, vol. 166; 881-893 (2016).
Torrens-Spence, M.P., et al., (2012). "Biochemical evaluation of a parsley tyrosine decarboxylase results in a novel 4-hydroxyphenylacetaldehyde synthase enzyme," Biochemical and biophysical research communications 418, 211-216.
Torrens-Spence, M.P., et al., (2014). "Investigation of a substrate-specifying residue within Papaver somniferum and Catharanthus roseus aromatic amino acid decarboxylases," Phytochemistry 106, 37-43.
Tu, Y., et al., (2008). "Rhodiola crenulata induces death and inhibits growth of breast cancer cell lines," Journal of medicinal food 11, 413-423.
Wang, H., et al., (2013). "Functional characterization of Dihydroflavonol-4-reductase in anthocyanin biosynthesis of purple sweet potato underlies the direct evidence of anthocyanins function against abiotic stresses," PloS one 8, e78484.
Wang, M., et al., (2017). "Aromatic amino acid aminotransferases in plants," Phytochemistry Reviews.
Wyk (LONG???), et al., (2010). "The ethnobotany and pharmacognosy of *Olea europaea* subsp. africana (Oleaceae)," South African Journal of Botany 76, 324-331.
Xia, J., et al., (2016). "Using MetaboAnalyst 3.0 for Comprehensive Metabolomics Data Analysis," Current protocols in bioinformatics 55, 14 10 11-14 10 91.
Xie, D.Y., et al., (2003). "Role of anthocyanidin reductase, encoded by BANYULS in plant flavonoid biosynthesis," Science 299, 396-399.
Yang, Y.N., et al., (2012). "Lignans from the Root of Rhodiola crenulate," J. Agr. Food Chem. 60, 964-972.
Yousef, G.G., et al., (2006). "Comparative phytochemical characterization of three *Rhodiola* species," Phytochemistry 67, 2380-2391.
Yuan, T., et al., (2007). "BEN1, a gene encoding a dihydroflavonol 4-reductase (DFR)-like protein, regulates the levels of brassinosteroids in *Arabidopsis thaliana*," The Plant journal for cell and molecular biology 51, 220-233.
Zhang, L., et al., (2007). "Protective effects of salidroside on hydrogen peroxide-induced apoptosis in SH-SY5Y human neuroblastoma cells," Eur. J. Pharmacol. 564, 18-25.
Zuckerkandl et al., "Evolutionary divergence and convergence in proteins," Evolving Genes and Proteins, 1965.
Altschul et al., "Basic local alignment search tool," J. Mol. Biol. 215, 403-410, 1990.
Ausubel et al., "Current protocols in molecular biology," John Wiley & Sons, Inc; ringbou edition (ISBN: 047150338X), 2003.
DeBoer et al.,"The tac promoter: A functional hybrid derived from the trp and lac promoters," Pro. Natl. Acad. Sci. USA, vol. 80, pp. 21-25, 1983.
Grabherr et al., "Trinity: reconstructing a full-length transcriptome without a genome from RNA-Seq data," Nat. Biotechnol., 29(7): 644-652, doi: 10.1038/nbt.1883, 2013.
Pearson et al., "Improved tools for biological sequence comparison," Proc. Natl. Acad. Sci. USA, vol. 85, pp. 2444-2448, 1988.
Priyam et al., "Sequenceserver: a modern graphical user interface for custom BLAST databases," bioRxiv preprint doi: https://doi.org/10.1101/033142; Nov. 27, 2015.
Romanos et al., "Foreign Gene Expression in Yeast: a Review," Yeast, vol. 8: 423-488 (1992).
Smith, T., "Comparison of Biosequences," Advances in Applied Mathematics 2, 482-489 (1981).
Villa-Komaroff et al., "A bacterial clone synthesizing proinsulin," Proc. Natl. Acad. Sci. USA, vol. 75, No. 8, pp. 3727-3731, 1978.
Anurag Priyam, et al., (2015). "Sequenceserver: a modern graphical user interface for custom BLAST databases," bioRxv 033142.
Bolger, A.M., et al., "Trimmomatic: a flexible trimmer for Illumina sequence data," (2014), Bioinformatics 30, 2114-2120.
Booker, A., et al., "From Traditional Resource to Global Commodities:—A Comparison of *Rhodiola* Species Using NMR Spectroscopy-Metabolomics and HPTLC," (2016), Frontiers in pharmacology 7, 254.
Burkhard, P., et al., "Structural insight into Parkinson's disease treatment from drug-inhibited DOPA decarboxylase," (2001), Nature structural biology 8, 963-967.
Chambers, M.C., et al. "A cross-platform toolkit for mass spectrometry and proteomics," (2012)., Nat Biotechnol 30, 918-920.
Chapple, C.C., et al., "Plant tyrosine decarboxylase can be strongly inhibited by L-alpha-aminooxy-beta-phenylpropionate," (1986), Planta 167, 101-105.
Cifani, C., et al., "Effect of salidroside, active principle of Rhodiola rosea extract, on binge eating," (2010), Physiology & behavior 101, 555-562.
De Luca, V., et al., "Molecular cloning and analysis of cDNA encoding a plant tryptophan decarboxylase: comparison with animal dopa decarboxylases," 1989, Proc Natl Acad Sci U S A 86, 2582-2586.
Dorji, et al., "Ecological status of high altitude medicinal plants and their sustainability: Lingshi, Bhutan," (2016), BMC Ecology.
Du, M., et al., "Flavonol Glycosides from Rhodiola-Crenulata," (1995), Phytochemistry 38, 809-810.
Facchini, P.J., et al., "Plant aromatic L-amino acid decarboxylases: evolution, biochemistry, regulation, and metabolic engineering applications," (2000), Phytochemistry 54, 121-138.
Gantt, R.W., et al., "Enzymatic methods for glyco(diversification/randomization) of drugs and small molecules," (2011), Natural product reports 28, 1811-1853.

(56) References Cited

OTHER PUBLICATIONS

Gauger, K.J., et al., "Rhodiola crenulata inhibits the tumorigenic properties of invasive mammary epithelial cells with stem cell characteristics," (2010), J. Med. Plants Res. 4, 446-454.
Gold, N.D., et al., "Metabolic engineering of a tyrosine-overproducing yeast platform using targeted metabolomics," (2015), Microb. Cell Fact 14.
Gouet, P., et al., "ESPript/ENDscript Extracting and rendering sequence and 3D information from atomic structures of proteins," (2003) Nucleic acids research 31, 3320-3323.
Grabherr, M.G., et al., Full-length transcriptome assembly from RNA-Seq data without a reference genome, (2011), Nat. Biotechnol. 29, 644-U130.
Guan, S., et al., "Protective effects of salidroside from Rhodiola rosea on LPS-induced acute lung injury in mice," (2012), Immunopharmacology and immunotoxicology 34, 667-672.
Gutensohn, M., et al., "Role of aromatic aldehyde synthase in wounding/herbivory response and flower scent production in different *Arabidopsis* ecotypes," (2011), The Plant journal: for cell and molecular biology 66, 591-602.
Haas, B.J., et al. "De novo transcript sequence reconstruction from RNA-seq using the Trinity platform for reference generation and analysis," (2013), Nat. Protoc. 8, 1494-1512.
Hagel, J.M., et al., "Benzylisoquinoline alkaloid metabolism: a century of discovery and a brave new world," (2013), Plant & cell physiology 54, 647-672.
Han, Q., et al., "Crystal structure and substrate specificity of *Drosophila* 3,4-dihydroxyphenylalanine decarboxylase," (2010), PloS one 5, e8826.
Kaminaga, Y., et al. "Plant phenylacetaldehyde synthase is a bifunctional homotetrameric enzyme that catalyzes phenylalanine decarboxylation and oxidation," (2006), The Journal of biological chemistry 281, 23357-23366.
Kawalleck, P., et al., "A pathogen-responsive gene of parsley encodes tyrosine decarboxylase," (1993), J. Biol. Chem. 268, 2189-2194.
Khanum, F., et al., "Rhodiola rosea: A versatile adaptogen," (2005), Compr. Rev. Food Sci. F 4, 55-62.
Kumar, S., et al., "MEGA7: Molecular Evolutionary Genetics Analysis Version 7.0 for Bigger Datasets," (2016), Mol. Biol. Evol. 33, 1870-1874.
Landtag, J., et al., (2002). "Accumulation of tyrosol glucoside in transgenic potato plants expressing a parsley tyrosine decarboxylase," Phytochemistry 60, 683-689.
Lee, M.E., et al., "A Highly Characterized Yeast Toolkit for Modular, Multipart Assembly," (2015), ACS synthetic biology 4, 975-986.
Lei, Y.D., et al., "Determination of genetic variation in Rhodiola crenulata from the Hengduan Mountains Region, China using inter-simple sequence repeats," (2006), Genet Mol Biol 29, 339-344.
Li, B., et al. (2010). "RNA-Seq gene expression estimation with read mapping uncertainty," Bioinformatics 26, 493-500.
Li, B., et al., (2011). "RSEM: accurate transcript quantification from RNA-Seq data with or without a reference genome," BMC Bioinformatics 12:323.
Ma, L.Q., et al., (2007). "Molecular cloning and overexpression of a novel UDP-glucosyltransferase elevating salidroside levels in Rhodiola sachalinensis." Plant cell reports 26, 989-999.
Mumberg, D., et al., (1995). "Yeast Vectors for the Controlled Expression of Heterologous Proteins in Different Genetic Backgrounds," Gene 156, 119-122.
Nelissen, H., et al., (2003). "DRL1, a homolog of the yeast TOT4/KT112 protein, has a function in meristem activity and organ growth in plants," The Plant cell 15, 639-654.
O'Connor, S.E. (2015). "Engineering of Secondary Metabolism," Annual review of genetics 49, 71-94.
Peyret, H., et al., (2013). "The pEAQ vector series: the easy and quick way to produce recombinant proteins in plants," Plant Mol. Biol. 83, 51-58.

Pluskal, T., et al., (2010). "MZmine 2: Modular framework for processing, visualizing, and analyzing mass spectrometry-based molecular profile data," Bmc Bioinformatics 11.
Rohloff, J. (2002). "Volatiles from rhizomes of *Rhodiola rosea* L." Phytochemistry 59, 655-661.
Sainsbury, F., et al., (2009). "pEAQ: versatile expression vectors for easy and quick transient expression of heterologous proteins in plants," Plant Biotechnol J 7, 682-693.
Samanani, N., et al., (2004). "Molecular cloning and characterization of norcoclaurine synthase, an enzyme catalyzing the first committed step in benzylisoquinoline alkaloid biosynthesis," The Plant journal for cell and molecular biology 40, 302-313.
Sanderson, M.J., et al., (2000). "Improved bootstrap confidence limits in large-scale phylogenies, with an example from Neo-Astragalus (Leguminosae)," Systematic biology 49, 671-685.
Schneider, C.A., et al., (2012). "NIH Image to ImageJ: 25 years of image analysis," Nat. Methods 9, 671-675.
Simao, F.A., et al., (2015). "BUSCO: assessing genome assembly and annotation completeness with single-copy orthologs," Bioinformatics 31, 3210-3212.
Strommer, J. (2011). "The plant ADH gene family," Plant Journal 66, 128-142.
Thompson, J.D., et al., (2002). "Multiple sequence alignment using ClustalW and ClustalX. Current protocols in bioinformatics," Chapter 2, Unit 2 3.
Tieman, D.M., et al., (2007). "Tomato phenylacetaldehyde reductases catalyze the last step in the synthesis of the aroma volatile 2-phenylethanol," Phytochemistry 68, 2660-2669.
Torrens-Spence, M.P., et al., (2016). "A Workflow for Studying Specialized Metabolism in Nonmodel Eukaryotic Organisms," Methods Enzymol. 576, 69-97.
Li et al., "Efficient O-Glycosylation of Triterpenes Enabled by Protein Engineering of Plant Glycosyltransferase UGT74AC1," ACSCatalysis, 10: 3620-3639 (2020).
Li et al., "Crystal Structure of Medicago truncatula UGT85H2 - Insights into the Structural Basis of a Multifunctional (Iso)flavonoid Glycosyltransferase," J. Mol. Biol., 370: 951-963 (2007).
Liu et al., "Structural Insights into the Catalytic Mechanism of a Plant Diterpene Glycosyltransferase SrUGT76G1," Plant Communications, 1, 100004: 1-11 (2020).
Pan et al., "Structural Studies of Cinnamoyl-CoA Reductase and Cinnamyl-Alcohol Dehydrogenase, Key Enzymes of Monolignol Biosynthesis," The Plant Cell, 26: 3709-3727 (2014).
Petit et al., "Crystal Structure of Grape Dihydroflavonol 4-Reductase, a Key Enzyme in Flavonoid Biosynthesis," J. Mol. Biol., 368: 1345-1357 (2007).
Sattler et al., "Structural and Biochemical Characterization of Cinnamoyl-CoA Reductases," Plant Physiology, 173: 1031-1044 (2017).
Shang et al., "Efficient Synthesis of (R)-2-Chloro-1-(2,4-dichlorophenyl) ethanol with a Ketoreductase from *Scheffersomyces stipitis* CBS 6045," Adv. Synth. Catal., 359: 426-431 (2017).
Shao et al., "Crystal Structure of Vestitone Reductase from Alfalfa (*Medicago sativa* L.)," J. Mol. Biol., 369: 265-276 (2007).
Trabelsi et al., "Structural evidence for the inhibition of grape dihydroflavonol 4-reductase by flavonols," Acta Cryst., D64: 883-891 (2008).
Thompson et al., "Differences in salicylic acid glucose conjugations by UGT74F1 and UGT74F2 from *Arabidopsis thaliana*," Scientific Reports, 7:46629, 1-11 (2017).
Yang et al., "Hydrophobic recognition allows the glycosyltransferase UGT76G1 to catalyze its substrate in two orientations," Nature Communications, 10(3214): 1-12 (2019).
Fan et al. (2017). Mining of efficient microbial UDP glycosyltransferases by motif evolution cross plant kingdom for application in biosynthesis of salidroside. Scientific Reports 7:463, 1-9.
Gachon et al. (2005) Plant secondary metabolism glycosyltransferases: the emerging functional analysis. Trends in plant science 10, 542-549.
Jones et al., "Glycosyltransferases in secondary plant metabolism: tranquilizers and stimulant controllers," Planta, 231:164-174 (2001).

(56) References Cited

OTHER PUBLICATIONS

Li et al. (2001). Phylogenetic analysis of the UDP-glycosyltransferase multigene family of *Arabidopsis thaliana*. J. Biol. Chem. 276, 4338-4343.
Ross et al. (2001). Higher plant glycosyltransferases. Genome Biol 2, REVIEWS3004.
Yu et al., "Characterization of glycosyltransferases responsible for salidroside biosynthesis in Rhodiola sachalinensis," Phytochemistry 72, pp. 862-870 (2011).

* cited by examiner

Substrate selectivity
Gly 370

| | | | | |
|---|---|---|---|---|
| Indolic Selective | C. roseus | P17770.1 | 360 | VDFNWQIATGKRSLKLL |
| | C. annuum | XP_016579458 | 360 | VDYDWQIGTGKRSLRLL |
| | O. pumila | BAC41515.1 | 359 | VDFDWQIGTGRKALRLL |
| | C. acuminata | AAB39708.1 | 360 | VDYDWQVGTGRKALRLF |
| | C. acuminata | AAB39709.1 | 357 | VDFDWQVGTGRKALRLF |
| | O. sativa | XP_015648701.1 | 371 | TDLDMQVGVGRRGLRLM |
| Phenolic Selective | P. hybrid | ABB72475.1 | 359 | VDYDWQITLSRRSLKLL |
| | P. crispum | Q06086.1 | 358 | VDYDWQIMLSRALKLF |
| | P. somniferum | AAC61842.1 | 362 | IDYDWQIALSRSMKLL |
| | P. somniferum | P54769.1 | 360 | VDYDWQIALSRRSLKLM |
| | T. flavum | AAG60665.1 | 359 | VDYDWQIALSRRAMKLL |
| | R. hybrid | ABB04522.1 | 360 | VDYDWQIALSRRALKLL |
| | R. crenulata | AFN89854.1 | 351 | VDYDWQISLSRRAIKMM |

SEQUENCE LISTING

```
<160> NUMBER OF SEQ ID NOS: 274

<210> SEQ ID NO 1
<211> LENGTH: 1473
<212> TYPE: DNA
<213> ORGANISM: Rhodiola rosea

<400> SEQUENCE: 1
atgggcagct tgccttctcc taatgatcca tcaaacacct tcaaccccat ggacctcacc      60
gagttatcca ccgagtcgaa actcgtcgta gatttcataa ctcagtacta ccaaaccta     120 gagacccgac ccgtccagcc acgggtcaag ccaggtttct taacgggcca gcttccagat    180
aaagcaccct ttcatggtga atcaatggaa gtaatattgt ctgatgtaaa tgagaagatt    240
gtccctggcc tcactcattg gcaaagccct aatttccatg catactttcc agccagttcc    300
agcaacgcag ggctgttggg agagttacta tgctccggac tcagtgtcat tgggttcaca    360
tggagctcct cccctgccgc gacggagctt gagaatgtcg tggttgactg gatggccaag    420
atgcttaacc ttccatcctc tttctgcttc tccggcggag gcggtggcgt tctgcaagca    480
aacacttgcg aggctgtgtt gtgcacttta gccgctgcga gggacaaggc tcttaaccgg    540
gtgggagatg atcagatcaa taaactggtc ctctactgct ccgaccaaac acatttcaca    600
atccacaagg gcgcaaagtt gataggaatc cgatcaaaga acataaaatc aatcactact    660
aagaaagaga acgagttaa actctgtcct aacgacctac gcgacgcgat aaggagtgat    720
ctggaagcag gactagttcc gttttacgta tgcggaacga ttggaacgac cgcgttagga    780
gttgtggatc cgattaaaga gctgggtaag gtggcaagag agtttgattt gtggttacat    840
gttgatggag cttatggtgg cagtgcatgc atatgccctg agtttcagca ttaccttgat    900
```

-continued

```
ggagttgacc ttgttgactc gatcagcatg aatgcacata aatggctttt atccaatcta    960
gattgctgct tcctgtggct tcaatctcct aacgccctaa tcgatccct ggccgcagaa    1020
gctaactttc tgaaaggtgg tagtgagatg gtggattaca aggactggca gatatcgttg    1080
agtcgtcgat ttagagcgat caagatgtgg atggtgataa ggcgatacgg tgtgagtaat    1140
ctcattgagc atattcgatc cgacgtgagc atggcggtga gattcgaaga gatggtggcg    1200
gcggacgacc ggtttgaaat cgtgtttcct agaaagtttg cgcttgtttg cttcaagctt    1260
agtagcgaga agacaccacc gggccgcgac tcggagttaa ctcgtgagct gatggagaga    1320
gtcaactcga gtgggaaggc ttacttgagt ggagttcaaa tgggtcggat cttcttcatc    1380
aggtgtgtga tcgggtcgag tttgactgag gagagacacg tcgataatct gtggaggctc    1440
attcaagaaa cagctcaaag catcgtgtct tag                                1473
```

<210> SEQ ID NO 2
<211> LENGTH: 490
<212> TYPE: PRT
<213> ORGANISM: Rhodiola rosea
<300> PUBLICATION INFORMATION:
<308> DATABASE ACCESSION NUMBER: GenBank MF674522

<400> SEQUENCE: 2

```
Met Gly Ser Leu Pro Ser Pro Asn Asp Pro Ser Asn Thr Phe Asn Pro
1               5                   10                  15

Met Asp Leu Thr Glu Leu Ser Thr Glu Ser Lys Leu Val Val Asp Phe
                20                  25                  30

Ile Thr Gln Tyr Tyr Gln Thr Leu Glu Thr Arg Pro Val Gln Pro Arg
            35                  40                  45

Val Lys Pro Gly Phe Leu Thr Gly Gln Leu Pro Asp Lys Ala Pro Phe
        50                  55                  60

His Gly Glu Ser Met Glu Val Ile Leu Ser Asp Val Asn Glu Lys Ile
65                  70                  75                  80

Val Pro Gly Leu Thr His Trp Gln Ser Pro Asn Phe His Ala Tyr Phe
                85                  90                  95

Pro Ala Ser Ser Ser Asn Ala Gly Leu Leu Gly Glu Leu Leu Cys Ser
            100                 105                 110

Gly Leu Ser Val Ile Gly Phe Thr Trp Ser Ser Ser Pro Ala Ala Thr
        115                 120                 125

Glu Leu Glu Asn Val Val Asp Trp Met Ala Lys Met Leu Asn Leu
    130                 135                 140

Pro Ser Ser Phe Cys Phe Ser Gly Gly Gly Gly Val Leu Gln Ala
145                 150                 155                 160

Asn Thr Cys Glu Ala Val Leu Cys Thr Leu Ala Ala Ala Arg Asp Lys
                165                 170                 175

Ala Leu Asn Arg Val Gly Asp Asp Gln Ile Asn Lys Leu Val Leu Tyr
            180                 185                 190

Cys Ser Asp Gln Thr His Phe Thr Ile His Lys Gly Ala Lys Leu Ile
        195                 200                 205

Gly Ile Arg Ser Lys Asn Ile Lys Ser Ile Thr Thr Lys Lys Glu Asn
    210                 215                 220

Glu Phe Lys Leu Cys Pro Asn Asp Leu Arg Asp Ala Ile Arg Ser Asp
225                 230                 235                 240

Leu Glu Ala Gly Leu Val Pro Phe Tyr Val Cys Gly Thr Ile Gly Thr
                245                 250                 255

Thr Ala Leu Gly Val Val Asp Pro Ile Lys Glu Leu Gly Lys Val Ala
```

```
                260              265              270
Arg Glu Phe Asp Leu Trp Leu His Val Asp Gly Ala Tyr Gly Gly Ser
            275              280              285
Ala Cys Ile Cys Pro Glu Phe Gln His Tyr Leu Asp Gly Val Asp Leu
            290              295              300
Val Asp Ser Ile Ser Met Asn Ala His Lys Trp Leu Leu Ser Asn Leu
305              310              315              320
Asp Cys Cys Phe Leu Trp Leu Gln Ser Pro Asn Ala Leu Ile Glu Ser
            325              330              335
Leu Ala Ala Glu Ala Asn Phe Leu Lys Gly Gly Ser Glu Met Val Asp
            340              345              350
Tyr Lys Asp Trp Gln Ile Ser Leu Ser Arg Arg Phe Arg Ala Ile Lys
            355              360              365
Met Trp Met Val Ile Arg Arg Tyr Gly Val Ser Asn Leu Ile Glu His
            370              375              380
Ile Arg Ser Asp Val Ser Met Ala Val Arg Phe Glu Glu Met Val Ala
385              390              395              400
Ala Asp Asp Arg Phe Glu Ile Val Phe Pro Arg Lys Phe Ala Leu Val
            405              410              415
Cys Phe Lys Leu Ser Ser Glu Lys Thr Pro Pro Gly Arg Asp Ser Glu
            420              425              430
Leu Thr Arg Glu Leu Met Glu Arg Val Asn Ser Ser Gly Lys Ala Tyr
            435              440              445
Leu Ser Gly Val Gln Met Gly Arg Ile Phe Phe Ile Arg Cys Val Ile
            450              455              460
Gly Ser Ser Leu Thr Glu Glu Arg His Val Asp Asn Leu Trp Arg Leu
465              470              475              480
Ile Gln Glu Thr Ala Gln Ser Ile Val Ser
            485              490
```

<210> SEQ ID NO 3
<211> LENGTH: 981
<212> TYPE: DNA
<213> ORGANISM: Rhodiola rosea

<400> SEQUENCE: 3

```
atgagtttaa gcggagcggg aaggtggtt tgcgttaccg gcgcgtctgg ctacatagcg    60
tcctggctcg tcaagcttct tctccagcgc ggttataccg tcaaggcctc cgttcgcgat   120
cctaatgatc cgaaaaagac tcagcacttg acggcacttg atggagctaa ggagaggctg   180
cagttgtaca agccaatttt gcttgaacaa ggctcgtttg atcccatagt tgaaggatgt   240
gaaggtgttt tccacaccgc gtctcccttt tatcatgcag tggatgatcc gcaggccgag   300
ttaattgacc ctgctgtcaa gggaacactc aatgttcttt cttcatgtgc taaagttgcg   360
tctcttaaaa gagtagtcct gacttcttcg attgctgctg ttgcatataa tgggaaaccc   420
cgtactccgg aggttgtagt tgacgagact tggttttcta acccagatgt tgtaaggag    480
atgaagcttt ggtatgtcat atccaagaca ctcgctgaag aagcagcatg gaagtttgtg   540
aaagagaaag gaatagacat ggttaccata aatccggcca tggtgattgg tccccttctg   600
caaccaacac tcaataccag tgctgctgct attctgaact tgatcaatgg atcggagaca   660
tacccaaatg cttcttttgg atgggtcaat gtgaaagatg ttgcagaagc acacgttctt   720
gcatttgagg ttccttcagc taatggtaga tactgcttgg tggaaagagt tgcccacagt   780
tctgaagtgg tgaacatgct ccatgagctc taccctgata tcaaacttcc cgccaagtgt   840
```

```
gcagatgaca aaccatttgt gccaatttat caagtttcaa agaaaaggc acatacttta    900 ggggtaaaat tcattccttt agaggtaagc ctcaaggaaa cagttgaaag cttgaaggaa    960
aagggtttcg ccaaactctg a                                              981
```

<210> SEQ ID NO 4
<211> LENGTH: 326
<212> TYPE: PRT
<213> ORGANISM: Rhodiola rosea
<300> PUBLICATION INFORMATION:
<308> DATABASE ACCESSION NUMBER: GenBank MF674524

<400> SEQUENCE: 4

```
Met Ser Leu Ser Gly Ala Gly Lys Val Val Cys Val Thr Gly Ala Ser
1               5                   10                  15

Gly Tyr Ile Ala Ser Trp Leu Val Lys Leu Leu Leu Gln Arg Gly Tyr
            20                  25                  30

Thr Val Lys Ala Ser Val Arg Asp Pro Asn Asp Pro Lys Lys Thr Gln
        35                  40                  45

His Leu Thr Ala Leu Asp Gly Ala Lys Glu Arg Leu Gln Leu Tyr Lys
    50                  55                  60

Ala Asn Leu Leu Glu Gln Gly Ser Phe Asp Pro Ile Val Glu Gly Cys
65                  70                  75                  80

Glu Gly Val Phe His Thr Ala Ser Pro Phe Tyr His Ala Val Asp Asp
                85                  90                  95

Pro Gln Ala Glu Leu Ile Asp Pro Ala Val Lys Gly Thr Leu Asn Val
            100                 105                 110

Leu Ser Ser Cys Ala Lys Val Ala Ser Leu Lys Arg Val Val Leu Thr
        115                 120                 125

Ser Ser Ile Ala Ala Val Ala Tyr Asn Gly Lys Pro Arg Thr Pro Glu
    130                 135                 140

Val Val Asp Glu Thr Trp Phe Ser Asn Pro Asp Val Cys Lys Glu
145                 150                 155                 160

Met Lys Leu Trp Tyr Val Ile Ser Lys Thr Leu Ala Glu Glu Ala Ala
                165                 170                 175

Trp Lys Phe Val Lys Glu Lys Gly Ile Asp Met Val Thr Ile Asn Pro
            180                 185                 190

Ala Met Val Ile Gly Pro Leu Leu Gln Pro Thr Leu Asn Thr Ser Ala
        195                 200                 205

Ala Ala Ile Leu Asn Leu Ile Asn Gly Ser Glu Thr Tyr Pro Asn Ala
    210                 215                 220

Ser Phe Gly Trp Val Asn Val Lys Asp Val Ala Glu Ala His Val Leu
225                 230                 235                 240

Ala Phe Glu Val Pro Ser Ala Asn Gly Arg Tyr Cys Leu Val Glu Arg
                245                 250                 255

Val Ala His Ser Ser Glu Val Val Asn Met Leu His Glu Leu Tyr Pro
            260                 265                 270

Asp Ile Lys Leu Pro Ala Lys Cys Ala Asp Asp Lys Pro Phe Val Pro
        275                 280                 285

Ile Tyr Gln Val Ser Lys Glu Lys Ala His Thr Leu Gly Val Lys Phe
    290                 295                 300

Ile Pro Leu Glu Val Ser Leu Lys Glu Thr Val Glu Ser Leu Lys Glu
305                 310                 315                 320

Lys Gly Phe Ala Lys Leu
                325
```

<210> SEQ ID NO 5
<211> LENGTH: 1425
<212> TYPE: DNA
<213> ORGANISM: Rhodiola rosea

<400> SEQUENCE: 5

| | | |
|---|---|---|
| atgggttctg attcacggcc tctacgcgtc ttcttctttc ccttcatggc tcacggccat | 60 |
| ctgattccga tggtcgacat cgccagactc ttctcttctc aaggagtcca ctccaccatc | 120 |
| atcaccaccc cactaaacgc caattacatc tccaaaacga cgtctctatc catcaaaacg | 180 |
| ataccgtttc ctgctgcgga agttgggctt ccggacggct gcgagaatat cgacatgctt | 240 |
| ccttcgcccg atctcttctt caaattttc caagccgcca atttactcca gcgccgttc | 300 |
| gagaaccttc tagaactcga aaggcccgat tgcttaatct ccgacatctt cttcccctgg | 360 |
| tcagtcgact ccgccgagaa attcaacatc ccgagactcg ttttccacgg cacgagcttc | 420 |
| ttcgccatgt gcgccatgga gagcttgaag acccacaagc cctataaatc ggtaagcacc | 480 |
| gactctgaac cgttcttaat cccgaatctc cctgatgaaa tcaaaatgac taaaagtcag | 540 |
| ttcacggttg acgcttggga agacaccgaa aagggccttg ggaagctgtt ggctgatgcg | 600 |
| agagcttcag ggctgaggag cttcggcatg atcgtaaaca gcttccacga gctcgaaccg | 660 |
| gcttacgcgg attattacaa gaatgtgttg aacatgaaag cgtggtgtgt cgggcctgtt | 720 |
| tcgttatata accgaaacga tgacgagaaa attgcaagag ggaagaaatc agcaatcgat | 780 |
| gatcatgagt gtttaaaatg gctggaggga aagcagccag actccgtcgt gtacgtttgt | 840 |
| ttcgggagca gcgcgagctt ccctgatgag cagttgcgcg atatcgcatt ggggctggaa | 900 |
| gaatctggag taaatttcat ctgggtgatc aggagaagtt ccgagtcagg atcagaagat | 960 |
| tacttgccgg aggggtttga ggaccgggtg aaggacagag ggctcgtgat ccgaggttgg | 1020 |
| gcgccacagg tactgatttt ggaccatccg tcggttgggg gatttgtgac tcactgcgga | 1080 |
| tggaattcgg cattggaggg gatttcagct ggcttgccga tggtgacttg gccactgttc | 1140 |
| gcagagcagt ttttcaacca gaaattgatt acgatgtgt tgaaagttgg ggttgaggtt | 1200 |
| ggagtgcaga aatggtctcg gaacggggag gatcgcgtga cgaaggagaa ggttgagaag | 1260 |
| gcggtgaggg ctgttatggt tggggaggac gctgaggaga gcgtggcag agctcgtcag | 1320 |
| cttgggaaat tggcaaagaa agctgtggcg aaagatggg cttcgtacat tgatctccac | 1380 |
| aatttgcttg atgaattgaa gttgagaaga gagactttgt cctag | 1425 |

<210> SEQ ID NO 6
<211> LENGTH: 474
<212> TYPE: PRT
<213> ORGANISM: Rhodiola rosea
<300> PUBLICATION INFORMATION:
<308> DATABASE ACCESSION NUMBER: GenBank MF674527

<400> SEQUENCE: 6

Met Gly Ser Asp Ser Arg Pro Leu Arg Val Phe Phe Pro Phe Met
1               5                   10                  15

Ala His Gly His Leu Ile Pro Met Val Asp Ile Ala Arg Leu Phe Ser
            20                  25                  30

Ser Gln Gly Val His Ser Thr Ile Ile Thr Thr Pro Leu Asn Ala Asn
        35                  40                  45

Tyr Ile Ser Lys Thr Thr Ser Leu Ser Ile Lys Thr Ile Pro Phe Pro
    50                  55                  60

```
Ala Ala Glu Val Gly Leu Pro Asp Gly Cys Glu Asn Ile Asp Met Leu
 65                  70                  75                  80

Pro Ser Pro Asp Leu Phe Phe Lys Phe Gln Ala Ala Asn Leu Leu
                 85                  90                  95

Gln Ala Pro Phe Glu Asn Leu Leu Glu Leu Glu Arg Pro Asp Cys Leu
                100                 105                 110

Ile Ser Asp Ile Phe Phe Pro Trp Ser Val Asp Ser Ala Glu Lys Phe
            115                 120                 125

Asn Ile Pro Arg Leu Val Phe His Gly Thr Ser Phe Phe Ala Met Cys
            130                 135                 140

Ala Met Glu Ser Leu Lys Thr His Lys Pro Tyr Lys Ser Val Ser Thr
145                 150                 155                 160

Asp Ser Glu Pro Phe Leu Ile Pro Asn Leu Pro Asp Glu Ile Lys Met
                165                 170                 175

Thr Lys Ser Gln Phe Thr Val Asp Ala Trp Glu Asp Thr Glu Lys Gly
            180                 185                 190

Leu Gly Lys Leu Leu Ala Asp Ala Arg Ala Ser Gly Leu Arg Ser Phe
        195                 200                 205

Gly Met Ile Val Asn Ser Phe His Glu Leu Glu Pro Ala Tyr Ala Asp
    210                 215                 220

Tyr Tyr Lys Asn Val Leu Asn Met Lys Ala Trp Cys Val Gly Pro Val
225                 230                 235                 240

Ser Leu Tyr Asn Arg Asn Asp Asp Glu Lys Ile Ala Arg Gly Lys Lys
                245                 250                 255

Ser Ala Ile Asp Asp His Glu Cys Leu Lys Trp Leu Glu Gly Lys Gln
            260                 265                 270

Pro Asp Ser Val Val Tyr Val Cys Phe Gly Ser Ser Ala Ser Phe Pro
            275                 280                 285

Asp Glu Gln Leu Arg Asp Ile Ala Leu Gly Leu Glu Glu Ser Gly Val
        290                 295                 300

Asn Phe Ile Trp Val Ile Arg Arg Ser Ser Glu Ser Gly Ser Glu Asp
305                 310                 315                 320

Tyr Leu Pro Glu Gly Phe Glu Asp Arg Val Lys Asp Arg Gly Leu Val
                325                 330                 335

Ile Arg Gly Trp Ala Pro Gln Val Leu Ile Leu Asp His Pro Ser Val
            340                 345                 350

Gly Gly Phe Val Thr His Cys Gly Trp Asn Ser Ala Leu Glu Gly Ile
        355                 360                 365

Ser Ala Gly Leu Pro Met Val Thr Trp Pro Leu Phe Ala Glu Gln Phe
    370                 375                 380

Phe Asn Gln Lys Leu Ile Thr Asp Val Leu Lys Val Gly Val Glu Val
385                 390                 395                 400

Gly Val Gln Lys Trp Ser Arg Asn Gly Glu Asp Arg Val Thr Lys Glu
                405                 410                 415

Lys Val Glu Lys Ala Val Arg Ala Val Met Val Gly Glu Asp Ala Glu
            420                 425                 430

Glu Arg Arg Gly Arg Ala Arg Gln Leu Gly Lys Leu Ala Lys Lys Ala
        435                 440                 445

Val Ala Lys Asp Gly Ser Ser Tyr Ile Asp Leu His Asn Leu Leu Asp
    450                 455                 460

Glu Leu Lys Leu Arg Arg Glu Thr Leu Ser
465                 470
```

<210> SEQ ID NO 7
<211> LENGTH: 1419
<212> TYPE: DNA
<213> ORGANISM: Rhodiola rosea

<400> SEQUENCE: 7

| | | | | | |
|---|---|---|---|---|---|
| atgtcaggca | caccacacat | cgccatcctc | cccagccccg | gcatgggcca | cctcatcccc | 60 |
| atggccgagt | tcgccaagcg | cctagtccac | caccacaact | tcagtatcac | cttcgtcatc | 120 |
| cctaccgacg | gccacccttc | ctccgcctac | caacaagtcc | tcacctccct | cccatcttcc | 180 |
| atagatcaca | tcttccttcc | acaagtcgac | ttaaccgacg | tcgtatcaca | atcaccagct | 240 |
| catcccagaa | tcgaaaccct | aatctccctc | accgtcgctc | gctccctctc | ctccctccgc | 300 |
| accaccttat | cctctctcca | atcgtctaaa | acctcgtct | cgctcgtcgt | tgatcttttc | 360 |
| ggcactgatg | cattcgaccc | ggccatcgag | ctcggcatct | cgccctacat | tttcttccct | 420 |
| tccacagcca | tgacgctctc | gctcttccta | tacatgcctc | agcttgacaa | atcagtcacg | 480 |
| tgcgaatttc | gtcacatgac | ggatttggtt | cgaattcctg | gatgcgttcc | tgtccgtgga | 540 |
| tcggatttat | tcgacccggt | tcaagacagg | accgacgagg | cttataaatg | ggtcatacat | 600 |
| cactccaaca | ggtaccctat | ggcggagggt | gttatagaga | atagcttcat | ggagttggaa | 660 |
| catggtgcgt | taaagtattt | gcaaacggtt | caatcgggta | agccgcctgt | ctacgcggtc | 720 |
| ggaccgttga | ttaaaatgga | ttatgatgtt | gacgattccg | ggtcgaagat | aatcgagtgg | 780 |
| ctcgatgatc | aaccggttgg | ttcggtttta | tttgtttcgt | ttggaagcgg | cggaacgctc | 840 |
| tcgtatgagc | aaatgaccga | gctggctcac | ggtttggaat | cgagccagca | acggttctta | 900 |
| tgggtggttc | ggagtccgaa | tcaaatcccc | aacagcacgt | atttcagtgt | acaaagccaa | 960 |
| aaagacccgt | tggcttactt | gccagaagga | ttttttaaacc | gaaccgaggg | taggggtctg | 1020 |
| gtcgtatcga | attgggcccc | acaggctcaa | attttgagtc | acggttcgac | cggtgggttc | 1080 |
| atgagccact | gtggttggaa | ttcgattttg | gagagtgtgg | tgcacggcgt | gccgatcata | 1140 |
| gcgtggccgt | tgtacgccga | gcagaagatg | aattcgataa | tcgtggtgga | ggacgttaag | 1200 |
| gtggcgctga | ggccggcggg | ggtaggggag | agggtggtgg | agaggtcgga | gataaccgca | 1260 |
| gtggtgaagg | cgttgatgga | gggtgaggag | gggaagaagg | taaggaatag | gatgaaggaa | 1320 |
| ctcaaggaag | cggcggcacg | tgcggttagt | gatgacggtg | cgtcgaccat | agcgattgcg | 1380 |
| gacttggcgc | aaaaatggcg | gagttcgatg | aagcattga | | | 1419 |

<210> SEQ ID NO 8
<211> LENGTH: 472
<212> TYPE: PRT
<213> ORGANISM: Rhodiola rosea
<300> PUBLICATION INFORMATION:
<308> DATABASE ACCESSION NUMBER: GenBank MF674528

<400> SEQUENCE: 8

Met Ser Gly Thr Pro His Ile Ala Ile Leu Pro Ser Pro Gly Met Gly
1               5                   10                  15

His Leu Ile Pro Met Ala Glu Phe Ala Lys Arg Leu Val His His His
                20                  25                  30

Asn Phe Ser Ile Thr Phe Val Ile Pro Thr Asp Gly Pro Ser Ser
            35                  40                  45

Ala Tyr Gln Gln Val Leu Thr Ser Leu Pro Ser Ser Ile Asp His Ile
        50                  55                  60

Phe Leu Pro Gln Val Asp Leu Thr Asp Val Val Ser Gln Ser Pro Ala
65                  70                  75                  80

His Pro Arg Ile Glu Thr Leu Ile Ser Leu Thr Val Ala Arg Ser Leu
                85                  90                  95

Ser Ser Leu Arg Thr Thr Leu Ser Ser Leu Gln Ser Ser Lys Asn Leu
            100                 105                 110

Val Ser Leu Val Val Asp Leu Phe Gly Thr Asp Ala Phe Asp Pro Ala
        115                 120                 125

Ile Glu Leu Gly Ile Ser Pro Tyr Ile Phe Phe Pro Ser Thr Ala Met
    130                 135                 140

Thr Leu Ser Leu Phe Leu Tyr Met Pro Gln Leu Asp Lys Ser Val Thr
145                 150                 155                 160

Cys Glu Phe Arg His Met Thr Asp Leu Val Arg Ile Pro Gly Cys Val
                165                 170                 175

Pro Val Arg Gly Ser Asp Leu Phe Asp Pro Val Gln Asp Arg Thr Asp
            180                 185                 190

Glu Ala Tyr Lys Trp Val Ile His Ser Asn Arg Tyr Pro Met Ala
        195                 200                 205

Glu Gly Val Ile Glu Asn Ser Phe Met Glu Leu Glu His Gly Ala Leu
    210                 215                 220

Lys Tyr Leu Gln Thr Val Gln Ser Gly Lys Pro Pro Val Tyr Ala Val
225                 230                 235                 240

Gly Pro Leu Ile Lys Met Asp Tyr Asp Val Asp Asp Ser Gly Ser Lys
                245                 250                 255

Ile Ile Glu Trp Leu Asp Asp Gln Pro Val Gly Ser Val Leu Phe Val
            260                 265                 270

Ser Phe Gly Ser Gly Gly Thr Leu Ser Tyr Glu Gln Met Thr Glu Leu
        275                 280                 285

Ala His Gly Leu Glu Ser Ser Gln Gln Arg Phe Leu Trp Val Val Arg
    290                 295                 300

Ser Pro Asn Gln Ile Pro Asn Ser Thr Tyr Phe Ser Val Gln Ser Gln
305                 310                 315                 320

Lys Asp Pro Leu Ala Tyr Leu Pro Glu Gly Phe Leu Asn Arg Thr Glu
                325                 330                 335

Gly Arg Gly Leu Val Val Ser Asn Trp Ala Pro Gln Ala Gln Ile Leu
            340                 345                 350

Ser His Gly Ser Thr Gly Gly Phe Met Ser His Cys Gly Trp Asn Ser
        355                 360                 365

Ile Leu Glu Ser Val Val His Gly Val Pro Ile Ile Ala Trp Pro Leu
    370                 375                 380

Tyr Ala Glu Gln Lys Met Asn Ser Ile Ile Val Glu Asp Val Lys
385                 390                 395                 400

Val Ala Leu Arg Pro Ala Gly Val Gly Glu Arg Val Val Glu Arg Ser
                405                 410                 415

Glu Ile Thr Ala Val Val Lys Ala Leu Met Glu Gly Glu Glu Gly Lys
            420                 425                 430

Lys Val Arg Asn Arg Met Lys Glu Leu Lys Glu Ala Ala Arg Ala
        435                 440                 445

Val Ser Asp Asp Gly Ala Ser Thr Ile Ala Ile Ala Asp Leu Ala Gln
    450                 455                 460

Lys Trp Arg Ser Ser Met Lys His
465                 470

<210> SEQ ID NO 9
<211> LENGTH: 1431

```
<212> TYPE: DNA
<213> ORGANISM: Rhodiola rosea

<400> SEQUENCE: 9
atggctgaaa acactcatgc tcatgccata gtggtaccat ttccagttca aggacacata        60
aagccctcgc tgaatctagc cctcaagcta gcatctcaag gcttcaccat cactttgtc        120
accactcatt tcacccacca gcaaatctcc caagctcaca aaacagtac aaatacaaac        180
catgacatgt ttttccaggc acgaaactcc agtctcgata ccgccatgt aacggtgaca        240
gacactttc ctttgggatt cgatcgcgca gggaatcagg atcagttttg ggagggcatg        300
cttcacgtat tccctgcaca tgttgatgaa ctggtggatc agttaatgaa ttcttcgaag        360
ccgagaccaa cttgtttgat tctggataca ttttataact ggggttccaa aattgctaac        420
aagtttaatt tagtgcatat ttcatttttgg actcagtctg ctctttcttt cactttgttt        480
taccattggg aacttttaaa gaaaaatggt cactttggct ctccagataa tcgcacggat        540
gtcatcgatt atattcccgg tgtgcaagag atcaagcccg cagacttaat atcctacctt        600
cagatgagtg atacaactac tgtggctcac aggacttgtt tcacagcatt tgaagatgtc        660
aggaaggcag atttcatcct ggctaataca atccaagaat ttgaaactga tacaatttct        720
tctatccgat tcaccagcc attttttctac ccaattggac ctgtttttttt aacaaagtct        780
gaacaacaag ctagctcagc tttgtggtct gagtcagact gtgagcagtg gctaagtaca        840
aaaccaaaag ggtctgttct ctatgcctca tttgggagct atgctcgtgt aactaggcat        900
gatatcgcag agatagccta cggattgatg caaagtgagg tgaattttat ttgggtgatt        960
cgcgacgata ttgtgggtgc acacgagact gattttttac caacagaatt cataaatgga       1020
atcaaactca aagatcaggg actactagtt tcctggtgct ctcaaactga agttttgtcc       1080
aatgcggcga ttggaggatt tctgactcat tgtggatgga actcgatact cgaaagcgta       1140
tggtgtgaag ttccattatt gtgttttcca ataatgactg atcagcctag taacaggaaa       1200
ctggtggtgg atgactggag gatcggcgtc aacctatctg cggcgagga ggtcagtaga       1260
gaagaagtgt caatgaaggt caggaacttg atttctggag aattgggaa tgagttgaga       1320
gtgcagattc aaaagtacaa aaagttgatg agaatggta taatgaagg tggatcatca       1380
cattccaatt ggaacaagtt catccacgac ctacaaatct tcaagaaatg a              1431

<210> SEQ ID NO 10
<211> LENGTH: 476
<212> TYPE: PRT
<213> ORGANISM: Rhodiola rosea
<300> PUBLICATION INFORMATION:
<308> DATABASE ACCESSION NUMBER: GenBank MF674532

<400> SEQUENCE: 10
```

Met Ala Glu Asn Thr His Ala His Ala Ile Val Val Pro Phe Pro Val
1               5                   10                  15

Gln Gly His Ile Lys Pro Ser Leu Asn Leu Ala Leu Lys Leu Ala Ser
            20                  25                  30

Gln Gly Phe Thr Ile Thr Phe Val Thr Thr His Phe Thr His Gln Gln
        35                  40                  45

Ile Ser Gln Ala His Lys Asn Ser Thr Asn Thr Asn His Asp Met Phe
    50                  55                  60

Phe Gln Ala Arg Asn Ser Ser Leu Asp Ile Arg His Val Thr Val Thr
65                  70                  75                  80

Asp Thr Phe Pro Leu Gly Phe Asp Arg Ala Gly Asn Gln Asp Gln Phe

```
             85                  90                  95
Trp Glu Gly Met Leu His Val Phe Pro Ala His Val Asp Glu Leu Val
            100                 105                 110
Asp Gln Leu Met Asn Ser Ser Lys Pro Arg Pro Thr Cys Leu Ile Leu
            115                 120                 125
Asp Thr Phe Tyr Asn Trp Gly Ser Lys Ile Ala Asn Lys Phe Asn Leu
        130                 135                 140
Val His Ile Ser Phe Trp Thr Gln Ser Ala Leu Ser Phe Thr Leu Phe
145                 150                 155                 160
Tyr His Trp Glu Leu Leu Lys Lys Asn Gly His Phe Gly Ser Pro Asp
                165                 170                 175
Asn Arg Thr Asp Val Ile Asp Tyr Ile Pro Gly Val Gln Glu Ile Lys
            180                 185                 190
Pro Ala Asp Leu Ile Ser Tyr Leu Gln Met Ser Asp Thr Thr Thr Val
            195                 200                 205
Ala His Arg Thr Cys Phe Thr Ala Phe Glu Asp Val Arg Lys Ala Asp
        210                 215                 220
Phe Ile Leu Ala Asn Thr Ile Gln Glu Phe Glu Thr Asp Thr Ile Ser
225                 230                 235                 240
Ser Ile Arg Phe His Gln Pro Phe Phe Tyr Pro Ile Gly Pro Val Phe
                245                 250                 255
Leu Thr Lys Ser Glu Gln Gln Ala Ser Ser Ala Leu Trp Ser Glu Ser
            260                 265                 270
Asp Cys Glu Gln Trp Leu Ser Thr Lys Pro Lys Gly Ser Val Leu Tyr
        275                 280                 285
Ala Ser Phe Gly Ser Tyr Ala Arg Val Thr Arg His Asp Ile Ala Glu
        290                 295                 300
Ile Ala Tyr Gly Leu Met Gln Ser Glu Val Asn Phe Ile Trp Val Ile
305                 310                 315                 320
Arg Asp Asp Ile Val Gly Ala His Glu Thr Asp Phe Leu Pro Thr Glu
                325                 330                 335
Phe Ile Asn Gly Ile Lys Leu Lys Asp Gln Gly Leu Leu Val Ser Trp
            340                 345                 350
Cys Ser Gln Thr Glu Val Leu Ser Asn Ala Ala Ile Gly Gly Phe Leu
        355                 360                 365
Thr His Cys Gly Trp Asn Ser Ile Leu Glu Ser Val Trp Cys Glu Val
        370                 375                 380
Pro Leu Leu Cys Phe Pro Ile Met Thr Asp Gln Pro Ser Asn Arg Lys
385                 390                 395                 400
Leu Val Val Asp Asp Trp Arg Ile Gly Val Asn Leu Ser Ala Ala Glu
                405                 410                 415
Glu Val Ser Arg Glu Val Ser Met Lys Val Arg Asn Leu Ile Ser
            420                 425                 430
Gly Glu Leu Gly Asn Glu Leu Arg Val Gln Ile Gln Lys Tyr Lys Lys
        435                 440                 445
Leu Met Glu Asn Gly Ile Met Glu Gly Gly Ser Ser His Ser Asn Trp
        450                 455                 460
Asn Lys Phe Ile His Asp Leu Gln Ile Phe Lys Lys
465                 470                 475

<210> SEQ ID NO 11
<211> LENGTH: 1458
<212> TYPE: DNA
<213> ORGANISM: Rhodiola rosea
```

<400> SEQUENCE: 11

```
atggcagaaa taagtctcat cttcatccct tttcccgtaa tcagccatct cactcccaca      60
atcgaaatcg ccaaaatcct cctcagcaga gaccaccgcc tttccatcac cttcctcgtc     120
atcgacatcc cccaacgaga cgcctcactc gcctccctca ccacctccat catctccgat     180
cgcctccact tcctcgatgt cgtacttcct cccaaccaac actcccaatc atccaagcca     240
tcaggcatcg cggctatcga gtccgccaaa cccgcagtca agaaaacgat cagcgatctt     300
gttgtacgat ctcagtccgc cgcatctggt ccgcggatag ctggcttcgt gctggacatg     360
ttctgcacgg ccatgatcga catcgcaact gagtttaacc ttccttcgta tatttactac     420
acttgcggct cttcgtttct ttcaatcgtg ctccacgtcc agaagctctg cgatgacgac     480
gctctcgata tcgccgattt caaaaactcg agtgtggagt tttcgttacc tgagttttca     540
aacttgattc cggctaggct gcttccatcc atggcgctcg ataaggactt ctcggcttca     600
ttcgtcggca agctagagc gttcaggaag acgaagggca ttttggtcaa ctcgcttgta     660
gagttggagc ctcacgcaat cgagtcgatg aaattagacc ggtctgttcc tccgatttac     720
tcggtcggac cagtgctcaa catgaatagc aacactgcat ttatcagaca ggagcaggag     780
aaggagatca tggagtggct ggaccaacag cctccagcat ctgtagtttt cttgtgtttt     840
ggcagcaggg gagcgttcaa gccggaccag gtgaaggaaa tcgcacgggg gttggagtcg     900
agcggctgcc ggttcctctg ggcgcttcgg cagccttcat caagcaatgt gaggttttca     960
cctcctacag attatgaaga tttctctgag gttctgcctg aagggttttt gcagcggaca    1020
tatggtgttg ggaaagtgat tggttgggca ccccagacag ctgttttaga ccaccccttcg    1080
gtgggtggat tcgtatcgca ttgcggttgg aactcgatac tggaatctct ttggtttggt    1140
gtgccgattg cgacttggcc tctgtatgct gagcagcaga tgaatgcgtt tgaggttgtg    1200
aaggagatga agattggagt ggagataagt ttggattatc ggcttgaaat gggcggtaaa    1260
caagcagaag gttctgggat tataagtggt gaacagattg agagagggat tagagatgtg    1320
atgcaggagg atagtgaagt gaggaagaag gtgaagctga tgatggaaaa gagtagagag    1380
gcagttgtgg agggaggctc ctcttataat tatatccaaa acttcatcag tgatctcagg    1440
accaacattg gcttgtaa                                                  1458
```

<210> SEQ ID NO 12
<211> LENGTH: 485
<212> TYPE: PRT
<213> ORGANISM: Rhodiola rosea
<300> PUBLICATION INFORMATION:
<308> DATABASE ACCESSION NUMBER: GenBank MF674538

<400> SEQUENCE: 12

```
Met Ala Glu Ile Ser Leu Ile Phe Ile Pro Phe Pro Val Ile Ser His
1               5                   10                  15

Leu Thr Pro Thr Ile Glu Ile Ala Lys Ile Leu Leu Ser Arg Asp His
            20                  25                  30

Arg Leu Ser Ile Thr Phe Leu Val Ile Asp Ile Pro Gln Arg Asp Ala
        35                  40                  45

Ser Leu Ala Ser Leu Thr Thr Ser Ile Ile Ser Asp Arg Leu His Phe
    50                  55                  60

Leu Asp Val Val Leu Pro Pro Asn Gln His Ser Gln Ser Ser Lys Pro
65                  70                  75                  80

Ser Gly Ile Ala Ala Ile Glu Ser Ala Lys Pro Ala Val Lys Lys Thr
```

```
            85                  90                  95
Ile Ser Asp Leu Val Val Arg Ser Gln Ser Ala Ala Ser Gly Pro Arg
            100                 105                 110

Ile Ala Gly Phe Val Leu Asp Met Phe Cys Thr Ala Met Ile Asp Ile
            115                 120                 125

Ala Thr Glu Phe Asn Leu Pro Ser Tyr Ile Tyr Tyr Thr Cys Gly Ser
        130                 135                 140

Ser Phe Leu Ser Ile Val Leu His Val Gln Lys Leu Cys Asp Asp Asp
145                 150                 155                 160

Ala Leu Asp Ile Ala Asp Phe Lys Asn Ser Ser Val Glu Phe Ser Leu
                165                 170                 175

Pro Glu Phe Ser Asn Leu Ile Pro Ala Arg Leu Leu Pro Ser Met Ala
            180                 185                 190

Leu Asp Lys Asp Phe Ser Ala Ser Phe Val Gly Lys Ala Arg Ala Phe
            195                 200                 205

Arg Lys Thr Lys Gly Ile Leu Val Asn Ser Leu Val Glu Leu Glu Pro
        210                 215                 220

His Ala Ile Glu Ser Met Lys Leu Asp Arg Ser Val Pro Pro Ile Tyr
225                 230                 235                 240

Ser Val Gly Pro Val Leu Asn Met Asn Ser Asn Thr Ala Phe Ile Arg
                245                 250                 255

Gln Glu Gln Glu Lys Glu Ile Met Glu Trp Leu Asp Gln Pro Pro
            260                 265                 270

Ala Ser Val Val Phe Leu Cys Phe Gly Ser Arg Gly Ala Phe Lys Pro
        275                 280                 285

Asp Gln Val Lys Glu Ile Ala Arg Gly Leu Glu Ser Ser Gly Cys Arg
        290                 295                 300

Phe Leu Trp Ala Leu Arg Gln Pro Ser Ser Ser Asn Val Arg Phe Ser
305                 310                 315                 320

Pro Pro Thr Asp Tyr Glu Asp Phe Ser Glu Val Leu Pro Glu Gly Phe
            325                 330                 335

Leu Gln Arg Thr Tyr Gly Val Gly Lys Val Ile Gly Trp Ala Pro Gln
            340                 345                 350

Thr Ala Val Leu Asp His Pro Ser Val Gly Gly Phe Val Ser His Cys
        355                 360                 365

Gly Trp Asn Ser Ile Leu Glu Ser Leu Trp Phe Gly Val Pro Ile Ala
        370                 375                 380

Thr Trp Pro Leu Tyr Ala Glu Gln Gln Met Asn Ala Phe Glu Val Val
385                 390                 395                 400

Lys Glu Met Lys Ile Gly Val Glu Ile Ser Leu Asp Tyr Arg Leu Glu
            405                 410                 415

Met Gly Gly Lys Gln Ala Glu Gly Gly Ile Ile Ser Gly Glu Gln
            420                 425                 430

Ile Glu Arg Gly Ile Arg Asp Val Met Gln Glu Asp Ser Glu Val Arg
        435                 440                 445

Lys Lys Val Lys Leu Met Met Glu Lys Ser Arg Glu Ala Val Val Glu
        450                 455                 460

Gly Gly Ser Ser Tyr Asn Tyr Ile Gln Asn Phe Ile Ser Asp Leu Arg
465                 470                 475                 480

Thr Asn Ile Gly Leu
            485

<210> SEQ ID NO 13
```

<211> LENGTH: 1443
<212> TYPE: DNA
<213> ORGANISM: Rhodiola rosea

<400> SEQUENCE: 13

```
atgggctcac ttccttccac aaaatcccat gcagtcctcg tcccataccc tgcccaaggc      60
cacatcaacc ctttcatgca acttgccaag ctcctacact caaaaggttt ccacataacc     120
ttcgtcaaca atgaccacaa ccatcgccgt ttgctcagaa caaaagggca tgattttgtt     180
caagggttgg aaggtttaag gtttgaagct gtgccggatg gcctacctcc atctgaccgt     240
gatgccactc aggatgtccc taagctgact gaatctattt acaataagag catgaaccaa     300
ccgttcagtg atctgcttca gaggctaaac tcaacgcccg ttcccctcc ggtcacttgt      360
gtcatatccg atgttgccat gttttttgct tgggacgtgg cggatgagct tggcatccct     420
aatgttcagt tttggacagc ttcagcttgt ggccttttgg gatacttaca gtatgatgag     480
ctcctaagaa gagccatagt cccattcaaa gatgaaaatt tcatgacgga tggttcgttg     540
gaggctttga ttgactggat tcctggcatg cctaacatga ggctgaagga cttgccaagc     600
ttcatgcgga ccacaagccc tgacgacgtg ttgttcaatt acttgcgtac aataaccacg     660
aaagctctaa atcctcggc cttgttgctg aacacatttg atgattttga acatgaagta     720
gttgaagaga tgaagaaaat gcaaccaaac atattcctag gaggtccact caacatgctt     780
ctcaggcaca catcaaaaac tgaaatcaca tccttaacaa caagtttatg aaagaggac      840
actcattgtt tagaatggct ggacaagcaa gaaccggagt cagtggtata catcaattac     900
ggatcggtga cgataatgtc tgatcaccat ttaaatgagt ttgcttgggg tttggctaac     960
agcaagcacc cttttttgtg gatcgtgagg ccggatgttg tgagggggcga gtcggggact    1020
ttgcccaagg agttttatga tgagatcaag acaggggat tgataacgag ctggtgtccg     1080
caaccagagg tgcttaaaca tccatccgta ggtgtatact tgacgcattg tggttggaac    1140
tctatcacga gagtgtggc cggaggagtg ccattgatgt gctggccgtt tttcgctgag    1200
caacagacga atagccgatt cgcgtgtacg gtgtggggca ctggagtgga ggtgaatgcg    1260
gatgtgaaga gggaggagct agcggaacaa gtgatggaga tgttggaagg aaagagggg     1320
caagagttga ggaaaaatgc taaggagtgg aggaggaagg cggaggaggc gacggacatt    1380
ggcggttctg cctatgctga tttcgatagg tttatggaaa aagtggtcca gtttagcgtc    1440
tga                                                                  1443
```

<210> SEQ ID NO 14
<211> LENGTH: 480
<212> TYPE: PRT
<213> ORGANISM: Rhodiola rosea
<300> PUBLICATION INFORMATION:
<308> DATABASE ACCESSION NUMBER: GenBank MF674542

<400> SEQUENCE: 14

Met Gly Ser Leu Pro Ser Thr Lys Ser His Ala Val Leu Val Pro Tyr
1               5                   10                  15

Pro Ala Gln Gly His Ile Asn Pro Phe Met Gln Leu Ala Lys Leu Leu
            20                  25                  30

His Ser Lys Gly Phe His Ile Thr Phe Val Asn Asp His Asn His
        35                  40                  45

Arg Arg Leu Leu Arg Thr Lys Gly His Asp Phe Val Gln Gly Leu Glu
    50                  55                  60

Gly Leu Arg Phe Glu Ala Val Pro Asp Gly Leu Pro Pro Ser Asp Arg

```
            65                  70                  75                  80
Asp Ala Thr Gln Asp Val Pro Lys Leu Thr Glu Ser Ile Tyr Asn Lys
                85                  90                  95
Ser Met Asn Gln Pro Phe Ser Asp Leu Leu Gln Arg Leu Asn Ser Thr
                100                 105                 110
Pro Gly Ser Pro Pro Val Thr Cys Val Ile Ser Asp Ala Met Phe
                115                 120                 125
Phe Ala Trp Asp Val Ala Asp Glu Leu Gly Ile Pro Asn Val Gln Phe
            130                 135                 140
Trp Thr Ala Ser Ala Cys Gly Leu Leu Gly Tyr Leu Gln Tyr Asp Glu
145                 150                 155                 160
Leu Leu Arg Arg Ala Ile Val Pro Phe Lys Asp Glu Asn Phe Met Thr
                165                 170                 175
Asp Gly Ser Leu Glu Ala Leu Ile Asp Trp Ile Pro Gly Met Pro Asn
                180                 185                 190
Met Arg Leu Lys Asp Leu Pro Ser Phe Met Arg Thr Thr Ser Pro Asp
            195                 200                 205
Asp Val Leu Phe Asn Tyr Leu Arg Thr Ile Thr Lys Ala Leu Lys
        210                 215                 220
Ser Ser Ala Leu Leu Leu Asn Thr Phe Asp Asp Phe Glu His Glu Val
225                 230                 235                 240
Val Glu Glu Met Lys Lys Met Gln Pro Asn Ile Phe Leu Gly Gly Pro
                245                 250                 255
Leu Asn Met Leu Leu Arg His Thr Ser Lys Thr Glu Ile Thr Ser Leu
                260                 265                 270
Thr Thr Ser Leu Trp Lys Glu Asp Thr His Cys Leu Glu Trp Leu Asp
            275                 280                 285
Lys Gln Glu Pro Glu Ser Val Val Tyr Ile Asn Tyr Gly Ser Val Thr
        290                 295                 300
Ile Met Ser Asp His His Leu Asn Glu Phe Ala Trp Gly Leu Ala Asn
305                 310                 315                 320
Ser Lys His Pro Phe Leu Trp Ile Val Arg Pro Asp Val Val Arg Gly
                325                 330                 335
Glu Ser Gly Thr Leu Pro Lys Glu Phe Tyr Asp Glu Ile Lys Asp Arg
                340                 345                 350
Gly Leu Ile Thr Ser Trp Cys Pro Gln Pro Glu Val Leu Lys His Pro
            355                 360                 365
Ser Val Gly Val Tyr Leu Thr His Cys Gly Trp Asn Ser Ile Thr Glu
        370                 375                 380
Ser Val Ala Gly Gly Val Pro Leu Met Cys Trp Pro Phe Phe Ala Glu
385                 390                 395                 400
Gln Gln Thr Asn Ser Arg Phe Ala Cys Thr Val Trp Gly Thr Gly Val
                405                 410                 415
Glu Val Asn Ala Asp Val Lys Arg Glu Glu Leu Ala Glu Gln Val Met
                420                 425                 430
Glu Met Leu Glu Gly Lys Arg Gly Gln Glu Leu Arg Lys Asn Ala Lys
            435                 440                 445
Glu Trp Arg Arg Lys Ala Glu Glu Ala Thr Asp Ile Gly Gly Ser Ala
        450                 455                 460
Tyr Ala Asp Phe Asp Arg Phe Met Glu Lys Val Val Gln Phe Ser Val
465                 470                 475                 480

<210> SEQ ID NO 15
```

```
<211> LENGTH: 1488
<212> TYPE: DNA
<213> ORGANISM: Rhodiola rosea

<400> SEQUENCE: 15
atgggatctc taggaaagaa gattcaacaa aagccacatg caatatgcac cccatacccca      60 gcacaaggcc atattaatcc catgcttaaa ctagccaagc tcctacacca ctcaggcttc     120
tacataacct tgttcacac aacctacaac tacaatcgcc ttctcaagac ccacgggtct      180
gattccttaa gtggtctacc agatttccaa tttgagacca tccctgatgg actaccacca     240
tcagatgcag ctgatgtcac acaagacatc cctgccttgt gtaaatcaac caccgaaacc     300
tgcttagtcc cattcaaaga gctcctggct aagctgcata caagtcaat ggcgtcaccg      360 gaggaagttc ctccagtgac atgcatagtt tctgatggtt gcatgtcatt tactgtggat     420
gctgcagaag aggcaggggt tcctaatgtg cttctttgga ctaccagtgc atgcggattt     480
ttaggatatg ctaattaccc gaaacttatt gacagaggca taattccact caaagatgag     540
agctacttta cgaatgggta cctagacaag acagtagatg aataccctgg aatgaaaggc     600
atacggctac gagacttccc aaactttgta tgcaccacaa acccagatga gtttatggtg     660
aaatatgcaa ttcaagagat cactagagct gccagagcag atgctgttat tttgaacacc     720
tttgacgctt tggaacatga tttcttagat ggcctatcaa acatatacc aaaggtcctc      780 cctattggcc cgctccagct tccgctcaac caaatcccag agagctcacc tctacattca     840
atctgttcta gtctctggaa agatgaacca cagtgcatta cctggttaaa ctcccaaaaa     900
ccaaaatcag tcgtttatgt taactacgga agtatcacag ttatgactcc gcaacaaatg     960
gtggagttcg catggggact ggctaataca aaatacccctt ttctgtggat tattagacct    1020
gatttggttg ctggtgagac agctgtccta cctccagatt ttttggaagt gacaaaagga    1080
aggagctgct tggctagttg gtgcccacag gaacaagttc ttagtcacac atccatagga    1140
gggttcttaa cccattgtgg gtggaactca atgctagaaa gcgtggtcga aggagttcca    1200
atggtatgct ggccgttttt tgctgagcaa cagactaatt gctgggctgc tcggacaaaa    1260 tgggtatag gtatggaaat tgacaatgat gttaagaggg ataaggttca gaaaatggtg    1320
acagagctta tggagggcga aaagggaaag gagatgaaga ggaagggcgg agaatggaag    1380
aagcttgggg cagaagctgc cggtcctaat ggctcagcta ccttaaactt cagcagactt    1440
ataaatgacg tacttctgtc caaaaaaaaa attgtagtta caacctaa                 1488

<210> SEQ ID NO 16
<211> LENGTH: 495
<212> TYPE: PRT
<213> ORGANISM: Rhodiola rosea
<300> PUBLICATION INFORMATION:
<308> DATABASE ACCESSION NUMBER: GenBank MF674554

<400> SEQUENCE: 16

Met Gly Ser Leu Gly Lys Lys Ile Gln Gln Lys Pro His Ala Ile Cys
1               5                   10                  15

Thr Pro Tyr Pro Ala Gln Gly His Ile Asn Pro Met Leu Lys Leu Ala
            20                  25                  30

Lys Leu Leu His His Ser Gly Phe Tyr Ile Thr Phe Val His Thr Thr
        35                  40                  45

Tyr Asn Tyr Asn Arg Leu Leu Lys Thr His Gly Ser Asp Ser Leu Ser
    50                  55                  60

Gly Leu Pro Asp Phe Gln Phe Glu Thr Ile Pro Asp Gly Leu Pro Pro
```

-continued

```
                65                  70                  75                  80
Ser Asp Ala Ala Asp Val Thr Gln Asp Ile Pro Ala Leu Cys Lys Ser
                        85                  90                  95

Thr Thr Glu Thr Cys Leu Val Pro Phe Lys Glu Leu Leu Ala Lys Leu
                    100                 105                 110

His Asn Lys Ser Met Ala Ser Pro Glu Glu Val Pro Pro Val Thr Cys
                115                 120                 125

Ile Val Ser Asp Gly Cys Met Ser Phe Thr Val Asp Ala Ala Glu Glu
            130                 135                 140

Ala Gly Val Pro Asn Val Leu Leu Trp Thr Thr Ser Ala Cys Gly Phe
145                 150                 155                 160

Leu Gly Tyr Ala Asn Tyr Pro Lys Leu Ile Asp Arg Gly Ile Ile Pro
                    165                 170                 175

Leu Lys Asp Glu Ser Tyr Phe Thr Asn Gly Tyr Leu Lys Thr Val
                180                 185                 190

Asp Gly Ile Pro Gly Met Lys Gly Ile Arg Leu Arg Asp Phe Pro Asn
                195                 200                 205

Phe Val Cys Thr Thr Asn Pro Asp Glu Phe Met Val Lys Tyr Ala Ile
            210                 215                 220

Gln Glu Ile Thr Arg Ala Ala Arg Ala Asp Ala Val Ile Leu Asn Thr
225                 230                 235                 240

Phe Asp Ala Leu Glu His Asp Phe Leu Asp Gly Leu Ser Asn Ile Tyr
                    245                 250                 255

Pro Lys Val Leu Pro Ile Gly Pro Leu Gln Leu Pro Leu Asn Gln Ile
                260                 265                 270

Pro Glu Ser Ser Pro Leu His Ser Ile Cys Ser Ser Leu Trp Lys Asp
            275                 280                 285

Glu Pro Gln Cys Ile Thr Trp Leu Asn Ser Gln Lys Pro Lys Ser Val
290                 295                 300

Val Tyr Val Asn Tyr Gly Ser Ile Thr Val Met Thr Pro Gln Gln Met
305                 310                 315                 320

Val Glu Phe Ala Trp Gly Leu Ala Asn Thr Lys Tyr Pro Phe Leu Trp
                    325                 330                 335

Ile Ile Arg Pro Asp Leu Val Ala Gly Glu Thr Ala Val Leu Pro Pro
                340                 345                 350

Asp Phe Leu Glu Val Thr Lys Gly Arg Ser Cys Leu Ala Ser Trp Cys
            355                 360                 365

Pro Gln Glu Gln Val Leu Ser His Thr Ser Ile Gly Gly Phe Leu Thr
370                 375                 380

His Cys Gly Trp Asn Ser Met Leu Glu Ser Val Val Glu Gly Val Pro
385                 390                 395                 400

Met Val Cys Trp Pro Phe Phe Ala Glu Gln Gln Thr Asn Cys Trp Ala
                    405                 410                 415

Ala Arg Thr Lys Trp Gly Ile Gly Met Glu Ile Asp Asn Asp Val Lys
                420                 425                 430

Arg Asp Lys Val Gln Lys Met Val Thr Glu Leu Met Glu Gly Glu Lys
            435                 440                 445

Gly Lys Glu Met Lys Arg Lys Gly Gly Glu Trp Lys Lys Leu Gly Ala
450                 455                 460

Glu Ala Ala Gly Pro Asn Gly Ser Ala Thr Leu Asn Phe Ser Arg Leu
465                 470                 475                 480

Ile Asn Asp Val Leu Leu Ser Lys Lys Lys Ile Val Val Thr Thr
                485                 490                 495
```

<210> SEQ ID NO 17
<211> LENGTH: 1476
<212> TYPE: DNA
<213> ORGANISM: Rhodiola rosea

<400> SEQUENCE: 17

```
atgggatctc taggaaagaa gattcaacaa aagccacatg caatatgcac cccataccca      60
gcacaaggcc atattaatcc catgcttaaa ctagccaagc tcctacacca ctcaggcttc     120
tacataacct tgttcacac aacctacaac tacaatcgcc ttctcaagac ccacgggtct      180
gattccttaa gtggtctacc agatttccaa tttgagacca tccctgatgg actaccacca     240
tcagatgcag ctgatgtcac acaagacatc cctgccttgt gtaaatcaac caccgaaacc     300
tgcttagtcc cattcaaaga gctcctggct aagctgcata caagtcaat ggcgtcaccg      360
gaggaagttc ctccagtgac atgcatagtt tctgatggtt gcatgtcatt tactgtggat     420
gctgcagaag aggcaggggt tcctaatgtg cttctttgga ctaccagtgc atgcggattt     480
ttaggatatg ctaattaccc gaaacttatt gacagaggca taattccact caagatgag      540
agctacttta cgaatgggta cctagacaag acagtagatg aataccctgg aatgaaaggc     600
atacggctac gagacttccc aaactttgta tgcaccacaa acccagatga gtttatggtg     660
aaatatgcaa ttcaagagat cactagagct gccagagcag atgctgttat tttgaacacc     720
tttgacgctt tggaacatga tttcttagat ggcctatcaa acatataccc aaaggtcctc     780
cctattggcc cgctccagct tccgctcaac caaatcccag agagctcacc tctacattca     840
atctgttcta gtctctggaa agatgaacca cagtgcatta cctggttaaa ctcccaaaaa     900
ccaaaatcag tcgtttatgt taactacgga agtatcacag ttatgactcc gcaacaaatg     960
gtggagttcg catggggact ggctaataca aaatacccct ttctgtggat tattagacct    1020
gatttggttg ctggtgagac agctgtccta cctccagatt ttttggaagt gacaaaagga    1080
aggagctgct tggctagttg gtgcccacag gaacaagttc ttagtcacac atccatagga    1140
gggttcttaa cccattgtgg gtggaactca atgctagaaa gcgtggtcga aggagttcca    1200
atggtatgct ggccgttttt tgctgagcaa cagactaatt gctgggctgc tcggacaaaa    1260
tggggtatag gtatggaaat tgacaatgat gttaagaggg ataaggttca gaaaatggtg    1320
acagagctta tggagggcga aaagggaaag gagatgaaga ggaagggcgg agaatggaag    1380
aagcttgggg cagaagctgc cggtcctaat ggctcagcta ccttaaactt cagcagactt    1440
ataaatgacg tacttctgtc caaaaaaaaa ttgtag                              1476
```

<210> SEQ ID NO 18
<211> LENGTH: 491
<212> TYPE: PRT
<213> ORGANISM: Rhodiola rosea
<300> PUBLICATION INFORMATION:
<308> DATABASE ACCESSION NUMBER: GenBank MF674557

<400> SEQUENCE: 18

```
Met Gly Ser Leu Gly Lys Lys Ile Gln Gln Lys Pro His Ala Ile Cys
1               5                   10                  15

Thr Pro Tyr Pro Ala Gln Gly His Ile Asn Pro Met Leu Lys Leu Ala
            20                  25                  30

Lys Leu Leu His His Ser Gly Phe Tyr Ile Thr Phe Val His Thr Thr
        35                  40                  45

Tyr Asn Tyr Asn Arg Leu Leu Lys Thr His Gly Ser Asp Ser Leu Ser
```

-continued

```
            50                  55                  60
Gly Leu Pro Asp Phe Gln Phe Glu Thr Ile Pro Asp Gly Leu Pro Pro
 65                  70                  75                  80

Ser Asp Ala Ala Asp Val Thr Gln Asp Ile Pro Ala Leu Cys Lys Ser
                 85                  90                  95

Thr Thr Glu Thr Cys Leu Val Pro Phe Lys Glu Leu Leu Ala Lys Leu
            100                 105                 110

His Asn Lys Ser Met Ala Ser Pro Glu Glu Val Pro Pro Val Thr Cys
            115                 120                 125

Ile Val Ser Asp Gly Cys Met Ser Phe Thr Val Asp Ala Ala Glu Glu
            130                 135                 140

Ala Gly Val Pro Asn Val Leu Leu Trp Thr Thr Ser Ala Cys Gly Phe
145                 150                 155                 160

Leu Gly Tyr Ala Asn Tyr Pro Lys Leu Ile Asp Arg Gly Ile Ile Pro
                165                 170                 175

Leu Lys Asp Glu Ser Tyr Phe Thr Asn Gly Tyr Leu Asp Lys Thr Val
                180                 185                 190

Asp Gly Ile Pro Gly Met Lys Gly Ile Arg Leu Arg Asp Phe Pro Asn
                195                 200                 205

Phe Val Cys Thr Thr Asn Pro Asp Glu Phe Met Val Lys Tyr Ala Ile
                210                 215                 220

Gln Glu Ile Thr Arg Ala Ala Arg Ala Asp Ala Val Ile Leu Asn Thr
225                 230                 235                 240

Phe Asp Ala Leu Glu His Asp Phe Leu Asp Gly Leu Ser Asn Ile Tyr
                245                 250                 255

Pro Lys Val Leu Pro Ile Gly Pro Leu Gln Leu Pro Leu Asn Gln Ile
                260                 265                 270

Pro Glu Ser Ser Pro Leu His Ser Ile Cys Ser Ser Leu Trp Lys Asp
                275                 280                 285

Glu Pro Gln Cys Ile Thr Trp Leu Asn Ser Gln Lys Pro Lys Ser Val
                290                 295                 300

Val Tyr Val Asn Tyr Gly Ser Ile Thr Val Met Thr Pro Gln Gln Met
305                 310                 315                 320

Val Glu Phe Ala Trp Gly Leu Ala Asn Thr Lys Tyr Pro Phe Leu Trp
                325                 330                 335

Ile Ile Arg Pro Asp Leu Val Ala Gly Glu Thr Ala Val Leu Pro Pro
                340                 345                 350

Asp Phe Leu Glu Val Thr Lys Gly Arg Ser Cys Leu Ala Ser Trp Cys
                355                 360                 365

Pro Gln Glu Gln Val Leu Ser His Thr Ser Ile Gly Gly Phe Leu Thr
                370                 375                 380

His Cys Gly Trp Asn Ser Met Leu Glu Ser Val Val Glu Gly Val Pro
385                 390                 395                 400

Met Val Cys Trp Pro Phe Phe Ala Glu Gln Gln Thr Asn Cys Trp Ala
                405                 410                 415

Ala Arg Thr Lys Trp Gly Ile Gly Met Glu Ile Asp Asn Asp Val Lys
                420                 425                 430

Arg Asp Lys Val Gln Lys Met Val Thr Glu Leu Met Glu Gly Glu Lys
                435                 440                 445

Gly Lys Glu Met Lys Arg Lys Gly Glu Trp Lys Lys Leu Gly Ala
                450                 455                 460

Glu Ala Ala Gly Pro Asn Gly Ser Ala Thr Leu Asn Phe Ser Arg Leu
465                 470                 475                 480
```

```
Ile Asn Asp Val Leu Leu Ser Lys Lys Lys Leu
            485                 490
```

<210> SEQ ID NO 19
<211> LENGTH: 1497
<212> TYPE: DNA
<213> ORGANISM: Rhodiola rosea

<400> SEQUENCE: 19

```
atgagcttaa ttgaaaaacc actcacggcc atagagactc gtgaaaaacc acacgctgtg    60
tgcatcccat acccagctca aggccatatc aatcccatga tgcaacttgc aaagctcctc   120
caccactctg gtttccacat aacgtttgtc cacactgagt ataattatga ccgtctagtg   180
aagtctcaag gttcagcttg tgtggctggt ttaccggatt ccgctttga agccatccca    240
gatggcttgc cctcgacgaa tggtgatgtt actcaagaca ttcctctgtt gagtagctct   300
acttctaaaa cctgcttgaa gccgtttaag gagttattga agaggttgca ggacaaatgc   360
aaagagttac ctgatgatgt tccgcctctg tcgtgcatcg tgtctgatgc agccatgtcg   420
tttacgatcg atgcatctga ggagtttgga gtgcccatag cgcttctttg gactgcaagt   480
gcctgcgggt tcttgggtta cacgcattac ccatatctaa ttgacagagg tgtcatccca   540
ttgaaagatg agagccaatt aacaaacgga tacctagata tgagcataga tggcatacct   600
tgtatggaag gtatccgctt acgagacctc ccaagctttc tacgcacaac tgatttagat   660
gatatgatgt ttagttatat actgcacgaa ataaaacaag tttcaagagg cagtgctatc   720
attctgaaca ccttttgaagc tttggaccat gatgtcttgg atagtctctc caaaatttac   780
caaaatgtca tcctgccagt tggccctcta catgtctcgc tcaacaagat cccaaaacac   840
tacccacttc aatctttaag ctcgaattta tggaaagatg acacagactg cattccctgg   900
ctgagctcta aggcttcaaa atcagttata tacgttaact ttgggagcat cacgacggta   960
tcaccaaaac aaattgtgga gtttgcgtgg ggattggcta acagcaaaca ccctttcctt  1020
tggataatca gaccggactt ggtggcaggt gaggcatcca tcattccgca ggacttcatg  1080
gatgaaacaa aaggaagagg tttgttggct ggttggtgtg accaagagct tgttctcaac  1140
catccatcca ttggagggtt tcttacgcac tgtggctgga actcaattat tgaaagcatt  1200
agcgcaggag tccctacggt ctgctggcca tttttttgctg agcagcaaac aaattgttgg  1260
tttgcttgca aaaaatggtg cattgggatg agatgcata ctgatgtaaa gagggatgag  1320
gttgacaagc tgttgagaga gctaatgaa ggtgacaaag gggaggagtt gaagaggaag  1380
gcaaccaact ggaagaggct ggcagaagaa gctgtttcct ccactggctt atcaacctta  1440
aacttcagga cgttagtgaa tcaagtcctg ctctcaaaaa caaaacatat ccgttag     1497
```

<210> SEQ ID NO 20
<211> LENGTH: 498
<212> TYPE: PRT
<213> ORGANISM: Rhodiola rosea
<300> PUBLICATION INFORMATION:
<308> DATABASE ACCESSION NUMBER: GenBank MF674558

<400> SEQUENCE: 20

```
Met Ser Leu Ile Glu Lys Pro Leu Thr Ala Ile Glu Thr Arg Glu Lys
1               5                   10                  15

Pro His Ala Val Cys Ile Pro Tyr Pro Ala Gln Gly His Ile Asn Pro
                20                  25                  30

Met Met Gln Leu Ala Lys Leu Leu His His Ser Gly Phe His Ile Thr
```

```
             35                  40                  45
Phe Val His Thr Glu Tyr Asn Tyr Asp Arg Leu Val Lys Ser Gln Gly
 50                  55                  60

Ser Ala Cys Val Ala Gly Leu Pro Asp Phe Arg Phe Glu Ala Ile Pro
 65                  70                  75                  80

Asp Gly Leu Pro Ser Thr Asn Gly Asp Val Thr Gln Asp Ile Pro Leu
                 85                  90                  95

Leu Ser Ser Ser Thr Ser Lys Thr Cys Leu Lys Pro Phe Lys Glu Leu
                100                 105                 110

Leu Lys Arg Leu Gln Asp Lys Cys Lys Glu Leu Pro Asp Asp Val Pro
            115                 120                 125

Pro Leu Ser Cys Ile Val Ser Asp Ala Ala Met Ser Phe Thr Ile Asp
        130                 135                 140

Ala Ser Glu Glu Phe Gly Val Pro Ile Ala Leu Leu Trp Thr Ala Ser
145                 150                 155                 160

Ala Cys Gly Phe Leu Gly Tyr Thr His Tyr Pro Tyr Leu Ile Asp Arg
                165                 170                 175

Gly Val Ile Pro Leu Lys Asp Glu Ser Gln Leu Thr Asn Gly Tyr Leu
            180                 185                 190

Asp Met Ser Ile Asp Gly Ile Pro Cys Met Glu Gly Ile Arg Leu Arg
        195                 200                 205

Asp Leu Pro Ser Phe Leu Arg Thr Thr Asp Leu Asp Asp Met Met Phe
210                 215                 220

Ser Tyr Ile Leu His Glu Ile Lys Gln Val Ser Arg Gly Ser Ala Ile
225                 230                 235                 240

Ile Leu Asn Thr Phe Glu Ala Leu Asp His Asp Val Leu Asp Ser Leu
                245                 250                 255

Ser Lys Ile Tyr Gln Asn Val Ile Leu Pro Val Gly Pro Leu His Val
            260                 265                 270

Ser Leu Asn Lys Ile Pro Lys His Tyr Pro Leu Gln Ser Leu Ser Ser
        275                 280                 285

Asn Leu Trp Lys Asp Asp Thr Asp Cys Ile Pro Trp Leu Ser Ser Lys
290                 295                 300

Ala Ser Lys Ser Val Ile Tyr Val Asn Phe Gly Ser Ile Thr Thr Val
305                 310                 315                 320

Ser Pro Lys Gln Ile Val Glu Phe Ala Trp Gly Leu Ala Asn Ser Lys
                325                 330                 335

His Pro Phe Leu Trp Ile Ile Arg Pro Asp Leu Val Ala Gly Glu Ala
            340                 345                 350

Ser Ile Ile Pro Gln Asp Phe Met Asp Glu Thr Lys Gly Arg Gly Leu
        355                 360                 365

Leu Ala Gly Trp Cys Asp Gln Glu Leu Val Leu Asn His Pro Ser Ile
370                 375                 380

Gly Gly Phe Leu Thr His Cys Gly Trp Asn Ser Ile Ile Glu Ser Ile
385                 390                 395                 400

Ser Ala Gly Val Pro Thr Val Cys Trp Pro Phe Phe Ala Glu Gln Gln
                405                 410                 415

Thr Asn Cys Trp Phe Ala Cys Lys Lys Trp Cys Ile Gly Met Glu Met
            420                 425                 430

His Thr Asp Val Lys Arg Asp Glu Val Asp Lys Leu Leu Arg Glu Leu
        435                 440                 445

Met Glu Gly Asp Lys Gly Glu Glu Leu Lys Arg Lys Ala Thr Asn Trp
450                 455                 460
```

```
Lys Arg Leu Ala Glu Glu Ala Val Ser Ser Thr Gly Leu Ser Thr Leu
465                 470                 475                 480

Asn Phe Arg Thr Leu Val Asn Gln Val Leu Ser Lys Thr Lys His
            485                 490                 495

Ile Arg

<210> SEQ ID NO 21
<211> LENGTH: 490
<212> TYPE: PRT
<213> ORGANISM: Arabidopsis thaliana
<300> PUBLICATION INFORMATION:
<308> DATABASE ACCESSION NUMBER: AT2G20340.1

<400> SEQUENCE: 21

Met Glu Asn Gly Ser Gly Lys Val Leu Lys Pro Met Asp Ser Glu Gln
1               5                   10                  15

Leu Arg Glu Tyr Gly His Leu Met Val Asp Phe Ile Ala Asp Tyr Tyr
                20                  25                  30

Lys Thr Ile Glu Asp Phe Pro Val Leu Ser Gln Val Gln Pro Gly Tyr
            35                  40                  45

Leu His Lys Leu Leu Pro Asp Ser Ala Pro Asp His Pro Glu Thr Leu
    50                  55                  60

Asp Gln Val Leu Asp Asp Val Arg Ala Lys Ile Leu Pro Gly Val Thr
65                  70                  75                  80

His Trp Gln Ser Pro Ser Phe Phe Ala Tyr Tyr Pro Ser Asn Ser Ser
                85                  90                  95

Val Ala Gly Phe Leu Gly Glu Met Leu Ser Ala Gly Leu Gly Ile Val
                100                 105                 110

Gly Phe Ser Trp Val Thr Ser Pro Ala Ala Thr Glu Leu Glu Met Ile
            115                 120                 125

Val Leu Asp Trp Val Ala Lys Leu Leu Asn Leu Pro Glu Gln Phe Met
    130                 135                 140

Ser Lys Gly Asn Gly Gly Gly Val Ile Gln Gly Ser Ala Ser Glu Ala
145                 150                 155                 160

Val Leu Val Val Leu Ile Ala Ala Arg Asp Lys Val Leu Arg Ser Val
                165                 170                 175

Gly Lys Asn Ala Leu Glu Lys Leu Val Val Tyr Ser Ser Asp Gln Thr
            180                 185                 190

His Ser Ala Leu Gln Lys Ala Cys Gln Ile Ala Gly Ile His Pro Glu
    195                 200                 205

Asn Cys Arg Val Leu Thr Thr Asp Ser Ser Thr Asn Tyr Ala Leu Arg
210                 215                 220

Pro Glu Ser Leu Gln Glu Ala Val Ser Arg Asp Leu Glu Ala Gly Leu
225                 230                 235                 240

Ile Pro Phe Phe Leu Cys Ala Asn Val Gly Thr Thr Ser Ser Thr Ala
                245                 250                 255

Val Asp Pro Leu Ala Ala Leu Gly Lys Ile Ala Asn Ser Asn Gly Ile
            260                 265                 270

Trp Phe His Val Asp Ala Ala Tyr Ala Gly Ser Ala Cys Ile Cys Pro
    275                 280                 285

Glu Tyr Arg Gln Tyr Ile Asp Gly Val Glu Thr Ala Asp Ser Phe Asn
290                 295                 300

Met Asn Ala His Lys Trp Phe Leu Thr Asn Phe Asp Cys Ser Leu Leu
305                 310                 315                 320
```

```
Trp Val Lys Asp Gln Asp Ser Leu Thr Leu Ala Leu Ser Thr Asn Pro
            325                 330                 335

Glu Phe Leu Lys Asn Lys Ala Ser Gln Ala Asn Leu Val Val Asp Tyr
            340                 345                 350

Lys Asp Trp Gln Ile Pro Leu Gly Arg Arg Phe Arg Ser Leu Lys Leu
            355                 360                 365

Trp Met Val Leu Arg Leu Tyr Gly Ser Glu Thr Leu Lys Ser Tyr Ile
370                 375                 380

Arg Asn His Ile Lys Leu Ala Lys Glu Phe Glu Gln Leu Val Ser Gln
385                 390                 395                 400

Asp Pro Asn Phe Glu Ile Val Thr Pro Arg Ile Phe Ala Leu Val Cys
            405                 410                 415

Phe Arg Leu Val Pro Val Lys Asp Glu Glu Lys Lys Cys Asn Asn Arg
            420                 425                 430

Asn Arg Glu Leu Leu Asp Ala Val Asn Ser Ser Gly Lys Leu Phe Met
            435                 440                 445

Ser His Thr Ala Leu Ser Gly Lys Ile Val Leu Arg Cys Ala Ile Gly
450                 455                 460

Ala Pro Leu Thr Glu Glu Lys His Val Lys Glu Ala Trp Lys Ile Ile
465                 470                 475                 480

Gln Glu Glu Ala Ser Tyr Leu Leu His Lys
            485                 490

<210> SEQ ID NO 22
<211> LENGTH: 498
<212> TYPE: PRT
<213> ORGANISM: Brachypodium distachyon
<300> PUBLICATION INFORMATION:
<308> DATABASE ACCESSION NUMBER: 1g28960.3

<400> SEQUENCE: 22

Met Asp Gly Ser Thr Thr Ser Asn Gly Gly Gly Gly Trp Met Arg Pro
1               5                   10                  15

Met Asp Glu Glu Gln Leu Arg Glu Cys Gly His Arg Met Val Asp Phe
            20                  25                  30

Ile Ala Asp Tyr Tyr Lys Ser Ile Glu Thr Tyr Pro Val Leu Ser Gln
        35                  40                  45

Val Gln Pro Gly Tyr Leu Lys Glu Leu Leu Pro Asp Ser Ala Pro Asn
    50                  55                  60

Gln Pro Asp Thr Leu Asp Ala Leu Phe Asp Asp Ile Arg Glu Lys Ile
65                  70                  75                  80

Val Pro Gly Val Thr His Trp Gln Ser Pro Asn Tyr Phe Ala Tyr Tyr
                85                  90                  95

Pro Ser Asn Ser Ser Thr Ala Gly Phe Leu Gly Glu Met Leu Ser Ala
            100                 105                 110

Ala Phe Asn Ile Val Gly Phe Ser Trp Ile Thr Ser Pro Ala Ala Thr
        115                 120                 125

Glu Leu Glu Val Ile Val Leu Asp Trp Val Ala Lys Met Leu Lys Leu
    130                 135                 140

Pro Ser Glu Phe Leu Ser Ala Ala Leu Gly Gly Gly Val Ile Gln Gly
145                 150                 155                 160

Thr Ala Ser Glu Ala Ile Leu Val Val Leu Ser Ala Arg Asp Arg
                165                 170                 175

Thr Leu Arg Lys His Gly Lys Lys Ser Leu Glu Lys Ile Val Val Tyr
            180                 185                 190
```

```
Ala Ser Asp Gln Thr His Ser Ala Leu Lys Lys Ala Cys Gln Ile Ala
            195                 200                 205

Gly Ile Phe Pro Glu Asn Ile Arg Ile Val Lys Ala Asp Cys Ser Met
        210                 215                 220

Asn Tyr Ala Val Thr Pro Gly Ala Val Ser Glu Ala Ile Ser Ile Asp
225                 230                 235                 240

Leu Ser Ala Gly Leu Ile Pro Phe Phe Ile Cys Ala Thr Val Gly Thr
                245                 250                 255

Thr Ser Ser Ser Ala Val Asp Pro Leu His Glu Leu Gly Gln Ile Ala
            260                 265                 270

Gln Ala His Asp Met Trp Phe His Ile Asp Ala Ala Tyr Ala Gly Ser
        275                 280                 285

Ala Cys Ile Cys Pro Glu Tyr Arg Lys Tyr Leu Asn Gly Val Glu Glu
    290                 295                 300

Ala Asp Ser Phe Asn Met Asn Ala His Lys Trp Phe Leu Thr Asn Phe
305                 310                 315                 320

Asp Cys Ser Leu Leu Trp Val Lys Asp Arg Asn Tyr Leu Ile Gln Ala
                325                 330                 335

Leu Ser Thr Asn Pro Glu Phe Leu Lys Asn Lys Ala Ser Gln Glu Asn
            340                 345                 350

Ser Val Ile Asp Phe Lys Asp Trp Gln Ile Pro Leu Gly Arg Arg Phe
        355                 360                 365

Arg Ser Leu Lys Leu Trp Met Val Leu Arg Leu Tyr Gly Val Glu Asn
    370                 375                 380

Leu Gln Ser Tyr Ile Arg Lys His Ile Gln Leu Ala Gln His Phe Glu
385                 390                 395                 400

Gln Leu Val Ile Ser Asp Pro Arg Phe Glu Val Val Thr Pro Arg Asn
                405                 410                 415

Phe Ser Leu Val Cys Phe Cys Leu Val Pro Pro Thr Cys Glu Val Asp
            420                 425                 430

Asn Gly His Lys Leu Asn Tyr Asp Leu Met Asp Ser Ala Asn Ser Ser
        435                 440                 445

Gly Lys Ile Phe Ile Ser His Thr Val Leu Ser Gly Lys Phe Val Leu
    450                 455                 460

Arg Phe Val Val Gly Ala Pro Leu Thr Glu Glu Gln His Val Asp Ala
465                 470                 475                 480

Ala Trp Lys Leu Leu Gln Asp Glu Ala Thr Lys Leu Leu Gly Asn Val
                485                 490                 495

Val Gln

<210> SEQ ID NO 23
<211> LENGTH: 480
<212> TYPE: PRT
<213> ORGANISM: Carica papaya
<300> PUBLICATION INFORMATION:
<308> DATABASE ACCESSION NUMBER: 16427710

<400> SEQUENCE: 23

Met Asp Ala Glu Gln Leu Arg Glu Asn Gly His Lys Met Val Asp Phe
1               5                   10                  15

Ile Ala Asp Tyr Tyr Lys Thr Ile Glu Asn Phe Pro Val Leu Ser Gln
                20                  25                  30

Val Glu Pro Gly Tyr Leu Arg Asp Leu Ile Pro Asp Ser Ala Pro Asn
            35                  40                  45

Ser Pro Glu Ser Phe Gln Gln Leu Leu Asp Asp Val Arg Thr Lys Ile
```

-continued

```
            50                  55                  60
Leu Pro Gly Val Thr His Trp Gln Ser Pro Asn Tyr Phe Ala Tyr Tyr
65                  70                  75                  80

Pro Ser Asn Ser Ser Val Ala Gly Phe Leu Gly Glu Met Leu Ser Ala
                85                  90                  95

Gly Leu Asn Ile Val Gly Phe Ser Trp Ile Thr Ser Pro Ala Ala Thr
                100                 105                 110

Glu Leu Glu Met Ile Val Leu Asp Trp Leu Ala Lys Leu Leu Lys Leu
                115                 120                 125

Pro Glu Asp Phe His Ser Thr Gly Asn Gly Gly Val Ile Gln Gly
    130                 135                 140

Thr Ala Ser Glu Ala Ile Leu Val Val Leu Leu Ala Ala Arg Asp Lys
145                 150                 155                 160

Val Leu Lys Arg Val Gly Lys Asn Ala Leu Glu Lys Leu Val Val Tyr
                165                 170                 175

Thr Ser Asp Gln Thr His Ser Ala Phe Gln Lys Ala Cys Gln Ile Gly
                180                 185                 190

Gly Ile His Pro Glu Asn Cys Arg Val Leu Lys Thr Asp Ser Ser Thr
                195                 200                 205

Asn Tyr Ala Leu Ser Pro Asp Leu Leu Lys Glu Ala Ile Ser Cys Asp
210                 215                 220

Val Ala Ala Gly Leu Ile Pro Phe Phe Cys Ala Thr Val Gly Thr
225                 230                 235                 240

Thr Ser Ser Thr Ala Val Asp Pro Leu Met Ala Leu Gly Lys Ile Ala
                245                 250                 255

Thr Ser Asn Glu Ile Trp Phe His Val Asp Ala Ala Tyr Ala Gly Ser
                260                 265                 270

Ala Cys Ile Cys Pro Glu Tyr Arg Pro Tyr Ile Asp Gly Val Glu Glu
                275                 280                 285

Ala Asp Ser Phe Asn Met Asn Ala His Lys Trp Phe Leu Thr Asn Phe
    290                 295                 300

Asp Cys Ser Val Leu Trp Val Lys Asp Lys Tyr Ser Leu Ile Gln Ser
305                 310                 315                 320

Leu Ser Thr Asn Pro Glu Phe Leu Lys Asn Lys Ala Ser Gln Ala Asp
                325                 330                 335

Met Val Val Asp Tyr Lys Asp Trp Gln Ile Pro Leu Gly Arg Arg Phe
                340                 345                 350

Arg Ser Leu Lys Leu Trp Met Val Leu Arg Leu Tyr Gly Val Glu Asn
                355                 360                 365

Leu Lys Ser Tyr Ile Arg Asn His Ile Lys Leu Ala Lys His Phe Glu
370                 375                 380

Glu Leu Val Thr Gln Asp Pro Arg Phe Glu Val Thr Pro Arg Ile
385                 390                 395                 400

Phe Ser Leu Val Cys Phe Arg Leu Leu Pro Pro Gly Asn Asp Glu Asn
                405                 410                 415

His Gly Asn Lys Leu Asn Gln Asp Leu Leu Glu Thr Val Asn Ser Thr
                420                 425                 430

Gly Lys Leu Phe Ile Ser His Thr Val Leu Ser Gly Lys Tyr Ile Leu
                435                 440                 445

Arg Phe Ala Val Gly Ala Pro Leu Thr Glu Glu Arg His Val Asn Glu
    450                 455                 460

Ala Trp Lys Ile Leu Gln Asp Glu Ala Ser Thr Leu Leu Glu Asn Pro
465                 470                 475                 480
```

<210> SEQ ID NO 24
<211> LENGTH: 492
<212> TYPE: PRT
<213> ORGANISM: Ricinus communis
<300> PUBLICATION INFORMATION:
<308> DATABASE ACCESSION NUMBER: 16804377

<400> SEQUENCE: 24

| Met | Phe | Arg | Glu | Gly | Glu | Leu | Arg | Pro | Met | Asp | Ala | Glu | Gln | Leu | Arg |
|---|---|---|---|---|---|---|---|---|---|---|---|---|---|---|---|
| 1 | | | | 5 | | | | | 10 | | | | | 15 | |

| Glu | His | Gly | His | Lys | Met | Val | Asp | Phe | Ile | Ala | Asp | Tyr | Tyr | Lys | Thr |
|---|---|---|---|---|---|---|---|---|---|---|---|---|---|---|---|
| | | | 20 | | | | | 25 | | | | | 30 | | |

| Ile | Glu | Asn | Phe | Pro | Val | Leu | Ser | Gln | Val | Glu | Pro | Gly | Tyr | Leu | Arg |
|---|---|---|---|---|---|---|---|---|---|---|---|---|---|---|---|
| | | | 35 | | | | | 40 | | | | | 45 | | |

| Lys | Leu | Leu | Pro | Asp | Ser | Ala | Pro | Asn | Gln | Pro | Glu | Ser | Leu | Gln | Asn |
|---|---|---|---|---|---|---|---|---|---|---|---|---|---|---|---|
| | 50 | | | | | 55 | | | | | 60 | | | | |

| Val | Leu | Asp | Asp | Val | Gln | Ala | Lys | Ile | Leu | Pro | Gly | Val | Thr | His | Trp |
|---|---|---|---|---|---|---|---|---|---|---|---|---|---|---|---|
| 65 | | | | | 70 | | | | | 75 | | | | | 80 |

| Gln | Ser | Pro | Asn | Tyr | Phe | Ala | Tyr | Tyr | Pro | Ser | Asn | Ser | Ser | Val | Ala |
|---|---|---|---|---|---|---|---|---|---|---|---|---|---|---|---|
| | | | | 85 | | | | | 90 | | | | | 95 | |

| Gly | Phe | Leu | Gly | Glu | Met | Leu | Ser | Ala | Gly | Ile | Asn | Met | Val | Gly | Phe |
|---|---|---|---|---|---|---|---|---|---|---|---|---|---|---|---|
| | | | 100 | | | | | 105 | | | | | 110 | | |

| Ser | Trp | Ile | Thr | Ser | Pro | Ala | Ala | Thr | Glu | Leu | Glu | Met | Ile | Val | Leu |
|---|---|---|---|---|---|---|---|---|---|---|---|---|---|---|---|
| | | | 115 | | | | | 120 | | | | | 125 | | |

| Asp | Trp | Leu | Gly | Lys | Met | Leu | Lys | Leu | Pro | Glu | Glu | Phe | Leu | Ser | Thr |
|---|---|---|---|---|---|---|---|---|---|---|---|---|---|---|---|
| | 130 | | | | | 135 | | | | | 140 | | | | |

| Gly | Gln | Gly | Gly | Gly | Val | Ile | Gln | Gly | Thr | Ala | Ser | Glu | Ala | Val | Leu |
|---|---|---|---|---|---|---|---|---|---|---|---|---|---|---|---|
| 145 | | | | | 150 | | | | | 155 | | | | | 160 |

| Val | Ala | Leu | Val | Ala | Ala | Arg | Asp | Lys | Val | Leu | Arg | Arg | Val | Gly | Lys |
|---|---|---|---|---|---|---|---|---|---|---|---|---|---|---|---|
| | | | | 165 | | | | | 170 | | | | | 175 | |

| Asp | Ala | Leu | Arg | Lys | Leu | Val | Val | Tyr | Gly | Ser | Asp | Gln | Thr | His | Ser |
|---|---|---|---|---|---|---|---|---|---|---|---|---|---|---|---|
| | | | 180 | | | | | 185 | | | | | 190 | | |

| Ala | Leu | Gln | Lys | Ala | Cys | Gln | Ile | Gly | Gly | Ile | His | Pro | Val | Asn | Cys |
|---|---|---|---|---|---|---|---|---|---|---|---|---|---|---|---|
| | | | 195 | | | | | 200 | | | | | 205 | | |

| Arg | Leu | Leu | Glu | Thr | Asp | Ser | Ser | Thr | Asn | Tyr | Ala | Leu | Ala | Pro | Asp |
|---|---|---|---|---|---|---|---|---|---|---|---|---|---|---|---|
| | 210 | | | | | 215 | | | | | 220 | | | | |

| Leu | Leu | Ser | Arg | Ala | Ile | Ser | Glu | Asp | Ile | Ser | Leu | Gly | Leu | Ile | Pro |
|---|---|---|---|---|---|---|---|---|---|---|---|---|---|---|---|
| 225 | | | | | 230 | | | | | 235 | | | | | 240 |

| Phe | Phe | Leu | Cys | Ala | Thr | Val | Gly | Thr | Thr | Ser | Ser | Thr | Ala | Val | Asp |
|---|---|---|---|---|---|---|---|---|---|---|---|---|---|---|---|
| | | | | 245 | | | | | 250 | | | | | 255 | |

| Pro | Leu | Leu | Ala | Leu | Gly | Lys | Ile | Ala | Lys | Ser | Asn | Gly | Met | Trp | Phe |
|---|---|---|---|---|---|---|---|---|---|---|---|---|---|---|---|
| | | | 260 | | | | | 265 | | | | | 270 | | |

| His | Val | Asp | Ala | Ala | Tyr | Ala | Gly | Ser | Ala | Cys | Val | Cys | Pro | Glu | Tyr |
|---|---|---|---|---|---|---|---|---|---|---|---|---|---|---|---|
| | | | 275 | | | | | 280 | | | | | 285 | | |

| Arg | Cys | Tyr | Met | Asp | Gly | Val | Glu | Glu | Ala | Asp | Ser | Phe | Asn | Met | Asn |
|---|---|---|---|---|---|---|---|---|---|---|---|---|---|---|---|
| | 290 | | | | | 295 | | | | | 300 | | | | |

| Ala | His | Lys | Trp | Phe | Leu | Thr | Asn | Phe | Asp | Cys | Ser | Ala | Leu | Trp | Val |
|---|---|---|---|---|---|---|---|---|---|---|---|---|---|---|---|
| 305 | | | | | 310 | | | | | 315 | | | | | 320 |

| Lys | Asp | Arg | Asn | Ala | Leu | Ile | Gln | Ser | Leu | Ser | Thr | Ser | Pro | Glu | Phe |
|---|---|---|---|---|---|---|---|---|---|---|---|---|---|---|---|
| | | | | 325 | | | | | 330 | | | | | 335 | |

| Leu | Gln | Asn | Lys | Pro | Ser | Gln | Thr | Asn | Thr | Val | Val | Asp | Tyr | Lys | Asp |
|---|---|---|---|---|---|---|---|---|---|---|---|---|---|---|---|
| | | | 340 | | | | | 345 | | | | | 350 | | |

| Trp | Gln | Ile | Pro | Leu | Gly | Arg | Arg | Phe | Arg | Ser | Leu | Lys | Leu | Trp | Met |
|---|---|---|---|---|---|---|---|---|---|---|---|---|---|---|---|
| | | | 355 | | | | | 360 | | | | | 365 | | |

```
Val Leu Arg Leu Tyr Gly Val Glu Lys Leu Gln Cys Tyr Ile Arg Asn
        370                 375                 380

His Ile Asn Leu Ala Lys Tyr Phe Glu Gly Leu Ile Ala Glu Asp Thr
385                 390                 395                 400

Arg Phe Glu Val Val Ser Pro Pro Ile Phe Ala Leu Val Cys Phe Arg
                405                 410                 415

Leu Leu Pro Pro Asp Asn Asn Val Asp His Gly Asn Lys Leu Ser His
                420                 425                 430

Asp Leu Asp Ala Val Asn Ser Thr Gly Lys Ile Phe Ile Ser His
                435                 440                 445

Thr Val Leu Ser Gly Lys Tyr Ile Leu Arg Phe Ala Val Gly Ala Pro
450                 455                 460

Leu Thr Glu Glu Arg His Val Thr Ala Ala Trp Lys Val Leu Gln Asp
465                 470                 475                 480

Glu Ala Cys Ala Leu Leu Glu Thr Ser Arg Ile Ser
                485                 490

<210> SEQ ID NO 25
<211> LENGTH: 486
<212> TYPE: PRT
<213> ORGANISM: Cucumis sativus
<300> PUBLICATION INFORMATION:
<308> DATABASE ACCESSION NUMBER: 16963476

<400> SEQUENCE: 25

Met Asp Asn Glu Leu Lys Pro Met Asp Ala Glu Gln Leu Arg Glu His
1               5                   10                  15

Ala His Lys Met Val Asp Phe Ile Ala Asp Tyr Tyr Lys Asn Ile Glu
                20                  25                  30

Asp Phe Pro Val Leu Ser Gln Val Glu Pro Gly Tyr Leu Gln Asn Leu
            35                  40                  45

Leu Pro Glu Ser Ala Pro Leu Asn Pro Glu Ser Leu Gln Ser Val Leu
        50                  55                  60

Asp Asp Val Gln Lys Lys Ile Phe Pro Gly Val Thr His Trp Gln Ser
65                  70                  75                  80

Pro Asn Tyr Phe Ala Tyr Tyr Pro Ser Asn Ser Ser Ile Ala Gly Phe
                85                  90                  95

Leu Gly Glu Met Leu Ser Ala Ala Phe Asn Val Ile Gly Phe Ser Trp
                100                 105                 110

Val Thr Ser Pro Ala Ala Thr Glu Leu Glu Met Ile Val Leu Asp Trp
            115                 120                 125

Leu Ala Lys Leu Leu Lys Leu Pro Asp Asp Phe Leu Ser Ser Gly Asn
        130                 135                 140

Gly Gly Gly Val Ile Gln Gly Thr Ala Ser Glu Ala Val Leu Val Val
145                 150                 155                 160

Leu Leu Ala Ala Arg Asp Arg Ala Leu Arg Arg Phe Gly Lys Asp Tyr
                165                 170                 175

Leu Lys Lys Leu Val Val Tyr Ala Ser Asp Gln Thr His Ser Ala Leu
                180                 185                 190

Gln Lys Ala Cys Gln Ile Gly Gly Ile His Pro Glu Asn Cys Arg Trp
            195                 200                 205

Leu Lys Ala Asp Ile Ser Thr Asn Tyr Ala Leu Ser Pro Asp Val Leu
        210                 215                 220

Ser Glu Glu Leu Ser Arg Asp Thr Ala Arg Gly Leu Ile Pro Phe Phe
225                 230                 235                 240
```

Leu Cys Ala Thr Val Gly Thr Thr Ser Ser Thr Ala Val Asp Pro Leu
            245                 250                 255

Pro Glu Leu Gly Thr Ile Ala Lys Arg His Glu Met Trp Phe His Val
            260                 265                 270

Asp Ala Ala Tyr Ala Gly Ser Ala Cys Val Cys Pro Glu Tyr Arg Gln
            275                 280                 285

Tyr Ile Asp Gly Val Glu Glu Ala Asp Ser Phe Asn Met Asn Leu His
            290                 295                 300

Lys Trp Phe Leu Thr Asn Phe Asp Cys Ser Ala Leu Trp Ile Lys Asp
305                 310                 315                 320

Arg His Ala Leu Ile Arg Ser Leu Ser Thr Asn Pro Glu Phe Leu Lys
                325                 330                 335

Asn Lys Ala Ser Glu Ala Glu Leu Val Val Asp Tyr Lys Asp Trp Gln
            340                 345                 350

Ile Pro Leu Gly Arg Arg Phe Arg Ser Leu Lys Val Trp Met Val Leu
            355                 360                 365

Arg Leu Tyr Gly Thr Glu Asn Leu Gln Lys Tyr Ile Arg Asn His Ile
            370                 375                 380

Ser Leu Ala Glu Arg Phe Glu Ala Leu Val Arg Glu Asp Pro Arg Phe
385                 390                 395                 400

Glu Ile Val Thr Pro Arg Ile Phe Ser Leu Val Cys Phe Arg Leu Leu
            405                 410                 415

Pro Ser Arg Lys Asn Glu Asp Gly Gly Asn Arg Leu Asn Gln Ser Leu
            420                 425                 430

Leu Asp Ala Val Asn Ala Ser Gly Asn Ile Phe Ile Ser His Thr Val
            435                 440                 445

Leu Ser Gly Lys Tyr Ile Leu Arg Phe Ala Val Gly Ala Pro Leu Thr
            450                 455                 460

Glu Glu Lys His Ile Asn Ser Ala Trp Lys Leu Leu Gln Asp Val Ala
465                 470                 475                 480

Ser Thr Leu Leu Ala Ile
            485

<210> SEQ ID NO 26
<211> LENGTH: 508
<212> TYPE: PRT
<213> ORGANISM: Vitis vinifera
<300> PUBLICATION INFORMATION:
<308> DATABASE ACCESSION NUMBER: 17835588

<400> SEQUENCE: 26

Met Asp Ala Glu Gln Leu Arg Glu Asn Gly His Lys Met Val Asp Phe
1               5                   10                  15

Ile Ala Asp Tyr Tyr Lys Ser Ile Glu Asn Phe Pro Val Leu Ser Gln
            20                  25                  30

Val Glu Pro Gly Tyr Leu Arg Glu Leu Leu Pro Asp Ser Ala Pro Asn
            35                  40                  45

Gln Pro Glu Ser Leu Gln Gln Val Phe Asp Asp Leu Gln Ala Lys Ile
            50                  55                  60

Leu Pro Gly Val Thr His Trp Gln Ser Pro Asn Phe Phe Ala Tyr Tyr
65                  70                  75                  80

Pro Ser Asn Ser Ser Thr Ala Gly Phe Leu Gly Glu Met Leu Ser Ala
            85                  90                  95

Gly Leu Asn Ile Val Gly Phe Ser Trp Ile Thr Ser Pro Ala Ala Thr
            100                 105                 110

```
Glu Leu Glu Met Ile Val Leu Asp Trp Leu Ala Lys Leu Leu Asn Leu
            115                 120                 125
Pro Asp Asp Phe Leu Ser Ala Gly Asn Gly Gly Val Ile Gln Gly
130                 135                 140
Thr Ala Ser Glu Ala Val Leu Val Val Leu Leu Ala Ala Arg Asp Arg
145                 150                 155                 160
Val Leu Arg Thr Val Gly Lys Thr Ala Leu Glu Lys Leu Val Val Tyr
                165                 170                 175
Gly Ser Asp Gln Thr His Ser Ala Leu Gln Lys Ala Cys Gln Ile Gly
                180                 185                 190
Gly Ile His Pro Glu Asn Cys Lys Leu Leu Lys Ala Asp Ser Ser Thr
                195                 200                 205
Gly Tyr Ala Leu Ser Pro Asp Leu Leu Ser Glu Ala Val Ser His Asp
210                 215                 220
Ile Thr Asn Gly Leu Ile Pro Phe Phe Leu Cys Ala Asn Val Gly Thr
225                 230                 235                 240
Thr Ser Ser Thr Ala Val Asp Pro Leu Leu Glu Leu Gly Lys Val Thr
                245                 250                 255
Lys Ser Asn Gly Ile Trp Phe His Val Asp Ala Ala Tyr Ala Gly Ser
                260                 265                 270
Ala Cys Val Cys Pro Glu Tyr Arg His Tyr Ile Asp Gly Val Glu Glu
                275                 280                 285
Ala Asp Ser Phe Asn Met Asn Ala His Lys Trp Phe Leu Thr Asn Phe
290                 295                 300
Asp Cys Ser Val Leu Trp Val Lys Asp Arg Asn Ala Leu Val Gln Ala
305                 310                 315                 320
Leu Ser Thr Asn Pro Val Phe Leu Lys Asn Lys Ala Ser Asp Ala Asn
                325                 330                 335
Met Val Val Asp Tyr Lys Asp Trp Gln Val Pro Leu Gly Arg Arg Phe
                340                 345                 350
Arg Ser Leu Lys Leu Trp Met Val Leu Arg Leu Tyr Gly Val Glu Asn
                355                 360                 365
Leu Gln Arg Tyr Ile Arg Asn His Ile Lys Leu Ala Lys Gln Phe Glu
370                 375                 380
Glu Leu Val Ala Gln Asp Pro Arg Phe Glu Ile Val Ala Pro Arg Lys
385                 390                 395                 400
Phe Ala Leu Val Cys Phe Arg Leu Leu Pro Pro His Arg Asn Glu Asp
                405                 410                 415
Phe Ser Asn Lys Leu Asn His Asn Leu Leu Asp Thr Val Asn Ser Thr
                420                 425                 430
Gly Lys Val Tyr Ile Ser His Thr Ala Leu Ser Gly Lys Tyr Thr Leu
                435                 440                 445
Arg Leu Ala Val Gly Ala Pro Leu Thr Glu Glu Arg His Val Asn Ala
450                 455                 460
Ala Trp Lys Val Ile Gln Glu Lys Ala Ser Val Leu Leu Ser Glu Phe
465                 470                 475                 480
Gly Met Asn Gly Leu Phe Asp Asn Ile Asn Leu Lys Phe Ile Leu Asn
                485                 490                 495
His Gln Ile Asp Ile Ser Ile Leu Leu Asn Tyr Asn
                500                 505

<210> SEQ ID NO 27
<211> LENGTH: 486
```

```
<212> TYPE: PRT
<213> ORGANISM: Citrus sinensis
<300> PUBLICATION INFORMATION:
<308> DATABASE ACCESSION NUMBER: 18113817

<400> SEQUENCE: 27

Met Asp Ala Glu Gln Leu Arg Glu Asn Ala His Lys Met Val Asp Phe
1               5                   10                  15

Ile Ala Asp Tyr Tyr Lys Ser Ile Glu Asn Phe Pro Val Leu Ser Gln
            20                  25                  30

Val Gln Pro Gly Tyr Leu His Asn Leu Ile Pro Asp Ser Ala Pro His
        35                  40                  45

His Pro Glu Ser Leu Gln Asn Val Leu Asp Gly Tyr Ile Asp Ile Gln
    50                  55                  60

Glu Lys Ile Leu Pro Gly Val Thr His Trp Gln Ser Pro Asn Tyr Phe
65                  70                  75                  80

Ala Tyr Tyr Pro Ser Asn Ser Ser Val Ala Gly Phe Leu Gly Glu Met
                85                  90                  95

Leu Ser Ala Gly Leu Asn Ile Val Gly Phe Ser Trp Ile Thr Ser Pro
            100                 105                 110

Ala Ala Thr Glu Leu Glu Met Ile Val Leu Asp Trp Leu Ala Lys Leu
        115                 120                 125

Leu Lys Leu Pro Glu Asp Phe Leu Ser Ser Gly Gln Gly Gly Gly Val
    130                 135                 140

Ile Gln Gly Thr Ala Ser Glu Ala Val Leu Val Val Leu Leu Ala Ala
145                 150                 155                 160

Arg Asp Lys Ala Leu Lys Arg Val Gly Lys Asn Ser Leu Glu Lys Leu
                165                 170                 175

Val Val Tyr Ala Ser Asp Gln Thr His Ser Ala Leu Gln Lys Ala Cys
            180                 185                 190

Gln Ile Gly Gly Ile His Pro Gln Asn Phe Arg Val Leu Lys Thr Asp
        195                 200                 205

Ser Ser Thr Asn Tyr Ser Leu Ser Pro Asp Ser Leu Ala Glu Ala Ile
    210                 215                 220

Ser Arg Asp Leu Thr Ile Gly Leu Ile Pro Phe Phe Leu Cys Ala Thr
225                 230                 235                 240

Val Gly Thr Thr Ser Ser Thr Ala Val Asp Pro Leu Leu Ala Leu Gly
                245                 250                 255

Asn Ile Ala Lys Ser Asn Gly Met Trp Phe His Val Asp Ala Ala Tyr
            260                 265                 270

Ala Gly Ser Ala Cys Ile Cys Pro Glu Tyr Arg Gln Tyr Ile Asp Gly
        275                 280                 285

Val Glu Glu Ala Asp Ser Phe Asn Met Asn Ala His Lys Trp Phe Leu
    290                 295                 300

Thr Asn Phe Asp Cys Ser Ala Leu Trp Val Lys Asp Arg Asn Thr Leu
305                 310                 315                 320

Ile Gln Ser Leu Ser Thr Asn Pro Glu Phe Leu Lys Asn Lys Ala Ser
                325                 330                 335

Gln Ala Asn Met Val Val Asp Tyr Lys Asp Trp Gln Ile Pro Leu Gly
            340                 345                 350

Arg Arg Phe Arg Ser Leu Lys Leu Trp Met Val Leu Arg Leu Tyr Gly
        355                 360                 365

Leu Glu Asn Leu Gln Gly Tyr Ile Arg Asn His Ile Gln Leu Ala Lys
    370                 375                 380
```

```
His Phe Glu Gly Leu Val Ala Gln Asp Leu Arg Phe Glu Val Val Thr
385                 390                 395                 400

Pro Arg Ile Phe Ser Leu Val Cys Phe Arg Leu Leu Pro Pro His Asn
            405                 410                 415

Asp Glu Asp His Gly Asn Lys Leu Asn His Lys Leu Leu Asp Asp Ile
        420                 425                 430

Asn Ser Thr Gly Lys Ile Phe Ile Ser His Thr Val Leu Ser Gly Lys
    435                 440                 445

Tyr Ile Leu Arg Phe Ala Val Gly Ala Pro Leu Thr Glu Trp Arg His
450                 455                 460

Val Asn Ala Ala Trp Glu Val Met Gln Asp Lys Ala Ser Ala Leu Leu
465                 470                 475                 480

Ala Arg Leu Ser Ile Glu
                485

<210> SEQ ID NO 28
<211> LENGTH: 507
<212> TYPE: PRT
<213> ORGANISM: Capsella rubella
<300> PUBLICATION INFORMATION:
<308> DATABASE ACCESSION NUMBER: 20900667

<400> SEQUENCE: 28

Met Gly Phe Cys Gln Ile Glu Leu Leu Arg His Ile Asn Lys His Asn
1               5                   10                  15

Met Gln Asn Gly Ser Gly Lys Asn Val Leu Lys Pro Met Asp Ser Glu
            20                  25                  30

Gln Leu Arg Glu Tyr Gly His Arg Met Val Asp Phe Ile Ala Asp Tyr
        35                  40                  45

Tyr Lys Thr Ile Glu Asp Phe Pro Val Leu Ser Gln Val Gln Pro Gly
    50                  55                  60

Tyr Leu His Gln Leu Leu Pro Asp Ser Ala Pro Asp His Pro Glu Thr
65                  70                  75                  80

Leu Asp Gln Val Leu Asp Asp Val Arg Ala Lys Ile Leu Pro Gly Val
                85                  90                  95

Thr His Trp Gln Ser Pro Gly Phe Phe Ala Tyr Tyr Pro Ser Asn Ser
            100                 105                 110

Ser Val Ala Gly Phe Leu Gly Glu Met Leu Ser Ala Gly Leu Gly Ile
        115                 120                 125

Val Gly Phe Ser Trp Val Thr Ser Pro Ala Ala Thr Glu Leu Glu Met
    130                 135                 140

Ile Val Leu Asp Trp Leu Ala Lys Leu Leu Asn Leu Pro Lys Glu Phe
145                 150                 155                 160

Leu Ser Lys Gly Asn Gly Gly Val Ile Gln Gly Ser Ala Ser Glu
                165                 170                 175

Ala Val Leu Val Val Leu Ile Ala Ala Arg Asp Lys Val Leu Arg Ser
        180                 185                 190

Ala Gly Lys Asn Ala Leu Gly Lys Leu Val Val Tyr Ser Ser Asp Gln
    195                 200                 205

Thr His Ser Ala Leu Gln Lys Ala Cys Gln Ile Ala Gly Ile His Pro
210                 215                 220

Glu Asn Cys Arg Val Leu Glu Thr Asp Ala Ser Thr Asn Tyr Ala Leu
225                 230                 235                 240

Arg Pro Glu Leu Leu Gln Glu Ala Val Ser Lys Asp Leu Lys Ala Gly
                245                 250                 255
```

```
Leu Ile Pro Phe Phe Leu Cys Ala Asn Val Gly Thr Thr Ser Ser Thr
            260                 265                 270

Ala Val Asp Pro Leu Ala Ala Leu Gly Lys Ile Ala Asn Ser Asn Glu
        275                 280                 285

Ile Trp Phe His Val Asp Ala Ala Tyr Ala Gly Ser Ala Cys Ile Cys
    290                 295                 300

Pro Glu Tyr Arg Lys Tyr Ile Asp Gly Val Glu Thr Ala Asp Ser Phe
305                 310                 315                 320

Asn Met Asn Ala His Lys Trp Phe Leu Thr Asn Phe Asp Cys Ser Leu
                325                 330                 335

Leu Trp Val Lys Glu Gln Asp Ser Leu Thr Glu Ala Leu Ser Thr Asn
            340                 345                 350

Pro Glu Phe Leu Lys Asn Lys Ala Ser Gln Ala Asn Leu Val Val Asp
        355                 360                 365

Tyr Lys Asp Trp Gln Ile Pro Leu Gly Arg Arg Phe Arg Ser Leu Lys
    370                 375                 380

Leu Trp Met Val Leu Arg Leu Tyr Gly Ala Glu Thr Leu Lys Ser Tyr
385                 390                 395                 400

Ile Arg Asn His Ile Lys Leu Ala Lys Tyr Phe Glu Lys Leu Val Ser
                405                 410                 415

Gln Asp Pro Asn Phe Glu Ile Val Thr Pro Arg Ile Phe Ser Leu Val
            420                 425                 430

Cys Phe Arg Leu Val Pro Lys Asn Asp Glu Lys Lys Cys Asn Asn
        435                 440                 445

Gln Asn Arg Lys Leu Leu Glu Ala Ala Asn Ser Ser Gly Lys Leu Phe
    450                 455                 460

Met Ser His Thr Ala Leu Ser Gly Lys Ile Val Leu Arg Cys Ala Ile
465                 470                 475                 480

Gly Ala Pro Leu Thr Glu Glu Lys His Met Lys Glu Ala Trp Lys Val
                485                 490                 495

Ile Gln Asp Glu Ala Ser Phe Leu Leu His Lys
            500                 505

<210> SEQ ID NO 29
<211> LENGTH: 486
<212> TYPE: PRT
<213> ORGANISM: Malus domestica
<300> PUBLICATION INFORMATION:
<308> DATABASE ACCESSION NUMBER: 22636618

<400> SEQUENCE: 29

Met Ser Gly Leu Lys Pro Met Asp Ala Glu Gln Leu Arg Glu Asn Ala
1               5                   10                  15

His Lys Met Val Asp Phe Ile Ala Asp Tyr Tyr Lys Thr Ile Glu Asp
            20                  25                  30

Phe Pro Val Leu Ser Gln Val Gln Pro Gly Tyr Leu Arg Asp Leu Leu
        35                  40                  45

Pro Asp Ser Ala Pro Thr His Pro Glu Ser Leu Gln Gln Val Phe Asp
    50                  55                  60

Asp Ile Gln Ala Lys Ile Leu Pro Gly Val Thr His Trp Gln Ser Pro
65                  70                  75                  80

Asn Phe Phe Gly Tyr Tyr Pro Ser Asn Ser Ser Val Ala Gly Phe Leu
                85                  90                  95

Gly Glu Met Leu Ser Ala Gly Leu Asn Ile Val Gly Phe Ser Trp Ile
            100                 105                 110
```

```
Thr Ser Pro Ala Ala Thr Glu Leu Glu Met Ile Val Leu Asp Trp Phe
            115                 120                 125

Ala Lys Met Leu Lys Leu Pro Glu Glu Phe Leu Ser Ala Gly Gln Gly
130                 135                 140

Gly Gly Val Ile Gln Gly Thr Ala Ser Glu Ala Val Leu Val Val Leu
145                 150                 155                 160

Leu Ala Ala Arg Asp Arg Ile Leu Arg Ala Glu Gly Lys Lys Ala Leu
                165                 170                 175

Glu Lys Leu Val Val Tyr Ala Ser Asp Gln Thr His Ser Ala Leu Gln
                180                 185                 190

Lys Ala Cys Gln Ile Gly Gly Ile His Pro Glu Asn Cys Arg Val Leu
            195                 200                 205

Ser Thr Asp Ser Ser Thr Asn Tyr Ala Leu Ser Pro Asn Val Leu Asn
210                 215                 220

Glu Ala Ile Ser Asn Asp Ile Ala Ser Gly Leu Val Pro Phe Phe Leu
225                 230                 235                 240

Cys Ala Thr Val Gly Thr Thr Ser Ser Thr Ala Val Asp Pro Leu Leu
                245                 250                 255

Glu Leu Gly Lys Ile Thr Lys Ser Asn Gly Met Trp Phe His Val Asp
                260                 265                 270

Ala Ala Tyr Ala Gly Ser Ala Cys Ile Cys Pro Glu Tyr Arg His His
            275                 280                 285

Ile Asp Gly Val Glu Glu Ala Asp Ser Phe Asn Met Asn Ala His Lys
290                 295                 300

Trp Phe Leu Thr Asn Phe Asp Cys Ser Leu Leu Trp Ile Lys Asp Arg
305                 310                 315                 320

Asn Ala Leu Val Gln Ala Leu Ser Thr Asn Pro Glu Phe Leu Lys Asn
                325                 330                 335

Lys Ala Ser Gln Ala Asn Leu Val Val Asp Tyr Lys Asp Trp Gln Ile
            340                 345                 350

Pro Leu Gly Arg Arg Phe Arg Ser Leu Lys Leu Trp Met Val Leu Arg
        355                 360                 365

Leu Tyr Gly Leu Glu Asn Leu Gln Ser Tyr Ile Arg Asn His Ile Asp
370                 375                 380

Leu Ala Lys Cys Phe Glu Asp Leu Val Ala Gln Asp Ser Arg Phe Glu
385                 390                 395                 400

Ile Val Thr Pro Arg Ile Phe Ser Leu Val Cys Phe Arg Leu Leu Pro
                405                 410                 415

Pro His Asn Asp Glu Thr Tyr Ala Thr Lys Leu Asn His Asp Leu Leu
            420                 425                 430

Asp Thr Val Asn Ser Thr Gly Lys Ile Phe Val Ser His Thr Val Leu
            435                 440                 445

Ser Gly Lys Tyr Val Leu Arg Phe Ala Val Gly Ala Pro Leu Thr Glu
    450                 455                 460

Glu Arg His Val Leu Ala Ala Trp Lys Leu Leu Gln Glu Glu Ala Ser
465                 470                 475                 480

Ala Leu Leu Ala Pro Leu
                485

<210> SEQ ID NO 30
<211> LENGTH: 483
<212> TYPE: PRT
<213> ORGANISM: Linum usitatissimum
<300> PUBLICATION INFORMATION:
<308> DATABASE ACCESSION NUMBER: 23178995
```

```
<400> SEQUENCE: 30

Met Gly Gly Tyr Arg Ser Leu Asn Leu Ile Phe Ile Phe Ile Ser Phe
1               5                   10                  15

Val Ala Asp Ile Arg Asp Leu Gly Tyr Asn Thr Lys Glu Gly Asp Asp
                20                  25                  30

Gly Gly Gly Ala Leu Lys Pro Met Asp Ala Glu Gln Leu Arg Gln Asn
            35                  40                  45

Ala His Gln Met Val Asp Phe Ile Ala Asp Tyr Tyr Lys Asn Ile Glu
        50                  55                  60

Thr Tyr Pro Val Leu Ser Gln Val Glu Pro Gly Tyr Leu Arg Glu Leu
65                  70                  75                  80

Leu Pro Asp Ser Ala Pro Asn Arg Pro Glu Ser Leu Gln Ser Val Leu
                85                  90                  95

Asp Asp Val Gln Ser Lys Ile Met Pro Gly Val Thr His Trp Gln Ser
            100                 105                 110

Pro Asn Tyr Phe Ala Tyr Tyr Pro Ser Asn Ser Ser Val Ala Gly Phe
        115                 120                 125

Leu Gly Glu Met Leu Ser Ala Gly Ile Asn Met Val Gly Phe Ser Trp
130                 135                 140

Ile Thr Ser Pro Ala Ala Thr Glu Leu Glu Met Ile Val Leu Asp Trp
145                 150                 155                 160

Leu Gly Lys Leu Leu Lys Leu Pro Glu Glu Phe Leu Ser Ser Gly His
                165                 170                 175

Gly Gly Gly Val Ile Gln Gly Thr Ala Ser Glu Ala Ile Leu Val Val
            180                 185                 190

Leu Leu Ala Ala Arg Asp Lys Met Leu Arg Lys Phe Gly Lys Ser Ala
        195                 200                 205

Leu Glu Lys Leu Val Val Tyr Ala Ser Asp Gln Thr His Ser Ala Leu
210                 215                 220

Gln Lys Ala Cys Gln Ile Gly Gly Ile Tyr Pro Glu Asn Cys Arg Leu
225                 230                 235                 240

Leu Lys Thr Asp Ser Ser Val Asn Tyr Ser Leu Thr Pro Glu Leu Val
                245                 250                 255

Ser Glu Ala Val Ser Gln Asp Ile Ser Ala Gly Leu Ile Pro Phe Phe
            260                 265                 270

Leu Cys Gly Thr Val Gly Thr Thr Ser Ser Ala Thr Val Asp Pro Leu
        275                 280                 285

Gly Thr Leu Gly Lys Ile Ala Lys Asn Asn Asp Met Trp Phe His Val
290                 295                 300

Asp Ala Ala Tyr Ala Gly Ser Ala Cys Ile Cys Pro Glu Tyr Arg Gln
305                 310                 315                 320

Tyr Leu Asp Gly Val Glu Glu Ala Asp Ser Phe Asn Met Asn Ala His
                325                 330                 335

Lys Trp Phe Leu Thr Asn Phe Asp Cys Ser Thr Leu Trp Val Lys Asp
            340                 345                 350

Lys Ser Ala Leu Ile Gln Ala Leu Ser Thr Asn Pro Glu Phe Leu Lys
        355                 360                 365

Asn Lys Ala Ser Gln Ala Asn Leu Val Val Asp Tyr Lys Asp Trp Gln
370                 375                 380

Ile Pro Leu Gly Arg Arg Phe Arg Ser Leu Lys Leu Trp Met Val Leu
385                 390                 395                 400

Arg Leu Tyr Gly Val Glu Asn Leu Gln Gln Tyr Leu Arg Asn His Ile
```

```
                    405                 410                 415
Glu Leu Ala Arg His Phe Glu Glu Cys Val Asn His Asp Pro Arg Phe
            420                 425                 430

Glu Ala Leu Ser Gly Lys Tyr Thr Leu Arg Val Ala Ile Gly Ala Pro
            435                 440                 445

Leu Thr Glu Lys Arg His Val Ala Ala Leu Lys Val Leu Gln Asp
        450                 455                 460

Glu Ala Thr Ser Leu Leu Val Ala Thr Ser Pro Leu Leu Glu Asn Gly
465                 470                 475                 480

Asn Ser Ser

<210> SEQ ID NO 31
<211> LENGTH: 490
<212> TYPE: PRT
<213> ORGANISM: Eutrema salsugineum
<300> PUBLICATION INFORMATION:
<308> DATABASE ACCESSION NUMBER: 20200788

<400> SEQUENCE: 31

Met Glu Asn Gly Asn Lys Asn Val Leu Lys Pro Met Asp Ser Glu Gln
1               5                   10                  15

Leu Arg Glu Tyr Gly His Arg Met Val Asp Phe Ile Ala Asp Tyr Tyr
            20                  25                  30

Lys Thr Ile Glu Asp Phe Pro Val Leu Ser Gln Val Gln Pro Gly Tyr
        35                  40                  45

Leu His Asn Leu Leu Pro Asp Ser Ala Pro Asp Gln Pro Glu Thr Leu
    50                  55                  60

Glu Glu Val Leu Asp Asp Val Lys Gly Lys Ile Leu Pro Gly Val Thr
65                  70                  75                  80

His Trp Gln Ser Pro Ser Phe Phe Ala Tyr Tyr Pro Ser Asn Ser Ser
                85                  90                  95

Val Ala Gly Phe Leu Gly Glu Met Leu Ser Ala Gly Leu Gly Ile Val
            100                 105                 110

Gly Phe Ser Trp Ile Thr Ser Pro Ala Ala Thr Glu Leu Glu Met Ile
        115                 120                 125

Val Leu Asp Trp Leu Ala Lys Leu Leu Asn Leu Pro Glu Gln Phe Leu
    130                 135                 140

Ser Arg Gly Asn Gly Gly Gly Val Ile Gln Gly Ser Ala Ser Glu Ala
145                 150                 155                 160

Glu Leu Val Val Leu Ile Ala Ala Arg Asp Lys Val Leu Arg Ser Val
                165                 170                 175

Gly Lys Lys Ala Leu Glu Lys Leu Val Val Tyr Ser Ser Asp Gln Thr
            180                 185                 190

His Ser Ala Leu Gln Lys Ala Cys Gln Ile Ala Gly Ile His Pro Glu
        195                 200                 205

Asn Cys Arg Val Leu Lys Ala Asp Tyr Ser Thr Asn Tyr Ala Leu Arg
    210                 215                 220

Pro Glu Thr Leu Gln Glu Ala Val Ser Lys Asp Leu Glu Ala Gly Leu
225                 230                 235                 240

Ile Pro Phe Phe Leu Cys Ala Asn Val Gly Thr Thr Ser Ser Thr Ala
                245                 250                 255

Val Asp Pro Leu Ala Ala Leu Gly Glu Ile Ala Lys Ser Asn Glu Met
            260                 265                 270

Trp Phe His Val Asp Ala Ala Tyr Ala Gly Ser Ala Cys Ile Cys Pro
        275                 280                 285
```

```
Glu Tyr Arg Gln Tyr Ile Asp Gly Val Glu Thr Ala Asp Ser Phe Asn
            290                 295                 300

Met Asn Ala His Lys Trp Phe Leu Thr Asn Phe Asp Cys Ser Leu Leu
305                 310                 315                 320

Trp Val Lys Asp Gln Tyr Ala Leu Thr Glu Ala Arg Ser Thr Asn Pro
                325                 330                 335

Glu Phe Leu Lys Asn Lys Ala Ser Gln Ala Asn Leu Val Val Asp Tyr
            340                 345                 350

Lys Asp Trp Gln Ile Pro Leu Gly Arg Arg Phe Arg Ser Leu Lys Leu
        355                 360                 365

Trp Met Val Leu Arg Leu Tyr Gly Ser Glu Asn Leu Lys Ser Tyr Ile
    370                 375                 380

Arg Asn His Ile Lys Leu Ala Lys Asp Phe Glu Gln Leu Val Ser Glu
385                 390                 395                 400

Asp Pro Asn Phe Glu Ile Val Thr Pro Arg Ile Phe Ser Leu Val Cys
                405                 410                 415

Phe Arg Ile Val Pro Ala Glu Asn Asp Glu Lys Lys Cys Asn Asn Gln
            420                 425                 430

Asn Arg Asn Leu Leu Asp Ala Val Asn Ser Ser Gly Lys Leu Phe Leu
        435                 440                 445

Ser His Thr Ala Leu Ser Gly Lys Ile Val Leu Arg Cys Ala Ile Gly
    450                 455                 460

Ala Pro Leu Thr Glu Glu Lys His Val Lys Glu Ala Trp Lys Val Ile
465                 470                 475                 480

Gln Glu Glu Ala Ser Tyr Leu Leu Arg Lys
                485                 490

<210> SEQ ID NO 32
<211> LENGTH: 488
<212> TYPE: PRT
<213> ORGANISM: Populus trichocarpa
<300> PUBLICATION INFORMATION:
<308> DATABASE ACCESSION NUMBER: 27022899

<400> SEQUENCE: 32

Met Glu Ser Lys Gly Leu Gln Pro Met Asp Ser Glu Gln Leu Arg Glu
1               5                   10                  15

Asn Ala His Lys Met Val Asp Phe Ile Ala Asp Tyr Tyr Lys Ser Ile
            20                  25                  30

Glu Asn Phe Pro Val Leu Ser Gln Val Glu Pro Gly Tyr Leu Arg Glu
        35                  40                  45

Leu Leu Pro Asp Ser Ala Pro Asn Gln Pro Glu Thr Leu Gln Asn Val
    50                  55                  60

Leu Asp Asp Val Gln Ala Lys Ile Leu Pro Gly Val Thr His Trp Gln
65                  70                  75                  80

Ser Pro Ser Tyr Phe Ala Tyr Tyr Pro Ser Asn Ser Ser Val Ala Gly
                85                  90                  95

Phe Leu Gly Glu Met Leu Ser Ala Gly Ile Asn Met Val Gly Phe Ser
            100                 105                 110

Trp Ile Thr Ser Pro Ala Ala Thr Glu Leu Glu Met Ile Val Leu Asp
        115                 120                 125

Trp Leu Gly Lys Leu Leu Lys Leu Pro Glu Asp Phe Leu Ser Thr Gly
    130                 135                 140

Gln Gly Gly Gly Val Ile Gln Gly Thr Ala Ser Glu Ala Val Leu Val
145                 150                 155                 160
```

Val Leu Leu Ala Ala Arg Asp Arg Val Leu Arg Lys Leu Gly Lys Asn
            165                 170                 175

Ala Leu Glu Lys Leu Val Val Tyr Ala Ser Asp Gln Thr His Ser Ala
        180                 185                 190

Leu Gln Lys Ala Cys Gln Ile Gly Gly Ile His Pro Glu Asn Cys Lys
    195                 200                 205

Leu Leu Lys Thr Gly Ser Ser Thr Asn Tyr Ala Leu Ser Pro Asp Leu
210                 215                 220

Leu Gly Lys Ala Ile Ser Asp Asp Ile Ser Thr Gly Leu Val Pro Phe
225                 230                 235                 240

Phe Leu Cys Ala Thr Val Gly Thr Thr Ser Ser Thr Ala Val Asp Pro
                245                 250                 255

Leu Leu Ser Leu Gly Lys Ile Ala Lys Asn Asn Gly Ile Trp Phe His
            260                 265                 270

Val Asp Ala Ala Tyr Ala Gly Ser Ala Cys Ile Cys Pro Glu Tyr Arg
        275                 280                 285

Cys Tyr Ile Asp Gly Val Glu Glu Ala Asp Ser Phe Asn Met Asn Ala
    290                 295                 300

His Lys Trp Phe Leu Thr Asn Phe Asp Cys Ser Ala Leu Trp Val Lys
305                 310                 315                 320

Asp Arg Asn Ala Leu Ile Gln Ser Leu Ser Thr Asn Pro Glu Phe Leu
                325                 330                 335

Lys Asn Lys Ala Ser Gln Ala Asn Met Val Val Asp Tyr Lys Asp Trp
            340                 345                 350

Gln Ile Pro Leu Gly Arg Arg Phe Arg Ser Leu Lys Leu Trp Met Val
        355                 360                 365

Leu Arg Leu Tyr Gly Leu Glu Asn Leu Gln Cys Tyr Ile Arg Asn His
    370                 375                 380

Ile Asn Leu Ala Lys Tyr Phe Glu Gly Leu Val Ala Ala Asp Ser Arg
385                 390                 395                 400

Phe Glu Val Val Thr Pro Arg Ile Phe Ser Leu Val Cys Phe Arg Leu
                405                 410                 415

Leu Pro Pro Asn Asn Asn Glu Asp His Gly Asn Asn Leu Asn His Asp
            420                 425                 430

Leu Leu Asp Ala Val Asn Ser Thr Gly Lys Ile Phe Ile Ser His Thr
        435                 440                 445

Val Leu Ser Gly Lys Tyr Ile Leu Arg Phe Ala Val Gly Ala Pro Leu
    450                 455                 460

Thr Glu Glu Arg His Val Thr Ala Ala Trp Lys Val Leu Gln Asp Glu
465                 470                 475                 480

Ala Ser Ala Leu Leu Gly Ser Leu
                485

<210> SEQ ID NO 33
<211> LENGTH: 500
<212> TYPE: PRT
<213> ORGANISM: Brachypodium stacei
<300> PUBLICATION INFORMATION:
<308> DATABASE ACCESSION NUMBER: 06G160800.1

<400> SEQUENCE: 33

Met Asp Gly Ser Thr Thr Ser Asn Gly Asp Gly Gly Gly Gly Trp Met
1               5                   10                  15

Arg Pro Met Asp Glu Glu Gln Leu Arg Glu Cys Gly His Arg Met Val
            20                  25                  30

-continued

Asp Phe Ile Ala Asp Tyr Tyr Lys Ser Ile Glu Thr Tyr Pro Val Leu
         35                  40                  45

Ser Gln Val Gln Pro Gly Tyr Leu Lys Glu Leu Leu Pro Asp Ser Ala
 50                  55                  60

Pro Asn Gln Pro Asp Thr Leu Asp Ala Leu Phe Asp Asp Ile Gln Glu
 65                  70                  75                  80

Lys Ile Val Pro Gly Val Thr His Trp Gln Ser Pro Asn Tyr Phe Ala
                 85                  90                  95

Tyr Tyr Pro Ser Asn Ser Ser Thr Ala Gly Phe Leu Gly Glu Met Leu
             100                 105                 110

Ser Ala Ala Phe Asn Ile Val Gly Phe Ser Trp Ile Thr Ser Pro Ala
             115                 120                 125

Ala Thr Glu Leu Glu Val Ile Val Leu Asp Trp Val Ala Lys Met Leu
         130                 135                 140

Lys Leu Pro Ser Gln Phe Leu Ser Ala Gly Leu Gly Gly Gly Val Ile
145                 150                 155                 160

Gln Gly Thr Ala Ser Glu Ala Ile Leu Val Val Leu Leu Ser Ala Arg
                 165                 170                 175

Asp Arg Thr Leu Arg Lys His Gly Lys Lys Ser Leu Glu Lys Leu Val
             180                 185                 190

Val Tyr Ala Ser Asp Gln Thr His Ser Ala Leu Gln Lys Ala Cys Gln
             195                 200                 205

Ile Ala Gly Ile Phe Ser Asp Asn Ile Arg Ile Val Lys Ala Asp Cys
         210                 215                 220

Ser Met Asn Tyr Ala Val Thr Pro Gly Ser Val Ser Glu Ala Ile Ser
225                 230                 235                 240

Ile Asp Leu Ser Ser Gly Leu Ile Pro Phe Phe Ile Cys Ala Thr Leu
                 245                 250                 255

Gly Thr Thr Ser Ser Ser Ala Val Asp Pro Leu His Glu Leu Gly Gln
             260                 265                 270

Ile Ala Gln Ala His Asp Met Trp Phe His Ile Asp Ala Ala Tyr Ala
         275                 280                 285

Gly Ser Ala Cys Ile Cys Pro Glu Tyr Gln Gln Tyr Leu Asn Gly Val
         290                 295                 300

Glu Glu Ala Asp Ser Phe Asn Met Asn Ala His Lys Trp Phe Leu Thr
305                 310                 315                 320

Asn Phe Asp Cys Ser Leu Leu Trp Val Lys Asp Arg Asn Tyr Leu Ile
                 325                 330                 335

Gln Ala Leu Ser Thr Asn Pro Glu Phe Leu Lys Asn Lys Ala Ser Gln
             340                 345                 350

Glu Asn Ser Val Ile Asp Phe Lys Asp Trp Gln Ile Pro Leu Gly Arg
             355                 360                 365

Arg Phe Arg Ser Leu Lys Leu Trp Met Val Leu Arg Leu Tyr Gly Val
         370                 375                 380

Glu Asn Leu Gln Ser Tyr Ile Arg Lys His Ile Gln Leu Ala Gln Arg
385                 390                 395                 400

Phe Glu Gln Leu Val Ile Ser Asp Ser Arg Phe Glu Val Val Thr Pro
                 405                 410                 415

Arg Asn Phe Ser Leu Val Cys Phe Cys Leu Val Pro Pro Thr Ser Glu
             420                 425                 430

Val Asp Asn Gly His Lys Leu Asn Tyr Asp Leu Met Asp Ser Val Asn
             435                 440                 445

-continued

```
Ser Ser Gly Lys Ile Phe Ile Ser His Thr Val Leu Ser Gly Lys Phe
    450                 455                 460
Val Leu Arg Phe Ala Val Gly Ala Pro Leu Thr Glu Glu Gln His Val
465                 470                 475                 480
Asn Ala Ala Trp Lys Leu Leu Gln Asp Glu Thr Lys Leu Leu Gly
                485                 490                 495
Ser Val Val Val
        500

<210> SEQ ID NO 34
<211> LENGTH: 503
<212> TYPE: PRT
<213> ORGANISM: Physcomitrella patens
<300> PUBLICATION INFORMATION:
<308> DATABASE ACCESSION NUMBER: Pp3c4_30790V3.1

<400> SEQUENCE: 34

Met Gly Ser Glu Ala Gly Ser Arg Ser Leu Thr Lys Pro Phe Asp
1               5                  10                  15
Pro Glu Glu Phe Arg Lys His Ala His Arg Met Val Asp Phe Ile Ala
                20                  25                  30
Asp Tyr His Arg Asp Ile Glu Asn Phe Pro Val Gln Ser Gln Val Glu
            35                  40                  45
Pro Gly Tyr Leu Gln Lys Leu Leu Pro Glu Asn Ala Pro Asp Glu Pro
        50                  55                  60
Glu Ser Leu Asp Asp Ile Leu Ala Asp Val Gln Ser Lys Ile Val Pro
65                  70                  75                  80
Gly Val Thr His Trp Gln Ser Pro Asn Phe Tyr Gly Tyr Tyr Pro Ser
                85                  90                  95
Asn Gly Ser Thr Ala Gly Phe Leu Gly Glu Met Leu Ser Gly Gly Phe
                100                 105                 110
Asn Ile Ile Gly Phe Ser Trp Ile Thr Ser Pro Ala Ala Thr Glu Leu
            115                 120                 125
Glu Ile Ile Val Met Asp Trp Leu Gly Lys Leu Leu Lys Leu Pro Asn
        130                 135                 140
Glu Phe Leu Ser Ser Gly Lys Gly Gly Val Ile Gln Gly Thr Ala
145                 150                 155                 160
Ser Glu Ala Val Leu Val Val Met Leu Ala Ala Arg Lys Arg Ala Val
                165                 170                 175
Glu Lys Leu Thr Lys Glu Gln Gly Ile Ser Glu Phe Glu Ala Leu Ala
                180                 185                 190
Lys Leu Val Ala Tyr Thr Ser Asp Gln Ala His Ser Cys Val Asn Lys
            195                 200                 205
Ala Ser Gln Ile Ala Gly Ile Ser Ile Glu Asn Leu Arg Leu Ile Pro
        210                 215                 220
Thr Asp Val Ser Thr Asn Tyr Ala Met Ser Ser Lys Val Leu Ala Asn
225                 230                 235                 240
Thr Leu Ala Asn Asp Val Lys Ala Gly Leu Val Pro Phe Phe Leu Cys
                245                 250                 255
Gly Val Ile Gly Ser Thr Ser Ser Ala Ala Val Asp Pro Leu Ser Glu
                260                 265                 270
Leu Gly Asp Leu Ala Gln Glu Tyr Gly Met Trp Phe His Val Asp Gly
            275                 280                 285
Ala Tyr Ala Gly Asn Ala Cys Ile Cys Pro Glu Phe Arg Pro Tyr Leu
        290                 295                 300
```

Asn Gly Val Glu Lys Ala Asp Ser Phe Asp Met Asn Pro His Lys Trp
305                 310                 315                 320

Leu Leu Thr Asn Phe Asp Cys Ser Thr Leu Trp Val Lys Asn Pro Ser
            325                 330                 335

Leu Leu Val Asp Ala Leu Ser Thr Asn Pro Val Phe Leu Arg Asn Lys
            340                 345                 350

Gln Ser Asp Asn Asn Leu Val Val Asp Tyr Lys Asp Trp Gln Ile Pro
            355                 360                 365

Leu Gly Arg Arg Phe Arg Ser Leu Lys Leu Trp Met Val Leu Arg Met
    370                 375                 380

Tyr Gly Ser Asn Gly Leu Arg Ser Tyr Ile Thr Asn His Cys Asn Leu
385                 390                 395                 400

Ala Lys His Phe Glu Glu Leu Leu Arg Thr Asp Ser Arg Phe Glu Val
            405                 410                 415

Val Ala Pro Arg Val Phe Ser Leu Val Cys Phe Arg Leu Lys Ser Pro
            420                 425                 430

Ala Asn Asp Ala Asp Asn Ser Cys Ser Leu Ser Ala Lys Leu Val Asp
            435                 440                 445

Ala Leu Asn Ser Asp Gly Asn Ile Leu Ile Thr Asn Thr Val Leu Gly
    450                 455                 460

Gly Arg Tyr Thr Ile Arg Phe Thr Val Gly Ala Ser Arg Thr Glu Leu
465                 470                 475                 480

Arg His Val Asp Ala Ala Trp Lys Val Ile Gln Gln Leu Ala Ser Lys
            485                 490                 495

Leu Leu Lys Glu Cys Ser Ser
            500

<210> SEQ ID NO 35
<211> LENGTH: 487
<212> TYPE: PRT
<213> ORGANISM: Ananas comosus
<300> PUBLICATION INFORMATION:
<308> DATABASE ACCESSION NUMBER: 33033299

<400> SEQUENCE: 35

Met Glu Ser Glu Leu Lys Pro Met Asp Ser Gln Leu Arg Glu Tyr
1               5                   10                  15

Ala His Lys Met Val Asp Phe Ile Ala Asp Tyr Tyr Lys Met Ile Glu
            20                  25                  30

Ser Phe Pro Val Leu Ser Gln Val Lys Pro Gly Tyr Leu Lys Glu Leu
            35                  40                  45

Leu Pro Asp Ser Ala Pro Cys Lys Pro Glu Asn Leu Glu Asp Val Phe
    50                  55                  60

Asp Asp Ile Arg Gln Lys Ile Ile Pro Gly Ile Thr His Trp Gln Ser
65                  70                  75                  80

Pro Asp Tyr Phe Ala Tyr Tyr Pro Ser Asn Ser Ser Thr Ala Gly Phe
            85                  90                  95

Leu Gly Glu Met Leu Ser Ala Gly Phe Asn Ile Ile Gly Phe Ser Trp
            100                 105                 110

Ile Ala Ser Pro Ala Ala Thr Glu Leu Glu Met Ile Val Leu Asp Trp
            115                 120                 125

Phe Ala Lys Met Leu Lys Leu Pro Glu Gln Phe Leu Ser Thr Gly Gln
    130                 135                 140

Gly Gly Gly Val Ile Gln Gly Thr Ala Ser Glu Ala Val Leu Val Val
145                 150                 155                 160

Leu Leu Ala Ala Arg Asp Lys Ile Leu Leu Lys Ala Gly Arg Lys Ser
            165                 170                 175

Leu Glu Lys Leu Val Val Tyr Cys Ser Asp Gln Thr His Ser Ala Met
            180                 185                 190

Gln Lys Ala Cys Gln Ile Ala Gly Ile Phe Pro Glu Asn Phe Arg Val
            195                 200                 205

Leu Lys Thr Asp Ser Ser Asn Tyr Ala Leu Leu Pro Glu Val Leu
            210                 215                 220

Ser Glu Ala Ile Ser Lys Asp Leu Ser Phe Gly Leu Ile Pro Phe Phe
225                 230                 235                 240

Leu Cys Ala Thr Val Gly Thr Thr Ser Ser Ala Ala Val Asp Pro Leu
            245                 250                 255

Leu Lys Leu Gly Asn Ile Ser Lys Val His Asp Met Trp Phe His Val
            260                 265                 270

Asp Ala Ala His Ala Gly Ser Ala Cys Ile Cys Pro Glu Tyr Arg His
            275                 280                 285

His Ile Asp Gly Val Glu Glu Ala Asp Ser Phe Cys Met Asn Ala His
            290                 295                 300

Lys Trp Phe Leu Thr Asn Phe Asp Cys Ser Leu Leu Trp Val Lys Asp
305                 310                 315                 320

Arg Ser Ala Leu Ile Gln Ser Leu Ser Thr Asn Pro Glu Phe Leu Lys
            325                 330                 335

Asn Lys Ala Ser Gln Glu Asn Ser Val Val Asp Phe Lys Asp Trp Gln
            340                 345                 350

Ile Pro Leu Gly Arg Arg Phe Arg Ser Leu Lys Leu Trp Met Val Leu
            355                 360                 365

Arg Leu Tyr Gly Leu Glu Asn Leu Gln Ser Tyr Ile Arg Glu His Ile
            370                 375                 380

Lys Leu Ala Glu Gln Phe Glu Gln Leu Ile Ser Ser Asp Ser Arg Phe
385                 390                 395                 400

Glu Ile Val Ala Pro Arg Thr Phe Ser Leu Val Cys Phe Arg Leu Leu
            405                 410                 415

Pro Pro Leu Tyr Asp Gln Asp Gly Tyr Lys Leu Asn Tyr Asn Leu
            420                 425                 430

Leu Asp Ala Val Asn Arg Ser Gly Lys Ile Phe Met Ser His Thr Val
            435                 440                 445

Leu Ser Gly Lys Phe Val Leu Arg Phe Ala Ile Gly Ala Pro Leu Thr
            450                 455                 460

Glu Glu Arg His Val Val Ala Ala Trp Lys Val Leu Gln Asp Glu Ala
465                 470                 475                 480

Thr Ile Leu Leu Arg Gly Ser
            485

<210> SEQ ID NO 36
<211> LENGTH: 511
<212> TYPE: PRT
<213> ORGANISM: Zostera marina
<300> PUBLICATION INFORMATION:
<308> DATABASE ACCESSION NUMBER: 33182387

<400> SEQUENCE: 36

Met Leu Asn Gly Asn Met Gly Glu Asn Glu Pro Phe Lys Pro Met Asp
1               5                   10                  15

Ser Glu Gln Leu Arg Glu Tyr Gly His Lys Met Val Asp Phe Ile Ala
            20                  25                  30

```
Asp Tyr Tyr Lys Ser Ile Glu Lys Phe Pro Val Leu Ser Gln Val Gln
             35                  40                  45

Pro Tyr Tyr Leu Lys Asp Leu Leu Pro Asp Ala Ala Pro Asp Gln Pro
 50                  55                  60

Glu Lys Phe Gln Asp Val Leu Asp Asp Ile Thr Lys Lys Ile Ile Pro
 65                  70                  75                  80

Gly Val Thr His Trp Gln Ser Pro Asn Phe Phe Gly Tyr Tyr Pro Gly
                 85                  90                  95

Asn Ser Ser Ile Ala Gly Phe Leu Gly Glu Met Ile Cys Ser Gly Leu
                100                 105                 110

Asn Val Ile Gly Phe Ser Trp Ile Thr Ser Pro Ala Ser Thr Glu Leu
                115                 120                 125

Glu Val Ile Val Leu Asp Trp Leu Ala Lys Leu Leu Asn Leu Pro Asp
                130                 135                 140

Gln Phe Leu Ser Ser Gly His Gly Gly Gly Val Ile Gln Gly Thr Ala
145                 150                 155                 160

Ser Glu Ala Ile Leu Val Val Leu Leu Ala Ala Arg Asp Lys Ile Leu
                165                 170                 175

Gly Arg Ile Gly Arg Asn Ser Leu Asp Lys Leu Val Val Tyr Ser Ser
                180                 185                 190

Asp Gln Val His Ala Ala Phe Lys Lys Ala Cys Gln Ile Ala Gly Ile
                195                 200                 205

Tyr Thr Glu Asn Phe Arg Val Leu Lys Thr Asp Ala Ser Ser Gly Tyr
                210                 215                 220

Gly Ile Asp Pro Lys Lys Phe Asp Gln Ala Ile His Asp Asp Met Glu
225                 230                 235                 240

Ala Gly Leu Ile Pro Phe Phe Leu Cys Ser Thr Val Gly Thr Thr Ser
                245                 250                 255

Ser Ala Ser Val Asp Pro Leu Val Glu Ile Gly Gln Ile Thr Glu Glu
                260                 265                 270

Asn Asp Met Trp Phe His Val Asp Ala Ala Tyr Ala Gly Ser Ala Cys
                275                 280                 285

Ile Cys Pro Glu Tyr Arg His Tyr Leu Asp Gly Val Glu Tyr Ala Asp
                290                 295                 300

Ser Phe Cys Met Asn Ala His Lys Trp Leu Leu Thr Asn Phe Asp Cys
305                 310                 315                 320

Ser Ala Leu Trp Val Lys Asp Ser Ser Ala Leu Val Asn Ser Leu Ser
                325                 330                 335

Thr Asn Pro Glu Phe Leu Lys Asn Lys Met Ser Glu Gln Lys Lys Val
                340                 345                 350

Val Asp Phe Lys Asp Trp Gln Ile Pro Leu Gly Arg Arg Phe Arg Ser
                355                 360                 365

Leu Lys Leu Trp Met Val Leu Arg Leu Tyr Gly Ala Glu Asn Leu Arg
                370                 375                 380

Glu Tyr Ile Arg Asn His Ile Lys Leu Ala Asn Leu Phe Glu Gln Leu
385                 390                 395                 400

Val Arg Ser Asp Ser Arg Phe Glu Ile Val Cys Pro Thr Leu Phe Ser
                405                 410                 415

Leu Val Cys Phe Arg Phe Leu Pro Ser Asn Asp Asn Asp Gly Tyr
                420                 425                 430

Glu Leu Asn Ser Met Leu Leu Asp Ala Val Asn Ser Thr Gly Gln Leu
                435                 440                 445

Phe Phe Thr His Thr Ile Ile Ser Asp Lys Tyr Ile Leu Arg Phe Ala
```

```
                450             455             460
Val Gly Ala Ala Leu Thr Glu Arg His Val Arg Glu Ser Trp Lys
465                 470                 475                 480

Val Ile Gln Asn Gln Ala Thr Ile Ile Ser Arg Gln His Ile Leu Ser
                485                 490                 495

Lys Thr Asn Met Lys Ser Lys Cys Glu Gly Met Ile Ala Asn Glu
                500                 505                 510
```

<210> SEQ ID NO 37
<211> LENGTH: 497
<212> TYPE: PRT
<213> ORGANISM: Daucus carota subsp. sativus
<300> PUBLICATION INFORMATION:
<308> DATABASE ACCESSION NUMBER: 36055203

<400> SEQUENCE: 37

```
Met Asp Gly Val Leu Lys Pro Met Asp Ala Glu Gln Leu Arg Glu Asn
1               5                   10                  15

Ala His Lys Met Val Asp Phe Ile Ala Asp Tyr Tyr Lys Asn Ile Glu
                20                  25                  30

Thr Phe Pro Val Leu Ser Gln Val Glu Pro Gly Tyr Leu Arg Asp Leu
            35                  40                  45

Leu Pro His Ser Ala Pro Asp Gln Pro Glu Ser Leu Gln Asn Ile Leu
    50                  55                  60

Asp Asp Ile Gln Ala Lys Ile Leu Pro Gly Val Thr His Trp Gln Ser
65                  70                  75                  80

Pro Asn Tyr Phe Ala Tyr Phe Pro Ser Asn Ser Ser Val Ala Gly Phe
                85                  90                  95

Leu Gly Glu Met Leu Ser Ala Gly Ile Asn Met Val Gly Phe Ser Trp
                100                 105                 110

Ile Thr Ser Pro Ala Ala Thr Glu Leu Glu Met Ile Val Leu Asp Trp
            115                 120                 125

Leu Ala Lys Leu Leu Lys Leu Pro Asp His Phe Leu Ser Thr Gly Gln
    130                 135                 140

Gly Gly Gly Val Ile Gln Gly Thr Ala Ser Glu Ala Val Leu Val Val
145                 150                 155                 160

Leu Leu Ala Ala Arg Asp Lys Val Leu Arg Ile Thr Gly Lys Asp Ala
                165                 170                 175

Leu Gly Lys Leu Val Val Tyr Cys Ser Asp Gln Thr His Ser Ala Leu
                180                 185                 190

Gln Lys Ala Cys Gln Ile Ala Gly Ile His Pro Gly Asn Cys Arg Val
            195                 200                 205

Leu Lys Thr Glu Ser Cys Asn Asp Tyr Ser Leu Ser Pro Glu Thr Phe
    210                 215                 220

Glu Gln Ala Ile Ser Thr Asp Val Ala Ser Gly Leu Ile Pro Leu Leu
225                 230                 235                 240

Leu Cys Ala Thr Val Gly Thr Thr Ser Thr Ala Val Asp Pro Leu
                245                 250                 255

Leu Glu Leu Gly Lys Ile Thr Lys Met Lys Gly Ile Trp Leu His Val
                260                 265                 270

Asp Ala Ala Tyr Ala Gly Ser Ala Cys Val Cys Pro Glu Phe Arg His
            275                 280                 285

Tyr Ile Asp Gly Val Glu Glu Ala Asp Ser Phe Asn Met Asn Ala His
    290                 295                 300

Lys Trp Phe Leu Thr Asn Phe Asp Cys Ser Ala Leu Trp Val Lys Asp
```

```
                 305                 310                 315                 320
Arg Ser Ala Leu Ile His Ser Leu Ser Thr Asn Pro Glu Phe Leu Lys
                325                 330                 335

Asn Lys Ala Ser Gln Glu Asn Leu Val Val Asp Tyr Lys Asp Trp Gln
                340                 345                 350

Ile Pro Leu Gly Arg Arg Phe Arg Ser Leu Lys Leu Trp Met Val Leu
                355                 360                 365

Arg Leu Tyr Gly Leu Glu Asn Leu Gln Ser Tyr Ile Arg Asn His Ile
                370                 375                 380

Gln Leu Ala Ala Thr Phe Glu Ser Phe Val Thr Glu Asp Pro Arg Phe
385                 390                 395                 400

Glu Val Val Ala Pro Arg Lys Phe Ala Leu Val Cys Phe Arg Leu Leu
                405                 410                 415

Pro Pro Ser His Lys Asp Glu Asp Cys Ser Asn Gln Leu Asn Arg Asp
                420                 425                 430

Leu Leu Asp Ala Val Asn Ala Thr Gly Lys Ala Phe Val Ser His Thr
                435                 440                 445

Ala Leu Ser Gly Arg Tyr Val Val Arg Phe Ala Ile Gly Ala Pro Leu
                450                 455                 460

Thr Glu Glu Ser His Ile Ile Glu Ala Trp Lys Ile Phe Gln Glu Val
465                 470                 475                 480

Ala Thr Val Leu Leu Lys Ser Leu Lys Met Asn His Thr Arg Pro Leu
                485                 490                 495

Asn

<210> SEQ ID NO 38
<211> LENGTH: 468
<212> TYPE: PRT
<213> ORGANISM: Trifolium pratense
<300> PUBLICATION INFORMATION:
<308> DATABASE ACCESSION NUMBER: 35974269

<400> SEQUENCE: 38

Met Val Asp Phe Ile Ala Asp Tyr Tyr Lys Thr Ile Glu Asn Phe Pro
1               5                   10                  15

Val Leu Ser Gln Val Glu Pro Gly Tyr Leu Gly Lys Leu Leu Pro Asp
                20                  25                  30

Ser Ala Pro Thr Tyr Pro Thr Thr Leu Glu His Val Leu Asn Asp Val
                35                  40                  45

Gln His Lys Ile Leu Pro Gly Val Thr His Trp Gln Ser Pro Asn Tyr
            50                  55                  60

Phe Ala Tyr Phe Pro Ser Asn Ser Ser Ile Ala Gly Phe Leu Gly Glu
65              70                  75                  80

Met Leu Ser Ala Gly Ile Asn Ile Val Gly Phe Ser Trp Ile Thr Ser
                85                  90                  95

Pro Ala Ala Thr Glu Leu Glu Ser Ile Val Leu Asp Trp Leu Ala Lys
                100                 105                 110

Ala Leu Phe Leu Pro Gln Asp Phe Leu Ser Asn Gly Lys Gly Gly Gly
                115                 120                 125

Val Ile Gln Gly Thr Ala Ser Glu Ala Val Leu Val Val Leu Leu Ala
                130                 135                 140

Ala Arg Asp Lys Ile Leu Arg Thr Val Gly Arg Ser Ala Leu Pro Lys
145                 150                 155                 160

Leu Val Thr Tyr Ala Ser Asp His Val His Ser Ser Leu Leu Lys Ala
                165                 170                 175
```

```
Cys Gln Ile Gly Gly Leu Asp Pro Glu Leu Cys Arg Leu Leu Lys Thr
                180                 185                 190

Asp Ser Ser Thr Asn Phe Ala Leu Ser Pro Asp Val Leu Ser Glu Ala
            195                 200                 205

Ile Ser Asn Asp Ile Ala Ser Gly Leu Ile Pro Phe Phe Leu Cys Ala
210                 215                 220

Asn Val Gly Thr Thr Ser Ser Thr Ala Val Asp Pro Leu Pro Ala Leu
225                 230                 235                 240

Ala Lys Val Thr Lys Thr Asn Asn Ile Trp Leu His Val Asp Ala Ala
                245                 250                 255

Tyr Ala Gly Ser Ala Cys Ile Cys Pro Glu Tyr Arg His Phe Ile Asp
            260                 265                 270

Gly Val Glu Glu Ala Asp Ser Phe Asn Met Asn Ala His Lys Trp Phe
        275                 280                 285

Leu Thr Asn Phe Asp Cys Ser Leu Leu Trp Val Lys Asp Arg Ser Ala
    290                 295                 300

Leu Ile Gln Ser Leu Ser Thr Asn Pro Glu Phe Leu Lys Asn Lys Ala
305                 310                 315                 320

Ser Glu Gly Asn Met Val Ile Asp Tyr Lys Asp Trp Gln Ile Pro Leu
                325                 330                 335

Gly Arg Arg Phe Arg Ser Leu Lys Leu Trp Met Val Leu Arg Leu Tyr
            340                 345                 350

Gly Leu Glu Gly Leu Arg Ser His Ile Arg Asn His Ile Ala Leu Ala
        355                 360                 365

Ala Ser Phe Glu Glu Leu Val Val Gln Asp Ala Arg Phe Lys Val Val
    370                 375                 380

Thr Pro Arg Thr Phe Ser Leu Val Cys Phe Arg Leu Leu Pro Pro Pro
385                 390                 395                 400

Asn Ser Glu Asp Asn Gly Asn Lys Leu Asn His Asp Leu Leu Asp Leu
                405                 410                 415

Val Asn Ser Thr Gly Ser Val Phe Ile Thr His Thr Val Leu Ser Gly
            420                 425                 430

Glu Tyr Ile Leu Arg Leu Ala Val Gly Ala Pro Leu Thr Glu Val Arg
        435                 440                 445

His Val Asn Ala Ala Trp Gln Ile Leu Gln Glu Lys Ala Thr Ala Leu
    450                 455                 460

Leu Glu Asn Leu
465

<210> SEQ ID NO 39
<211> LENGTH: 475
<212> TYPE: PRT
<213> ORGANISM: Arabidopsis lyrata
<300> PUBLICATION INFORMATION:
<308> DATABASE ACCESSION NUMBER: 35943929

<400> SEQUENCE: 39

Met Asp Ser Glu Gln Leu Arg Glu Tyr Gly His Arg Met Val Asp Phe
1               5                   10                  15

Ile Ala Asp Tyr Tyr Lys Thr Ile Glu Asp Phe Pro Val Leu Ser Gln
            20                  25                  30

Val Gln Pro Gly Tyr Leu His Lys Leu Leu Pro Asp Ser Ala Pro Asp
        35                  40                  45

His Pro Glu Thr Leu Asp Gln Val Leu Asp Asp Val Arg Ala Lys Ile
    50                  55                  60
```

```
Leu Pro Gly Val Thr His Trp Gln Ser Pro Ser Phe Ala Tyr Tyr
 65                  70                  75                  80

Pro Ser Asn Ser Ser Val Ala Gly Phe Leu Gly Glu Met Leu Ser Ala
             85                  90                  95

Gly Leu Gly Ile Val Gly Phe Ser Trp Val Thr Ser Pro Ala Ala Thr
            100                 105                 110

Glu Leu Glu Met Ile Val Leu Asp Trp Leu Ala Lys Leu Leu Asn Leu
            115                 120                 125

Pro Glu Gln Phe Met Ser Lys Gly Asn Gly Gly Val Ile Gln Gly
            130                 135                 140

Ser Ala Ser Glu Ala Val Leu Val Val Leu Ile Ala Ala Arg Asp Lys
145                 150                 155                 160

Val Leu Arg Ser Val Gly Lys Asn Ala Leu Gln Lys Leu Val Val Tyr
                165                 170                 175

Ser Ser Asp Gln Thr His Ser Ala Leu Gln Lys Ala Cys Gln Ile Ala
            180                 185                 190

Gly Ile His Pro Glu Asn Cys Arg Val Leu Lys Thr Asp Ser Ser Thr
        195                 200                 205

Asn Tyr Ala Leu Arg Pro Glu Leu Leu Gln Glu Ala Val Ser Gln Asp
210                 215                 220

Leu Asp Ala Gly Leu Ile Pro Phe Phe Leu Cys Ala Asn Val Gly Thr
225                 230                 235                 240

Thr Ser Ser Thr Ala Val Asp Pro Leu Ala Ala Leu Gly Lys Ile Ala
                245                 250                 255

Asn Arg Asn Glu Met Trp Phe His Val Asp Ala Ala Tyr Ala Gly Ser
            260                 265                 270

Ala Cys Ile Cys Pro Glu Tyr Arg Gln Tyr Ile Asp Gly Val Glu Thr
        275                 280                 285

Ala Asp Ser Phe Asn Met Asn Ala His Lys Trp Phe Leu Thr Asn Phe
290                 295                 300

Asp Cys Ser Leu Leu Trp Val Lys Asp Gln Asp Ser Leu Thr Leu Ala
305                 310                 315                 320

Leu Ser Thr Asn Pro Glu Phe Leu Lys Asn Lys Ala Ser Gln Ala Asn
                325                 330                 335

Leu Val Val Asp Tyr Lys Asp Trp Gln Ile Pro Leu Gly Arg Arg Phe
            340                 345                 350

Arg Ser Leu Lys Leu Trp Met Val Leu Arg Leu Tyr Gly Ser Glu Thr
        355                 360                 365

Leu Lys Ser Tyr Ile Arg Asn His Ile Lys Leu Ala Lys Glu Phe Glu
370                 375                 380

Gln Leu Val Ser Gln Asp Pro Asn Phe Glu Ile Val Thr Pro Arg Ile
385                 390                 395                 400

Phe Ser Leu Val Cys Phe Arg Leu Val Pro Val Lys Asn Glu Glu Lys
                405                 410                 415

Lys Cys Asn Asn Arg Asn Arg Glu Leu Leu Asp Ala Val Asn Ser Ser
            420                 425                 430

Gly Lys Leu Phe Ile Ser His Thr Val Ser Asp Phe Ser Ser Phe Phe
        435                 440                 445

Leu Leu Phe Phe Leu Leu Asp Asn Val Leu Asn Leu Arg Gly Asn Arg
450                 455                 460

Leu Cys Arg Gly Lys Ser Tyr Cys Val Ala Gln
465                 470                 475
```

```
<210> SEQ ID NO 40
<211> LENGTH: 505
<212> TYPE: PRT
<213> ORGANISM: Sorghum bicolor
<300> PUBLICATION INFORMATION:
<308> DATABASE ACCESSION NUMBER: 002G120700.1

<400> SEQUENCE: 40
```

| | | | | | | | | | | | | | | |
|---|---|---|---|---|---|---|---|---|---|---|---|---|---|---|
|Met|Asp|Gly|Ser|Gly|Ser|Ser|Gly|Gly|Thr|Asn|Gly|Gly|Ser|Gly|
|1| | | |5| | | | |10| | | | |15|

| | | | | | | | | | | | | | | |
|---|---|---|---|---|---|---|---|---|---|---|---|---|---|---|
|Asp|Gly|Ala|Gly|Trp|Leu|Arg|Pro|Met|Asp|Ala|Glu|Gln|Leu|Arg|Glu|
| | | |20| | | | |25| | | | |30| |

| | | | | | | | | | | | | | |
|---|---|---|---|---|---|---|---|---|---|---|---|---|---|
|Cys|Gly|His|Arg|Met|Val|Asp|Phe|Val|Ala|Asp|Tyr|Tyr|Lys|Ser|Ile|
| | |35| | | | |40| | | | |45| |

|Glu|Thr|Phe|Pro|Val|Leu|Ser|Gln|Val|Gln|Pro|Gly|Tyr|Leu|Lys|Glu|
|---|---|---|---|---|---|---|---|---|---|---|---|---|---|---|---|
| |50| | | | |55| | | | |60| | | | |

|Leu|Leu|Pro|Asp|Thr|Ala|Pro|Asn|Lys|Pro|Thr|Leu|Glu|Ala|Leu|
|---|---|---|---|---|---|---|---|---|---|---|---|---|---|---|
|65| | | | |70| | | | |75| | | | |80|

|Phe|Asp|Asp|Ile|Arg|Glu|Lys|Ile|Val|Pro|Gly|Val|Thr|His|Trp|Gln|
|---|---|---|---|---|---|---|---|---|---|---|---|---|---|---|---|
| | | | |85| | | | |90| | | | |95| |

|Ser|Pro|Asn|Tyr|Phe|Ala|Tyr|Tyr|Pro|Ser|Asn|Ser|Thr|Ala|Gly|
|---|---|---|---|---|---|---|---|---|---|---|---|---|---|---|
| | | |100| | | | |105| | | | |110| |

|Phe|Leu|Gly|Glu|Met|Leu|Ser|Ala|Ala|Phe|Asn|Ile|Val|Gly|Phe|Ser|
|---|---|---|---|---|---|---|---|---|---|---|---|---|---|---|---|
| | |115| | | | |120| | | | |125| | | |

|Trp|Ile|Thr|Ser|Pro|Ala|Ala|Thr|Glu|Leu|Glu|Val|Ile|Val|Leu|Asp|
|---|---|---|---|---|---|---|---|---|---|---|---|---|---|---|---|
| |130| | | | |135| | | | |140| | | | |

|Trp|Phe|Ala|Lys|Met|Leu|Arg|Leu|Pro|Ser|Gln|Phe|Leu|Ser|Thr|Ala|
|---|---|---|---|---|---|---|---|---|---|---|---|---|---|---|---|
|145| | | | |150| | | | |155| | | | |160|

|Leu|Gly|Gly|Gly|Val|Ile|Gln|Gly|Thr|Ala|Ser|Glu|Ala|Val|Leu|Val|
|---|---|---|---|---|---|---|---|---|---|---|---|---|---|---|---|
| | | |165| | | | |170| | | | |175| | |

|Val|Leu|Leu|Ala|Ala|Arg|Asp|Arg|Thr|Leu|Arg|Lys|His|Gly|Lys|Thr|
|---|---|---|---|---|---|---|---|---|---|---|---|---|---|---|---|
| | | |180| | | | |185| | | | |190| | |

|Ser|Leu|Glu|Lys|Leu|Val|Val|Tyr|Ala|Ser|Asp|Gln|Thr|His|Ser|Ala|
|---|---|---|---|---|---|---|---|---|---|---|---|---|---|---|---|
| | |195| | | | |200| | | | |205| | | |

|Leu|Gln|Lys|Ala|Cys|Gln|Ile|Ala|Gly|Ile|Phe|Pro|Glu|Asn|Val|Arg|
|---|---|---|---|---|---|---|---|---|---|---|---|---|---|---|---|
| |210| | | | |215| | | | |220| | | | |

|Leu|Val|Lys|Ala|Asp|Cys|Asn|Arg|Asn|Tyr|Ala|Val|Ala|Pro|Leu|Ala|
|---|---|---|---|---|---|---|---|---|---|---|---|---|---|---|---|
|225| | | | |230| | | | |235| | | | |240|

|Ile|Ser|Asp|Ala|Ile|Ala|Thr|Asp|Leu|Ser|Ser|Gly|Leu|Ile|Pro|Phe|
|---|---|---|---|---|---|---|---|---|---|---|---|---|---|---|---|
| | | |245| | | | |250| | | | |255| | |

|Phe|Ile|Cys|Ala|Thr|Val|Gly|Thr|Thr|Ser|Ser|Ser|Ala|Val|Asp|Pro|
|---|---|---|---|---|---|---|---|---|---|---|---|---|---|---|---|
| | | |260| | | | |265| | | | |270| | |

|Leu|Pro|Glu|Leu|Gly|Gln|Ile|Ala|Lys|Ala|Asn|Asp|Met|Trp|Leu|His|
|---|---|---|---|---|---|---|---|---|---|---|---|---|---|---|---|
| | |275| | | | |280| | | | |285| | | |

|Ile|Asp|Ala|Ala|Tyr|Ala|Gly|Ser|Ala|Cys|Ile|Cys|Pro|Glu|Tyr|Arg|
|---|---|---|---|---|---|---|---|---|---|---|---|---|---|---|---|
| |290| | | | |295| | | | |300| | | | |

|His|His|Leu|Asn|Gly|Val|Glu|Glu|Ala|Asp|Ser|Phe|Asn|Met|Asn|Ala|
|---|---|---|---|---|---|---|---|---|---|---|---|---|---|---|---|
|305| | | | |310| | | | |315| | | | |320|

|His|Lys|Trp|Phe|Leu|Thr|Asn|Phe|Asp|Cys|Ser|Leu|Leu|Trp|Val|Lys|
|---|---|---|---|---|---|---|---|---|---|---|---|---|---|---|---|
| | | |325| | | | |330| | | | |335| | |

|Asp|Arg|Ser|Tyr|Leu|Ile|Gln|Ser|Leu|Ser|Thr|Asn|Pro|Glu|Phe|Leu|
|---|---|---|---|---|---|---|---|---|---|---|---|---|---|---|---|
| | |340| | | | |345| | | | |350| | | |

|Lys|Asn|Lys|Ala|Ser|Glu|Ala|Asn|Ser|Val|Phe|Asp|Phe|Lys|Asp|Trp|
|---|---|---|---|---|---|---|---|---|---|---|---|---|---|---|---|
| | |355| | | | |360| | | | |365| | | |

```
Gln Ile Pro Leu Gly Arg Arg Phe Arg Ser Leu Lys Leu Trp Met Val
    370                 375                 380

Leu Arg Leu Tyr Gly Val Glu Asn Leu Gln Ser Tyr Ile Arg Lys His
385                 390                 395                 400

Ile Glu Leu Ala Lys Glu Phe Glu Gln Leu Val Ile Ser Asp Ser Arg
                405                 410                 415

Phe Glu Val Val Thr Pro Arg Thr Phe Ser Leu Val Cys Phe Arg Leu
                420                 425                 430

Val Pro Leu Ala Ser Asp Gln Asp Asn Gly Arg Lys Leu Asn Tyr Asp
                435                 440                 445

Leu Met Asp Ala Ala Asn Ser Ser Gly Lys Ile Phe Ile Ser His Thr
450                 455                 460

Val Leu Ser Gly Lys Phe Val Leu Arg Phe Ala Val Gly Ala Pro Leu
465                 470                 475                 480

Thr Glu Gly Gln His Ile Phe Ser Ala Trp Lys Ile Leu Gln Asp Leu
                485                 490                 495

Ala Thr Lys Gln Leu Leu Glu Ser Ser
                500                 505

<210> SEQ ID NO 41
<211> LENGTH: 504
<212> TYPE: PRT
<213> ORGANISM: Sphagnum fallax
<300> PUBLICATION INFORMATION:
<308> DATABASE ACCESSION NUMBER: 0166s0011.1

<400> SEQUENCE: 41

Met Gly Ser Glu Ala Gly Glu Gly Ser Arg Leu Ser Lys Pro Leu Asp
1               5                   10                  15

Val Glu Glu Phe Arg Lys His Ala His Gln Met Val Asp Phe Val Ala
                20                  25                  30

Asp Tyr His Arg Asp Ile Glu Ser Phe Pro Val Arg Ser Gln Val Lys
            35                  40                  45

Pro Gly Tyr Leu Arg Pro Leu Leu Pro Asp Ser Ala Pro Ala Glu Pro
    50                  55                  60

Glu Thr Val Glu Asp Val Phe Ala Asp Leu Trp Ser Lys Ile Leu Pro
65                  70                  75                  80

Gly Leu Thr His Trp Gln Ser Pro Lys Phe Phe Gly Tyr Tyr Pro Cys
                85                  90                  95

Asn Val Ser Thr Ala Gly Met Leu Gly Glu Met Leu Cys Gly Gly Leu
                100                 105                 110

Asn Val Asn Gly Phe Ser Trp Ile Thr Ser Pro Ala Ala Thr Glu Leu
            115                 120                 125

Glu Thr Ile Val Leu Asp Trp Leu Gly Lys Leu Leu His Leu Pro Glu
    130                 135                 140

Glu Phe Leu Ser Thr Ser Gly Lys Gly Gly Val Ile Gln Gly Thr
145                 150                 155                 160

Ala Ser Glu Ala Val Leu Val Val Met Leu Ala Ala Arg Lys Arg Ala
                165                 170                 175

Leu Lys Gln Val Ser Ser Ala Ala Gln Gly Met Ser Glu Ala Glu Ala
            180                 185                 190

Leu Ser Lys Leu Val Val Tyr Ser Ser Asp Gln Thr His Ser Cys Val
    195                 200                 205

Ile Lys Ala Cys Gln Val Ala Ser Ile Ala Thr Glu Asn Phe Arg Pro
    210                 215                 220
```

Leu Pro Thr Asp Ala Ser Thr Asn Phe Ala Leu Ser Pro Ala Val Val
225                 230                 235                 240

Arg Lys Ala Ile Ala Thr Asp Val Glu Ala Gly Leu Ile Pro Phe Phe
            245                 250                 255

Leu Cys Gly Thr Leu Gly Thr Thr Ser Ser Ala Ala Val Asp Pro Leu
            260                 265                 270

Glu Glu Leu Gly Asp Ile Ala Lys Glu Tyr Gly Met Trp Tyr His Ile
        275                 280                 285

Asp Ala Ala Tyr Ala Gly Asn Ala Cys Ile Cys Pro Glu Phe Arg His
        290                 295                 300

Tyr Leu Asn Gly Val Glu Lys Ala Asp Ser Tyr Asn Met Asn Pro His
305                 310                 315                 320

Lys Trp Leu Leu Thr Asn Phe Asp Cys Ser Thr Leu Trp Met Lys Asp
                325                 330                 335

Ser Glu Phe Leu Leu Ala Ala Leu Ser Asn Lys Pro Val Phe Leu Arg
            340                 345                 350

Asn Glu Ala Thr Asp Asn Asn Leu Val Val Asp Tyr Lys Asp Trp Gln
        355                 360                 365

Ile Pro Leu Gly Arg Arg Phe Arg Ala Leu Lys Leu Trp Met Val Met
370                 375                 380

Arg Leu Tyr Gly Thr Ser Gly Leu Gln Ser Phe Ile Arg Ser His Val
385                 390                 395                 400

Ser Ser Ala Lys His Phe Glu Ser Leu Val Arg Ala Asp Ser Arg Phe
                405                 410                 415

Glu Val Met Ala Pro Met Thr Phe Ser Leu Val Cys Phe Arg Leu Arg
            420                 425                 430

Thr Leu Pro Gly Ser Gln Asp Asn Ser Asn Ser Leu Asn Ser Lys Leu
            435                 440                 445

Val Asp Ala Leu Asn Arg Lys Gly Asn Ile Leu Val Thr His Thr Glu
        450                 455                 460

Leu Ser Gly Ile Tyr Thr Val Arg Phe Ala Val Gly Ala Thr His Thr
465                 470                 475                 480

Glu Leu Gln His Val Gln Ala Ala Trp Glu Val Ile Gln Ala Glu Ala
                485                 490                 495

Ser His Leu Leu Asn Gly Lys Gln
            500

<210> SEQ ID NO 42
<211> LENGTH: 524
<212> TYPE: PRT
<213> ORGANISM: Kalanchoe laxiflora
<300> PUBLICATION INFORMATION:
<308> DATABASE ACCESSION NUMBER: 1398s0003.1

<400> SEQUENCE: 42

Met Ile Leu Ser Ile His Pro Phe Pro Phe Thr Leu Ser Ala Arg Phe
1               5                   10                  15

Ser Gly Ala Ala Ala Asn Ile Leu Ser Lys Ala Ser Cys Trp Leu
            20                  25                  30

Arg Cys Leu Arg Ser Met Glu Gly Glu Leu Lys Pro Met Asp Ala Glu
            35                  40                  45

Gln Leu Arg Glu Tyr Gly His Arg Met Val Asp Phe Val Ala Asp Tyr
        50                  55                  60

Tyr Lys Thr Ile Glu Asp His Pro Val Leu Ser Gln Val Glu Pro Gly
65                  70                  75                  80

-continued

```
Tyr Leu Arg Lys Leu Leu Pro Asp Ser Ala Pro Asp Lys Pro Glu Ser
                85                  90                  95
Phe Glu Asn Val Leu Ser Asp Val Lys Thr Lys Ile Ile Pro Gly Val
            100                 105                 110
Thr His Trp Gln Ser Pro Asn Tyr Phe Ala Tyr Phe Pro Ser Asn Ser
        115                 120                 125
Ser Thr Ala Gly Phe Leu Gly Glu Met Leu Ser Ala Cys Phe Asn Ile
    130                 135                 140
Val Gly Phe Ser Trp Ile Thr Ser Pro Ala Ala Thr Glu Leu Glu Met
145                 150                 155                 160
Ile Val Leu Asp Trp Phe Ala Lys Met Leu Lys Leu Pro Asp Phe Phe
                165                 170                 175
Leu Ser Thr Gly Gln Gly Gly Val Ile Gln Gly Thr Ala Ser Glu
            180                 185                 190
Ala Val Leu Val Val Leu Leu Ala Ala Arg Asp Ile Phe Leu Arg Lys
            195                 200                 205
Leu Gly Lys Gly Phe Leu Glu Lys Leu Val Val Tyr Ala Ser Asp Gln
    210                 215                 220
Thr His Ser Ala Leu Gln Lys Ala Cys Gln Ile Ala Gly Ile His Pro
225                 230                 235                 240
Glu Asn Val Arg Ala Leu Lys Thr Asp Ser Ser Thr Asn Tyr Gly Leu
                245                 250                 255
Ser Pro Asp Leu Leu Ser Lys Glu Ile Cys His Asp Ile Ala Asn Gly
            260                 265                 270
Leu Val Pro Phe Phe Ala Cys Ala Ser Val Gly Thr Thr Ser Ser Thr
        275                 280                 285
Ala Val Asp Pro Ile Leu Glu Leu Ala Asn Val Thr Lys Ser Tyr Asn
    290                 295                 300
Ile Trp Leu His Val Asp Ser Ala Tyr Ala Gly Ser Ala Cys Val Cys
305                 310                 315                 320
Pro Glu Tyr Arg His His Ile Asp Gly Val Glu Glu Val Asp Ser Phe
                325                 330                 335
Asn Met Asn Ala His Lys Trp Phe Leu Thr Asn Phe Asp Cys Ser Leu
            340                 345                 350
Leu Trp Val Lys Asp Arg Asn Ala Leu Ile Gln Ser Leu Ser Thr Asn
        355                 360                 365
Pro Glu Phe Leu Lys Asn Lys Ala Ser Gln Ser Asn Ser Val Leu Asp
    370                 375                 380
Tyr Lys Asp Trp Gln Ile Pro Leu Gly Arg Arg Phe Arg Ser Leu Lys
385                 390                 395                 400
Leu Trp Leu Val Leu Arg Leu Tyr Gly Val Glu Asn Leu Gln Ala Tyr
                405                 410                 415
Ile Arg Asn His Ile Glu Leu Ala Leu Asn Phe Glu Glu Leu Val Ser
            420                 425                 430
Gln Asp Met Arg Phe Glu Ile Val Ala Pro Arg Thr Phe Ala Leu Val
        435                 440                 445
Cys Phe Arg Leu Leu Pro Cys Gly Phe Glu Asp His Thr Asn Asp
    450                 455                 460
Val Asn Ser Asp Leu Leu Gln Ala Val Asn Ser Thr Gly Lys Ile Phe
465                 470                 475                 480
Ile Ser His Thr Val Leu Ser Gly Thr Tyr Val Leu Arg Phe Ala Val
                485                 490                 495
Gly Ala Pro Leu Thr Glu Glu Arg His Ile Asp Ala Ala Trp Lys Leu
```

```
                    500                 505                 510
Ile Gln Asp Gln Ala Ser Ser Leu Leu Glu Lys Leu
            515                 520

<210> SEQ ID NO 43
<211> LENGTH: 487
<212> TYPE: PRT
<213> ORGANISM: Manihot esculenta
<300> PUBLICATION INFORMATION:
<308> DATABASE ACCESSION NUMBER: 12G038600.1

<400> SEQUENCE: 43

Met Glu Gly Glu Leu Arg Pro Met Asp Ala Glu Gln Leu Arg Glu Tyr
1               5                   10                  15

Gly His Gln Met Val Asp Phe Ile Ala Asp Tyr Tyr Lys Thr Ile Glu
            20                  25                  30

Asn Phe Pro Val Leu Ser Gln Val Glu Pro Gly Tyr Leu His Lys Leu
        35                  40                  45

Leu Pro Asp Ser Ala Pro Asn Gln Pro Glu Ala Leu Gln Asn Val Leu
    50                  55                  60

Asp Asp Val Arg Val Lys Ile Leu Pro Gly Val Thr His Trp Gln Ser
65                  70                  75                  80

Pro Asn Tyr Phe Ala Tyr Tyr Pro Ser Asn Ser Ser Val Ala Gly Phe
                85                  90                  95

Leu Gly Glu Met Leu Ser Ala Gly Ile Asn Met Ile Gly Phe Ser Trp
            100                 105                 110

Ile Thr Ser Pro Ala Ala Thr Glu Leu Glu Met Ile Val Leu Asp Trp
        115                 120                 125

Leu Gly Lys Met Leu Lys Leu Pro Glu Glu Phe Leu Ser Ser Gly Gln
    130                 135                 140

Gly Gly Gly Val Ile Gln Gly Thr Ala Ser Glu Ala Val Leu Val Val
145                 150                 155                 160

Leu Leu Ala Ala Arg Asp Lys Val Leu Thr Arg Val Gly Lys Asp Ser
                165                 170                 175

Leu Lys Lys Leu Val Val Tyr Gly Ser Asp Gln Thr His Ser Ala Leu
            180                 185                 190

Gln Lys Ala Cys Gln Ile Ala Gly Val His Leu Asp Asn Cys Arg Leu
        195                 200                 205

Leu Lys Thr Asp Ser Ser Lys Asn Tyr Ala Leu Ser Pro Asp Ile Leu
    210                 215                 220

Cys Asp Ala Ile Ser Gln Asp Met Ser Asn Gly Leu Ile Pro Phe Phe
225                 230                 235                 240

Leu Cys Ala Thr Val Gly Thr Thr Ser Ser Ala Thr Val Asp Pro Leu
                245                 250                 255

Leu Ala Leu Gly Lys Ile Ala Lys Lys Tyr Gly Met Trp Phe His Val
            260                 265                 270

Asp Ala Ala Tyr Ala Gly Ser Ala Cys Ile Cys Pro Glu Tyr Arg Cys
        275                 280                 285

Tyr Ile Asp Gly Val Glu Glu Ala Asp Ser Phe Asn Met Asn Ala His
    290                 295                 300

Lys Trp Phe Leu Thr Asn Phe Asp Cys Ser Ala Leu Trp Val Lys Asp
305                 310                 315                 320

Arg Asn Ala Leu Ile Gln Ser Leu Ser Thr Asn Pro Glu Phe Leu Lys
                325                 330                 335

Asn Lys Ala Ser Gln Ala Asn Met Val Val Asp Tyr Lys Asp Trp Gln
```

Ile Pro Leu Gly Arg Arg Phe Arg Ser Leu Lys Leu Trp Met Val Leu
           340                 345                 350

Arg Leu Tyr Gly Val Ala Asn Leu Gln Ser Tyr Ile Arg Asn His Ile
    355                 360                 365

Asn Leu Ala Lys Tyr Phe Glu Gly Leu Val Ala Gly Asp Ser Arg Phe
370                 375                 380

Glu Val Val Ala Pro Arg Leu Phe Ser Leu Val Cys Phe Arg Leu Leu
385                 390                 395                 400

Pro Pro Asp Asn Asp Glu Asn His Gly Asn Lys Leu Asn His Asp Leu
            405                 410                 415

Leu Asp Ala Ala Asn Ser Thr Gly Lys Ile Phe Ile Ser His Thr Val
            420                 425                 430

Leu Ser Gly Lys Tyr Ile Leu Arg Phe Ala Val Gly Ala Pro Leu Thr
            435                 440                 445

Glu Glu Arg His Val Thr Ala Ala Trp Lys Val Leu Gln Asp Glu Ala
            450                 455                 460

Ser Ala Leu Leu Gly Ser Leu
465                 470                 475                 480

485

<210> SEQ ID NO 44
<211> LENGTH: 487
<212> TYPE: PRT
<213> ORGANISM: Prunus persica
<300> PUBLICATION INFORMATION:
<308> DATABASE ACCESSION NUMBER: 8G214500.1

<400> SEQUENCE: 44

Met Glu Ser Gly Leu Lys Pro Met Asp Ala Glu Gln Leu Arg Glu Asn
1               5                   10                  15

Ala His Lys Met Val Asp Phe Ile Ala Asp Tyr Tyr Lys Thr Ile Glu
            20                  25                  30

Asn Phe Pro Val Leu Ser Gln Val Gln Pro Gly Tyr Leu Arg Glu Leu
        35                  40                  45

Leu Pro Asp Ser Ala Pro Thr His Pro Glu Pro Leu Gln His Ile Phe
    50                  55                  60

Asp Asp Ile Gln Ala Lys Ile Leu Pro Gly Val Thr His Trp Gln Ser
65                  70                  75                  80

Pro Asn Phe Phe Gly Tyr Tyr Pro Ser Asn Ser Ser Ile Ala Gly Phe
                85                  90                  95

Leu Gly Glu Met Met Ser Ala Gly Leu Asn Ile Val Gly Phe Ser Trp
            100                 105                 110

Ile Thr Ser Pro Ala Ala Thr Glu Leu Glu Met Ile Val Leu Asp Trp
        115                 120                 125

Phe Gly Lys Met Leu Lys Leu Pro Glu Glu Phe Leu Ser Ala Gly Lys
    130                 135                 140

Gly Gly Gly Val Ile Gln Gly Thr Ala Ser Glu Ala Val Leu Val Val
145                 150                 155                 160

Leu Leu Ala Ala Arg Asp Lys Ile Leu Arg Arg Val Gly Lys Asn Ser
                165                 170                 175

Leu Glu Lys Leu Val Val Tyr Ala Ser Asp Gln Thr His Ser Ala Leu
            180                 185                 190

Gln Lys Ala Cys Gln Ile Gly Gly Ile His Pro Glu Asn Cys Arg Leu
        195                 200                 205

Leu Arg Thr Asp Ser Ser Thr Asn Tyr Ala Leu Ser Pro Asn Val Leu

```
            210                 215                 220
Asn Glu Ala Ile Ser Asn Asp Val Thr Ser Gly Leu Ile Pro Phe Phe
225                 230                 235                 240

Leu Cys Ala Thr Val Gly Thr Thr Ser Ser Thr Ala Val Asp Pro Leu
                    245                 250                 255

Leu Glu Leu Gly Lys Ile Ala Lys Ser Asn Asp Met Trp Phe His Val
                260                 265                 270

Asp Ala Ala Tyr Ala Gly Ser Ala Cys Ile Cys Pro Glu Tyr Arg His
                    275                 280                 285

Tyr Ile Asp Gly Val Glu Glu Ala Asp Ser Phe Asn Thr Asn Ala His
                290                 295                 300

Lys Trp Phe Leu Thr Asn Phe Asp Cys Ser Val Leu Trp Ile Lys Asp
305                 310                 315                 320

Arg Asn Ala Leu Ile Gln Ala Leu Ser Thr Asn Pro Glu Phe Leu Lys
                    325                 330                 335

Asn Lys Ala Ser Gln Ala Asn Leu Val Val Asp Tyr Lys Asp Trp Gln
                340                 345                 350

Ile Pro Leu Gly Arg Arg Phe Arg Ser Leu Lys Leu Trp Met Val Leu
                355                 360                 365

Arg Leu Tyr Gly Leu Glu Asn Leu Gln Ser Tyr Ile Arg Asn His Ile
370                 375                 380

Asn Leu Ala Lys His Phe Lys Glu Leu Ala Gln Asp Pro Arg Phe
385                 390                 395                 400

Glu Ile Val Thr Pro Arg Leu Phe Ser Leu Val Cys Phe Arg Leu Leu
                    405                 410                 415

Pro Pro His Asn Asp Glu Thr Cys Ala Thr Lys Leu Asn His Gly Leu
                420                 425                 430

Leu Asp Ala Val Asn Ala Thr Gly Lys Ile Phe Ile Ser His Thr Val
                    435                 440                 445

Leu Ser Gly Lys Tyr Leu Leu Arg Leu Ala Val Gly Ala Pro Leu Thr
                450                 455                 460

Glu Glu Arg His Val Asn Ala Ala Trp Lys Leu Leu Gln Asp Glu Ala
465                 470                 475                 480

Ser Ala Leu Leu Ala Thr Leu
                485

<210> SEQ ID NO 45
<211> LENGTH: 490
<212> TYPE: PRT
<213> ORGANISM: Eucalyptus grandis
<300> PUBLICATION INFORMATION:
<308> DATABASE ACCESSION NUMBER: K01418.1

<400> SEQUENCE: 45

Met Glu Glu Arg Leu Lys Pro Met Asp Ala Glu Gln Leu Arg Glu Ser
1               5                   10                  15

Ala His Arg Met Val Asp Phe Ile Ala Asp Tyr Tyr Lys Ser Ile Glu
                20                  25                  30

Ser Phe Pro Val Leu Ser Gln Val Glu Pro Gly Tyr Leu Arg Lys Leu
            35                  40                  45

Leu Pro Asp Ser Ala Pro Asp His Pro Glu Ser Leu Gln Gln Val Leu
        50                  55                  60

Glu Asp Val Gln Ala Lys Ile Leu Pro Gly Val Thr His Trp Gln Ser
65                  70                  75                  80

Pro Asn Tyr Phe Ala Tyr Tyr Pro Ser Asn Ser Ser Ile Ala Gly Phe
```

```
                    85                  90                  95
Met Gly Glu Met Leu Ser Ala Gly Leu Asn Ile Val Gly Phe Ser Trp
                100                 105                 110

Ile Thr Ser Pro Ala Ala Thr Glu Leu Glu Ile Ile Val Leu Asp Trp
                115                 120                 125

Leu Ala Lys Leu Leu Asn Leu Pro Asp Asp Phe Leu Ser Thr Gly Pro
            130                 135                 140

Gly Gly Gly Val Ile Gln Gly Thr Ala Ser Glu Ala Val Leu Val Val
145                 150                 155                 160

Leu Leu Ala Ala Arg Asp Lys Phe Leu Ser Arg Ile Gly Lys Ser Ser
                165                 170                 175

Leu Asp Lys Leu Val Val Tyr Ser Ser Asp Gln Thr His Ser Ala Leu
                180                 185                 190

Gln Lys Ala Cys Gln Ile Gly Gly Ile Tyr Pro Glu Asn Cys Arg Val
            195                 200                 205

Leu Lys Thr Asp Ala Ser Thr Asn Tyr Ala Leu Ser Pro Asp Leu Leu
        210                 215                 220

Asn Glu Val Ile Ser Gln Asp Ile Ser Thr Gly Leu Val Pro Phe Leu
225                 230                 235                 240

Leu Cys Ala Thr Val Gly Thr Thr Ser Ser Thr Ala Val Asp Pro Leu
                245                 250                 255

Pro Ala Leu Ala Thr Val Ala Lys Arg Asn Gly Met Trp Phe His Ile
            260                 265                 270

Asp Ala Ala Tyr Ala Gly Ser Ala Cys Ile Cys Pro Glu Tyr Arg Pro
        275                 280                 285

Tyr Ile Asp Gly Val Glu Glu Ala Asp Ser Phe Asn Met Asn Ala His
    290                 295                 300

Lys Trp Phe Leu Thr Asn Phe Asp Cys Ser Ala Leu Trp Ile Lys Asp
305                 310                 315                 320

Arg Lys Ala Leu Ile Gln Ala Leu Ser Thr Asn Pro Glu Phe Leu Lys
                325                 330                 335

Asn Lys Ala Ser Gln Ala Asn Met Val Val Asp Tyr Arg Asp Trp Gln
            340                 345                 350

Ile Pro Leu Gly Arg Arg Phe Arg Ser Leu Lys Leu Trp Met Val Leu
        355                 360                 365

Arg Leu Tyr Gly Val Gln Asn Leu Gln Gln Tyr Ile Arg Asn His Ile
    370                 375                 380

Glu Leu Ala Arg Gln Phe Glu Asp Leu Val Ile Gln Asp Pro Arg Phe
385                 390                 395                 400

Glu Val Val Thr Pro Arg Ile Phe Ser Leu Val Cys Phe Arg Leu Leu
                405                 410                 415

Ser Pro Asp Asn Asp Gly Asp Lys Gly Asn Lys Leu Asn Arg Asp Leu
            420                 425                 430

Leu Asp Thr Val Asn Ser Thr Gly Lys Ile Phe Ile Ser His Thr Val
        435                 440                 445

Leu Ser Gly Thr Tyr Ile Leu Arg Phe Ala Val Gly Ala Pro Leu Thr
    450                 455                 460

Glu Glu Arg His Val Asn Glu Ala Trp Lys Val Leu Gln Asp Glu Ala
465                 470                 475                 480

Ser Lys Leu Leu Ala Thr Ile Gln Asn Asn
                485                 490

<210> SEQ ID NO 46
```

```
<211> LENGTH: 480
<212> TYPE: PRT
<213> ORGANISM: Amborella trichopoda
<300> PUBLICATION INFORMATION:
<308> DATABASE ACCESSION NUMBER: 31565185

<400> SEQUENCE: 46
```

| | | | | | | | | | | | | | | |
|---|---|---|---|---|---|---|---|---|---|---|---|---|---|---|
|Met|Asp|Ala|Glu|Glu|Leu|Arg|Glu|His|Gly|His|Arg|Met|Val|Asp|Phe
|1| | | |5| | | | |10| | | | |15|
|Ile|Ser|Asp|Tyr|Tyr|Lys|Glu|Ile|Glu|Ser|Tyr|Pro|Val|Arg|Ser|Gln
| | | |20| | | | |25| | | | |30| | |
|Val|Gln|Pro|Gly|Tyr|Leu|Arg|Asn|Leu|Ile|Pro|Asp|Ser|Ala|Pro|Asp
| | | | |35| | | | |40| | | | |45| |
|Met|Pro|Glu|Ser|Phe|Glu|Ser|Ile|Leu|Glu|Asp|Ile|Arg|His|Lys|Ile
| |50| | | | |55| | | | |60| | | | |
|Ile|Pro|Gly|Val|Thr|His|Trp|Gln|Ser|Pro|Lys|Tyr|Phe|Ala|Tyr|Tyr
|65| | | | |70| | | | |75| | | | |80|
|Pro|Ser|Asn|Ser|Ser|Thr|Ala|Gly|Phe|Leu|Gly|Glu|Met|Leu|Ser|Ala
| | | | |85| | | | |90| | | | |95| |
|Gly|Phe|Asn|Ile|Val|Gly|Phe|Ser|Trp|Val|Thr|Ser|Pro|Ala|Ala|Thr
| | | | |100| | | | |105| | | | |110| |
|Glu|Leu|Glu|Val|Ile|Val|Leu|Asp|Trp|Leu|Ala|Lys|Val|Leu|Lys|Leu
| | | |115| | | | |120| | | | |125| | |
|Pro|Glu|Gln|Phe|Leu|Ser|Thr|Gly|Lys|Gly|Gly|Val|Ile|Gln|Gly|
| | |130| | | | |135| | | | |140| | | |
|Thr|Ala|Ser|Glu|Ala|Met|Leu|Val|Ala|Leu|Leu|Ala|Ala|Arg|Asp|Lys
|145| | | | |150| | | | |155| | | | |160|
|Ala|Leu|Arg|Arg|Val|Gly|Gln|Asn|Leu|Leu|Glu|Asn|Leu|Val|Val|Tyr
| | | | |165| | | | |170| | | | |175| |
|Gly|Ser|Asp|Gln|Thr|His|Ser|Ala|Leu|Ile|Lys|Ala|Cys|Lys|Ile|Ala
| | | | |180| | | | |185| | | | |190| |
|Gly|Ile|Asn|Pro|Met|Asn|Cys|Arg|Leu|Leu|Gln|Ala|Thr|Phe|Met|Thr
| | | |195| | | | |200| | | | |205| | |
|Asn|Tyr|Ala|Leu|Ser|Pro|Glu|Val|Ala|Ser|Glu|Ser|Ile|Ser|Asn|Asp
| |210| | | | |215| | | | |220| | | | |
|Ile|Ala|Ala|Gly|Leu|Leu|Pro|Ile|Phe|Leu|Cys|Ala|Thr|Val|Gly|Thr
|225| | | | |230| | | | |235| | | | |240|
|Thr|Ser|Ser|Thr|Ala|Val|Asp|Pro|Leu|Ala|Ala|Leu|Gly|Arg|Leu|Ala
| | | | |245| | | | |250| | | | |255| |
|Lys|Ala|Asn|Asp|Met|Trp|Phe|His|Ile|Asp|Ala|Ala|Tyr|Ala|Gly|Ser
| | | |260| | | | |265| | | | |270| | |
|Ala|Cys|Ile|Cys|Pro|Glu|Tyr|Arg|His|Tyr|Ile|Asp|Gly|Val|Glu|Glu
| | | |275| | | | |280| | | | |285| | |
|Ala|Asp|Ser|Phe|Asn|Met|Pro|His|Lys|Trp|Leu|Leu|Thr|Asn|Phe|
| |290| | | | |295| | | | |300| | | | |
|Asp|Cys|Ser|Thr|Leu|Trp|Val|Lys|Asp|Ser|Ser|Asn|Leu|Ile|Gln|Ser
|305| | | | |310| | | | |315| | | | |320|
|Leu|Ser|Thr|Asn|Pro|Glu|Phe|Leu|Arg|Asn|Lys|Ala|Ser|Glu|Glu|Asp
| | | | |325| | | | |330| | | | |335| |
|Leu|Val|Val|Asp|Tyr|Lys|Asp|Trp|Gln|Ile|Pro|Leu|Gly|Arg|Arg|Phe
| | | |340| | | | |345| | | | |350| | |
|Arg|Ser|Leu|Lys|Leu|Trp|Met|Val|Leu|Arg|Met|Tyr|Gly|Val|Ala|Asn
| | | | |355| | | | |360| | | | |365| |
|Leu|Gln|Asn|His|Ile|Arg|Thr|His|Ile|Asn|Leu|Ala|Lys|His|Phe|Glu
| | |370| | | | |375| | | | |380| | | |

Glu Leu Ile Ala Thr Asp Thr Arg Phe Glu Ile Val Pro Arg Val
385                 390                 395                 400

Phe Ala Leu Val Cys Phe Ala Leu Lys Pro Met Pro Asn Gly Gln Asp
                405                 410                 415

Asp Ala Ser Lys Leu Asn Leu Lys Leu Leu Glu Ala Val Asn Asn Ser
            420                 425                 430

Gly Ala Met Phe Leu Thr His Thr Val Leu Ser Gly Arg Phe Val Leu
        435                 440                 445

Arg Phe Val Gly Ala Pro Leu Thr Glu Glu Arg His Val Asn Thr
    450                 455                 460

Ala Trp Lys Val Leu Gln Asp His Ala Asn Leu Ile Leu Gly Thr Val
465                 470                 475                 480

<210> SEQ ID NO 47
<211> LENGTH: 488
<212> TYPE: PRT
<213> ORGANISM: Salix purpurea
<300> PUBLICATION INFORMATION:
<308> DATABASE ACCESSION NUMBER: 0252s0200.1

<400> SEQUENCE: 47

Met Glu Ser Lys Gly Leu Lys Pro Met Asp Ser Glu Gln Leu Arg Glu
1               5                   10                  15

Asn Ala His Lys Met Val Asp Phe Ile Ala Asp Tyr Tyr Lys Ser Ile
            20                  25                  30

Glu Asn Phe Pro Val Leu Ser Gln Val Glu Pro Gly Tyr Leu Arg Glu
        35                  40                  45

Leu Leu Pro Asp Ser Ala Pro Asn Gln Pro Glu Thr Leu Gln Asn Val
50                  55                  60

Leu Asp Asp Val Gln Ala Lys Ile Leu Pro Gly Val Thr His Trp Gln
65                  70                  75                  80

Ser Pro Ser Tyr Phe Ala Tyr Tyr Pro Ser Asn Ser Ser Val Ala Gly
                85                  90                  95

Phe Leu Gly Glu Met Leu Ser Ala Gly Ile Asn Met Val Gly Phe Ser
            100                 105                 110

Trp Ile Thr Ser Pro Ala Ala Thr Glu Leu Glu Met Ile Val Leu Glu
        115                 120                 125

Trp Leu Gly Lys Leu Leu Lys Leu Pro Glu Asp Phe Leu Ser Thr Gly
    130                 135                 140

Gln Gly Gly Gly Val Ile Gln Gly Thr Ala Ser Glu Ser Val Leu Val
145                 150                 155                 160

Val Leu Leu Ala Ala Arg Asp Arg Val Leu Thr Lys Leu Gly Lys Asn
                165                 170                 175

Ala Leu Glu Lys Leu Val Val Tyr Ala Ser Asp Gln Thr His Ser Ala
            180                 185                 190

Leu Gln Lys Ala Cys Lys Ile Gly Gly Ile His Pro Glu Asn Cys Lys
        195                 200                 205

Leu Leu Lys Thr Asp Ser Ser Thr Asn Tyr Ala Leu Ser Pro Asp Leu
    210                 215                 220

Leu Ser Lys Ala Ile Ser Asp Ile Ser Thr Gly Leu Ile Pro Phe
225                 230                 235                 240

Phe Leu Cys Ala Thr Val Gly Thr Thr Ser Ser Thr Ala Val Asp Pro
                245                 250                 255

Leu His Ala Leu Gly Lys Ile Ala Lys Asn Asn Gly Ile Trp Phe His
            260                 265                 270

```
Val Asp Ala Ala Tyr Ala Gly Ser Ala Cys Ile Cys Pro Glu Tyr Arg
        275                 280                 285

Cys Tyr Ile Asp Gly Val Glu Glu Ala Asp Ser Phe Asn Met Asn Ala
        290                 295                 300

His Lys Trp Leu Leu Thr Asn Phe Asp Cys Ser Ala Leu Trp Val Lys
305                 310                 315                 320

Asp Arg Asn Ala Leu Ile Gln Ala Leu Ser Thr Asn Pro Glu Phe Leu
                325                 330                 335

Lys Asn Lys Ala Ser Gln Ala Asn Met Val Val Asp Tyr Lys Asp Trp
            340                 345                 350

Gln Ile Pro Leu Gly Arg Arg Phe Arg Ser Leu Lys Leu Trp Met Val
        355                 360                 365

Leu Arg Leu Tyr Gly Leu Glu Asn Leu Gln Cys Tyr Ile Arg Asn His
    370                 375                 380

Ile Asn Leu Ala Lys Tyr Phe Glu Gly Leu Val Ala Ala Asp Ser Arg
385                 390                 395                 400

Phe Glu Val Val Thr Pro Arg Ile Phe Ser Leu Val Cys Phe Arg Leu
                405                 410                 415

Leu Pro Pro Ser Asn Asn Glu Asp His Gly Asn Asn Leu Asn Arg Asp
            420                 425                 430

Leu Leu Asp Ala Val Asn Ser Ser Gly Lys Ile Phe Ile Ser His Thr
        435                 440                 445

Val Leu Ser Gly Lys Tyr Ile Leu Arg Phe Ala Val Gly Ala Pro Leu
    450                 455                 460

Thr Glu Glu Arg His Val Ile Ala Ala Trp Lys Val Leu Gln Asp Glu
465                 470                 475                 480

Ser Thr Ser Leu Leu Gly Ser Leu
                485

<210> SEQ ID NO 48
<211> LENGTH: 532
<212> TYPE: PRT
<213> ORGANISM: Medicago truncatula
<300> PUBLICATION INFORMATION:
<308> DATABASE ACCESSION NUMBER: 31080941

<400> SEQUENCE: 48

Met Val Leu Gln Ile Trp Cys Leu Thr His Asp Ser Asp Lys Lys Leu
1               5                   10                  15

Gly Gly Gly Tyr Leu Leu Phe Pro Val Ile Lys Val Ala Tyr Thr Val
            20                  25                  30

His Thr Leu Thr Glu Trp Cys Cys Val Thr Glu Glu Gly Gly Gly Ser
        35                  40                  45

Glu Leu Lys Ala Met Asp Ala Glu Gln Leu Arg Glu Gln Gly His Met
    50                  55                  60

Met Val Asp Phe Ile Ala Asp Tyr Tyr Lys Thr Ile Glu Asn Phe Pro
65                  70                  75                  80

Val Leu Ser Gln Val Gln Pro Gly Tyr Leu Gly Lys Leu Leu Pro Asp
                85                  90                  95

Ser Ala Pro Thr His Pro Glu Ser Leu Gln His Val Leu Asn Asp Val
            100                 105                 110

Gln Glu Lys Ile Leu Pro Gly Val Thr His Trp Gln Ser Pro Asn Tyr
        115                 120                 125

Phe Ala Tyr Phe Pro Ser Asn Ser Ser Ile Ala Gly Phe Leu Gly Glu
    130                 135                 140
```

Met Leu Ser Ala Gly Leu Ser Ile Val Gly Phe Ser Trp Ile Ser Ser
145                 150                 155                 160

Pro Ala Ala Thr Glu Leu Glu Thr Ile Val Leu Asp Trp Leu Ala Lys
                165                 170                 175

Ala Leu Leu Leu Pro His Asp Phe Phe Ser Thr Gly Gln Gly Gly Gly
            180                 185                 190

Val Ile Gln Gly Thr Ala Ser Glu Ala Val Leu Val Val Leu Val Ala
            195                 200                 205

Ala Arg Asp Lys Ile Leu Arg Thr Val Gly Arg Ser Ala Leu Pro Lys
210                 215                 220

Leu Val Thr Tyr Ala Ser Asp Gln Thr His Ser Ser Leu Gln Lys Ala
225                 230                 235                 240

Cys Gln Ile Ala Gly Leu Asn Pro Glu Leu Cys Arg Leu Leu Lys Thr
                245                 250                 255

Asp Ser Ser Thr Asn Phe Ala Leu Ser Pro Asp Val Leu Ser Glu Ala
            260                 265                 270

Ile Ser Asn Asp Ile Ala Ser Gly Leu Thr Pro Phe Phe Leu Cys Ala
            275                 280                 285

Thr Val Gly Thr Thr Ser Ser Thr Ala Val Asp Pro Leu Pro Ala Leu
            290                 295                 300

Ala Lys Val Thr Lys Pro Asn Asn Ile Trp Leu His Val Asp Ala Ala
305                 310                 315                 320

Tyr Ala Gly Ser Ala Cys Ile Cys Pro Glu Tyr Arg His Phe Ile Asp
                325                 330                 335

Gly Val Glu Glu Ala Asp Ser Phe Asn Met Asn Ala His Lys Trp Phe
            340                 345                 350

Leu Thr Asn Phe Asp Cys Ser Val Leu Trp Val Lys Asp Arg Ser Ala
            355                 360                 365

Leu Ile Gln Ser Leu Ser Thr Asn Pro Glu Phe Leu Lys Asn Lys Ala
370                 375                 380

Ser Gln Glu Asn Thr Val Ile Asp Tyr Lys Asp Trp Gln Ile Pro Leu
385                 390                 395                 400

Gly Arg Arg Phe Arg Ser Leu Lys Leu Trp Met Val Met Arg Leu Tyr
                405                 410                 415

Gly Leu Glu Gly Leu Arg Thr His Ile Arg Ser His Ile Ala Leu Ala
            420                 425                 430

Val Tyr Phe Glu Glu Leu Val Val Gln Asp Thr Arg Phe Lys Val Val
            435                 440                 445

Ala Pro Arg Thr Phe Ser Leu Val Cys Phe Arg Leu Leu Pro Pro Gln
    450                 455                 460

Asn Ser Glu Asp Asn Gly Asn Lys Leu Asn His Asp Leu Leu Asp Ala
465                 470                 475                 480

Val Asn Ser Thr Gly Asp Val Phe Ile Thr His Thr Val Leu Ser Gly
                485                 490                 495

Glu Tyr Ile Leu Arg Leu Ala Val Gly Ala Pro Leu Thr Glu Val Arg
            500                 505                 510

His Val His Ala Ala Trp Gln Ile Leu Gln Glu Lys Ala Thr Ala Leu
            515                 520                 525

Leu Glu Ser Leu
        530

<210> SEQ ID NO 49
<211> LENGTH: 501

```
<212> TYPE: PRT
<213> ORGANISM: Brassica rapa
<300> PUBLICATION INFORMATION:
<308> DATABASE ACCESSION NUMBER: I01156.1

<400> SEQUENCE: 49
```

| | | | | | | | | | | | | | | |
|---|---|---|---|---|---|---|---|---|---|---|---|---|---|---|
| Met | Gln | Ile | Arg | Ala | Lys | Ile | Pro | Val | Phe | Gly | Arg | Glu | Asn | Gly | Ser |
| 1 | | | | 5 | | | | | 10 | | | | | 15 | |
| Arg | His | Val | Leu | Lys | Pro | Met | Asp | Ser | Glu | Gln | Leu | Arg | Glu | Tyr | Gly |
| | | | 20 | | | | | 25 | | | | | 30 | | |
| His | Arg | Met | Val | Asp | Phe | Ile | Ala | Asp | Tyr | Tyr | Lys | Thr | Ile | Glu | Ser |
| | | 35 | | | | | 40 | | | | | 45 | | | |
| Phe | Pro | Val | Leu | Ser | Gln | Val | Gln | Pro | Gly | Tyr | Leu | His | Asn | Leu | Leu |
| | 50 | | | | | 55 | | | | | 60 | | | | |
| Pro | Asp | Ser | Ala | Pro | Asp | His | Pro | Glu | Thr | Val | Glu | Gln | Val | Leu | Asp |
| 65 | | | | | 70 | | | | | 75 | | | | | 80 |
| Asp | Val | Lys | Thr | Lys | Ile | Leu | Pro | Gly | Val | Thr | His | Trp | Gln | Ser | Pro |
| | | | | 85 | | | | | 90 | | | | | 95 | |
| Asn | Phe | Phe | Ala | Tyr | Tyr | Pro | Ser | Asn | Ser | Ser | Val | Ala | Gly | Phe | Leu |
| | | | | 100 | | | | | 105 | | | | | 110 | |
| Gly | Glu | Met | Leu | Ser | Ala | Gly | Val | Gly | Ile | Val | Gly | Phe | Ser | Trp | Val |
| | | | 115 | | | | | 120 | | | | | 125 | | |
| Thr | Ser | Pro | Ala | Ala | Thr | Glu | Leu | Glu | Met | Ile | Val | Leu | Asp | Trp | Leu |
| | 130 | | | | | 135 | | | | | 140 | | | | |
| Ala | Lys | Leu | Leu | Asn | Leu | Pro | Glu | His | Phe | Leu | Ser | Lys | Gly | Asn | Gly |
| 145 | | | | | 150 | | | | | 155 | | | | | 160 |
| Gly | Gly | Val | Ile | Gln | Gly | Ser | Ala | Ser | Glu | Ala | Ile | Leu | Val | Val | Met |
| | | | | 165 | | | | | 170 | | | | | 175 | |
| Ile | Ala | Ala | Arg | Asp | Lys | Val | Leu | Arg | Ser | Ala | Gly | Lys | Asn | Ala | Leu |
| | | | 180 | | | | | 185 | | | | | 190 | | |
| Gly | Lys | Leu | Val | Val | Tyr | Ser | Ser | Asp | Gln | Thr | His | Ser | Ala | Leu | Gln |
| | | | 195 | | | | | 200 | | | | | 205 | | |
| Lys | Ala | Cys | Gln | Ile | Ala | Gly | Ile | His | Pro | Glu | Asn | Cys | Arg | Val | Leu |
| 210 | | | | | 215 | | | | | 220 | | | | | |
| Lys | Ala | Asp | Ser | Ser | Thr | Asn | Tyr | Ala | Leu | Arg | Pro | Glu | Leu | Leu | Gln |
| 225 | | | | | 230 | | | | | 235 | | | | | 240 |
| Glu | Ala | Val | Ser | Arg | Asp | Leu | Glu | Ala | Gly | Leu | Ile | Pro | Phe | Phe | Leu |
| | | | | 245 | | | | | 250 | | | | | 255 | |
| Cys | Gly | Asn | Val | Gly | Thr | Thr | Ser | Ser | Ala | Ala | Val | Asp | Pro | Leu | Ala |
| | | | | 260 | | | | | 265 | | | | | 270 | |
| Ala | Leu | Gly | Lys | Ile | Ala | Lys | Ser | Asn | Glu | Ile | Trp | Phe | His | Val | Asp |
| | | | 275 | | | | | 280 | | | | | 285 | | |
| Ala | Ala | Tyr | Ala | Gly | Ser | Ala | Cys | Ile | Cys | Pro | Glu | Tyr | Arg | Gln | Tyr |
| | | 290 | | | | | 295 | | | | | 300 | | | |
| Ile | Asp | Gly | Val | Glu | Thr | Ala | Asp | Ser | Phe | Asn | Met | Asn | Ala | His | Lys |
| 305 | | | | | 310 | | | | | 315 | | | | | 320 |
| Trp | Phe | Leu | Thr | Asn | Phe | Asp | Cys | Ser | Leu | Leu | Trp | Val | Lys | Asp | Gln |
| | | | | 325 | | | | | 330 | | | | | 335 | |
| His | Ala | Leu | Thr | Glu | Ala | Leu | Ser | Thr | Asn | Pro | Glu | Phe | Leu | Lys | Asn |
| | | | 340 | | | | | 345 | | | | | 350 | | |
| Lys | Ala | Ser | Gln | Ala | Asn | Leu | Val | Val | Asp | Tyr | Lys | Asp | Trp | Gln | Ile |
| | | | 355 | | | | | 360 | | | | | 365 | | |
| Pro | Leu | Gly | Arg | Arg | Phe | Arg | Ser | Leu | Lys | Leu | Trp | Met | Val | Leu | Arg |
| | 370 | | | | | 375 | | | | | 380 | | | | |

```
Leu Tyr Gly Ala Glu Ala Leu Lys Asn Tyr Ile Arg Asn His Ile Lys
385                 390                 395                 400

Leu Ala Lys Asp Leu Glu Gln Leu Val Ser Gln Asp Pro Asn Phe Glu
                405                 410                 415

Val Ile Thr Pro Arg Ile Phe Ser Leu Val Cys Phe Arg Ile Val Pro
            420                 425                 430

Thr Asp Asn Asp Glu Lys Lys Cys Asn Ser Arg Asn Leu Glu Leu Leu
        435                 440                 445

Glu Ala Val Asn Ser Ser Gly Lys Leu Phe Ile Ser His Thr Ala Leu
    450                 455                 460

Ser Gly Lys Ile Val Leu Arg Cys Ala Ile Gly Ala Pro Leu Thr Glu
465                 470                 475                 480

Glu Lys His Val Lys Glu Thr Trp Lys Val Ile Gln Glu Lys Val Ser
                485                 490                 495

Tyr Leu Leu Arg Lys
            500

<210> SEQ ID NO 50
<211> LENGTH: 479
<212> TYPE: PRT
<213> ORGANISM: Brassica rapa
<300> PUBLICATION INFORMATION:
<308> DATABASE ACCESSION NUMBER: I04706.1

<400> SEQUENCE: 50

Met Asp Ser Glu Gln Leu Arg Glu Tyr Gly His Arg Met Val Asp Phe
1               5                   10                  15

Ile Ala Asp Tyr Tyr Lys Thr Ile Glu Thr Phe Pro Val Leu Ser Gln
                20                  25                  30

Val Gln Pro Gly Tyr Leu His Asn Leu Leu Pro Asp Ser Ala Pro Asp
            35                  40                  45

Gln Pro Glu Thr Val Glu Gln Val Leu Asp Asp Val Lys Thr Lys Ile
        50                  55                  60

Leu Pro Gly Ile Thr His Trp Gln Ser Pro Thr Phe Tyr Ala Tyr Tyr
65                  70                  75                  80

Pro Ser Asn Ser Ser Val Ala Gly Phe Leu Gly Glu Met Leu Ser Ala
                85                  90                  95

Gly Leu Gly Ile Val Gly Phe Ser Trp Val Thr Ser Pro Ala Ala Thr
                100                 105                 110

Glu Leu Glu Met Ile Val Leu Asp Trp Leu Ala Lys Leu Leu Asn Leu
            115                 120                 125

Pro Glu Gln Phe Leu Ser Lys Gly Asn Gly Gly Val Ile Gln Gly
        130                 135                 140

Ser Ala Ser Glu Ala Ile Leu Val Val Met Ile Gly Ala Arg Glu Lys
145                 150                 155                 160

Val Leu Arg Arg Val Gly Lys Asn Ala Leu Gly Lys Leu Val Val Tyr
                165                 170                 175

Ser Ser Asp Gln Thr His Ser Ala Leu Gln Lys Ala Cys Gln Ile Ala
            180                 185                 190

Gly Ile His Pro Glu Asn Cys Arg Val Leu Lys Ala Asp Ser Ser Thr
        195                 200                 205

Asn Tyr Ala Leu Arg Pro Glu Leu Leu Gln Glu Ala Val Ser Lys Asp
    210                 215                 220

Ile Glu Ala Gly Leu Ile Pro Phe Phe Leu Cys Gly Asn Val Gly Thr
225                 230                 235                 240
```

```
Thr Ser Ser Thr Ala Val Asp Pro Leu Ala Ala Leu Gly Lys Ile Ala
            245                 250                 255

Lys Ser Asn Glu Ile Trp Phe His Val Asp Ala Ala Tyr Ala Gly Ser
        260                 265                 270

Ala Cys Ile Cys Pro Glu Tyr Arg Gln Tyr Ile Asp Gly Val Glu Thr
        275                 280                 285

Ala Asp Ser Phe Asn Met Asn Ala His Lys Trp Phe Leu Thr Asn Phe
        290                 295                 300

Asp Cys Ser Leu Leu Trp Val Lys Asp Gln Tyr Val Leu Thr Glu Ala
305                 310                 315                 320

Leu Ser Thr Asn Pro Glu Phe Leu Lys Asn Lys Ala Ser Gln Ala Asn
            325                 330                 335

Leu Val Val Asp Tyr Lys Asp Trp Gln Ile Pro Leu Gly Arg Arg Phe
            340                 345                 350

Arg Ser Leu Lys Leu Trp Met Val Leu Arg Leu Tyr Gly Ala Glu Thr
        355                 360                 365

Leu Lys Ser Tyr Ile Arg Asn His Ile Lys Leu Ala Lys Asp Leu Glu
        370                 375                 380

Gln Leu Val Ser Gln Asp Pro Asn Phe Glu Val Val Thr Pro Arg Ile
385                 390                 395                 400

Phe Ser Leu Val Cys Phe Arg Ile Leu Pro Val Asp Asn Asp Glu Lys
            405                 410                 415

Glu Cys Asn Asn Arg Asn Arg Asn Leu Leu Asp Ala Val Asn Ser Ser
            420                 425                 430

Gly Lys Leu Phe Leu Ser His Thr Ala Leu Ser Gly Lys Ile Val Leu
            435                 440                 445

Arg Cys Ala Ile Gly Ala Pro Leu Thr Glu Glu Arg His Val Lys Glu
450                 455                 460

Thr Trp Lys Val Ile Gln Glu Glu Ala Ser Arg Leu Leu Gly Lys
465                 470                 475

<210> SEQ ID NO 51
<211> LENGTH: 482
<212> TYPE: PRT
<213> ORGANISM: Brassica rapa
<300> PUBLICATION INFORMATION:
<308> DATABASE ACCESSION NUMBER: G00043.1

<400> SEQUENCE: 51

Met Asp Ser Glu Gln Leu Arg Glu Tyr Gly His Arg Met Val Asp Phe
1               5                   10                  15

Ile Ala Asp Tyr Tyr Lys Thr Ile Glu Thr Phe Pro Val Leu Ser Gln
            20                  25                  30

Val Gln Pro Gly Tyr Leu His Asn Leu Leu Pro Asp Ser Ala Pro Asp
        35                  40                  45

Gln Pro Glu Thr Leu Glu Gln Val Leu Asp Asp Val Lys Glu Lys Ile
    50                  55                  60

Leu Pro Gly Val Thr His Trp Gln Ser Pro Phe Phe Ala Tyr Tyr
65                  70                  75                  80

Pro Ala Asn Ser Ser Val Ala Gly Phe Leu Gly Glu Met Leu Ser Ala
                85                  90                  95

Ala Leu Asn Ile Val Gly Phe Ser Trp Val Ser Ser Pro Ala Ala Thr
            100                 105                 110

Glu Leu Glu Met Ile Val Leu Asp Trp Phe Ala Lys Leu Leu Asn Leu
        115                 120                 125
```

-continued

```
Pro Glu Gln Phe Leu Ser Arg Gly Asn Gly Gly Val Ile Gln Gly
        130                 135                 140

Thr Ala Ser Glu Ala Ile Leu Val Val Met Ile Ala Ala Arg Asp Lys
145                 150                 155                 160

Val Leu Arg Ser Leu Gly Lys Lys Ala Leu Glu Lys Leu Val Val Tyr
                165                 170                 175

Ser Ser Asp Gln Thr His Ser Ser Leu Leu Lys Ala Cys Gln Ile Ala
            180                 185                 190

Gly Ile His Leu Glu Asn Cys Arg Met Leu Lys Thr Asp Ser Ser Thr
        195                 200                 205

Asn Tyr Ala Leu Arg Pro Glu Ser Leu Gln Glu Ala Val Ser Gly Asp
210                 215                 220

Leu Glu Ala Gly Leu Ile Pro Phe Phe Leu Cys Gly Thr Val Gly Thr
225                 230                 235                 240

Thr Ser Ser Thr Ala Val Asp Pro Leu Ala Glu Leu Gly Lys Ile Ala
                245                 250                 255

Lys Ser Asn Glu Met Trp Phe His Val Asp Ala Ala Tyr Ala Gly Ser
            260                 265                 270

Ala Cys Ile Cys Pro Glu Tyr Arg Gln Tyr Ile Asp Gly Val Glu Thr
        275                 280                 285

Ala Asp Ser Phe Asn Met Asn Ala His Lys Trp Phe Leu Thr Asn Phe
290                 295                 300

Asp Cys Ser Leu Leu Trp Val Lys Asp Arg Tyr Ala Leu Thr Glu Ala
305                 310                 315                 320

Leu Ser Thr Asn Pro Glu Phe Leu Lys Asn Lys Ala Ser Gln Ala Asn
                325                 330                 335

Leu Val Val Asp Tyr Lys Asp Trp Gln Ile Pro Leu Gly Arg Arg Phe
            340                 345                 350

Arg Ser Leu Lys Leu Trp Met Val Leu Arg Leu Tyr Gly Ala Glu Thr
        355                 360                 365

Leu Lys Ser Tyr Ile Lys Asn His Ile Lys Leu Ala Lys Asp Leu Glu
370                 375                 380

Gln Leu Val Ser Gln Asp Pro Asn Phe Glu Val Val Thr Pro Arg Ile
385                 390                 395                 400

Phe Ser Leu Val Cys Phe Arg Ile Val Pro Val Asp Asn Asp Glu Lys
                405                 410                 415

Thr Cys Asn Asn Leu Asn Arg Ser Leu Leu Asp Ala Val Asn Ser Ser
            420                 425                 430

Gly Lys Leu Phe Ile Ser His Thr Thr Leu Ser Gly Lys Phe Val Leu
        435                 440                 445

Arg Leu Ala Ile Gly Ala Pro Leu Thr Glu Glu Lys His Val Met Asp
450                 455                 460

Ala Trp Lys Val Ile Gln Glu Ala Ser Phe Leu Leu Ala Ser Gln
465                 470                 475                 480

Val Lys
```

<210> SEQ ID NO 52
<211> LENGTH: 489
<212> TYPE: PRT
<213> ORGANISM: Glycine max
<300> PUBLICATION INFORMATION:
<308> DATABASE ACCESSION NUMBER: 03G167900.1

<400> SEQUENCE: 52

Met Glu Glu Glu Ser Ala Leu Arg Pro Met Asp Ala Glu Gln Leu Arg

-continued

```
1               5                   10                  15
Glu Gln Ala His Lys Met Val Asp Phe Ile Ala Asp Tyr Tyr Lys Thr
            20                  25                  30

Ile Glu Asp Phe Pro Val Leu Ser Gln Val Gln Pro Gly Tyr Leu Gly
            35                  40                  45

Lys Leu Leu Pro Asp Ser Ala Pro Asp Ser Pro Glu Ser Leu Gln Asn
            50                  55                  60

Val Leu Asp Asp Val Gln Glu Lys Ile Leu Pro Gly Val Thr His Trp
65                  70                  75                  80

Gln Ser Pro Asn Tyr Phe Ala Tyr Phe Pro Ser Asn Ser Ser Ile Ala
                85                  90                  95

Gly Phe Leu Gly Glu Met Leu Ser Ala Gly Leu Asn Ile Val Gly Phe
                100                 105                 110

Ser Trp Ile Thr Ser Pro Ala Ala Thr Glu Leu Glu Thr Ile Val Leu
                115                 120                 125

Asp Trp Leu Ala Lys Ala Phe Gln Leu Pro Asp Tyr Phe Tyr Ser Ser
            130                 135                 140

Gly Lys Gly Gly Gly Val Ile Gln Gly Thr Ala Ser Glu Ala Val Leu
145                 150                 155                 160

Val Val Leu Leu Ala Ala Arg Asp Lys Ile Leu Arg Arg Val Gly Arg
                165                 170                 175

Asn Ala Leu Pro Lys Leu Val Met Tyr Ala Ser Asp Gln Thr His Ser
                180                 185                 190

Ala Leu Leu Lys Ala Cys Gln Ile Ala Gly Ile Asn Pro Glu Leu Cys
            195                 200                 205

Arg Leu Leu Lys Thr Asp Ser Ser Thr Asn Tyr Ala Leu Ser Pro Asp
            210                 215                 220

Val Leu Ser Glu Ala Ile Ser Asn Asp Ile Ala Gly Gly Leu Val Pro
225                 230                 235                 240

Phe Phe Leu Cys Ala Thr Val Gly Thr Thr Ser Ser Thr Ala Val Asp
                245                 250                 255

Pro Leu Pro Ala Leu Gly Lys Ile Ala Lys Thr Asn Lys Leu Trp Phe
                260                 265                 270

His Val Asp Ala Ala Tyr Ala Gly Ser Ala Cys Val Cys Pro Glu Tyr
            275                 280                 285

Arg His Cys Ile Asp Gly Val Glu Glu Ala Asp Ser Phe Asn Met Asn
            290                 295                 300

Ala His Lys Trp Phe Leu Thr Asn Phe Asp Cys Ser Leu Leu Trp Val
305                 310                 315                 320

Lys Asp Arg Ser Ser Leu Ile Gln Ser Leu Ser Thr Asn Pro Glu Phe
                325                 330                 335

Leu Lys Asn Lys Ala Ser Gln Gly Asn Met Val Ile Asp Tyr Lys Asp
                340                 345                 350

Trp Gln Ile Pro Leu Gly Arg Arg Phe Arg Ser Leu Lys Leu Trp Met
            355                 360                 365

Val Leu Arg Leu Tyr Gly Leu Asp Gly Leu Arg Ser His Ile Arg Asn
            370                 375                 380

His Ile Glu Leu Ala Ala Asn Phe Glu Glu Leu Val Arg Gln Asp Thr
385                 390                 395                 400

Arg Phe Lys Val Val Ala Pro Arg Thr Phe Ser Leu Val Cys Phe Arg
                405                 410                 415

Leu Leu Pro His Pro Asn Ser Ala Asp His Gly Asn Lys Leu Asn Ser
                420                 425                 430
```

-continued

```
Asp Leu Leu Asp Ser Val Asn Ser Thr Gly Asn Ala Phe Ile Thr His
        435                 440                 445

Thr Val Leu Ser Gly Glu Tyr Ile Leu Arg Phe Ala Val Gly Ala Pro
    450                 455                 460

Leu Thr Glu Arg Arg His Val Asn Met Ala Trp Gln Ile Leu Gln Asp
465                 470                 475                 480

Lys Ala Thr Ala Leu Leu Glu Ser Leu
                485

<210> SEQ ID NO 53
<211> LENGTH: 520
<212> TYPE: PRT
<213> ORGANISM: Fragaria vesca
<300> PUBLICATION INFORMATION:
<308> DATABASE ACCESSION NUMBER: 27261550

<400> SEQUENCE: 53

Met Asp Ala Glu Gln Leu Arg Glu Asn Ala His Lys Met Val Asp Phe
1               5                   10                  15

Ile Ala Asp Tyr Tyr Lys Thr Ile Glu Asp Phe Pro Val Leu Ser Gln
            20                  25                  30

Val Gln Pro Gly Tyr Leu Arg Glu Leu Leu Pro Asp Ser Ala Pro Thr
        35                  40                  45

Gln Pro Glu Ser Leu Gln His Ile Phe Asp Ile Gln Ala Lys Ile
    50                  55                  60

Leu Pro Gly Val Thr His Trp Gln Ser Pro Asn Phe Phe Ala Tyr Tyr
65                  70                  75                  80

Pro Ser Asn Ser Ser Ile Ala Gly Phe Leu Gly Glu Met Leu Ser Ala
                85                  90                  95

Gly Leu Asn Ile Val Gly Phe Ser Trp Val Thr Ser Pro Ala Ala Thr
            100                 105                 110

Glu Leu Glu Met Ile Val Leu Asp Trp Leu Ala Lys Leu Ile Lys Leu
        115                 120                 125

Pro Asp Glu Phe Leu Ser Ala Gly Gln Gly Gly Gly Val Ile Gln Gly
    130                 135                 140

Thr Ala Ser Glu Ala Ile Leu Val Val Met Leu Ala Ala Arg Asp Lys
145                 150                 155                 160

Ile Leu Arg Arg Val Gly Lys Asn Ala Leu Glu Lys Leu Val Val Tyr
                165                 170                 175

Ala Ser Asp Gln Thr His Ser Ala Leu Gln Lys Ala Cys Gln Ile Ala
            180                 185                 190

Gly Ile His Pro Glu Asn Cys Arg Ile Leu Ser Thr Asn Ser Thr Thr
        195                 200                 205

Asn Tyr Ala Leu Ser Pro Ser Val Gly Thr Thr Ser Ser Thr Ala Val
    210                 215                 220

Asp Pro Leu Gly Glu Leu Gly Lys Ile Ala Lys Asn Asn Glu Met Trp
225                 230                 235                 240

Phe His Val Asp Ala Ala Tyr Ala Gly Ser Ala Cys Ile Cys Pro Glu
                245                 250                 255

Tyr Arg His Tyr Ile Asp Gly Val Glu Lys Ala Asp Ser Phe Asn Met
            260                 265                 270

Asn Ala His Lys Trp Phe Leu Thr Asn Phe Asp Cys Ser Val Leu Trp
        275                 280                 285

Ile Lys Asp Arg Asn Ala Leu Val Gln Ser Leu Ser Thr Asn Pro Glu
    290                 295                 300
```

```
Phe Leu Lys Asn Lys Ala Ser Gln Ala Asn Met Val Asp Tyr Lys
305                 310                 315                 320

Asp Trp Gln Val Pro Leu Gly Arg Arg Phe Arg Ser Leu Lys Leu Trp
            325                 330                 335

Met Val Leu Arg Leu Tyr Gly Leu Glu Asn Leu Gln Ser Tyr Ile Arg
            340                 345                 350

Thr His Ile Asn Leu Ala Lys His Phe Glu Glu Leu Val Ala Gln Asp
                355                 360                 365

Pro Arg Phe Glu Ile Val Thr Pro Arg Leu Tyr Ser Leu Val Cys Phe
    370                 375                 380

Arg Leu Leu Pro Pro His Gly Asn Glu Ala Cys Ala Ser Lys Leu Asn
385                 390                 395                 400

His Asp Leu Leu Asp Ala Val Asn Ser Thr Gly Lys Ile Tyr Ile Ser
                405                 410                 415

His Thr Val Leu Ser Gly Ala Tyr Ile Leu Arg Phe Ala Val Gly Ala
            420                 425                 430

Pro Leu Thr Glu Glu Lys His Val Thr Ala Ala Trp Lys Lys Leu Lys
            435                 440                 445

Ser Val Ile Arg Asp Val Leu Ala Leu Ala Asn Ser Phe Val Ser Ile
450                 455                 460

Thr Phe Ser His Met Tyr Arg Glu Ala Asn Phe Leu Thr Asp Ala Leu
465                 470                 475                 480

Ala Ser Val Gly His Ser Leu Ser Ser Ser Met Cys Trp Phe Asp Gly
                485                 490                 495

Ile Pro Pro Gln Ala Gln Met Ala Leu Leu Met Asp Ser Ser Cys Ile
            500                 505                 510

Gly His Leu Arg Gly Ser Ser Leu
            515                 520

<210> SEQ ID NO 54
<211> LENGTH: 487
<212> TYPE: PRT
<213> ORGANISM: Kalanchoe fedtschenkoi
<300> PUBLICATION INFORMATION:
<308> DATABASE ACCESSION NUMBER: 0172s0035.1

<400> SEQUENCE: 54

Met Glu Gly Glu Leu Lys Pro Met Asp Ala Glu Gln Leu Arg Glu Tyr
1               5                   10                  15

Gly His Arg Met Val Asp Phe Val Ala Asp Tyr Tyr Lys Thr Ile Glu
            20                  25                  30

Asp His Pro Val Leu Ser Gln Val Glu Pro Gly Tyr Leu Arg Lys Leu
        35                  40                  45

Leu Pro Asp Ser Ala Pro Asp Lys Pro Glu Ser Phe Glu Asn Val Leu
    50                  55                  60

Ser Asp Val Lys Thr Lys Ile Ile Pro Gly Val Thr His Trp Gln Ser
65                  70                  75                  80

Pro Asn Tyr Phe Ala Tyr Phe Pro Ser Asn Ser Ser Thr Ala Gly Phe
                85                  90                  95

Leu Gly Glu Met Leu Ser Ala Cys Phe Asn Ile Val Gly Phe Ser Trp
            100                 105                 110

Ile Thr Ser Pro Ala Ala Thr Glu Leu Glu Met Ile Val Leu Asp Trp
        115                 120                 125

Phe Ala Lys Met Leu Lys Leu Pro Asp Phe Phe Leu Ser Thr Gly Gln
    130                 135                 140
```

-continued

Gly Gly Gly Val Ile Gln Gly Thr Ala Ser Glu Ala Val Leu Val Val
145                 150                 155                 160

Leu Leu Ala Ala Arg Asp Ile Phe Leu Arg Lys Leu Gly Lys Gly Phe
                165                 170                 175

Leu Glu Lys Leu Val Val Tyr Ala Ser Asp Gln Thr His Ser Ala Leu
            180                 185                 190

Gln Lys Ala Cys Gln Ile Ala Gly Ile His Pro Glu Asn Val Lys Ala
        195                 200                 205

Leu Lys Thr Asp Ser Ser Thr Asn Tyr Gly Leu Ser Pro Asp Leu Leu
210                 215                 220

Ser Lys Glu Ile Cys His Asp Ile Ala Asn Gly Leu Val Pro Phe Phe
225                 230                 235                 240

Ala Cys Ala Ser Val Gly Thr Thr Ser Ser Thr Ala Ile Asp Pro Ile
                245                 250                 255

Leu Glu Leu Ala Asn Val Thr Lys Ser Tyr Asn Ile Trp Leu His Val
            260                 265                 270

Asp Ser Ala Tyr Ala Gly Ser Ala Cys Val Cys Pro Glu Tyr Arg His
        275                 280                 285

His Ile Asp Gly Val Glu Glu Val Asp Ser Phe Asn Met Asn Ala His
    290                 295                 300

Lys Trp Phe Leu Thr Asn Phe Asp Cys Ser Leu Leu Trp Val Lys Asp
305                 310                 315                 320

Arg Asn Ala Leu Ile Gln Ser Leu Ser Thr Asn Pro Glu Phe Leu Lys
                325                 330                 335

Asn Lys Ala Ser Gln Ser Lys Ser Val Leu Asp Tyr Lys Asp Trp Gln
            340                 345                 350

Ile Pro Leu Gly Arg Arg Phe Arg Ser Leu Lys Leu Trp Leu Val Leu
        355                 360                 365

Arg Leu Tyr Gly Val Glu Asn Leu Gln Ala Tyr Ile Arg Asn His Ile
370                 375                 380

Glu Leu Ala Ile His Phe Glu Glu Leu Val Ser Gln Asp Met Arg Phe
385                 390                 395                 400

Glu Ile Val Ala Pro Arg Thr Phe Ala Leu Val Cys Phe Arg Leu Leu
                405                 410                 415

Leu Pro Cys Gly Phe Glu Asp Arg Thr Asn Asp Val Asn Gly Asp Leu
            420                 425                 430

Leu Gln Ala Val Asn Ser Thr Gly Lys Ile Phe Ile Ser His Thr Val
        435                 440                 445

Leu Ser Gly Thr Tyr Val Met Arg Phe Ala Val Gly Ala Pro Leu Thr
    450                 455                 460

Glu Glu Arg His Ile Asp Ala Ala Trp Lys Leu Ile Gln Asp Gln Ala
465                 470                 475                 480

Ser Ser Leu Leu Glu Lys Leu
                485

<210> SEQ ID NO 55
<211> LENGTH: 479
<212> TYPE: PRT
<213> ORGANISM: Capsella grandiflora
<300> PUBLICATION INFORMATION:
<308> DATABASE ACCESSION NUMBER: 22666s0001.1

<400> SEQUENCE: 55

Met Asp Ser Glu Gln Leu Arg Glu Tyr Gly His Arg Met Val Asp Phe
1               5                   10                  15

Ile Ala Asp Tyr Tyr Lys Thr Ile Glu Asp Phe Pro Val Leu Ser Gln
            20                  25                  30

Val Gln Pro Gly Tyr Leu His Lys Leu Leu Pro Asp Ser Ala Pro Asp
        35                  40                  45

Gln Pro Glu Thr Leu Asp Gln Val Leu Asp Asp Val Arg Ala Lys Ile
50                  55                  60

Leu Pro Gly Val Thr His Trp Gln Ser Pro Gly Phe Phe Ala Tyr Tyr
65                  70                  75                  80

Pro Ser Asn Ser Ser Val Ala Gly Phe Leu Gly Glu Met Leu Ser Ala
                85                  90                  95

Gly Leu Gly Ile Val Gly Phe Ser Trp Val Thr Ser Pro Ala Ala Thr
            100                 105                 110

Glu Leu Glu Met Ile Val Leu Asp Trp Leu Ala Lys Leu Leu Asn Leu
            115                 120                 125

Pro Lys Glu Phe Leu Ser Lys Gly Asn Gly Gly Val Ile Gln Gly
            130                 135                 140

Ser Ala Ser Glu Ala Val Leu Val Val Leu Ile Ala Ala Arg Asp Lys
145                 150                 155                 160

Val Leu Arg Ser Ala Gly Lys Asn Ala Leu Gly Lys Leu Val Val Tyr
                165                 170                 175

Ser Ser Asp Gln Thr His Ser Ala Leu Gln Lys Ala Cys Gln Ile Ala
            180                 185                 190

Gly Ile His Pro Glu Asn Cys Arg Val Leu Glu Thr Asp Ala Ser Thr
            195                 200                 205

Asn Tyr Ala Leu Arg Pro Glu Leu Leu Gln Glu Ala Val Ser Lys Asp
        210                 215                 220

Leu Lys Ala Gly Leu Ile Pro Phe Phe Leu Cys Ala Asn Val Gly Thr
225                 230                 235                 240

Thr Ser Ser Thr Ala Val Asp Pro Leu Ala Ala Leu Gly Lys Ile Ala
                245                 250                 255

Asn Ser Asn Glu Ile Trp Phe His Val Asp Ala Ala Tyr Ala Gly Ser
            260                 265                 270

Ala Cys Ile Cys Pro Glu Tyr Arg Lys Tyr Ile Asp Gly Val Glu Thr
            275                 280                 285

Ala Asp Ser Phe Asn Met Asn Ala His Lys Trp Phe Leu Thr Asn Phe
        290                 295                 300

Asp Cys Ser Leu Leu Trp Val Lys Glu Gln Asp Ser Leu Thr Glu Ala
305                 310                 315                 320

Leu Ser Thr Asn Pro Glu Phe Leu Lys Asn Lys Ala Ser Gln Ala Asn
                325                 330                 335

Leu Val Val Asp Tyr Lys Asp Trp Gln Ile Pro Leu Gly Arg Arg Phe
            340                 345                 350

Arg Ser Leu Lys Leu Trp Met Val Leu Arg Leu Tyr Gly Ala Glu Thr
            355                 360                 365

Leu Lys Ser Tyr Ile Arg Asn His Ile Lys Leu Ala Lys Tyr Tyr Glu
        370                 375                 380

Lys Leu Val Ser Gln Asp Pro Asn Phe Glu Ile Val Thr Pro Arg Ile
385                 390                 395                 400

Phe Ser Leu Val Cys Phe Arg Leu Val Pro Lys Asn Glu Asp Glu Lys
                405                 410                 415

Lys Cys Asn Asn Gln Asn Arg Lys Leu Leu Glu Ala Ala Asn Ser Ser
            420                 425                 430

```
Gly Lys Leu Phe Met Ser His Thr Ala Leu Ser Gly Lys Ile Val Leu
            435                 440                 445

Arg Cys Ala Ile Gly Ala Pro Leu Thr Glu Lys His Met Lys Glu
450                 455                 460

Ala Trp Lys Val Ile Gln Asp Glu Ala Ser Phe Leu Leu His Lys
465                 470                 475

<210> SEQ ID NO 56
<211> LENGTH: 527
<212> TYPE: PRT
<213> ORGANISM: Selaginella moellendorffii
<300> PUBLICATION INFORMATION:
<308> DATABASE ACCESSION NUMBER: 15420188

<400> SEQUENCE: 56

Met Gly Glu Ala Asn Ile Gly Pro Lys Pro Ile Asp Ala Glu Phe
1               5                   10                  15

Arg Lys His Ala His Glu Met Val Asp Phe Ile Ala Asp Tyr Tyr Arg
            20                  25                  30

Asp Ile Glu Ser Phe Pro Val Arg Ser Gln Val Ser Gln Pro Gly Tyr
            35                  40                  45

Leu Lys Thr Leu Leu Pro Ala Ala Pro Glu Asp Pro Glu Ala Leu
    50                  55                  60

Glu Glu Val Phe Ala Asp Ile Gln Ser Lys Ile Ile Pro Gly Val Thr
65                  70                  75                  80

His Trp Gln Ser Pro Asn Phe Phe Gly Tyr Tyr Pro Ser Asn Ser Ser
                85                  90                  95

Thr Ala Gly Leu Leu Gly Glu Met Leu Ser Ala Gly Leu Asn Ile Val
            100                 105                 110

Gly Phe Ser Trp Ile Thr Ser Pro Ala Ala Thr Glu Leu Glu Ile Ile
        115                 120                 125

Val Leu Asp Trp Leu Ala Lys Leu Leu Lys Leu Pro Asp Glu Phe Leu
130                 135                 140

Phe Gly Gly Asn Gly Gly Gly Val Ile Gln Gly Thr Ala Ser Glu Ala
145                 150                 155                 160

Val Ser Val Val Leu Leu Ala Ala Arg Thr Arg Ala Ile Ser Glu Asn
                165                 170                 175

Lys Arg Lys Gly Leu Ser Glu Ala Glu Ile Leu Ser Lys Leu Ala Val
            180                 185                 190

Tyr Thr Ser Asp Gln Thr His Ser Cys Leu Gln Lys Gly Cys Ala Ile
        195                 200                 205

Ala Gly Ile Pro Leu Glu Asn Leu Val Ile Val Pro Thr Asp Ser Ser
    210                 215                 220

Thr Asn Tyr Ala Val Ser Pro Ala Ala Met Arg Gln Ala Leu Glu Asp
225                 230                 235                 240

Gly Val Lys Gln Gly Leu Leu Pro Phe Phe Leu Cys Gly Thr Val Gly
                245                 250                 255

Thr Thr Ser Ser Ser Ala Val Asp Pro Leu Ser Ala Leu Gly Asp Ile
            260                 265                 270

Ala Lys Asp Phe Gly Met Trp Phe His Val Asp Ala Ala Tyr Ala Gly
        275                 280                 285

Ser Ala Cys Ile Cys Pro Glu Phe Arg His His Leu Asp Gly Val Glu
    290                 295                 300

Lys Ala Asp Ser Phe Asn Met Asn Ala His Lys Trp Leu Leu Thr Asn
305                 310                 315                 320
```

```
Phe Asp Cys Ser Ala Leu Trp Val Lys Glu Ser Ser His Leu Val Ser
                325                 330                 335

Ala Leu Ser Thr Thr Pro Glu Phe Leu Arg Asn Lys Ala Ser Asp Leu
            340                 345                 350

Asn Gln Val Val Asp Tyr Lys Asp Trp Gln Ile Pro Leu Gly Arg Arg
        355                 360                 365

Phe Arg Ser Leu Lys Leu Trp Phe Val Met Arg Met Asn Gly Ala Ser
370                 375                 380

Gly Leu Arg Ser Tyr Ile Arg Asn His Val Arg Leu Ala Lys Arg Phe
385                 390                 395                 400

Glu Gly Phe Val Arg Glu Asp Pro Arg Phe Gln Leu Leu Val Pro Arg
                405                 410                 415

Thr Phe Gly Leu Ile Cys Phe Arg Leu Lys Pro Glu Ser Asp Asp Pro
            420                 425                 430

Asp Asn Gly Arg Thr Leu Asn Ser Thr Leu Leu Glu Ala Val Asn Ser
        435                 440                 445

Ser Gly Arg Met Phe Ile Thr His Thr Val Leu Ser Gly Val Tyr Thr
450                 455                 460

Leu Arg Met Ala Ile Gly Gly Pro Leu Thr Gln Asp Lys His Val Asp
465                 470                 475                 480

Ala Ala Trp Lys Leu Ile Gln Glu Ala Thr Thr Leu Leu Val Lys
                485                 490                 495

Gly Pro Ser His Ile Leu Ala Asn Asn Leu Arg Leu Ser Pro Ile Leu
            500                 505                 510

Ala Asn Asn Leu Arg Leu Ser Pro Ile Leu Ala Asn Asn Arg Ile
        515                 520                 525

<210> SEQ ID NO 57
<211> LENGTH: 572
<212> TYPE: PRT
<213> ORGANISM: Setaria italica
<300> PUBLICATION INFORMATION:
<308> DATABASE ACCESSION NUMBER: 3G188200.1

<400> SEQUENCE: 57

Met Asp Ile Leu Asn His Ala Asp Thr Thr Ala Asn Gly Thr Ser
1               5                   10                  15

Pro Ala Ala Ala Ala Ala Ala Val Val Ala Pro Thr Pro Ser
            20                  25                  30

Ser Leu Val Thr Pro Pro Leu Asp Ala Asp Glu Phe Arg Arg Gln Gly
            35                  40                  45

Arg Leu Val Val Asp Phe Ile Ala Asp Tyr Tyr Thr Arg Ile Asn Glu
        50                  55                  60

Tyr Pro Val Arg Pro Ala Val Ala Pro Gly Phe Leu Ala Arg Gln Leu
65                  70                  75                  80

Pro Glu Thr Ala Pro Ala Arg Pro Glu Arg Asp Ala Leu Ala Ala Ala
                85                  90                  95

Leu Arg Asp Val Arg Asp Leu Ile Leu Pro Gly Val Thr His Trp Gln
            100                 105                 110

Ser Pro Arg His Phe Ala His Phe Ala Ala Thr Ala Ser Asn Val Gly
        115                 120                 125

Ala Leu Gly Glu Ala Leu Ala Ala Gly Leu Asn Ile Asn Pro Phe Thr
    130                 135                 140

Trp Ala Ala Ser Pro Ala Ala Thr Glu Leu Glu Val Val Val Thr Asp
145                 150                 155                 160
```

```
Trp Leu Gly Lys Ala Leu His Leu Pro Glu Arg Leu Leu Phe Ser Gly
            165                 170                 175

Gly Gly Gly Gly Thr Leu Leu Gly Thr Ser Cys Glu Ala Met Leu Cys
            180                 185                 190

Thr Ile Val Ala Ala Arg Asp Arg Lys Leu Ala Glu Ile Gly Glu Glu
            195                 200                 205

Arg Ile Gly Asp Leu Val Val Tyr Phe Ser Asp Gln Thr His Phe Ser
210                 215                 220

Phe Gln Lys Ala Ala Arg Ile Ala Gly Ile Arg Gly Asn Cys Arg
225                 230                 235                 240

Glu Ile Pro Thr Ser Arg Glu Ser Gly Phe Thr Leu Ser Pro Lys Ala
            245                 250                 255

Leu Arg Ala Ala Val Arg Ala Asp Glu Ala Ser Gly Arg Val Pro Leu
            260                 265                 270

Phe Leu Cys Ala Thr Val Gly Thr Thr Pro Thr Ala Ala Ile Asp Pro
            275                 280                 285

Leu Arg Glu Leu Cys Ala Ala Val Ser Gly His Gly Val Trp Val His
            290                 295                 300

Val Asp Ala Ala Tyr Ala Gly Ala Ala Cys Val Cys Pro Glu Phe Arg
305                 310                 315                 320

His Ala Ile Ala Gly Ala Glu Ala Val Asp Ser Phe Ser Thr Asn Pro
            325                 330                 335

His Lys Trp Leu Leu Ala Asn Met Asp Cys Cys Ala Leu Trp Val Thr
            340                 345                 350

Arg Pro Ala Ala Leu Val Ala Ala Leu Gly Thr Asp His Asp Val Ile
            355                 360                 365

Leu Lys Asp Pro Ser Ala Ala Ala Gln Asp Gly His Asp Val Val Val
            370                 375                 380

Asp Tyr Lys Asp Trp Gln Val Ala Leu Ser Arg Arg Phe Arg Ala Leu
385                 390                 395                 400

Lys Leu Trp Leu Val Leu Arg Cys His Gly Val Glu Gly Leu Arg Gly
            405                 410                 415

Phe Val Arg Ala His Val Arg Met Ala Ala Ala Phe Glu Ala Met Val
            420                 425                 430

Arg Ala Asp Thr Arg Phe Glu Val Pro Val Pro Arg Gln Phe Ala Leu
            435                 440                 445

Val Cys Phe Arg Leu Arg Pro Ala Ser Ala Gly Glu Lys Arg Thr Arg
            450                 455                 460

Gly Gly Glu Val Val Glu Pro Asn Glu Leu Asn Arg Arg Leu Leu Glu
465                 470                 475                 480

Ala Val Asn Ala Thr Gly Arg Ala Tyr Ile Ser Ser Ala Val Val Gly
            485                 490                 495

Gly Val Tyr Val Leu Arg Cys Ala Ile Gly Asn Ser Leu Thr Glu Glu
            500                 505                 510

Arg His Val Arg Glu Ala Trp Ser Val Val Gln Glu Gln Ala Asn Val
            515                 520                 525

Val Leu Ala Ala Ala Thr Ala Thr Cys Pro Asp Glu Arg Ala Val His
            530                 535                 540

Arg Ala Arg Cys Val Glu Thr Asp Ala Ala Asp Ala Pro Ala Ser Val
545                 550                 555                 560

Pro Pro Val Gln Met Arg Phe Pro Ser Ala Gln Ser
            565                 570
```

<210> SEQ ID NO 58
<211> LENGTH: 505
<212> TYPE: PRT
<213> ORGANISM: Kalanchoe fedtschenkoi
<300> PUBLICATION INFORMATION:
<308> DATABASE ACCESSION NUMBER: 0033s0078.1

<400> SEQUENCE: 58

Met Gly Ser Leu Pro Ser Pro His Asp Pro Ser Asn Ala Phe Asn Pro
1               5                   10                  15

Met Asp Val Ala Glu Leu Ser Ile Glu Ser Arg Leu Val Met Asp Phe
            20                  25                  30

Ile Thr Gln Tyr Tyr Gln Thr Leu Glu Thr Arg Pro Val Gln Pro Arg
        35                  40                  45

Val Lys Pro Gly Phe Leu Thr Gly Gln Leu Pro Glu Lys Ala Pro Phe
    50                  55                  60

His Ala Glu Ser Met Glu Glu Ile Leu Ser Asp Val Ser Glu Lys Ile
65                  70                  75                  80

Val Pro Gly Leu Thr His Trp Gln Ser Pro Asn Phe His Ala Tyr Phe
                85                  90                  95

Pro Ala Ser Ser Ser Asn Ala Gly Leu Leu Gly Glu Met Leu Cys Ser
            100                 105                 110

Gly Leu Ser Val Ile Gly Phe Thr Trp Asn Ser Ser Pro Ala Ala Thr
        115                 120                 125

Glu Leu Glu Asn Val Val Val Asp Trp Leu Ala Asp Met Leu Asn Leu
    130                 135                 140

Pro Pro Ser Phe Arg Phe Ser Gly Gly Gly Gly Gly Gly Val Leu
145                 150                 155                 160

Gln Ser Asn Thr Cys Glu Ala Val Leu Cys Thr Leu Ala Ala Ala Arg
                165                 170                 175

Asp Lys Val Leu Glu Arg Ile Gly Asp Asp Lys Ile Asn Lys Leu Val
            180                 185                 190

Ala Tyr Cys Ser Asp Gln Thr His Phe Thr Leu His Lys Gly Ala Lys
        195                 200                 205

Leu Ile Gly Ile Arg Arg Ala Asn Ile Lys Ser Ile Gly Thr Arg Arg
    210                 215                 220

Glu Asn Gly Phe Gly Leu Cys Pro Asn Asp Leu Arg Asn Ala Ile Thr
225                 230                 235                 240

Gly Asp Leu Glu Ala Gly Leu Val Pro Phe Tyr Leu Cys Gly Thr Ile
                245                 250                 255

Gly Thr Thr Ala Leu Gly Ala Val Asp Pro Ile Lys Glu Leu Gly Lys
            260                 265                 270

Val Ala Arg Glu Phe Asp Leu Trp Phe His Ile Asp Ala Ala Tyr Gly
        275                 280                 285

Gly Ser Ala Cys Ile Cys Pro Glu Phe Arg His Tyr Leu Asp Gly Val
    290                 295                 300

Glu Leu Val Asp Ser Ile Ser Met Asn Ala His Lys Trp Leu Leu Ser
305                 310                 315                 320

Asn Leu Asp Cys Cys Phe Leu Trp Leu Gln Asn Pro Lys Cys Leu Ile
                325                 330                 335

Gln Cys Leu Ala Ala Glu Ala Glu Phe Leu Lys Gly Ser Gly Glu Met
            340                 345                 350

Val Asp Tyr Lys Asp Trp Gln Ile Ser Leu Ser Arg Arg Phe Arg Ala
        355                 360                 365

Ile Lys Met Trp Met Val Phe Arg Arg Tyr Gly Val Ser Asn Leu Met

```
                    370                 375                 380
Glu His Ile Arg Ser Asp Val Ser Met Ala Ala Arg Phe Glu Glu Met
385                 390                 395                 400

Val Ser Ala Asp Asp Arg Phe Glu Ile Val Phe Pro Arg Lys Phe Ala
                405                 410                 415

Leu Val Cys Phe Lys Leu Asn Thr Lys Gly Ser Val Gln His Gly Glu
            420                 425                 430

Asp Asp Gly Glu Asp Gly Leu Asp Gly Asp Ser Val Leu Thr Arg Glu
        435                 440                 445

Leu Met Gly Arg Val Asn Ser Ser Gly Lys Ala Tyr Leu Ser Gly Val
    450                 455                 460

Glu Met Gly Arg Ile Phe Phe Ile Arg Cys Val Ile Gly Ser Ser Leu
465                 470                 475                 480

Thr Glu Glu Arg His Val Asp Asn Leu Trp Asn Leu Ile Gln Glu Lys
                485                 490                 495

Thr Gln Ser Ile Met Pro Cys Arg Ala
            500                 505

<210> SEQ ID NO 59
<211> LENGTH: 493
<212> TYPE: PRT
<213> ORGANISM: Daucus carota subsp. sativus
<300> PUBLICATION INFORMATION:
<308> DATABASE ACCESSION NUMBER: 36068870

<400> SEQUENCE: 59

Met Gly Ser Leu Ser Thr Gln Lys Phe Asn Pro Leu Asn Leu Asp Phe
1               5                   10                  15

Phe Ser Ser Glu Ser Asn Lys Val Ile Glu Phe Ile Thr Ala Tyr Tyr
                20                  25                  30

Lys Asn Val Glu Lys Tyr Pro Val Arg Ser Gln Val Glu Pro Gly Phe
            35                  40                  45

Leu Leu Asn Met Tyr Pro Lys Lys Ala Pro Ser Gln Pro Val Ser Leu
        50                  55                  60

Asp Thr Ile Leu Gln Glu Leu Glu Ala Asp Ile Ile Pro Gly Met Thr
65                  70                  75                  80

His Trp Gln Ser Pro Asn Phe Tyr Ala Tyr Phe Arg Thr Thr Thr Ser
                85                  90                  95

Asn Ala Ala Phe Gln Gly Glu Met Leu Cys Asn Ala Leu Asn Val Ala
            100                 105                 110

Gly Phe Asn Trp Ile Cys Ser Pro Ala Ala Thr Glu Leu Glu Met Ile
        115                 120                 125

Val Met Asp Trp Leu Gly Lys Met Leu Ser Leu Pro Gln Ser Phe Leu
    130                 135                 140

Phe Ala Gly Asn Gly Gly Gly Val Leu Gln Gly Ser Thr Ser Glu Ala
145                 150                 155                 160

Leu Ile Cys Val Leu Ser Ala Ala Arg Asp Arg Ala Leu Lys Gln Tyr
                165                 170                 175

Gly Glu Asp Ser Ile Thr Lys Leu Val Val Tyr Ala Ser Asp Gln Thr
            180                 185                 190

His Phe Val Val Lys Lys Ala Ala Lys Leu Val Gly Ile Pro Thr Lys
        195                 200                 205

Asn Phe Arg Val Ile Pro Thr Ser Ile Ala Thr Cys Phe Ala Leu Lys
    210                 215                 220

Pro Asn Asp Ile Lys Met Ala Ile Glu Arg Asp Leu Glu Ser Gly Leu
```

```
            225                 230                 235                 240
    Val Pro Leu Phe Val Cys Ala Thr Val Gly Ala Thr Pro Ser Gly Ser
                    245                 250                 255

Val Asp Pro Val Glu Gly Leu Gly Leu Leu Ala Lys Asn Tyr Gly Leu
                    260                 265                 270

Trp Leu His Ile Glu Ala Ala Tyr Ala Gly Ser Ala Phe Ile Cys Pro
                    275                 280                 285

Glu Leu Thr His Tyr Leu Arg Gly Ile Glu His Ala His Ser Ile Ser
                    290                 295                 300

Ile Asn Leu His Lys Trp Leu Thr Asn Met Asp Cys Ser Cys Leu
    305                 310                 315                 320

Trp Val Lys Ser Pro Asp Val Leu Leu Glu Ser Leu Ser Met Thr Asp
                    325                 330                 335

Glu Ile Leu Arg Asn Glu Ala Ser Glu Ser Lys Lys Val Val Asp Phe
                    340                 345                 350

Met Asp Trp Gln Ile Ala Thr Ser Lys Leu Phe Arg Ala Leu Lys Leu
                    355                 360                 365

Trp Phe Val Leu Arg Arg Tyr Gly Val Asp Asn Leu Met Ala His Ile
                    370                 375                 380

Arg Ser Asp Ile Glu Leu Ala Lys His Phe Glu Ala Leu Val Asn Ser
    385                 390                 395                 400

Asp Lys Arg Phe Glu Val Val Pro Val Asn Phe Ser Leu Val Cys
                    405                 410                 415

Phe Arg Leu Lys Pro Asn Glu Glu Gly Glu Ser Leu Lys Val Leu
                    420                 425                 430

Met Asn Trp Asn Leu Met Glu Ala Val Asn Ser Ser Gly Arg Ala Tyr
                    435                 440                 445

Met Thr His Ala Val Leu Gly Asp Ile Phe Val Ile Arg Cys Ala Ile
                    450                 455                 460

Gly Thr Ser Leu Thr Glu Glu Arg His Val Asn Glu Leu Trp Lys Leu
    465                 470                 475                 480

Ile Leu Glu Lys Thr Glu Val Ile Leu Lys Arg Asp Gln
                    485                 490

<210> SEQ ID NO 60
<211> LENGTH: 441
<212> TYPE: PRT
<213> ORGANISM: Daucus carota subsp. sativus
<300> PUBLICATION INFORMATION:
<308> DATABASE ACCESSION NUMBER: 36056758

<400> SEQUENCE: 60

Met Asn Thr Phe Asp Thr Glu Asp Phe Arg Lys Gln Ala His Leu Ile
1               5                   10                  15

Ile Asp Phe Leu Ala Asp Tyr Tyr Gln Asn Ile Glu Lys Phe Pro Val
                20                  25                  30

Arg Ser Gln Val Ser Pro Gly Tyr Leu Gly Ile Leu Pro Asp Ser
            35                  40                  45

Ala Pro His Asp Pro Glu Pro Ile Glu Lys Ile Leu Glu Asp Val Arg
        50                  55                  60

Ser Asn Ile Ile Pro Gly Ile Thr His Trp Gln Ser Pro Asn Phe Phe
65                  70                  75                  80

Ala Tyr Phe Pro Ser Cys Gly Ser Thr Ala Gly Phe Leu Gly Glu Met
                85                  90                  95

Leu Ala Asn Gly Phe Asn Val Val Gly Phe Asn Trp Ile Ser Ser Pro
```

```
            100                 105                 110
Ala Ala Thr Glu Leu Glu Thr Ile Val Met Asp Trp Leu Gly Lys Met
        115                 120                 125

Leu Gln Leu Pro Glu Ala Phe Leu Phe Ser Gly Gly Gly Gly Gly Val
    130                 135                 140

Leu Gln Gly Thr Thr Cys Glu Ala Met Leu Cys Thr Leu Val Ala Ala
145                 150                 155                 160

Arg Asp Arg Thr Leu Arg Glu Gln Gly Met Glu Asn Phe Asp Lys Leu
                165                 170                 175

Leu Cys Pro Val Gln Leu Glu Leu Glu Ile Leu Ser Asp Val Gln Asn
            180                 185                 190

Gly Leu Ile Pro Leu Phe Leu Cys Val Thr Ile Gly Thr Thr Pro Ser
        195                 200                 205

Thr Ala Val Asp Pro Leu Ala Thr Leu Ser Glu Val Ala Lys Lys Tyr
    210                 215                 220

Lys Leu Trp Val His Val Asp Ala Ala Tyr Ala Gly Ser Ala Cys Ile
225                 230                 235                 240

Cys Pro Glu Phe Arg His Phe Leu Asp Gly Leu Glu Asn Val Asn Ser
                245                 250                 255

Phe Ser Met Asn Ala His Lys Trp Phe Leu Thr Thr Leu Asp Cys Cys
            260                 265                 270

Cys Leu Trp Val Asn Asp Pro Ser Ala Leu Ile Lys Ser Leu Ser Thr
        275                 280                 285

Tyr Pro Glu Phe Leu Arg Asn His Ala Ser Glu Ser Asn Lys Val Val
    290                 295                 300

Asp Tyr Lys Asp Trp Gln Ile Met Leu Ser Arg Arg Phe Arg Ala Leu
305                 310                 315                 320

Lys Leu Trp Phe Val Leu Arg Ser Tyr Gly Val Glu Lys Leu Arg Glu
                325                 330                 335

Phe Ile Arg Val His Val Glu Met Ala Lys Tyr Phe Glu Gly Leu Val
            340                 345                 350

Ala Met Asp Gln Arg Phe Glu Val Val Val Pro Arg Leu Phe Ala Met
        355                 360                 365

Val Cys Phe Arg Val Val Cys Cys Gly Glu Asn Asp Val Asn Glu Ile
    370                 375                 380

Asn Glu Lys Leu Leu Glu Ser Val Asn Gln Ser Gly Arg Ile Tyr Val
385                 390                 395                 400

Ser His Ala Val Leu Asp Gly Val Tyr Val Ile Arg Phe Ala Ile Gly
                405                 410                 415

Ala Thr Leu Thr Asp Tyr Ser His Val Ser Ala Ala Trp Glu Val Val
            420                 425                 430

Gln Glu His Ala Asp Ala Leu Leu Ala
        435                 440

<210> SEQ ID NO 61
<211> LENGTH: 510
<212> TYPE: PRT
<213> ORGANISM: Solanum tuberosum
<300> PUBLICATION INFORMATION:
<308> DATABASE ACCESSION NUMBER: 3DMP400026166

<400> SEQUENCE: 61

Met Gly Thr Leu Asn Ile Asn His Glu Leu Asp Asp Gln Ile Phe Asn
1               5                   10                  15

Thr Ile Asn Pro Leu Asp Pro Glu Glu Phe Arg Arg Gln Gly His Lys
```

```
            20                  25                  30
Ile Val Asn Phe Leu Ala Asp Tyr Tyr Gln Asn Ile Glu Gln Tyr Pro
            35                  40                  45
Val Cys Ser Gln Val Asn Pro Gly Tyr Leu Gln Lys Ile Val Pro Asn
            50                  55                  60
Ser Ala Pro Asn Asn Ser Glu Ser Leu Glu Lys Ile Leu Lys Asp Val
 65                  70                  75                  80
Glu Arg Asp Ile Ile Pro Gly Leu Thr His Trp Gln Ser Pro Asn Phe
                    85                  90                  95
Phe Ala Tyr Phe Pro Ser Ser Gly Ser Thr Ala Gly Phe Leu Gly Glu
                100                 105                 110
Met Leu Ser Val Gly Phe Asn Val Gly Phe Asn Trp Ile Ser Ser
            115                 120                 125
Pro Ala Ala Thr Glu Leu Glu Ser Ile Val Met Asp Trp Phe Gly Lys
            130                 135                 140
Met Leu Asn Leu Pro Asn Cys Phe Leu Phe Ala Ser Gly Gly Gly Gly
145                 150                 155                 160
Val Leu Gln Gly Thr Thr Cys Glu Ala Met Leu Cys Thr Ile Val Ala
                165                 170                 175
Ala Arg Asp Gln Met Leu Arg Lys Ile Ser Arg Glu Asn Phe Gly Lys
                180                 185                 190
Leu Val Val Tyr Ala Ser Asp Gln Thr His Phe Ser Leu Lys Lys Ala
                195                 200                 205
Ala His Ile Ala Gly Ile Asp Pro Gly Asn Phe Arg Val Ile Pro Thr
            210                 215                 220
Ile Lys Ala Asn Glu Tyr Thr Leu Cys Pro Lys Ser Leu Arg Leu Ala
225                 230                 235                 240
Ile Leu Asn Asp Leu Lys Glu Gly Asn Val Pro Leu Phe Leu Cys Ala
                245                 250                 255
Thr Ile Gly Thr Thr Ala Thr Thr Ser Val Asp Pro Leu Arg Leu Leu
            260                 265                 270
Cys Glu Ile Ala Lys Glu Phe Gly Ile Trp Val His Val Asp Ala Ala
            275                 280                 285
Tyr Ala Gly Ser Ala Cys Ile Cys Pro Glu Phe Gln Val Phe Leu Asp
            290                 295                 300
Gly Val Glu Asn Ala Asn Ser Phe Ser Leu Asn Ala His Lys Trp Phe
305                 310                 315                 320
Phe Ser Thr Leu Asp Cys Cys Cys Leu Trp Val Lys Asp Pro Ser Ala
                325                 330                 335
Leu Thr Asn Ala Leu Ser Thr Asn Pro Glu Cys Leu Arg Asn Lys Ala
            340                 345                 350
Thr Glu Leu Asn Gln Val Ile Asp Tyr Lys Asp Trp Gln Ile Ala Leu
            355                 360                 365
Ser Lys Arg Phe Arg Ala Leu Lys Leu Trp Leu Val Leu Arg Ser Tyr
            370                 375                 380
Gly Val Thr Asn Leu Arg Asn Leu Ile Arg Ser His Val Asn Met Ala
385                 390                 395                 400
Lys His Phe Glu Gly Leu Val Ala Thr Asp Lys Arg Phe Glu Ile Phe
                405                 410                 415
Val Pro Arg Lys Phe Ala Met Val Cys Phe Arg Ile Ser Pro Leu Val
            420                 425                 430
Leu Ser Gln Val Ser Thr Lys Phe Asp Asp Glu Lys Glu Val Asn Met
            435                 440                 445
```

```
Phe Asn Thr Lys Leu Val Glu Ser Ile Asn Ser Cys Gly Lys Leu Tyr
    450                 455                 460

Leu Thr His Gly Val Val Gly Gly Thr Tyr Ile Ile Arg Phe Ala Ile
465                 470                 475                 480

Gly Ala Ser Leu Thr His Tyr Arg His Val Asp Val Ala Trp Lys Val
                485                 490                 495

Ile Gln Asp His Ala Asn Ala Leu Leu Asn Gln Gly Tyr Val
                500                 505                 510

<210> SEQ ID NO 62
<211> LENGTH: 507
<212> TYPE: PRT
<213> ORGANISM: Solanum tuberosum
<300> PUBLICATION INFORMATION:
<308> DATABASE ACCESSION NUMBER: 3DMP400024738

<400> SEQUENCE: 62

Met Gly Thr Met Lys Ile Asn Pro Glu His Glu Phe Asp Gly Gln Phe
1               5                   10                  15

Ser Ile Asn Thr Ser Ser Arg Leu Leu Asp Pro Glu Glu Phe Arg
            20                  25                  30

Arg Gln Gly His Met Met Val Asp Phe Leu Ala Asp Tyr Phe Gln Asn
            35                  40                  45

Ile Glu Lys Tyr Pro Val Arg Ser Gln Val Glu Pro Gly Tyr Leu Lys
50                  55                  60

Lys Leu Leu Pro Asp Ser Ala Pro Tyr Lys Pro Glu Pro Ile Ala Lys
65                  70                  75                  80

Ile Leu Glu Asp Val Glu Arg Asp Ile Phe Pro Gly Leu Thr His Trp
                85                  90                  95

Gln Ser Pro Asn Phe Phe Ala Tyr Phe Pro Cys Thr Ser Ser Thr Ala
            100                 105                 110

Gly Ile Leu Gly Glu Met Leu Ser Ala Gly Leu Asn Val Val Gly Phe
            115                 120                 125

Ser Leu Ile Ala Ser Pro Ala Ala Thr Glu Leu Glu Ser Ile Val Met
130                 135                 140

Asp Trp Leu Gly Lys Met Ile Ser Leu Pro Lys Thr Tyr Leu Phe Ser
145                 150                 155                 160

Gly Gly His Gly Gly Gly Val Ile Gln Gly Thr Thr Cys Glu Ala
            165                 170                 175

Met Leu Cys Thr Ile Val Ala Ala Arg Glu Gln Met Leu Glu Lys Val
            180                 185                 190

Gly Arg Glu Lys Val Asp Lys Leu Val Val Tyr Ala Ser Asp Gln Thr
            195                 200                 205

His Phe Ser Phe Glu Lys Ala Val Lys Ile Ser Gly Ile Lys Leu Glu
            210                 215                 220

Asn Phe Arg Val Ile Pro Thr Thr Lys Asp Thr Glu Phe Ala Leu Asp
225                 230                 235                 240

Pro Lys Ser Leu Ser Arg Thr Ile Glu Gln Asp Ile Lys Ser Gly Phe
            245                 250                 255

Ile Pro Leu Phe Met Cys Ala Thr Ile Gly Thr Thr Ser Thr Thr Val
            260                 265                 270

Val Asp Pro Leu Lys Leu Leu Cys Glu Ile Thr Lys Asp Tyr Gly Ile
            275                 280                 285

Trp Val His Val Asp Ala Ala Tyr Ala Gly Gly Ala Cys Ile Cys Pro
            290                 295                 300
```

Glu Phe Gln His Phe Leu Asp Gly Ile Glu Asn Ala Asn Ser Phe Ser
305                 310                 315                 320

Phe Asn Ala His Lys Trp Leu Phe Ser Asn Leu Asp Cys Cys Cys Leu
            325                 330                 335

Trp Val Lys Asp Pro Ser Ala Leu Thr Asn Ala Leu Ser Thr Arg Pro
            340                 345                 350

Glu Cys Leu Arg Asn Lys Ala Thr Asp Thr Lys Gln Val Val Asp Tyr
            355                 360                 365

Lys Asp Trp Gln Leu Ser Leu Ser Arg Arg Phe Arg Ala Leu Lys Leu
            370                 375                 380

Trp Leu Val Leu Arg Ser Tyr Gly Ile Asp Asn Leu Arg Asn Phe Ile
385                 390                 395                 400

Arg Ser His Val Lys Met Ala Lys His Phe Glu Gln Leu Val Ser Met
                405                 410                 415

Asp Glu Arg Phe Glu Ile Val Ala Pro Arg Asn Phe Ser Met Val Cys
            420                 425                 430

Phe Arg Val Ser Pro Leu Ala Leu Gly Asn Lys Gln Val Asn Lys Phe
            435                 440                 445

Asn Met Glu Leu Leu Glu Ser Ile Asn Ser Cys Gly Asn Ile His Met
450                 455                 460

Thr His Ala Leu Val Gly Gly Val Tyr Met Ile Arg Phe Ala Ile Ala
465                 470                 475                 480

Ala Pro Leu Thr Glu Tyr Lys His Ile Asp Met Ala Trp Glu Val Ile
            485                 490                 495

Cys Asn His Ala Asn Ala Met Leu Asp Val Asn
            500                 505

<210> SEQ ID NO 63
<211> LENGTH: 476
<212> TYPE: PRT
<213> ORGANISM: Solanum lycopersicum
<300> PUBLICATION INFORMATION:
<308> DATABASE ACCESSION NUMBER: 36137005

<400> SEQUENCE: 63

Met Gly Thr Leu Asn Ile Asn His Glu Leu Asp Asp Gln Ile Phe Asn
1               5                   10                  15

Thr Ile Asn Pro Leu Asp Pro Glu Glu Phe Arg Arg Gln Gly His Lys
            20                  25                  30

Ile Val Asn Phe Leu Ala Asp Tyr Tyr Gln Asn Ile Glu Gln Tyr Pro
            35                  40                  45

Val Cys Ser Gln Val Asn Pro Gly Tyr Leu Gln Asn Ile Val Pro Asn
        50                  55                  60

Ser Ala Pro Asn Asn Pro Glu Ser Leu Asp Lys Ile Leu Lys Asp Val
65                  70                  75                  80

Gln Asn Asp Ile Ile Pro Gly Leu Thr His Trp Gln Ser Pro Asn Phe
                85                  90                  95

Phe Ala Tyr Phe Pro Ser Ser Gly Ser Thr Val Gly Phe Val Gly Glu
            100                 105                 110

Met Leu Ser Val Gly Phe Asn Val Val Gly Phe Asn Trp Ile Ser Ser
            115                 120                 125

Pro Ala Ala Thr Glu Leu Glu Ser Ile Val Met Asp Trp Phe Gly Lys
            130                 135                 140

Met Leu Asn Leu Pro Asn Cys Phe Leu Phe Ala Ser Gly Gly Gly Gly
145                 150                 155                 160

```
Val Leu Gln Gly Thr Thr Cys Glu Ala Ile Leu Cys Thr Ile Val Ala
                165                 170                 175

Ala Arg Asp Gln Met Leu Arg Lys Ile Ser Arg Glu Asn Phe Gly Lys
            180                 185                 190

Leu Val Val Tyr Ala Ser Gly Gln Thr His Phe Ser Leu Lys Lys Ser
        195                 200                 205

Ala His Ile Ala Gly Ile Asp Pro Gly Asn Phe Arg Val Ile Pro Thr
    210                 215                 220

Ile Lys Ala Lys Glu Tyr Thr Leu Cys Pro Lys Ser Leu Arg Leu Ala
225                 230                 235                 240

Ile Leu Asn Asp Leu Lys Glu Gly Asn Val Pro Leu Phe Leu Cys Ala
                245                 250                 255

Thr Ile Gly Thr Thr Ser Thr Thr Ser Val Asp Pro Leu Arg Leu Leu
            260                 265                 270

Cys Asp Ile Ser Lys Glu Phe Gly Ile Trp Val His Val Asp Ala Ala
        275                 280                 285

Tyr Val Gly Ser Ala Cys Ile Cys Pro Glu Phe Gln Val Phe Leu Asp
    290                 295                 300

Gly Val Glu Asn Ala Asn Ser Phe Ser Leu Asn Asp Pro Ser Ala Leu
305                 310                 315                 320

Thr Asn Ala Leu Ser Thr Asn Leu Glu Phe Leu Arg Asn Lys Ala Thr
                325                 330                 335

Glu Leu Asn Gln Val Ile Asp Tyr Lys Asp Trp Gln Ile Ala Leu Ser
            340                 345                 350

Arg Arg Phe Arg Ala Leu Lys Leu Trp Leu Val Leu Arg Ser Tyr Gly
        355                 360                 365

Val Thr Asn Leu Arg Asn Leu Ile Arg Ser His Val Asn Met Thr Lys
    370                 375                 380

His Phe Glu Gly Leu Ile Ala Met Asp Lys Arg Phe Glu Ile Phe Val
385                 390                 395                 400

Pro Arg Lys Phe Ala Met Val Cys Phe Arg Ile Ser Pro Leu Val Leu
                405                 410                 415

Ser Gln Val Ser Ile Lys Phe Asp Asp Glu Lys Glu Val Asn Met Phe
            420                 425                 430

Asn Thr Lys Leu Leu Glu Ser Ile Asn Ser Cys Ser Lys Leu Tyr Leu
        435                 440                 445

Thr His Gly Ile Val Gly Gly Thr Tyr Ile Ile Arg Phe Ala Ile Gly
    450                 455                 460

Ala Ser Leu Thr His Tyr Arg His Val Asp Ile Ala
465                 470                 475

<210> SEQ ID NO 64
<211> LENGTH: 440
<212> TYPE: PRT
<213> ORGANISM: Daucus carota subsp. sativus
<300> PUBLICATION INFORMATION:
<308> DATABASE ACCESSION NUMBER: 36065781

<400> SEQUENCE: 64

Met Cys Lys Pro Lys Ser Ser Pro Ala Ser His Ile Asn Trp Gln Ser
1               5                   10                  15

Pro Asn Phe Phe Ala Tyr Phe Pro Ser Ser Gly Ser Thr Ala Gly Phe
            20                  25                  30

Leu Gly Glu Met Leu Ser Thr Gly Phe Asn Val Val Gly Phe His Trp
        35                  40                  45
```

Met Ala Ser Pro Ala Ala Thr Glu Leu Glu Asn Val Val Thr Asp Trp
    50                  55                  60

Phe Gly Lys Met Leu Gln Leu Pro Lys Ser Phe Leu Phe Ser Gly Gly
65                  70                  75                  80

Gly Gly Gly Val Leu Gln Gly Thr Thr Cys Glu Ala Met Leu Cys Thr
                85                  90                  95

Leu Val Ala Ala Arg Asp Lys Asn Leu Arg Gln His Gly Met Glu Asn
                100                 105                 110

Ile Gly Lys Leu Val Val Tyr Cys Ser Asp Gln Thr His Ser Ala Met
                115                 120                 125

Gln Lys Ala Ala Lys Ile Ala Gly Ile Asp Pro Lys Asn Phe Arg Thr
                130                 135                 140

Val Glu Thr Ser Arg Ala Ser Asn Phe Gln Leu Cys Pro Arg Arg Leu
145                 150                 155                 160

Glu Ser Ala Ile Leu Thr Asp Ile Gln Asn Gly Leu Ile Pro Leu Tyr
                165                 170                 175

Leu Cys Ala Thr Val Gly Thr Thr Ser Ser Thr Ala Val Asp Pro Leu
                180                 185                 190

Pro Ala Leu Thr Glu Val Ala Lys Lys Tyr Asp Leu Trp Val His Val
                195                 200                 205

Asp Ala Ala Tyr Ala Gly Ser Ala Cys Ile Cys Pro Glu Leu Arg Gln
                210                 215                 220

Tyr Leu Asn Gly Val Glu Asn Ala Asp Ser Phe Ser Leu Asn Ala His
225                 230                 235                 240

Lys Trp Phe Leu Thr Thr Leu Asp Cys Cys Cys Leu Trp Val Lys Asn
                245                 250                 255

Pro Ser Ala Leu Ile Lys Ser Leu Ser Thr Tyr Pro Glu Phe Leu Arg
                260                 265                 270

Asn Asn Ala Ser Glu Thr Asn Lys Val Val Asp Tyr Lys Asp Trp Gln
                275                 280                 285

Ile Met Leu Ser Arg Arg Phe Arg Ala Leu Lys Leu Trp Phe Val Leu
                290                 295                 300

Arg Ser Tyr Gly Val Gly Gln Leu Arg Glu Phe Ile Arg Gly His Val
305                 310                 315                 320

Asp Met Ala Lys Tyr Phe Glu Gly Leu Val Gly Lys Asp Lys Arg Phe
                325                 330                 335

Glu Val Val Pro Arg Leu Phe Ser Met Val Cys Ile Arg Val Arg
                340                 345                 350

Pro Ser Ala Met Thr Gly Lys Ser Cys Gly Asn Asp Val Asn Glu Leu
                355                 360                 365

Asn Arg Lys Leu Leu Glu Ser Leu Asn Glu Ser Gly Arg Ile Tyr Val
                370                 375                 380

Ser His Thr Val Leu Asp Gly Ile Tyr Ile Ile Arg Phe Ala Ile Gly
385                 390                 395                 400

Ala Thr Leu Thr Asp Ile Asn His Val Ser Ala Ala Trp Lys Val Val
                405                 410                 415

Gln Asp His Ala Thr Ala Leu Leu Asp Asp Thr Asn Phe Leu Ala Lys
                420                 425                 430

Lys Val Ala Asp Ile Ile Leu Ser
                435                 440

<210> SEQ ID NO 65
<211> LENGTH: 577

```
<212> TYPE: PRT
<213> ORGANISM: Oropetium thomaeum
<300> PUBLICATION INFORMATION:
<308> DATABASE ACCESSION NUMBER: 35995617

<400> SEQUENCE: 65
```

| | | | | | | | | | | | | | | |
|---|---|---|---|---|---|---|---|---|---|---|---|---|---|---|
| Met | Ala | Ile | Leu | Asn | His | Ala | Asp | Asp | Ala | Ser | Pro | Ala | Asn | Asp | Asp |
| 1 | | | | 5 | | | | | 10 | | | | | 15 | |
| Asn | Pro | Ala | Thr | Ala | Pro | Ala | Met | Ala | Pro | Thr | Asn | Pro | Arg | Pro | |
| | | | 20 | | | | | 25 | | | | | 30 | | |
| Leu | Asp | Ala | Asp | Glu | Phe | Arg | Arg | Gln | Gly | Arg | Leu | Val | Val | Asp | Phe |
| | | | 35 | | | | | 40 | | | | | 45 | | |
| Ile | Ala | Asp | Tyr | Tyr | Ala | Arg | Val | Glu | Glu | Tyr | Pro | Val | Arg | Pro | Ser |
| | 50 | | | | | 55 | | | | | 60 | | | | |
| Val | Thr | Pro | Gly | Phe | Leu | Ser | Arg | Lys | Leu | Pro | Glu | Thr | Ala | Pro | Glu |
| 65 | | | | | 70 | | | | | 75 | | | | | 80 |
| Gln | Pro | Glu | Pro | Gly | His | Gly | Asp | Ala | Phe | Ala | Ser | Ala | Leu | Arg | Asp |
| | | | | 85 | | | | | 90 | | | | | 95 | |
| Val | Arg | Asp | Leu | Ile | Leu | Pro | Gly | Ile | Thr | His | Trp | Gln | Ser | Pro | Asn |
| | | | 100 | | | | | 105 | | | | | 110 | | |
| His | Phe | Ala | His | Phe | Ala | Ala | Thr | Ala | Ser | Asn | Val | Gly | Ala | Leu | Gly |
| | | | 115 | | | | | 120 | | | | | 125 | | |
| Glu | Ala | Leu | Ala | Ala | Gly | Leu | Asn | Ile | Asn | Pro | Phe | Thr | Trp | Ala | Ala |
| | 130 | | | | | 135 | | | | | 140 | | | | |
| Ser | Ser | Ala | Ala | Thr | Glu | Leu | Glu | Val | Val | Val | Thr | Asp | Trp | Leu | Gly |
| 145 | | | | | 150 | | | | | 155 | | | | | 160 |
| Lys | Ala | Leu | His | Leu | Pro | Gln | Glu | Leu | Leu | Phe | Ser | Gly | Gly | Gly | Gly |
| | | | | 165 | | | | | 170 | | | | | 175 | |
| Gly | Thr | Leu | Leu | Gly | Thr | Ser | Cys | Glu | Ala | Met | Leu | Cys | Thr | Val | Val |
| | | | 180 | | | | | 185 | | | | | 190 | | |
| Ala | Ala | Arg | Asp | Arg | Lys | Leu | Gly | Glu | Ile | Gly | Glu | His | Arg | Ile | Gly |
| | | | 195 | | | | | 200 | | | | | 205 | | |
| Asp | Leu | Val | Val | Tyr | Cys | Ser | Asp | Gln | Thr | His | Phe | Ser | Phe | Arg | Lys |
| | 210 | | | | | 215 | | | | | 220 | | | | |
| Ala | Ala | Arg | Val | Ala | Gly | Ile | Arg | Arg | Ala | Asn | Cys | Arg | Glu | Ile | Pro |
| 225 | | | | | 230 | | | | | 235 | | | | | 240 |
| Thr | Ser | Leu | Glu | Ser | Asp | Phe | Ala | Leu | Ser | Pro | Ser | Ala | Leu | Leu | Ala |
| | | | | 245 | | | | | 250 | | | | | 255 | |
| Ala | Val | Arg | Ala | Asp | Glu | Ala | Ala | Gly | Leu | Val | Pro | Leu | Tyr | Leu | Cys |
| | | | 260 | | | | | 265 | | | | | 270 | | |
| Val | Thr | Val | Gly | Thr | Thr | Pro | Thr | Ala | Ala | Val | Asp | Pro | Val | Arg | Glu |
| | 275 | | | | | 280 | | | | | 285 | | | | |
| Leu | Cys | Ala | Ala | Val | Ala | Gly | Arg | Gly | Val | Trp | Val | His | Val | Asp | Ala |
| | 290 | | | | | 295 | | | | | 300 | | | | |
| Ala | Tyr | Ala | Gly | Ala | Ala | Arg | Val | Cys | Pro | Glu | Leu | Leu | Arg | His | Ala |
| 305 | | | | | 310 | | | | | 315 | | | | | 320 |
| Gly | Ala | Ile | Val | Asp | Gly | Val | Asp | Ser | Phe | Ser | Thr | Asn | Pro | His | Lys |
| | | | | 325 | | | | | 330 | | | | | 335 | |
| Trp | Leu | Leu | Ala | Asn | Met | Asp | Cys | Cys | Ala | Leu | Trp | Val | Gln | Gln | Pro |
| | | | 340 | | | | | 345 | | | | | 350 | | |
| Asp | Ala | Leu | Val | Ala | Ala | Leu | Gly | Thr | Asp | His | Asp | Val | Ile | Leu | Lys |
| | | | 355 | | | | | 360 | | | | | 365 | | |
| Asp | Pro | Ala | Ala | Ala | Ala | Gly | Asp | Val | Val | Val | Asp | Tyr | Lys | Asp | |
| | 370 | | | | | 375 | | | | | 380 | | | | |

```
Trp Gln Val Ala Leu Ser Arg Arg Phe Arg Ala Leu Lys Leu Trp Leu
385                 390                 395                 400

Leu Leu Arg Cys His Gly Val Glu Gly Leu Arg Ala His Val Arg Asp
            405                 410                 415

Gly Leu Arg Met Ala Glu Ala Phe Glu Ala Met Val Arg Ala Asp Ala
            420                 425                 430

Arg Phe Glu Val Pro Val Arg Arg Gln Leu Ser Leu Val Cys Phe Arg
435                 440                 445

Leu Arg Pro Thr Ala Val Ile Arg Glu Lys Gln Gln Gln Arg Gly
    450                 455                 460

Arg Arg Arg Asp His Asp Asp Thr Ala Ala Asn Glu Leu Asn
465                 470                 475                 480

Arg Arg Leu Leu Glu Ala Val Asn Ala Thr Gly Arg Thr Tyr Met Ser
            485                 490                 495

Cys Ala Val Val Gly Val Tyr Met Leu Arg Cys Ala Ile Gly Asn
            500                 505                 510

Ser Leu Thr Glu Asp Arg His Val Glu Ala Trp Asn Val Val Gln
    515                 520                 525

Glu Gln Ala Ser Ala Ile Leu Asp Ala Ala Met Val Val Arg Ala Asp
530                 535                 540

Glu Cys Thr Val Cys Thr Ala Ala His Cys Val Gln Met Gly Met Val
545                 550                 555                 560

Asp Asp Ile Leu Ala Ala Ser Phe Pro Thr Gly Asn Glu Val Thr Ile
            565                 570                 575

Arg
```

<210> SEQ ID NO 66
<211> LENGTH: 565
<212> TYPE: PRT
<213> ORGANISM: Oryza sativa
<300> PUBLICATION INFORMATION:
<308> DATABASE ACCESSION NUMBER: 33157740

<400> SEQUENCE: 66

```
Met Ala Ile Leu Asn His Ser Asp Ala Ala Phe Pro Val Ala Ala Thr
1               5                   10                  15

Thr Pro Leu Leu Gly Arg Arg Pro Leu Asp Ala Gly Glu Phe Arg Arg
            20                  25                  30

Gln Gly Arg Gln Val Val Asp Phe Ile Ala Asp Tyr Ala Gly Ile
        35                  40                  45

Asn Asp Tyr Pro Val Arg Pro Ala Val Ala Pro Gly Phe Leu Ala Gly
50                  55                  60

Lys Leu Pro Ala Thr Ala Pro Ser Thr Pro Glu Pro Asp Ala Leu Thr
65                  70                  75                  80

Ala Gly Leu Arg Asp Val Arg Glu Leu Met Leu Pro Gly Leu Thr His
            85                  90                  95

Trp Gln Ser Pro Arg His Phe Ala His Phe Ser Ala Thr Ala Ser Asn
            100                 105                 110

Val Gly Ala Leu Gly Glu Ala Leu Ala Ala Gly Leu Asn Val Asn Pro
        115                 120                 125

Phe Thr Trp Glu Ala Ser Pro Ala Ala Thr Glu Leu Glu Val Val Val
    130                 135                 140

Thr Asp Trp Leu Gly Lys Ala Leu His Leu Pro Glu Arg Leu Leu Phe
145                 150                 155                 160

Ala Gly Gly Gly Gly Gly Thr Leu Leu Gly Thr Ser Cys Glu Ala Met
```

```
            165                 170                 175
Leu Cys Thr Ile Val Ala Ala Arg Asp Glu Lys Leu Ala Glu Ile Gly
            180                 185                 190

Glu Glu Arg Ile Gly Asp Leu Val Val Tyr Cys Ser Asp Gln Thr His
            195                 200                 205

Phe Ser Phe Gln Lys Ala Ala Arg Ile Ala Gly Ile Arg Arg Gly Asn
            210                 215                 220

Cys Arg Glu Ile Pro Thr Cys Arg Glu Ser Gly Phe Val Leu Thr Ala
225                 230                 235                 240

Thr Ala Leu Gln Ala Ala Val Ala Ala Asp Glu Ala Ala Gly Arg Val
            245                 250                 255

Pro Leu Phe Leu Cys Ala Thr Val Gly Thr Thr Pro Thr Ala Ala Val
            260                 265                 270

Asp Pro Leu Arg Glu Leu Cys Ala Ala Val Glu Gly Arg Gly Val Trp
            275                 280                 285

Val His Val Asp Ala Ala Tyr Ala Gly Ala Ala Cys Val Cys Pro Glu
            290                 295                 300

Phe Arg His Ala Ile Ala Gly Ala Glu Ala Val Asp Ser Phe Ser Thr
305                 310                 315                 320

Asn Pro His Lys Trp Leu Leu Ala Asn Met Asp Cys Cys Ala Leu Trp
            325                 330                 335

Val Ala Arg Pro Ala Ala Leu Val Ala Ala Leu Gly Thr Asp Asp Asp
            340                 345                 350

Val Ile Leu Lys Asp Ala Ala Ala Ala Arg Pro Ala Arg Gly Asp
            355                 360                 365

His His His His Ala Ala Val Asp Tyr Lys Asp Trp Gln Val Ala Leu
            370                 375                 380

Ser Arg Arg Phe Arg Ala Leu Lys Leu Trp Leu Val Leu Arg Cys His
385                 390                 395                 400

Gly Val Asp Gly Leu Arg Ala Val Val Arg Ser His Val Arg Met Ala
            405                 410                 415

Ala Ala Leu Glu Arg Met Val Arg Ala Asp Ala Arg Phe Glu Val Pro
            420                 425                 430

Val Pro Arg Gln Phe Ala Leu Val Cys Phe Arg Leu Arg Gly Gly Gly
            435                 440                 445

Ala Ala Ala Gln Leu Val Gly Gly Asp Glu Leu Thr Ala Ser Asn Glu
            450                 455                 460

Leu Asn Arg Arg Leu Leu Glu Ala Val Asn Ala Thr Gly Arg Ala Tyr
465                 470                 475                 480

Met Ser Ser Ala Val Val Gly Gly Met Tyr Val Leu Arg Cys Ala Val
            485                 490                 495

Gly Asn Ser Leu Thr Glu Glu His His Val Arg Glu Ala Trp Ser Val
            500                 505                 510

Val Gln Gly Gln Ala Ala Val Leu Ala Thr Ala Gly Ala Ala Ala
            515                 520                 525

Asp Thr Ala Arg Thr Lys Asp His Ala Ala Gly Asp His Gly Ala
            530                 535                 540

Asp Gln Pro His Ala Met Thr Thr Thr Thr Met Gly Cys Arg Ser
545                 550                 555                 560

Gly Pro Trp Glu Leu
            565

<210> SEQ ID NO 67
```

```
<211> LENGTH: 509
<212> TYPE: PRT
<213> ORGANISM: Brachypodium stacei
<300> PUBLICATION INFORMATION:
<308> DATABASE ACCESSION NUMBER: 01G392300.1

<400> SEQUENCE: 67
```

| | | | | | | | | | | | | | | |
|---|---|---|---|---|---|---|---|---|---|---|---|---|---|---|
|Met|Ala|Pro|Ala|Ser|Ser|Thr|Arg|Gln|Val|Ile|Thr|Asp|His|Lys|Thr
1| | | |5| | | | |10| | | | |15| |

Gln Lys Glu Asn Ser Ser Cys Thr Val Ile Asn His Leu Leu Asp Ala
                20                  25                  30

Asp Glu Phe Arg Arg Gln Gly His Lys Val Ile Asp Phe Ile Ala Asp
            35                  40                  45

Tyr Tyr Ser Gly Ile Ala Asp Tyr Pro Val His Pro Ser Val Thr Pro
50                  55                  60

Gly Phe Leu Leu Asn Gln Leu Pro Ala Asp Pro Glu Asp Pro Asp
65                  70                  75                  80

Thr Phe Ala Ser Ala Leu Gln Asp Val Arg Asp Leu Ile Leu Pro Gly
                85                  90                  95

Met Thr His Trp Gln Ser Pro Arg His Leu Ala His Phe Pro Ala Ser
            100                 105                 110

Ser Ser Val Thr Gly Ala Leu Gly Glu Ala Leu Ala Ala Gly Ile Asn
        115                 120                 125

Ala Val Pro Phe Met Trp Ser Ala Ser Pro Ala Ala Thr Glu Leu Glu
130                 135                 140

Met Val Ala Val Asp Trp Leu Gly Lys Ala Leu His Leu Pro Lys Thr
145                 150                 155                 160

Leu Leu Phe Ser Gly Ala Gly Gly Gly Thr Leu Leu Gly Thr Ser Tyr
                165                 170                 175

Arg Lys Leu Ala Glu Thr Gly Ala Gly Arg Ile Gly Asp Leu Val Val
            180                 185                 190

Tyr Gly Ser Asp Gln Thr His Phe Ala Leu Arg Lys Ala Ala Arg Ile
        195                 200                 205

Ala Gly Ile Arg His Gly Arg Cys Arg Glu Leu Arg Thr Cys Ile Ala
210                 215                 220

Asp Met Phe Ala Leu Ser Pro Ala Ala Leu Ser Ala Ala Met Asp Ala
225                 230                 235                 240

Asp Ala Gly Ala Gly Leu Val Pro Leu Phe Leu Cys Ala Thr Val Gly
                245                 250                 255

Thr Thr Gln Thr Lys Ala Val Asp Pro Ile Gly Ala Leu Cys Ala Glu
            260                 265                 270

Ala Ala Pro His Gly Val Trp Val His Val Asp Ala Ala Tyr Gly Gly
        275                 280                 285

Ser Ala Leu Val Cys Pro Glu Leu Ala Arg Asp Ala Ile Asp Gly Val
290                 295                 300

Glu Ala Val Asp Ser Phe Ser Met Asn Ala His Lys Trp Leu Leu Val
305                 310                 315                 320

Asn Thr Asp Cys Cys Ala Leu Trp Val Lys Arg Pro Ala Leu Leu Val
                325                 330                 335

Ser Ala Leu Gly Thr Gln Asp Glu Asp Glu Val Ile Leu Arg Asp Ala
            340                 345                 350

Ala Ala Gln Gly His Asp Val Val Asp Tyr Lys Asp Trp Ala Val Thr
        355                 360                 365

Leu Thr Arg Arg Phe Arg Ala Leu Lys Leu Trp Leu Val Leu Arg Cys
370                 375                 380

```
Tyr Gly Val Glu Gly Leu Arg Glu His Ile Arg Gly His Val Arg Met
385                 390                 395                 400

Ala Ala Leu Phe Glu Gly Met Val Asn Ala Asp Pro Arg Phe Glu Val
            405                 410                 415

Val Thr Glu Arg Arg Phe Ala Leu Val Cys Phe Arg Leu Arg Pro Asp
        420                 425                 430

Gln Leu Pro Asp Glu Gly Asn Lys Lys Thr Met Ala Ala Ala Asn
            435                 440                 445

Glu Leu Asn Arg Arg Leu Leu Gln Glu Val Asn Ala Ala Leu Gly
        450                 455                 460

Pro Tyr Met Ser Ala Ala Asn Val Gly Gly Ile Tyr Val Leu Arg Cys
465                 470                 475                 480

Ala Val Gly Ser Thr Leu Thr Glu Lys Arg His Val Arg Gln Ala Trp
            485                 490                 495

Glu Val Val Gln Glu Lys Ala Thr Ser Ile Leu Arg Ala
            500                 505
```

<210> SEQ ID NO 68
<211> LENGTH: 475
<212> TYPE: PRT
<213> ORGANISM: Amaranthus hypochondriacus
<300> PUBLICATION INFORMATION:
<308> DATABASE ACCESSION NUMBER: 32828676

<400> SEQUENCE: 68

```
Ser Leu His Asp Glu Thr Leu Gln Gly Ile Lys Tyr Val Thr Gln Tyr
1               5                   10                  15

Tyr Lys Asn Val Glu Lys Tyr Pro Val Val Ser Lys Val Lys Trp Gly
            20                  25                  30

Tyr Leu Arg Gln Ile Leu Pro Glu Asn Ala Pro Ser Leu Pro Glu Ser
        35                  40                  45

Ile Asp Gln Ile Leu Glu Asp Val Asp Thr Lys Ile Val Pro Gly Leu
    50                  55                  60

Thr His Trp Gln Ser Pro Asn Phe Phe Ala Tyr Phe Pro Ala Thr Ala
65                  70                  75                  80

Ser Asn Ala Ala Met Leu Gly Asp Ile Val Cys Ser Gly Leu Asn Val
                85                  90                  95

Val Gly Phe Ser Trp Ile Ser Pro Ala Ala Thr Glu Leu Glu Ala
            100                 105                 110

Ile Val Met Asp Trp Met Ala Lys Leu Leu Met Leu Pro Pro Thr Phe
            115                 120                 125

Leu Phe Ser Gly Gly Gly Gly Val Ile His Gly Ser Thr Cys Glu
    130                 135                 140

Ala Ile Val Cys Thr Gln Ala Ala Ala Arg Asp Val Ala Leu Asn Ile
145                 150                 155                 160

His Gly Glu Glu Lys Ile Thr Lys Leu Val Val Tyr Ala Ser Asp Gln
                165                 170                 175

Thr His Ile Ser Phe Gln Lys Ala Ala Lys Leu Ile Gly Ile Pro Pro
            180                 185                 190

Arg Asn Phe Arg Val Leu Pro Thr Ser Ala Thr Asp Phe Ala Leu
        195                 200                 205

Ser Pro Thr Thr Leu Arg Ala Ser Ile Glu Val Asp Leu Ser Gln Gly
    210                 215                 220

Leu Val Pro Phe Tyr Ile Cys Ala Thr Ile Gly Ala Thr Pro Ser Gly
225                 230                 235                 240
```

```
Ala Val Asp Pro Ile Asp Gly Leu Gly Gln Ile Ala Arg Asp Tyr Gly
            245                 250                 255

Ala Trp Leu His Val Asp Ala Ala Phe Ala Gly Asn Ala Cys Ile Cys
                260                 265                 270

Pro Glu Tyr Arg His Tyr Leu Asp Gly Val Glu Leu Ala Asp Ser Ile
            275                 280                 285

Ser Met Asn Pro His Lys Trp Leu Leu Thr Asn Met Glu Cys Ser Cys
        290                 295                 300

Leu Trp Leu Lys Asn Pro Lys Leu Met Val Asp Ser Leu Ser Thr Lys
305                 310                 315                 320

Pro Glu Ile Leu Asn Asn Lys Ala Thr Gln Ser Gly Asp Val Ile Asp
                325                 330                 335

Tyr Lys Asp Trp Gln Ile Ala Leu Ser Arg Arg Phe Arg Ala Leu Lys
            340                 345                 350

Leu Trp Ile Val Ile Arg Arg Tyr Gly Ser Thr Tyr Leu Met Asn His
        355                 360                 365

Val Arg Ser Asp Ile Glu Leu Ala Lys Tyr Phe Glu Ser Leu Ile Lys
    370                 375                 380

Gln Asp Glu Arg Phe Glu Leu Val Val Pro Arg Lys Phe Ser Leu Val
385                 390                 395                 400

Cys Phe Arg Met Lys Leu Val Gly Arg Glu Asp Val Glu Thr Leu Thr
                405                 410                 415

Asn Gln Lys Leu Leu Glu Asp Val Asn Ser Ser Gly Lys Ala Tyr Met
            420                 425                 430

Thr His Ala Val Ile Gly Gly Lys Phe Val Ile Arg Cys Ala Ile Gly
        435                 440                 445

Gly Thr Leu Thr Glu Lys Arg His Ile Asp Ser Leu Trp Lys Leu Ile
    450                 455                 460

Ile Glu Lys Val Pro Leu Thr Thr Cys Glu Leu
465                 470                 475

<210> SEQ ID NO 69
<211> LENGTH: 553
<212> TYPE: PRT
<213> ORGANISM: Brachypodium distachyon
<300> PUBLICATION INFORMATION:
<308> DATABASE ACCESSION NUMBER: 5g21770.1

<400> SEQUENCE: 69

Met Ser Ser Asn Ser Cys Pro Ala Ala Ala Ala Thr Phe Thr Thr
1               5                   10                  15

Pro Pro Gly Ala His Pro Leu Pro Leu Asp Ala Asp Ala Phe Arg Arg
                20                  25                  30

Gln Gly Arg Gln Val Ala Asp Phe Ile Ala Asp Tyr Tyr Asp Arg Ile
            35                  40                  45

Glu Asp Tyr Pro Val Arg Pro Asn Val Ser Pro Gly Phe Leu Ala Ala
        50                  55                  60

Gln Leu Pro Asp Ala Ala Pro Ser Trp Pro Glu Glu Pro Asp Ala Leu
65                  70                  75                  80

Ala Ser Ala Leu Arg Asp Val Arg Asp Leu Ile Leu Pro Gly Leu Thr
                85                  90                  95

His Trp Gln Ser Pro Arg His Phe Ala His Phe Ala Ala Thr Ala Ser
            100                 105                 110

Asn Ala Gly Ala Leu Gly Glu Phe Leu Ala Ala Gly Leu Asn Val Asn
        115                 120                 125
```

```
Pro Phe Thr Trp Ala Ala Ser Pro Ala Ala Glu Leu Glu Val Val
    130                 135                 140

Val Thr Asp Trp Leu Gly Gln Ala Leu Gly Leu Pro Glu Lys Leu Leu
145                 150                 155                 160

Phe Arg Gly Gly Ser Gly Gly Gly Thr Leu Leu Gly Thr Ser Cys
                165                 170                 175

Glu Ala Met Leu Cys Thr Ile Val Ala Ala Arg Asp Gln Lys Leu Leu
            180                 185                 190

Lys Ile Gly Glu Asp Arg Ile Gly Asp Leu Val Val Tyr Cys Ser Asp
        195                 200                 205

Gln Thr His Phe Ser Phe Lys Lys Ala Ala Arg Val Ala Gly Ile Arg
    210                 215                 220

Arg Gly Asn Cys Arg Val Ile Pro Thr Arg Phe Glu Asp Gly Phe Ala
225                 230                 235                 240

Leu Ser Pro Ala Ala Leu Ala Ala Val Arg Asp Asp Val Ala Arg
                245                 250                 255

Gly Lys Val Pro Leu Phe Leu Cys Ala Thr Val Gly Thr Thr Ala Thr
                260                 265                 270

Gly Ala Val Asp Pro Val Arg Glu Leu Cys Ala Val Gly Ala Gly
            275                 280                 285

His Gly Ser Gly Val Trp Val His Val Asp Ala Ala Tyr Ala Gly Gly
    290                 295                 300

Ala Cys Val Cys Pro Glu Phe Arg His Val Ala Ala Gly Ala Glu Glu
305                 310                 315                 320

Ala Asp Ser Phe Ser Thr Asn Pro His Lys Trp Leu Leu Ala Asn Met
                325                 330                 335

Asp Cys Cys Ala Leu Trp Ile Arg Arg Pro Gly Leu Leu Val Ala Ala
            340                 345                 350

Leu Gly Ala Gly Glu Asp Glu Asp Ala Ile Leu Asn Lys Ala Pro Pro
        355                 360                 365

Ala Ala Arg Gly Met Gln Ala Asp Leu Met Val Asp Tyr Lys Asp Trp
    370                 375                 380

Gln Val Pro Leu Ser Arg Arg Phe Arg Ala Leu Lys Leu Trp Leu Val
385                 390                 395                 400

Leu Arg Cys His Gly Val Glu Gly Leu Arg Gly Val Val Arg Gly His
                405                 410                 415

Val Arg Met Ala Ala Ala Phe Glu Ala Met Val Arg Ala Asp Pro Arg
            420                 425                 430

Phe Glu Val Pro Val Pro Pro Ala Phe Ala Leu Val Cys Phe Arg Leu
        435                 440                 445

Arg Pro Leu Ala Ala His Pro Gly Ser Ser Ser Gly Ile Asp Glu Val
    450                 455                 460

Asn Gly Arg Leu Leu Glu Ala Val Asn Gly Thr Gly Arg Ala Tyr Met
465                 470                 475                 480

Ser Gly Ala Val Val Gly Gly Ala Tyr Val Leu Arg Cys Ala Val Gly
                485                 490                 495

Asn Ser Leu Thr Glu Asp Arg His Val Arg Glu Ala Trp Ser Val Val
            500                 505                 510

Gln Glu Gln Ala Asp Ala Ile Leu Ala Pro Ser Asp Asp Glu Asp Arg
        515                 520                 525

Cys Cys Thr Asp Gln Ile Gln Thr Glu Met Glu Leu Gln Arg Arg Pro
    530                 535                 540
```

Leu Gly Ala Ala Ala Asp Val Phe Ala
545                 550

<210> SEQ ID NO 70
<211> LENGTH: 543
<212> TYPE: PRT
<213> ORGANISM: Brachypodium distachyon
<300> PUBLICATION INFORMATION:
<308> DATABASE ACCESSION NUMBER: 2g02360.1

<400> SEQUENCE: 70

Met Ala Pro Ala Ser Ser Lys Leu His Ala Ile Thr Asp Asp Lys Thr
1               5                   10                  15

Gln Gln Gln Asn Ser Ser Cys Pro Ala Ala Ser Asn Gly Ala Ile Glu
            20                  25                  30

Pro Ser Asn Ala Lys Cys Ala Ala Ser Ser Asn His Leu Leu Asp Ala
        35                  40                  45

Asp Glu Phe Arg Arg Gln Gly His Lys Val Ile Asp Phe Ile Ala Asp
    50                  55                  60

Tyr Tyr Ala Gly Ile Ala Asp Tyr Pro Val His Pro Ser Val Thr Pro
65                  70                  75                  80

Gly Phe Leu Leu Asn Gln Leu Pro Ala Asp Pro Pro Ser Arg Pro Glu
                85                  90                  95

Asp His Pro Asp Gly Ala Phe Gly Pro Ala Leu Gln Asp Val Arg Asp
            100                 105                 110

Val Ile Leu Pro Gly Met Thr His Trp Gln Ser Pro Arg His Phe Ala
        115                 120                 125

His Phe Pro Ala Ser Ser Ser Val Ala Gly Val Leu Gly Glu Ala Leu
    130                 135                 140

Ala Ala Gly Ile Asn Ala Val Pro Phe Thr Trp Ala Ala Ser Pro Ala
145                 150                 155                 160

Ala Ala Glu Leu Glu Met Val Ala Val Asp Trp Leu Gly Lys Ala Leu
                165                 170                 175

His Leu Pro Glu Ser Leu Leu Phe Ser Gly Ala Gly Gly Gly Thr Leu
            180                 185                 190

Leu Gly Thr Ser Cys Glu Ala Ile Leu Cys Ala Leu Val Ala Ala Arg
        195                 200                 205

Asp Arg Lys Leu Ala Asp Ile Gly Thr Asp Arg Ile Gly Asp Leu Val
    210                 215                 220

Val Tyr Gly Ser Asp Gln Thr His Phe Ala Leu Arg Lys Ala Ala Arg
225                 230                 235                 240

Ile Ala Gly Ile Arg His Asp Arg Cys Arg Glu Leu Gln Thr Cys Leu
                245                 250                 255

Ala Asp Met Phe Ala Leu Ser Pro Ala Ala Leu Ser Ala Met Asp
            260                 265                 270

Ala Asp Ala Gly Ala Gly Leu Val Pro Leu Phe Leu Cys Ala Thr Val
    275                 280                 285

Gly Thr Thr Gln Thr Thr Ala Val Asp Gln Val Gly Ala Leu Cys Ala
        290                 295                 300

Ala Ala Ala Pro His Gly Val Trp Val His Val Asp Ala Ala Tyr Ala
305                 310                 315                 320

Gly Ser Ala Leu Val Cys Pro Glu Leu Ala Arg Asp Ala Ile Asp Gly
                325                 330                 335

Ile Glu Val Val Asp Ser Phe Ser Met Asn Ala His Lys Trp Leu Leu
            340                 345                 350

```
Ala Asn Thr Asp Cys Cys Ala Leu Trp Val Lys Gln Pro Lys Leu Leu
        355                 360                 365

Val Val Ser Leu Gly Thr Gln Asn Glu Glu Leu Ile Leu Arg Asp Ala
    370                 375                 380

Ala Ala Glu Gly His Asp Val Val Asp Tyr Lys Asp Trp Ala Ile Thr
385                 390                 395                 400

Leu Thr Arg Arg Phe Arg Ala Leu Lys Leu Trp Leu Val Phe Arg Cys
                405                 410                 415

Tyr Gly Val Glu Gly Leu Arg Glu His Ile Arg Ala His Val Arg Met
                420                 425                 430

Ala Ala Leu Phe Glu Gly Leu Val Lys Asp Asp Pro Arg Phe Glu Val
            435                 440                 445

Val Thr Glu Arg Arg Phe Ala Leu Val Cys Phe Arg Leu Arg Ala Pro
    450                 455                 460

Asp Gln Leu Met Asp Glu Gly Asn Glu Lys Lys Lys Thr Thr Ala Ala
465                 470                 475                 480

Ala Asn Glu Leu Asn Arg Arg Leu Leu Arg Glu Val Asn Gly Val Ala
                485                 490                 495

Leu Gly Pro Tyr Met Ser Ala Val Val Gly Gly Ile Tyr Ile Leu
            500                 505                 510

Arg Cys Ala Val Gly Ser Thr Leu Thr Glu Glu Arg His Val Arg Gln
    515                 520                 525

Ala Trp Glu Val Val Gln Glu Arg Ala Thr Ser Ile Leu Arg Gly
            530                 535                 540

<210> SEQ ID NO 71
<211> LENGTH: 588
<212> TYPE: PRT
<213> ORGANISM: Sorghum bicolor
<300> PUBLICATION INFORMATION:
<308> DATABASE ACCESSION NUMBER: 009G192600.1

<400> SEQUENCE: 71

Met Gly Val Ala Val Thr Ala Glu Val Val His Ala Arg Ser Cys Lys
1               5                   10                  15

Gly Thr Pro Pro Val Gly Ala Ala Ser Val Met Val Trp Asp Gly
            20                  25                  30

Ala Gly Gln Gly Tyr Ser Cys Gln Pro Val Gly Thr Thr Thr Ala Asn
        35                  40                  45

Gly Gly Thr Thr Pro Ala Ala Pro Val Ala Ile Ala Met Pro Ser Leu
    50                  55                  60

Pro His Pro Leu Leu Asp Ala Asp Glu Phe Arg Arg Gln Gly Arg Leu
65                  70                  75                  80

Val Val Asp Phe Ile Ala Asp Tyr Tyr Ala Arg Ile Asp Glu Tyr Pro
                85                  90                  95

Val Arg Pro Ala Val Ala Pro Gly Phe Leu Ala Arg Gln Leu Pro Glu
            100                 105                 110

Thr Ala Pro Ala Arg Pro Glu Pro Asp Ala Leu Ala Ala Leu Arg
        115                 120                 125

Asp Val Arg Asp Leu Ile Leu Pro Gly Val Thr His Trp Gln Ser Pro
130                 135                 140

Arg His Phe Ala His Phe Ala Ala Thr Ala Ser Asn Val Gly Ala Leu
145                 150                 155                 160

Gly Glu Ala Leu Ala Ala Gly Leu Asn Ile Asn Pro Thr Phe Thr Trp Ala
                165                 170                 175
```

```
Ala Ser Pro Ala Ala Thr Glu Leu Glu Val Val Thr Asp Trp Leu
            180                 185                 190

Gly Lys Ala Leu His Leu Pro Glu Ser Leu Leu Phe Ser Gly Gly
        195                 200                 205

Gly Gly Thr Leu Leu Gly Thr Ser Cys Glu Ala Met Leu Cys Thr Ile
        210                 215                 220

Val Ala Ala Arg Asp Arg Lys Leu Ala Glu Val Gly Glu Arg Met
225                 230                 235                 240

Gly Asp Leu Val Val Tyr Cys Ser Asp Gln Thr His Phe Ser Phe Gln
                245                 250                 255

Lys Ala Ala Arg Ile Ala Gly Ile Arg Arg Gly Asn Cys Arg Glu Ile
            260                 265                 270

Pro Thr Ser Met Glu Ala Gly Phe Thr Leu Ser Pro Lys Ala Leu Ala
            275                 280                 285

Ala Ala Val Arg Ala Asp Glu Ala Ala Gly Arg Val Pro Leu Phe Leu
            290                 295                 300

Cys Ala Thr Val Gly Thr Thr Pro Thr Ala Ala Val Asp Pro Val Arg
305                 310                 315                 320

Glu Leu Cys Ala Ala Val Ala Gly Arg Gly Val Trp Val His Val Asp
                325                 330                 335

Ala Ala Tyr Ala Gly Ala Ala Ser Val Cys Pro Glu Leu Arg His Ala
            340                 345                 350

Val Ala Gly Val Glu Arg Val Asp Ser Phe Ser Thr Asn Pro His Lys
            355                 360                 365

Trp Leu Leu Ala Asn Met Asp Cys Cys Ala Leu Trp Val Arg Arg Pro
370                 375                 380

Ala Ala Leu Thr Ala Ala Leu Gly Thr Asp His Asp Val Ile Leu Lys
385                 390                 395                 400

Asp Pro Ser Ala Gln Ala Ala Gln Glu Gly Gly Ala Val Val Asp Tyr
                405                 410                 415

Lys Asp Trp Gln Val Ala Leu Ser Arg Arg Phe Arg Ala Leu Lys Leu
            420                 425                 430

Trp Leu Val Leu Arg Cys His Gly Val Glu Gly Leu Arg Gly Leu Val
            435                 440                 445

Arg Ala His Val Arg Met Ala Ala Ala Phe Glu Ala Met Val Arg Thr
450                 455                 460

Asp Ala Arg Phe Glu Val Pro Val Pro Arg Gln Phe Ala Leu Val Cys
465                 470                 475                 480

Phe Arg Leu Arg Ala Ala Val Leu Val Gly Glu Lys Arg Ala
                485                 490                 495

Arg Asp Gly Asp Asp Glu Val Val Thr Ala Gly Asn Glu Leu Asn Arg
            500                 505                 510

Arg Leu Leu Glu Ala Val Asn Ala Thr Gly Arg Val Tyr Met Ser Ser
            515                 520                 525

Ala Val Val Gly Gly Thr Tyr Ile Leu Arg Cys Ala Ile Gly Asn Ser
            530                 535                 540

Leu Thr Glu Glu Arg His Val Arg Glu Ala Trp Ser Val Val Gln Glu
545                 550                 555                 560

Gln Ala Thr Ala Ile Leu Ala Ala Arg Arg Pro Thr Ala Arg Thr
                565                 570                 575

Asn Arg Arg Thr Val Arg Arg Ala His Ala Ala Leu
            580                 585
```

<210> SEQ ID NO 72
<211> LENGTH: 502
<212> TYPE: PRT
<213> ORGANISM: Kalanchoe laxiflora
<300> PUBLICATION INFORMATION:
<308> DATABASE ACCESSION NUMBER: 0994s0009.1

<400> SEQUENCE: 72

```
Met Gly Ser Leu Gln Ser Pro His Asp Pro Asn Ala Phe Asn Pro Met
1               5                   10                  15

Asp Val Ala Glu Leu Ser Ile Glu Ser Arg Leu Val Met Asp Phe Ile
            20                  25                  30

Thr Gln Tyr Tyr Gln Thr Leu Glu Thr Arg Pro Val Gln Pro Arg Val
        35                  40                  45

Lys Pro Gly Phe Leu Thr Gly Gln Leu Pro Glu Lys Pro Pro Phe His
50                  55                  60

Ala Glu Ser Met Glu Glu Ile Leu Ser Asp Val Ser Glu Lys Ile Val
65                  70                  75                  80

Pro Gly Leu Thr His Trp Gln Ser Pro Asn Phe His Ala Tyr Phe Pro
                85                  90                  95

Ala Ser Ser Ser Asn Ala Gly Leu Leu Gly Glu Met Leu Cys Ser Gly
            100                 105                 110

Leu Ser Val Ile Gly Phe Thr Trp Asn Ser Ser Pro Ala Ala Thr Glu
        115                 120                 125

Leu Glu Asn Val Val Val Asp Trp Leu Ala Asp Met Leu Asn Leu Pro
    130                 135                 140

Pro Ser Phe Arg Phe Ser Gly Gly Gly Gly Val Leu Gln Ser Asn
145                 150                 155                 160

Thr Cys Glu Ala Val Leu Cys Thr Leu Ala Ala Arg Asp Lys Val
                165                 170                 175

Leu Glu Arg Ile Gly Asp Asp Lys Ile Asn Lys Leu Val Val Tyr Cys
            180                 185                 190

Ser Asp Gln Thr His Phe Thr Leu His Lys Gly Ala Lys Leu Ile Gly
        195                 200                 205

Ile Arg Arg Ala Asn Ile Lys Ser Ile Ser Thr Arg Arg Glu Asn Gly
    210                 215                 220

Phe Gly Leu Cys Pro Asn Asp Leu Arg Asn Ala Ile Lys Ser Asp Leu
225                 230                 235                 240

Glu Ala Gly Leu Val Pro Phe Tyr Leu Cys Gly Thr Ile Gly Thr Thr
                245                 250                 255

Ala Leu Gly Ala Val Asp Pro Ile Lys Glu Leu Gly Lys Val Ala Arg
            260                 265                 270

Glu Phe Asp Leu Trp Phe His Ile Asp Ala Ala Tyr Gly Gly Ser Ala
        275                 280                 285

Cys Ile Cys Pro Glu Phe Arg His Tyr Leu Asp Gly Val Glu Leu Val
    290                 295                 300

Asp Ser Ile Ser Met Asn Ala His Lys Trp Leu Leu Ser Asn Leu Asp
305                 310                 315                 320

Cys Cys Phe Leu Trp Leu Gln Asn Pro Lys Cys Leu Ile Gln Cys Leu
                325                 330                 335

Ala Ala Glu Gly Glu Phe Leu Lys Gly Ser Gly Glu Met Val Asp Tyr
            340                 345                 350

Lys Asp Trp Gln Ile Ser Leu Ser Arg Arg Phe Arg Ala Ile Lys Met
        355                 360                 365

Trp Met Val Phe Arg Arg Tyr Gly Val Ser Asn Leu Met Glu His Ile
```

```
                370                 375                 380
Arg Ser Asp Val Ser Met Ala Ala Arg Phe Glu Glu Met Val Ala Ala
385                 390                 395                 400

Asp Asp Arg Phe Glu Ile Val Phe Pro Arg Lys Phe Ala Leu Val Cys
                405                 410                 415

Phe Lys Leu Asn Thr Lys Gly Ser Val Gln His Gly Glu Val Asp Gly
            420                 425                 430

Glu Asp Gly Leu Asp Gly Asp Ser Val Leu Thr Arg Glu Leu Met Gly
        435                 440                 445

Arg Val Asn Ser Ser Gly Lys Ala Tyr Leu Ser Gly Val Glu Met Gly
    450                 455                 460

Arg Ile Phe Phe Ile Arg Cys Val Ile Gly Ser Ser Leu Thr Glu Glu
465                 470                 475                 480

Arg His Val Asp Asn Leu Trp Asn Leu Ile Gln Glu Lys Thr Gln Ser
                485                 490                 495

Ile Met Pro Arg Arg Ala
            500

<210> SEQ ID NO 73
<211> LENGTH: 509
<212> TYPE: PRT
<213> ORGANISM: Kalanchoe laxiflora
<300> PUBLICATION INFORMATION:
<308> DATABASE ACCESSION NUMBER: 0003s0173.1

<400> SEQUENCE: 73

Met Gly Ser Leu Ser Ser Pro Arg Asp Leu Thr Lys Pro Phe Asn Pro
1               5                   10                  15

Leu Asp Pro Thr Glu Leu Ala Val Glu Ser Ser Leu Val Thr Asp Phe
            20                  25                  30

Ile Ala Glu Tyr Tyr Arg Thr Val Glu Gln Arg Pro Val Gln Pro His
        35                  40                  45

Val Thr Pro Gly Phe Leu Thr Ser Gln Leu Pro Ser Ala Ala Pro Phe
    50                  55                  60

Ala Ser Glu Ser Val Glu Ser Ile Leu Gln Asp Val Tyr Asp Lys Ile
65                  70                  75                  80

Leu Pro Gly Leu Val Gln Trp Gln Ser Pro Asn Phe His Ala Tyr Tyr
                85                  90                  95

Pro Ala Thr Cys Ser Asn Ala Gly Leu Leu Gly Glu Met Leu Cys Ser
            100                 105                 110

Gly Leu Asn Val Val Gly Phe Thr Trp Ser Ala Ser Pro Ala Ala Ala
        115                 120                 125

Glu Leu Glu Gln Val Val Asp Trp Met Gly Lys Met Met Gly Leu
    130                 135                 140

Pro Gln Ser Phe Leu Phe Ser Gly Gly Gly Gly Val Leu Gln Gly
145                 150                 155                 160

Ser Thr Cys Glu Ala Val Val Cys Thr Leu Ala Ala Arg Asp Arg
                165                 170                 175

Ala Leu Glu Arg Val Gly Asp Asp Met Phe Asn Lys Leu Val Val Tyr
            180                 185                 190

Cys Ser Asp Gln Thr His Phe Thr Leu Lys Lys Gly Ser Lys Leu Val
        195                 200                 205

Gly Ile Arg Pro Ala Asn Val Lys Ala Ile Lys Thr Thr Lys Asn Asn
    210                 215                 220

Glu Tyr Gly Leu Cys Pro Thr Asp Leu Arg Asn Leu Val Ala Ser Asp
```

-continued

```
            225                 230                 235                 240

Val Lys Ala Gly Phe Ile Pro Ile Tyr Leu Cys Gly Thr Ile Gly Thr
                245                 250                 255

Thr Ala Phe Gly Ala Val Asp Pro Ile Arg Glu Leu Gly Lys Val Ala
                260                 265                 270

Arg Glu Phe Asn Met Trp Phe His Val Asp Ala Ala Tyr Ala Gly Ser
                275                 280                 285

Ala Phe Ile Cys Pro Glu Phe Arg His Tyr Met Asp Gly Val Glu Leu
290                 295                 300

Ala Asp Ser Phe Ser Thr Asn Pro His Lys Trp Leu Leu Ser Asn Met
305                 310                 315                 320

Asp Cys Cys Val Leu Trp Leu Lys Phe Pro Lys Arg Val Ile Lys Ser
                325                 330                 335

Leu Ala Ala Glu Gly Val Phe Leu Glu Gly Gly Ser Glu Thr Met Val
                340                 345                 350

Asp Tyr Lys Asp Trp Gln Ile Ala Leu Ser Arg Arg Phe Arg Ala Ile
                355                 360                 365

Lys Leu Trp Met Val Ile Lys Arg Tyr Gly Leu Lys Asn Leu Ile Ser
370                 375                 380

His Ile Arg Ser Asp Val Ser Met Ala Lys Arg Phe Glu Glu Leu Leu
385                 390                 395                 400

Leu Ser Asp Arg Arg Phe Glu Val Val Phe Pro Arg Lys Phe Ser Leu
                405                 410                 415

Val Cys Phe Lys Leu Asp Val Met Lys Asn Val Pro Glu Val Val Asp
                420                 425                 430

Glu Asp Asp Gly Glu Leu Ser His Asp Ser Lys Leu Thr Arg Glu Leu
                435                 440                 445

Met Ala Ser Val Asn Val Thr Gly Lys Ala Phe Leu Thr Gly Val Arg
                450                 455                 460

Leu Gly Arg Ile Phe Phe Ile Arg Cys Ala Ile Gly Ser Thr Leu Thr
465                 470                 475                 480

Glu Asp Arg His Ile Gln Asp Leu Trp Lys Leu Ile Gln Glu Lys Ala
                485                 490                 495

His Lys Ile Cys Ala Asn His Asp Leu Lys Phe Arg Val
                500                 505
```

<210> SEQ ID NO 74
<211> LENGTH: 607
<212> TYPE: PRT
<213> ORGANISM: Panicum hallii
<300> PUBLICATION INFORMATION:
<308> DATABASE ACCESSION NUMBER: 32512198

<400> SEQUENCE: 74

```
Met Ala Ile Leu Asn His Gly Asp Thr Thr Thr Ala Asn Gly Ser Ser
1               5                   10                  15

Pro Ala Asp Ala Ala Val Ala Pro Ala Met Pro Ser Leu Val Gln
                20                  25                  30

Pro Pro Leu Asp Ala Asp Glu Phe Arg Arg Gln Gly Arg Leu Val Val
                35                  40                  45

Asp Phe Ile Ala Asp Tyr Tyr Thr Arg Ile Asp Glu His Pro Val Arg
                50                  55                  60

Pro Ala Val Ala Pro Gly Phe Leu Ala Arg Gln Leu Pro Asp Thr Ala
65                  70                  75                  80

Pro Ala Arg Pro Glu Pro Gly Asp Asp Ala Leu Ala Ala Ala Leu Arg
```

-continued

```
                85                  90                  95
Asp Val Arg Asp Leu Ile Leu Pro Gly Val Thr His Trp Gln Ser Pro
            100                 105                 110
Arg His Phe Ala His Phe Ala Ala Thr Ala Ser Asn Val Gly Ala Leu
            115                 120                 125
Gly Glu Ala Leu Thr Ala Gly Leu Asn Ile Asn Pro Phe Thr Trp Ala
            130                 135                 140
Ala Ser Pro Ala Ala Thr Glu Leu Glu Val Val Thr Asp Trp Leu
145                 150                 155                 160
Gly Lys Ala Leu His Leu Pro Glu Ser Leu Leu Phe Ser Gly Gly
                165                 170                 175
Gly Ala Thr Leu Leu Gly Thr Ser Cys Glu Ala Met Leu Cys Thr Leu
            180                 185                 190
Val Ala Ala Arg Asp Arg Lys Leu Ala Glu Ile Gly Glu Glu Arg Ile
            195                 200                 205
Gly Asp Leu Val Val Tyr Cys Ser Asp Gln Thr His Phe Ser Phe Gln
            210                 215                 220
Lys Ala Ala Arg Ile Ala Gly Ile Arg Arg Gly Asn Tyr Arg Glu Ile
225                 230                 235                 240
Pro Thr Ser Arg Glu Ser Gly Phe Thr Leu Ser Pro Lys Val Leu Arg
                245                 250                 255
Ala Ala Val Arg Ala Asp Glu Ala Ala Gly Arg Val Pro Leu Phe Leu
            260                 265                 270
Cys Ala Thr Val Gly Thr Thr Pro Thr Ala Ala Val Asp Pro Leu Arg
            275                 280                 285
Glu Leu Cys Ala Thr Val Ala Gly His Gly Val Trp Val His Val Asp
            290                 295                 300
Ala Ala Tyr Ala Gly Ala Ala Cys Val Cys Pro Glu Phe Arg His Ala
305                 310                 315                 320
Ile Ala Gly Ala Glu Ala Val Asp Ser Phe Ser Thr Asn Pro His Lys
                325                 330                 335
Trp Leu Leu Ala Asn Met Asp Cys Cys Ala Leu Trp Val Arg Arg Pro
            340                 345                 350
Glu Ala Leu Thr Ala Ala Leu Gly Thr Asp His Asp Val Ile Leu Lys
            355                 360                 365
Asp Pro Ser Ser Glu Arg Asp Cys Gly Arg Gly Val Val Asp Tyr Lys
            370                 375                 380
Asp Trp Gln Val Ala Leu Ser Arg Arg Phe Arg Ala Leu Lys Leu Trp
385                 390                 395                 400
Leu Val Leu Arg Cys His Gly Val Glu Gly Leu Arg Gly Phe Val Arg
                405                 410                 415
Ala His Val Arg Met Ala Ala Phe Glu Asp Met Val Arg Ala Asp
            420                 425                 430
Ala Arg Phe Glu Val Pro Val Pro Arg Gln Phe Ala Leu Val Cys Phe
            435                 440                 445
Arg Leu Arg Ser Ala Ala Ala Gly Glu Lys Arg Ala Arg Asp Gly Asp
            450                 455                 460
Asp Ala Glu Pro Asn Glu Leu Asn Arg Leu Leu Glu Ala Val Asn
465                 470                 475                 480
Ala Thr Gly Arg Ala Tyr Met Ser Ser Ala Val Val Gly Gly Ile Tyr
                485                 490                 495
Val Leu Arg Cys Ala Ile Gly Asn Ser Leu Thr Glu Glu Arg His Val
            500                 505                 510
```

```
Arg Glu Ala Trp Cys Val Val Gln Glu Gln Ala Thr Val Val Leu Ala
        515                 520                 525

Ala Ala Ala Cys Thr Glu Glu Arg Ala Val His Ser Ala Arg Cys Ala
    530                 535                 540

Asp Ala Pro Ala Val Pro Val Gln Asn Glu Gly Tyr Gly Glu
545                 550                 555                 560

Pro Thr Ser Ile Ala Ala Lys Ile Phe Gly Thr Ser Ile Ala Arg Cys
                565                 570                 575

Ser Ile Lys Ser Glu Ala Ser Thr Tyr His Ser Trp Ser Thr Leu Trp
        580                 585                 590

Arg Thr Leu Met Phe Lys Leu Leu Thr Trp Ile Ile Ser Arg Leu
        595                 600                 605

<210> SEQ ID NO 75
<211> LENGTH: 510
<212> TYPE: PRT
<213> ORGANISM: Prunus persica
<300> PUBLICATION INFORMATION:
<308> DATABASE ACCESSION NUMBER: 6G202600.1

<400> SEQUENCE: 75

Met Thr Ser Ala Leu Asp Pro Val Glu Phe Arg Arg Gln Gly His Met
1               5                   10                  15

Met Val Asp Phe Ile Ala Asp Tyr Tyr Gln Asn Ile Asp Lys Tyr Pro
            20                  25                  30

Val Leu Ser Gln Val Asp Pro Gly Tyr Leu Arg Lys Arg Leu Pro Glu
        35                  40                  45

Ser Ala Pro Asp Asn Pro Glu Pro Ile Glu Thr Ile Leu Gln Asp Val
    50                  55                  60

Gln Glu His Ile Val Pro Gly Leu Thr His Trp Gln Ser Pro Ser Phe
65                  70                  75                  80

Phe Ala Tyr Phe Ala Ser Asn Val Ser Ile Ala Gly Phe Leu Gly Glu
                85                  90                  95

Met Leu Ser Thr Gly Phe Asn Val Val Gly Phe Asn Trp Val Ser Ser
            100                 105                 110

Pro Ala Ala Thr Glu Leu Glu Ser Ile Val Met Asp Trp Leu Gly Asn
        115                 120                 125

Leu Leu Ser Leu Pro Lys Ser Phe Leu Phe Ser Gly Asn Gly Gly Gly
    130                 135                 140

Val Ile His Gly Ser Thr Cys Glu Ala Ile Val Cys Thr Met Ala Ala
145                 150                 155                 160

Ser Arg Asp Gln Met Leu Ser Arg Ile Gly Gly Asp Asn Ile Gly Lys
                165                 170                 175

Leu Val Val Tyr Gly Ser Asp Gln Thr His Ser Ala Leu Gln Lys Ala
            180                 185                 190

Ser Gln Ile Val Gly Ile Asn Pro Lys Asn Phe Arg Ala Ile Glu Ala
        195                 200                 205

Thr Arg Ser Thr Thr Phe Ala Leu Ser Pro Glu Ser Leu Lys Leu Ala
    210                 215                 220

Ile Ser Ser Asp Ile Glu Ala Gly Leu Val Pro Leu Phe Leu Cys Ala
225                 230                 235                 240

Thr Val Gly Thr Thr Ala Thr Thr Ala Val Asp Pro Leu Gly Pro Leu
                245                 250                 255

Cys Asp Val Ala Lys His His Gly Met Trp Val His Val Asp Ala Ala
            260                 265                 270
```

-continued

```
Tyr Ala Gly Ser Ala Cys Ile Cys Pro Glu Phe Arg His Phe Ile Asp
            275                 280                 285

Gly Ile Glu Gly Val Asp Ser Phe Ser Phe Asn Ala His Lys Trp Phe
290                 295                 300

Phe Thr Gly Leu Asp Cys Cys Cys Leu Trp Val Lys Asn Pro Gly Ala
305                 310                 315                 320

Leu Ile Ser Ser Leu Ser Ala Asn Pro Glu Phe Leu Arg Asn Lys Pro
            325                 330                 335

Thr Asp Ser Lys Gln Val Val Asp Tyr Lys Asp Trp Gln Ile Ala Leu
            340                 345                 350

Ser Arg Arg Phe Arg Ala Met Lys Leu Trp Leu Val Leu Arg Ser Tyr
            355                 360                 365

Gly Val Val Asn Leu Arg Asn Phe Leu Arg Ser His Val Lys Met Ala
370                 375                 380

Lys Leu Phe Glu Gly Leu Val Ala Met Asp Gln Arg Phe Glu Ile Val
385                 390                 395                 400

Val Pro Arg Asn Phe Ser Met Val Pro Pro Thr Thr Pro Thr Ser Asn
                405                 410                 415

Ser Phe His Gln Asn Gly Ile Glu Ile Asn Val Glu Lys Cys Thr Asn
            420                 425                 430

Glu Val Asn Cys Lys Leu Leu Glu Ala Ile Asn Ala Ser Gly Arg Val
            435                 440                 445

Phe Met Thr His Ala Met Val Gly Gly Met Tyr Val Ile Arg Cys Ala
450                 455                 460

Val Gly Val Thr Gln Thr Glu Glu Lys His Ile Ala Met Ala Trp Lys
465                 470                 475                 480

Val Val Gln Glu His Ala Asp Val Ile Leu Lys Asn Asn Gly Asp Asp
            485                 490                 495

Gly Asp Ala Asn Leu Lys Leu Pro Leu Leu Asp Lys Ile Ala
            500                 505                 510

<210> SEQ ID NO 76
<211> LENGTH: 510
<212> TYPE: PRT
<213> ORGANISM: Prunus persica
<300> PUBLICATION INFORMATION:
<308> DATABASE ACCESSION NUMBER: 4G086700.1

<400> SEQUENCE: 76

Met Gly Ser Leu Asn Phe Asp His Pro Gln Glu Asn Asn Ser Ala His
1               5                   10                  15

Met Ser Gly Pro Leu Asp Leu Val Glu Leu Arg Arg Gln Gly His Met
            20                  25                  30

Ile Ile Asp Phe Ile Thr Asp Tyr Tyr Gln Asn Ile Glu Lys His Pro
        35                  40                  45

Val Leu Ser Gln Val Gln Pro Gly Tyr Leu Lys Gln Arg Leu Pro Glu
    50                  55                  60

Ser Ala Pro Tyr Asn Pro Glu Pro Ile Glu Thr Ile Leu Arg Asp Val
65                  70                  75                  80

Gln Asp His Ile Val Pro Gly Leu Thr His Trp Gln Ser Pro Asn His
                85                  90                  95

Phe Ala Tyr Phe Pro Ala Thr Ile Ser Thr Ala Gly Phe Leu Gly Glu
            100                 105                 110

Met Leu Thr Thr Cys Phe Asn Val Val Gly Phe Asn Trp Met Ala Ser
        115                 120                 125
```

```
Pro Ala Ala Thr Glu Leu Glu Thr Ile Val Met Asp Trp Leu Gly Asp
        130                 135                 140

Met Leu Lys Leu Pro Asn Ser Phe Leu Phe Ser Gly Thr Gly Gly Gly
145                 150                 155                 160

Val Leu His Gly Ser Thr His Glu Ser Val Val Cys Thr Met Ala Ala
            165                 170                 175

Ala Arg Asp Gln Ile Leu Ser Arg Ile Gly Glu Glu Asn Ile Gly Lys
        180                 185                 190

Leu Val Val Tyr Gly Ser Asp Gln Thr His Ser Val Ile Gln Lys Val
            195                 200                 205

Ser Gln Ile Val Gly Ile Pro Ser Lys Asn Phe Arg Ala Ile Glu Thr
        210                 215                 220

Thr Ile Ser Ser Ser Phe Thr Leu Ser Pro Glu Thr Leu Arg Leu Thr
225                 230                 235                 240

Val Cys Ser Asp Met Glu Ala Gly Leu Val Pro Phe Tyr Leu Cys Ala
            245                 250                 255

Thr Val Gly Thr Thr Ala Thr Thr Ala Val Asp Pro Leu Gly Pro Leu
        260                 265                 270

Cys Asp Val Ala Lys Asp Tyr Gly Met Trp Val His Val Asp Ala Ala
        275                 280                 285

Tyr Ala Gly Ser Ala Cys Ile Cys Pro Glu Phe Arg Gln Tyr Ile Asp
        290                 295                 300

Gly Ile Glu Gly Ala Asn Ser Phe Ser Phe Asn Ala Gln Lys Trp Phe
305                 310                 315                 320

Phe Thr Ala Leu Asp Cys Cys Cys Leu Trp Val Lys Asn Pro Ser Ala
            325                 330                 335

Leu Thr Lys Ser Met Ser Thr Asp Leu Glu Val Leu Arg Asn Lys Ala
        340                 345                 350

Ser Glu Ser Lys Arg Val Val Asp Phe Lys Asp Trp Gln Ile Ala Leu
        355                 360                 365

Thr Arg Arg Phe Arg Ala Ile Lys Leu Trp Leu Val Leu Arg Ser Tyr
        370                 375                 380

Gly Val Ala Asn Leu Arg Asn Phe Leu Arg Ser His Val Lys Met Ala
385                 390                 395                 400

Lys Arg Phe Glu Gly Leu Val Arg Thr Asp Glu Arg Phe Glu Val Val
            405                 410                 415

Val Pro Arg Ile Phe Ala Leu Val Cys Phe Arg Ile Ser Pro Ser Ala
        420                 425                 430

Ile Ser Lys Ala Asn Pro Thr Pro Ser Asp Glu Lys Cys Val Asn Glu
        435                 440                 445

Val Asn Cys Lys Leu Leu Glu Ala Ile Asn Gly Ser Gly Trp Val Tyr
450                 455                 460

Met Thr His Ala Val Val Gly Gly Met Tyr Val Leu Arg Cys Ala Ile
465                 470                 475                 480

Gly Ala Ser Leu Thr Lys Glu Lys His Val Ala Met Ala Trp Lys Val
            485                 490                 495

Val Gln Glu His Val Asp Ala Ile Leu Pro Leu Thr Met Tyr
            500                 505                 510

<210> SEQ ID NO 77
<211> LENGTH: 533
<212> TYPE: PRT
<213> ORGANISM: Prunus persica
<300> PUBLICATION INFORMATION:
```

<308> DATABASE ACCESSION NUMBER: 4G087100.1

<400> SEQUENCE: 77

```
Met Met Gly Ser Val Glu Phe Glu His Pro Gln Glu Asn Asn Ser Ala
1               5                   10                  15

His Met Thr Thr Ser Pro Leu Asp Pro Glu Glu Phe Arg Arg Gln Gly
            20                  25                  30

His Met Val Ile Asp Phe Ile Ala Asp Tyr Tyr Lys Thr Ile Glu Lys
        35                  40                  45

Tyr Pro Val Leu Ser Gln Val Gln Pro Gly Tyr Leu Lys Lys Arg Leu
50                  55                  60

Pro Glu Ser Ala Pro Tyr Asp Pro Glu Pro Ile Glu Thr Ile Leu Gln
65                  70                  75                  80

Asp Val Gln Asp His Leu Val Pro Gly Leu Thr His Trp Leu Ser Pro
                85                  90                  95

Asn His Phe Gly Tyr Phe Pro Ala Ala Ile Ser Thr Ala Ala Phe Leu
            100                 105                 110

Gly Glu Met Leu Thr Thr Gly Phe Asn Val Val Gly Phe Asn Trp Met
        115                 120                 125

Ala Ser Pro Ala Ala Thr Glu Leu Glu Asn Ile Val Met Asp Trp Leu
130                 135                 140

Gly Asp Met Leu Lys Leu Pro Lys Ser Phe Leu Phe Ser Gly Asn Gly
145                 150                 155                 160

Gly Gly Val Leu Gln Gly Thr Thr Cys Glu Ala Ile Val Cys Thr Met
                165                 170                 175

Ala Ala Ala Arg Asp Gln Met Leu Arg Gln Ile Gly Arg Glu Asn Ile
            180                 185                 190

Gly Lys Leu Val Val Tyr Gly Ser Asp Gln Thr His Ser Ala Leu Gln
        195                 200                 205

Lys Ala Ser Gln Ile Val Gly Ile His Pro Lys Asn Phe Arg Ala Ile
210                 215                 220

Glu Thr Thr Thr Ser Thr Ser Phe Ala Leu Ser Pro Glu Val Leu Lys
225                 230                 235                 240

Ser Thr Ile Cys Ser Asp Ile Glu Ala Gly Leu Val Pro Leu Phe Leu
                245                 250                 255

Cys Ala Thr Val Gly Thr Thr Ala Ile Thr Ala Val Asp Pro Leu Gly
            260                 265                 270

Pro Leu Cys Glu Val Ala Lys Glu His Asp Met Trp Val His Val Asp
        275                 280                 285

Ala Ala Tyr Ala Gly Ser Ala Phe Ile Cys Pro Glu Phe Gln Tyr Phe
290                 295                 300

Ile Asp Gly Val Glu Gly Ala Asp Ser Phe Ser Leu Asn Ala His Lys
305                 310                 315                 320

Trp Phe Phe Thr Thr Leu Asp Cys Cys Cys Leu Trp Val Lys Asn Pro
                325                 330                 335

Ser Ala Leu Val Ser Ser Leu Ser Thr Asn Pro Glu Phe Leu Arg Asn
            340                 345                 350

Lys Ala Thr Asp Ser Lys Gln Val Val Asp Tyr Lys Asp Trp Gln Ile
        355                 360                 365

Ala Leu Ser Arg Arg Phe Lys Ala Ile Lys Leu Trp Leu Val Leu Arg
370                 375                 380

Ser Tyr Gly Val Gly Asn Leu Arg Asn Phe Leu Arg Ser His Val Lys
385                 390                 395                 400
```

```
Met Ala Lys Ile Phe Glu Gly Leu Val Gly Met Asp Lys Arg Phe Glu
                405                 410                 415

Ile Val Ala Pro Arg His Phe Ser Leu Val Cys Phe Arg Val Ser Pro
            420                 425                 430

Ser Ala Ile Ser Lys Ala Asn Pro Ser Leu Ser Asp His Asp Asn Gly
            435                 440                 445

Lys Leu Lys Ala His Asn Tyr Glu Leu Leu Asn Gly Val Lys Cys Val
    450                 455                 460

Val Asn Glu Val Asn Ser Lys Leu Leu Glu Ala Ile Asn Gly Ser Gly
465                 470                 475                 480

Leu Val Tyr Met Ser His Ala Val Val Gly Gly Met Tyr Val Leu Arg
                485                 490                 495

Cys Ala Ile Gly Ala Ser Leu Thr Glu Glu Lys His Val Ala Met Ala
            500                 505                 510

Trp Lys Val Val Gln Glu His Ala Asp Ala Ile Leu Gly Thr Lys Ile
        515                 520                 525

Ile Val Asp Gln Thr
        530

<210> SEQ ID NO 78
<211> LENGTH: 502
<212> TYPE: PRT
<213> ORGANISM: Medicago truncatula
<300> PUBLICATION INFORMATION:
<308> DATABASE ACCESSION NUMBER: 31073039

<400> SEQUENCE: 78

Met Asn Thr Ser Ser Asn Pro Pro Gln Ser Asp Pro Gln Lys Thr
1               5                   10                  15

Met Asn Pro Leu Asp Leu Glu Glu Phe Lys Arg Gln Gly Tyr Met Met
            20                  25                  30

Ile Asp Phe Leu Thr Asp Tyr Tyr Lys Asn Ile Glu Asn Tyr Pro Val
        35                  40                  45

Leu Ser Lys Val Glu Pro Gly Tyr Leu Ala Lys Ile Leu Pro Ser Ser
    50                  55                  60

Ala Pro Phe Gln Pro Glu Ser Ile Glu Ser Ile Leu Glu Asp Val Gln
65                  70                  75                  80

Gln His Ile Ile Pro Gly Ile Thr His Trp Met Ser Pro Asn Tyr Tyr
                85                  90                  95

Ala Tyr Phe Pro Ser Ser Gly Ser Ile Ala Gly Phe Ile Gly Glu Met
            100                 105                 110

Leu Ser Thr Gly Phe Asn Val Val Gly Phe Asn Trp Leu Ser Ser Pro
        115                 120                 125

Ala Ala Thr Glu Leu Glu Thr Ile Val Met Asn Trp Leu Gly Lys Leu
    130                 135                 140

Leu Asn Leu Pro Lys Ser Phe Ile Phe Ser Asn Ile Lys Gly Gly
145                 150                 155                 160

Gly Glu Ile Lys Lys Leu Ser Gln Ile Gly Lys Asp Asn Ile Gly Lys
                165                 170                 175

Leu Val Val Tyr Cys Ser Asp Gln Thr His Ser Ala Leu Gln Lys Ala
            180                 185                 190

Thr Gln Ile Val Gly Ile His Ser Glu Asn Phe Arg Val Ile Lys Thr
        195                 200                 205

Lys Gly Ser Asn Leu Phe Ala Leu Ser Pro Asp Ser Leu Leu Ser Thr
    210                 215                 220
```

Ile Leu Leu Asp Val Asp Asn Gly Leu Ile Pro Tyr Phe Leu Cys Ala
225                 230                 235                 240

Thr Ile Gly Thr Thr Ser Thr Asn Ala Val Asp Pro Ile Lys Leu Leu
            245                 250                 255

Cys Asn Val Thr Lys Glu Tyr Asp Ile Trp Val His Val Asp Ala Ala
            260                 265                 270

Tyr Ala Gly Ser Val Cys Ile Cys Pro Glu Phe Arg His Cys Ile Asp
            275                 280                 285

Gly Ile Glu Glu Leu Asn Ser Phe Ser Phe Asn Ala His Lys Trp Phe
            290                 295                 300

Leu Thr Asn Leu Ala Cys Cys Cys Leu Trp Val Lys Asp His Asn Ala
305                 310                 315                 320

Leu Thr Thr Ser Leu Ser Thr Asn Pro Glu Phe Leu Arg Asn Lys Lys
            325                 330                 335

Ser Asp Ser Lys Glu Val Ile Asp Tyr Lys Asp Trp Gln Ile Pro Leu
            340                 345                 350

Ser Arg Lys Phe Asn Ala Leu Lys Leu Trp Ile Val Leu Arg Ser Tyr
            355                 360                 365

Gly Val Glu Asn Leu Lys Asn Phe Leu Arg Asn His Val Glu Met Ala
370                 375                 380

Lys Ile Phe Glu Gly Leu Val Arg Lys Asp Glu Arg Phe Glu Ile Val
385                 390                 395                 400

Val Pro Ser Lys Phe Ser Leu Val Cys Phe Arg Ile Ser Pro Phe Ala
            405                 410                 415

Ile Ser Ile Ala Asn Asp Ser Glu Gly Tyr Tyr Val Gly Lys Met Met
            420                 425                 430

Asn Asp Ala Tyr Leu Val Asn Glu Met Asn His Lys Leu Leu Asp Leu
            435                 440                 445

Ile Asn Ser Ser Gly Lys Ala Tyr Met Ser His Gly Glu Val Glu Gly
            450                 455                 460

Ser Phe Val Ile Arg Cys Ala Ile Gly Ala Thr Leu Thr Glu Glu His
465                 470                 475                 480

His Val Thr Met Thr Trp Lys Leu Val Gln Gln Ile Ala Ser Phe Leu
            485                 490                 495

Leu Gly Thr Pro Leu Asn
            500

<210> SEQ ID NO 79
<211> LENGTH: 577
<212> TYPE: PRT
<213> ORGANISM: Zea mays
<300> PUBLICATION INFORMATION:
<308> DATABASE ACCESSION NUMBER: GRMZM2G009400

<400> SEQUENCE: 79

Met Ala Ile Leu Asn Arg Ala Asp Thr Ser His Thr Thr Thr Ala Ser
1               5                   10                  15

Asn Gly Ser Ala Thr Pro Ala Ala Pro Val Ala Ile Ala Met Pro Ser
            20                  25                  30

Leu Pro His Pro Pro Leu Asp Ala Asp Glu Phe Arg Arg Gln Gly Arg
            35                  40                  45

Leu Val Val Asp Phe Ile Ala Asp Tyr Tyr Arg Ile Asp Gly Tyr
        50                  55                  60

Pro Val Arg Pro Ala Val Ala Pro Gly Phe Leu Ile Arg Gln Leu Pro
65                  70                  75                  80

-continued

Glu Ala Ala Pro Ala Arg Pro Glu Pro Asp Ala Leu Ala Ala Leu
                85                  90                  95

Arg Asp Val Arg Asp Leu Ile Leu Pro Gly Val Thr His Trp Gln Ser
            100                 105                 110

Pro Arg His Phe Ala His Phe Ala Ala Thr Ala Ser Asn Val Gly Ala
            115                 120                 125

Leu Gly Glu Ala Leu Ala Ala Gly Leu Asn Val Asn Pro Phe Thr Trp
        130                 135                 140

Ala Ala Ser Pro Ala Ala Thr Glu Leu Glu Val Val Thr Asp Trp
145                 150                 155                 160

Leu Gly Lys Ala Leu His Leu Pro Glu Ser Leu Leu Phe Ser Gly Gly
                165                 170                 175

Gly Gly Gly Thr Leu Leu Gly Thr Ser Cys Glu Ala Met Leu Cys Thr
            180                 185                 190

Ile Val Ala Ala Arg Asp Arg Lys Leu Ala Glu Val Gly Glu Arg
        195                 200                 205

Ile Gly Asp Leu Val Val Tyr Cys Ser Asp Gln Thr His Phe Ser Phe
210                 215                 220

Gln Lys Ala Ala Arg Ile Ala Gly Ile Arg Arg Gly Asn Cys Arg Glu
225                 230                 235                 240

Ile Pro Thr Ser Arg Glu Ser Gly Phe Thr Leu Ser Pro Lys Ala Leu
            245                 250                 255

Ala Ala Ala Val Arg Ala Asp Glu Ala Ala Gly Arg Val Pro Leu Phe
                260                 265                 270

Leu Cys Ala Thr Val Gly Thr Thr Pro Thr Ala Ala Val Asp Pro Leu
        275                 280                 285

Arg Glu Leu Cys Ala Ala Val Ala Gly His Asp Val Trp Val His Val
    290                 295                 300

Asp Ala Ala Tyr Ala Gly Ala Ala Cys Val Cys Pro Glu Phe Ser His
305                 310                 315                 320

Val Val Ala Gly Val Glu Ala Ala Glu Ser Phe Ser Thr Asn Pro His
            325                 330                 335

Lys Trp Leu Leu Ala Asn Met Asp Cys Cys Ala Leu Trp Val Arg Arg
        340                 345                 350

Pro Ala Ala Leu Thr Ala Ala Leu Gly Thr Asp His Asp Val Ile Leu
            355                 360                 365

Lys Asp Pro Ala Ala Ala Gln Ala Gln Ala Gln Gln Gln Cys Ser
        370                 375                 380

Asp Gly Gly Val Val Asp Tyr Lys Asp Trp Gln Val Ala Leu Ser Arg
385                 390                 395                 400

Arg Phe Arg Ala Leu Lys Leu Trp Leu Val Leu Arg Cys His Gly Val
                405                 410                 415

Glu Gly Leu Arg Gly Leu Val Arg Ala His Val Arg Met Ala Ala Ala
            420                 425                 430

Phe Glu Ala Met Val Arg Gly Asp Ala Arg Phe Glu Val His Val Pro
        435                 440                 445

Arg Gln Phe Ala Leu Val Cys Phe Arg Leu Arg Ala Val Ala Val Ala
    450                 455                 460

Val Ala Gly Glu Lys Arg Ala Gly Asp Tyr Asp Gly Val Ala Ala Gly
465                 470                 475                 480

Asn Glu Leu Asn Arg Arg Leu Leu Glu Ala Val Asn Ala Thr Gly Arg
            485                 490                 495

Val Tyr Met Ser Ser Ala Val Val Gly Gly Ala Tyr Ile Leu Arg Cys

```
                500                  505                  510
Ala Ile Gly Asn Ser Leu Thr Glu Glu Arg His Val Arg Glu Ala Trp
            515                  520                  525

Ser Val Val Gln Glu Gln Ala Thr Ala Ile Leu Ser Ala Ala Thr Ala
            530                  535                  540

Thr Ala Arg Thr Asn Gly Leu Thr Val Arg Arg Ala Arg Cys Asp Ala
545                 550                  555                  560

Glu Ala Asp Val Ser Asp Val Pro Thr Pro Gln Gln Pro Leu Pro Leu
                565                  570                  575

Gly

<210> SEQ ID NO 80
<211> LENGTH: 519
<212> TYPE: PRT
<213> ORGANISM: Glycine max
<300> PUBLICATION INFORMATION:
<308> DATABASE ACCESSION NUMBER: 07G059000.1

<400> SEQUENCE: 80

Met Glu Met Lys Asn Thr Met Asn Arg Asn Pro Gln Ser Asp Ala Pro
1               5                   10                  15

Ile Ile Lys Pro Leu Asp Pro Glu Glu Phe Lys Arg Gln Gly Tyr Met
                20                  25                  30

Met Val Asp Phe Leu Ala Asp Tyr Ile Arg Asn Val Ser His Tyr Pro
            35                  40                  45

Val Leu Ser Lys Val Glu Pro Gly Tyr Leu Lys Gln Arg Leu Pro Thr
        50                  55                  60

Ser Ala Pro Cys Gly Pro Glu Pro Ile Glu Ser Ile Leu Lys Asp Val
65                  70                  75                  80

Gln Asp His Ile Ile Pro Gly Leu Thr His Trp Gln Ser Pro Asn Phe
                85                  90                  95

Tyr Gly Tyr Phe Pro Ser Ser Gly Ser Ile Ala Gly Phe Met Gly Glu
            100                 105                 110

Met Leu Ser Ala Gly Leu Asn Val Val Gly Phe Asn Trp Val Ser Ser
        115                 120                 125

Pro Ser Ala Thr Glu Leu Glu Ser Ile Val Met Asp Trp Leu Gly Gln
130                 135                 140

Val Leu Asn Leu Pro Lys Ser Phe Leu Phe Cys Gly Asp His Gly Gly
145                 150                 155                 160

Gly Val Val Leu Gly Thr Thr Cys Glu Ala Ile Leu Cys Thr Leu Val
                165                 170                 175

Ala Ala Arg Glu Lys Lys Leu Ser Gln Val Gly Lys Glu Asn Ile Gly
            180                 185                 190

Lys Leu Val Val Tyr Gly Ser Asp Gln Thr His Ser Ala Leu Gln Lys
        195                 200                 205

Ala Ala Gln Ile Ala Gly Ile His Pro Ala Asn Phe Arg Val Ile Lys
    210                 215                 220

Thr Lys Arg Ser Asn Ser Phe Ala Leu Ser Pro Asp Ser Leu Leu Ser
225                 230                 235                 240

Thr Ile Leu Leu Asp Val Glu Arg Gly Leu Ile Pro Cys Phe Leu Cys
                245                 250                 255

Ala Thr Val Gly Thr Thr Ala Ile Ala Thr Ile Asp Pro Ile Gly Pro
            260                 265                 270

Leu Cys Asn Val Ala Lys Asp Tyr Gly Ile Trp Val His Val Asp Ala
        275                 280                 285
```

```
Ala Tyr Ala Gly Ser Ala Cys Ile Cys Pro Glu Phe Arg His Cys Ile
            290                 295                 300

Asp Gly Val Glu Glu Val Asn Ser Phe Ser Leu Asn Ala His Lys Trp
305                 310                 315                 320

Phe Leu Thr Asn Leu Thr Cys Cys Cys Leu Trp Val Lys Asp His Ile
                325                 330                 335

Ala Leu Thr Lys Ser Leu Thr Val Asn Pro Gln Phe Leu Arg Asn Lys
            340                 345                 350

Ala Ser Glu Ser Lys Arg Val Ile Asp Tyr Lys Asp Trp Gln Ile Pro
        355                 360                 365

Leu Ser Arg Lys Phe Asn Ala Leu Lys Leu Trp Leu Val Leu Arg Ser
370                 375                 380

Tyr Gly Val Glu Asn Ile Arg Asn Phe Leu Arg Asn His Val Gln Met
385                 390                 395                 400

Ala Lys Thr Phe Glu Gly Leu Val Arg Leu Asp Lys Arg Phe Glu Ile
                405                 410                 415

Val Val Pro Pro Lys Phe Ser Leu Val Cys Phe Arg Ile Ala Pro Ser
            420                 425                 430

Ala Ile Ile Ala Asn Gly Leu Ser Lys Gly Val Glu Ala Cys Tyr Asn
        435                 440                 445

Gly Lys Leu Val Asn Asp Glu Tyr Met Val Asn Glu Val Asn Arg Lys
450                 455                 460

Leu Leu Asp Ser Val Asn Ser Ser Gly Asp Ala Phe Met Thr His Gly
465                 470                 475                 480

Glu Val Glu Gly Ala Phe Met Ile Arg Cys Ala Ile Gly Gly Thr Leu
                485                 490                 495

Thr Glu Glu His His Val Ile Met Ala Trp Lys Leu Val Gln Glu His
            500                 505                 510

Ala Asn Ser Leu Leu Gly Leu
        515

<210> SEQ ID NO 81
<211> LENGTH: 531
<212> TYPE: PRT
<213> ORGANISM: Panicum virgatum
<300> PUBLICATION INFORMATION:
<308> DATABASE ACCESSION NUMBER: Ca01381.1

<400> SEQUENCE: 81

Met Ala Ile Leu Asn His Gly Asp Thr Thr Ala Ala Ser Gly Thr Ser
1               5                   10                  15

Pro Ala Ala Ala Val Asn Val Ala Pro Pro Met His Ser Leu Val
            20                  25                  30

Gln Pro Val Leu Asp Ala Asp Glu Phe Arg Arg Gln Gly Arg Leu Val
        35                  40                  45

Val Asp Phe Ile Ala Asp Tyr Tyr Thr Arg Ile Asp Glu Tyr Pro Val
    50                  55                  60

Arg Pro Ala Val Ala Pro Gly Phe Leu Ala Arg Gln Leu Pro Glu Ala
65                  70                  75                  80

Ala Pro Ala Arg Pro Glu Pro Gly Gly Asp Ala Leu Ala Ala Leu
            85                  90                  95

Arg Asp Val Arg Asp Leu Ile Leu Pro Gly Val Thr His Trp Gln Ser
            100                 105                 110

Pro Arg His Phe Ala His Phe Ala Thr Thr Gly Ser Asn Val Gly Ala
        115                 120                 125
```

-continued

```
Leu Gly Glu Ala Leu Ala Ala Gly Leu Asn Ile Asn Pro Phe Thr Trp
    130                 135                 140

Ala Ala Ser Pro Ala Ala Thr Glu Leu Glu Val Val Thr Asp Trp
145                 150                 155                 160

Leu Gly Lys Ala Leu His Leu Pro Glu Arg Leu Leu Phe Ser Gly Gly
                165                 170                 175

Gly Gly Gly Thr Leu Leu Gly Thr Ser Cys Glu Ala Met Leu Cys Thr
            180                 185                 190

Leu Val Ala Ala Arg Asp Arg Lys Leu Ala Glu Ile Gly Glu Glu Arg
        195                 200                 205

Met Gly Asp Leu Val Val Tyr Cys Ser Asp Gln Thr His Phe Ser Phe
    210                 215                 220

Arg Lys Ala Ala Arg Ile Ala Gly Ile Arg Arg Gly Asn Cys Arg Glu
225                 230                 235                 240

Ile Pro Thr Ser Arg Glu Ser Gly Phe Ala Leu Gln Pro Arg Thr Leu
                245                 250                 255

Leu Ala Ala Val Arg Ala Asp Glu Ala Ala Gly Arg Val Pro Met Phe
            260                 265                 270

Leu Cys Ala Thr Val Gly Thr Thr Pro Thr Ala Ala Val Asp Pro Leu
        275                 280                 285

Arg Glu Leu Cys Ala Ala Val Ala Gly Arg Gly Val Trp Val His Val
    290                 295                 300

Asp Ala Ala Tyr Ala Gly Ala Ala Cys Val Cys Pro Glu Phe Arg Gly
305                 310                 315                 320

Ala Thr Ala Gly Ala Glu Ala Val Asp Ser Phe Ser Thr Asn Pro His
                325                 330                 335

Lys Trp Leu Leu Ala Asn Met Asp Cys Cys Ala Leu Trp Val Arg Arg
            340                 345                 350

Pro Glu Ala Leu Thr Ala Ala Leu Gly Thr Asp His Asp Val Ile Leu
        355                 360                 365

Lys Asp Pro Ser Ser Glu Arg Gly Gly Val Val Asp Tyr Lys Asp
    370                 375                 380

Trp Gln Val Ala Leu Ser Arg Arg Phe Arg Ala Leu Lys Leu Trp Leu
385                 390                 395                 400

Val Leu Arg Cys His Gly Val Glu Gly Leu Arg Gly Leu Val Arg Ala
                405                 410                 415

Asp Ala Arg Phe Glu Val Pro Val Pro Arg Gln Phe Ala Leu Val Cys
            420                 425                 430

Phe Arg Leu Arg Ala Ala Ala Ala Ala Val Gly Glu Lys Arg Gly
        435                 440                 445

Arg Asp Arg Asp Asn Asp Ala Glu Pro Asn Glu Leu Asn Arg Arg Leu
450                 455                 460

Leu Glu Ala Val Asn Ala Thr Gly Arg Ala Tyr Met Ser Ser Ala Val
465                 470                 475                 480

Val Gly Gly Ile Tyr Val Leu Arg Cys Ala Ile Gly Asn Ser Leu Thr
                485                 490                 495

Glu Glu Arg His Val Arg Glu Ala Trp Arg Val Val Gln Gln Ala
            500                 505                 510

Thr Ala Val Leu Ala Ala Ala Cys Thr Glu Glu Arg Ala Val Arg
        515                 520                 525

Ser Ala Arg
    530
```

<210> SEQ ID NO 82
<211> LENGTH: 489
<212> TYPE: PRT
<213> ORGANISM: Theobroma cacao
<300> PUBLICATION INFORMATION:
<308> DATABASE ACCESSION NUMBER: 27425420

<400> SEQUENCE: 82

```
Met Ser Ser Ala Ser Arg Lys Thr Phe Leu Pro Leu Glu Pro Thr Ser
1               5                   10                  15

Phe Thr Asn Glu Ser Lys Ala Val Ile Asp Phe Ile Ala Asp Tyr Tyr
            20                  25                  30

Lys Asn Ile Glu Glu Tyr Pro Val Gln Ser Gly Val Glu Pro Gly Tyr
        35                  40                  45

Leu Ser Ala Lys Leu Pro Asp Ser Ala Pro Tyr Cys Pro Glu Ser Leu
    50                  55                  60

Glu Asp Ile Leu Lys Asp Val Asn Asp Cys Ile Ile Pro Gly Leu Thr
65                  70                  75                  80

His Trp Gln Ser Pro Asn Phe Phe Ala Tyr Phe Gln Ala Asn Ala Ser
                85                  90                  95

Thr Ala Gly Phe Leu Gly Glu Met Leu Cys Ser Gly Phe Asn Val Val
            100                 105                 110

Gly Phe Asn Trp Ile Ser Ser Pro Ala Ala Thr Glu Leu Glu Ser Ile
        115                 120                 125

Val Leu Asp Trp Met Gly Lys Leu Leu Lys Leu Pro Ser Ser Phe Leu
    130                 135                 140

Phe Ser Gly Thr Gly Gly Gly Val Leu His Gly Ser Thr Cys Glu Ala
145                 150                 155                 160

Ala Val Cys Thr Leu Ala Ala Ala Arg Asp Lys Ala Leu Lys Glu Leu
                165                 170                 175

Gly Gly Trp Glu Asn Ile Thr Lys Leu Met Val Tyr Ala Ser Asp Gln
            180                 185                 190

Thr His Phe Thr Phe Gln Lys Ala Ala Lys Leu Val Gly Ile Pro Pro
        195                 200                 205

Ser Asn Phe Arg Phe Ile Glu Thr Ser Leu Ser Thr Gly Phe Ser Met
    210                 215                 220

Ser Ser Asp Gln Val Arg Leu Ala Ile Glu His Asp Ile Lys Ser Gly
225                 230                 235                 240

Leu Val Pro Leu Phe Leu Cys Ala Thr Ile Gly Thr Thr Ala Cys Gly
                245                 250                 255

Ala Ile Asp Pro Ile Ala Glu Leu Gly Gln Val Ala Arg Glu Tyr Lys
            260                 265                 270

Leu Trp Leu His Ile Asp Ala Ala Tyr Ala Gly Ser Ala Cys Ile Cys
        275                 280                 285

Pro Glu Leu Arg His Phe Leu Asp Gly Val Glu Leu Ala Asn Ser Val
    290                 295                 300

Ser Met Asn Pro His Lys Trp Phe Leu Thr Asn Met Asp Cys Cys Cys
305                 310                 315                 320

Leu Trp Ile Thr Glu Pro Arg Leu Leu Val Asp Ser Leu Ser Thr Asp
                325                 330                 335

Pro Glu Ile Leu Arg Asn Lys Ala Ser Glu Phe Lys Ala Val Leu Asp
            340                 345                 350

Tyr Lys Asp Trp Gln Val Ala Leu Ser Arg Arg Phe Arg Ala Leu Lys
        355                 360                 365
```

```
Leu Trp Ile Val Ile Arg Arg His Gly Leu Ala Asn Leu Val Tyr His
    370                 375                 380

Ile Arg Ser Asp Ile Ser Met Ala Glu Arg Phe Glu Ala Phe Val Ala
385                 390                 395                 400

Lys Asp Asp Arg Phe Asp Ile Val Val Pro Arg Lys Phe Ala Leu Val
                405                 410                 415

Cys Phe Arg Leu Lys Pro Lys Gln Glu Leu Glu Gly Leu Glu Leu Asn
                420                 425                 430

Ser Arg Leu Leu Glu Ala Ile Asn Ser Ser Gly Arg Ala Phe Met Thr
            435                 440                 445

His Ala Val Val Gly Gly Ile Tyr Val Ile Arg Cys Ala Ile Gly Thr
450                 455                 460

Thr Met Thr Glu Glu Arg His Val Asp Ala Leu Trp Lys Leu Ile Gln
465                 470                 475                 480

Glu Lys Ala Gln Gly Leu Leu Met Glu
                485
```

<210> SEQ ID NO 83
<211> LENGTH: 625
<212> TYPE: PRT
<213> ORGANISM: Fragaria vesca
<300> PUBLICATION INFORMATION:
<308> DATABASE ACCESSION NUMBER: 27274768

<400> SEQUENCE: 83

```
Met Gly Ser Leu Asp Phe His His Val Pro Glu Lys Thr Asn Ser Asp
1               5                   10                  15

Pro Pro Met Ala Asn Pro Met Asp Pro Glu Glu Phe Arg Arg Gln Gly
                20                  25                  30

His Ile Met Ile Asp Phe Ile Ala Asp Tyr Tyr Lys Asn Ile Glu Lys
            35                  40                  45

Tyr Pro Val Leu Ser Gln Val Gln Pro Gly Tyr Leu Lys Lys Leu Leu
        50                  55                  60

Pro Glu Ser Ala Pro Tyr Asn Pro Glu Pro Ile Glu Thr Ile Leu Gln
65                  70                  75                  80

Asp Val Gln Asp His Ile Val Pro Gly Ile Thr His Trp Gln Ser Pro
                85                  90                  95

Ser Tyr Phe Ala Tyr Phe Pro Ser Ser Gly Ser Ile Ala Gly Phe Leu
                100                 105                 110

Gly Glu Met Leu Ser Thr Gly Phe Asn Val Val Gly Phe Asn Trp Met
            115                 120                 125

Ser Ser Pro Ala Ala Thr Glu Leu Glu Arg Thr Thr Cys Glu Ala Ile
        130                 135                 140

Val Cys Thr Met Ala Ala Arg Asp Gln Met Leu Ser Arg Ile Gly
145                 150                 155                 160

Lys Asp Asn Ile Gly Lys Leu Val Val Tyr Gly Ser Asp Gln Thr His
                165                 170                 175

Ser Ala Leu Lys Lys Ala Ser Gln Ile Val Gly Ile His Pro Asn Asn
            180                 185                 190

Phe Arg Ala Ile Lys Thr Thr Lys Ser Thr Glu Phe Ala Leu Ser Pro
        195                 200                 205

Glu Leu Leu Arg Ser Thr Ile Cys Ser Asp Ile Asp Lys Gly Leu Val
    210                 215                 220

Pro Leu Phe Leu Cys Ala Thr Met Gly Thr Thr Ala Thr Thr Ser Val
225                 230                 235                 240
```

```
Asp Pro Leu Arg Gly Leu Cys Asp Val Ala Lys Asp Tyr Asp Leu Trp
            245                 250                 255

Val His Val Asp Ala Ala Tyr Ala Gly Ser Ile Cys Ile Cys Pro Glu
        260                 265                 270

Phe Arg His Phe Ile Glu Gly Val Asp Gly Ala Asn Ser Phe Ser Phe
            275                 280                 285

Asn Ala His Lys Trp Phe Phe Thr Thr Leu Asp Cys Cys Cys Leu Trp
        290                 295                 300

Val Lys Asn Pro Thr Ala Leu Ile Asn Ser Leu Ser Thr Asn Pro Glu
305                 310                 315                 320

Phe Leu Arg Asn Lys Ala Ser Asp Ser Lys Gln Val Val Asp Tyr Lys
            325                 330                 335

Asp Trp Gln Val Ala Leu Ser Arg Arg Phe Arg Ala Leu Lys Leu Trp
        340                 345                 350

Leu Val Leu Arg Ser Tyr Gly Val Ala Asn Leu Arg Ser Phe Leu Arg
            355                 360                 365

Ser His Val Lys Met Ala Glu Val Phe Glu Lys Leu Val Arg Glu Asn
        370                 375                 380

Lys Trp Phe Glu Val Val Pro Arg Asn Phe Ala Met Val Cys Phe
385                 390                 395                 400

Arg Ile Ser Pro Ser Ala Ile Arg Lys Ala Pro Thr Asp Asp Gly
            405                 410                 415

Ile Asp Val Val Ile Asn Glu Val Asn Ser Lys Leu Leu Glu Ala Met
        420                 425                 430

Asn Thr Ser Gly Ser Val Tyr Met Thr His Ala Val Val Gly Gly Met
            435                 440                 445

Tyr Val Leu Arg Cys Ala Ile Gly Ala Thr Met Thr Glu Glu Lys His
        450                 455                 460

Val Leu Met Ala Trp Lys Cys Gly Ser Ala Leu Glu Arg Lys Asp Val
465                 470                 475                 480

Ala Ala Asn Glu Thr Leu Ser Phe Asn Phe Gln Arg Arg Phe Asp Arg
            485                 490                 495

Arg Ala Arg Gln Arg Arg Gly His Val Gly Phe Arg Leu Ala Ile Thr
        500                 505                 510

Met Leu Asp Leu Lys Thr Ser Glu Arg Asp Gly Ala Arg Arg Trp Ser
            515                 520                 525

Ile Gly Ala Tyr Ala Asn Gln Ile Thr Thr Ile Ser Gln Ala Asn Ser
        530                 535                 540

Ser Val Ala Trp Thr Met Glu Phe His Ser Cys Phe Ile Phe Cys
545                 550                 555                 560

Gly Ser Ile Lys Leu Asp Thr Gln Val Pro Asn Asp Phe Val Leu
            565                 570                 575

Ser Ala Arg Trp Pro Pro Ser Phe Pro Val Ser Gly Trp Ser Thr Ile
        580                 585                 590

Asn Phe His Glu Thr Ile Lys Ile Tyr Val Gly Ser Leu Asp Ser Leu
            595                 600                 605

Asp Ser Trp Thr Met Glu Phe His Ser Cys Phe Thr Phe Phe Cys Gly
        610                 615                 620

Ser
625

<210> SEQ ID NO 84
<211> LENGTH: 486
<212> TYPE: PRT
```

<213> ORGANISM: Gossypium raimondii
<300> PUBLICATION INFORMATION:
<308> DATABASE ACCESSION NUMBER: 26786642

<400> SEQUENCE: 84

| | | | | | | | | | | | | | | |
|---|---|---|---|---|---|---|---|---|---|---|---|---|---|---|
| Met | Val | Ser | Ala | Ser | Arg | Lys | Thr | Phe | Leu | Pro | Leu | Asp | Pro | Val | Thr |
| 1 | | | | 5 | | | | | 10 | | | | | 15 | |

Phe Ser Asn Glu Ser Lys Ala Val Ile Asp Phe Ile Ala Asp Tyr Tyr
              20                  25                  30

Glu Asn Val Glu Lys Tyr Pro Val Gln Ser Thr Val Glu Pro Gly Tyr
          35                  40                  45

Leu Ser Ala Met Leu Pro Glu Ser Ala Pro Tyr Cys Pro Glu Pro Leu
 50                  55                  60

Gln Asp Ile Leu Glu Asp Val Ser Asn Cys Ile Ile Pro Gly Leu Thr
65                  70                  75                  80

His Trp Gln Ser Pro Asn Phe Phe Ala Tyr Phe His Ala Asn Ala Ser
                85                  90                  95

Thr Ala Gly Phe Phe Gly Glu Met Leu Cys Ser Gly Phe Asn Val Val
            100                 105                 110

Gly Phe Asn Trp Ile Ser Ser Pro Ala Ala Thr Glu Leu Glu Ser Ile
        115                 120                 125

Val Leu Asp Trp Met Gly Lys Met Leu Lys Leu Pro Ser Ser Phe Leu
130                 135                 140

Phe Ser Gly Thr Gly Gly Gly Val Leu His Gly Ser Ser Cys Glu Ala
145                 150                 155                 160

Ala Val Cys Val Leu Ala Ala Arg Asp Lys Ala Leu Lys Glu Leu
                165                 170                 175

Gly Gly Trp Glu Asn Ile Thr Lys Leu Val Val Tyr Ala Ser Asp Gln
            180                 185                 190

Ala His Phe Thr Phe Gln Lys Ala Ala Lys Leu Val Gly Ile Pro Pro
        195                 200                 205

Ser Asn Phe Arg Leu Ile Glu Thr Ser Phe Ser Thr Gly Phe Ser Leu
210                 215                 220

Ser Pro Glu Asn Leu Arg Phe Val Ile Glu Asp Asn Ile Arg Ser Gly
225                 230                 235                 240

Leu Val Pro Leu Phe Leu Cys Ala Thr Ile Gly Thr Thr Pro Ser Gly
                245                 250                 255

Ala Val Asp Pro Ile Ala Glu Leu Gly Lys Val Ala Met Glu Phe Lys
            260                 265                 270

Leu Trp Leu His Ile Asp Ala Ala Tyr Ala Gly Ser Gly Cys Ile Cys
        275                 280                 285

Pro Glu Leu Arg His Tyr Leu Asp Gly Val Glu Leu Ala Asn Ser Ile
290                 295                 300

Ser Met Asn Pro His Lys Trp Phe Leu Thr Asn Met Asp Cys Cys Cys
305                 310                 315                 320

Leu Trp Ile Lys Glu Pro Lys Leu Leu Val Asp Ser Leu Ser Thr Asp
                325                 330                 335

Pro Glu Ile Leu Arg Asn Asn Ala Ser Lys Ser Lys Ala Val Val Asp
            340                 345                 350

Cys Lys Asp Trp Gln Ile Ala Leu Ser Arg Arg Phe Arg Ala Leu Lys
        355                 360                 365

Leu Trp Val Val Ile Arg Arg His Gly Leu Ala Asn Leu Met Cys His
370                 375                 380

Ile Arg Ser Asp Ile Ala Met Ala Lys Arg Phe Glu Ala Leu Val Gly

```
                385              390              395              400
Glu Asp Glu Arg Phe Glu Ile Val Val Pro Arg Lys Phe Ala Leu Val
                    405              410              415

Cys Phe Arg Leu Lys Pro Lys Val Glu Glu Asp Leu Asn Cys Lys
                    420              425          430

Leu Val Glu Ala Ile Asn Ser Ser Gly Arg Ala Phe Met Ser His Ala
            435              440              445

Val Leu Ser Gly Ile Tyr Val Ile Arg Cys Ala Ile Gly Thr Thr Leu
        450              455              460

Thr Gln Gln His His Val Asp Ala Leu Trp Lys Leu Ile Gln Asp Lys
465              470              475              480

Ala Gln Ser Leu Leu Met
                485

<210> SEQ ID NO 85
<211> LENGTH: 495
<212> TYPE: PRT
<213> ORGANISM: Populus trichocarpa
<300> PUBLICATION INFORMATION:
<308> DATABASE ACCESSION NUMBER: 26994989

<400> SEQUENCE: 85

Met Gly Ser Leu Ser Thr Asn Thr Phe Ser Pro Leu Asp Pro Asn Gly
1               5                   10                  15

Phe Thr Asn Asp Ser Lys Met Val Ile Asp Phe Ile Ala Asp Tyr Tyr
            20                  25                  30

Lys Asn Ile Glu Asn Asn Pro Val Gln Ser Gln Val Lys Pro Gly Tyr
        35                  40                  45

Leu Leu Thr Gln Leu Pro Asp Thr Ala Pro Tyr Cys Glu Glu Ser Leu
    50                  55                  60

Glu Asp Val Leu Lys Asp Val Thr Asp Ser Ile Ile Pro Gly Leu Thr
65                  70                  75                  80

His Trp Gln Ser Pro Asn Phe Phe Ala Tyr Phe Gln Ala Asn Ala Ser
                85                  90                  95

Thr Ala Gly Phe Val Gly Glu Met Leu Cys Thr Gly Leu Asn Val Val
            100                 105                 110

Gly Phe Asn Trp Ile Ala Ser Pro Ala Ala Thr Glu Leu Glu Ser Ile
        115                 120                 125

Val Met Asp Trp Met Gly Lys Met Leu Lys Leu Pro Ser Thr Phe Leu
    130                 135                 140

Phe Ser Gly Asn Gly Gly Gly Val Leu His Gly Ser Thr Cys Glu Ala
145                 150                 155                 160

Ile Val Cys Thr Leu Val Ala Ala Arg Asp Glu Thr Leu Arg Met Ile
                165                 170                 175

Gly Ala Glu Asn Ile Thr Lys Leu Val Val Tyr Ala Ser Asp Gln Thr
            180                 185                 190

His Ser Thr Leu Leu Lys Gly Val Lys Leu Val Gly Ile Pro Ser Ser
        195                 200                 205

Asn Phe Arg Cys Leu Ser Thr Ser Phe Ser Ser Glu Phe Ser Leu Ser
    210                 215                 220

Pro Gln Ala Leu Glu Asp Ala Ile Glu Asn Asp Ile Lys Ala Gly Leu
225                 230                 235                 240

Val Pro Leu Phe Leu Cys Ala Thr Val Gly Thr Thr Ala Cys Gly Ala
                245                 250                 255

Val Asp Pro Val Met Asp Leu Gly Glu Ile Ala Arg Lys Tyr Asn Leu
```

```
                  260                 265                 270
Trp Phe His Ile Asp Ala Ala Tyr Ala Gly Ser Ala Cys Ile Cys Pro
            275                 280                 285

Glu Phe Arg His Tyr Leu Asp Gly Val Glu Leu Ala Asp Ser Leu Ser
            290                 295                 300

Met Asn Pro His Lys Trp Leu Leu Thr Asn Met Asp Cys Cys Cys Leu
305                 310                 315                 320

Trp Val Lys Gln Pro Arg Leu Leu Ile Glu Ser Leu Ser Ser Asp Ala
            325                 330                 335

Glu Phe Leu Arg Asn Asn Ala Ser Glu Ser Ser Asp Val Val Asp Tyr
            340                 345                 350

Lys Asp Trp Gln Ile Ala Leu Ser Arg Arg Phe Arg Ala Leu Lys Leu
            355                 360                 365

Trp Ile Val Ile Arg Arg His Gly Leu Ala Asn Leu Met Cys His Ile
            370                 375                 380

Arg Ser Asp Val Asn Leu Ala Lys Arg Phe Glu Ser Leu Val Ala Lys
385                 390                 395                 400

Asp Ser Arg Phe Glu Val Val Arg Arg Phe Ser Leu Val Cys
            405                 410                 415

Phe Arg Leu Lys His Asn Asp Glu Cys Gln Gly Leu Glu Leu Asn Arg
            420                 425                 430

Lys Leu Leu Ala Ala Val Asn Glu Ser Gly Arg Ala Phe Met Thr His
            435                 440                 445

Ala Val Val Gly Gly Leu Phe Ile Ile Arg Cys Ala Ile Gly Ser Thr
            450                 455                 460

Leu Thr Glu Glu Arg His Val Asp Asp Leu Trp Lys Leu Ile Gln Glu
465                 470                 475                 480

Lys Ala Ala Asp Leu Leu Ser Lys Lys Gln Val Leu Leu Asp Asn
            485                 490                 495

<210> SEQ ID NO 86
<211> LENGTH: 565
<212> TYPE: PRT
<213> ORGANISM: Malus domestica
<300> PUBLICATION INFORMATION:
<308> DATABASE ACCESSION NUMBER: 22679008

<400> SEQUENCE: 86

Met Ser Leu Leu Ala Phe Tyr Ser Asn Ser Gly Glu Arg Ser Lys Arg
1               5                   10                  15

Val His Leu Ser Ala Ser Thr Tyr Gly Asn Ser Thr Pro Asn Ser Tyr
            20                  25                  30

Ile Ser Leu Pro Tyr Ala Leu Phe Ser Ser Ala Thr Gln Leu Ile Asn
            35                  40                  45

Ile His Ser Asn Ser Ser Asn Phe Gln Met Gly Ser Leu Ile Ser Gln
        50                  55                  60

Glu Asn Asn Ser Pro Asn Val Pro Thr Asn Pro Leu Asp Pro Glu Glu
65                  70                  75                  80

Phe Arg Arg Gln Gly His Leu Val Ile Asp Phe Ile Ala Asp Tyr Tyr
            85                  90                  95

Lys Ser Ile Glu Lys His Pro Val Leu Ser Gln Val Gln Pro Gly Tyr
            100                 105                 110

Leu Lys Lys Arg Leu Pro Asp Thr Ala Pro Tyr Asn Pro Glu Pro Leu
            115                 120                 125

Glu Thr Ile Leu Gln Asp Val Gln Asp His Ile Val Pro Gly Ile Thr
```

-continued

```
            130                 135                 140
His Trp Gln Ser Pro Asn Tyr Phe Ala Tyr Phe Pro Ser Ser Gly Ser
145                 150                 155                 160

Val Ala Gly Phe Leu Gly Glu Met Leu Ser Ser Gly Phe Asn Val Val
                165                 170                 175

Gly Phe Asn Trp Met Ser Ser Pro Ala Ala Thr Glu Leu Glu Ser Thr
            180                 185                 190

Val Arg Asp Trp Phe Gly Asn Met Leu Lys Leu Pro Lys Ser Phe Leu
        195                 200                 205

Phe Ser Gly Asn Gly Gly Asp Val Ile Gln Gly Thr Thr Cys Glu Ala
    210                 215                 220

Leu Val Cys Ala Met Val Ala Ala Arg Asp Gln Lys Leu Ser Lys Phe
225                 230                 235                 240

Gly Arg His Asn Ile Gly Lys Leu Val Val Tyr Gly Ser Asp Gln Thr
                245                 250                 255

His Ser Ala Leu Gln Lys Ala Ser Gln Ile Val Gly Ile His Pro Glu
            260                 265                 270

Asn Phe Arg Ser Ile Glu Thr Thr Arg Ser Thr Ser Phe Ala Leu Ser
        275                 280                 285

Pro Glu Ser Leu Lys Val Ile Ile Tyr Ser Asp Ile Glu Ala Gly Leu
    290                 295                 300

Val Pro Leu Phe Leu Cys Ala Thr Val Gly Thr Thr Ala Ile Ala Thr
305                 310                 315                 320

Val Asp Pro Leu Gly Pro Leu Cys Gly Val Ala Gly Asp Tyr Gly Met
                325                 330                 335

Trp Val His Val Asp Ala Ala Tyr Ala Gly Ser Ala Cys Ile Cys Pro
            340                 345                 350

Ser Phe Asp Ile Ser Leu Met Ala Ser Arg Val Gln Ile His Ser Val
        355                 360                 365

Ser Thr Arg Thr Asn Gly Ser Ser Pro Leu Ser Thr Val Val Ala Phe
    370                 375                 380

Gly Leu Arg Ile Pro Thr Arg Trp Asn Lys Ala Thr Glu Leu Lys Gln
385                 390                 395                 400

Val Val Asp Tyr Lys Asp Trp Gln Ile Ala Leu Ser Arg Arg Phe Arg
                405                 410                 415

Ser Met Lys Leu Trp Leu Val Arg Ser Tyr Gly Val Ala Asn Leu
            420                 425                 430

Arg Asn Phe Leu Arg Ser His Val Lys Met Ala Lys Ile Phe Glu Gly
        435                 440                 445

Leu Val Ala Met Asp Lys Arg Phe Glu Ile Val Ala Pro Arg Asn Phe
    450                 455                 460

Ser Leu Val Cys Phe Arg Val Ser Pro Ser Ser Ile Ser Asn Lys Ala
465                 470                 475                 480

Ser Ser Asp Gln Asn Gly Lys Thr Asp Tyr Cys Cys Asp Ala Asn Gly
                485                 490                 495

Asp Glu Asn Ser Val Ile Ile Asn Glu Val Asn Arg Lys Leu Leu Glu
            500                 505                 510

Ser Ile Asn Val Ser Gly His Val Tyr Met Thr His Gly Val Val Gly
        515                 520                 525

Gly Leu Tyr Met Leu Arg Phe Ala Val Gly Ala Thr Leu Thr Glu Glu
    530                 535                 540

His His Ile Ala Leu Ala Trp Lys Val Val Gln Glu His Ala Asp Gln
545                 550                 555                 560
```

Ile Leu Thr Lys Tyr
            565

<210> SEQ ID NO 87
<211> LENGTH: 523
<212> TYPE: PRT
<213> ORGANISM: Citrus clementina
<300> PUBLICATION INFORMATION:
<308> DATABASE ACCESSION NUMBER: 20801973

<400> SEQUENCE: 87

Met Arg Ala Gly Glu Ala Ser Ile Ile Lys Met Gly Ser Phe Gly Leu
1               5                   10                  15

Ser Ala Asn Asn Ile Thr His Gly Ser Ser Phe Ser Ala Asp Leu Glu
            20                  25                  30

Pro Lys Ser Phe Ser Asp Glu Ser Lys Ala Val Ile Asp Phe Ile Ala
        35                  40                  45

Asp Tyr Tyr Lys Asn Ile Glu Lys Tyr Pro Val Gln Ser Lys Val Glu
    50                  55                  60

Pro Gly Tyr Leu Ser Ala Arg Leu Pro Asp Thr Ala Pro His Ser Pro
65                  70                  75                  80

Glu Ser Leu Asp Asp Ile Leu Lys Asp Val Thr Asp Cys Ile Leu Pro
                85                  90                  95

Gly Leu Thr His Trp Gln Ser Pro Asn Phe Phe Gly Tyr Phe Gln Ala
            100                 105                 110

Asn Ala Ser Thr Ala Gly Phe Leu Gly Glu Met Leu Cys Ser Gly Phe
        115                 120                 125

Asn Val Val Gly Phe Asn Trp Leu Ala Ser Pro Val Ala Thr Glu Leu
    130                 135                 140

Glu Ser Ile Val Met Asp Trp Met Gly Lys Met Leu Lys Leu Pro Ser
145                 150                 155                 160

Ser Phe Leu Phe Ser Gly Thr Gly Gly Val Leu His Gly Ser Thr
                165                 170                 175

Cys Glu Ser Leu Val Cys Thr Leu Ala Ala Ala Arg Asp Lys Ala Leu
            180                 185                 190

Glu Lys Leu Gly Gly Gly Phe Asp Asn Ile Thr Lys Leu Ala Val Tyr
        195                 200                 205

Ala Ser Asp Gln Thr His Phe Ala Leu Gln Lys Ser Ala Lys Leu Ile
    210                 215                 220

Gly Ile Pro Pro Ala Asn Phe Arg Pro Leu Arg Thr Ser Phe Ser Thr
225                 230                 235                 240

Glu Phe Ser Leu Ser Pro Asp Thr Val Arg Ala Ala Ile Glu Asp Asp
                245                 250                 255

Ile Lys Ser Gly His Val Pro Leu Tyr Leu Cys Ala Thr Val Gly Thr
            260                 265                 270

Thr Gly Ala Gly Ala Val Asp Pro Ile Glu Glu Leu Gly Lys Ile Ala
        275                 280                 285

Asn Glu Tyr Lys Leu Trp Leu His Ile Asp Ala Ala Tyr Ala Gly Ser
    290                 295                 300

Ala Cys Ile Cys Pro Glu Tyr Arg His Tyr Leu Asn Gly Val Glu Leu
305                 310                 315                 320

Ala Asp Ser Ile Ser Leu Asn Pro His Lys Trp Phe Leu Thr Asn Met
                325                 330                 335

Asp Cys Cys Cys Leu Trp Val Lys His Pro Ser Phe Leu Val Asp Ser
            340                 345                 350

```
Leu Ser Thr Glu Ser Asp Ile Met Arg Asn Arg Ser Pro Ala Ser Asn
            355                 360                 365

Thr Ser Thr Asn Ala Ala Pro Val Ile Asp Tyr Lys Asp Trp Gln Ile
        370                 375                 380

Ala Leu Ser Arg Arg Phe Lys Ala Leu Lys Leu Trp Thr Val Ile Arg
385                 390                 395                 400

Lys His Gly Tyr Ser Gly Leu Met Tyr His Ile Arg Ser Asp Val Ser
            405                 410                 415

Met Ala Lys Arg Phe Ala Ala Met Val Ala Lys Asp Glu Arg Phe Glu
            420                 425                 430

Ile Val Val Pro Arg Lys Phe Ala Leu Val Cys Phe Arg Leu Lys Pro
            435                 440                 445

Lys Arg Glu Ser Glu Gly Ser Glu Leu Asn Arg Glu Leu Val Asp Ala
            450                 455                 460

Leu Asn Gly Ser Gly Arg Ala Phe Leu Thr Gln Ala Met Leu Gly Gly
465                 470                 475                 480

Val Tyr Val Ile Arg Cys Ser Ile Gly Thr Thr Leu Thr Gln Asp Arg
                485                 490                 495

His Val Asp Asp Leu Trp Lys Leu Ile Gln Gly Lys Ala Asp Arg Leu
            500                 505                 510

Leu Ser Leu Gln Glu Pro Glu His Ala Ser Arg
            515                 520

<210> SEQ ID NO 88
<211> LENGTH: 506
<212> TYPE: PRT
<213> ORGANISM: Citrus clementina
<300> PUBLICATION INFORMATION:
<308> DATABASE ACCESSION NUMBER: 20818150

<400> SEQUENCE: 88

Met Gly Ser Leu Asn Ser Asp His Glu Leu Lys Thr Asn Ser Ala Ser
1               5                   10                  15

Phe Asn Asn Pro Met Asp Ser Glu Glu Phe Arg Arg Gln Gly His Met
            20                  25                  30

Ile Ile Asp Phe Ile Ala Asp Tyr Tyr Arg Asp Val Glu Lys Tyr Pro
        35                  40                  45

Val Leu Ser Gln Val Glu Pro Gly Tyr Leu Gln Lys Arg Leu Pro Glu
    50                  55                  60

Ser Ala Pro Tyr Asn Pro Glu Pro Ile Glu Thr Ile Leu Gln Asp Val
65                  70                  75                  80

Gln Gln His Ile Val Pro Gly Ile Thr His Trp Gln Ser Pro Tyr Tyr
                85                  90                  95

Phe Ala Tyr Phe Pro Ser Ser Gly Ser Ile Ala Gly Phe Leu Gly Glu
            100                 105                 110

Met Leu Ser Ser Gly Phe Asn Val Val Gly Phe Asn Trp Met Ser Ser
            115                 120                 125

Pro Ala Ala Thr Glu Leu Glu Asn Ile Val Met Asp Trp Leu Gly Glu
        130                 135                 140

Met Leu Lys Leu Pro Lys Ser Phe Leu Phe Ser Gly Thr Gly Gly Gly
145                 150                 155                 160

Val Ile Gln Gly Thr Thr Cys Glu Ala Ile Leu Cys Thr Leu Ala Ala
                165                 170                 175

Ala Arg Asp Gln Ile Leu Asn Glu Ile Gly Arg Glu Asn Ile Ser Arg
            180                 185                 190
```

Leu Val Val Tyr Gly Ser Asp Gln Thr His Ser Ala Leu Gln Lys Ala
            195                 200                 205

Ala Gln Ile Ala Gly Ile Asp Pro Lys Asn Phe Arg Ala Ile Lys Thr
    210                 215                 220

Thr Lys Ser Ser Phe Thr Leu Thr Pro Glu Ser Leu Gln Ala Ala
225                 230                 235                 240

Ile Asp Leu Asp Ile Gln Ser Gly Leu Ile Pro Leu Phe Leu Cys Ala
                245                 250                 255

Thr Val Gly Thr Thr Ala Ile Thr Thr Val Asp Pro Leu Gly Pro Leu
            260                 265                 270

Cys Asp Ile Ala Lys Arg Tyr Ser Ile Trp Ile His Val Asp Ala Ala
            275                 280                 285

Tyr Ala Gly Ser Ala Cys Ile Cys Pro Glu Phe Arg His Phe Ile Asp
            290                 295                 300

Gly Ile Glu Ser Ala Asp Ser Phe Ser Leu Asn Ala His Lys Trp Phe
305                 310                 315                 320

Phe Thr Thr Leu Asp Cys Cys Cys Met Trp Val Lys Asn Pro Asn Ala
                325                 330                 335

Leu Ile Lys Ala Leu Ser Thr Asn Pro Glu Phe Leu Arg Asn Lys Ala
            340                 345                 350

Ser Asp Ser Lys Gln Val Val Asp Tyr Lys Asp Trp Gln Ile Ser Leu
            355                 360                 365

Ser Arg Arg Phe Arg Ala Leu Lys Leu Trp Leu Val Leu Arg Ser Phe
            370                 375                 380

Gly Val Ala Asn Leu Arg Asn Phe Leu Arg Ser His Val Gly Met Ala
385                 390                 395                 400

Gln Leu Phe Gln Glu Leu Val Gly Gly Asp Asn Arg Phe Glu Ile Val
                405                 410                 415

Ala Pro Arg Asn Phe Ala Val Val Cys Phe Arg Val Leu Pro Ser Ala
            420                 425                 430

Ser Gly Leu Gly Asn Gly Lys Ala Asn Glu Gly Ala Asn Glu Leu Asn
            435                 440                 445

Arg Lys Leu Leu Glu Ser Ile Asn Ala Ser Gly Gln Leu Tyr Val Ser
    450                 455                 460

His Gly Met Val Ala Gly Ile Tyr Phe Ile Arg Phe Ala Val Gly Ala
465                 470                 475                 480

Thr Leu Thr Glu Asp Arg His Val Ile Ala Ala Trp Lys Val Val Gln
                485                 490                 495

Glu Lys Leu Asp Gly Ile Leu Ala Thr Ser
            500                 505

<210> SEQ ID NO 89
<211> LENGTH: 467
<212> TYPE: PRT
<213> ORGANISM: Vitis vinifera
<300> PUBLICATION INFORMATION:
<308> DATABASE ACCESSION NUMBER: 17834108

<400> SEQUENCE: 89

Met Gly Ser Leu Ser Phe Asn Thr Phe Ser Pro Leu Asp Pro Gln Ser
1               5                   10                  15

Phe Ser Glu Glu Ser Lys Met Val Val Asp Phe Ile Ala Asp Tyr Tyr
            20                  25                  30

Lys Asn Val Glu Lys Tyr Pro Val Gln Ser Gln Val Asp Pro Gly Tyr
        35                  40                  45

```
Leu Met His His Cys Pro Asp Thr Ala Pro Tyr Cys Pro Glu Pro Leu
    50                  55                  60
Glu Thr Ile Leu Lys Asp Val Ser Asp Gly Ile Ile Pro Gly Leu Thr
65                  70                  75                  80
His Trp Gln Ser Pro Asn Phe Phe Gly Tyr Phe Gln Ala Asn Ala Ser
                85                  90                  95
Thr Ala Gly Phe Leu Gly Glu Met Leu Cys Thr Gly Leu Asn Val Val
            100                 105                 110
Gly Phe Asn Trp Ile Ala Ser Pro Ala Thr Glu Leu Glu Ser Ile
            115                 120                 125
Ala Ile Ile Cys Ser Leu Ala Ala Arg Asp Lys Val Leu Lys Lys
130                 135                 140
Leu Gly His His Lys Ile Thr Lys Leu Val Tyr Gly Ser Asp Gln
145                 150                 155                 160
Thr His Ser Thr Leu Gln Lys Ala Ser Lys Leu Val Gly Ile Pro Ala
                165                 170                 175
Ser Asn Phe Arg Ser Leu Pro Thr Ser Phe Ser Asn Tyr Phe Ala Leu
            180                 185                 190
Cys Pro Asp Asp Val Arg Thr Ala Met Glu Glu Asp Ile Gly Ala Gly
            195                 200                 205
Leu Val Pro Leu Phe Leu Cys Ala Thr Val Gly Thr Thr Ser Ser Gly
210                 215                 220
Ala Val Asp Pro Leu Glu Ala Leu Gly His Val Ala Lys Asp Phe Lys
225                 230                 235                 240
Val His His Leu Asn Gly Val Glu Leu Ala His Ser Ile Ser Met Asn
                245                 250                 255
Pro His Lys Trp Leu Leu Thr Asn Met Asp Cys Cys Cys Leu Trp Ile
            260                 265                 270
Lys Glu Pro Lys Leu Phe Val Asp Ser Leu Ser Thr Ala Pro Glu Phe
            275                 280                 285
Leu Arg Asn Asn Ala Ser Glu Ser Lys Lys Val Ile Asp Tyr Lys Asp
290                 295                 300
Trp Gln Ile Ala Leu Ser Arg Arg Phe Arg Ala Ile Lys Val Trp Ala
305                 310                 315                 320
Val Val Pro Arg Arg Phe Ala Leu Val Cys Phe Arg Leu Arg Pro Arg
                325                 330                 335
Glu Glu Gly Glu Ser Thr Glu Leu Asn Ser Arg Leu Leu Met Ala Val
            340                 345                 350
Asn Gly Ser Gly Ala Ala Phe Met Thr His Ala Val Val Gly Gly Ile
            355                 360                 365
Tyr Ile Ile Arg Cys Ala Ile Gly Ser Thr Leu Thr Glu Thr Arg His
370                 375                 380
Val Asp Ser Leu Trp Lys Leu Ile Gln Glu Lys Ala Gln Leu Val Leu
385                 390                 395                 400
Gln Glu Pro Gly Leu Ala Leu Glu Glu Asp Tyr Ile Asp Pro Cys Ile
                405                 410                 415
Gly Val Ser Ala Thr Ser Leu His Ala Val Val Arg Trp Tyr Cys Asn
            420                 425                 430
Tyr Ser Ser Glu Ile Asn Ala His Leu Val Phe Ile Ala Phe Phe Val
            435                 440                 445
Val Val Cys Lys Glu Asn Arg Glu Asn Tyr Val Leu Gly Val Asn Gly
450                 455                 460
```

-continued

Pro Pro Asn
465

<210> SEQ ID NO 90
<211> LENGTH: 506
<212> TYPE: PRT
<213> ORGANISM: Petunia hybrida
<300> PUBLICATION INFORMATION:
<308> DATABASE ACCESSION NUMBER: ABB72475.1

<400> SEQUENCE: 90

Met Asp Thr Ile Lys Ile Asn Pro Glu Phe Asp Gly Gln Phe Cys Lys
1               5                   10                  15

Thr Thr Ser Leu Leu Asp Pro Glu Glu Phe Arg Arg Asn Gly His Met
            20                  25                  30

Met Val Asp Phe Leu Ala Asp Tyr Phe His Asn Ile Glu Lys Tyr Pro
        35                  40                  45

Val Arg Ser Gln Val Glu Pro Gly Tyr Leu Glu Arg Leu Leu Pro Asp
    50                  55                  60

Ser Ala Pro Ile Gln Pro Glu Pro Ile Glu Lys Ile Leu Lys Asp Val
65                  70                  75                  80

Arg Ser Asp Ile Phe Pro Gly Leu Thr His Trp Gln Ser Pro Asn Phe
                85                  90                  95

Phe Ala Tyr Phe Pro Cys Ser Ser Ser Thr Ala Gly Ile Leu Gly Glu
            100                 105                 110

Met Leu Ser Ala Gly Leu Asn Val Val Gly Phe Ser Trp Ile Ala Ser
        115                 120                 125

Pro Ala Ala Thr Glu Leu Glu Ser Ile Val Met Asp Trp Leu Gly Lys
    130                 135                 140

Leu Ile Asn Leu Pro Lys Thr Tyr Leu Phe Ser Gly Gly Gly Gly Gly
145                 150                 155                 160

Val Met Gln Gly Thr Thr Cys Glu Val Met Leu Cys Thr Ile Val Ala
                165                 170                 175

Ala Arg Asp Lys Met Leu Glu Lys Phe Gly Arg Glu Asn Ile Asp Lys
            180                 185                 190

Leu Val Val Tyr Ala Ser Asp Gln Thr His Phe Ser Phe Gln Lys Ala
        195                 200                 205

Val Lys Ile Ser Gly Ile Lys Pro Glu Asn Phe Arg Ala Ile Pro Thr
    210                 215                 220

Thr Lys Ala Thr Glu Phe Ser Leu Asn Pro Glu Ser Leu Arg Arg Ala
225                 230                 235                 240

Ile Gln Glu Asp Lys Lys Ala Gly Leu Ile Pro Leu Phe Leu Cys Thr
                245                 250                 255

Ser Ile Gly Thr Thr Ser Thr Thr Ala Val Asp Pro Leu Lys Pro Leu
            260                 265                 270

Cys Glu Ile Ala Glu Glu Tyr Gly Ile Trp Val His Val Asp Ala Ala
        275                 280                 285

Tyr Ala Gly Ser Ala Cys Ile Cys Pro Glu Phe Gln His Phe Leu Asp
    290                 295                 300

Gly Val Glu His Ala Asn Ser Phe Ser Phe Asn Ala His Lys Trp Leu
305                 310                 315                 320

Phe Thr Thr Leu Asp Cys Cys Cys Leu Trp Leu Lys Asp Pro Ser Ser
                325                 330                 335

Leu Thr Lys Ala Leu Ser Thr Asn Pro Glu Val Leu Arg Asn Asp Ala
            340                 345                 350

Thr Asp Ser Glu Gln Val Val Asp Tyr Lys Asp Trp Gln Ile Thr Leu
            355                 360                 365

Ser Arg Arg Phe Arg Ser Leu Lys Leu Trp Leu Val Leu Lys Ser Tyr
370                 375                 380

Gly Val Ala Asn Leu Arg Asn Phe Ile Arg Ser His Ile Glu Met Ala
385                 390                 395                 400

Lys His Phe Glu Glu Leu Val Ala Met Asp Glu Arg Phe Glu Ile Met
                405                 410                 415

Ala Pro Arg Asn Phe Ser Leu Val Cys Phe Arg Val Ser Leu Leu Ala
                420                 425                 430

Leu Glu Lys Lys Phe Asn Phe Val Asp Glu Thr Gln Val Asn Glu Phe
            435                 440                 445

Asn Ala Lys Leu Leu Glu Ser Ile Ile Ser Ser Gly Asn Val Tyr Met
        450                 455                 460

Thr His Thr Val Val Glu Gly Val Tyr Met Ile Arg Phe Ala Val Gly
465                 470                 475                 480

Ala Pro Leu Thr Asp Tyr Pro His Ile Asp Met Ala Trp Asn Val Val
                485                 490                 495

Arg Asn His Ala Thr Met Met Leu Asn Ala
            500                 505

<210> SEQ ID NO 91
<211> LENGTH: 494
<212> TYPE: PRT
<213> ORGANISM: Carica papaya
<300> PUBLICATION INFORMATION:
<308> DATABASE ACCESSION NUMBER: 16421889

<400> SEQUENCE: 91

Met Ser Ser Leu Ser Arg Asp Leu Asn Ala Ser Pro Leu Glu Pro Glu
1               5                   10                  15

Asn Phe Arg Val Glu Ser Lys Arg Val Ile Asp Phe Ile Ala Asp Tyr
                20                  25                  30

Tyr Lys Asn Ile Glu Thr Tyr Pro Val Gln Ser Arg Val Lys Pro Gly
            35                  40                  45

Tyr Leu Ala Gly Arg Leu Pro Ser Ser Ala Pro Phe Ser Pro Glu Ser
50                  55                  60

Leu Glu Thr Ile Leu Gln Asp Ile Ala Glu Asn Ile Ser Pro Gly Leu
65                  70                  75                  80

Thr His Trp Gln Ser Pro Asn Phe Phe Gly Tyr Phe Gln Ala Asn Ala
                85                  90                  95

Ser Thr Ala Gly Phe His Gly Glu Met Leu Cys Ser Gly Leu Asn Val
            100                 105                 110

Val Gly Phe Asn Trp Ile Ser Ser Pro Ala Ala Thr Glu Leu Glu Ser
        115                 120                 125

Leu Val Met Asp Trp Met Gly Asn Met Leu Lys Leu Pro Ser Ser Phe
130                 135                 140

Leu Phe Ser Gly Ser Gly Gly Gly Val Leu His Gly Ser Thr Cys Glu
145                 150                 155                 160

Ala Val Val Cys Thr Leu Ala Ala Ala Arg Asp Lys Thr Leu Asn Gln
                165                 170                 175

Leu Gly Gly Asn Tyr Gln Asn Ile Thr Lys Phe Val Val Tyr Ala Ser
            180                 185                 190

Asp Gln Thr His Phe Thr Leu Gln Lys Ala Ala Lys Leu Ile Gly Ile
        195                 200                 205

Pro Pro Ser Asn Phe Arg Ser Leu Thr Thr Ser Phe Pro Ser Gly Phe
        210                 215                 220

Ser Leu Ser Pro Glu Lys Leu Gln Ser Ala Ile Lys Asp Asp Ile Lys
225                 230                 235                 240

Ser Gly Tyr Val Pro Leu Tyr Val Cys Ala Thr Val Gly Thr Thr Ala
                245                 250                 255

Ala Gly Ala Val Asp Pro Ile Leu Glu Leu Gly Lys Val Ala Gln Glu
            260                 265                 270

Tyr Asn Leu Trp Phe His Ile Asp Ala Ala Tyr Ala Gly Ser Ala Cys
        275                 280                 285

Ile Cys Thr Glu Phe Arg His Tyr Leu Asn Gly Val Glu Leu Ala Asp
    290                 295                 300

Ser Ile Ser Thr Asn Pro His Lys Trp Leu Leu Thr Asn Met Glu Cys
305                 310                 315                 320

Ser Cys Leu Trp Val Lys Ser Pro Ser Ser Leu Val Asp Ser Leu Ser
                325                 330                 335

Thr Lys Ser Glu Ile Met Arg Asn Ala Ala Thr Asp Ser Asn Gln Val
            340                 345                 350

Ile Asp Tyr Lys Asp Trp Gln Ile Ala Leu Ser Arg Arg Phe Arg Ala
        355                 360                 365

Leu Lys Leu Trp Ile Val Ile Arg Arg His Gly Leu Ser Gly Leu Thr
    370                 375                 380

Ser His Ile His Lys Asp Ile Lys Met Ala Glu Leu Phe Glu Ser Leu
385                 390                 395                 400

Val Ala Lys Asp Lys Arg Phe Glu Ile Val Pro Arg Lys Phe Ala
                405                 410                 415

Leu Val Cys Phe Arg Phe Lys Pro Glu Lys Glu Asn Gln Asp Leu Ser
                420                 425                 430

Glu Leu Asn Ser Lys Leu Leu Asn Ala Val Asn Ser Ser Gly Cys Ala
            435                 440                 445

Phe Met Thr His Ala Val Leu Glu Gly Val Tyr Thr Ile Arg Cys Ala
        450                 455                 460

Ile Gly Thr Thr Leu Thr Glu Glu His His Val Val Asn Leu Trp Lys
465                 470                 475                 480

Leu Ile Gln Glu Lys Ala Gln Ser Leu Ile Ile Asn Glu Tyr
                485                 490

<210> SEQ ID NO 92
<211> LENGTH: 452
<212> TYPE: PRT
<213> ORGANISM: Sphagnum fallax
<300> PUBLICATION INFORMATION:
<308> DATABASE ACCESSION NUMBER: 0042s0024.1

<400> SEQUENCE: 92

Met Ser Ser Lys Val Ala Pro Trp Ser Arg Leu Ser Lys Pro Leu Asp
1               5                   10                  15

Val Glu Glu Phe Arg Thr His Ala Arg Met Val Asp Phe Ile Ala
            20                  25                  30

Asp Tyr His His Asn Ile Gln Ser Phe Pro Val His Ser Gln Leu Lys
        35                  40                  45

Pro Gly Tyr Leu Arg Pro Leu Leu Pro Asp Thr Ala Pro Thr Glu Pro
    50                  55                  60

Glu Val Val Glu Asp Val Phe Ala Asp Val Trp Asn Lys Ile Leu Pro
65                  70                  75                  80

```
Gly Ile Thr His Trp Gln Ser Pro Lys Phe Gly Tyr Tyr Pro Phe
                 85                  90                  95

Asn Val Ser Thr Ala Gly Ile Leu Gly Glu Ile Leu Ser Gly Val
            100                 105                 110

Asn Val Thr Gly Phe Ser Trp Ile Thr Ser Pro Val Val Thr Glu Leu
            115                 120                 125

Glu Ile Ile Val Leu Asp Trp Leu Gly Lys Leu Leu His Leu Pro Glu
            130                 135                 140

Glu Phe Leu Ser Ser Gly Lys Gly Gly Val Ile Gln Gly Thr Ser
145                 150                 155                 160

Ser Glu Ala Val Val Cys Thr Ser Gln His Met Ser Glu Ala Glu Ala
                165                 170                 175

Leu Thr Lys Leu Val Val Tyr Thr Ser Asp Gln Ala Gln Ser Cys Val
            180                 185                 190

Leu Arg Ala Cys Gln Ile Ala Gly Ile Ala Thr Ala Asn Phe Arg Pro
            195                 200                 205

Leu Pro Thr Asp Ala Ser Ser His Phe Ser Leu Ser Pro Ala Val Leu
            210                 215                 220

Ile Lys Ala Ala Ala Thr Asp Val Ala Ala Gly Leu Phe Pro Phe Phe
225                 230                 235                 240

Leu Cys Gly Lys Val Gly Thr Thr Ser Ser Ser Ala Val Asp Pro Leu
            245                 250                 255

Leu Glu Leu Gly Asp Ile Ala Lys Arg Tyr Gly Met Trp Tyr His Ile
            260                 265                 270

Asp Ala Ala Tyr Ala Gly Ser Ala Cys Ile Cys Pro Glu Phe Arg His
            275                 280                 285

Tyr Leu Asn Gly Val Glu Lys Ala Asp Ser Tyr Asn Met Asn Pro His
            290                 295                 300

Asp Trp Met Leu Thr Asn Phe Asp Cys Ser Thr Leu Trp Val Lys Asn
305                 310                 315                 320

Ser Glu Leu Leu Val Ala Ala Leu Ser Asn Lys Pro Val Tyr Leu Gln
            325                 330                 335

Asn Glu Ala Thr Asp Asn Asn Leu Val Asp Cys Ser His Ile Arg Asn
            340                 345                 350

His Ile Ser Ile Ala Lys His Phe Glu Ser Leu Val Arg Ala Asp Phe
            355                 360                 365

Arg Phe Glu Met Ile Val Pro Thr Asn Phe Ser Leu Val Cys Phe Arg
            370                 375                 380

Leu Arg Thr Pro Ala Gly Ser Lys Asp Asn Ser Arg Thr Leu Asn Ser
385                 390                 395                 400

Lys Leu Val Glu Ala Leu Asn Arg Lys Gly Asp Ile Leu Val Thr His
                405                 410                 415

Thr Glu Leu Ser Gly Arg Tyr Thr Leu Arg Phe Ala Val Gly Gly Thr
            420                 425                 430

His Met Glu Leu His His Val Gln Ala Ala Trp Asn Leu Arg Leu Gln
            435                 440                 445

Arg Gln Val Phe
    450

<210> SEQ ID NO 93
<211> LENGTH: 486
<212> TYPE: PRT
<213> ORGANISM: Eucalyptus grandis
<300> PUBLICATION INFORMATION:
<308> DATABASE ACCESSION NUMBER: E01788.1
```

<400> SEQUENCE: 93

```
Met Asn Pro Leu Asp Pro Gly Glu Phe Arg Arg Gln Gly His Met Val
1               5                   10                  15

Val Asp Phe Leu Ala Lys Tyr Tyr Glu Asn Ile Glu Lys Tyr Pro Val
            20                  25                  30

Leu Ser Gln Val Glu Pro Gly Tyr Leu Ser Lys Arg Leu Pro Ser Ser
        35                  40                  45

Ala Pro Gln Asp Glu Glu Pro Met Glu Ala Ile Leu Asp Asp Val His
    50                  55                  60

Gln His Ile Phe Pro Gly Leu Thr His Trp Gln Ser Pro Asn Phe Phe
65                  70                  75                  80

Ala Tyr Tyr Gln Thr Asn Thr Ser Thr Ala Ala Ile Leu Gly Glu Met
            85                  90                  95

Leu Cys Ala Gly Phe Asn Val Ala Gly Phe Asn Trp Val Ser Ser Pro
        100                 105                 110

Ala Ala Thr Glu Leu Glu Ser Leu Val Met Asp Trp Leu Gly Lys Met
    115                 120                 125

Leu Asp Leu Pro Arg Pro Phe Leu Pro Phe Gly Asn Gly Gly Val
130                 135                 140

Ile Glu Gly Asn Thr Ser Glu Ala Ile Ile Cys Thr Leu Thr Ala Ala
145                 150                 155                 160

Arg Asp Arg Val Leu Arg Lys Leu Gly His Asn Ser Ile Ala Lys Leu
                165                 170                 175

Val Val Tyr Gly Ser Asp Gln Thr Asn Cys Ser Phe Gln Lys Ala Ala
            180                 185                 190

Arg Val Val Gly Ile Asp Pro Arg Asn Phe Arg Ala Leu Lys Met Thr
        195                 200                 205

Arg Ser Thr Leu Phe Gly Leu Ser Pro Asp Ser Leu Glu Lys Ala Ile
    210                 215                 220

Arg Leu Asp Ile Asn Ala Gly Leu Ile Pro Leu Tyr Leu Cys Ala Thr
225                 230                 235                 240

Val Gly Thr Thr Ser Cys Ala Ala Val Asp Pro Leu Glu Pro Leu Cys
                245                 250                 255

Lys Val Ala Ser Lys Phe Ser Met Trp Ile His Val Asp Ala Ala Tyr
            260                 265                 270

Ala Gly Ala Ser Cys Ile Cys Pro Glu Tyr Arg Lys Phe Ile Asn Gly
        275                 280                 285

Val Glu Phe Ala Asp Ser Phe Ser Phe Asn Ala His Lys Trp Leu Leu
    290                 295                 300

Thr Pro Leu Asp Cys Cys Cys Leu Trp Val Lys Asp Pro Asn Ala Leu
305                 310                 315                 320

Val Lys Ser Leu Ser Thr Asp Pro Glu Tyr Leu Lys Asn Glu Ala Thr
                325                 330                 335

Glu Ser Lys Gln Val Ile Asp Tyr Ala Asp Trp Gln Leu Ser Leu Ser
            340                 345                 350

Arg Arg Phe Arg Ala Leu Lys Leu Trp Leu Val Leu Arg Ser His Gly
        355                 360                 365

Val Gln Asn Leu Arg Ser His Ile Lys Asn His Cys Arg Leu Ala Lys
    370                 375                 380

Leu Phe Glu Glu Leu Val Glu Glu Asp Pro Gln Phe Glu Val Val Phe
385                 390                 395                 400

Pro Arg Asn Phe Ala Leu Val Cys Phe Arg Ile His Pro Ser Gly Val
```

```
                  405                 410                 415
Ala Gly Met Leu Asn Ala Gln Leu Leu His Ala Ile Asn Ala Ser Gly
            420                 425                 430

Arg Val Phe Met Ser His Thr Thr Val Gly Gly Val Tyr Val Leu Arg
        435                 440                 445

Phe Ala Val Gly Ala Thr Leu Val Thr Glu Lys His Val Ile Met Ala
    450                 455                 460

Trp Lys Val Val Gln Glu His Ala Asn Ser Leu Leu Ser Met Pro Ala
465                 470                 475                 480

Ser Glu Gln His Ser Ala
            485

<210> SEQ ID NO 94
<211> LENGTH: 5336
<212> TYPE: DNA
<213> ORGANISM: Artificial Sequence
<220> FEATURE:
<223> OTHER INFORMATION: pHis8-4 vector

<400> SEQUENCE: 94
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tcccttaagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta tagggattt tgccgatttc ggcctattgg ttaaaaaatg agctgattta      420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatatttt gaaaaagccg tttctgtaat gaaggagaaa      660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga cgcgaaatac gcgatcgctg ttaaaaggac     960
aattacaaac aggaatcgaa tgcaaccggc gcaggaacac tgccagcgca tcaacaatat    1020
tttcacctga tcaggatat tcttctaata cctggaatgc tgttttcccg gggatcgcag     1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa atcccttaa     1440 cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
```

```
gtggtttgtt tgccggatca agagctacca actcttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata gtcgtgtct taccgggttg gactcaagac gatagttacc ggataaggcg    1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100 gccttttac ggttcctggc cttttgctgg ccttttgctc acatgttctt tcctgcgtta    2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
```

```
tcggctgaat tgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactt tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa agacaccgg    4560 catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatatacc atgaaacacc accaccaca ccaccacca    5100 ggtggtgaaa acttgtactt ccaggcccat ggcggatccg aattcgagct ccgtcgacaa   5160
gcttgcggcc gcactcgagc accaccacca ccaccactga gatccggctg ctaacaaagc   5220
ccgaaaggaa gctgagttgg ctgctgccac cgctgagcaa taactagcat aaccccttgg   5280
ggcctctaaa cgggtcttga gggggttttt gctgaaagga ggaactatat ccggat       5336
```

<210> SEQ ID NO 95
<211> LENGTH: 10003
<212> TYPE: DNA
<213> ORGANISM: Artificial Sequence
<220> FEATURE:
<223> OTHER INFORMATION: pEAQ-HT vector

<400> SEQUENCE: 95

```
cctgtggttg gcatgcacat acaaatggac gaacggataa accttttcac gccctttaa     60 atatccgatt attctaataa acgctctttt ctcttaggtt tacccgccaa tatatcctgt    120
caaacactga tagtttgtga accatcaccc aaatcaagtt ttttgggtc gaggtgccgt    180 aaagcactaa atcggaaccc taaagggagc cccgattta gagcttgacg ggaaagccg     240 gcgaacgtgg cgagaaagga agggaagaaa gcgaaaggag cgggcgccat tcaggctgcg   300
caactgttgg gaagggcgat cggtgcgggc ctcttcgcta ttacgccagc tggcgaaagg   360
gggatgtgct gcaaggcgat taagttgggt aacgccaggg ttttcccagt cacgacgttg   420
taaaacgacg gccagtgaat tgttaattaa gaattcgagc tccaccgcgg aaacctcctc   480
ggattccatt gcccagctat ctgtcacttt attgagaaga tagtggaaaa ggaaggtggc   540
tcctacaaat gccatcattg cgataaagga aaggccatcg ttgaagatgc ctctgccgac   600
agtggtccca agatggaccc cccacccacg aggagcatcg tggaaaaaga agacgttcca   660
```

```
accacgtctt caaagcaagt ggattgatgt gatatctcca ctgacgtaag ggatgacgca    720
caatcccact atccttcgca agacccttcc tctatataag gaagttcatt tcatttggag    780
aggtattaaa atcttaatag gttttgataa aagcgaacgt ggggaaaccc gaaccaaacc    840
ttcttctaaa ctctctctca tctctcttaa agcaaacttc tctcttgtct ttcttgcgtg    900
agcgatcttc aacgttgtca gatcgtgctt cggcaccagt acaacgtttt ctttcactga    960
agcgaaatca aagatctctt tgtggacacg tagtgcggcg ccattaaata acgtgtactt   1020
gtcctattct tgtcggtgtg gtcttgggaa aagaaagctt gctggaggct gctgttcagc   1080
cccatacatt acttgttacg attctgctga cttcggcgg gtgcaatatc tctacttctg   1140
cttgacgagg tattgttgcc tgtacttctt tcttcttctt cttgctgatt ggttctataa   1200
gaaatctagt atttcttg aaacagagtt ttcccgtggt tttcgaactt ggagaaagat   1260
tgttaagctt ctgtatattc tgcccaaatt cgcgaccggt atgcatcacc atcaccatca   1320
tcccgggcat caccatcacc atcactagct cgaggccttt aactctggtt tcattaaatt   1380
ttctttagtt tgaatttact gttattcggt gtgcatttct atgtttggtg agcggttttc   1440
tgtgctcaga gtgtgtttat tttatgtaat ttaatttctt tgtgagctcc tgtttagcag   1500
gtcgtcccctt cagcaaggac acaaaaagat tttaattta ttaaaaaaaa aaaaaaaaa   1560
gaccgggaat tcgatatcaa gcttatcgac ctgcagatcg ttcaaacatt tggcaataaa   1620
gtttcttaag attgaatcct gttgccggtc ttgcgatgat tatcatataa tttctgttga   1680
attacgttaa gcatgtaata attaacatgt aatgcatgac gttatttatg agatgggttt   1740
ttatgattag agtcccgcaa ttatacattt aatacgcgat agaaaacaaa atatagcgcg   1800
caaactagga taaattatcg cgcgcggtgt catctatgtt actagatctc tagagtctca   1860
agcttggcgc gccagcttgg cgtaatcatg gtcatagctg ttgcgattaa gaattcgagc   1920
tcggtaccc cctactccaa aaatgtcaaa gatacagtct cagaagacca aagggctatt   1980
gagacttttc aacaaagggt aatttcggga aacctcctcg gattccattg cccagctatc   2040
tgtcacttca tcgaaggac agtagaaaag gaaggtggct cctacaaatg ccatcattgc   2100
gataaaggaa aggctatcat tcaagatgcc tctgccgaca gtggtcccaa agatggaccc   2160
ccacccacga ggagcatcgt ggaaaaagaa gacgttccaa ccacgtcttc aaagcaagtg   2220
gattgatgtg acatctccac tgacgtaagg gatgacgcac aatcccacta tccttcgcaa   2280
gacccttcct ctatataagg aagttcattt catttggaga ggacagccca agcttcgact   2340
ctagaggatc cccttaaatc gatatggaac gagctataca aggaaacgac gctagggaac   2400
aagctaacag tgaacgttgg gatggaggat caggaggtac cacttctccc ttcaaacttc   2460
ctgacgaaag tccgagttgg actgagtggc ggctacataa cgatgagacg aattcgaatc   2520
aagataatcc ccttggtttc aaggaaagct ggggtttcgg gaaagttgta tttaagagat   2580
atctcagata cgacaggacg gaagcttcac tgcacagagt ccttggatct tggacgggag   2640
attcggttaa ctatgcagca tctcgatttt tcggtttcga ccagatcgga tgtacctata   2700
gtattcggtt tcgaggagtt agtatcaccg tttctggagg gtctcgaact cttcagcatc   2760
tctgtgagat ggcaattcgg tctaagcaag aactgctaca gcttgcccca atcgaagtgg   2820
aaagtaatgt atcaagagga tgccctgaag gtactgagac cttcgaaaaa gaaagcgagt   2880
aaggggagct cgaattcgct gaaatcacca gtctctctct acaaatctat ctctctctat   2940
tttctccata ataatgtgt gagtagtttc ccgataaggg aaattagggt tcttataggg   3000
tttcgctcat gtgttgagca tataagaaac ccttagtatg tatttgtatt tgtaaaatac   3060
```

```
ttctatcaat aaaatttcta attcctaaaa ccaaaatcca gtactaaaat ccagatctcc    3120
taaagtccct atagatcttt gtcgtgaata taaaccagac acgagacgac taaacctgga    3180
gcccagacgc cgttcgaagc tagaagtacc gcttaggcag gaggccgtta gggaaaagat    3240
gctaaggcag ggttggttac gttgactccc ccgtaggttt ggtttaaata tgatgaagtg    3300
gacggaagga aggaggaaga caaggaagga taaggttgca ggccctgtgc aaggtaagaa    3360
gatggaaatt tgatagaggt acgctactat acttatacta tacgctaagg gaatgcttgt    3420
atttataccc tatacccct aataacccct tatcaattta agaaataatc cgcataagcc    3480
cccgcttaaa aattggtatc agagccatga ataggtctat gaccaaaact caagaggata    3540
aaacctcacc aaaatacgaa agagttctta actctaaaga taaaagatgg cgcgtggccg    3600
gcctacagta tgagcggaga attaagggag tcacgttatg accccgccg atgacgcggg    3660 acaagccgtt ttacgtttgg aactgacaga accgcaacgt tgaaggagcc actcagccgc    3720
gggtttctgg agtttaatga gctaagcaca tacgtcagaa accattattg cgcgttcaaa    3780
agtcgcctaa ggtcactatc agctagcaaa tatttcttgt caaaaatgct ccactgacgt    3840
tccataaatt cccctcggta tccaattaga gtctcatatt cactctcaat ccaaataatc    3900
tgcaccggat ctggatcgtt tcgcatgatt gaacaagatg gattgcacgc aggttctccg    3960
gccgcttggg tggagaggct attcggctat gactgggcac aacagacaat cggctgctct    4020
gatgccgccg tgttccggct gtcagcgcag gggcgcccgg ttcttttttgt caagaccgac    4080 ctgtccggtg ccctgaatga actgcaggac gaggcagcgc ggctatcgtg gctggccacg    4140
acgggcgttc cttgcgcagc tgtgctcgac gttgtcactg aagcgggaag ggactggctg    4200
ctattgggcg aagtgccggg gcaggatctc ctgtcatctc accttgctcc tgccgagaaa    4260
gtatccatca tggctgatgc aatgcggcgg ctgcatacgc ttgatccggc tacctgccca    4320
ttcgaccacc aagcgaaaca tcgcatcgag cgagcacgta ctcggatgga agccggtctt    4380
gtcgatcagg atgatctgga cgaagagcat caggggctcg cgccagccga actgttcgcc    4440
aggctcaagg cgcgcatgcc cgacggcgat gatctcgtcg tgacccatgg cgatgcctgc    4500
ttgccgaata tcatggtgga aaatggccgc ttttctggat tcatcgactg tggccggctg    4560
ggtgtggcgg accgctatca ggacatagcg ttggctaccc gtgatattgc tgaagagctt    4620
ggcggcgaat gggctgaccg cttcctcgtg ctttacggta tcgccgctcc cgattcgcag    4680
cgcatcgcct tctatcgcct tcttgacgag ttcttctgag cgggactctg gggttcgaaa    4740
tgaccgacca agcgacgccc aacctgccat cacgagattt cgattccacc gccgccttct    4800
atgaaaggtt gggcttcgga atcgttttcc gggacgccgg ctggatgatc ctccagcgcg    4860
gggatctcat gctggagttc ttcgcccacg gatctctgc ggaacaggcg gtcgaaggtg    4920
ccgatatcat tacgacagca acggccgaca agcacaacgc cacgatcctg agcgacaata    4980
tgatcgcggc gtccacatca acggcgtcgg cggcgactgc ccaggcaaga ccagatgca    5040 ccgcgatatc ttgctgcgtt cggatatttt cgtggagttc ccgccacaga cccggatgat    5100
ccccgatcgt tcaaacattt ggcaataaag tttcttaaga ttgaatcctg ttgccggtct    5160
tgcgatgatt atcatataat ttctgttgaa ttacgttaag catgtaataa ttaacatgta    5220
atgcatgacg ttatttatga gatgggtttt tatgattaga gtcccgcaat tatacattta    5280
atacgcgata gaaaacaaaa tatagcgcgc aaactaggat aaattatcgc gcgcggtgtc    5340
atctatgtta ctagatcggg actgtaggcc ggccctcact ggtgaaaaga aaaaccaccc    5400
```

```
cagtacatta aaaacgtccg caatgtgtta ttaagttgtc taagcgtcaa tttgtttaca   5460
ccacaatata tcctgccacc agccagccaa cagctcccg accggcagct cggcacaaaa    5520
tcaccactcg atacaggcag cccatcagtc cgggacggcg tcagcgggag agccgttgta   5580
aggcggcaga ctttgctcat gttaccgatg ctattcggaa gaacggcaac taagctgccg   5640
ggtttgaaac acggatgatc tcgcggaggg tagcatgttg attgtaacga tgacagagcg   5700
ttgctgcctg tgatcaaata tcatctccct cgcagagatc cgaattatca gccttcttat   5760
tcatttctcg cttaaccgtg acagagtaga caggctgtct cgcggccgag gggcgcagcc   5820
cctgggggg atgggaggcc cgcgttagcg ggcggagg gttcgagaag ggggggcacc       5880
cccttcggc gtgcgcggtc acgcgcacag ggcgcagccc tggttaaaaa caaggtttat    5940
aaatattggt ttaaaagcag gttaaaagac aggttagcgg tggccgaaaa acgggcggaa   6000
acccttgcaa atgctggatt ttctgcctgt ggacagcccc tcaaatgtca ataggtgcgc   6060
ccctcatctg tcagcactct gcccctcaag tgtcaaggat cgcgcccctc atctgtcagt   6120
agtcgcgccc ctcaagtgtc aataccgcag ggcacttatc cccaggcttg tccacatcat   6180
ctgtgggaaa ctcgcgtaaa atcaggcgtt ttcgccgatt tgcgaggctg ccagctcca    6240
cgtcgccggc cgaaatcgag cctgcccctc atctgtcaac gccgcgccgg gtgagtcggc   6300
ccctcaagtg tcaacgtccg cccctcatct gtcagtgagg ccaagttttt ccgcgaggta   6360
tccacaacgc cggcggccgc ggtgtctcgc acacggcttc gacggcgttt ctggcgcgtt   6420
tgcagggcca tagacggccg ccagcccagc ggcgagggca accagcccgg tgagcgtcgg   6480
aaaggcgctc ggtcttgcct tgctcgtcgg tgatgtacac tagtcgctgg ctgctgaacc   6540
cccagccgga actgaccca caaggcccta gcgtttgcaa tgcaccaggt catcattgac     6600
ccaggcgtgt tccaccaggc cgctgcctcg caactcttcg caggcttcgc cgacctgctc   6660
gcgccacttc ttcacgcggg tggaatccga tccgcacatg aggcggaagg tttccagctt   6720
gagcgggtac ggctcccggt gcgagctgaa atagtcgaac atccgtcggg ccgtcggcga   6780
cagcttgcgg tacttctccc atatgaattt cgtgtagtgg tcgccagcaa acagcacgac   6840
gatttcctcg tcgatcagga cctggcaacg ggacgttttc ttgccacggt ccaggacgcg   6900
gaagcggtgc agcagcgaca ccgattccag gtgcccaacg cggtcggacg tgaagcccat   6960
cgccgtcgcc tgtaggcgcg acaggcattc ctcggccttc gtgtaatacc ggccattgat   7020
cgaccagccc aggtcctggc aaagctcgta gaacgtgaag gtgatcggct cgccgatagg   7080
ggtgcgcttc gcgtactcca acacctgctg ccacaccagt tcgtcatcgt cggcccgcag   7140
ctcgacgccg gtgtaggtga tcttcacgtc cttgttgacg tggaaaatga ccttgttttg   7200
cagcgcctcg cgcgggattt tcttgttgcg cgtggtgaac agggcagagc gggccgtgtc   7260
gtttggcatc gctcgcatcg tgtccggcca cggcgcaata tcgaacaagg aaagctgcat   7320
ttccttgatc tgctgcttcg tgtgtttcag caacgcggcc tgcttggcct cgctgacctg   7380
ttttgccagg tcctcgccgg cggttttttcg cttcttggtc gtcatagttc ctcgcgtgtc   7440
gatggtcatc gacttcgcca aacctgccgc ctcctgttcg agacgacgcg aacgctccac   7500
ggcggccgat ggcgcgggca gggcagggg agccagttgc acgctgtcgc gctcgatctt    7560
ggccgtagct tgctggacca tcgagccgac ggactggaag gtttcgcggg gcgcacgcat   7620
gacggtgcgg cttgcgatgg tttcggcatc tcggcggaa accccgcgt cgatcagttc     7680
ttgcctgtat gccttccggt caaacgtccg attcattcac cctccttgcg ggattgcccc   7740
gactcacgcc ggggcaatgt gcccttattc ctgatttgac ccgcctggtg ccttggtgtc   7800
```

```
cagataatcc accttatcgg caatgaagtc ggtcccgtag accgtctggc cgtccttctc    7860
gtacttggta ttccgaatct tgccctgcac gaataccagc gaccccttgc ccaaatactt    7920
gccgtgggcc tcggcctgag agccaaaaca cttgatgcgg aagaagtcgg tgcgctcctg    7980
cttgtcgccg gcatcgttgc gccacatcta ggtactaaaa caattcatcc agtaaaatat    8040
aatattttat tttctcccaa tcaggcttga tccccagtaa gtcaaaaaat agctcgacat    8100
actgttcttc cccgatatcc tccctgatcg accggacgca gaaggcaatg tcataccact    8160
tgtccgccct gccgcttctc ccaagatcaa taaagccact tactttgcca tctttcacaa    8220
agatgttgct gtctcccagg tcgccgtggg aaaagacaag ttcctcttcg ggcttttccg    8280
tctttaaaaa atcatacagc tcgcgcggat ctttaaatgg agtgtcttct tcccagtttt    8340
cgcaatccac atcggccaga tcgttattca gtaagtaatc caattcggct aagcggctgt    8400
ctaagctatt cgtataggga caatccgata tgtcgatgga gtgaaagagc ctgatgcact    8460
ccgcatacag ctcgataatc ttttcagggc tttgttcatc ttcatactct ccgagcaaa    8520
ggacgccatc ggcctcactc atgagcagat tgctccagcc atcatgccgt tcaaagtgca    8580
ggacctttgg aacaggcagc tttccttcca gccatagcat catgtccttt tcccgttcca    8640
catcataggt ggtcccttta taccggctgt ccgtcatttt taaatatagg ttttcatttt    8700
ctcccaccag cttatatacc ttagcaggag acattcctcc cgtatctttt acgcagcggt    8760
atttttcgat cagttttttc aattccggtg atattctcat tttagccatt tattatttcc    8820
ttcctctttt ctacagtatt taaagatacc ccaagaagct aattataaca agacgaactc    8880
caattcactg ttccttgcat tctaaaacct taaataccag aaaacagctt tttcaaagtt    8940
gttttcaaag ttggcgtata acatagtatc gacggagccg attttgaaac cacaattatg    9000
ggtgatgctg ccaacttact gatttagtgt atgatggtgt ttttgaggtg ctccagtggc    9060
ttctgtttct atcagctgtc cctcctgttc agctactgac ggggtggtgc gtaacggcaa    9120
aagcaccgcc ggacatcagc gctatctctg ctctcactgc cgtaaaacat ggcaactgca    9180
gttcacttac accgcttctc aacccggtac gcaccagaaa atcattgata tggccatgaa    9240
tggcgttgga tgccgggcaa cagcccgcat tatgggcgtt ggcctcaaca cgattttacg    9300
tcacttaaaa aactcaggcc gcagtcggta actatgcgt gtgaaatacc gcacagatgc    9360
gtaaggagaa ataccgcat caggcgctct tccgcttcct cgctcactga ctcgctgcgc    9420
tcggtcgttc ggctgcggcg agcggtatca gctcactcaa aggcggtaat acggttatcc    9480
acagaatcag gggataacgc aggaaagaac atgtgagcaa aaggccagca aaaggccagg    9540
aaccgtaaaa aggccgcgtt gctggcgttt ttccataggc tccgcccccc tgacgagcat    9600
cacaaaaatc gacgctcaag tcagaggtgg cgaaacccga caggactata agataccag    9660
gcgtttcccc ctggaagctc cctcgtgcgc tctcctgttc cgaccctgcc gcttaccgga    9720
tacctgtccg cctttctccc ttcgggaagc gtggcgcttt ctcatagctc acgctgtagg    9780
tatctcagtt cggtgtaggt cgttcgctcc aagctgggct gtgtgcacga accccccgtt    9840
cagcccgacc gctgcgcctt atccggtaac tatcgtcttg agtccaaccc ggtaagacac    9900
gacttatcgc cactggcagc aggtaacctc gcgcatacag ccgggcagtg acgtcatcgt    9960
ctgcgcggaa atggacgggc ccccggcgcc agatctgggg aac                      10003

<210> SEQ ID NO 96
<211> LENGTH: 5291
<212> TYPE: DNA
```

<213> ORGANISM: Artificial Sequence
<220> FEATURE:
<223> OTHER INFORMATION: pJKW 1410 vector

<400> SEQUENCE: 96

```
ccctgaattc gcatctagac tgatgagacg tggtagagcc acaaacagcc ggtacaagca      60
acgatctcca ggaccatctg aatcatgcgc ggatgacacg aactcacgac ggcgatcaca     120
gacattaacc cacagtacag acactgcgac aacgtggcaa ttcgtcgcaa tacaacgtga     180
gaccgaaagt gaaacgtgat tcatgcgtc attttgaaca ttttgtaaat cttatttaat      240
aatgtgtgcg gcaattcaca tttaatttat gaatgttttc ttaacatcgc ggcaactcaa     300
gaaacggcag gttcggatct tagctactag agaaagagga gaaatactag atgcgtaaag     360
gcgaagagct gttcactggt gtcgtcccta ttctggtgga actggatggt gatgtcaacg     420
gtcataagtt ttccgtgcgt ggcgagggtg aaggtgacgc aactaatggt aaactgacgc     480
tgaagttcat ctgtactact ggtaaactgc cggttccttg ccgactctg gtaacgacgc      540
tgacttatgg tgttcagtgc tttgctcgtt atccggacca tatgaagcag catgacttct     600
tcaagtccgc catgccggaa ggctatgtgc aggaacgcac gatttccttt aaggatgacg     660
gcacgtacaa aacgcgtgcg gaagtgaaat ttgaaggcga taccctggta aaccgcattg     720
agctgaaagg cattgacttt aaagaggacg gcaatatcct gggccataag ctggaataca     780
attttaacag ccacaatgtt tacatcaccg ccgataaaca aaaaaatggc attaaagcga     840
attttaaaat tcgccacaac gtggaggatg gcagcgtgca gctggctgat cactaccagc     900
aaaacactcc aatcggtgat ggtcctgttc tgctgccaga caatcactat ctgagcacgc     960
aaagcgttct gtctaaagat ccgaacgaga acgcgatca tatggttctg ctggagttcg    1020
taaccgcagc gggcatcacg catggtatgg atgaactgta caatgacca ggcatcaaat    1080
aaaacgaaag gctcagtcga aagactgggc ctttcgtttt atctgttgtt tgtcggtgaa    1140
cgctctctac tagagtcaca ctggctcacc ttcgggtggg cctttctgcg tttataggtc    1200
tcagctggaa atctgctcgt cagtggtgct cacactgacg aatcatgtac agatcatacc    1260
gatgactgcc tggcgactca caactaagca agacagccgg aaccagcgcc ggcgaacacc    1320
actgcatata tggcatatca caacagtcca cgtctcaagc agttacagag atgttacgaa    1380
ccactagtgc actgcagtac aaaacacagtc ctttcccgca attttctttt tctattactc    1440
ttggcctcct ctagtacact ctatattttt ttatgcctcg gtaatgattt tcattttttt    1500
ttttccacct agcggatgac tcttttttt tcttagcgat tggcattatc acataatgaa    1560
ttatacatta tataaagtaa tgtgatttct tcgaagaata tactaaaaaa tgagcaggca    1620
agataaacga aggcaaagat gacagagcag aaagccctag taaagcgtat tacaaatgaa    1680
accaagattc agattgcgat ctcttaaag ggtggtcccc tagcgataga gcactcgatc     1740
ttcccagaaa aagaggcaga agcagtagca gaacaggcca cacaatcgca agtgattaac    1800
gtccacacag gtatagggtt tctggaccat atgatacatg ctctggccaa gcattccggc    1860
tggtcgctaa tcgttgagtg cattggtgac ttacacatag acgaccatca caccactgag    1920
gactgcggga ttgctctcgg tcaagctttt aagagggccc tagggccgt gcgtggagta    1980
aaaaggtttg gatcaggatt tgcgcctttg gatgaggcac tttccagagc ggtggttgat    2040
ctttcgaaca ggccgtacgc agttgtcgaa cttggtttgc aaaggagaa agtaggtgat    2100
ctctcttgcg agatgatccc gcattttctt gaaagctttg cagaggctag cagaattacc    2160
ctccacgttg attgtctgcg aggcaagaat gatcatcacc gtagtgagag tgcgttcaag    2220
```

```
gctcttgcgg ttgccataag agaagccacc tcgcccaatg gtaccaacga tgttccctcc    2280
accaaaggtg ttcttatgta gtgacaccga ttatttaaag ctgctgcata cgatatatat    2340
acatgtgtat atatgtatac ctatgaatgt cagtaagtat gtatacgaac agtatgatac    2400
tgaagatgac aagtaatgc atcattctat acgtgtcatt ctgaacgagg cgcgctttcc     2460
ttttttcttt ttgcttttc ttttttttc tcttgaactc gacggatcat agagtaacga      2520
agcatctgtg cttcattttg tagaacaaaa atgcaacgcg agagcgctaa ttttcaaac     2580 aaagaatctg agctgcattt ttacagaaca gaaatgcaac gcgaaagcgc tattttacca    2640
acgaagaatc tgtgcttcat ttttgtaaaa caaaaatgca acgcgagagc gctaattttt    2700
caaacaaaga atctgagctg cattttaca gaacagaaat gcaacgcgag agcgctattt    2760
taccaacaaa gaatctatac ttcttttttg ttctacaaaa atgcatcccg agagcgctat    2820
ttttctaaca aagcatctta gattactttt tttctccttt gtgcgctcta taatgcagtc    2880
tcttgataac ttttgcact gtaggtccgt taaggttaga agaaggctac tttggtgtct     2940
attttctctt ccataaaaaa agcctgactc cacttcccgc gtttactgat tactagcgaa    3000
gctgcgggtg catttttca agataaaggc atccccgatt atattctata ccgatgtgga    3060
ttgcgcatac tttgtgaaca gaaagtgata gcgttgatga ttcttcattg gtcagaaaat    3120
tatgaacggt ttcttctatt ttgtctctat atactacgta taggaaatgt ttacattttc    3180
gtattgtttt cgattcactc tatgaatagt tcttactaca atttttttgt ctaaagagta    3240
atactagaga taaacataaa aaatgtagag gtcgagttta gatgcaagtt caaggagcga    3300
aaggtggatg ggtaggttat ataggggatat agcacagaga tatatagcaa agagatactt    3360
ttgagcaatg tttgtggaag cggtattcgc aatattttag tagctcgtta cagtccggtg    3420 cgttttggt tttttgaaag tgcgtcatca gagcgctttt ggttttcaaa agcgctctga    3480
agttcctata ctttctagct agagaatagg aacttcccga gcggccgcgt gttacaacca    3540
attaaccaat tctgattaga aaaactcatc gagcatcaaa tgaaactgca atttattcat    3600
atcaggatta tcaataccat atttttgaaa aagccgtttc tgtaatgaag gagaaaactc    3660
accgaggcag ttccatagga tggcaagatc ctggtatcgg tctgcgattc cgactcgtcc    3720
aacatcaata caacctatta atttcccctc gtcaaaaata aggttatcaa gtgagaaatc    3780
accatgagtg acgactgaat ccggtgagaa tggcaaaagc ttatgcattt ctttccagac    3840
ttgttcaaca ggccagccat tacgctcgtc atcaaaatca ctcgcatcaa ccaaaccgtt    3900
attcattcgt gattgcgcct gagcgaggcg aaatacgcga tcgctgttaa aaggacaatt    3960
acaaacagga atcgaatgca accggcgcag gaacactgcc agcgcatcaa caatattttc    4020
acctgaatca ggatattctt ctaatacctg gaatgctgtt ttcccgggga tcgcagtggt    4080
gagtaaccat gcatcatcag gagtacggat aaaatgcttg atggtcggaa gaggcataaa    4140
ttccgtcagc cagtttagtc tgaccatctc atctgtaaca tcattggcaa cgctacctt     4200 gccatgtttc agaaacaact ctggcgcatc gggcttccca tacaatcgat agattgtcgc    4260
acctgattgc ccgacattat cgcgagccca tttatacca tataaatcag catccatgtt     4320
ggaatttaat cgcggcctgg agcaagacgt ttcccgttga atatggctca taacacccct    4380
tgtattactg tttatgtaag cagacagttt tattgttcat gatgatatat ttttatcttg    4440
tgcaatgtaa catcagagat tttgagacac aacgtggctt tgttgaataa atcgaacttt    4500
tgctgagttg aaggatcagt catgaccaaa atcccttaac gtgagttttc gttccactga    4560
```

```
gcgtcagacc ccgtagaaaa gatcaaagga tcttcttgag atccttttt tctgcgcgta      4620 atctgctgct tgcaaacaaa aaaccaccg ctaccagcgg tggtttgttt gccggatcaa      4680
gagctaccaa ctcttttcc gaaggtaact ggcttcagca gagcgcagat accaaatact      4740
gttcttctag tgtagccgta gttaggccac cacttcaaga actctgtagc accgcctaca      4800
tacctcgctc tgctaatcct gttaccagtg gctgctgcca gtggcgataa gtcgtgtctt      4860
accgggttgg actcaagacg atagttaccg gataaggcgc agcggtcggg ctgaacgggg      4920
ggttcgtgca cacagcccag cttggagcga acgacctaca ccgaactgag atacctacag      4980
cgtgagctat gagaaagcgc cacgcttccc gaagggagaa aggcggacag gtatccggta      5040
agcggcaggg tcggaacagg agagcgcacg agggagcttc caggggggaaa cgcctggtat      5100 ctttatagtc ctgtcgggtt cgccacctc tgacttgagc gtcgatttt gtgatgctcg      5160 tcagggggc ggagcctatg gaaaaacgcc agcaacgcgg cctttttacg gttcctggcc      5220
ttttgctggc cttttgctca catgttcttt cctgcgttat cccctgattc tgtggataac      5280
cgtgcggccg c                                                         5291

<210> SEQ ID NO 97
<211> LENGTH: 52
<212> TYPE: DNA
<213> ORGANISM: Artificial Sequence
<220> FEATURE:
<223> OTHER INFORMATION: pHis8-4 Forward primer for Rr4HPAAS

<400> SEQUENCE: 97
gaaaacttgt acttccaggc ccatggcatg ggcagcttgc cttctcctaa tg            52

<210> SEQ ID NO 98
<211> LENGTH: 52
<212> TYPE: DNA
<213> ORGANISM: Artificial Sequence
<220> FEATURE:
<223> OTHER INFORMATION: pHis8-4 Reverse primer for Rr4HPAAS

<400> SEQUENCE: 98
ctcgaattcg gatccgccat ggctaagaca cgatgctttg agctgtttct tg            52

<210> SEQ ID NO 99
<211> LENGTH: 53
<212> TYPE: DNA
<213> ORGANISM: Artificial Sequence
<220> FEATURE:
<223> OTHER INFORMATION: pEAQ-HT Forward primer for Rr4HPAAS

<400> SEQUENCE: 99
gtatattctg cccaaattcg cgaccggtat gggcagcttg ccttctccta atg           53

<210> SEQ ID NO 100
<211> LENGTH: 65
<212> TYPE: DNA
<213> ORGANISM: Artificial Sequence
<220> FEATURE:
<223> OTHER INFORMATION: pEAQ-HT Reverse primer for Rr4HPAAS

<400> SEQUENCE: 100
gaaaatttaa tgaaaccaga gttaaaggcc tcgagctaag acacgatgct ttgagctgtt    60
tcttg                                                               65

<210> SEQ ID NO 101
<211> LENGTH: 55
```

-continued

```
<212> TYPE: DNA
<213> ORGANISM: Artificial Sequence
<220> FEATURE:
<223> OTHER INFORMATION: p423TEF Forward primer for Rr4HPAAS

<400> SEQUENCE: 101
gcatagcaat ctaatctaag ttttctagaa ctagtatggg cagcttgcct tctcc          55

<210> SEQ ID NO 102
<211> LENGTH: 51
<212> TYPE: DNA
<213> ORGANISM: Artificial Sequence
<220> FEATURE:
<223> OTHER INFORMATION: p423TEF Reverse primer for Rr4HPAAS

<400> SEQUENCE: 102
cagcccgggg gatccactag tctaagacac gatgctttga gctgtttctt g              51

<210> SEQ ID NO 103
<211> LENGTH: 48
<212> TYPE: DNA
<213> ORGANISM: Artificial Sequence
<220> FEATURE:
<223> OTHER INFORMATION: pHis8-4 Forward primer for RrAAS

<400> SEQUENCE: 103
gaaaacttgt acttccaggc ccatggcatg gaggaggagt tgaagccg                  48

<210> SEQ ID NO 104
<211> LENGTH: 56
<212> TYPE: DNA
<213> ORGANISM: Artificial Sequence
<220> FEATURE:
<223> OTHER INFORMATION: pHis8-4 Reverse primer for RrAAS

<400> SEQUENCE: 104
ctcgaattcg gatccgccat ggtcatgcat ttatatgctt ttgtagcagt gaagtg         56

<210> SEQ ID NO 105
<211> LENGTH: 48
<212> TYPE: DNA
<213> ORGANISM: Artificial Sequence
<220> FEATURE:
<223> OTHER INFORMATION: pHis8-4 Forward primer for RrPAR1

<400> SEQUENCE: 105
gaaaacttgt acttccaggc ccatggcatg agtttaagcg agcgggg                   48

<210> SEQ ID NO 106
<211> LENGTH: 47
<212> TYPE: DNA
<213> ORGANISM: Artificial Sequence
<220> FEATURE:
<223> OTHER INFORMATION: pHis8-4 Reverse primer for RrPAR1

<400> SEQUENCE: 106
ctcgaattcg gatccgccat ggtcagagtt tggcgaaacc cttttcc                   47

<210> SEQ ID NO 107
<211> LENGTH: 56
<212> TYPE: DNA
<213> ORGANISM: Artificial Sequence
<220> FEATURE:
<223> OTHER INFORMATION: p425TEF Forward primer for RrPAR1

<400> SEQUENCE: 107
```

```
gcatagcaat ctaatctaag ttttctagaa ctagtatgag tttaagcgga gcgggg       56
```

<210> SEQ ID NO 108
<211> LENGTH: 46
<212> TYPE: DNA
<213> ORGANISM: Artificial Sequence
<220> FEATURE:
<223> OTHER INFORMATION: p425TEF Reverse primer for RrPAR1

<400> SEQUENCE: 108

```
cagcccgggg gatccactag ttcagagttt ggcgaaaccc ttttcc                 46
```

<210> SEQ ID NO 109
<211> LENGTH: 55
<212> TYPE: DNA
<213> ORGANISM: Artificial Sequence
<220> FEATURE:
<223> OTHER INFORMATION: pHis8-4 Forward primer for RrPAR2

<400> SEQUENCE: 109

```
gaaaacttgt acttccaggc ccatggcatg ggtttatctg aagagaagaa gttag       55
```

<210> SEQ ID NO 110
<211> LENGTH: 54
<212> TYPE: DNA
<213> ORGANISM: Artificial Sequence
<220> FEATURE:
<223> OTHER INFORMATION: pHis8-4 Reverse primer for RrPAR2

<400> SEQUENCE: 110

```
ctcgaattcg gatccgccat ggtcatttgt ctttcaaact tcgacagtg tctc         54
```

<210> SEQ ID NO 111
<211> LENGTH: 60
<212> TYPE: DNA
<213> ORGANISM: Artificial Sequence
<220> FEATURE:
<223> OTHER INFORMATION: p426TEF Forward primer for RrUGT1

<400> SEQUENCE: 111

```
caatctaatc taagttttct agaactagta tggtgacgaa aaaaactcac attcttatcc  60
```

<210> SEQ ID NO 112
<211> LENGTH: 48
<212> TYPE: DNA
<213> ORGANISM: Artificial Sequence
<220> FEATURE:
<223> OTHER INFORMATION: p426TEF Reverse primer for RrUGT1

<400> SEQUENCE: 112

```
cagcccgggg gatccactag ttcaggtaag accagacaca aacttgac               48
```

<210> SEQ ID NO 113
<211> LENGTH: 51
<212> TYPE: DNA
<213> ORGANISM: Artificial Sequence
<220> FEATURE:
<223> OTHER INFORMATION: p426TEF Forward primer for RrUGT2

<400> SEQUENCE: 113

```
caatctaatc taagttttct agaactagta tgggttctga ttcacggcct c           51
```

<210> SEQ ID NO 114
<211> LENGTH: 54
<212> TYPE: DNA
<213> ORGANISM: Artificial Sequence
<220> FEATURE:
<223> OTHER INFORMATION: p426TEF Reverse primer for RrUGT2

<400> SEQUENCE: 114
cagcccgggg gatccactag tctaggacaa agtctctctt ctcaacttca attc    54

<210> SEQ ID NO 115
<211> LENGTH: 49
<212> TYPE: DNA
<213> ORGANISM: Artificial Sequence
<220> FEATURE:
<223> OTHER INFORMATION: pHis8-4 Forward primer for RrUGT2

<400> SEQUENCE: 115
gaaaacttgt acttccaggc ccatggcatg ggttctgatt cacggcctc    49

<210> SEQ ID NO 116
<211> LENGTH: 55
<212> TYPE: DNA
<213> ORGANISM: Artificial Sequence
<220> FEATURE:
<223> OTHER INFORMATION: pHis8-4 Reverse primer for RrUGT2

<400> SEQUENCE: 116
ctcgaattcg gatccgccat ggctaggaca aagtctctct tctcaacttc aattc    55

<210> SEQ ID NO 117
<211> LENGTH: 50
<212> TYPE: DNA
<213> ORGANISM: Artificial Sequence
<220> FEATURE:
<223> OTHER INFORMATION: pEAQ-HT Forward primer for RrUGT2

<400> SEQUENCE: 117
gtatattctg cccaaattcg cgaccggtat gggttctgat tcacggcctc    50

<210> SEQ ID NO 118
<211> LENGTH: 63
<212> TYPE: DNA
<213> ORGANISM: Artificial Sequence
<220> FEATURE:
<223> OTHER INFORMATION: pEAQ-HT Reverse primer for RrUGT2

<400> SEQUENCE: 118
gaaaatttaa tgaaaccaga gttaaaggcc tcgagctagg acaaagtctc tcttctcaac    60
ttc    63

<210> SEQ ID NO 119
<211> LENGTH: 51
<212> TYPE: DNA
<213> ORGANISM: Artificial Sequence
<220> FEATURE:
<223> OTHER INFORMATION: p426TEF Forward primer for RrUGT3

<400> SEQUENCE: 119
caatctaatc taagttttct agaactagta tgtcaggcac accacacatc g    51

<210> SEQ ID NO 120
<211> LENGTH: 44
<212> TYPE: DNA
<213> ORGANISM: Artificial Sequence
<220> FEATURE:
<223> OTHER INFORMATION: p426TEF Reverse primer for RrUGT3

<400> SEQUENCE: 120
cagcccgggg gatccactag ttcaatgctt catcgaactc cgcc         44

<210> SEQ ID NO 121
<211> LENGTH: 49
<212> TYPE: DNA
<213> ORGANISM: Artificial Sequence
<220> FEATURE:
<223> OTHER INFORMATION: pHis8-4 Forward primer for RrUGT3

<400> SEQUENCE: 121
gaaaacttgt acttccaggc ccatggcatg tcaggcacac cacacatcg   49

<210> SEQ ID NO 122
<211> LENGTH: 45
<212> TYPE: DNA
<213> ORGANISM: Artificial Sequence
<220> FEATURE:
<223> OTHER INFORMATION: pHis8-4 Reverse primer for RrUGT3

<400> SEQUENCE: 122
ctcgaattcg gatccgccat ggtcaatgct tcatcgaact ccgcc       45

<210> SEQ ID NO 123
<211> LENGTH: 50
<212> TYPE: DNA
<213> ORGANISM: Artificial Sequence
<220> FEATURE:
<223> OTHER INFORMATION: pEAQ-HT Forward primer for RrUGT3

<400> SEQUENCE: 123
gtatattctg cccaaattcg cgaccggtat gtcaggcaca ccacacatcg  50

<210> SEQ ID NO 124
<211> LENGTH: 58
<212> TYPE: DNA
<213> ORGANISM: Artificial Sequence
<220> FEATURE:
<223> OTHER INFORMATION: pEAQ-HT Reverse primer for RrUGT3

<400> SEQUENCE: 124
gaaaatttaa tgaaaccaga gttaaaggcc tcgagtcaat gcttcatcga actccgcc   58

<210> SEQ ID NO 125
<211> LENGTH: 55
<212> TYPE: DNA
<213> ORGANISM: Artificial Sequence
<220> FEATURE:
<223> OTHER INFORMATION: p426TEF Forward primer for RrUGT4

<400> SEQUENCE: 125
caatctaatc taagtttcct agaactagta tgggttcaca gcctctcca aaacc        55

<210> SEQ ID NO 126
<211> LENGTH: 56
<212> TYPE: DNA
<213> ORGANISM: Artificial Sequence
<220> FEATURE:
<223> OTHER INFORMATION: p426TEF Reverse primer for RrUGT4

<400> SEQUENCE: 126
cagcccgggg gatccactag ttcattcctt gaactggaga atatctttca caagcc      56

<210> SEQ ID NO 127
<211> LENGTH: 51
<212> TYPE: DNA
<213> ORGANISM: Artificial Sequence
<220> FEATURE:
<223> OTHER INFORMATION: p426TEF Forward primer for RrUGT5

<400> SEQUENCE: 127
caatctaatc taagttttct agaactagta tggaaccgag acctcacgca g            51

<210> SEQ ID NO 128
<211> LENGTH: 58
<212> TYPE: DNA
<213> ORGANISM: Artificial Sequence
<220> FEATURE:
<223> OTHER INFORMATION: p426TEF Reverse primer for RrUGT5

<400> SEQUENCE: 128
cagcccgggg gatccactag tttaattagt gtcaccaaga tgagtttct ttagtaag      58

<210> SEQ ID NO 129
<211> LENGTH: 60
<212> TYPE: DNA
<213> ORGANISM: Artificial Sequence
<220> FEATURE:
<223> OTHER INFORMATION: p426TEF Forward primer for RrUGT6

<400> SEQUENCE: 129
caatctaatc taagttttct agaactagta tggaatctgt acaaggtgtt caagaaaagc   60

<210> SEQ ID NO 130
<211> LENGTH: 48
<212> TYPE: DNA
<213> ORGANISM: Artificial Sequence
<220> FEATURE:
<223> OTHER INFORMATION: p426TEF Reverse primer for RrUGT6

<400> SEQUENCE: 130
cagcccgggg gatccactag ttcagtttga attcctcgac aggagcac               48

<210> SEQ ID NO 131
<211> LENGTH: 55
<212> TYPE: DNA
<213> ORGANISM: Artificial Sequence
<220> FEATURE:
<223> OTHER INFORMATION: p426TEF Forward primer for RrUGT7

<400> SEQUENCE: 131
caatctaatc taagttttct agaactagta tggctgaaaa cactcatgct catgc        55

<210> SEQ ID NO 132
<211> LENGTH: 52
<212> TYPE: DNA
<213> ORGANISM: Artificial Sequence
<220> FEATURE:
<223> OTHER INFORMATION: p426TEF Reverse primer for RrUGT7

<400> SEQUENCE: 132
cagcccgggg gatccactag ttcatttctt gaagatttgt aggtcgtgga tg           52

<210> SEQ ID NO 133
<211> LENGTH: 58
<212> TYPE: DNA
<213> ORGANISM: Artificial Sequence
<220> FEATURE:
<223> OTHER INFORMATION: p426TEF Forward primer for RrUGT8

<400> SEQUENCE: 133
caatctaatc taagttttct agaactagta tggcttcctc ctctttagct tgtgattc    58

<210> SEQ ID NO 134
<211> LENGTH: 61
<212> TYPE: DNA
<213> ORGANISM: Artificial Sequence
<220> FEATURE:
<223> OTHER INFORMATION: p426TEF Reverse primer for RrUGT8

<400> SEQUENCE: 134
cagcccgggg gatccactag tttatttaac tgtttcttgt ttttgcagga cagaatgaat    60
g                                                                   61

<210> SEQ ID NO 135
<211> LENGTH: 51
<212> TYPE: DNA
<213> ORGANISM: Artificial Sequence
<220> FEATURE:
<223> OTHER INFORMATION: p426TEF Forward primer for RrUGT9

<400> SEQUENCE: 135
caatctaatc taagttttct agaactagta tgggtctga gccactagtc c              51

<210> SEQ ID NO 136
<211> LENGTH: 51
<212> TYPE: DNA
<213> ORGANISM: Artificial Sequence
<220> FEATURE:
<223> OTHER INFORMATION: p426TEF Reverse primer for RrUGT9

<400> SEQUENCE: 136
cagcccgggg gatccactag tttatgctga aattgcatcc ttagcaactg g             51

<210> SEQ ID NO 137
<211> LENGTH: 47
<212> TYPE: DNA
<213> ORGANISM: Artificial Sequence
<220> FEATURE:
<223> OTHER INFORMATION: p426TEF Forward primer for RrUGT10

<400> SEQUENCE: 137
caatctaatc taagttttct agaactagta tgacgaggcg ccaccac                  47

<210> SEQ ID NO 138
<211> LENGTH: 47
<212> TYPE: DNA
<213> ORGANISM: Artificial Sequence
<220> FEATURE:
<223> OTHER INFORMATION: p426TEF Reverse primer for RrUGT10

<400> SEQUENCE: 138
cagcccgggg gatccactag ttcatccaag gccattgaca aaacgac                  47

<210> SEQ ID NO 139
<211> LENGTH: 56
<212> TYPE: DNA
<213> ORGANISM: Artificial Sequence
<220> FEATURE:
<223> OTHER INFORMATION: p426TEF Forward primer for RrUGT11

<400> SEQUENCE: 139
caatctaatc taagttttct agaactagta tggcaggcga gattctaata cttccg        56

<210> SEQ ID NO 140
<211> LENGTH: 49
<212> TYPE: DNA
<213> ORGANISM: Artificial Sequence

```
<220> FEATURE:
<223> OTHER INFORMATION: p426TEF Reverse primer for RrUGT11

<400> SEQUENCE: 140
cagcccgggg gatccactag ttcacttgtg ggagataatg aagtccctg                49

<210> SEQ ID NO 141
<211> LENGTH: 46
<212> TYPE: DNA
<213> ORGANISM: Artificial Sequence
<220> FEATURE:
<223> OTHER INFORMATION: p426TEF Forward primer for RrUGT12

<400> SEQUENCE: 141
caatctaatc taagttttct agaactagta tggaggaggc ggccag                   46

<210> SEQ ID NO 142
<211> LENGTH: 49
<212> TYPE: DNA
<213> ORGANISM: Artificial Sequence
<220> FEATURE:
<223> OTHER INFORMATION: p426TEF Reverse primer for RrUGT12

<400> SEQUENCE: 142
cagcccgggg gatccactag tttaacacag agtccaaatg tccagcaac                49

<210> SEQ ID NO 143
<211> LENGTH: 58
<212> TYPE: DNA
<213> ORGANISM: Artificial Sequence
<220> FEATURE:
<223> OTHER INFORMATION: p426TEF Forward primer for RrUGT13

<400> SEQUENCE: 143
caatctaatc taagttttct agaactagta tgctacctct cttacatgtt acactaac      58

<210> SEQ ID NO 144
<211> LENGTH: 50
<212> TYPE: DNA
<213> ORGANISM: Artificial Sequence
<220> FEATURE:
<223> OTHER INFORMATION: p426TEF Reverse primer for RrUGT13

<400> SEQUENCE: 144
cagcccgggg gatccactag tttacaagcc aatgttggtc ctgagatcac                50

<210> SEQ ID NO 145
<211> LENGTH: 46
<212> TYPE: DNA
<213> ORGANISM: Artificial Sequence
<220> FEATURE:
<223> OTHER INFORMATION: p426TEF Forward primer for RrUGT14

<400> SEQUENCE: 145
caatctaatc taagttttct agaactagta tggacaccac cgccgc                   46

<210> SEQ ID NO 146
<211> LENGTH: 49
<212> TYPE: DNA
<213> ORGANISM: Artificial Sequence
<220> FEATURE:
<223> OTHER INFORMATION: p426TEF Reverse primer for RrUGT14

<400> SEQUENCE: 146
cagcccgggg gatccactag tttatcccct tccaagttga gtcaacgac                49
```

<210> SEQ ID NO 147
<211> LENGTH: 53
<212> TYPE: DNA
<213> ORGANISM: Artificial Sequence
<220> FEATURE:
<223> OTHER INFORMATION: p426TEF Forward primer for RrUGT15

<400> SEQUENCE: 147
caatctaatc taagttttct agaactagta tggctgatgc tgctcaacat gtc         53

<210> SEQ ID NO 148
<211> LENGTH: 58
<212> TYPE: DNA
<213> ORGANISM: Artificial Sequence
<220> FEATURE:
<223> OTHER INFORMATION: p426TEF Reverse primer for RrUGT15

<400> SEQUENCE: 148
cagcccgggg gatccactag tttattgaac tttgtgaaat tgaagatgac tcaaaagg    58

<210> SEQ ID NO 149
<211> LENGTH: 53
<212> TYPE: DNA
<213> ORGANISM: Artificial Sequence
<220> FEATURE:
<223> OTHER INFORMATION: p426TEF Forward primer for RrUGT16

<400> SEQUENCE: 149
caatctaatc taagttttct agaactagta tggcagagga aaacagaacc agc         53

<210> SEQ ID NO 150
<211> LENGTH: 57
<212> TYPE: DNA
<213> ORGANISM: Artificial Sequence
<220> FEATURE:
<223> OTHER INFORMATION: p426TEF Reverse primer for RrUGT16

<400> SEQUENCE: 150
cagcccgggg gatccactag ttcatacagc tgaagatatt ttggatatga attggtc     57

<210> SEQ ID NO 151
<211> LENGTH: 49
<212> TYPE: DNA
<213> ORGANISM: Artificial Sequence
<220> FEATURE:
<223> OTHER INFORMATION: p426TEF Forward primer for RrUGT17

<400> SEQUENCE: 151
caatctaatc taagttttct agaactagta tgggctcact tccttccac              49

<210> SEQ ID NO 152
<211> LENGTH: 49
<212> TYPE: DNA
<213> ORGANISM: Artificial Sequence
<220> FEATURE:
<223> OTHER INFORMATION: p426TEF Reverse primer for RrUGT17

<400> SEQUENCE: 152
cagcccgggg gatccactag ttcagacgct aaactggacc acttttttcc             49

<210> SEQ ID NO 153
<211> LENGTH: 54
<212> TYPE: DNA
<213> ORGANISM: Artificial Sequence
<220> FEATURE:
<223> OTHER INFORMATION: p426TEF Forward primer for RrUGT18

<400> SEQUENCE: 153
caatctaatc taagtttttct agaactagta tgggctcccg aggaaagcca catg    54

<210> SEQ ID NO 154
<211> LENGTH: 46
<212> TYPE: DNA
<213> ORGANISM: Artificial Sequence
<220> FEATURE:
<223> OTHER INFORMATION: p426TEF Reverse primer for RrUGT18

<400> SEQUENCE: 154
cagcccgggg gatccactag ttcattttgg ggaattagac agcagg    46

<210> SEQ ID NO 155
<211> LENGTH: 54
<212> TYPE: DNA
<213> ORGANISM: Artificial Sequence
<220> FEATURE:
<223> OTHER INFORMATION: p426TEF Forward primer for RrUGT19

<400> SEQUENCE: 155
caatctaatc taagtttttct agaactagta tgacgtcatc aacacctcct cctc    54

<210> SEQ ID NO 156
<211> LENGTH: 53
<212> TYPE: DNA
<213> ORGANISM: Artificial Sequence
<220> FEATURE:
<223> OTHER INFORMATION: p426TEF Reverse primer for RrUGT19

<400> SEQUENCE: 156
cagcccgggg gatccactag tctaaaaaaa tgctttaaca tagctagcgt ccg    53

<210> SEQ ID NO 157
<211> LENGTH: 50
<212> TYPE: DNA
<213> ORGANISM: Artificial Sequence
<220> FEATURE:
<223> OTHER INFORMATION: p426TEF Forward primer for RrUGT20

<400> SEQUENCE: 157
caatctaatc taagtttttct agaactagta tgggttcact cgacgtcgtc    50

<210> SEQ ID NO 158
<211> LENGTH: 53
<212> TYPE: DNA
<213> ORGANISM: Artificial Sequence
<220> FEATURE:
<223> OTHER INFORMATION: p426TEF Reverse primer for RrUGT20

<400> SEQUENCE: 158
cagcccgggg gatccactag ttcatttcat aatagcttca tcaatcaact cgg    53

<210> SEQ ID NO 159
<211> LENGTH: 56
<212> TYPE: DNA
<213> ORGANISM: Artificial Sequence
<220> FEATURE:
<223> OTHER INFORMATION: p426TEF Forward primer for RrUGT21

<400> SEQUENCE: 159
caatctaatc taagtttttct agaactagta tgaagtccaa cactcatcta ttcctc    56

<210> SEQ ID NO 160

```
<211> LENGTH: 44
<212> TYPE: DNA
<213> ORGANISM: Artificial Sequence
<220> FEATURE:
<223> OTHER INFORMATION: p426TEF Reverse primer for RrUGT21

<400> SEQUENCE: 160
cagcccgggg gatccactag ttcatacaac cggctccagt tgac                44

<210> SEQ ID NO 161
<211> LENGTH: 57
<212> TYPE: DNA
<213> ORGANISM: Artificial Sequence
<220> FEATURE:
<223> OTHER INFORMATION: p426TEF Forward primer for RrUGT22

<400> SEQUENCE: 161
caatctaatc taagttttct agaactagta tgaaaactcc tcaaaatcca cacgtag    57

<210> SEQ ID NO 162
<211> LENGTH: 55
<212> TYPE: DNA
<213> ORGANISM: Artificial Sequence
<220> FEATURE:
<223> OTHER INFORMATION: p426TEF Reverse primer for RrUGT22

<400> SEQUENCE: 162
cagcccgggg gatccactag ttcaatcctg ataaatcttt gaactcatct tgctc       55

<210> SEQ ID NO 163
<211> LENGTH: 54
<212> TYPE: DNA
<213> ORGANISM: Artificial Sequence
<220> FEATURE:
<223> OTHER INFORMATION: p426TEF Forward primer for RrUGT23

<400> SEQUENCE: 163
caatctaatc taagttttct agaactagta tggaaaggca gagtgatcac caag        54

<210> SEQ ID NO 164
<211> LENGTH: 54
<212> TYPE: DNA
<213> ORGANISM: Artificial Sequence
<220> FEATURE:
<223> OTHER INFORMATION: p426TEF Reverse primer for RrUGT23

<400> SEQUENCE: 164
cagcccgggg gatccactag ttcatttggt ggatatcaca tctctaacaa actg        54

<210> SEQ ID NO 165
<211> LENGTH: 45
<212> TYPE: DNA
<213> ORGANISM: Artificial Sequence
<220> FEATURE:
<223> OTHER INFORMATION: p426TEF Forward primer for RrUGT24

<400> SEQUENCE: 165
caatctaatc taagttttct agaactagta tgagcaacgc cgccg                  45

<210> SEQ ID NO 166
<211> LENGTH: 55
<212> TYPE: DNA
<213> ORGANISM: Artificial Sequence
<220> FEATURE:
<223> OTHER INFORMATION: p426TEF Reverse primer for RrUGT24

<400> SEQUENCE: 166
```
cagcccgggg gatccactag tttagtttat gacttcattc acttgctcca acaac       55

<210> SEQ ID NO 167
<211> LENGTH: 48
<212> TYPE: DNA
<213> ORGANISM: Artificial Sequence
<220> FEATURE:
<223> OTHER INFORMATION: p426TEF Forward primer for RrUGT25

<400> SEQUENCE: 167
caatctaatc taagttttct agaactagta tggcgcgcca ccactttg              48

<210> SEQ ID NO 168
<211> LENGTH: 57
<212> TYPE: DNA
<213> ORGANISM: Artificial Sequence
<220> FEATURE:
<223> OTHER INFORMATION: p426TEF Reverse primer for RrUGT25

<400> SEQUENCE: 168
cagcccgggg gatccactag tttagcaggt aacaaggtta ttaaccaaat ccttgag     57

<210> SEQ ID NO 169
<211> LENGTH: 57
<212> TYPE: DNA
<213> ORGANISM: Artificial Sequence
<220> FEATURE:
<223> OTHER INFORMATION: p426TEF Forward primer for RrUGT26

<400> SEQUENCE: 169
caatctaatc taagttttct agaactagta tgtcatcaga ttccggccac attatcc     57

<210> SEQ ID NO 170
<211> LENGTH: 58
<212> TYPE: DNA
<213> ORGANISM: Artificial Sequence
<220> FEATURE:
<223> OTHER INFORMATION: p426TEF Reverse primer for RrUGT26

<400> SEQUENCE: 170
cagcccgggg gatccactag tctatattat ttttcttaat gccatgactt gtcggacc   58

<210> SEQ ID NO 171
<211> LENGTH: 55
<212> TYPE: DNA
<213> ORGANISM: Artificial Sequence
<220> FEATURE:
<223> OTHER INFORMATION: p426TEF Forward primer for RrUGT27

<400> SEQUENCE: 171
caatctaatc taagttttct agaactagta tgagttcagt caatgctcaa aagcc       55

<210> SEQ ID NO 172
<211> LENGTH: 53
<212> TYPE: DNA
<213> ORGANISM: Artificial Sequence
<220> FEATURE:
<223> OTHER INFORMATION: p426TEF Reverse primer for RrUGT27

<400> SEQUENCE: 172
cagcccgggg gatccactag ttcaaaagtg cattagtagt ccttccacaa atc         53

<210> SEQ ID NO 173
<211> LENGTH: 53
<212> TYPE: DNA

```
<213> ORGANISM: Artificial Sequence
<220> FEATURE:
<223> OTHER INFORMATION: p426TEF Forward primer for RrUGT28

<400> SEQUENCE: 173
caatctaatc taagttttct agaactagta tggactcggt tgatctgaac aag        53

<210> SEQ ID NO 174
<211> LENGTH: 47
<212> TYPE: DNA
<213> ORGANISM: Artificial Sequence
<220> FEATURE:
<223> OTHER INFORMATION: p426TEF Reverse primer for RrUGT28

<400> SEQUENCE: 174
cagcccgggg gatccactag tctagttggc acttggcaac acaatcg              47

<210> SEQ ID NO 175
<211> LENGTH: 57
<212> TYPE: DNA
<213> ORGANISM: Artificial Sequence
<220> FEATURE:
<223> OTHER INFORMATION: p426TEF Forward primer for RrUGT29

<400> SEQUENCE: 175
caatctaatc taagttttct agaactagta tgggatctct aggaaagaag attcaac    57

<210> SEQ ID NO 176
<211> LENGTH: 52
<212> TYPE: DNA
<213> ORGANISM: Artificial Sequence
<220> FEATURE:
<223> OTHER INFORMATION: p426TEF Reverse primer for RrUGT29

<400> SEQUENCE: 176
cagcccgggg gatccactag tttaggttgt aactacaatt ttttttttgg ac         52

<210> SEQ ID NO 177
<211> LENGTH: 55
<212> TYPE: DNA
<213> ORGANISM: Artificial Sequence
<220> FEATURE:
<223> OTHER INFORMATION: pHis8-4 Forward primer for RrUGT29

<400> SEQUENCE: 177
gaaaacttgt acttccaggc ccatggcatg ggatctctag aaagaagat tcaac       55

<210> SEQ ID NO 178
<211> LENGTH: 53
<212> TYPE: DNA
<213> ORGANISM: Artificial Sequence
<220> FEATURE:
<223> OTHER INFORMATION: pHis8-4 Reverse primer for RrUGT29

<400> SEQUENCE: 178
ctcgaattcg gatccgccat ggttaggttg taactacaat ttttttttg gac         53

<210> SEQ ID NO 179
<211> LENGTH: 56
<212> TYPE: DNA
<213> ORGANISM: Artificial Sequence
<220> FEATURE:
<223> OTHER INFORMATION: pEAQ-HT Forward primer for RrUGT29

<400> SEQUENCE: 179
gtatattctg cccaaattcg cgaccggtat gggatctcta ggaaagaaga ttcaac     56
```

<210> SEQ ID NO 180
<211> LENGTH: 66
<212> TYPE: DNA
<213> ORGANISM: Artificial Sequence
<220> FEATURE:
<223> OTHER INFORMATION: pEAQ-HT Reverse primer for RrUGT29

<400> SEQUENCE: 180
gaaaatttaa tgaaaccaga gttaaaggcc tcgagttagg ttgtaactac aattttttt    60 ttggac                                                              66

<210> SEQ ID NO 181
<211> LENGTH: 54
<212> TYPE: DNA
<213> ORGANISM: Artificial Sequence
<220> FEATURE:
<223> OTHER INFORMATION: p426TEF Forward primer for RrUGT30

<400> SEQUENCE: 181
caatctaatc taagtttcct agaactagta tgggctcccg aggaaagcca catg          54

<210> SEQ ID NO 182
<211> LENGTH: 46
<212> TYPE: DNA
<213> ORGANISM: Artificial Sequence
<220> FEATURE:
<223> OTHER INFORMATION: p426TEF Reverse primer for RrUGT30

<400> SEQUENCE: 182
cagcccgggg gatccactag ttcattttgg ggaattagac agcagg                   46

<210> SEQ ID NO 183
<211> LENGTH: 59
<212> TYPE: DNA
<213> ORGANISM: Artificial Sequence
<220> FEATURE:
<223> OTHER INFORMATION: p426TEF Forward primer for RrUGT31

<400> SEQUENCE: 183
caatctaatc taagtttcct agaactagta tggaatctgt acaaggtgtt caagaaaag     59

<210> SEQ ID NO 184
<211> LENGTH: 48
<212> TYPE: DNA
<213> ORGANISM: Artificial Sequence
<220> FEATURE:
<223> OTHER INFORMATION: p426TEF Reverse primer for RrUGT31

<400> SEQUENCE: 184
cagcccgggg gatccactag ttcagtttga attcctcgac aggagcac                 48

<210> SEQ ID NO 185
<211> LENGTH: 58
<212> TYPE: DNA
<213> ORGANISM: Artificial Sequence
<220> FEATURE:
<223> OTHER INFORMATION: p426TEF Forward primer for RrUGT32

<400> SEQUENCE: 185
caatctaatc taagtttcct agaactagta tggactcggt tgatctgaac aagaaacc      58

<210> SEQ ID NO 186
<211> LENGTH: 62
<212> TYPE: DNA

```
<213> ORGANISM: Artificial Sequence
<220> FEATURE:
<223> OTHER INFORMATION: p426TEF Reverse primer for RrUGT32

<400> SEQUENCE: 186
cagcccgggg gatccactag tctacaattt tttttttggac agaagtacgt catttataag     60
tc                                                                    62

<210> SEQ ID NO 187
<211> LENGTH: 56
<212> TYPE: DNA
<213> ORGANISM: Artificial Sequence
<220> FEATURE:
<223> OTHER INFORMATION: p426TEF Forward primer for RrUGT33

<400> SEQUENCE: 187
caatctaatc taagttttct agaactagta tgagcttaat tgaaaaacca ctcacg         56

<210> SEQ ID NO 188
<211> LENGTH: 54
<212> TYPE: DNA
<213> ORGANISM: Artificial Sequence
<220> FEATURE:
<223> OTHER INFORMATION: p426TEF Reverse primer for RrUGT33

<400> SEQUENCE: 188
cagcccgggg gatccactag tctaacggat atgttttgtt tttgagagca ggac           54

<210> SEQ ID NO 189
<211> LENGTH: 54
<212> TYPE: DNA
<213> ORGANISM: Artificial Sequence
<220> FEATURE:
<223> OTHER INFORMATION: pHis8-4 Forward primer for RrUGT33

<400> SEQUENCE: 189
gaaaacttgt acttccaggc ccatggcatg agcttaattg aaaaaccact cacg           54

<210> SEQ ID NO 190
<211> LENGTH: 55
<212> TYPE: DNA
<213> ORGANISM: Artificial Sequence
<220> FEATURE:
<223> OTHER INFORMATION: pHis8-4 Reverse primer for RrUGT33

<400> SEQUENCE: 190
ctcgaattcg gatccgccat ggctaacgga tatgttttgt tttgagagc aggac           55

<210> SEQ ID NO 191
<211> LENGTH: 55
<212> TYPE: DNA
<213> ORGANISM: Artificial Sequence
<220> FEATURE:
<223> OTHER INFORMATION: pEAQ-HT Forward primer for RrUGT33

<400> SEQUENCE: 191
gtatattctg cccaaattcg cgaccggtat gagcttaatt gaaaaccac tcacg           55

<210> SEQ ID NO 192
<211> LENGTH: 68
<212> TYPE: DNA
<213> ORGANISM: Artificial Sequence
<220> FEATURE:
<223> OTHER INFORMATION: pEAQ-HT Reverse primer for RrUGT33

<400> SEQUENCE: 192
```

```
gaaaatttaa tgaaaccaga gttaaaggcc tcgagctaac ggatatgttt tgtttttgag      60
agcaggac                                                                68

<210> SEQ ID NO 193
<211> LENGTH: 58
<212> TYPE: DNA
<213> ORGANISM: Artificial Sequence
<220> FEATURE:
<223> OTHER INFORMATION: p426TEF Forward primer for RrUGT34

<400> SEQUENCE: 193
gcatagcaat ctaatctaag ttttctagaa ctagttggac cctgacgaca gcgttttg       58

<210> SEQ ID NO 194
<211> LENGTH: 60
<212> TYPE: DNA
<213> ORGANISM: Artificial Sequence
<220> FEATURE:
<223> OTHER INFORMATION: p426TEF Reverse primer for RrUGT34

<400> SEQUENCE: 194
cagcccgggg gatccactag tttagttttt gttctcgtac aaataatgca caaactcatc      60

<210> SEQ ID NO 195
<211> LENGTH: 46
<212> TYPE: DNA
<213> ORGANISM: Artificial Sequence
<220> FEATURE:
<223> OTHER INFORMATION: pHis8-4 Forward primer for Pc4HPAAS

<400> SEQUENCE: 195
gaaaacttgt acttccaggc ccatggcatg ggctccatcg ataatc                    46

<210> SEQ ID NO 196
<211> LENGTH: 48
<212> TYPE: DNA
<213> ORGANISM: Artificial Sequence
<220> FEATURE:
<223> OTHER INFORMATION: pHis8-4 Reverse primer for Pc4HPAAS

<400> SEQUENCE: 196
ctcgaattcg gatccgccat ggttaggata aatattcac gatcttct                   48

<210> SEQ ID NO 197
<211> LENGTH: 47
<212> TYPE: DNA
<213> ORGANISM: Artificial Sequence
<220> FEATURE:
<223> OTHER INFORMATION: pEAQ-HT Forward primer for Pc4HPAAS

<400> SEQUENCE: 197
gtatattctg cccaaattcg cgaccggtat gggctccatc gataatc                   47

<210> SEQ ID NO 198
<211> LENGTH: 60
<212> TYPE: DNA
<213> ORGANISM: Artificial Sequence
<220> FEATURE:
<223> OTHER INFORMATION: pEAQ-HT Reverse primer for Pc4HPAAS

<400> SEQUENCE: 198
gaaaatttaa tgaaaccaga gttaaaggcc tcgagttagg ataaaatatt cacgatcttc      60

<210> SEQ ID NO 199
```

```
<211> LENGTH: 55
<212> TYPE: DNA
<213> ORGANISM: Artificial Sequence
<220> FEATURE:
<223> OTHER INFORMATION: pHis8-4 Forward primer for PsTyDC

<400> SEQUENCE: 199
gaaaacttgt acttccaggc ccatggcatg ggaagccttc cgactaataa ccttg      55

<210> SEQ ID NO 200
<211> LENGTH: 49
<212> TYPE: DNA
<213> ORGANISM: Artificial Sequence
<220> FEATURE:
<223> OTHER INFORMATION: pHis8-4 Reverse primer for PsTyDC

<400> SEQUENCE: 200
ctcgaattcg gatccgccat ggctaggcac caagtatggc atctgtatg            49

<210> SEQ ID NO 201
<211> LENGTH: 56
<212> TYPE: DNA
<213> ORGANISM: Artificial Sequence
<220> FEATURE:
<223> OTHER INFORMATION: pEAQ-HT Forward primer for PsTyDC

<400> SEQUENCE: 201
gtatattctg cccaaattcg cgaccggtat gggaagcctt ccgactaata accttg    56

<210> SEQ ID NO 202
<211> LENGTH: 62
<212> TYPE: DNA
<213> ORGANISM: Artificial Sequence
<220> FEATURE:
<223> OTHER INFORMATION: pEAQ-HT Reverse primer for PsTyDC

<400> SEQUENCE: 202
gaaaatttaa tgaaaccaga gttaaaggcc tcgagctagg caccaagtat ggcatctgta   60
tg                                                                  62

<210> SEQ ID NO 203
<211> LENGTH: 48
<212> TYPE: DNA
<213> ORGANISM: Artificial Sequence
<220> FEATURE:
<223> OTHER INFORMATION: p426TEF Forward primer for AAS55083
<300> PUBLICATION INFORMATION:
<308> DATABASE ACCESSION NUMBER: GenBank AAS55083

<400> SEQUENCE: 203
caatctaatc taagttttct agaactagta tggcaggcag tgggactg              48

<210> SEQ ID NO 204
<211> LENGTH: 54
<212> TYPE: DNA
<213> ORGANISM: Artificial Sequence
<220> FEATURE:
<223> OTHER INFORMATION: p426TEF Reverse primer for AAS55083
<300> PUBLICATION INFORMATION:
<308> DATABASE ACCESSION NUMBER: GenBank AAS55083

<400> SEQUENCE: 204
cagcccgggg gatccactag ttcagtgttt aactgaggat ctccactttt tagc      54

<210> SEQ ID NO 205
<211> LENGTH: 59
```

```
<212> TYPE: DNA
<213> ORGANISM: Artificial Sequence
<220> FEATURE:
<223> OTHER INFORMATION: p426TEF Forward primer for EU567325
<300> PUBLICATION INFORMATION:
<308> DATABASE ACCESSION NUMBER: GenBank EU567325

<400> SEQUENCE: 205
gcatagcaat ctaatctaag ttttctagaa ctagtatggg ttctgaaact cggcctttg      59

<210> SEQ ID NO 206
<211> LENGTH: 54
<212> TYPE: DNA
<213> ORGANISM: Artificial Sequence
<220> FEATURE:
<223> OTHER INFORMATION: p426TEF Reverse primer for EU567325
<300> PUBLICATION INFORMATION:
<308> DATABASE ACCESSION NUMBER: GenBank EU567325

<400> SEQUENCE: 206
cagcccgggg gatccactag tctagacttt ctttaacttg agttcctgaa gcag           54

<210> SEQ ID NO 207
<211> LENGTH: 21
<212> TYPE: PRT
<213> ORGANISM: C. roseus

<400> SEQUENCE: 207

Val Asp Phe Lys Asn Trp Gln Ile Ala Thr Gly Arg Lys Phe Arg Ser
1               5                   10                  15

Leu Lys Leu Trp Leu
            20

<210> SEQ ID NO 208
<211> LENGTH: 21
<212> TYPE: PRT
<213> ORGANISM: C. annuum

<400> SEQUENCE: 208

Val Asp Tyr Lys Asp Trp Gln Ile Gly Thr Gly Arg Lys Phe Lys Ser
1               5                   10                  15

Leu Arg Leu Trp Leu
            20

<210> SEQ ID NO 209
<211> LENGTH: 21
<212> TYPE: PRT
<213> ORGANISM: O. pumila

<400> SEQUENCE: 209

Val Asp Phe Lys Asp Trp Gln Ile Gly Thr Gly Arg Arg Phe Lys Ala
1               5                   10                  15

Leu Arg Leu Trp Leu
            20

<210> SEQ ID NO 210
<211> LENGTH: 21
<212> TYPE: PRT
<213> ORGANISM: C. acuminata

<400> SEQUENCE: 210

Val Asp Tyr Lys Asp Trp Gln Val Gly Thr Gly Arg Arg Phe Lys Ala
1               5                   10                  15

Leu Arg Leu Trp Phe
```

-continued

20

<210> SEQ ID NO 211
<211> LENGTH: 21
<212> TYPE: PRT
<213> ORGANISM: C. acuminata

<400> SEQUENCE: 211

Val Asp Phe Lys Asp Trp Gln Val Gly Thr Gly Arg Arg Phe Lys Ala
1               5                   10                  15

Leu Arg Leu Trp Phe
          20

<210> SEQ ID NO 212
<211> LENGTH: 21
<212> TYPE: PRT
<213> ORGANISM: O. sativa

<400> SEQUENCE: 212

Thr Asp Leu Lys Asp Met Gln Val Gly Val Gly Arg Arg Phe Arg Gly
1               5                   10                  15

Leu Lys Leu Trp Met
          20

<210> SEQ ID NO 213
<211> LENGTH: 21
<212> TYPE: PRT
<213> ORGANISM: P. hybrid

<400> SEQUENCE: 213

Val Asp Tyr Lys Asp Trp Gln Ile Thr Leu Ser Arg Arg Phe Arg Ser
1               5                   10                  15

Leu Lys Leu Trp Leu
          20

<210> SEQ ID NO 214
<211> LENGTH: 21
<212> TYPE: PRT
<213> ORGANISM: P. crispum

<400> SEQUENCE: 214

Val Asp Tyr Lys Asp Trp Gln Ile Met Leu Ser Arg Arg Phe Arg Ala
1               5                   10                  15

Leu Lys Leu Trp Phe
          20

<210> SEQ ID NO 215
<211> LENGTH: 21
<212> TYPE: PRT
<213> ORGANISM: P. somniferum

<400> SEQUENCE: 215

Ile Asp Tyr Lys Asp Trp Gln Ile Ala Leu Ser Arg Arg Phe Arg Ser
1               5                   10                  15

Met Lys Leu Trp Leu
          20

<210> SEQ ID NO 216
<211> LENGTH: 21
<212> TYPE: PRT
<213> ORGANISM: P. somniferum

<400> SEQUENCE: 216

-continued

Val Asp Tyr Lys Asp Trp Gln Ile Ala Leu Ser Arg Arg Phe Arg Ser
1               5                   10                  15

Leu Lys Leu Trp Met
            20

<210> SEQ ID NO 217
<211> LENGTH: 21
<212> TYPE: PRT
<213> ORGANISM: T. flavum

<400> SEQUENCE: 217

Val Asp Tyr Lys Asp Trp Gln Ile Ala Leu Ser Arg Arg Phe Arg Ala
1               5                   10                  15

Met Lys Leu Trp Leu
            20

<210> SEQ ID NO 218
<211> LENGTH: 21
<212> TYPE: PRT
<213> ORGANISM: R. hybrid

<400> SEQUENCE: 218

Val Asp Tyr Lys Asp Trp Gln Ile Ala Leu Ser Arg Arg Phe Arg Ala
1               5                   10                  15

Leu Lys Leu Trp Leu
            20

<210> SEQ ID NO 219
<211> LENGTH: 21
<212> TYPE: PRT
<213> ORGANISM: R. crenulata

<400> SEQUENCE: 219

Val Asp Tyr Lys Asp Trp Gln Ile Ser Leu Ser Arg Arg Phe Arg Ala
1               5                   10                  15

Ile Lys Met Trp Met
            20

<210> SEQ ID NO 220
<211> LENGTH: 20
<212> TYPE: PRT
<213> ORGANISM: P. somniferum

<400> SEQUENCE: 220

Leu Val Lys Ala Leu Ser Thr Ser Ala Glu Tyr Leu Lys Asn Lys Ala
1               5                   10                  15

Thr Glu Ser Lys
            20

<210> SEQ ID NO 221
<211> LENGTH: 21
<212> TYPE: PRT
<213> ORGANISM: B. distachyon

<400> SEQUENCE: 221

Leu Ile Ala Ala Leu Gly Thr Glu Gln Glu Tyr Ile Leu Lys Asp Ser
1               5                   10                  15

Ala Ser Glu Gly His
            20

<210> SEQ ID NO 222

```
<211> LENGTH: 21
<212> TYPE: PRT
<213> ORGANISM: O. sativa

<400> SEQUENCE: 222

Leu Val Ala Ala Leu Gly Thr Glu Gln Glu Tyr Ile Leu Arg Asp Ala
1               5                   10                  15

Ala Ala Glu Gly His
            20

<210> SEQ ID NO 223
<211> LENGTH: 20
<212> TYPE: PRT
<213> ORGANISM: T. flavum

<400> SEQUENCE: 223

Leu Ile Lys Ala Leu Ser Thr Asn Pro Glu Tyr Leu Arg Asn Lys Ala
1               5                   10                  15

Thr Glu Ser His
            20

<210> SEQ ID NO 224
<211> LENGTH: 20
<212> TYPE: PRT
<213> ORGANISM: P. somniferum

<400> SEQUENCE: 224

Leu Val Lys Ala Leu Ser Thr Asn Pro Glu Tyr Leu Arg Asn Lys Ala
1               5                   10                  15

Thr Glu Ser Arg
            20

<210> SEQ ID NO 225
<211> LENGTH: 19
<212> TYPE: PRT
<213> ORGANISM: C. acuminata

<400> SEQUENCE: 225

Leu Val Lys Ala Leu Ser Thr Asp Pro Glu Tyr Leu Lys Asn Pro Ser
1               5                   10                  15

Glu Ser Lys

<210> SEQ ID NO 226
<211> LENGTH: 20
<212> TYPE: PRT
<213> ORGANISM: C. acuminata

<400> SEQUENCE: 226

Leu Val Lys Ala Leu Ser Thr Asp Pro Glu Tyr Leu Lys Asn Lys Pro
1               5                   10                  15

Ser Glu Ser Asn
            20

<210> SEQ ID NO 227
<211> LENGTH: 20
<212> TYPE: PRT
<213> ORGANISM: O. pumila

<400> SEQUENCE: 227

Met Val Lys Ala Leu Ser Thr Asn Pro Glu Tyr Leu Arg Asn Lys Arg
1               5                   10                  15

Ser Glu Phe Asp
```

-continued

20

<210> SEQ ID NO 228
<211> LENGTH: 20
<212> TYPE: PRT
<213> ORGANISM: O. sativa

<400> SEQUENCE: 228

Leu Thr Gly Ser Leu Glu Thr Asn Pro Glu Tyr Leu Lys Asn His Ala
1               5                   10                  15

Ser Asp Ser Gly
            20

<210> SEQ ID NO 229
<211> LENGTH: 20
<212> TYPE: PRT
<213> ORGANISM: C. annuum

<400> SEQUENCE: 229

Leu Ile Gln Ser Leu Ser Thr Asn Pro Glu Tyr Leu Lys Asn Lys Ala
1               5                   10                  15

Ser Gln Gly Asn
            20

<210> SEQ ID NO 230
<211> LENGTH: 20
<212> TYPE: PRT
<213> ORGANISM: A. thaliana

<400> SEQUENCE: 230

Leu Ile Asp Ala Leu Lys Thr Asn Pro Glu Tyr Leu Glu Phe Lys Val
1               5                   10                  15

Ser Lys Lys Asp
            20

<210> SEQ ID NO 231
<211> LENGTH: 20
<212> TYPE: PRT
<213> ORGANISM: C. annuum

<400> SEQUENCE: 231

Leu Ile Gln Ser Leu Ser Thr Asn Pro Glu Tyr Leu Lys Asn Lys Ala
1               5                   10                  15

Ser Gln Gly Asn
            20

<210> SEQ ID NO 232
<211> LENGTH: 20
<212> TYPE: PRT
<213> ORGANISM: C. roseus

<400> SEQUENCE: 232

Leu Leu Arg Ala Leu Thr Thr Asn Pro Glu Tyr Leu Lys Asn Lys Gln
1               5                   10                  15

Ser Asp Leu Asp
            20

<210> SEQ ID NO 233
<211> LENGTH: 20
<212> TYPE: PRT
<213> ORGANISM: R. rosea

<400> SEQUENCE: 233

```
Leu Thr Lys Ala Leu Ser Thr Asn Pro Glu Tyr Leu Arg Asn Gln Gln
1               5                   10                  15

Ser Glu Leu Asn
            20

<210> SEQ ID NO 234
<211> LENGTH: 20
<212> TYPE: PRT
<213> ORGANISM: R. hybrid

<400> SEQUENCE: 234

Leu Ala Ser Ser Leu Ser Thr Asn Pro Glu Phe Leu Arg Asn Lys Ala
1               5                   10                  15

Ser Asp Ser Lys
            20

<210> SEQ ID NO 235
<211> LENGTH: 20
<212> TYPE: PRT
<213> ORGANISM: P. crispum

<400> SEQUENCE: 235

Leu Ile Lys Ser Leu Ser Thr Tyr Pro Glu Phe Leu Lys Asn Asn Ala
1               5                   10                  15

Ser Glu Thr Asn
            20

<210> SEQ ID NO 236
<211> LENGTH: 20
<212> TYPE: PRT
<213> ORGANISM: A. thaliana

<400> SEQUENCE: 236

Leu Thr Leu Ala Leu Ser Thr Asn Pro Glu Phe Leu Lys Asn Lys Ala
1               5                   10                  15

Ser Gln Ala Asn
            20

<210> SEQ ID NO 237
<211> LENGTH: 20
<212> TYPE: PRT
<213> ORGANISM: O. europaea

<400> SEQUENCE: 237

Leu Ile Gln Ser Leu Ser Thr Asn Pro Glu Phe Leu Lys Asn Lys Ala
1               5                   10                  15

Ser Glu Gly Asn
            20

<210> SEQ ID NO 238
<211> LENGTH: 17
<212> TYPE: PRT
<213> ORGANISM: R. crenulata

<400> SEQUENCE: 238

Leu Ile Glu Ser Leu Ala Ala Glu Ala Asn Phe Leu Lys Gly Asn Ser
1               5                   10                  15

Glu

<210> SEQ ID NO 239
<211> LENGTH: 20
```

```
<212> TYPE: PRT
<213> ORGANISM: R. rosea

<400> SEQUENCE: 239

Leu Ile Gln Ser Leu Ser Thr Tyr Pro Glu Phe Leu Lys Asn Lys Ala
1               5                   10                  15

Ser Gln Ser Asn
            20

<210> SEQ ID NO 240
<211> LENGTH: 16
<212> TYPE: PRT
<213> ORGANISM: R. rosea

<400> SEQUENCE: 240

Leu Ile Glu Ser Leu Ala Ala Glu Ala Asn Phe Leu Lys Gly Gly Ser
1               5                   10                  15

<210> SEQ ID NO 241
<211> LENGTH: 37
<212> TYPE: PRT
<213> ORGANISM: R. rosea

<400> SEQUENCE: 241

Val Leu Tyr Cys Ser Asp Gln Thr His Phe Thr Ile His Lys Gly Ala
1               5                   10                  15

Lys Ala Leu Ile Glu Ser Leu Ala Ala Glu Ala Asn Phe Leu Lys Gly
                20                  25                  30

Gly Ser Glu Met Val
            35

<210> SEQ ID NO 242
<211> LENGTH: 41
<212> TYPE: PRT
<213> ORGANISM: A. thaliana

<400> SEQUENCE: 242

Val Val Tyr Ser Ser Asp Gln Thr His Ser Ala Leu Gln Lys Ala Cys
1               5                   10                  15

Gln Ser Leu Thr Leu Ala Leu Ser Thr Asn Pro Glu Phe Leu Lys Asn
                20                  25                  30

Lys Ala Ser Gln Ala Asn Leu Val Val
            35                  40

<210> SEQ ID NO 243
<211> LENGTH: 43
<212> TYPE: PRT
<213> ORGANISM: A. thaliana

<400> SEQUENCE: 243

Val Val Tyr Gly Ser Asp Gln Thr His Ser Ser Phe Arg Lys Ala Cys
1               5                   10                  15

Leu Ser Leu Ile Asp Ala Leu Lys Thr Asn Pro Glu Tyr Leu Glu Phe
                20                  25                  30

Lys Val Lys Val Ser Lys Lys Asp Thr Val Val
            35                  40

<210> SEQ ID NO 244
<211> LENGTH: 41
<212> TYPE: PRT
<213> ORGANISM: C. annuum
```

```
<400> SEQUENCE: 244

Val Val Tyr Cys Ser Asp Gln Thr His Ser Ser Leu Gln Lys Ala Cys
1               5                   10                  15

Gln Ala Leu Ile Gln Ser Leu Ser Thr Asn Pro Glu Tyr Leu Lys Asn
                20                  25                  30

Lys Ala Ser Gln Gly Asn Leu Val Val
            35                  40

<210> SEQ ID NO 245
<211> LENGTH: 41
<212> TYPE: PRT
<213> ORGANISM: O. sativa

<400> SEQUENCE: 245

Val Val Tyr Ala Ser Asp Gln Thr His Ser Ala Leu Gln Lys Ala Cys
1               5                   10                  15

Gln Phe Leu Ile Gln Ser Leu Ser Thr Asn Pro Glu Phe Leu Lys Asn
                20                  25                  30

Lys Ala Ser Gln Ala Asn Ser Val Val
            35                  40

<210> SEQ ID NO 246
<211> LENGTH: 41
<212> TYPE: PRT
<213> ORGANISM: O. sativa

<400> SEQUENCE: 246

Ala Val Tyr Ala Ala Asp Gln Thr His Ser Thr Phe Phe Lys Ala Cys
1               5                   10                  15

Arg Arg Leu Thr Gly Ser Leu Glu Thr Asn Pro Glu Tyr Leu Lys Asn
                20                  25                  30

His Ala Ser Asp Ser Gly Glu Val Thr
            35                  40

<210> SEQ ID NO 247
<211> LENGTH: 41
<212> TYPE: PRT
<213> ORGANISM: C. acuminate

<400> SEQUENCE: 247

Val Val Tyr Gly Ser Asp Gln Thr His Ser Thr Tyr Ala Lys Ala Cys
1               5                   10                  15

Lys Leu Leu Val Lys Ala Leu Ser Thr Asp Pro Glu Tyr Leu Lys Asn
                20                  25                  30

Gln Pro Ser Glu Ser Lys Ser Val Val
            35                  40

<210> SEQ ID NO 248
<211> LENGTH: 41
<212> TYPE: PRT
<213> ORGANISM: C. acuminate

<400> SEQUENCE: 248

Val Val Tyr Gly Ser Asp Gln Thr His Ser Thr Tyr Ala Lys Ala Cys
1               5                   10                  15

Asn Val Leu Val Lys Ala Leu Ser Thr Asp Pro Glu Tyr Leu Lys Asn
                20                  25                  30

Lys Pro Ser Glu Ser Asn Ser Val Val
            35                  40
```

<210> SEQ ID NO 249
<211> LENGTH: 41
<212> TYPE: PRT
<213> ORGANISM: C. annuum

<400> SEQUENCE: 249

Val Val Tyr Gly Ser Asp Gln Thr His Ser Met Tyr Ala Lys Ala Cys
1               5                   10                  15

Lys Val Leu Val Lys Ala Leu Ser Thr Asn Pro Glu Tyr Leu Arg Asn
            20                  25                  30

Lys Arg Ser Glu His Gly Ser Val Val
        35                  40

<210> SEQ ID NO 250
<211> LENGTH: 41
<212> TYPE: PRT
<213> ORGANISM: O. pumila

<400> SEQUENCE: 250

Val Val Tyr Gly Ser Asp Gln Thr His Ser Phe Phe Gln Lys Thr Cys
1               5                   10                  15

Lys Leu Met Val Lys Ala Leu Ser Thr Asn Pro Glu Tyr Leu Arg Asn
            20                  25                  30

Lys Arg Ser Glu Phe Asp Gly Val Val
        35                  40

<210> SEQ ID NO 251
<211> LENGTH: 41
<212> TYPE: PRT
<213> ORGANISM: C. roseus

<400> SEQUENCE: 251

Val Cys Tyr Gly Ser Asp Gln Thr His Thr Met Phe Pro Lys Thr Cys
1               5                   10                  15

Lys Leu Leu Leu Arg Ala Leu Thr Thr Asn Pro Glu Tyr Leu Lys Asn
            20                  25                  30

Lys Gln Ser Asp Leu Asp Lys Val Val
        35                  40

<210> SEQ ID NO 252
<211> LENGTH: 41
<212> TYPE: PRT
<213> ORGANISM: P. crispum

<400> SEQUENCE: 252

Val Val Tyr Cys Ser Asp Gln Thr His Ser Ala Leu Gln Lys Ala Ala
1               5                   10                  15

Lys Ala Leu Ile Lys Ser Leu Ser Thr Tyr Pro Glu Phe Leu Lys Asn
            20                  25                  30

Asn Ala Ser Glu Thr Asn Lys Val Val
        35                  40

<210> SEQ ID NO 253
<211> LENGTH: 41
<212> TYPE: PRT
<213> ORGANISM: R. hybrid

<400> SEQUENCE: 253

Val Val Tyr Gly Ser Asp Gln Thr His Ser Thr Leu Gln Lys Ala Thr
1               5                   10                  15

Gln Val Leu Ala Ser Ser Leu Ser Thr Asn Pro Glu Phe Leu Arg Asn
            20                  25                  30

Lys Ala Ser Asp Ser Lys Gln Val Val
            35                  40

<210> SEQ ID NO 254
<211> LENGTH: 41
<212> TYPE: PRT
<213> ORGANISM: P. hybrida

<400> SEQUENCE: 254

Val Val Tyr Ala Ser Asp Gln Thr His Phe Ser Phe Gln Lys Ala Val
1               5                   10                  15

Lys Ser Leu Thr Lys Ala Leu Ser Thr Asn Pro Glu Val Leu Arg Asn
            20                  25                  30

Asp Ala Thr Asp Ser Glu Gln Val Val
            35                  40

<210> SEQ ID NO 255
<211> LENGTH: 41
<212> TYPE: PRT
<213> ORGANISM: T. flavum

<400> SEQUENCE: 255

Val Val Tyr Gly Ser Asp Gln Thr His Cys Ala Leu Gln Lys Ala Ala
1               5                   10                  15

Gln Ala Leu Ile Lys Ala Leu Ser Thr Asn Pro Glu Tyr Leu Arg Asn
            20                  25                  30

Lys Ala Thr Glu Ser His Gln Val Val
            35                  40

<210> SEQ ID NO 256
<211> LENGTH: 42
<212> TYPE: PRT
<213> ORGANISM: B. distachyon

<400> SEQUENCE: 256

Val Val Tyr Cys Ser Asp Gln Thr His Phe Ala Phe Arg Lys Ala Ala
1               5                   10                  15

Arg Glu Leu Ile Ala Ala Leu Gly Thr Glu Gln Glu Tyr Ile Leu Lys
            20                  25                  30

Asp Ser Ala Ser Glu Gly His Asp Ile Val
            35                  40

<210> SEQ ID NO 257
<211> LENGTH: 41
<212> TYPE: PRT
<213> ORGANISM: P. somniferum

<400> SEQUENCE: 257

Val Val Tyr Ala Ser Asn Gln Thr His Cys Ala Leu Gln Lys Ala Ala
1               5                   10                  15

Gln Ser Leu Val Lys Ala Leu Ser Thr Ser Ala Glu Tyr Leu Lys Asn
            20                  25                  30

Lys Ala Thr Glu Ser Lys Gln Val Ile
            35                  40

<210> SEQ ID NO 258
<211> LENGTH: 490
<212> TYPE: PRT
<213> ORGANISM: R. rosea

<400> SEQUENCE: 258

Met Gly Ser Leu Pro Ser Pro Asn Asp Pro Ser Asn Thr Phe Asn Pro
1               5                   10                  15

Met Asp Leu Thr Glu Leu Ser Thr Glu Ser Lys Leu Val Val Asp Phe
            20                  25                  30

Ile Thr Gln Tyr Tyr Gln Thr Leu Glu Thr Arg Pro Val Gln Pro Arg
        35                  40                  45

Val Lys Pro Gly Phe Leu Thr Gly Gln Leu Pro Asp Lys Ala Pro Phe
    50                  55                  60

His Gly Glu Ser Met Glu Val Ile Leu Ser Asp Val Asn Glu Lys Ile
65                  70                  75                  80

Val Pro Gly Leu Thr His Trp Gln Ser Pro Asn Phe His Ala Tyr Phe
                85                  90                  95

Pro Ala Ser Ser Ser Asn Ala Gly Leu Leu Gly Glu Leu Leu Cys Ser
            100                 105                 110

Gly Leu Ser Val Ile Gly Phe Thr Trp Ser Ser Pro Ala Ala Thr
            115                 120                 125

Glu Leu Glu Asn Val Val Asp Trp Met Ala Lys Met Leu Asn Leu
130                 135                 140

Pro Ser Ser Phe Cys Phe Ser Gly Gly Gly Gly Val Leu Gln Ala
145                 150                 155                 160

Asn Thr Cys Glu Ala Val Leu Cys Thr Leu Ala Ala Arg Asp Lys
            165                 170                 175

Ala Leu Asn Arg Val Gly Asp Asp Gln Ile Asn Lys Leu Val Leu Tyr
            180                 185                 190

Cys Ser Asp Gln Thr His Phe Thr Ile His Lys Gly Ala Lys Leu Ile
        195                 200                 205

Gly Ile Arg Ser Lys Asn Ile Lys Ser Ile Thr Thr Lys Lys Glu Asn
        210                 215                 220

Glu Phe Lys Leu Cys Pro Asn Asp Leu Arg Asp Ala Ile Arg Ser Asp
225                 230                 235                 240

Leu Glu Ala Gly Leu Val Pro Phe Tyr Val Cys Gly Thr Ile Gly Thr
            245                 250                 255

Thr Ala Leu Gly Val Val Asp Pro Ile Lys Glu Leu Gly Lys Val Ala
            260                 265                 270

Arg Glu Phe Asp Leu Trp Leu His Val Asp Gly Ala Tyr Gly Gly Ser
            275                 280                 285

Ala Cys Ile Cys Pro Glu Phe Gln His Tyr Leu Asp Gly Val Asp Leu
290                 295                 300

Val Asp Ser Ile Ser Met Asn Ala His Lys Trp Leu Leu Ser Asn Leu
305                 310                 315                 320

Asp Cys Cys Phe Leu Trp Leu Gln Ser Pro Asn Ala Leu Ile Glu Ser
            325                 330                 335

Leu Ala Ala Glu Ala Asn Phe Leu Lys Gly Gly Ser Glu Met Val Asp
            340                 345                 350

Tyr Lys Asp Trp Gln Ile Ser Leu Ser Arg Arg Phe Arg Ala Ile Lys
        355                 360                 365

Met Trp Met Val Ile Arg Arg Tyr Gly Val Ser Asn Leu Ile Glu His
        370                 375                 380

Ile Arg Ser Asp Val Ser Met Ala Val Arg Phe Glu Glu Met Val Ala
385                 390                 395                 400

Ala Asp Asp Arg Phe Glu Ile Val Phe Pro Arg Lys Phe Ala Leu Val

```
                    405                 410                 415
Cys Phe Lys Leu Ser Ser Glu Lys Thr Pro Pro Gly Arg Asp Ser Glu
        420                 425                 430

Leu Thr Arg Glu Leu Met Glu Arg Val Asn Ser Ser Gly Lys Ala Tyr
            435                 440                 445

Leu Ser Gly Val Gln Met Gly Arg Ile Phe Phe Ile Arg Cys Val Ile
    450                 455                 460

Gly Ser Ser Leu Thr Glu Glu Arg His Val Asp Asn Leu Trp Arg Leu
465                 470                 475                 480

Ile Gln Glu Thr Ala Gln Ser Ile Val Ser
                485                 490

<210> SEQ ID NO 259
<211> LENGTH: 490
<212> TYPE: PRT
<213> ORGANISM: A. thaliana

<400> SEQUENCE: 259

Met Glu Asn Gly Ser Gly Lys Val Leu Lys Pro Met Asp Ser Glu Gln
1               5                   10                  15

Leu Arg Glu Tyr Gly His Leu Met Val Asp Phe Ile Ala Asp Tyr Tyr
            20                  25                  30

Lys Thr Ile Glu Asp Phe Pro Val Leu Ser Gln Val Gln Pro Gly Tyr
        35                  40                  45

Leu His Lys Leu Leu Pro Asp Ser Ala Pro Asp His Pro Glu Thr Leu
    50                  55                  60

Asp Gln Val Leu Asp Asp Val Arg Ala Lys Ile Leu Pro Gly Val Thr
65                  70                  75                  80

His Trp Gln Ser Pro Ser Phe Phe Ala Tyr Tyr Pro Ser Asn Ser Ser
                85                  90                  95

Val Ala Gly Phe Leu Gly Glu Met Leu Ser Ala Gly Leu Gly Ile Val
            100                 105                 110

Gly Phe Ser Trp Val Thr Ser Pro Ala Ala Thr Glu Leu Glu Met Ile
        115                 120                 125

Val Leu Asp Trp Val Ala Lys Leu Leu Asn Leu Pro Glu Gln Phe Met
    130                 135                 140

Ser Lys Gly Asn Gly Gly Gly Val Ile Gln Gly Ser Ala Ser Glu Ala
145                 150                 155                 160

Val Leu Val Val Leu Ile Ala Ala Arg Asp Lys Val Leu Arg Ser Val
            165                 170                 175

Gly Lys Asn Ala Leu Glu Lys Leu Val Val Tyr Ser Ser Asp Gln Thr
        180                 185                 190

His Ser Ala Leu Gln Lys Ala Cys Gln Ile Ala Gly Ile His Pro Glu
    195                 200                 205

Asn Cys Arg Val Leu Thr Thr Asp Ser Ser Thr Asn Tyr Ala Leu Arg
210                 215                 220

Pro Glu Ser Leu Gln Glu Ala Val Ser Arg Asp Leu Glu Ala Gly Leu
225                 230                 235                 240

Ile Pro Phe Phe Leu Cys Ala Asn Val Gly Thr Thr Ser Ser Thr Ala
            245                 250                 255

Val Asp Pro Leu Ala Ala Leu Gly Lys Ile Ala Asn Ser Asn Gly Ile
        260                 265                 270

Trp Phe His Val Asp Ala Ala Tyr Ala Gly Ser Ala Cys Ile Cys Pro
    275                 280                 285
```

Glu Tyr Arg Gln Tyr Ile Asp Gly Val Glu Thr Ala Asp Ser Phe Asn
290                 295                 300

Met Asn Ala His Lys Trp Phe Leu Thr Asn Phe Asp Cys Ser Leu Leu
305                 310                 315                 320

Trp Val Lys Asp Gln Asp Ser Leu Thr Leu Ala Leu Ser Thr Asn Pro
                325                 330                 335

Glu Phe Leu Lys Asn Lys Ala Ser Gln Ala Asn Leu Val Val Asp Tyr
                340                 345                 350

Lys Asp Trp Gln Ile Pro Leu Gly Arg Arg Phe Arg Ser Leu Lys Leu
            355                 360                 365

Trp Met Val Leu Arg Leu Tyr Gly Ser Glu Thr Leu Lys Ser Tyr Ile
370                 375                 380

Arg Asn His Ile Lys Leu Ala Lys Glu Phe Glu Gln Leu Val Ser Gln
385                 390                 395                 400

Asp Pro Asn Phe Glu Ile Val Thr Pro Arg Ile Phe Ala Leu Val Cys
                405                 410                 415

Phe Arg Leu Val Pro Val Lys Asp Glu Lys Lys Cys Asn Asn Arg
                420                 425                 430

Asn Arg Glu Leu Leu Asp Ala Val Asn Ser Ser Gly Lys Leu Phe Met
            435                 440                 445

Ser His Thr Ala Leu Ser Gly Lys Ile Val Leu Arg Cys Ala Ile Gly
450                 455                 460

Ala Pro Leu Thr Glu Glu Lys His Val Lys Glu Ala Trp Lys Ile Ile
465                 470                 475                 480

Gln Glu Glu Ala Ser Tyr Leu Leu His Lys
                485                 490

<210> SEQ ID NO 260
<211> LENGTH: 547
<212> TYPE: PRT
<213> ORGANISM: A. thaliana

<400> SEQUENCE: 260

Met Phe Lys Pro Gln His Met Tyr Asp Arg Glu Phe Gly Thr Gly Asn
1               5                   10                  15

Gly Tyr Ser Asn Gly Asn Gly Tyr Thr Asn Gly Asn Gly His Thr Asn
                20                  25                  30

Gly Asn Gly Asn Tyr Asn Gly Asn Gly His Val Asn Gly Asn Gly Lys
            35                  40                  45

Ala Asn Gly Ala Lys Val Val Lys Met Lys Pro Met Asp Ser Glu Leu
50                  55                  60

Leu Arg Glu Gln Gly His Ile Met Val Asp Phe Ile Ala Asp Tyr Tyr
65                  70                  75                  80

Lys Asn Leu Gln Asp Ser Pro Gln Asp Phe Pro Val Leu Ser Gln Val
                85                  90                  95

Gln Pro Gly Tyr Leu Arg Asp Met Leu Pro Asp Ser Ala Pro Glu Arg
            100                 105                 110

Pro Glu Ser Leu Lys Glu Leu Leu Asp Asp Val Ser Lys Lys Ile Met
        115                 120                 125

Pro Gly Ile Thr His Trp Gln Ser Pro Ser Tyr Phe Ala Tyr Tyr Ala
    130                 135                 140

Ser Ser Thr Ser Val Ala Gly Phe Leu Gly Glu Met Leu Asn Ala Gly
145                 150                 155                 160

Leu Ser Val Val Gly Phe Thr Trp Leu Thr Ser Pro Ala Ala Thr Glu
                165                 170                 175

```
Leu Glu Ile Ile Val Leu Asp Trp Leu Ala Lys Leu Leu Gln Leu Pro
            180                 185                 190

Asp His Phe Leu Ser Thr Gly Asn Gly Gly Val Ile Gln Gly Thr
            195                 200                 205

Gly Cys Glu Ala Val Leu Val Val Leu Ala Arg Asp Arg Ile
210                 215                 220

Leu Lys Lys Val Gly Lys Thr Leu Leu Pro Gln Leu Val Tyr Gly
225                 230                 235                 240

Ser Asp Gln Thr His Ser Ser Phe Arg Lys Ala Cys Leu Ile Gly Gly
                245                 250                 255

Ile His Glu Glu Asn Ile Arg Leu Leu Lys Thr Asp Ser Ser Thr Asn
            260                 265                 270

Tyr Gly Met Pro Pro Glu Ser Leu Glu Glu Ala Ile Ser His Asp Leu
            275                 280                 285

Ala Lys Gly Phe Ile Pro Phe Ile Cys Ala Thr Val Gly Thr Thr
            290                 295                 300

Ser Ser Ala Ala Val Asp Pro Leu Val Pro Leu Gly Asn Ile Ala Lys
305                 310                 315                 320

Lys Tyr Gly Ile Trp Leu His Val Asp Ala Ala Tyr Ala Gly Asn Ala
                325                 330                 335

Cys Ile Cys Pro Glu Tyr Arg Lys Phe Ile Asp Gly Ile Glu Asn Ala
            340                 345                 350

Asp Ser Phe Asn Met Asn Ala His Lys Trp Leu Phe Ala Asn Gln Thr
            355                 360                 365

Cys Ser Pro Leu Trp Val Lys Asp Arg Tyr Ser Leu Ile Asp Ala Leu
            370                 375                 380

Lys Thr Asn Pro Glu Tyr Leu Glu Phe Lys Val Lys Val Ser Lys Lys
385                 390                 395                 400

Asp Thr Val Val Asn Tyr Lys Asp Trp Gln Ile Ser Leu Ser Arg Arg
                405                 410                 415

Phe Arg Ser Leu Lys Leu Trp Met Val Leu Arg Leu Tyr Gly Ser Glu
            420                 425                 430

Asn Leu Arg Asn Phe Ile Arg Asp His Val Asn Leu Ala Lys His Phe
            435                 440                 445

Glu Asp Tyr Val Ala Gln Asp Pro Ser Phe Glu Val Val Thr Thr Arg
450                 455                 460

Tyr Phe Ser Leu Val Cys Phe Arg Leu Ala Pro Val Asp Gly Asp Glu
465                 470                 475                 480

Asp Gln Cys Asn Glu Arg Asn Arg Glu Leu Leu Ala Ala Val Asn Ser
                485                 490                 495

Thr Gly Lys Ile Phe Ile Ser Thr Ala Leu Ser Gly Lys Phe Val
            500                 505                 510

Leu Arg Phe Ala Val Gly Ala Pro Leu Thr Glu Glu Lys His Val Thr
            515                 520                 525

Glu Ala Trp Gln Ile Ile Gln Lys His Ala Ser Lys Phe Thr Arg Asn
530                 535                 540

Asp His Tyr
545

<210> SEQ ID NO 261
<211> LENGTH: 487
<212> TYPE: PRT
<213> ORGANISM: C. annuum
```

```
<400> SEQUENCE: 261

Met Glu Gly Glu Leu Lys Pro Met Asp Ala Glu Gln Leu Arg Glu Tyr
1               5                   10                  15

Gly His Lys Met Val Asp Phe Ile Ala Asp Tyr Tyr Lys Asn Ile Glu
            20                  25                  30

Thr Leu Pro Val Leu Ser Gln Val Glu Pro Gly Tyr Leu Arg Lys Leu
        35                  40                  45

Leu Pro Glu Thr Ala Pro Ala His Ser Glu Thr Leu Gln Asn Val Leu
    50                  55                  60

Glu Asp Val Gln Thr Lys Ile Leu Pro Gly Val Thr His Trp Gln Ser
65                  70                  75                  80

Pro Asp Tyr Phe Ala Tyr Phe Pro Ser Asn Ser Ser Val Ala Gly Phe
                85                  90                  95

Leu Gly Glu Met Leu Ser Ala Gly Ile Asn Met Val Gly Phe Ser Trp
            100                 105                 110

Ile Thr Ser Pro Ala Ala Thr Glu Leu Glu Met Ile Val Leu Asp Trp
        115                 120                 125

Leu Ala Lys Ala Leu Lys Leu Pro Asp Glu Phe Leu Ser Thr Gly Gln
    130                 135                 140

Gly Gly Gly Val Ile Gln Gly Thr Ala Ser Glu Ala Val Leu Val Val
145                 150                 155                 160

Leu Leu Ala Ala Arg Asp Lys Val Leu Arg Arg Val Gly Lys Asp Ala
                165                 170                 175

Ile Ser Lys Leu Val Val Tyr Cys Ser Asp Gln Thr His Ser Ser Leu
            180                 185                 190

Gln Lys Ala Cys Gln Ile Gly Gly Ile His Pro Glu Asn Phe Arg Val
        195                 200                 205

Leu Lys Thr Asp Pro Ser Arg Asp Tyr Ala Leu Ser Pro Asp Thr Leu
    210                 215                 220

Ser Glu Ala Val Ser His Asp Met Ala Thr Asp Leu Ile Pro Phe Phe
225                 230                 235                 240

Phe Cys Ala Thr Ile Gly Thr Thr Ser Thr Ala Val Asp Pro Leu
                245                 250                 255

Leu Asp Leu Gly Lys Ile Ala Gln Ser Asn Ser Ile Trp Phe His Val
            260                 265                 270

Asp Ala Ala Tyr Ala Gly Ser Ala Cys Ile Cys Pro Glu Tyr Arg Gly
        275                 280                 285

Tyr Ile Asn Gly Val Glu Glu Ala His Ser Phe Asn Met Asn Ala His
    290                 295                 300

Lys Trp Phe Leu Thr Asn Phe Asp Cys Ser Ala Leu Trp Val Lys Asp
305                 310                 315                 320

Arg Ser Ala Leu Ile Gln Ser Leu Ser Thr Asn Pro Glu Tyr Leu Lys
                325                 330                 335

Asn Lys Ala Ser Gln Gly Asn Leu Val Val Asp Tyr Lys Asp Trp Gln
            340                 345                 350

Val Pro Leu Gly Arg Arg Phe Arg Ser Leu Lys Leu Trp Met Val Leu
        355                 360                 365

Arg Leu Tyr Gly Leu Glu Lys Leu Gln Ala Tyr Ile Arg Asn His Ile
    370                 375                 380

Gln Leu Ala Lys Leu Phe Glu Lys Leu Val Ala Gln Asp Gln Arg Phe
385                 390                 395                 400

Glu Ile Val Thr Pro Arg Lys Phe Ser Leu Val Cys Phe Arg Leu Leu
                405                 410                 415
```

```
Pro Pro Pro Ser Asn Glu Asp Tyr Ala Asn Lys Leu Asn His Asn Leu
            420                 425                 430

Leu Asp Ser Val Asn Ser Thr Gly Lys Leu Phe Ile Ser His Thr Leu
            435                 440                 445

Leu Ser Asp Lys Tyr Ile Leu Arg Phe Ala Val Gly Ala Pro Leu Thr
            450                 455                 460

Glu Glu Arg His Ile Val Gly Ala Trp Lys Val Leu Gln Asp Glu Ala
465                 470                 475                 480

Ala Thr Leu Leu Ser Lys Cys
                485

<210> SEQ ID NO 262
<211> LENGTH: 497
<212> TYPE: PRT
<213> ORGANISM: O. sativa

<400> SEQUENCE: 262

Met Glu Gly Val Gly Gly Gly Gly Gly Glu Glu Trp Leu Arg Pro
1               5                   10                  15

Met Asp Ala Glu Gln Leu Arg Glu Cys Gly His Arg Met Val Asp Phe
            20                  25                  30

Val Ala Asp Tyr Tyr Lys Ser Ile Glu Ala Phe Pro Val Leu Ser Gln
            35                  40                  45

Val Gln Pro Gly Tyr Leu Lys Glu Val Leu Pro Ser Ala Pro Arg
50                  55                  60

Gln Pro Asp Thr Leu Asp Ser Leu Phe Asp Asp Ile Gln Gln Lys Ile
65                  70                  75                  80

Ile Pro Gly Val Thr His Trp Gln Ser Pro Asn Tyr Phe Ala Tyr Tyr
                85                  90                  95

Pro Ser Asn Ser Ser Thr Ala Gly Phe Leu Gly Glu Met Leu Ser Ala
            100                 105                 110

Ala Phe Asn Ile Val Gly Phe Ser Trp Ile Thr Ser Pro Ala Ala Thr
            115                 120                 125

Glu Leu Glu Val Ile Val Leu Asp Trp Phe Ala Lys Met Leu Gln Leu
130                 135                 140

Pro Ser Gln Phe Leu Ser Thr Ala Leu Gly Gly Gly Val Ile Gln Gly
145                 150                 155                 160

Thr Ala Ser Glu Ala Val Leu Val Ala Leu Leu Ala Ala Arg Asp Arg
                165                 170                 175

Ala Leu Lys Lys His Gly Lys His Ser Leu Glu Lys Leu Val Val Tyr
            180                 185                 190

Ala Ser Asp Gln Thr His Ser Ala Leu Gln Lys Ala Cys Gln Ile Ala
            195                 200                 205

Gly Ile Phe Ser Glu Asn Val Arg Val Ile Ala Asp Cys Asn Lys
210                 215                 220

Asn Tyr Ala Val Ala Pro Glu Val Ser Glu Ala Leu Ser Ile Asp
225                 230                 235                 240

Leu Ser Ser Gly Leu Ile Pro Phe Phe Ile Cys Ala Thr Val Gly Thr
            245                 250                 255

Thr Ser Ser Ser Ala Val Asp Pro Leu Pro Glu Leu Gly Gln Ile Ala
            260                 265                 270

Lys Ser Asn Asp Met Trp Phe His Ile Asp Ala Ala Tyr Ala Gly Ser
            275                 280                 285

Ala Cys Ile Cys Pro Glu Tyr Arg His His Leu Asn Gly Val Glu Glu
```

```
                    290                 295                 300
Ala Asp Ser Phe Asn Met Asn Ala His Lys Trp Phe Leu Thr Asn Phe
305                 310                 315                 320

Asp Cys Ser Leu Leu Trp Val Lys Asp Arg Ser Phe Leu Ile Gln Ser
                325                 330                 335

Leu Ser Thr Asn Pro Glu Phe Leu Lys Asn Lys Ala Ser Gln Ala Asn
            340                 345                 350

Ser Val Val Asp Phe Lys Asp Trp Gln Ile Pro Leu Gly Arg Arg Phe
        355                 360                 365

Arg Ser Leu Lys Leu Trp Met Val Leu Arg Leu Tyr Gly Val Asp Asn
370                 375                 380

Leu Gln Ser Tyr Ile Arg Lys His Ile His Leu Ala Glu His Phe Glu
385                 390                 395                 400

Gln Leu Leu Leu Ser Asp Ser Arg Phe Glu Val Val Thr Pro Arg Thr
                405                 410                 415

Phe Ser Leu Val Cys Phe Arg Leu Val Pro Pro Thr Ser Asp His Glu
            420                 425                 430

Asn Gly Arg Lys Leu Asn Tyr Asp Met Met Asp Gly Val Asn Ser Ser
        435                 440                 445

Gly Lys Ile Phe Leu Ser His Thr Val Leu Ser Gly Lys Phe Val Leu
    450                 455                 460

Arg Phe Ala Val Gly Ala Pro Leu Thr Glu Glu Arg His Val Asp Ala
465                 470                 475                 480

Ala Trp Lys Leu Leu Arg Asp Glu Ala Thr Lys Val Leu Gly Lys Met
                485                 490                 495

Val
```

<210> SEQ ID NO 263
<211> LENGTH: 514
<212> TYPE: PRT
<213> ORGANISM: O. sativa

<400> SEQUENCE: 263

```
Met Gly Ser Leu Asp Thr Asn Pro Thr Ala Phe Ser Ala Phe Pro Ala
1               5                   10                  15

Gly Glu Gly Glu Thr Phe Gln Pro Leu Asn Ala Asp Asp Val Arg Ser
            20                  25                  30

Tyr Leu His Lys Ala Val Asp Phe Ile Ser Asp Tyr Lys Ser Val
        35                  40                  45

Glu Ser Met Pro Val Leu Pro Asn Val Lys Pro Gly Tyr Leu Gln Asp
    50                  55                  60

Glu Leu Arg Ala Ser Pro Pro Thr Tyr Ser Ala Pro Phe Asp Val Thr
65                  70                  75                  80

Met Lys Glu Leu Arg Ser Ser Val Pro Gly Met Thr His Trp Ala
                85                  90                  95

Ser Pro Asn Phe Phe Ala Phe Phe Pro Ser Thr Asn Ser Ala Ala Ala
            100                 105                 110

Ile Ala Gly Asp Leu Ile Ala Ser Ala Met Asn Thr Val Gly Phe Thr
        115                 120                 125

Trp Gln Ala Ser Pro Ala Ala Thr Glu Met Glu Val Leu Ala Leu Asp
    130                 135                 140

Trp Leu Ala Gln Met Leu Asn Leu Pro Thr Ser Phe Met Asn Arg Thr
145                 150                 155                 160

Gly Glu Gly Arg Gly Thr Gly Gly Gly Val Ile Leu Gly Thr Thr Ser
```

```
                    165                 170                 175
Glu Ala Met Leu Val Thr Leu Val Ala Ala Arg Asp Ala Ala Leu Arg
            180                 185                 190

Arg Ser Gly Ser Asp Gly Val Ala Gly Leu His Arg Leu Ala Val Tyr
        195                 200                 205

Ala Ala Asp Gln Thr His Ser Thr Phe Phe Lys Ala Cys Arg Leu Ala
    210                 215                 220

Gly Phe Asp Pro Ala Asn Ile Arg Ser Ile Pro Thr Gly Ala Glu Thr
225                 230                 235                 240

Asp Tyr Gly Leu Asp Pro Ala Arg Leu Leu Glu Ala Met Gln Ala Asp
                245                 250                 255

Ala Asp Ala Gly Leu Val Pro Thr Tyr Val Cys Ala Thr Val Gly Thr
            260                 265                 270

Thr Ser Ser Asn Ala Val Asp Pro Val Gly Ala Val Ala Asp Val Ala
        275                 280                 285

Ala Arg Phe Ala Ala Trp Val His Val Asp Ala Ala Tyr Ala Gly Ser
    290                 295                 300

Ala Cys Ile Cys Pro Glu Phe Arg His His Leu Asp Gly Val Glu Arg
305                 310                 315                 320

Val Asp Ser Ile Ser Met Ser Pro His Lys Trp Leu Met Thr Cys Leu
                325                 330                 335

Asp Cys Thr Cys Leu Tyr Val Arg Asp Thr His Arg Leu Thr Gly Ser
            340                 345                 350

Leu Glu Thr Asn Pro Glu Tyr Leu Lys Asn His Ala Ser Asp Ser Gly
        355                 360                 365

Glu Val Thr Asp Leu Lys Asp Met Gln Val Gly Val Gly Arg Arg Phe
    370                 375                 380

Arg Gly Leu Lys Leu Trp Met Val Met Arg Thr Tyr Gly Val Ala Lys
385                 390                 395                 400

Leu Gln Glu His Ile Arg Ser Asp Val Ala Met Ala Lys Val Phe Glu
                405                 410                 415

Asp Leu Val Arg Gly Asp Asp Arg Phe Glu Val Val Pro Arg Asn
            420                 425                 430

Phe Ala Leu Val Cys Phe Arg Ile Arg Ala Gly Ala Gly Ala Ala Ala
        435                 440                 445

Ala Thr Glu Glu Asp Ala Asp Glu Ala Asn Arg Glu Leu Met Glu Arg
    450                 455                 460

Leu Asn Lys Thr Gly Lys Ala Tyr Val Ala His Thr Val Val Gly Gly
465                 470                 475                 480

Arg Phe Val Leu Arg Phe Ala Val Gly Ser Ser Leu Gln Glu Glu His
                485                 490                 495

His Val Arg Ser Ala Trp Glu Leu Ile Lys Lys Thr Thr Thr Glu Met
            500                 505                 510

Met Asn

<210> SEQ ID NO 264
<211> LENGTH: 502
<212> TYPE: PRT
<213> ORGANISM: C. acuminate

<400> SEQUENCE: 264

Met Gly Ser Leu Asp Ser Asn Tyr Asp Thr Glu Ser Pro Ala Ser Val
1               5                   10                  15

Gly Gln Phe Asn Pro Leu Asp Pro Glu Glu Phe Arg Lys Gln Ala His
```

```
                20                  25                  30
Cys Ile Val Asp Phe Ile Ala Asp Tyr Tyr Lys Asn Ile Glu Ser Tyr
            35                  40                  45
Pro Val Leu Ser Gln Val Asp Pro Gly Tyr Arg His Ser Arg Leu Gly
        50                  55                  60
Lys Asn Ala Pro Tyr Arg Ser Glu Pro Phe Glu Ser Ile Leu Lys Asp
65                  70                  75                  80
Val Gln Lys Asp Ile Ile Pro Gly Met Thr His Trp Met Ser Pro Asn
                85                  90                  95
Phe Phe Ala His Phe Pro Ala Thr Val Ser Ser Ala Ala Phe Val Gly
            100                 105                 110
Glu Met Leu Cys Thr Cys Phe Asn Ser Val Gly Phe Asn Trp Leu Ala
        115                 120                 125
Ser Pro Ala Ala Thr Glu Leu Glu Met Val Val Ile Asp Trp Leu Ala
    130                 135                 140
Asn Met Leu Lys Leu Pro Lys Ser Phe Met Phe Ser Gly Thr Gly Gly
145                 150                 155                 160
Gly Val Leu Gln Gly Thr Thr Ser Glu Ala Ile Leu Cys Thr Leu Ile
                165                 170                 175
Ala Ala Ser Pro Met His Phe Glu Ile Val Gly Val Lys Thr Ser Thr
            180                 185                 190
Ser Phe Val Val Tyr Gly Ser Asp Gln Thr His Ser Thr Tyr Ala Lys
        195                 200                 205
Ala Cys Lys Leu Ala Gly Ile Leu Pro Cys Asn Ile Arg Ser Ile Pro
    210                 215                 220
Thr Thr Ala Asp Ser Asn Phe Ser Val Ser Pro Leu Leu Leu Arg Arg
225                 230                 235                 240
Ala Ile Glu Ala Asp Lys Ala Ala Gly Met Val Pro Leu Tyr Ile Cys
                245                 250                 255
Ala Thr Val Gly Thr Thr Ser Thr Thr Ala Ile Asp Pro Leu Ser Ser
            260                 265                 270
Leu Ala Asp Val Ala Asn Asp Tyr Gly Val Trp Phe His Val Asp Ala
        275                 280                 285
Ala Tyr Ala Gly Ser Ala Cys Ile Cys Pro Glu Phe Arg His Tyr Leu
    290                 295                 300
Asp Gly Ile Glu Arg Ala Asp Ser Leu Ser Leu Ser Pro His Lys Trp
305                 310                 315                 320
Leu Leu Ser Tyr Leu Asp Cys Cys Cys Leu Trp Val Lys Ser Pro Ser
                325                 330                 335
Leu Leu Val Lys Ala Leu Ser Thr Asp Pro Glu Tyr Leu Lys Asn Gln
            340                 345                 350
Pro Ser Glu Ser Lys Ser Val Val Asp Tyr Lys Asp Trp Gln Val Gly
        355                 360                 365
Thr Gly Arg Arg Phe Lys Ala Leu Arg Leu Trp Phe Val Met Arg Ser
    370                 375                 380
Tyr Gly Val Ala Asn Leu Gln Ser His Ile Arg Thr Asp Val Gln Met
385                 390                 395                 400
Ala Lys Met Phe Glu Gly Phe Val Lys Ser Asp Pro Arg Phe Glu Ile
                405                 410                 415
Leu Val Pro Arg Val Phe Ser Leu Val Cys Phe Arg Leu Asn Pro Ile
            420                 425                 430
Ser Gly Ser Asp Pro Thr Gly Thr Glu Ala Leu Asn Arg Lys Leu Leu
        435                 440                 445
```

```
Asp Trp Val Asn Ser Thr Gly Arg Val Tyr Met Thr His Thr Lys Val
        450                 455                 460

Gly Gly Ile Tyr Met Leu Arg Phe Ala Val Gly Ala Thr Leu Thr Glu
465                 470                 475                 480

Lys Arg His Val Ser Ser Ala Trp Lys Leu Ile Lys Glu Gly Ala Asp
                485                 490                 495

Val Leu Leu Lys Glu Asp
            500

<210> SEQ ID NO 265
<211> LENGTH: 498
<212> TYPE: PRT
<213> ORGANISM: C. acuminate

<400> SEQUENCE: 265

Met Gly Ser Ile Asp Ser Asn Tyr Asp Thr Glu Ser Ala Gly Gln Cys
1               5                   10                  15

Arg Pro Leu Glu Pro Glu Glu Phe Arg Lys Gln Ala His Gln Met Val
            20                  25                  30

Asp Phe Ile Ala Asp Tyr Tyr Lys Asn Ile Glu Ser Tyr Pro Val Leu
        35                  40                  45

Ser Gln Val Glu Pro Gly Tyr Leu Gln Ser Arg Leu Pro Glu Thr Ala
    50                  55                  60

Pro Tyr Arg Pro Glu Pro Phe Glu Ser Ile Leu Lys Asp Val His Lys
65                  70                  75                  80

Asp Ile Ile Pro Gly Val Thr His Trp Leu Ser Pro Asn Phe Phe Ala
                85                  90                  95

Tyr Phe Pro Ala Thr Val Ser Ser Ala Ala Phe Val Gly Glu Met Leu
            100                 105                 110

Cys Thr Cys Phe Asn Ala Val Gly Phe Asn Trp Leu Ala Ser Pro Ala
        115                 120                 125

Glu Leu Glu Leu Glu Met Val Val Met Asp Trp Leu Ala Ser Met Leu
    130                 135                 140

Lys Leu Pro Asn Ser Phe Thr Phe Leu Gly Thr Gly Gly Gly Val Ile
145                 150                 155                 160

Gln Gly Thr Thr Ser Glu Ala Ile Leu Cys Thr Leu Ile Ala Ala Arg
                165                 170                 175

Asp Arg Ala Leu Glu Ser Ile Gly Val Asp Ser Ile His Lys Leu Val
            180                 185                 190

Val Tyr Gly Ser Asp Gln Thr His Ser Thr Tyr Ala Lys Ala Cys Asn
        195                 200                 205

Leu Ala Gly Ile Leu Pro Cys Asn Ile Arg Ser Ile Arg Thr Glu Ala
    210                 215                 220

Val Ala Asn Phe Ser Leu Ser Pro Asp Ser Leu His Arg Glu Ile Glu
225                 230                 235                 240

Ala Asp Val Ala Ala Gly Met Val Pro Leu Tyr Leu Cys Ala Thr Val
                245                 250                 255

Gly Thr Thr Ser Thr Thr Ala Ile Asp Ser Leu Ser Pro Leu Ala Asp
            260                 265                 270

Val Ala Asn Asp Tyr Gly Leu Trp Phe His Val Asp Ala Ala Tyr Ala
        275                 280                 285

Gly Ser Ala Cys Ile Cys Pro Glu Phe Arg His Tyr Leu Asp Gly Ile
    290                 295                 300

Glu Arg Ala Asp Ser Leu Ser Leu Ser Pro His Lys Trp Leu Leu Ser
```

```
                305                 310                 315                 320
Tyr Leu Asp Cys Cys Cys Leu Trp Val Lys Arg Pro Ser Val Leu Val
                    325                 330                 335

Lys Ala Leu Ser Thr Asp Pro Glu Tyr Leu Lys Asn Lys Pro Ser Glu
                340                 345                 350

Ser Asn Ser Val Val Asp Phe Lys Asp Trp Gln Val Gly Thr Gly Arg
            355                 360                 365

Arg Phe Lys Ala Leu Arg Leu Trp Phe Val Met Arg Ser Tyr Gly Val
        370                 375                 380

Ala Asn Leu Gln Ser His Ile Arg Ser Asp Ile Gln Met Ala Lys Met
385                 390                 395                 400

Phe Glu Glu Phe Val Asn Ser Asp Pro Arg Phe Glu Ile Val Val Pro
                405                 410                 415

Arg Val Phe Ser Leu Val Cys Phe Arg Leu Asn Pro Phe Ser Lys Ser
                420                 425                 430

Asp Pro Cys Asn Thr Glu Leu Leu Asn Arg Lys Leu Leu Glu Trp Val
            435                 440                 445

Asn Ser Thr Gly Gln Val Tyr Ile Thr His Thr Lys Val Gly Gly Val
        450                 455                 460

Tyr Met Leu Arg Phe Ala Val Gly Ala Thr Leu Thr Glu Glu His His
465                 470                 475                 480

Val Ser Ala Ala Trp Lys Leu Ile Arg Glu Gly Ala Asp Ala Leu Leu
                485                 490                 495

Cys Ser

<210> SEQ ID NO 266
<211> LENGTH: 503
<212> TYPE: PRT
<213> ORGANISM: C. annuum

<400> SEQUENCE: 266

Met Gly Ser Leu Asp Ser Asn Asn Ser Thr Gln Thr Gln Ser Asn Val
1               5                   10                  15

Thr Lys Phe Asn Pro Leu Asp Pro Glu Glu Phe Arg Thr Gln Ala His
            20                  25                  30

Gln Met Val Asp Phe Ile Ala Asp Tyr Tyr Lys Asn Ile Glu Ser Tyr
        35                  40                  45

Pro Val Leu Ser Gln Val Glu Pro Gly Tyr Leu Arg Asn His Leu Pro
    50                  55                  60

Glu Asn Ala Pro Tyr Leu Pro Glu Ser Leu Asp Thr Ile Met Lys Asp
65                  70                  75                  80

Val Glu Lys His Ile Ile Pro Gly Met Thr His Trp Leu Ser Pro Asn
                85                  90                  95

Phe Phe Ala Phe Phe Pro Ala Thr Val Ser Ser Ala Ala Phe Leu Gly
            100                 105                 110

Glu Met Leu Cys Asn Cys Phe Asn Ser Val Gly Phe Asn Trp Leu Ala
        115                 120                 125

Ser Pro Ala Met Thr Glu Leu Glu Met Ile Ile Met Asp Trp Leu Ala
    130                 135                 140

Asn Met Leu Lys Leu Pro Glu Cys Phe Met Phe Ser Gly Thr Gly Gly
145                 150                 155                 160

Gly Val Ile Gln Gly Thr Thr Ser Glu Ala Ile Leu Cys Thr Leu Ile
                165                 170                 175

Ala Ala Arg Asp Arg Lys Leu Glu Asn Ile Gly Val Asp Asn Ile Gly
```

180                 185                 190
Lys Leu Val Val Tyr Gly Ser Asp Gln Thr His Ser Met Tyr Ala Lys
            195                 200                 205

Ala Cys Lys Ala Ala Gly Ile Phe Pro Cys Asn Ile Arg Ala Ile Ser
        210                 215                 220

Thr Cys Val Glu Asn Asp Phe Ser Leu Ser Pro Ala Val Leu Arg Gly
225                 230                 235                 240

Ile Val Glu Val Asp Ala Ala Gly Leu Val Pro Leu Phe Leu Cys
                245                 250                 255

Ala Thr Val Gly Thr Thr Ser Thr Thr Ala Ile Asp Pro Ile Ser Glu
            260                 265                 270

Leu Gly Glu Leu Ala Asn Glu Phe Asp Ile Trp Leu His Val Asp Ala
        275                 280                 285

Ala Tyr Gly Gly Ser Ala Cys Ile Cys Pro Glu Phe Arg Gln Tyr Leu
        290                 295                 300

Asp Gly Ile Glu Arg Ala Asn Ser Phe Ser Leu Ser Pro His Lys Trp
305                 310                 315                 320

Leu Leu Ser Tyr Leu Asp Cys Cys Met Trp Val Lys Glu Pro Ser
                325                 330                 335

Val Leu Val Lys Ala Leu Ser Thr Asn Pro Glu Tyr Leu Arg Asn Lys
            340                 345                 350

Arg Ser Glu His Gly Ser Val Val Asp Tyr Lys Asp Trp Gln Ile Gly
        355                 360                 365

Thr Gly Arg Lys Phe Lys Ser Leu Arg Leu Trp Leu Ile Met Arg Ser
370                 375                 380

Tyr Gly Val Ala Asn Leu Gln Ser His Ile Arg Ser Asp Val Arg Met
385                 390                 395                 400

Ala Lys Met Phe Glu Gly Leu Val Arg Ser Asp Pro Tyr Phe Glu Val
                405                 410                 415

Ile Val Pro Arg Arg Phe Ser Leu Val Cys Phe Arg Phe Asn Pro Asp
            420                 425                 430

Lys Glu Tyr Glu Pro Ala Tyr Thr Glu Leu Leu Asn Lys Arg Leu Leu
        435                 440                 445

Asp Asn Val Asn Ser Thr Gly Arg Val Tyr Met Thr His Thr Val Ala
        450                 455                 460

Gly Gly Ile Tyr Met Leu Arg Phe Ala Val Gly Ala Thr Phe Thr Glu
465                 470                 475                 480

Asp Arg His Leu Ile Cys Ala Trp Lys Leu Ile Lys Asp Cys Ala Asp
                485                 490                 495

Ala Leu Leu Arg Asn Cys Gln
            500

<210> SEQ ID NO 267
<211> LENGTH: 506
<212> TYPE: PRT
<213> ORGANISM: O. pumila

<400> SEQUENCE: 267

Met Gly Ser Ile Ser Glu Asn Cys Asp Asp Ser Ile Ser Leu Ala Ala
1               5                   10                  15

Pro Phe Arg Pro Leu Glu Pro Glu Glu Phe Arg Lys Gln Ala His Val
            20                  25                  30

Met Val Asp Phe Ile Ala Asp Tyr Tyr Lys Asn Ile Glu Asn Tyr Pro
        35                  40                  45

```
Val Leu Ser Gln Val Glu Pro Gly Tyr Leu Lys Asn Arg Leu Pro Glu
    50                  55                  60

Thr Ala Pro His Leu Pro Glu Ser Phe Glu Thr Ile Leu Lys Asp Ile
65                  70                  75                  80

Lys Lys Asp Ile Val Pro Gly Met Thr Asn Trp Leu Ser Pro Asn Phe
                85                  90                  95

Phe Ala Tyr Phe Pro Ala Thr Val Ser Ser Ala Ala Phe Val Gly Glu
            100                 105                 110

Met Leu Cys Thr Gly Phe Asn Ser Val Gly Phe Asn Trp Leu Ala Ser
            115                 120                 125

Pro Ala Ser Thr Glu Leu Glu Met Val Val Ile Asp Trp Leu Ala Asn
        130                 135                 140

Met Leu Lys Leu Pro Lys Ser Phe Met Phe His Gly Thr Gly Gly Gly
145                 150                 155                 160

Val Ile Gln Gly Thr Thr Ser Glu Ala Ile Leu Cys Thr Leu Ile Ala
                165                 170                 175

Ala Arg Asp Gly Ala Leu Glu Lys Ile Gly Met Glu Asn Val Gly Lys
            180                 185                 190

Leu Val Val Tyr Gly Ser Asp Gln Thr His Ser Phe Phe Gln Lys Thr
        195                 200                 205

Cys Lys Val Ala Gly Ile Phe Pro Cys Asn Ile Lys Leu Ile Pro Thr
210                 215                 220

Thr Arg Glu Asp Asn Phe Ser Met Ser Pro Ile Ala Leu Arg Glu Gln
225                 230                 235                 240

Ile Glu Ala Asp Val Ala Asp Gly Leu Val Pro Ile Phe Leu Cys Thr
                245                 250                 255

Thr Val Gly Thr Thr Ser Thr Ala Ala Ile Asp Pro Val Ser Glu Val
            260                 265                 270

Ala Lys Val Ala Asn Asp Phe Asn Ile Trp Val His Val Asp Ala Ala
        275                 280                 285

Tyr Ala Gly Ser Ala Cys Ile Cys Pro Glu Phe Arg Gln Tyr Leu Asp
290                 295                 300

Gly Ile Glu Leu Val Asp Ser Phe Ser Leu Ser Pro His Lys Trp Leu
305                 310                 315                 320

Leu Cys Phe Leu Asp Cys Cys Cys Leu Trp Leu Lys Lys Pro His Leu
                325                 330                 335

Met Val Lys Ala Leu Ser Thr Asn Pro Glu Tyr Leu Arg Asn Lys Arg
            340                 345                 350

Ser Glu Phe Asp Gly Val Val Asp Phe Lys Asp Trp Gln Ile Gly Thr
        355                 360                 365

Gly Arg Arg Phe Lys Ala Leu Arg Leu Trp Leu Val Met Arg Ser Tyr
370                 375                 380

Gly Val Glu Asn Leu Lys Arg His Ile Leu Ser Asp Val Gln Met Ala
385                 390                 395                 400

Lys Met Phe Glu Gly Leu Val Lys Ser Asp Pro Arg Phe Glu Ile Ile
                405                 410                 415

Val Pro Arg Ala Phe Ala Leu Val Cys Phe Arg Leu Asn Pro Gly Lys
            420                 425                 430

Gly Tyr Asp Asp Glu Ile Asp Lys Glu Ile Leu Asn Lys Glu Leu Leu
        435                 440                 445

Asp Leu Ile Asn Ser Thr Gly Arg Ala Tyr Met Thr His Thr Lys Ala
450                 455                 460

Gly Gly Ile Tyr Met Leu Arg Phe Ala Val Gly Thr Thr Leu Thr Glu
```

```
            465                 470                 475                 480
Glu His His Val Tyr Ala Ala Trp Glu Leu Ile Lys Glu Cys Thr Asp
                    485                 490                 495
Ala Ser Leu Thr Lys Thr Asn Ile Ile Glu
                500                 505

<210> SEQ ID NO 268
<211> LENGTH: 500
<212> TYPE: PRT
<213> ORGANISM: C. roseus

<400> SEQUENCE: 268

Met Gly Ser Ile Asp Ser Thr Asn Val Ala Met Ser Asn Ser Pro Val
 1               5                  10                  15

Gly Glu Phe Lys Pro Leu Glu Ala Glu Phe Arg Lys Gln Ala His
                20                  25                  30

Arg Met Val Asp Phe Ile Ala Asp Tyr Tyr Lys Asn Val Glu Thr Tyr
                35                  40                  45

Pro Val Leu Ser Glu Val Glu Pro Gly Tyr Leu Arg Lys Arg Ile Pro
 50                  55                  60

Glu Thr Ala Pro Tyr Leu Pro Glu Pro Leu Asp Asp Ile Met Lys Asp
65                  70                  75                  80

Ile Gln Lys Asp Ile Ile Pro Gly Met Thr Asn Trp Met Ser Pro Asn
                85                  90                  95

Phe Tyr Ala Phe Phe Pro Ala Thr Val Ser Ser Ala Ala Phe Leu Gly
                100                 105                 110

Glu Met Leu Ser Thr Ala Leu Asn Ser Val Gly Phe Thr Trp Val Ser
                115                 120                 125

Ser Pro Ala Ala Thr Glu Leu Glu Met Ile Val Met Asp Trp Leu Ala
            130                 135                 140

Gln Ile Leu Lys Leu Pro Lys Ser Phe Met Phe Ser Gly Thr Gly Gly
145                 150                 155                 160

Gly Val Ile Gln Asn Thr Thr Ser Glu Ser Ile Leu Cys Thr Ile Ile
                165                 170                 175

Ala Ala Arg Glu Arg Ala Leu Glu Lys Leu Gly Pro Asp Ser Ile Gly
            180                 185                 190

Lys Leu Val Cys Tyr Gly Ser Asp Gln Thr His Thr Met Phe Pro Lys
            195                 200                 205

Thr Cys Lys Leu Ala Gly Ile Tyr Pro Asn Asn Ile Arg Leu Ile Pro
210                 215                 220

Thr Thr Val Glu Thr Asp Phe Gly Ile Ser Pro Gln Val Leu Arg Lys
225                 230                 235                 240

Met Val Glu Asp Asp Val Ala Ala Gly Tyr Val Pro Leu Phe Leu Cys
                245                 250                 255

Ala Thr Leu Gly Thr Thr Ser Thr Thr Ala Thr Asp Pro Val Asp Ser
            260                 265                 270

Leu Ser Glu Ile Ala Asn Glu Phe Gly Ile Trp Ile His Val Asp Ala
            275                 280                 285

Ala Tyr Ala Gly Ser Ala Cys Ile Cys Pro Glu Phe Arg His Tyr Leu
            290                 295                 300

Asp Gly Ile Glu Arg Val Asp Ser Leu Ser Leu Ser Pro His Lys Trp
305                 310                 315                 320

Leu Leu Ala Tyr Leu Asp Cys Thr Cys Leu Trp Val Lys Gln Pro His
                325                 330                 335
```

```
Leu Leu Leu Arg Ala Leu Thr Thr Asn Pro Glu Tyr Leu Lys Asn Lys
                340                 345                 350

Gln Ser Asp Leu Asp Lys Val Val Asp Phe Lys Asn Trp Gln Ile Ala
            355                 360                 365

Thr Gly Arg Lys Phe Arg Ser Leu Lys Leu Trp Leu Ile Leu Arg Ser
        370                 375                 380

Tyr Gly Val Val Asn Leu Gln Ser His Ile Arg Ser Asp Val Ala Met
385                 390                 395                 400

Gly Lys Met Phe Glu Glu Trp Val Arg Ser Asp Ser Arg Phe Glu Ile
                405                 410                 415

Val Val Pro Arg Asn Phe Ser Leu Val Cys Phe Arg Leu Lys Pro Asp
            420                 425                 430

Val Ser Ser Leu His Val Glu Glu Val Asn Lys Lys Leu Leu Asp Met
        435                 440                 445

Leu Asn Ser Thr Gly Arg Val Tyr Met Thr His Thr Ile Val Gly Gly
    450                 455                 460

Ile Tyr Met Leu Arg Leu Ala Val Gly Ser Ser Leu Thr Glu Glu His
465                 470                 475                 480

His Val Arg Arg Val Trp Asp Leu Ile Gln Lys Leu Thr Asp Asp Leu
                485                 490                 495

Leu Lys Glu Ala
            500

<210> SEQ ID NO 269
<211> LENGTH: 514
<212> TYPE: PRT
<213> ORGANISM: P. crispum

<400> SEQUENCE: 269

Met Gly Ser Ile Asp Asn Leu Thr Glu Lys Leu Ala Ser Gln Phe Pro
1               5                   10                  15

Met Asn Thr Leu Glu Pro Glu Glu Phe Arg Arg Gln Gly His Met Met
            20                  25                  30

Ile Asp Phe Leu Ala Asp Tyr Tyr Arg Lys Val Glu Asn Tyr Pro Val
        35                  40                  45

Arg Ser Gln Val Ser Pro Gly Tyr Leu Arg Glu Ile Leu Pro Glu Ser
    50                  55                  60

Ala Pro Tyr Asn Pro Glu Ser Leu Glu Thr Ile Leu Gln Asp Val Gln
65                  70                  75                  80

Thr Lys Ile Ile Pro Gly Ile Thr His Trp Gln Ser Pro Asn Phe Phe
                85                  90                  95

Ala Tyr Phe Pro Ser Ser Gly Ser Thr Ala Gly Phe Leu Gly Glu Met
            100                 105                 110

Leu Ser Thr Gly Phe Asn Val Val Gly Phe Asn Trp Met Val Ser Pro
        115                 120                 125

Ala Ala Thr Glu Leu Glu Asn Val Val Thr Asp Trp Phe Gly Lys Met
    130                 135                 140

Leu Gln Leu Pro Lys Ser Phe Leu Phe Ser Gly Gly Gly Gly Gly Val
145                 150                 155                 160

Leu Gln Gly Thr Thr Cys Glu Ala Ile Leu Cys Thr Leu Val Ala Ala
                165                 170                 175

Arg Asp Lys Asn Leu Arg Gln His Gly Met Asp Asn Ile Gly Lys Leu
            180                 185                 190

Val Val Tyr Cys Ser Asp Gln Thr His Ser Ala Leu Gln Lys Ala Ala
        195                 200                 205
```

Lys Ile Ala Gly Ile Asp Pro Lys Asn Phe Arg Ala Ile Glu Thr Thr
210                 215                 220

Lys Ser Ser Asn Phe Gln Leu Cys Pro Lys Arg Leu Glu Ser Ala Ile
225                 230                 235                 240

Leu His Asp Leu Gln Asn Gly Leu Ile Pro Leu Tyr Leu Cys Ala Thr
            245                 250                 255

Val Gly Thr Thr Ser Ser Thr Thr Val Asp Pro Leu Pro Ala Leu Thr
            260                 265                 270

Glu Val Ala Lys Lys Tyr Asp Leu Trp Val His Val Asp Ala Ala Tyr
275                 280                 285

Ala Gly Ser Ala Cys Ile Cys Pro Glu Phe Arg Gln Tyr Leu Asp Gly
290                 295                 300

Val Glu Asn Ala Asp Ser Phe Ser Leu Asn Ala His Lys Trp Phe Leu
305                 310                 315                 320

Thr Thr Leu Asp Cys Cys Cys Leu Trp Val Arg Asn Pro Ser Ala Leu
            325                 330                 335

Ile Lys Ser Leu Ser Thr Tyr Pro Glu Phe Leu Lys Asn Asn Ala Ser
            340                 345                 350

Glu Thr Asn Lys Val Val Asp Tyr Lys Asp Trp Gln Ile Met Leu Ser
355                 360                 365

Arg Arg Phe Arg Ala Leu Lys Leu Trp Phe Val Leu Arg Ser Tyr Gly
370                 375                 380

Val Gly Gln Leu Arg Glu Phe Ile Arg Gly His Val Gly Met Ala Lys
385                 390                 395                 400

Tyr Phe Glu Gly Leu Val Asn Met Asp Lys Arg Phe Glu Val Val Ala
            405                 410                 415

Pro Arg Leu Phe Ser Met Val Cys Phe Arg Ile Lys Pro Ser Ala Met
            420                 425                 430

Ile Gly Lys Asn Asp Glu Asp Glu Val Asn Glu Ile Asn Arg Lys Leu
            435                 440                 445

Leu Glu Ser Val Asn Asp Ser Gly Arg Ile Tyr Val Ser His Thr Val
450                 455                 460

Leu Gly Gly Ile Tyr Val Ile Arg Phe Ala Ile Gly Thr Leu Thr
465                 470                 475                 480

Asp Ile Asn His Val Ser Ala Ala Trp Lys Val Leu Gln Asp His Ala
            485                 490                 495

Gly Ala Leu Leu Asp Asp Thr Phe Thr Ser Asn Lys Leu Val Glu Val
            500                 505                 510

Leu Ser

<210> SEQ ID NO 270
<211> LENGTH: 508
<212> TYPE: PRT
<213> ORGANISM: R. hybrid

<400> SEQUENCE: 270

Met Gly Ser Phe Pro Phe His Arg Asp Leu Gln Glu Ile Ala Ser Ser
1               5                   10                  15

Gln Leu Thr Lys Ala Leu Asp Pro Glu Glu Phe Arg Lys Gln Gly His
            20                  25                  30

Met Val Ile Asn Phe Ile Ala Asp Tyr Tyr Gln Asn Ile Glu Lys Tyr
        35                  40                  45

Pro Val Leu Ser Arg Val Glu Pro Gly Tyr Leu Lys Lys Cys Leu Pro
50                  55                  60

```
Val Ser Ala Pro Tyr Asp Pro Glu Pro Ile Ser Thr Ile Leu Arg Asp
 65                  70                  75                  80

Val Gln Asn His Ile Val Pro Gly Leu Thr His Trp Gln Ser Pro Asn
                 85                  90                  95

Phe Phe Ala Tyr Phe Ser Ser Thr Ala Ser Thr Ala Gly Phe Leu Gly
            100                 105                 110

Glu Ile Leu Thr Thr Gly Phe Asn Val Val Gly Phe Asn Trp Val Ser
        115                 120                 125

Ser Pro Ala Ala Thr Glu Leu Glu Asn Ile Val Met Asp Trp Leu Gly
    130                 135                 140

Asp Met Leu Gln Leu Pro Lys Ser Phe His Phe Ser Gly Asn Gly Gly
145                 150                 155                 160

Gly Val Leu His Gly Ser Thr Cys Glu Ala Ile Val Cys Thr Met Val
                165                 170                 175

Ala Ala Arg Asp Gln Met Leu Arg Arg Ile Gly Ser Glu Asn Leu Gly
            180                 185                 190

Lys Leu Val Val Tyr Gly Ser Asp Gln Thr His Ser Thr Leu Gln Lys
        195                 200                 205

Ala Thr Gln Ile Val Gly Ile Asn Thr Glu Asn Phe Arg Ala Ile Lys
    210                 215                 220

Thr Thr Lys Ser Thr Gly Phe Ala Leu Ser Pro Glu Met Leu Arg Leu
225                 230                 235                 240

Thr Ile Ser Ser Asp Leu Glu Lys Gly Leu Val Pro Leu Phe Leu Cys
                245                 250                 255

Ala Thr Ile Gly Thr Thr Ala Thr Thr Ala Ile Asp Pro Leu Glu Ala
            260                 265                 270

Leu Cys His Val Ala Lys Glu Tyr Gly Val Trp Val His Val Asp Ala
        275                 280                 285

Ala Tyr Ala Gly Ser Ala Cys Ile Cys Pro Glu Phe Arg His Phe Ile
    290                 295                 300

Asn Gly Val Glu Gly Ala Asn Ser Phe Ser Phe Asn Pro His Lys Trp
305                 310                 315                 320

Leu Phe Thr Gly Met Asp Cys Cys Cys Leu Trp Val Lys Asn Pro Ser
                325                 330                 335

Val Leu Ala Ser Ser Leu Ser Thr Asn Pro Glu Phe Leu Arg Asn Lys
            340                 345                 350

Ala Ser Asp Ser Lys Gln Val Val Asp Tyr Lys Asp Trp Gln Ile Ala
        355                 360                 365

Leu Ser Arg Arg Phe Arg Ala Leu Lys Leu Trp Leu Val Leu Arg Ser
    370                 375                 380

Tyr Gly Val Ala Asn Leu Arg Asn Phe Ile Arg Ile His Val Lys Met
385                 390                 395                 400

Ala Lys Thr Phe Glu Gly Leu Val Arg Met Asp Lys Arg Phe Glu Ile
                405                 410                 415

Leu Val Pro Arg Asn Phe Ser Leu Val Cys Phe Arg Ile Ser Pro Ser
            420                 425                 430

Ala Leu Ile Ser Ser Asn Glu Asp Asp Glu Ile Gly Met Val Asn Glu
        435                 440                 445

Val Asn Cys Lys Leu Leu Glu Ala Ile Asn Ala Ser Gly Lys Ala Tyr
    450                 455                 460

Met Thr His Ala Val Val Gly Gly Leu Tyr Val Leu Arg Cys Ala Val
465                 470                 475                 480
```

Gly Ala Thr Leu Thr Glu Glu Lys His Ile Val Glu Ala Trp Asn Val
            485                 490                 495

Val Gln Asp His Ala Gln Ala Ile Leu Ser Thr Tyr
            500                 505

<210> SEQ ID NO 271
<211> LENGTH: 506
<212> TYPE: PRT
<213> ORGANISM: P. hybrida

<400> SEQUENCE: 271

Met Asp Thr Ile Lys Ile Asn Pro Glu Phe Asp Gly Gln Phe Cys Lys
1               5                   10                  15

Thr Thr Ser Leu Leu Asp Pro Glu Glu Phe Arg Arg Asn Gly His Met
            20                  25                  30

Met Val Asp Phe Leu Ala Asp Tyr Phe His Asn Ile Glu Lys Tyr Pro
        35                  40                  45

Val Arg Ser Gln Val Glu Pro Gly Tyr Leu Glu Arg Leu Leu Pro Asp
    50                  55                  60

Ser Ala Pro Ile Gln Pro Glu Pro Ile Glu Lys Ile Leu Lys Asp Val
65                  70                  75                  80

Arg Ser Asp Ile Phe Pro Gly Leu Thr His Trp Gln Ser Pro Asn Phe
                85                  90                  95

Phe Ala Tyr Phe Pro Cys Ser Ser Ser Thr Ala Gly Ile Leu Gly Glu
            100                 105                 110

Met Leu Ser Ala Gly Leu Asn Val Val Gly Phe Ser Trp Ile Ala Ser
        115                 120                 125

Pro Ala Ala Thr Glu Leu Glu Ser Ile Val Met Asp Trp Leu Gly Lys
    130                 135                 140

Leu Ile Asn Leu Pro Lys Thr Tyr Leu Phe Ser Gly Gly Gly Gly Gly
145                 150                 155                 160

Val Met Gln Gly Thr Thr Cys Glu Val Met Leu Cys Thr Ile Val Ala
                165                 170                 175

Ala Arg Asp Lys Met Leu Glu Lys Phe Gly Arg Glu Asn Ile Asp Lys
            180                 185                 190

Leu Val Val Tyr Ala Ser Asp Gln Thr His Phe Ser Phe Gln Lys Ala
        195                 200                 205

Val Lys Ile Ser Gly Ile Lys Pro Glu Asn Phe Arg Ala Ile Pro Thr
    210                 215                 220

Thr Lys Ala Thr Glu Phe Ser Leu Asn Pro Glu Ser Leu Arg Arg Ala
225                 230                 235                 240

Ile Gln Glu Asp Lys Lys Ala Gly Leu Ile Pro Leu Phe Leu Cys Thr
                245                 250                 255

Ser Ile Gly Thr Thr Ser Thr Thr Ala Val Asp Pro Leu Lys Pro Leu
            260                 265                 270

Cys Glu Ile Ala Glu Glu Tyr Gly Ile Trp Val His Val Asp Ala Ala
        275                 280                 285

Tyr Ala Gly Ser Ala Cys Ile Cys Pro Glu Phe Gln His Phe Leu Asp
    290                 295                 300

Gly Val Glu His Ala Asn Ser Phe Ser Phe Asn Ala His Lys Trp Leu
305                 310                 315                 320

Phe Thr Thr Leu Asp Cys Cys Cys Leu Trp Leu Lys Asp Pro Ser Ser
                325                 330                 335

Leu Thr Lys Ala Leu Ser Thr Asn Pro Glu Val Leu Arg Asn Asp Ala
            340                 345                 350

```
Thr Asp Ser Glu Gln Val Val Asp Tyr Lys Asp Trp Gln Ile Thr Leu
            355                 360                 365

Ser Arg Arg Phe Arg Ser Leu Lys Leu Trp Leu Val Leu Lys Ser Tyr
370                 375                 380

Gly Val Ala Asn Leu Arg Asn Phe Ile Arg Ser His Ile Glu Met Ala
385                 390                 395                 400

Lys His Phe Glu Glu Leu Val Ala Met Asp Glu Arg Phe Glu Ile Met
            405                 410                 415

Ala Pro Arg Asn Phe Ser Leu Val Cys Phe Arg Val Ser Leu Leu Ala
            420                 425                 430

Leu Glu Lys Lys Phe Asn Phe Val Asp Glu Thr Gln Val Asn Glu Phe
            435                 440                 445

Asn Ala Lys Leu Leu Glu Ser Ile Ile Ser Ser Gly Asn Val Tyr Met
450                 455                 460

Thr His Thr Val Val Glu Gly Val Tyr Met Ile Arg Phe Ala Val Gly
465                 470                 475                 480

Ala Pro Leu Thr Asp Tyr Pro His Ile Asp Met Ala Trp Asn Val Val
            485                 490                 495

Arg Asn His Ala Thr Met Met Leu Asn Ala
            500                 505

<210> SEQ ID NO 272
<211> LENGTH: 518
<212> TYPE: PRT
<213> ORGANISM: T. flavum

<400> SEQUENCE: 272

Met Gly Ser Leu His Val Glu Asp Leu Asp Asn Ile Ser Lys Cys Thr
1               5                   10                  15

Val Glu Asn Pro Leu Asp Pro Glu Glu Phe Arg Arg Gln Gly His Met
            20                  25                  30

Met Ile Asp Phe Leu Ala Asp Tyr Tyr Arg Asp Ile Glu Lys Tyr Pro
        35                  40                  45

Val Arg Ser Gln Val Glu Pro Gly Tyr Leu Arg Lys Glu Ile Pro Asp
50                  55                  60

Ser Ala Pro Tyr Asn Pro Glu Ser Ile Glu Thr Ile Leu Glu Asp Val
65                  70                  75                  80

His Lys Gln Ile Ile Pro Gly Ile Thr His Trp Gln Ser Pro Asn Tyr
                85                  90                  95

Phe Ala Tyr Phe Pro Ser Ser Gly Ser Val Ala Gly Phe Leu Gly Glu
            100                 105                 110

Met Leu Ser Thr Gly Phe Asn Val Val Gly Phe Asn Trp Met Ser Ser
        115                 120                 125

Pro Ala Ala Thr Glu Leu Glu Ser Ile Val Met Asp Trp Leu Gly Lys
130                 135                 140

Met Leu Lys Leu Pro Lys Ser Phe Leu Phe Ser Gly Asn Gly Gly Gly
145                 150                 155                 160

Val Leu Gln Gly Thr Thr Cys Glu Ala Ile Leu Cys Thr Leu Thr Ala
                165                 170                 175

Ala Arg Asp Arg Met Leu Asn Lys Ile Gly Arg Glu Asn Ile Cys Lys
            180                 185                 190

Leu Val Val Tyr Gly Ser Asp Gln Thr His Cys Ala Leu Gln Lys Ala
        195                 200                 205

Ala Gln Ile Ala Gly Ile His Pro Asn Asn Phe Arg Ala Val Pro Thr
```

```
                  210                 215                 220

Thr Lys Ala Asn Asp Tyr Gly Leu Ser Ala Ser Ala Leu Arg Ser Thr
225                 230                 235                 240

Ile Leu Glu Asp Ile Glu Ala Gly Leu Val Pro Leu Phe Leu Cys Ala
                245                 250                 255

Thr Val Gly Thr Thr Ser Ser Thr Ala Val Asp Pro Ile Gly Pro Leu
            260                 265                 270

Cys Lys Val Ala Ser Asp Tyr Ser Ile Trp Val His Val Asp Ala Ala
            275                 280                 285

Tyr Ala Gly Ser Ala Cys Ile Cys Pro Glu Phe Arg His Phe Ile Asp
        290                 295                 300

Gly Val Glu Asn Ala Asp Ser Phe Ser Leu Asn Ala His Lys Trp Phe
305                 310                 315                 320

Phe Thr Thr Leu Asp Cys Cys Cys Leu Trp Val Lys Glu Pro Ser Ala
                325                 330                 335

Leu Ile Lys Ala Leu Ser Thr Asn Pro Glu Tyr Leu Arg Asn Lys Ala
            340                 345                 350

Thr Glu Ser His Gln Val Val Asp Tyr Lys Asp Trp Gln Ile Ala Leu
        355                 360                 365

Ser Arg Arg Phe Arg Ala Met Lys Leu Trp Leu Val Leu Arg Ser Tyr
    370                 375                 380

Gly Val Ala Asn Leu Arg Asn Phe Leu Arg Ser His Val Lys Met Ala
385                 390                 395                 400

Lys Asn Phe Glu Gly Phe Ile Ala Leu Asp Lys Arg Phe Glu Ile Val
                405                 410                 415

Val Pro Arg Thr Phe Ala Met Val Cys Phe Arg Leu Leu Pro Pro Arg
            420                 425                 430

Ser Pro Leu Ile Ile Lys Thr Asn Gly Tyr Gln Asn Gly Asn Gly Val
            435                 440                 445

Tyr His Lys Asp Glu Ser Arg Ala Asn Glu Leu Asn Arg Arg Leu Leu
        450                 455                 460

Glu Ser Ile Asn Ala Ser Gly Ser Ala Tyr Met Thr His Ser Met Val
465                 470                 475                 480

Gly Gly Val Tyr Met Ile Arg Phe Ala Val Gly Ala Ser Leu Thr Glu
                485                 490                 495

Glu Arg His Val Ile Leu Ala Trp Lys Val Val Gln Glu His Ala Asp
            500                 505                 510

Ala Val Leu Ala Thr Phe
        515

<210> SEQ ID NO 273
<211> LENGTH: 533
<212> TYPE: PRT
<213> ORGANISM: B. distachyon

<400> SEQUENCE: 273

Met Ala Pro Thr Ser Met Cys Phe Asp Ala Ile Asn Gly Ala Ala Ala
1               5                   10                  15

Ala Gln Asn Gly Thr Ala Pro Val Leu Ala Thr Lys Pro Ala Ala Gln
            20                  25                  30

Ala Leu Gln Cys Pro Asn Ala Leu Asn Ala Asp Asp Phe Arg Arg Gln
        35                  40                  45

Gly His Gln Val Ile Asp Phe Ile Ala Glu Tyr Tyr Gly Gly Met Ala
    50                  55                  60
```

```
Asp Tyr Pro Val His Pro Ser Val Thr Pro Gly Phe Leu Arg Asn Leu
 65                  70                  75                  80

Leu Pro Ala Ser Ala Pro Ser Arg Ala Glu Pro Asp Ala Phe Ser Ser
             85                  90                  95

Ala Leu Lys Asp Ile Arg Asp His Ile Leu Pro Gly Met Thr His Trp
        100                 105                 110

Gln Ser Pro Arg His Phe Ala His Phe Pro Ala Ser Ser Ser Thr Val
        115                 120                 125

Gly Ala Leu Gly Glu Ala Leu Thr Ala Gly Ile Asn Val Val Pro Phe
        130                 135                 140

Thr Trp Ala Ala Ser Pro Ala Ala Thr Glu Leu Glu Met Val Val Val
145                 150                 155                 160

Asp Trp Leu Gly Lys Ala Leu His Leu Pro Glu Thr Leu Leu Phe Ala
                165                 170                 175

Gly Gly Gly Gly Gly Thr Leu Leu Gly Thr Ser Cys Glu Ala Ile Leu
            180                 185                 190

Cys Ala Leu Val Ala Ala Arg Asp Arg Lys Leu Ala Glu Ile Gly Gly
        195                 200                 205

Arg Arg Ile Gly Asp Leu Val Val Tyr Cys Ser Asp Gln Thr His Phe
        210                 215                 220

Ala Phe Arg Lys Ala Ala Arg Ile Ala Gly Ile Leu Arg Glu His Ile
225                 230                 235                 240

Arg Glu Ile Gln Thr Cys His Ala Asn Met Phe Ala Leu Ser Ala Thr
                245                 250                 255

Ala Leu Glu Ala Ala Met Gln Ala Asp Val Glu Ala Gly Leu Val Pro
            260                 265                 270

Leu Phe Val Cys Ala Thr Val Gly Thr Thr Gln Thr Thr Ala Val Asp
        275                 280                 285

Pro Ile Gly Glu Leu Cys Thr Val Thr Ala Pro His Gly Val Trp Val
        290                 295                 300

His Val Asp Ala Ala Tyr Ala Gly Ser Ala Leu Val Cys Pro Glu Phe
305                 310                 315                 320

Arg His Val Ile Asn Gly Val Glu Ser Val Asp Ser Phe Ser Met Asn
                325                 330                 335

Ala His Lys Trp Leu Leu Thr Asn Asn Asp Cys Cys Ala Met Trp Val
            340                 345                 350

Lys Lys Pro Ser Glu Leu Ile Ala Ala Leu Gly Thr Glu Gln Glu Tyr
        355                 360                 365

Ile Leu Lys Asp Ser Ala Ser Glu Gly His Asp Ile Val Asp Tyr Lys
        370                 375                 380

Asp Trp Thr Met Thr Leu Thr Arg Arg Phe Arg Ala Leu Lys Met Trp
385                 390                 395                 400

Leu Val Leu Arg Cys Tyr Gly Ile Asp Gly Leu Arg Glu His Ile Arg
                405                 410                 415

Ser His Val Arg Met Ala Glu Ala Phe Glu Asn Leu Val Arg Ala Asp
            420                 425                 430

Glu Arg Phe Glu Val Val Thr Asp Arg Gln Phe Ala Leu Val Cys Phe
        435                 440                 445

Arg Leu Arg Ser Pro Glu Lys Tyr Gly Gly Lys Thr Ala Asn Glu
        450                 455                 460

Leu Asn Arg Ser Leu Leu Glu Glu Val Asn Ala Val Thr Leu Gly Pro
465                 470                 475                 480

Tyr Met Ser Ser Ala Asn Val Gly Gly Met Tyr Met Leu Arg Cys Ala
```

```
            485                 490                 495
Val Gly Ser Thr Leu Thr Glu Asp Cys His Val Thr Asp Gly Trp Lys
            500                 505                 510

Val Val Gln Asp Arg Ala Thr Ser Ile Leu Arg Lys Met Glu Ile Ile
            515                 520                 525

Tyr Ser Val Leu Gly
            530

<210> SEQ ID NO 274
<211> LENGTH: 512
<212> TYPE: PRT
<213> ORGANISM: P. somniferum

<400> SEQUENCE: 274

Met Gly Ser Leu Pro Thr Asn Asn Leu Glu Ser Ile Ser Leu Cys Ser
1               5                   10                  15

Gln Asn Pro Leu Asp Pro Asp Glu Phe Arg Arg Gln Gly His Met Ile
            20                  25                  30

Ile Asp Phe Leu Ala Asp Tyr Tyr Lys Asn Val Glu Asn Tyr Pro Val
        35                  40                  45

Arg Ser Gln Val Glu Pro Gly Tyr Leu Lys Arg Leu Pro Glu Ser
    50                  55                  60

Ala Pro Tyr Asn Pro Glu Ser Ile Glu Thr Ile Leu Glu Asp Val Thr
65                  70                  75                  80

Asn Asp Ile Ile Pro Gly Leu Thr His Trp Gln Ser Pro Asn Tyr Phe
                85                  90                  95

Ala Tyr Phe Pro Ser Ser Gly Ser Ile Ala Gly Phe Leu Gly Glu Met
            100                 105                 110

Leu Ser Thr Gly Phe Asn Val Val Gly Phe Asn Trp Met Ser Ser Pro
        115                 120                 125

Ala Ala Thr Glu Leu Glu Ser Ile Val Met Asn Trp Leu Gly Gln Met
    130                 135                 140

Leu Thr Leu Pro Lys Ser Phe Leu Phe Ser Ser Asp Gly Ser Ser Gly
145                 150                 155                 160

Gly Gly Gly Val Leu Gln Gly Thr Thr Cys Glu Ala Ile Leu Cys Thr
                165                 170                 175

Leu Thr Ala Ala Arg Asp Lys Met Leu Asn Lys Ile Gly Arg Glu Asn
            180                 185                 190

Ile Asn Lys Leu Val Val Tyr Ala Ser Asn Gln Thr His Cys Ala Leu
        195                 200                 205

Gln Lys Ala Ala Gln Ile Ala Gly Ile Asn Pro Lys Asn Val Arg Ala
    210                 215                 220

Ile Lys Thr Ser Lys Ala Thr Asn Phe Gly Leu Ser Pro Asn Ser Leu
225                 230                 235                 240

Gln Ser Ala Ile Leu Ala Asp Ile Glu Ser Gly Leu Val Pro Leu Phe
                245                 250                 255

Leu Cys Ala Thr Val Gly Thr Thr Ser Ser Thr Ala Val Asp Pro Ile
            260                 265                 270

Gly Pro Leu Cys Ala Val Ala Lys Leu Tyr Gly Ile Trp Val His Ile
        275                 280                 285

Asp Ala Ala Tyr Ala Gly Ser Ala Cys Ile Cys Pro Glu Phe Arg His
    290                 295                 300

Phe Ile Asp Gly Val Glu Asp Ala Asp Ser Phe Ser Leu Asn Ala His
305                 310                 315                 320
```

-continued

```
Lys Trp Phe Phe Thr Thr Leu Asp Cys Cys Cys Leu Trp Val Lys Asp
            325                 330                 335
Ser Asp Ser Leu Val Lys Ala Leu Ser Thr Ser Ala Glu Tyr Leu Lys
            340                 345                 350
Asn Lys Ala Thr Glu Ser Lys Gln Val Ile Asp Tyr Lys Asp Trp Gln
            355                 360                 365
Ile Ala Leu Ser Arg Arg Phe Arg Ser Met Lys Leu Trp Leu Val Leu
    370                 375                 380
Arg Ser Tyr Gly Val Ala Asn Leu Arg Thr Phe Leu Arg Ser His Val
385                 390                 395                 400
Lys Met Ala Lys His Phe Gln Gly Leu Met Gly Met Asp Asn Arg Phe
            405                 410                 415
Glu Ile Val Val Pro Arg Thr Phe Ala Met Val Cys Phe Arg Leu Lys
            420                 425                 430
Pro Ala Ala Ile Phe Lys Gln Lys Ile Val Asp Asn Asp Tyr Ile Glu
            435                 440                 445
Asp Gln Thr Asn Glu Val Asn Ala Lys Leu Leu Glu Ser Val Asn Ala
        450                 455                 460
Ser Gly Lys Ile Tyr Met Thr His Ala Val Val Gly Gly Val Tyr Met
465                 470                 475                 480
Ile Arg Phe Ala Val Gly Ala Thr Leu Thr Glu Glu Arg His Val Thr
            485                 490                 495
Gly Ala Trp Lys Val Val Gln Glu His Thr Asp Ala Ile Leu Gly Ala
            500                 505                 510
```

HOST CELL EXPRESSION OF 4-HYDROXYPHENYLACETALDEHYDE SYNTHASE FOR PRODUCTION OF SALIDROSIDE, ICARISIDE D2, AND PRECURSORS

CROSS-REFERENCE TO RELATED APPLICATIONS

This application claims the benefit of U.S. Provisional Application No. 62/607,271, filed on Dec. 18, 2017. The entire teachings of the above application are incorporated herein by reference.

INCORPORATION BY REFERENCE OF MATERIAL IN ASCII TEXT FILE

This application incorporates by reference the Sequence Listing contained in the following ASCII text file being submitted concurrently herewith:
  a) File name: 03992060001_SEQUENCE_LISTING_20191003.txt; created Oct. 3, 2019, 494 KB in size.

BACKGROUND

Salidroside, also known as tyrosol 8-O-glucoside, is naturally produced by plants within the *Rhodiola* genus. Salidroside is of particular interest and value because of its unique reported biological activities (Cifani et al., 2010; Guan et al., 2012; Panossian et al., 2014). However, commercially available salidroside in its pure form is currently obtained through a lengthy purification process from its native plant host, which poses a significant bottleneck hindering further clinical development of salidroside as a potential therapeutic agent. Accordingly, improved methods of making salidroside are needed.

SUMMARY

Salidroside is a bioactive tyrosine-derived phenolic natural product found in medicinal plants under the *Rhodiola* genus. In addition to their anti-fatigue and anti-anoxia roles in traditional medicine, *Rhodiola* total extract and salidroside have also displayed medicinal properties as anti-cardiovascular disease, and anti-cancer, agents. The resulting surge in global demand of *Rhodiola* plants and salidroside has driven some species close to extinction.

Described herein is a *Rhodiola* salidroside biosynthetic pathway that was elucidated utilizing comprehensive transcriptomics and metabolomics datasets for *Rhodiola rosea*. This pathway includes a pyridoxal phosphate (PLP)-dependent 4-hydroxyphenylacetaldehyde synthase (4HPAAS) that directly converts tyrosine to 4-HPAA. Genes encoding the subsequent 4-HPAA reductase (4HPAR) and tyrosol:UDP-glucose 8-O-glucosyltransferase (T8GT), respectively, were further identified to complete salidroside biosynthesis in *Rhodiola*. As described herein, heterologous production of salidroside can be achieved in yeast *Saccharomyces cerevisiae* as well as in plant *Nicotiana benthamiana* through transgenic expression of *Rhodiola* salidroside biosynthetic genes. Accordingly, the methods and compositions described herein provide useful tools for engineering sustainable production of salidroside in heterologous hosts.

Described herein are vectors and kits that include vectors. Those vectors include a nucleic acid encoding one or more of a 4-hydroxyphenylacetaldehyde synthase (4HPAAS), a 4-hydroxyphenylacetaldehyde reductase (4HPAR), a tyrosol:UDP-glucose 8-O-glucosyltransferase (T8GT), and a tyrosol:UDP-glucose 4-O-glucosyltransferase (T4GT). Described herein are methods of using the vectors and kits to make a transgenic host cell having a transgene encoding one or more of a 4HPAAS, a 4HPAR, a T8GT, and a T4GT. Described herein are methods of making one or more of 4-hydroxyphenylacetaldehyde (4-HPAA), tyrosol, tyrosol 8-O-glucoside (salidroside), and icariside D2 in a transgenic host cell. The tyrosol, salidroside, and/or icariside D2 can subsequently be obtained, e.g., by separation and purification processes. A variety of transgenic host cells can be used, such as yeast cells, plant cells, and bacterial cells. In some embodiments, the tyrosol, tyrosol 8-O-glucoside (salidroside), or icariside D2 can be obtained in greater quantities than by purification from the native plant host. In some embodiments, the tyrosol, tyrosol 8-O-glucoside (salidroside), or icariside D2 can be obtained more cost-effectively than by purification from the native plant host.

Certain embodiments provide a vector that includes a nucleic acid encoding a 4-hydroxyphenylacetaldehyde synthase (4HPAAS), wherein the 4HPAAS has at least 70% sequence identity to either SEQ ID NO: 2 (*Rhodiola rosea* 4HPAAS), or a biologically active fragment thereof. The 4HPAAS includes: a) an amino acid residue selected from the group consisting of F, L, I, M and V at a position corresponding to the F residue at position 343 in SEQ ID NO: 2; b) an amino acid residue selected from the group consisting of N and D at a position corresponding to the H residue at position 198 in SEQ ID NO: 2; or c) a combination thereof.

Certain embodiments provide a vector that includes a nucleic acid encoding a 4-hydroxyphenylacetaldehyde reductase (4HPAR), wherein the 4HPAR includes at least 70% amino acid sequence identity to SEQ ID NO: 4, or a biologically active fragment thereof.

Certain embodiments provide a vector that includes a nucleic acid encoding a tyrosol:UDP-glucose 8-O-glucosyltransferase (T8GT). In some embodiments, the T8GT comprises a plant secondary product glycosyltransferase (PSPG) motif. In some embodiments, the T8GT comprises at least 70% amino acid sequence identity to one or more of SEQ ID NO: 14, SEQ ID NO: 16, SEQ ID NO: 18, and SEQ ID NO: 20, or a biologically active fragment thereof.

Certain embodiments provide a vector that includes a nucleic acid encoding a tyrosol:UDP-glucose 4-O-glucosyltransferase (T4GT). In some embodiments, the T4GT comprises a plant secondary product glycosyltransferase (PSPG) motif. In some embodiments, the T4GT comprises at least 70% amino acid sequence identity to one or more of SEQ ID NO: 6, SEQ ID NO: 8, SEQ ID NO: 10, SEQ ID NO: 12, and SEQ ID NO: 14, or a biologically active fragment thereof.

Certain embodiments provide a kit that includes: a) a vector that includes a nucleic acid encoding a 4-hydroxyphenylacetaldehyde synthase (4HPAAS); b) a vector that includes a nucleic acid encoding a 4-hydroxyphenylacetaldehyde reductase (4HPAR); and c) one or more of i) a vector that includes a nucleic acid encoding a tyrosol:UDP-glucose 8-O-glucosyltransferase (T8GT) and ii) a vector that includes a nucleic acid encoding a tyrosol:UDP-glucose 4-O-glucosyltransferase (T4GT). In some embodiments, the kit includes both a T8GT and a T4GT.

Some embodiments provide a host cell that includes a transgene encoding a tyrosol:UDP-glucose 8-O-glucosyltransferase (T8GT). In some embodiments, the host cell further includes a transgene encoding 4-hydroxyphenylacetaldehyde reductase (4HPAR). In some embodiments, the host cell further includes a transgene encoding a 4-hydroxyphenylacetaldehyde synthase (4HPAAS). In some embodiments, the host cell further includes a transgene encoding both a 4HPAR and a 4HPAAS. In some embodiments, a single transgene encodes multiple genes, such as one or more of the T8GT, the 4HPAR, and the 4HPAAS. In some embodiments, separate transgenes encode one or more of T8GT, 4HPAR, and 4HPAAS.

Some embodiments provide a host cell that includes a transgene encoding a 4-hydroxyphenylacetaldehyde synthase (4HPAAS). In some embodiments, the host cell further includes a transgene encoding 4-hydroxyphenylacetaldehyde reductase (4HPAR). In some embodiments, the host cell further includes a transgene encoding tyrosol:UDP-glucose 8-O-glucosyltransferase (T8GT). In some embodiments, the host cell further includes a transgene encoding tyrosol:UDP-glucose 4-O-glucosyltransferase (T4GT). In some embodiments, the host cell further includes a transgene encoding both a 4HPAR and a T8GT. In some embodiments, the host cell further includes a transgene encoding both a 4HPAR and a T4GT. In some embodiments, a single transgene encodes multiple genes, such as one or more of the 4HPAAS, the 4HPAR, the T8GT, and the T4GT. In some embodiments, separate transgenes encode one or more of the 4HPAAS, the 4HPAR, the T8GT, and the T4GT.

Some embodiments provide a method of making a transgenic host cell. The method can include introducing a vector into the host cell, wherein the vector includes a nucleic acid encoding a tyrosol:UDP-glucose 8-O-glucosyltransferase (T8GT). The method can further include introducing into the host cell a vector that includes a nucleic acid encoding a 4-hydroxyphenylacetaldehyde reductase (4HPAR). The method can further include introducing into the host cell a vector that includes a nucleic acid encoding a 4-hydroxyphenylacetaldehyde synthase (4HPAAS).

Some embodiments provide a method of making a transgenic host cell. The method can include introducing a vector into the host cell, wherein the vector includes a nucleic acid encoding a 4-hydroxyphenylacetaldehyde synthase (4HPAAS). The method can further include introducing into the host cell a vector that includes a nucleic acid encoding a 4-hydroxyphenylacetaldehyde reductase (4HPAR). The method can further include introducing into the host cell a vector that includes a nucleic acid encoding tyrosol:UDP-glucose 8-O-glucosyltransferase (T8GT) or a tyrosol:UDP-glucose 4-O-glucosyltransferase (T4GT). In some embodiments, the method can further include introducing into the host cell a vector that includes a nucleic acid encoding a T8GT and a nucleic acid encoding a T4GT.

Certain embodiments provide a method of making tyrosol 8-O-glucoside (salidroside). In some embodiments, the salidroside is made in a host cell. In certain embodiments, the salidroside is made in a cell-free system or cell lysate. The method can include expressing in a host cell a transgene that encodes a tyrosol:UDP-glucose 8-O-glucosyltransferase (T8GT). In some embodiments, the host cell includes tyrosol, either produced endogenously or provided to the cell exogenously.

In some embodiments, the host cell further expresses a transgene that encodes a 4-hydroxyphenylacetaldehyde reductase (4HPAR). In some embodiments, the host cell further expresses a transgene that encodes a 4-hydroxyphenylacetaldehyde synthase (4HPAAS). In some embodiments, tyrosol is secreted by the host cell into the cell culture media, from which it can be obtained.

Certain embodiments provide a method of making 4-hydroxyphenylacetaldehyde (4-HPAA). In some embodiments, the 4-HPAA is made in a host cell. In some embodiments, the 4-HPAA is made in a cell-free system or lysate. The method can include expressing in the host cell a transgene that encodes a 4-hydroxyphenylacetaldehyde synthase (4HPAAS). In some embodiments, the host cell includes L-tyrosine, produced endogenously or provided to the cell exogenously. In some embodiments, the method further includes making tyrosol in the host cell, and the host cell further expresses a transgene encoding a 4-hydroxyphenylacetaldehyde reductase (4HPAR). In some embodiments, tyrosol is secreted by the host cell into the cell culture media, from which it can be obtained.

In some embodiments, the host cell is a yeast cell, such as *Saccharomyces cerevisiae*. In some embodiments, the host cell is a plant cell, such as a cell a from a *Nicotiana benthamiana* plant. In some embodiments, the host cell is a bacterial cell, such as *Escherichia coli* or *Agrobacterium tumefaciens*.

In some embodiments, nucleic acids encoding two or more of 4HPAAS, 4HPAR, T8GT, and T4GT are included in a single vector. In some embodiments, the transgene encoding an enzyme (e.g., 4HPAAS, 4HPAR, T8GT, and T4GT) can be integrated into the genome of the host transgenic cell.

Certain embodiments provide a transgenic plant, such as a *Nicotiana benthamiana* plant, that includes a transgene encoding a tyrosol:UDP-glucose 8-O-glucosyltransferase (T8GT).

Some embodiments provide a transgenic plant, such as a *Nicotiana benthamiana* plant, that includes a transgene encoding a tyrosol:UDP-glucose 4-O-glucosyltransferase (T4GT).

Some embodiments provide a transgenic plant, such as a *Nicotiana benthamiana* plant, that includes a transgene encoding a 4-hydroxyphenylacetaldehyde synthase (4HPAAS).

Certain embodiments provide a transgenic plant, such as a *Nicotiana benthamiana* plant, that includes a transgene encoding a 4-hydroxyphenylacetaldehyde reductase (4HPAR).

Certain embodiments provide an isolated deoxyribonucleic acid (DNA) coding sequence encoding a tyrosol: UDP-glucose 8-O-glucosyltransferase (T8GT). In some embodiments, the nucleic acid includes SEQ ID NO: 13. In some embodiments, the nucleic acid includes SEQ ID NO: 15. In some embodiments, the nucleic acid includes SEQ ID NO: 17. In some embodiments, the nucleic acid includes SEQ ID NO: 19.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 1A is a photograph of greenhouse-grown *R. rosea*. FIG. 1B is a chromatogram showing metabolic profiling of *R. rosea* root and crown tissues by LC-HRAM-MS. Enrichment of tyrosol and salidroside is observed in the root.

Extracted ion chromatogram (XIC) is shown with mass windows set to display the [M–H]⁻ ion for tyrosol and the [M+NH₄]⁺ ion for salidroside. The identity of the metabolites was verified in comparison to authentic standards. FIG. 1C is a schematic showing alternative salidroside biosynthetic pathways in *Rhodiola*.

FIG. 2A is a simplified maximum likelihood (ML) phylogenetic tree of land plant AAADs. A fully annotated version of this tree is shown in FIG. 11. The three major groups of the tree have been annotated as the basal (green), TyDC (blue) and TDC (red) clades based on taxonomic distribution, cladding, and conservation of the substrate-specifying active site residue. Representative characterized enzymes are labeled at the tree branches, while the *R. rosea* TDC, AAS and 4HPAAS are displayed in bold. The scale measures evolutionary distances in substitutions per amino acid. FIG. 2B is LC-UV chromatograms of the reaction product of L-tyrosine and Rr4HPAAS enzyme (with and without NaBH₄ reduction) in comparison to enzyme assay conducted using PsTyDC as a control. The identity of the products was verified by comparison with authentic standards. FIG. 2C is a graph showing kinetic characterization of Rr4HPAAS against various aromatic amino acid substrates.

FIG. 3A is a simplified ML phylogenetic tree of angiosperm ADHs. A fully annotated version of this tree is shown in FIG. 14. Major clades are annotated based on representative characterized enzymes when possible. The two *R. rosea* 4HPARs and the previously characterized SlPARs are labeled at the tree branches. The scale measures evolutionary distances in substitutions per amino acid. FIG. 3B is LC-MS chromatograms of the reaction product of 4-HPAA and 0.2 µg recombinant Rr4HPAR1 after incubation for various time points. FIG. 3C is LC-MS chromatograms of the reaction product of 4-HPAA and 15 µg recombinant Rr4HPAR2 after incubation for various time points. The identity of the tyrosol product was verified by comparison with an authentic standard.

FIG. 4A is a maximum likelihood (ML) phylogenetic tree of 34 *R. rosea* UGTs together with 88 full-length UGTs encoded by the *A. thaliana* genome. UGTs that show T4GT and T8GT activities are denoted by black circles and stars, respectively. Bootstrap values (based on 500 replicates) are indicated at the major nodes. The scale measures evolutionary distances in substitutions per amino acid. FIG. 4B a chart showing relative in vivo T4GT and T8GT activities of *R. rosea* UGTs as examined in engineered yeast. FIG. 4C is a graph showing Michaelis-Menten kinetic characterization of four *R. rosea* tyrosol-modifying UGTs.

FIG. 5A is a chromatogram showing that *N. benthamiana* transiently expressing Rr4HPAAS or Pc4HPAAS produces both salidroside and icariside D2. FIG. 5B is a chromatogram showing that *N. benthamiana* transiently expressing PsTyDC produces tyramine. FIG. 5C is a chromatogram showing that *N. benthamiana* leaves transiently co-expressing Rr4HPAAS and RrT4GT or RrT8GT produce predominantly icariside D2 or salidroside, respectively. XICs are shown with mass windows set to display the [M+NH₄]⁺ ion for salidroside and icariside D2, and the [M+H]⁺ ion for tyramine. The identity of the metabolites was verified by comparison with authentic standards.

FIG. 7 is a multiple sequence alignment highlighting the sequence regions that can influence enzyme substrate selectivity in select plant AAAD family members. Sequences represent various enzymes from the TyDC and TDC clades. The residue framed in black (identified as Gly 370 for *C. roseus*) can impact substrate selectivity (indolic vs. phenolic). Columns framed in blue indicate greater than 70% conservation of residue physico-chemical properties. Identical amino acids are in white font boxed in red, while similar residues are displayed in red font. FIG. 7 includes SEQ ID NOs: 207 through 219, in order from top-to-bottom.

FIG. 8A is a chromatogram of positive ion mode metabolites. FIG. 8B is a chromatogram of negative ion mode metabolites.

FIG. 10 includes SEQ ID NOs: 220 through 240, in order from top-to-bottom.

FIG. 19A is a chromatogram of the tyrosol glycoside [M+NH4]+ production using the newly described RrUGT3, RrUGT33 and the previously described R. sachalinensis UGTs (GenBank: AAS55083 and EU567325). FIG. 19B is a graph showing relative icariside D2 and salidroside production from RrT8HGT, RrT4GHT RsAAS55083 and RsEU567325. The identity of the ions was confirmed by comparison to NMR verified standards.

FIG. 29A is a chromatogram of salidroside production in wild type (WT), native Rr4HPAAS and RrT8GT expressing, coRr4HPAAS and coRrT8GT expressing or ARO4 K229L, ARO7 G141S, coRr4HPAAS and coRrT8GT expressing S. cerevisiae strains.

FIG. 29B is a chromatogram of salidroside production in S. cerevisiae expressing coRr4HPAAS and coRrT8GT with and without the addition of L-tyrosine and tyrosol.

FIG. 31 includes SEQ ID NOs: 241 through 257, in order from top-to-bottom.

FIG. 32 includes SEQ ID NOs: 258 through 274, in order from top-to-bottom.

FIG. 34A is a chromatogram showing the reduced enzyme product of tyrosine incubated with wildtype PsTyDC. FIG. 34B is a chromatogram showing the reduced enzyme product of tyrosine incubated with PsTyDC Y350F. FIG. 34C is a chromatogram showing the reduced enzyme product of tyrosine incubated with PsTyDC H204N.

DETAILED DESCRIPTION

A description of example embodiments follows.

Rhodiola and Salidroside Biosynthesis

Figure 1A:
FIGS. 1A-C show salidroside biosynthesis in *R. rosea*.

The *Rhodiola* genus consists of approximately 90 species of high-altitude and cold tolerant perennial plants of the Crassulaceae family native to the arctic regions of Eurasia and North America (FIG. 1A). Select species from this genus have a long history in traditional medicine with purported roles in bolstering immunity, memory and learning, while ameliorating depression, altitude sickness and fatigue (Fu, 2009; Lei et al., 2006). Recent studies of *Rhodiola* extract have also demonstrated antioxidant and anti-inflammatory properties with potential applications in the prevention of cardiovascular diseases and cancer (Gauger et al., 2010; Khanum et al., 2005; Skopinska-Rozewska et al., 2008; Tu et al., 2008; Zhang et al., 2007). Extensive phytochemical analysis of *Rhodiola* has identified a number of specialized glycosides, including rosiridin, rhodionin, rosarin, rosin, rosavin and salidroside (FIG. 6) (Du and Xie, 1995; Rohloff, 2002; Yang et al., 2012; Yousef et al., 2006). Salidroside, or tyrosol 8-O-glucoside, is of particular interest and value because of its unique reported biological activities (Cifani et al., 2010; Guan et al., 2012; Panossian et al., 2014). However, commercially available salidroside in its pure form is currently obtained through a lengthy purification process from its native plant host, which poses a significant bottleneck hindering further clinical development of salidroside as a potential therapeutic agent. Moreover, surging global demand of wild *Rhodiola* plants as a herbal supplement has led to overharvesting of these ecologically vulnerable plants from their native habitats with some species now threatened by extinction (Booker et al., 2016; Dorji, 2016).

Metabolic engineering is a promising approach to gain access to high-value plant natural products as an alternative to direct compound isolation from plant hosts (O'Connor, 2015). Previous attempts to engineer salidroside biosynthesis in heterologous hosts have utilized a selection of plant and yeast enzymes to assemble artificial salidroside biosynthetic pathways (Bai et al., 2014; Chung et al., 2017). Although these studies demonstrated the feasibility of engineering salidroside production in bacterial hosts (Bai et al., 2014), an unresolved native salidroside biosynthetic pathway in planta hinders further development and improvement of salidroside biosynthetic strategies in bacteria and other alternative chassis organisms. In postulated salidroside biosynthetic pathway, the salidroside aglycone tyrosol is generated from tyrosine through sequential decarboxylation, oxidative deamination, and aldehyde reduction reactions, catalyzed by three discrete enzymes, tyrosine decarboxylase (TyDC), monoamine oxidase (MAO) and 4HPAR, respectively (FIG. 1C) (Lan et al., 2013). Tyrosol is then glycosylated at its 8-OH group by a regio-specific uridine 5'-diphospho-glucosyltransferase (UGT) to yield salidroside. Although the proposed salidroside pathway seems plausible, to date, only one enzyme of this proposed pathway, *Rhodiola crenulata* TyDC (RcTyDC) (GenBank AFN89854.1), has been previously recombinantly expressed and experimentally examined (Lan et al., 2013). Overexpression of this TyDC-like gene in *R. crenulata* hairy roots culture led to increased accumulation of salidroside (Lan et al., 2013).

TyDCs, together with tryptophan decarboxylases (TDCs) and aromatic acetaldehyde synthases (AASs), encompass a large family of PLP-dependent enzymes broadly referred to as the plant AAAD family (Facchini et al., 2000; Kaminaga et al., 2006). As their respective names imply, TyDCs, TDCs and AAS catalyze discrete decarboxylation or decarboxylation-deamination reactions using specific aromatic amino acids as substrates.

To resolve *Rhodiola* salidroside biosynthesis, tissue-specific transcriptomics and metabolomics datasets were generated for *R. rosea*. Using a combination of differential expression analysis, phylogenetic analysis, biochemical characterization, and heterologous expression, a set of *Rhodiola* genes encoding 4HPAAS, 4HPAR, and T8GT to complete salidroside biosynthesis from tyrosine were identified. In addition, a number of regio-specific T4GTs capable of producing icariside D2 were identified. The newly acquired knowledge about phenolic glycoside biosynthesis in *Rhodiola* allowed reconstitution of salidroside or icariside D2 biosynthesis in yeast *S. cerevisiae* as well as in the plant *N. benthamiana*.

Aromatic Amino Acid Decarboxylases (AAAD) Family of Enzymes

Figure 35:
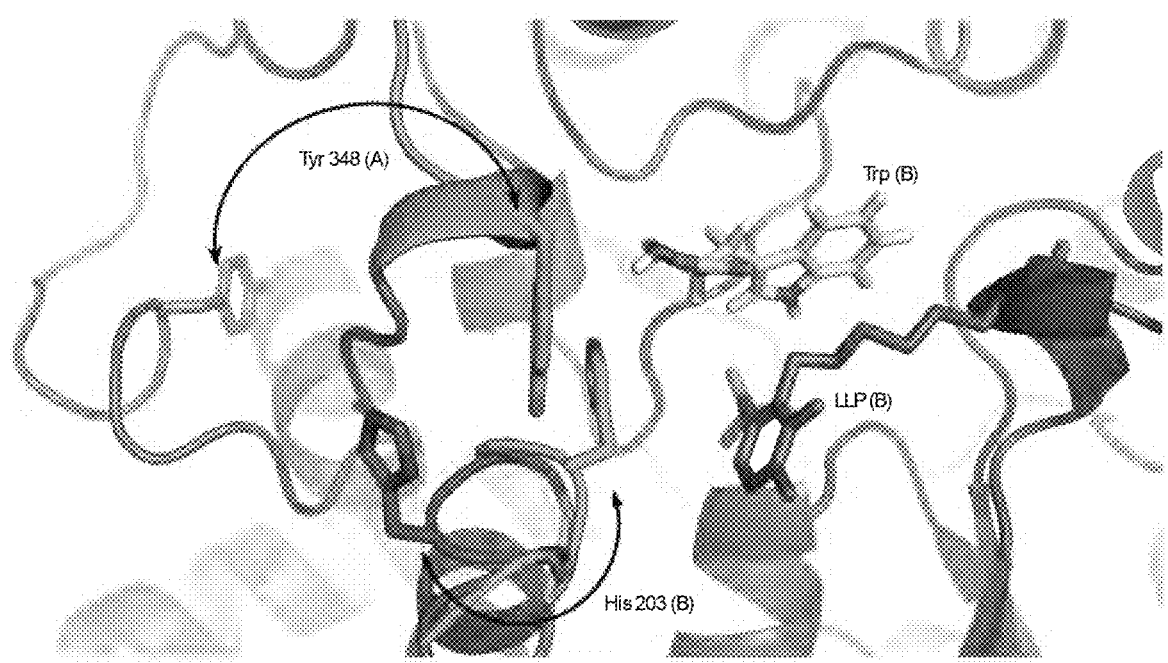
FIG. 35 is a depiction of active site conformations of *Catharanthus roseus* tryptophan decarboxylase. In this homodimer, the A chain is shown in green while the B chain is shown in blue. The active site ligand (tryptophan) is shown in yellow. The active site lysine bound pyridoxal phosphate (LLP) cofactor is visible in the B chain.

TyDCs, together with tryptophan decarboxylases (TDCs) and aromatic acetaldehyde synthases (AASs), encompass a large family of PLP-dependent enzymes broadly referred to as the plant AAAD family (Facchini et al., 2000; Kaminaga et al., 2006). Thus, the AAAD family encompasses enzymes with aromatic amino acid decarboxylase activity and enzymes with aromatic acetaldehyde synthase activity. (*Torrens*-Spence et al., 2012; *Torrens*-Spence et al., 2013). Without wishing to be bound by theory, the catalytic mechanism of the AAAD family of enzymes is contingent on the conformational change of two active site loops, which is illustrated in FIG. 35 with respect to a tryptophan decarboxylase from *Catharanthus roseus*. The large loop from the A chain (342-359) undergoes a dramatic conformational change from a solvent exposed active site "open" conformation to an active site obscured "closed" conformation. Concurrently, a small loop from chain B (201-205) undergoes a crank shaft conformational change to move from a solvent exposed "open" conformation to a pyridoxal phosphate (LLP) associated "closed" conformation. Key residues in these dynamic loops play important roles in the catalytic mechanism of AAAD enzymes. In the tryptophan decarboxylase from *Catharanthus roseus*, tyrosine 348 (Chain A) functions as a catalytic acid to donate a proton to the carbanion intermediate in the decarboxylation reaction mechanism while histidine 203 (Chain B) functions as a molecular chaperon responsible for coordinating and enabling proton donation of the acid tyrosine 348. Substitution of either residue abolishes the protonation and enables a peroxy-aldimine intermediate through the attack of molecular oxygen which spontaneously decomposes to yield the corresponding aromatic acetylaldehyde, peroxide and ammonia aldehyde synthase products. Consequently, substitutions at either location function as a primary sequence means for biochemical functional prediction. One of skill in the art will understand that the precise location within the sequence (here, tyrosine at 348 and histidine at 203) varies among related enzymes within the AAAD family.

Nucleic Acids

As used herein, the term "nucleic acid" refers to a polymer comprising multiple nucleotide monomers (e.g., ribonucleotide monomers or deoxyribonucleotide monomers). "Nucleic acid" includes, for example, DNA (e.g., genomic DNA and cDNA), RNA, and DNA-RNA hybrid molecules. Nucleic acid molecules can be naturally occurring, recombinant, or synthetic. In addition, nucleic acid molecules can be single-stranded, double-stranded or triple-stranded. In certain embodiments, nucleic acid molecules can be modified. In the case of a double-stranded polymer, "nucleic acid" can refer to either or both strands of the molecule.

The terms "nucleotide" and "nucleotide monomer" refer to naturally occurring ribonucleotide or deoxyribonucleotide monomers, as well as non-naturally occurring derivatives and analogs thereof. Accordingly, nucleotides can include, for example, nucleotides comprising naturally occurring bases (e.g., adenosine, thymidine, guanosine, cytidine, uridine, inosine, deoxyadenosine, deoxythymidine, deoxyguanosine, or deoxycytidine) and nucleotides comprising modified bases known in the art.

As used herein, "wildtype" refers to the canonical amino acid sequence as found in nature. As those of skill in the art would appreciate, a nucleic acid sequence can be modified, e.g., for codon optimization in a host cell (e.g., bacteria, yeast, and plant host cells).

As used herein, the term "sequence identity," refers to the extent to which two nucleotide sequences, or two amino acid sequences, have the same residues at the same positions when the sequences are aligned to achieve a maximal level of identity, expressed as a percentage. For sequence alignment and comparison, typically one sequence is designated as a reference sequence, to which a test sequences are compared. The sequence identity between reference and test sequences is expressed as the percentage of positions across the entire length of the reference sequence where the reference and test sequences share the same nucleotide or amino acid upon alignment of the reference and test sequences to achieve a maximal level of identity. As an example, two sequences are considered to have 70% sequence identity when, upon alignment to achieve a maximal level of identity, the test sequence has the same nucleotide or amino acid residue at 70% of the same positions over the entire length of the reference sequence.

Alignment of sequences for comparison to achieve maximal levels of identity can be readily performed by a person of ordinary skill in the art using an appropriate alignment method or algorithm. In some instances, the alignment can include introduced gaps to provide for the maximal level of identity. Examples include the local homology algorithm of Smith & Waterman, *Adv. Appl. Math.* 2:482 (1981), the homology alignment algorithm of Needleman & Wunsch, *J. Mol. Biol.* 48:443 (1970), the search for similarity method of Pearson & Lipman, *Proc. Nat'l. Acad. Sci. USA* 85:2444 (1988), computerized implementations of these algorithms (GAP, BESTFIT, FASTA, and TFASTA in the Wisconsin Genetics Software Package, Genetics Computer Group, 575 Science Dr., Madison, Wis.), and visual inspection (see generally Ausubel et al., *Current Protocols in Molecular Biology*).

When using a sequence comparison algorithm, test and reference sequences are input into a computer, subsequent coordinates are designated, if necessary, and sequence algorithm program parameters are designated. The sequence comparison algorithm then calculates the percent sequence identity for the test sequence(s) relative to the reference sequence, based on the designated program parameters. A commonly used tool for determining percent sequence identity is Protein Basic Local Alignment Search Tool (BLASTP) available through National Center for Biotechnology Information, National Library of Medicine, of the United States National Institutes of Health. (Altschul et al., 1990).

In various embodiments, two nucleotide sequences, or two amino acid sequences, can have at least, e.g., 70%, 75%, 80%, 85%, 86%, 87%, 88%, 89%, 90%, 91%, 92%, 93%, 94%, 95%, 96%, 97%, 98%, 99%, or more, sequence identity. When ascertaining percent sequence identity to one or more sequences described herein, the sequences described herein are the reference sequences.

Some embodiments of the invention relate to a nucleic acid coding sequence (e.g., dsDNA, cDNA) encoding one or more of the enzymes described herein, including those nucleic acid sequences provided in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and SEQ ID NO: 19.

Enzymes

As used herein, the term 4-hydroxyphenylacetaldehyde synthase (4HPAAS) refers to an enzyme that catalyzes conversion of L-tyrosine to 4-hydroxyphenylacetaldehyde. Methods and assays for determining whether an enzyme catalyzes conversion of L-tyrosine to 4-hydroxyphenylacetaldehyde are known in the art, and include enzyme activity assays and liquid chromatography to assess retention time of metabolites, as described herein. Chemical structure can also be assessed by nuclear magnetic resonance (NMR) or liquid chromatography-mass spectrometry. An example of a 4HPAAS is SEQ ID NO: 2, which is the amino acid sequence of a 4HPAAS identified in *Rhodiola rosea* (Rr4HPAAS). In some embodiments, a 4HPAAS has at least about 70%, 75%, 80%, 85%, 86%, 87%, 88%, 89%, 90%, 91%, 92%, 93%, 94%, 95%, 96%, 97%, 98%, 99%, or more sequence identity to SEQ ID NO: 2, or a biologically active fragment thereof. In some embodiments, a 4HPAAS has: a) an amino acid residue selected from the group consisting of F, L, I, M and V at a position corresponding to the F residue at position 343 in SEQ ID NO: 2; b) an amino acid residue selected from the group consisting of N and D at a position corresponding to the H residue at position 198 in SEQ ID NO: 2; or c) a combination thereof. Typically, a 4HPAAS has at least 70% sequence identity to SEQ ID NO: 2, or a biologically active fragment thereof, and also: a) an amino acid residue selected from the group consisting of F, L, I, M and V at a position corresponding to the F residue at position 343 in SEQ ID NO: 2; b) an amino acid residue selected from the group consisting of N and D at a position corresponding to the H residue at position 198 in SEQ ID NO: 2; or c) a combination thereof. An example of a nucleic acid coding sequence that encodes a 4HPAAS is SEQ ID NO: 1, which encodes an amino acid having SEQ ID NO: 2. Many different nucleic acids can encode the 4HPAAS of SEQ ID NO: 2 due to the degeneracy of the genetic code. Nucleic acids can also differ from SEQ ID NO: 1, for example, as a result of one or more substitutions (e.g., silent substitutions).

In some embodiments, modified enzymes can be used in the methods and host cells described herein to provide 4HPAAS activity in those host cells and methods. Typically, those modified enzymes have a) an amino acid residue selected from the group consisting of F, L, I, M and V at a position corresponding to the F residue at position 343 in SEQ ID NO: 2; b) an amino acid residue selected from the group consisting of N and D at a position corresponding to the H residue at position 198 in SEQ ID NO: 2; or c) a combination thereof. In certain embodiments, modified *Papaver somniferum* tyrosine decarboxylase (PsTyDC) enzymes comprising a substitution of the active site histidine (e.g., with N or D) at the position corresponding to the H residue at position 198 in SEQ ID NO: 2, and/or the active site tyrosine (e.g., with F, L, I, M or V) corresponding to the F residue at position 343 in SEQ ID NO: 2, can be used in the methods and host cells described herein to provide 4HPAAS activity in those host cells and methods. In some embodiments, modified nucleic acids encoding the modified enzymes can be used in the vectors, kits, and methods described herein. In some embodiments, those nucleic acids may be codon optimized for expression in a host cell.

As used herein, the term 4-hydroxyphenylacetaldehyde reductase (4HPAR) refers to an enzyme that catalyzes conversion of 4-hydroxyphenylacetaldehyde to tyrosol. Methods and assays for determining whether an enzyme catalyzes conversion of 4-hydroxyphenylacetaldehyde to tyrosol are known in the art, and include enzyme activity assays and liquid chromatography to assess retention time of metabolites, as described herein. Chemical structure can also be assessed by nuclear magnetic resonance (NMR) or liquid chromatography-mass spectrometry. An example of a 4HPAR is SEQ ID NO: 4, which is the amino acid sequence of a 4HPAR identified in *Rhodiola rosea* (Rr4HPAR). In some embodiments, a 4HPAR has at least about 70%, 75%, 80%, 85%, 86%, 87%, 88%, 89%, 90%, 91%, 92%, 93%, 94%, 95%, 96%, 97%, 98%, 99%, or more sequence identity to SEQ ID NO: 4, or a biologically active fragment thereof. An example of a nucleic acid that encodes a 41HPAR is SEQ ID NO: 3, which encodes an amino acid having SEQ ID NO: 4. Many different nucleic acids can encode the 4HPAR of SEQ ID NO: 4 due to the degeneracy of the genetic code. Nucleic acids can also differ from SEQ ID NO: 3, for example, as a result of one or more substitutions (e.g., conservative substitutions, non-conservative substitutions), deletions, or insertions, or a combination thereof, with respect to the wild-type Rr4HPAR sequence (SEQ ID NO: 3).

As used herein, the term tyrosol:UDP-glucose 8-O-glucosyltransferase (T8GT) refers to an enzyme that catalyzes conversion of tyrosol to tyrosol 8-O-glucoside (salidroside). Methods and assays for determining whether an enzyme catalyzes conversion of tyrosol to tyrosol 8-O-glucoside (salidroside) are known in the art, and include enzyme activity assays and liquid chromatography to assess retention time of metabolites, as described herein. Chemical structure can also be assessed by nuclear magnetic resonance (NMR) or liquid chromatography-mass spectrometry. Examples of T8GTs are SEQ ID NO: 14, SEQ ID NO: 16, SEQ ID NO: 18, and SEQ ID NO: 20, which are the amino acid sequences of T8GTs identified in *Rhodiola rosea* (RrT8GTs). In some embodiments, a T8GT has at least about 70%, 75%, 80%, 85%, 86%, 87%, 88%, 89%, 90%, 91%, 92%, 93%, 94%, 95%, 96%, 97%, 98%, 99%, or more sequence identity to one or more of SEQ ID NO: 14, SEQ ID NO: 16, SEQ ID NO: 18, and SEQ ID NO: 20, or biologically active fragments thereof. Examples of nucleic acids that encode T8GTs are SEQ ID NO: 13, SEQ ID NO: 15, SEQ ID NO: 17, and SEQ ID NO: 19, which encode amino acids having SEQ ID NO: 14, SEQ ID NO: 16, SEQ ID NO: 18, and SEQ ID NO: 20, respectively. Many different nucleic acids can encode the T8GTs due to the degeneracy of the genetic code. Nucleic acids can also differ, for example, as a result of one or more substitutions (e.g., silent substitutions), with respect to any of the wild-type RrT8GT nucleic acid sequences.

As used herein, the term tyrosol:UDP-glucose 4-O-glucosyltransferase (T4GT) refers to an enzyme that catalyzes conversion of tyrosol to tyrosol 4-O-glucoside (icariside D2). Methods and assays for determining whether an enzyme catalyzes conversion of tyrosol to tyrosol 4-O-glucoside (icariside D2) are known in the art, and include enzyme activity assays and liquid chromatography to assess retention time of metabolites, as described herein. Chemical structure can also be assessed by nuclear magnetic resonance (NMR) or liquid chromatography-mass spectrometry. Examples of T4GTs are SEQ ID NO: 6, SEQ ID NO: 8, SEQ ID NO: 10, SEQ ID NO: 12, and SEQ ID NO: 14, which are the amino acid sequences of T4GTs identified in *Rhodiola rosea* (RrT4GTs). In some embodiments, a T4GT has at least about 70%, 75%, 80%, 85%, 86%, 87%, 88%, 89%, 90%, 91%, 92%, 93%, 94%, 95%, 96%, 97%, 98%, 99%, or more sequence identity to one or more of SEQ ID NO: 6, SEQ ID NO: 8, SEQ ID NO: 10, SEQ ID NO: 12, and SEQ ID NO: 14, or biologically active fragments thereof. Examples of nucleic acids that encode T8GTs are SEQ ID NO: 5, SEQ ID NO: 7, SEQ ID NO: 9, SEQ ID NO: 11, and SEQ ID NO: 13, which encode amino acids having SEQ ID NO: 6, SEQ ID NO: 8, SEQ ID NO: 10, SEQ ID NO: 12, and SEQ ID NO: 14, respectively. Many different nucleic acids can encode the T4GTs due to the degeneracy of the genetic code. Nucleic acids can also differ, for example, as a result of one or more substitutions (e.g., silent substitutions) with respect to any of the wild-type RrT4GT nucleic acid sequences.

Vectors

The terms "vector", "vector construct" and "expression vector" mean the vehicle by which a DNA or RNA sequence (e.g. a foreign gene) can be introduced into a host cell, so as to transform the host and promote expression (e.g. transcription and translation) of the introduced sequence. Vectors typically comprise the DNA of a transmissible agent, into which foreign DNA encoding a protein is inserted by restriction enzyme technology. A common type of vector is a "plasmid", which generally is a self-contained molecule of double-stranded DNA that can readily accept additional (foreign) DNA and which can readily introduced into a suitable host cell. A large number of vectors, including plasmid and fungal vectors, have been described for replication and/or expression in a variety of eukaryotic and prokaryotic hosts.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter. Gene delivery vectors generally include a transgene (e.g., nucleic acid encoding an enzyme) operably linked to a promoter and other nucleic acid elements required for expression of the transgene in the host cells into which the vector is introduced. Suitable promoters for gene expression and delivery constructs are known in the art. For bacterial host cells, suitable promoters, include, but are not limited to promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xy1A and xy1B genes, and prokaryotic beta-lactamase gene (See e.g., Villa-Kamaroff et al., *Proc. Natl. Acad. Sci. USA* 75: 3727-3731, 1978), as well as the tac promoter (See e.g., DeBoer et al., *Proc. Natl. Acad. Sci. USA* 80: 21-25, 1983). Examples of promoters for filamentous fungal host cells, include, but are not limited to promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (See e.g., WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof. Examples of yeast cell promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are known in the art (See e.g., Romanos et al., Yeast 8:423-488, 1992). The selection of a suitable promoter is within the skill in the art. The recombinant plasmids can also comprise inducible, or regulatable, promoters for expression of an enzyme in cells.

Various gene delivery vehicles are known in the art and include both viral and non-viral (e.g., naked DNA, plasmid) vectors. Viral vectors suitable for gene delivery are known to those skilled in the art. Such viral vectors include, e.g., vector derived from the herpes virus, baculovirus vector, lentiviral vector, retroviral vector, adenoviral vector and adeno-associated viral vector (AAV). Vectors derived from plant viruses can also be used, such as the viral backbones of the RNA viruses Tobacco mosaic virus (TMV), Potato virus X (PVX) and Cowpea mosaic virus (CPMV), and the DNA geminivirus Bean yellow dwarf virus. The viral vector can be replicating or non-replicating.

Non-viral vectors include naked DNA and plasmids, among others. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and such vectors may be introduced into many appropriate host cells, using methods disclosed or cited herein or otherwise known to those skilled in the relevant art.

In certain embodiments, the vector comprises a transgene operably linked to a promoter. The transgene encodes a biologically active molecule, such as an enzyme described herein.

To facilitate the introduction of the gene delivery vector into host cells, the vector can be combined with different chemical means such as colloidal dispersion systems (macromolecular complex, nanocapsules, microspheres, beads) or lipid-based systems (oil-in-water emulsions, micelles, liposomes).

Some embodiments relate to a vector comprising a nucleic acid encoding any enzyme described herein. In certain embodiments, the vector is a plasmid, and includes any one or more plasmid sequences such as, e.g., a promoter sequence, a selection marker sequence, or a locus-targeting sequence. Suitable plasmid vectors include p423TEF 2µ, p425TEF 2µ, and p426TEF 2µ. Another suitable vector is pHis8-4 (Whitehead Institute, Cambridge, Mass., United States of America), which is identified as SEQ ID NO: 94. Another suitable vector is pEAQ-HT, which is identified as SEQ ID NO: 95. Another suitable vector is pJKW 1410, which is identified as SEQ ID NO: 96. pJKW 1410 is a backbone vector used to construct the multi gene yeast expression vector used for salidroside production in the work described in the Examples.

Although the genetic code is degenerate in that most amino acids are represented by multiple codons (called "synonyms" or "synonymous" codons), it is understood in the art that codon usage by particular organisms is nonrandom and biased towards particular codon triplets. Accordingly, in some embodiments, the vector includes a nucleotide sequence that has been optimized for expression in a particular type of host cell (e.g., through codon optimization). Codon optimization refers to a process in which a polynucleotide encoding a protein of interest is modified to replace particular codons in that polynucleotide with codons that encode the same amino acid(s), but are more commonly used/recognized in the host cell in which the nucleic acid is being expressed. In some aspects, the polynucleotides described herein are codon optimized for expression in a bacterial cell, e.g., *E. coli*. In some aspects, the polynucleotides described herein are codon optimized for expression in a yeast cell, e.g., *S. cerevisiae*.

Host Cells

A wide variety of host cells can be used, including fungal cells, bacterial cells, plant cells, insect cells, and mammalian cells.

In some embodiments, the host cell is a fungal cell, such as a yeast cell and an *Aspergillus* spp cell. A wide variety of yeast cells are suitable, such as cells of the genus *Pichia*, including *Pichia pastoris* and *Pichia stipitis*; cells of the genus *Saccharomyces*, including *Saccharomyces cerevisiae*; cells of the genus *Schizosaccharomyces*, including *Schizosaccharomyces pombe*; and cells of the genus *Candida*, including *Candida albicans*.

In some embodiments, the host cell is a bacterial cell. A wide variety of bacterial cells are suitable, such as cells of the genus *Escherichia*, including *Escherichia coli*; cells of the genus *Bacillus*, including *Bacillus subtilis*; cells of the genus *Pseudomonas*, including *Pseudomonas aeruginosa*; and cells of the genus *Streptomyces*, including *Streptomyces griseus*.

In some embodiments, the host cell is a plant cell. A wide variety of cells from a plant are suitable, including cells from a *Nicotiana benthamiana* plant. In other embodiments, the plant belongs to a genus selected from the group consisting of *Arabidopsis, Beta, Glycine, Helianthus, Solanum, Triticum, Oryza, Brassica, Medicago, Prunus, Malus, Hordeum, Musa, Phaseolus, Citrus, Piper, Sorghum, Daucus, Manihot, Capsicum*, and *Zea*.

In some embodiments, the host cell is an insect cell, such as a *Spodoptera frugiperda* cell, such as *Spodoptera frugiperda* Sf9 cell line and *Spodoptera frugiperda* Sf21

In some embodiments, the host cell is a mammalian cell.

In some embodiments, the host cell is an *Escherichia coli* cell, and the vector is pHis8-4. In some embodiments, the host cell is a *Nicotiana benthamiana* cell, and the vector is pEAQ-HT. In some embodiments, the cell is a *Saccharomyces cerevisiae* cell, and the vector is a p423TEF 2μ plasmid, a p425TEF 2μ plasmid, or a p426TEF 2μ plasmid.

As used herein, the term "host cell" encompasses cells in cell culture and also cells within an organism (e.g., a plant).

Some embodiments relate to a host cell comprising a vector as described herein. In certain embodiments, the host cell is an *Escherichia coli* cell, a *Nicotiana benthamiana* cell, or a *Saccharomyces cerevisiae* cell.

In some embodiments, the hosts cells are cultured in a cell culture medium, such as a standard cell culture medium known in the art to be suitable for the particular host cell. In some embodiments, the culture medium is supplemented with one or more of L-tyrosine, 4-hydroxyphenylacetaldehyde (4-HPAA), and tyrosol. In some embodiments, the culture medium is supplemented with tyrosine, for example, between 0.1 mM and 100 mM L-tyrosine. In some embodiments, the culture medium is supplemented with 4-HPAA, for example, between 0.1 mM and 100 mM of 4-HPAA. In some embodiments, the culture medium is supplemented with tyrosol, for example, between 0.1 mM and 100 mM of tyrosol.

Methods of Making Transgenic Host Cells

Described herein are methods of making a transgenic host cell. The transgenic host cells can be made, for example, by introducing one or more of the vector embodiments described herein into the host cell.

In one embodiment, the method comprises introducing into a host cell a vector that includes a nucleic acid encoding a tyrosol:UDP-glucose 8-O-glucosyltransferase (T8GT). In another embodiment, the method can also include introducing into the host cell a vector that includes a nucleic acid encoding a 4-hydroxyphenylacetaldehyde reductase (4HPAR) in addition to introducing a nucleic acid encoding a T8GT. In another embodiment, the method can further include introducing into the host cell a vector that includes a nucleic acid encoding a 4-hydroxyphenylacetaldehyde synthase (4HPAAS) in addition to introducing one or more nucleic acids encoding one or more of T8GT and 4HPAR.

In another embodiment, the method comprises introducing a vector that includes a nucleic acid encoding a 4-hydroxyphenylacetaldehyde synthase (4HPAAS). In another embodiment, the method can further include introducing into the host cell a vector that includes a nucleic acid encoding a 4-hydroxyphenylacetaldehyde reductase (4HPAR) in addition to introducing a nucleic acid encoding a 4HPAAS. In another embodiment, the method can further include introducing into the host cell a vector that includes one or more of a nucleic acid encoding tyrosol:UDP-glucose 8-O-glucosyltransferase (T8GT) and a tyrosol:UDP-glucose 4-O-glucosyltransferase (T4GT), in addition to introducing a nucleic acid encoding one or more of a 4HPAAS and a 4HPAR. In some embodiments, the method can further include introducing into the host cell a vector that includes a nucleic acid encoding a T8GT and a nucleic acid encoding a T4GT, in addition to introducing a nucleic acid encoding one or more of a 4HPAAS and a 4HPAR.

In some embodiments, nucleic acids encoding two or more of 4HPAAS, 4HPAR, T8GT, and T4GT are included in a single vector, such that a single vector encoding one or more enzymes is introduced into a host cell.

In some embodiments, one or more of the nucleic acids are integrated into the genome of the host cell. In some embodiments, the nucleic acids to be integrated into a host genome can be introduced into the host cell using any of a variety of suitable methodologies known in the art, including, for example, CRISPR-based systems (e.g., CRISPR/Cas9; CRISPR/Cpf1), TALEN systems and *Agrobacterium*-mediated transformation. However, as those skilled in the art would recognize, transient transformation techniques can be used that do not require integration into the genome of the host cell. In some embodiments, nucleic acid (e.g., plasmids) can be introduced that are maintained as episomes, which need not be integrated into the host cell genome.

In certain embodiments, the nucleic acid is introduced into a tissue, cell, or seed of a plant cell. Various methods of introducing nucleic acid into the tissue, cell, or seed of plants are known to one of ordinary skill in the art, such as protoplast transformation. The particular method can be selected based on several considerations, such as, e.g., the type of plant used. For example, the floral dip method, as described herein, is a suitable method for introducing genetic material into a plant. In certain embodiments, the nucleic acid can be delivered into the plant by an *Agrobacterium*.

In some embodiments, a host cell is selected or engineered to have increased activity of the synthesis pathway for one or more of L-tyrosine, 4-hydroxyphenylacetaldehyde (4-HPAA) and tyrosol. In some embodiments, a host cell is selected or engineered to have increased activity of the synthesis pathway for L-tyrosine. In some embodiments a host cell may be selected or engineered to have reduced feedback inhibition of one or more enzymes in the L-tyrosine synthesis pathway. In some embodiments, the host cell is engineered to increase uptake of a precursor, such as L-tyrosine, 4-HPAA, or tyrosol, from the medium.

Methods of Making Salidroside, Icariside D2, and Salidroside Precursors

Described herein are methods of making salidroside, icariside D2, and salidroside precursors. Salidroside, icariside D2, and salidroside precursors can be produced by expressing one or more of the enzymes described herein in a host cell.

Some embodiments provide a method of making tyrosol 8-O-glucoside (salidroside) in a host cell. The method can include expressing in a host cell a transgene that encodes a tyrosol:UDP-glucose 8-O-glucosyltransferase (T8GT). In some embodiments, the host cell synthesizes tyrosol and includes, either endogenously or transgenically, enzymes to synthesize tyrosol. In some embodiments, tyrosol is provided in the culture media. In some embodiments, the host cell further expresses a transgene that encodes a 4-hydroxyphenylacetaldehyde reductase (4HPAR). In some embodiments, the host cell further expresses a transgene that encodes a 4-hydroxyphenylacetaldehyde synthase (4HPAAS).

Some embodiments provide a method of making tyrosol 8-O-glucoside (salidroside) in a host cell. The method can include expressing in a host cell a transgene that encodes a 4-hydroxyphenylacetaldehyde synthase (4HPAAS) and a transgene that encodes a 4-hydroxyphenylacetaldehyde reductase (4HPAR). The host cell expresses, either endogenously or transgenically, one or more enzymes that catalyze conversion of tyrosol to tyrosol 8-O-glucoside (salidroside).

Certain embodiments provide a method of making 4-hydroxyphenylacetaldehyde (4-HPAA) in a host cell. The method can include expressing in the host cell a transgene that encodes a 4-hydroxyphenylacetaldehyde synthase (4HPAAS). In some embodiments, the host cell includes L-tyrosine, produced endogenously or provided to the cell exogenously. In some embodiments, L-tyrosine is provided in the cell culture medium. In some embodiments, the method further includes making tyrosol in the host cell, and the host cell further expresses a transgene encoding a 4-hydroxyphenylacetaldehyde reductase (4HPAR).

In some embodiments, particularly those optimized for producing salidroside, the host cell can have low or absent T4GT activity in order to reduce competition from T4GT for the substrate tyrosol. In some embodiments, the host cell is engineered to reduce or eliminate expression of T4GT.

In some embodiments, particularly those optimized for producing icariside D2, the host cell can have low or absent T8GT activity in order to reduce competition from T8GT for the substrate tyrosol. In some embodiments, the host cell is engineered to reduce or eliminate expression of T8GT.

In some embodiments, a host cell (e.g., a bacterial host cell) endogenously expresses enzymes that catalyze the production of salidroside or icariside D2 from tyrosol. For example, some bacteria express UGTs that exhibit T8GT and/or T4GT activity (Fan et al., 2017). In some embodiments, nucleic acids encoding the bacterial-derived T8GTs can be used in vectors and methods described herein. In some embodiments, host cells and methods can express a T8GT that is a bacterial-derived T8GT.

In some embodiments, one or more copies of one or more of the nucleic acids are integrated into the genome of the host cell. However, as those skilled in the art would recognize, transient transformation techniques can be used that do not require integration into the genome of the host cell.

Methods of obtaining, or extracting, salidroside, icariside D2, and precursors of salidroside and icariside D2 are described herein and are well known to one or ordinary skill in the art. For example, as described herein, salidroside, icariside D2, and/or precursors of salidroside and icariside D2 can be separated by liquid chromatography. Larger scale separation can be obtained by, e.g., simulated moving bed (SMB) chromatography and/or ion exchange chromatography. Any of the methods described herein can further include isolating salidroside, icariside D2, and/or a salidroside precursor from a host cell. Any of the methods described herein can include harvesting tissue (e.g., leaves, roots) of a transgenic plant described herein and processing the harvested tissue to obtain salidroside, icariside D2, and/or a precursor of salidroside and icariside D2 therefrom.

Values and Ranges

Unless otherwise indicated or otherwise evident from the context and understanding of one of ordinary skill in the art, values that are expressed as ranges can assume any specific value or subrange within the stated ranges in various embodiments, unless the context clearly dictates otherwise. "About" in reference to a numerical value generally refers to a range of values that fall within +8%, in some embodiments ±6%, in some embodiments ±4%, in some embodiments ±2%, in some embodiments ±1%, in some embodiments ±0.5% of the value unless otherwise stated or otherwise evident from the context.

EXEMPLIFICATION

Example #1: Results

Generating Metabolomics and Transcriptomics Resources for *R. rosea*

Figure 1B:
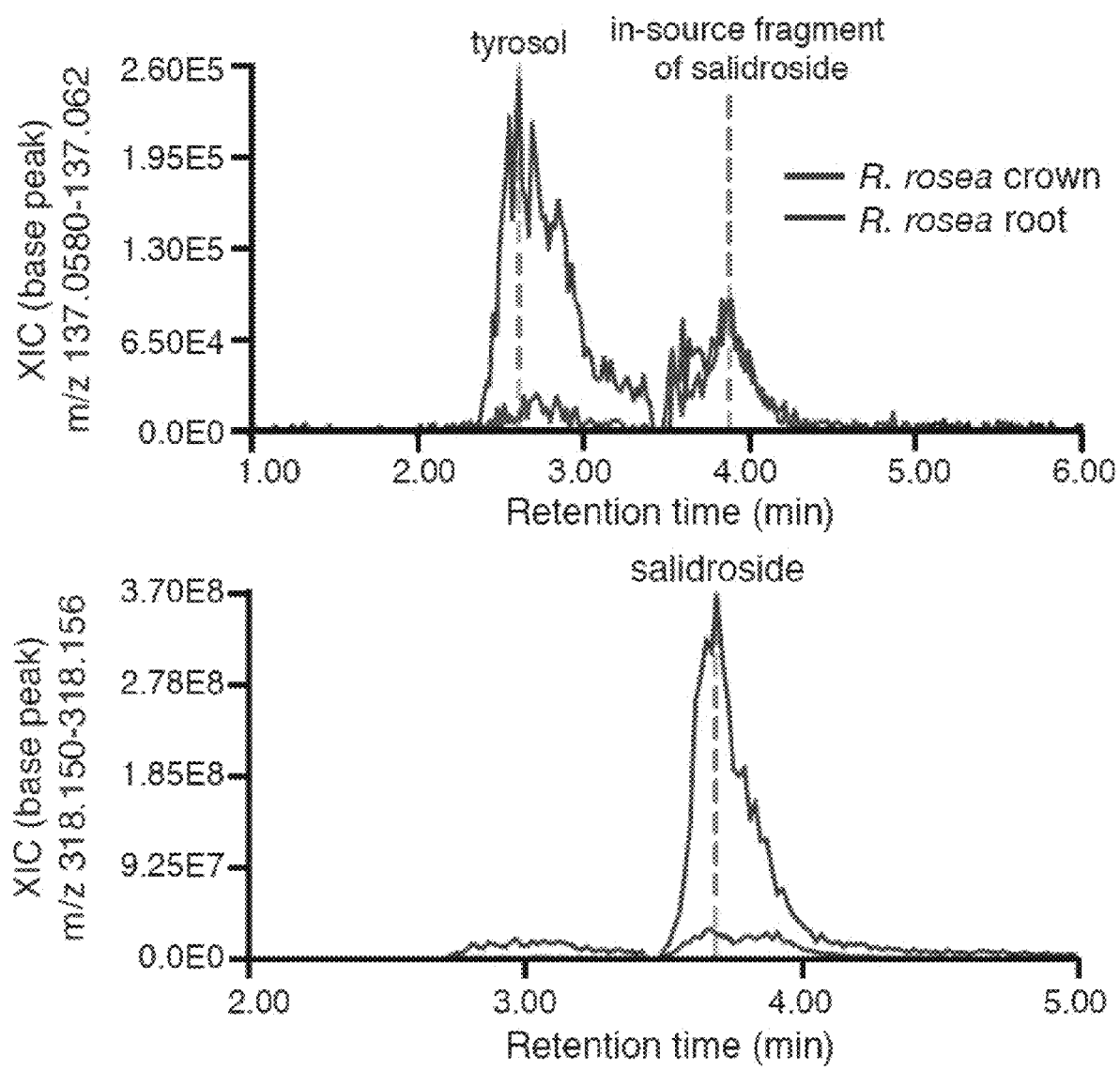
Figure 1C:
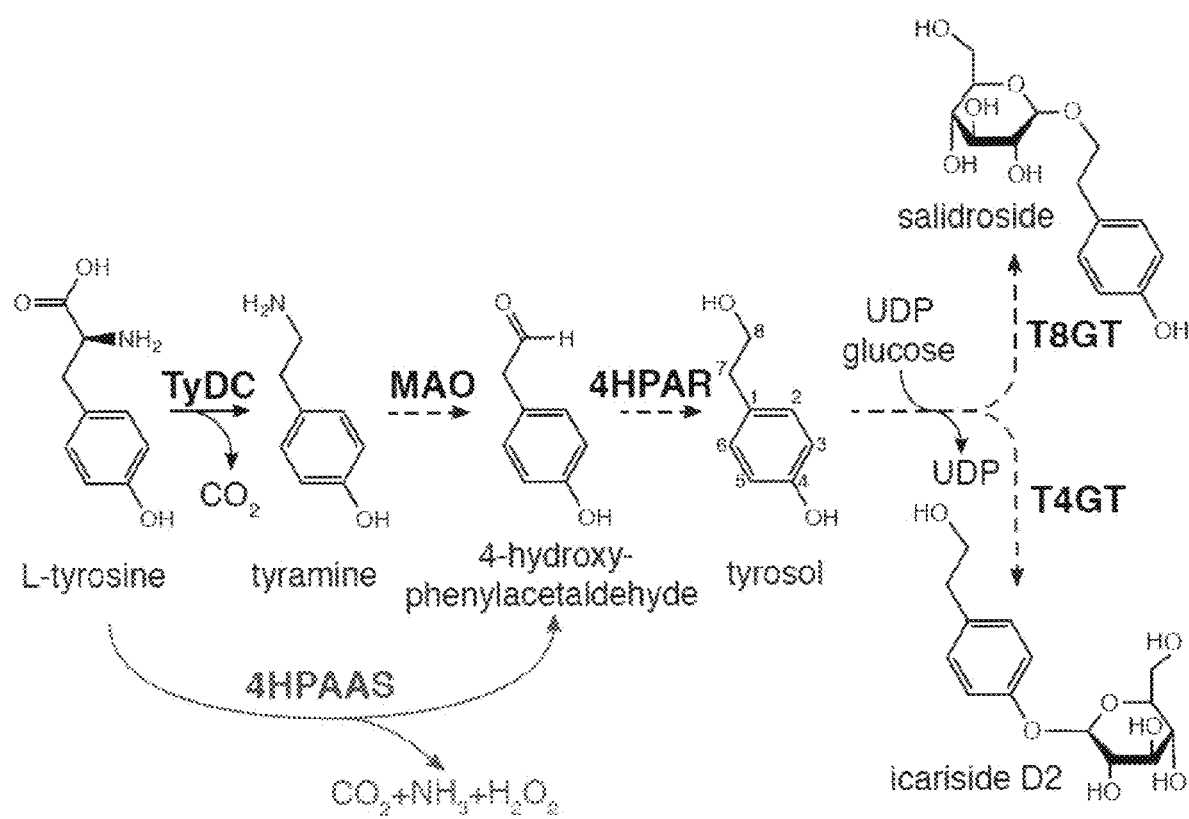
Figure 8A:
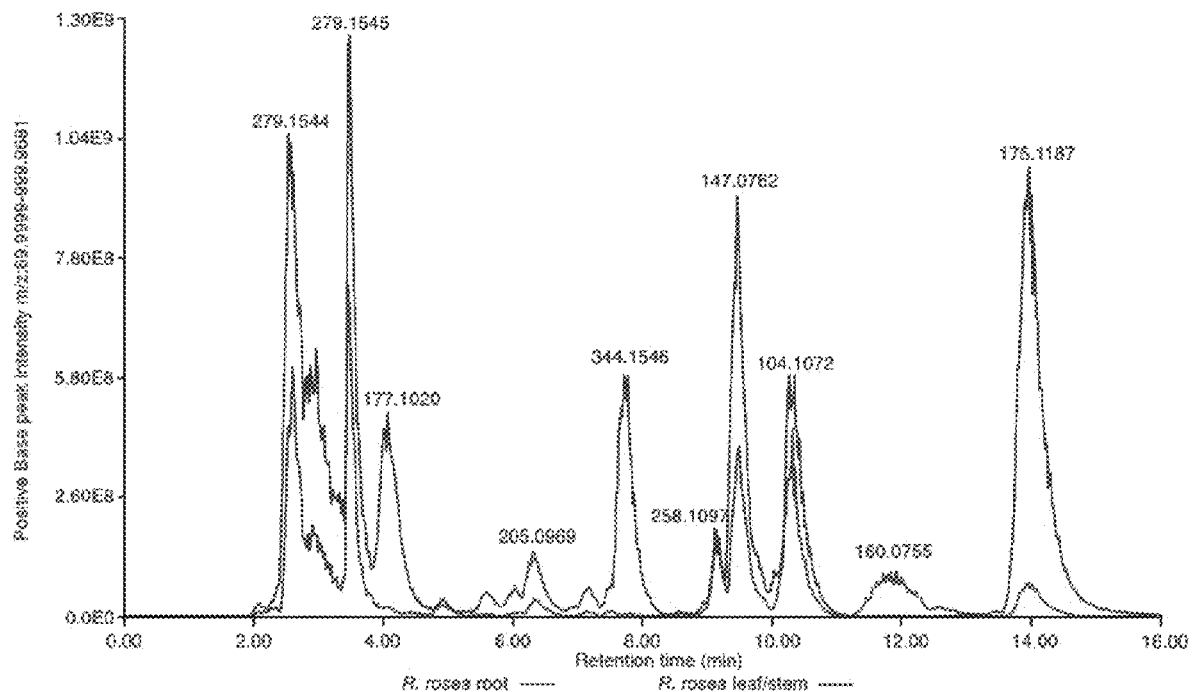
FIGS. 8A-B show total ion count of the root and crown *R. rosea* extractions.
Figure 8B:
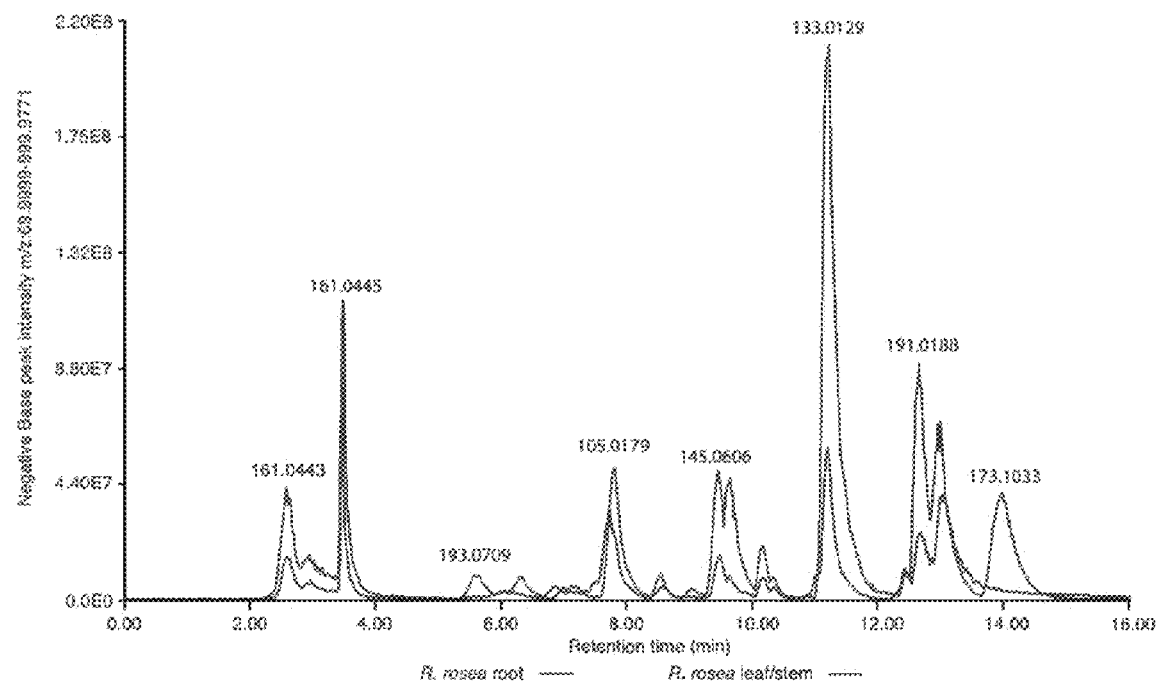
Figures 9, 10:
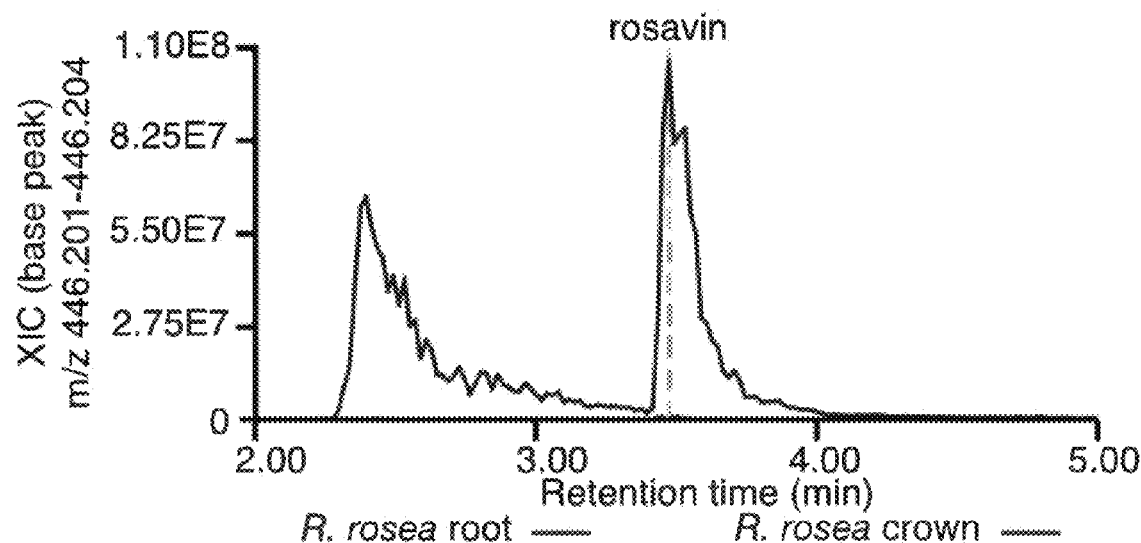
FIG. 9 is a chromatogram showing relative abundance of rosavin between *R. rosea* tissue types. The differential location of the natural product rosavin [M+NH4]⁺ ion between *R. rosea* root and crown. The identity of rosavin was verified by comparison to an authentic standard.
FIG. 10 is a multiple sequence alignment highlighting the residue that dictate decarboxylation and aldehyde synthase chemistry in plant AAADs family members. Sequences represent plant AAADs performing either decarboxylation chemistry or aldehyde synthase chemistry (highlighted in green). The three identified *R. rosea* AAAD sequences are also displayed. Investigation of the activity influencing residue (boxed in black) suggests that the *R. rosea* sequence from the TDC clade likely catalyzes decarboxylation chemistry while the basal and TyDC clade *R. rosea* AAS catalyze aldehyde synthase chemistry. Columns framed in blue indicate greater than 70% conservation of residue physico-chemical properties. Identical amino acids are in white font boxed in red, while similar residues are displayed in red font.

To survey the metabolic profile of *Rhodiola* cultivated under lab conditions, crown tissue (aerial tissue including leaves and stems) and root tissue were collected separately from a three-month old greenhouse-grown *R. rosea* plant (FIG. 1A). The fresh tissues were extracted by 50% methanol, and analyzed by untargeted liquid chromatography high-resolution accurate-mass mass spectrometry (LC-HRAM-MS). This analysis confirmed the presence of tyrosol, rosavin and salidroside in greenhouse-grown *R. rosea*, all of which accumulate at much higher levels in the root compared to the crown (FIGS. 1, 8, and 9).

The higher accumulation of these metabolites in the root suggests that the requisite biosynthetic genes may also obey a similar tissue-specific expression pattern. An RNA-Seq experiment was then performed using total RNAs prepared from the two tissues. This experiment yielded about 30 million paired-end sequencing reads (100×100 bp) per sample. While 84,645 and 105,132 unique transcripts were assembled de novo from the crown and root tissues separately, a total of 128,623 unique transcripts were assembled combining all raw sequencing reads from both tissues. The combined transcriptome was evaluated as 90.3% complete by the metric of Benchmarking Universal Single-Copy Orthologs (BUSCO) (Simao et al., 2015). The Transcripts Per Million (TPM) value of unique transcripts in each tissue type was calculated to infer the relative expression level of the corresponding genes (Li et al., 2010). The identification and prioritization of candidate salidroside biosynthetic genes from the *R. rosea* transcriptome were based upon our hypothetical salidroside biosynthetic model, subsequent large-scale phylogenetic analyses, and the relative expression level of plausible candidate genes in the two examined tissue types. The biochemical function of selected candidate genes was further investigated both in vitro and in vivo.

*R. rosea* Contains a Neofunctionalized 4HPAAS

Figure 2A:
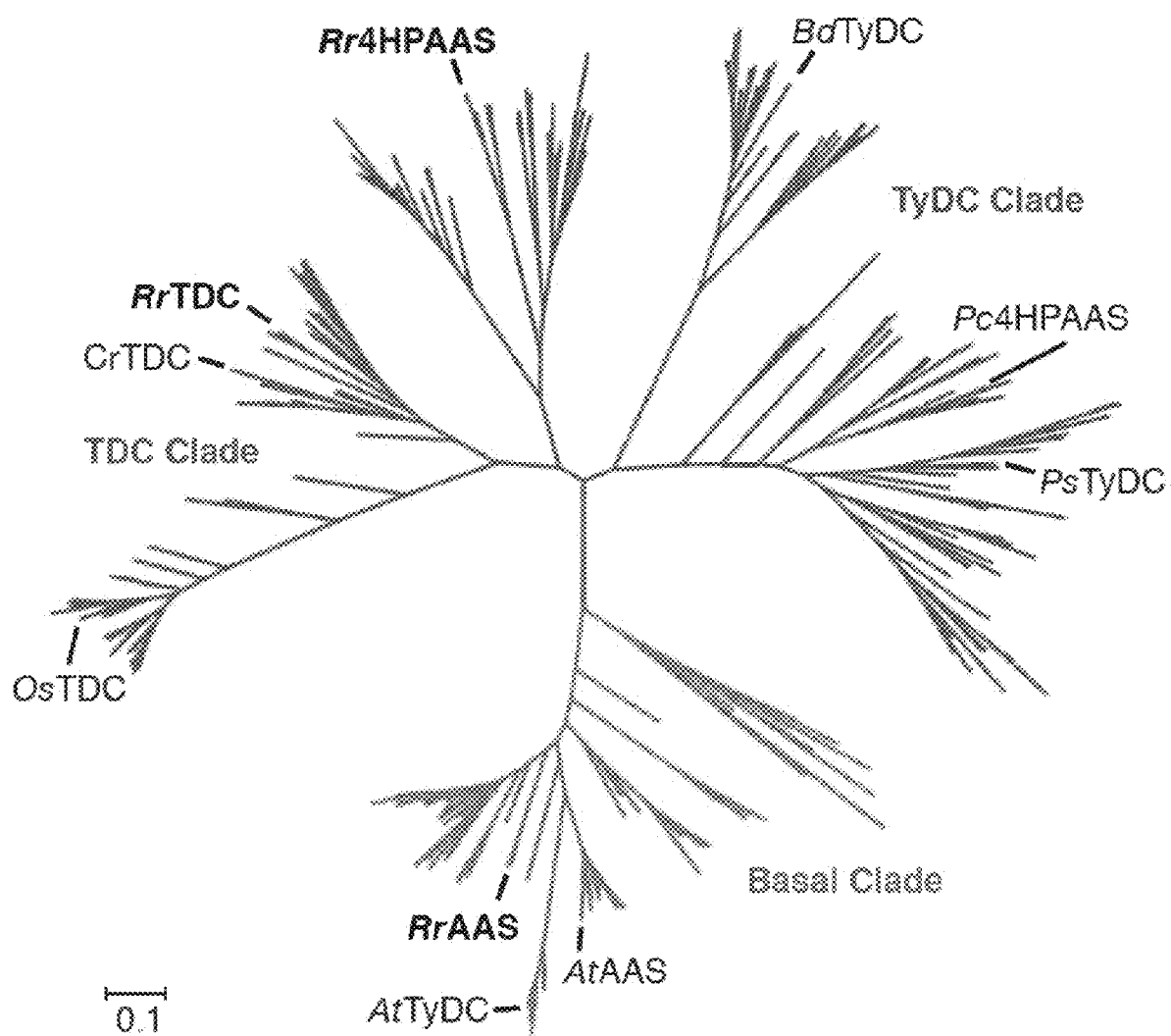
FIGS. 2A-C show identification and characterization of the Rr4HPAAS.
Figure 2B:
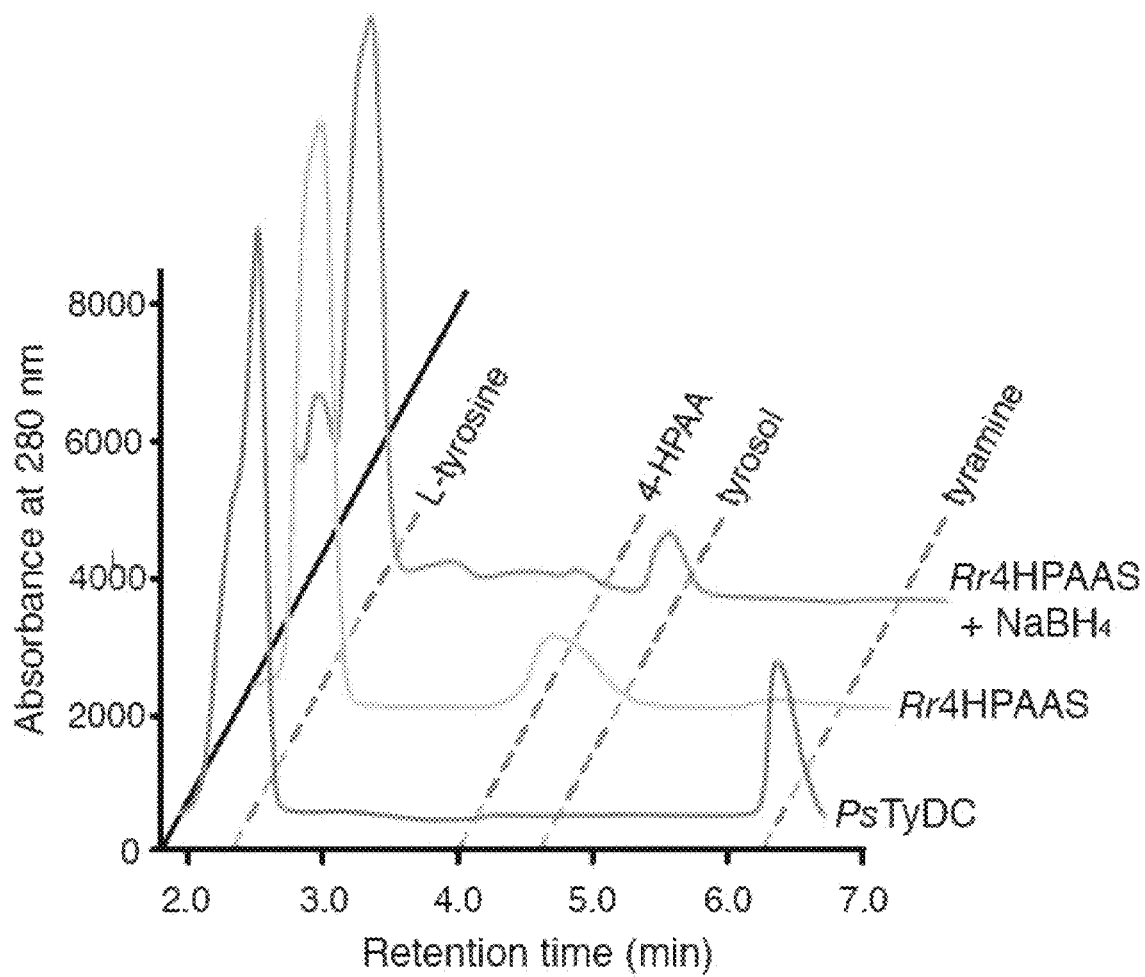
Figure 11:
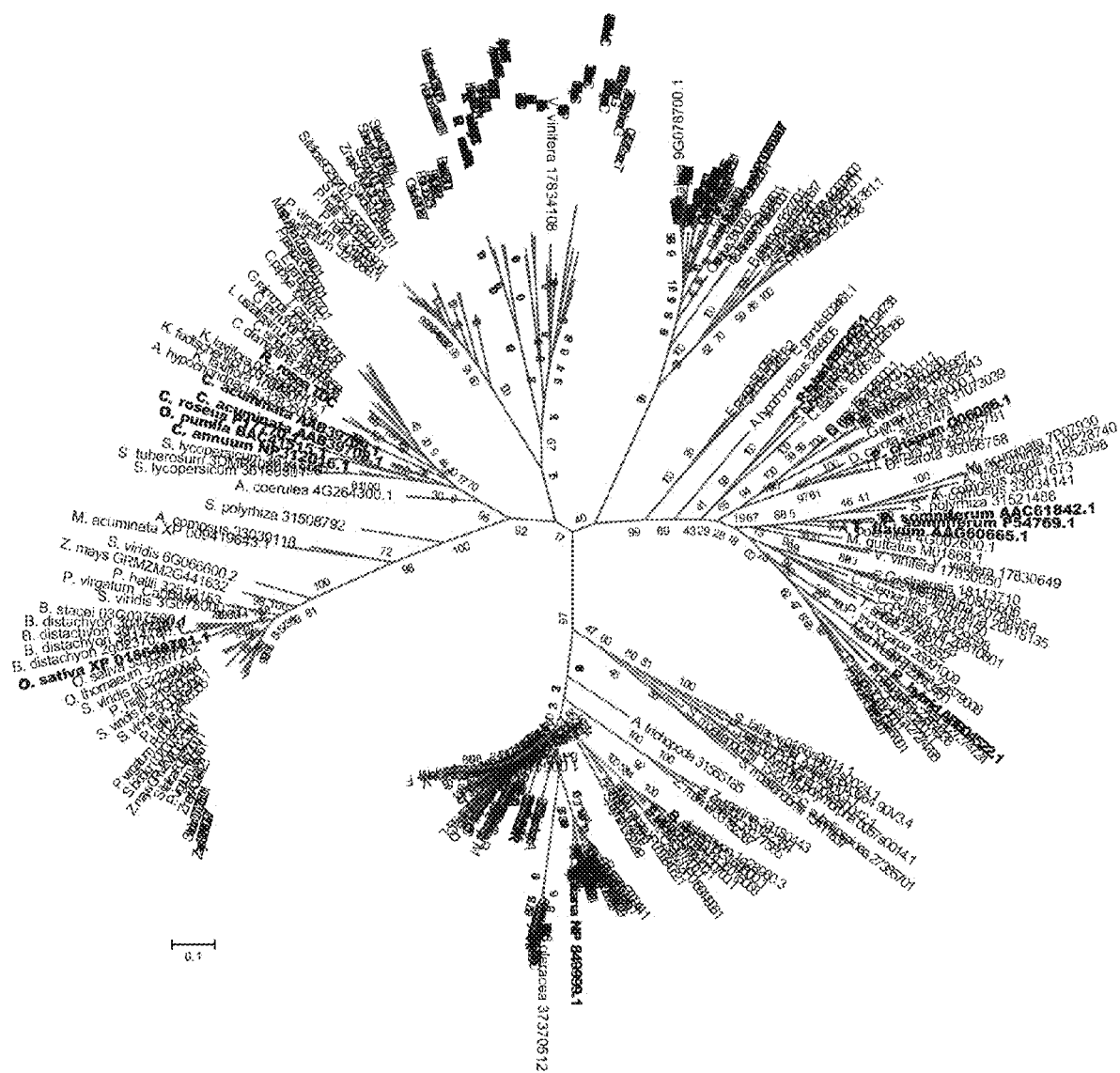
FIG. 11 is a phylogenetic tree of embryophyte AAADs. This tree is populated with sequences from all Phytozome V12 embryophyte species, the three AAAD like sequences from the *R. rosea* transcriptomes (shown in bold) and all attainable characterized NCBI AAAD sequences (also shown in bold). Green, red and blue branches correspond to the basal, TDC and TyDC clades, respectively. These clades were determined through the application of the indolic substrate selective active site glycine (red clade), the phenolic substrate selective serine (blue clade), their taxonomic distribution (green clade exists in all sampled species and is most closely related to chlorophytes species) and representative characterized sequences.

A BLAST search using PsTyDC as the query against the *R. rosea* transcriptome identified three AAAD homologs. Using the sequence motifs correlating to AAAD substrate specificity and catalytic mechanism (*Torrens*-Spence et al., 2014; *Torrens*-Spence et al., 2013), two of the three *R. rosea* AAAD homologs were predicted to possibly function as AASs, and the other is likely to catalyze decarboxylation chemistry (FIG. 10). A phylogenetic analysis including the three *R. rosea* AAAD homologs together with other AAAD sequences from taxonomically diverse plant species was conducted (FIGS. 2B and 11). Whereas the predicted *R. rosea* decarboxylase candidate clusters within the TDC clade (red) containing largely previously known TDCs, the two *R. rosea* AAS candidates fall into two distinct clades, designated as the basal clade (green) and the TyDC clade (blue), respectively (FIGS. 2B and 11). It is noted that the TyDC-type AAS candidate isolated in this study is likely orthologous to the RcTyDC previously reported by Bai et al. (Bai et al., 2014), sharing 96% sequence identity at the protein level.

Figure 12:
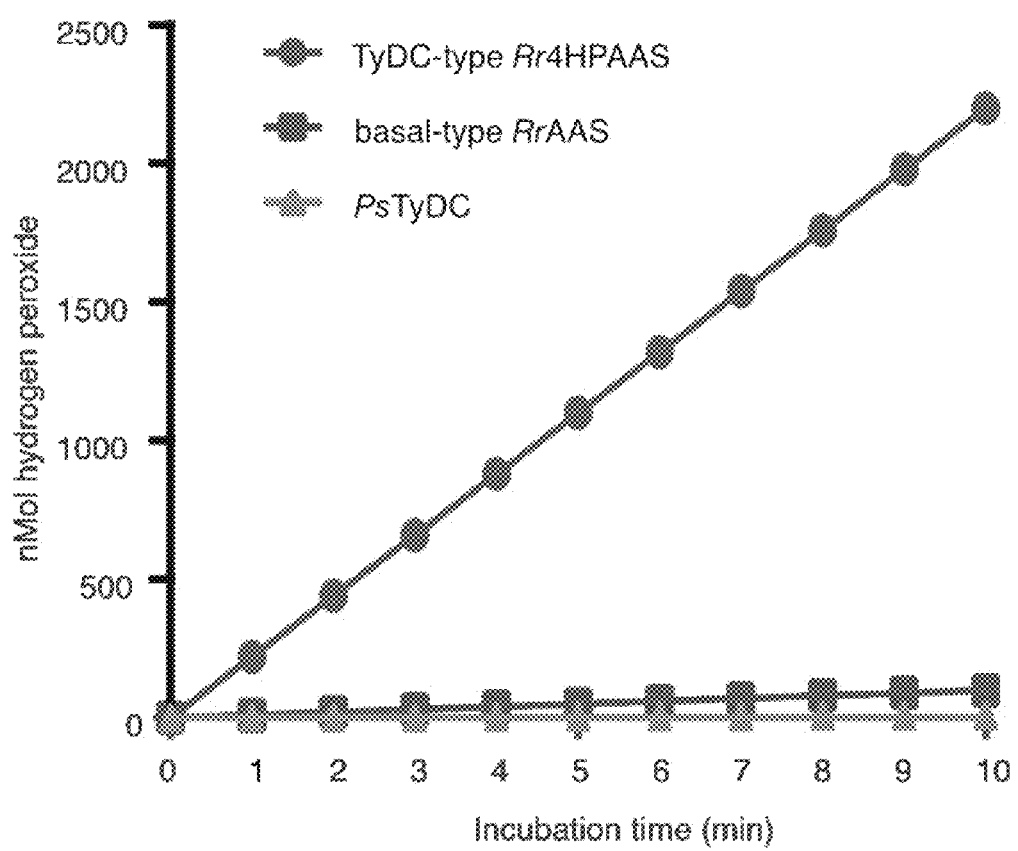
FIG. 12 is a graph showing relative hydrogen peroxide production for the Rr4HPAAS, the RrAAS and the PsTyDC. 100 µL reaction mixtures containing 50 µg of recombinant enzyme, 2 mM L-tyrosine, 50 mM Tris pH 8.0 and 200 µM PLP were incubated at 30° C. for various time points prior to quenching with 100 µL of 0.8 M formic acid. Hydrogen peroxide levels of quenched reaction mixtures were subsequently analyzed using Pierce Quantitative Peroxide Assay Kit against a standard curve of hydrogen peroxide.
Figure 13:
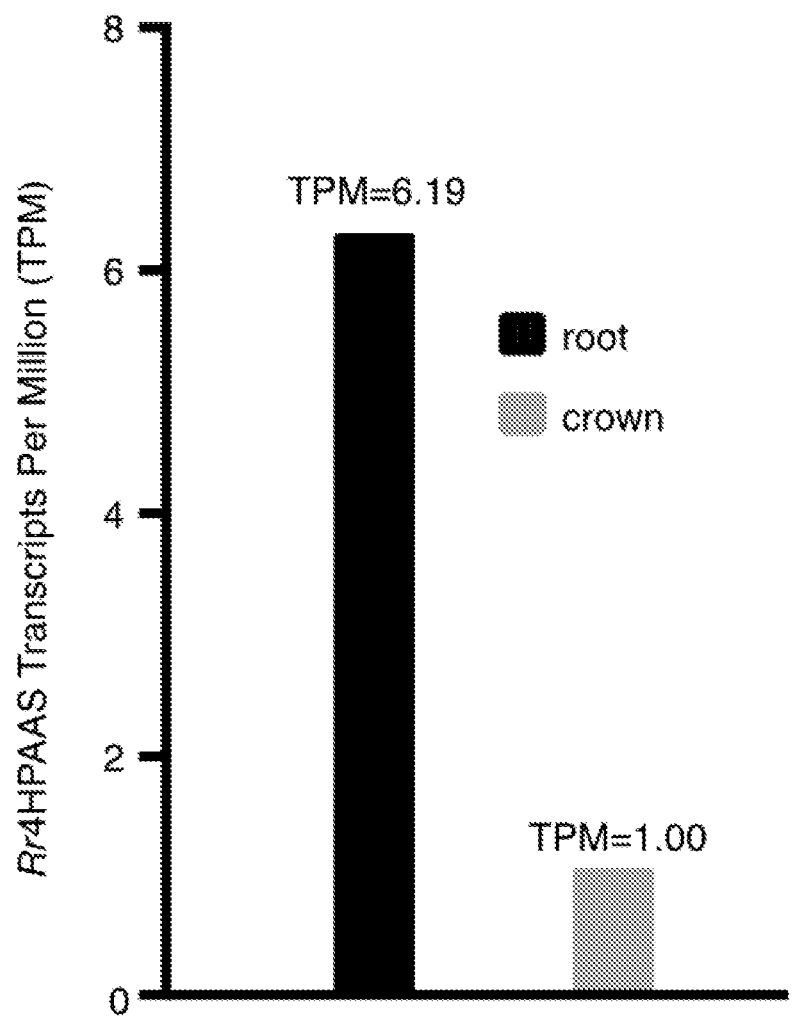
FIG. 13 is a chart showing relative TPM for the Rr4HPAAS transcript between the root and crown transcriptomes.

To experimentally assess the biochemical activities of the two *R. rosea* AAS candidates, full-length open reading frame corresponding to both the basal and TyDC-type AAS candidate genes from *R. rosea* cDNA were cloned. Their encoded proteins were recombinantly expressed in *E. coli*, purified to homogeneity, and tested for enzymatic activity using L-tyrosine as the substrate. Both enzymes readily yield hydrogen peroxide, a co-product of AAS as opposed to canonical TyDC (Kaminaga et al., 2006), while the TyDC-type AAS candidate exhibits much higher activity than the basal AAS candidate (FIG. 12). To confirm the chemical identity of the AAS reaction products, the enzyme assays were analyzed by LC coupled with a UV detector (FIG. 2B). Incubation of L-tyrosine with both AAS candidate enzymes led to the production of 4-HPAA, which is distinct from the tyramine product yielded by PsTyDC as a control (FIG. 2B). The identity of the 4-HPAA product was further confirmed by sodium borohydride reduction of 4-HPAA to yield tyrosol (FIG. 2B). Notably, the transcript corresponding to the TyDC-type AAS candidate is highly enriched in the root versus the crown (FIG. 13), whereas such pattern was not observed for the basal AAS candidate. In light of these results, the TyDC-type AAS candidate is likely the primary AAS involved in salidroside biosynthesis in R. rosea root. The TyDC-type AAS candidate is referred to as Rr4HPAAS hereafter.

Figure 2C:
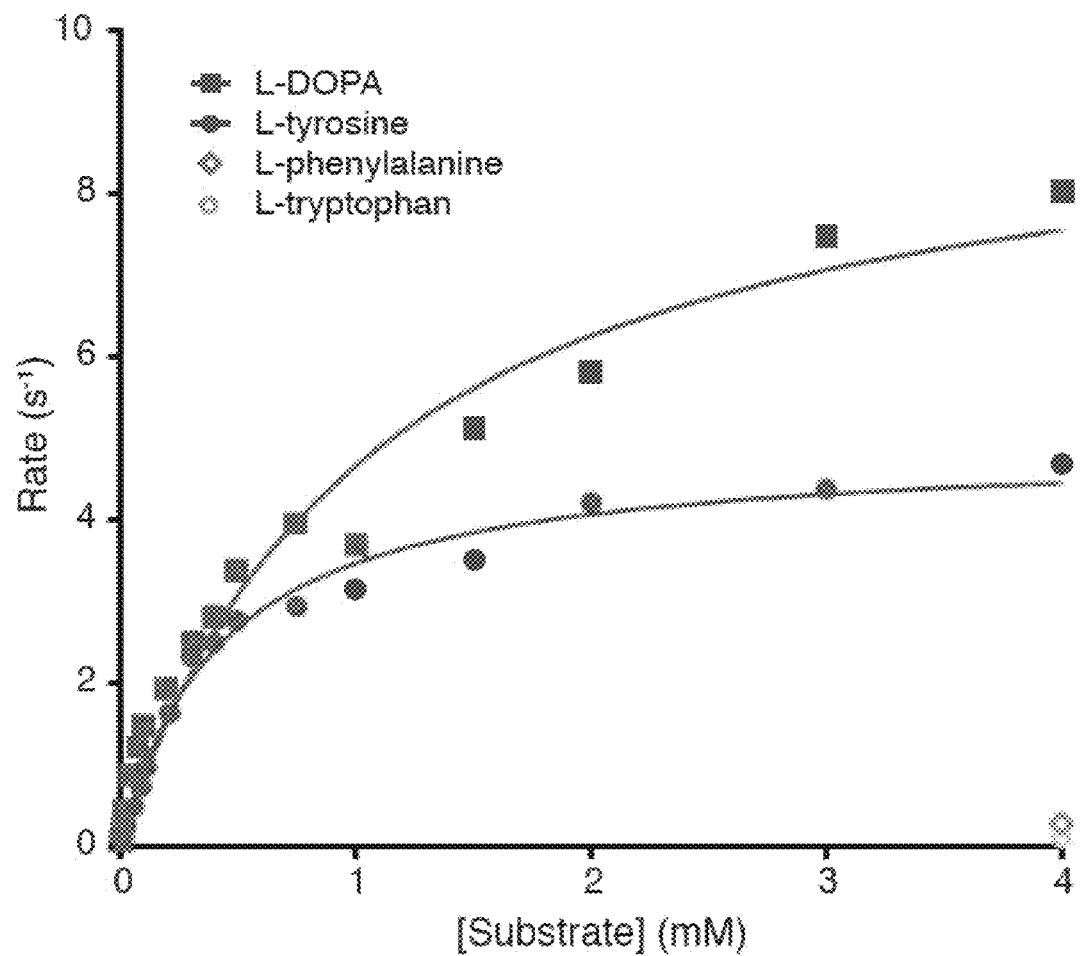

The Michaelis-Menten kinetics of Rr4HPAAS was measured against four aromatic amino acids, namely L-tyrosine, L-3,4-dihydroxyphenylalanine (L-DOPA), L-phenylalanine, and L-tryptophan (FIG. 2C and Table 1). Rr4HPAAS demonstrates the highest catalytic efficiency toward L-tyrosine ($k_{cat}/K_m$=11.7 s$^{-1}$ mM$^{-1}$) followed by L-DOPA ($k_{cat}/K_m$=9.1 s$^{-1}$ mM$^{-1}$), whereas L-phenylalanine and L-tryptophan are much less preferred substrates (FIG. 2C and Table 1). L-DOPA and any potential phenolic compound derived from it were not detected in the R. rosea metabolomics datasets, and thus the kinetic characteristics of Rr4HPAAS is consistent with its role in salidroside biosynthesis. These results also suggest that the previously reported RcTyDC was likely functionally mischaracterized (Bai et al., 2014).

Figure 3A:
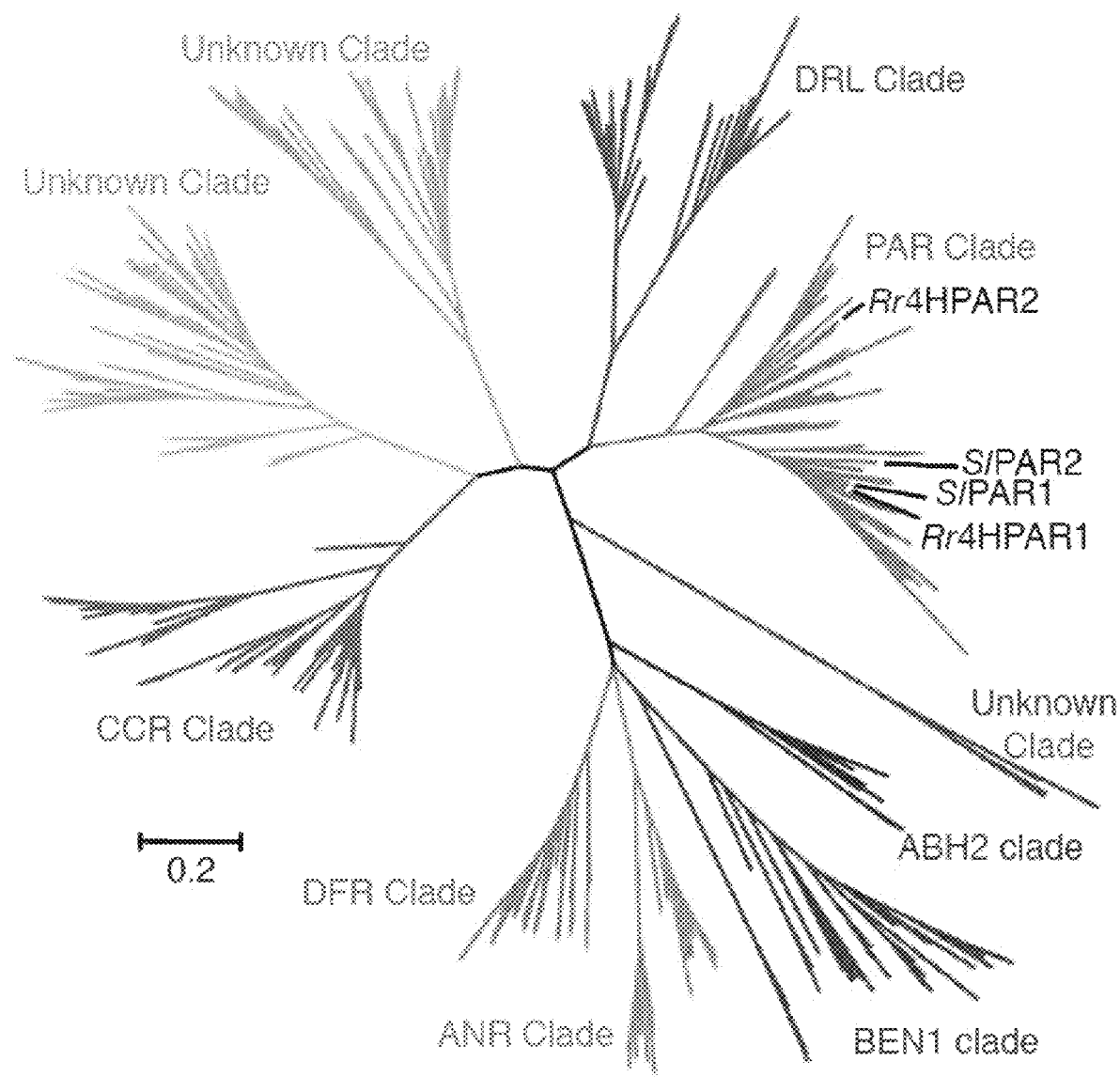
FIGS. 3A-C show identification and characterization of two *R. rosea* 4HPARs.
Figure 14:
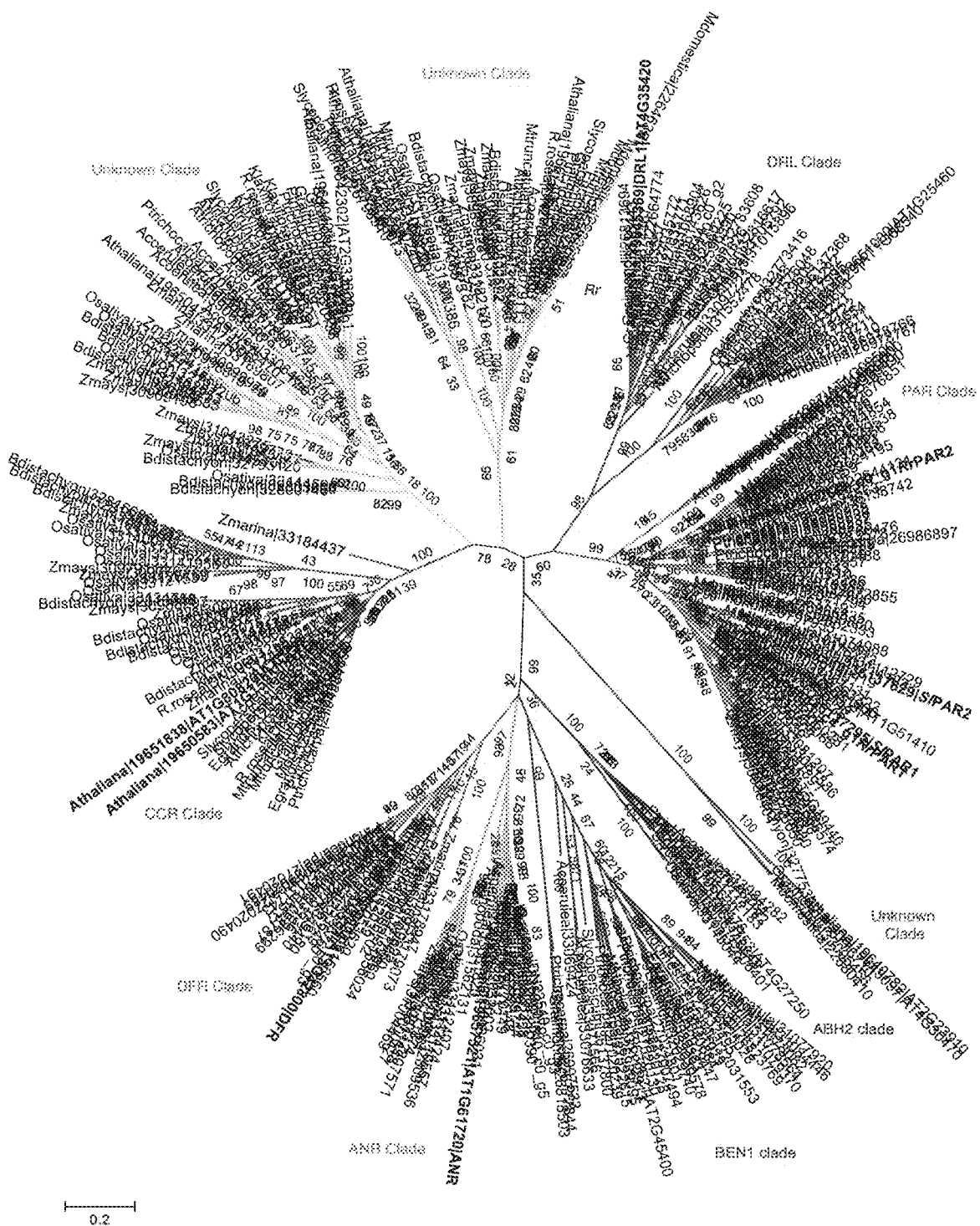
FIG. 14 is a phylogenetic tree of angiosperm ADHs. This tree is populated with sequences from various Phytozome V12 angiosperm species, ADLs like sequences from the R. rosea transcriptomes and two characterized SlPAR sequences. Characterized A. thaliana enzymes, the two SlPARs and the two Rr4HPARs are show in bold. The different colors have been applied to distinguish between various clades.

Identification and Biochemical Characterization of Rhodiola Phenolic Aldehyde Reductases To identify R. rosea enzymes involved in the next step of salidroside biosynthesis, a BLAST search was conducted using the previously characterized Solanum lycopersicum PAR (SlPAR, GenBank: ABR15768.1) as a query (Tieman et al., 2007) against our R. rosea transcriptome. A phylogenetic analysis was performed using the returned R. rosea hits together with other homologous ADHs from select plant species (FIGS. 3A and 14). This analysis revealed two R. rosea ADH homologs, referred to as RrPAR-like1 and RrPAR-like2, that cluster phylogenetically with SlPAR (Tieman et al., 2007), and share 76% and 58% protein sequence identity to SlPAR, respectively. Both genes were cloned from R. rosea cDNA as candidate genes encoding 4HPAR.

Figure 3B:
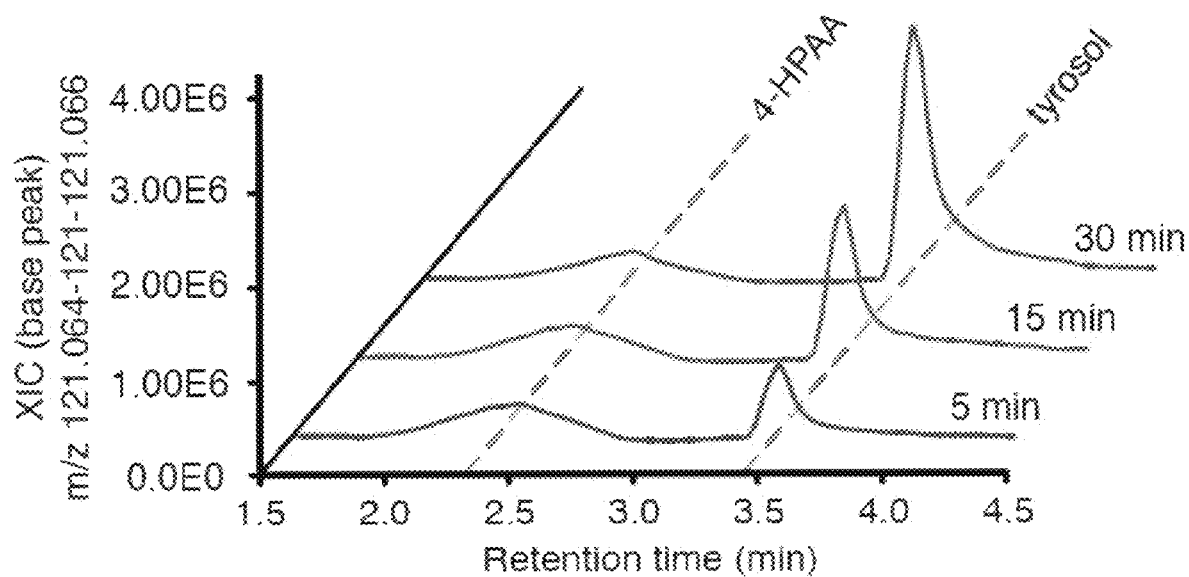
Figure 3C:
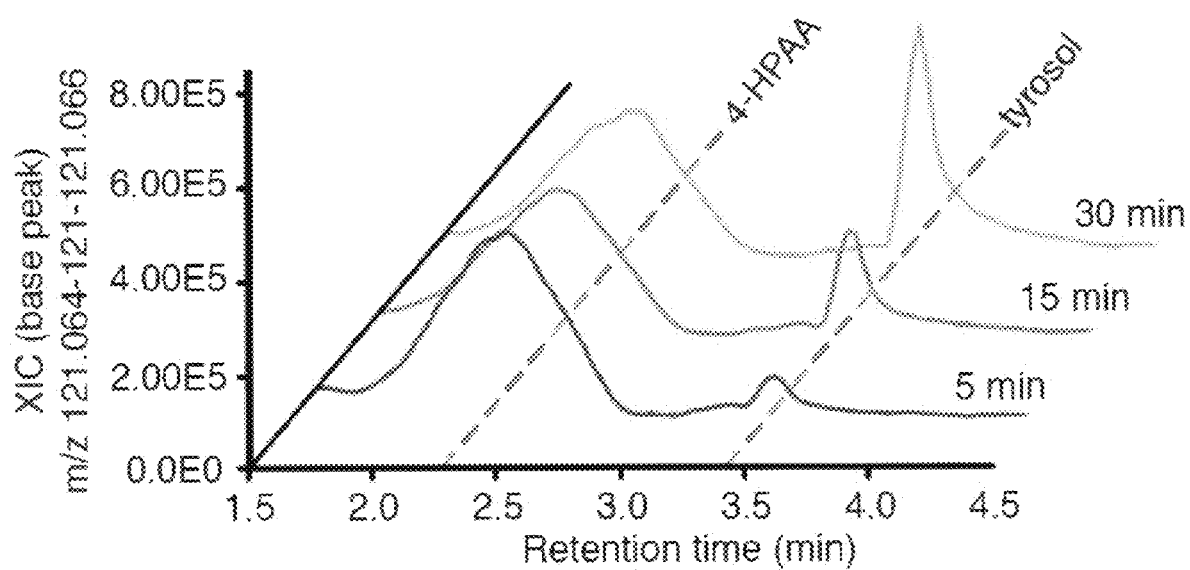
Figure 15:
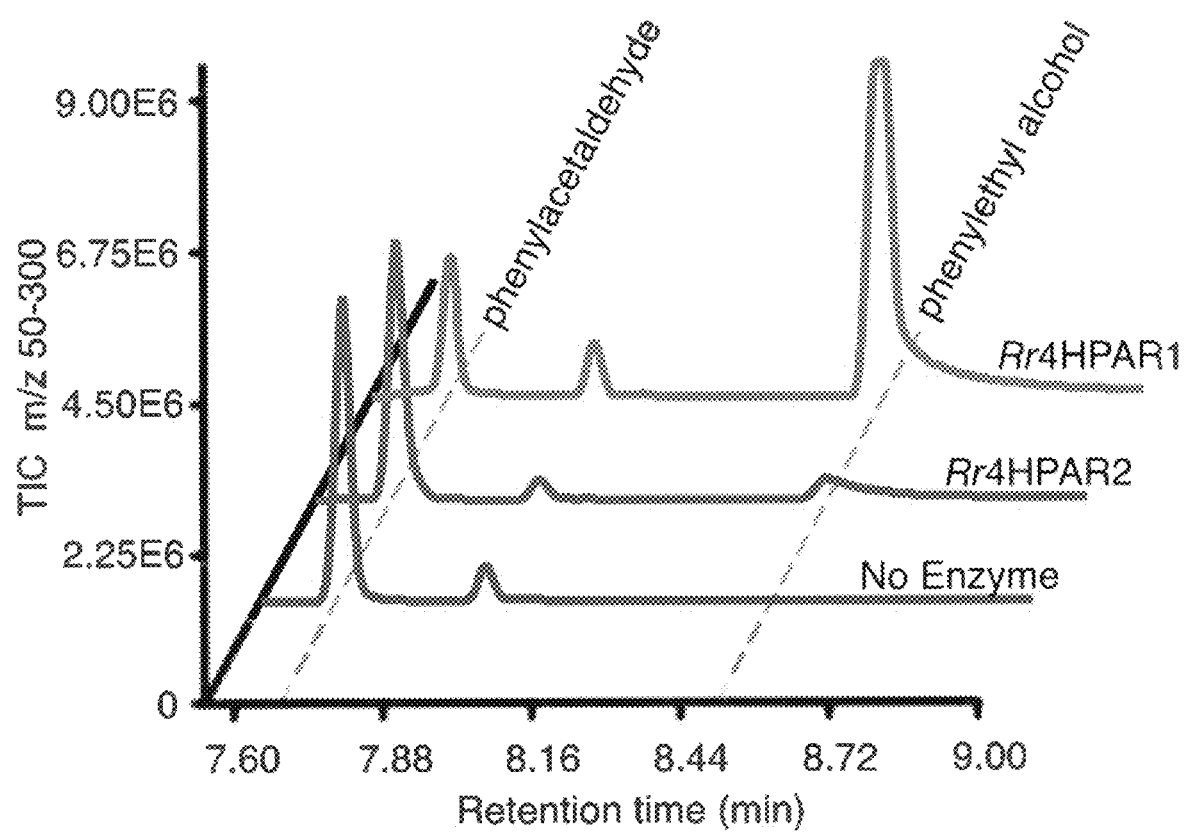
FIG. 15 is a chromatogram showing the enzymatic reduction of phenylacetaldehyde to phenylethyl alcohol by Rr4HPAR1 and Rr4HPAR2. Chromatogram of positive ion mode metabolites between 50 and 300 m/z show the depletion of phenylacetaldehyde and production of phenylethyl alcohol when exposed to NADPH and Rr4HPAR1 or RrPAR2. Reactions were carried out in 200 µL 50 mM Tris, pH 8.0 in the presence of 2 mM phenylacetaldehyde, 5 mM NADPH and 50 µg of recombinant enzyme. The reactions were incubated at 30° C. for 25 minutes prior to quenching with 200 µL of 0.8 M formic acid, extracted with 100 µL of ethyl acetate and analyzed by gas chromatography-mass spectrometry. Phenylethyl alcohol was verified by comparison to an authentic standard.
Figure 16:
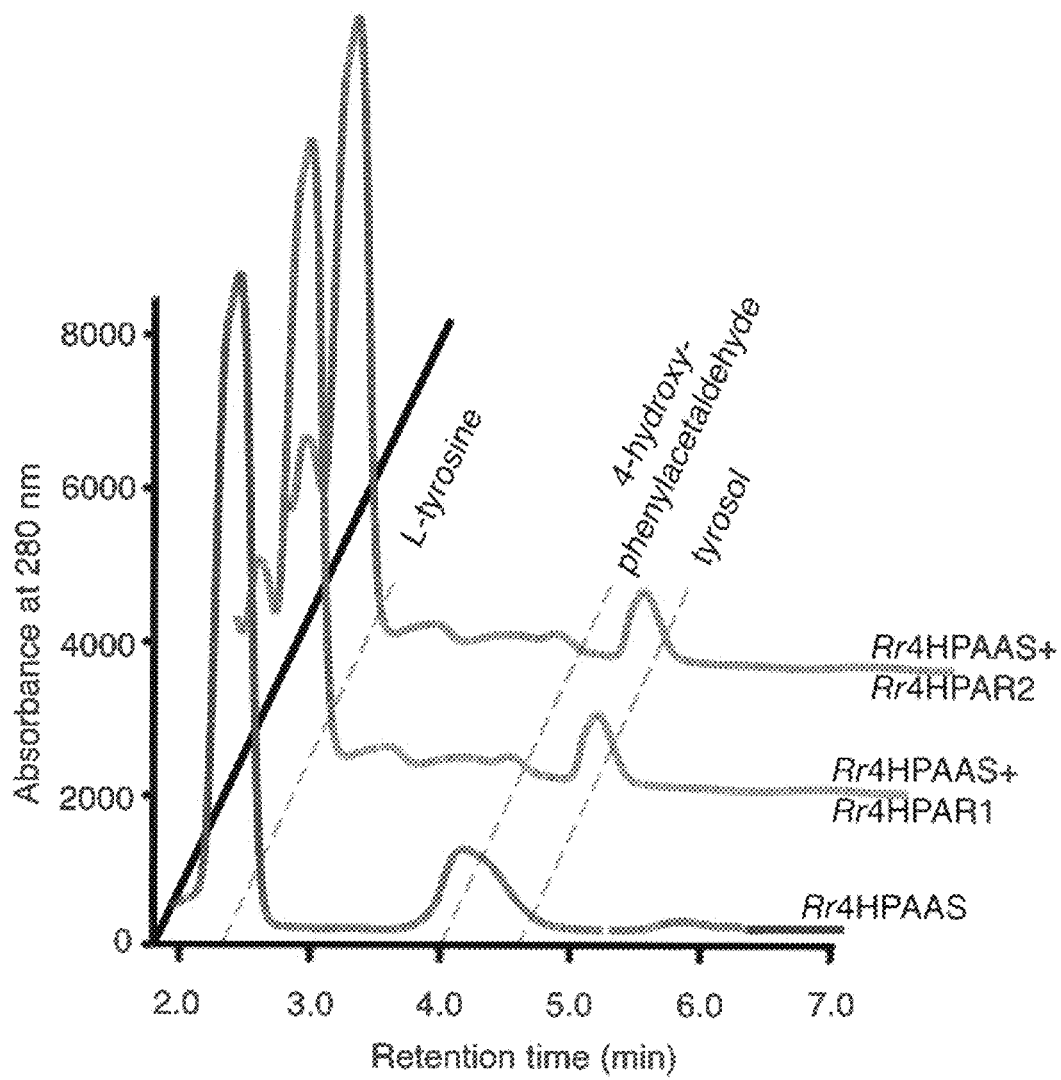
FIG. 16 is a chromatogram showing the enzymatic reduction of 4-HPAA to tyrosol by Rr4HPAR1 and Rr4HPAR2. LC-UV chromatograms of products generated from coupled enzyme assays conducted using Rr4HPAAS in combination with Rr4HPAR1 or Rr4HPAR2, respectively. Enzyme assay conducted using Rr4HPAAS alone is included as a control. 100 µl reaction mixtures containing 50 mM Tris pH 8.0, 4 mM tyrosine, 2 µg catalase and 100 µg of Rr4HPAAS were incubated at 30 degrees C. for 1 hour. 10 mM NADPH and 10 µg of Rr4HPAR1 or Rr4HPAR2 was then added and incubated for an additional 15 minutes at which point the reactions were quenched with an equal volume of 0.8 M formic acid and analyzed by LC-UV. The identity of the product was verified by comparing the elution profile and UV spectrum to that of an authentic tyrosol standard.

To examine the biochemical activity of the two 4HPAR candidates, recombinant enzymes were expressed in E. coli, purified to homogeneity, and assayed against 4-HPAA or phenylacetaldehyde in the presence of NADPH as the co-substrate. Both enzymes are capable of reducing phenylacetaldehyde to phenylethanol with RrPAR-like1 displaying higher activity (FIG. 15). Likewise, RrPAR-like1 exhibited orders of magnitude higher specific activity towards 4-HPAA (6.9 μmol min$^{-1}$ mg$^{-1}$) than RrPAR-like2 (8.4 nmol min$^{-1}$ mg$^{-1}$) (FIGS. 3B, 3C, and 16). Nonetheless, RrPAR-like1 and RrPAR-like2 were renamed as Rr4HPAR1 and Rr4HPAR2, respectively, as both enzymes displayed 4-HPAA reductase activity.

Identification of Regio-Specific Tyrosol-Modifying UGTs from R. rosea

Figure 17:
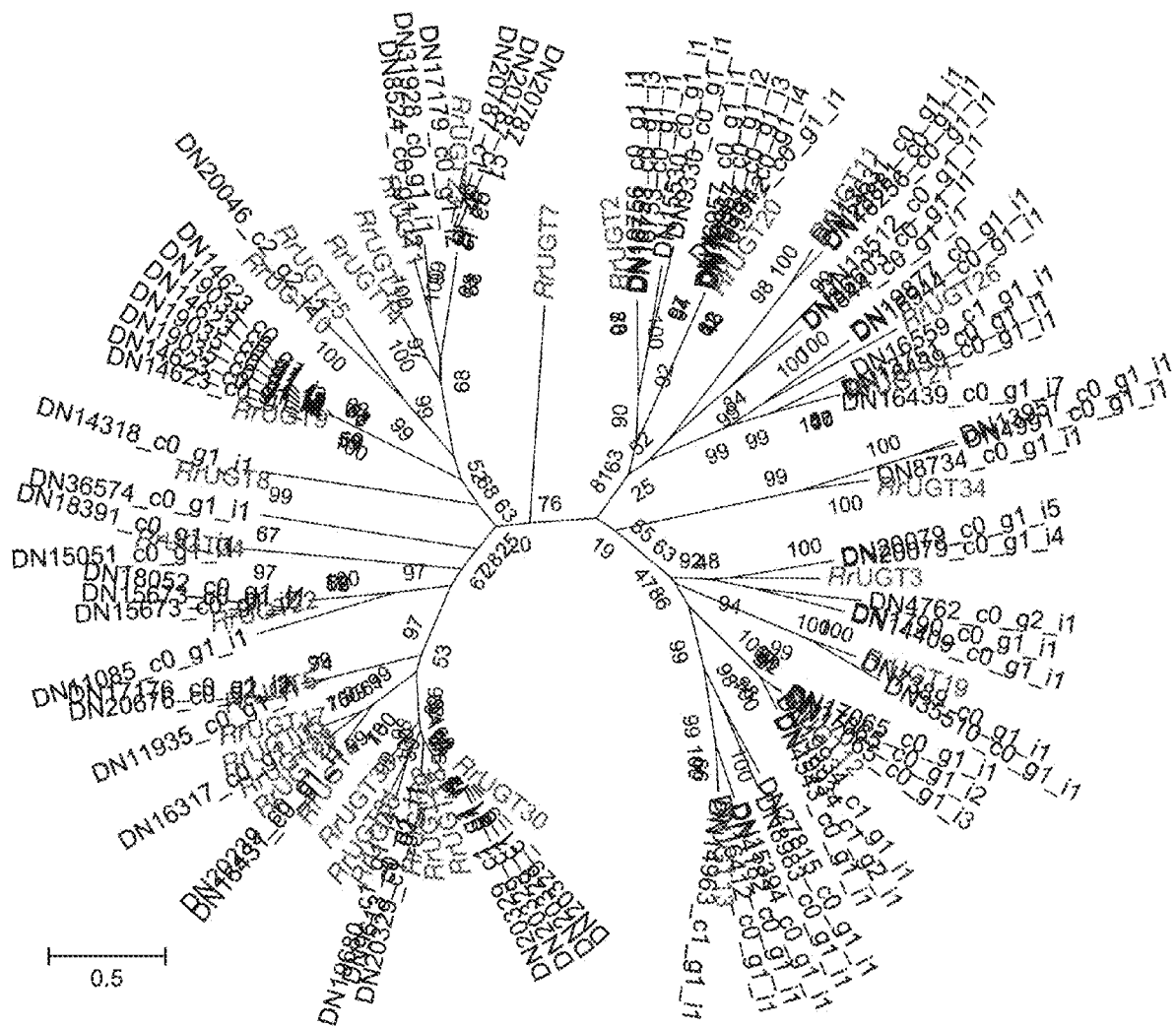
FIG. 17 is a phylogenetic tree of the 113 curated full-length non redundant R. rosea transcriptome UGTs. Sequences profiled for tyrosol glycosylation activity in yeast have been annotated RrUGT1-34.

To complete the salidroside biosynthetic pathway, candidate UGT genes encoding T8GT were identified. The UGT superfamily is one of the largest enzyme families in the plant kingdom (Li et al., 2001). The plant secondary product glycosyltransferase (PSPG) motif is described in Gachon et al., 2005, particularly at FIG. 2A and associated text. The transcriptome was queried using a UGT superfamily signature motif (Li et al., 2001), and conducted an unbiased phylogenetic analysis using 113 curated non-redundant full-length UGT homologs retrieved from the R. rosea transcriptome (FIG. 17). Thirty-four candidate UGT genes were then prioritized for further functional analysis according to a combination of criteria including phylogenetic distribution pattern and transcript levels in the root and crown transcriptome datasets.

Figure 4A:
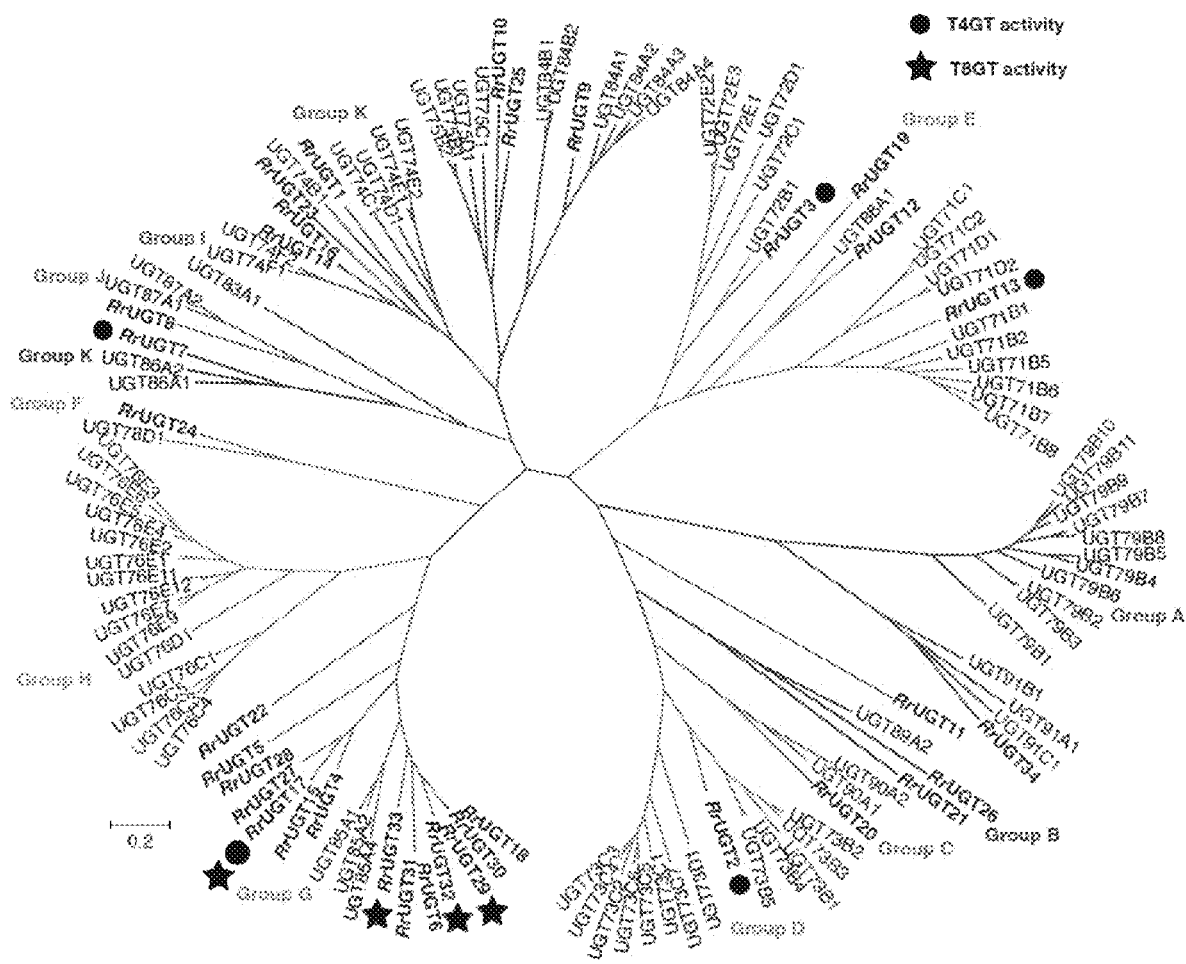
FIGS. 4A-C show identification and characterization of *R. rosea* tyrosol-modifying UGTs.
Figure 4B:
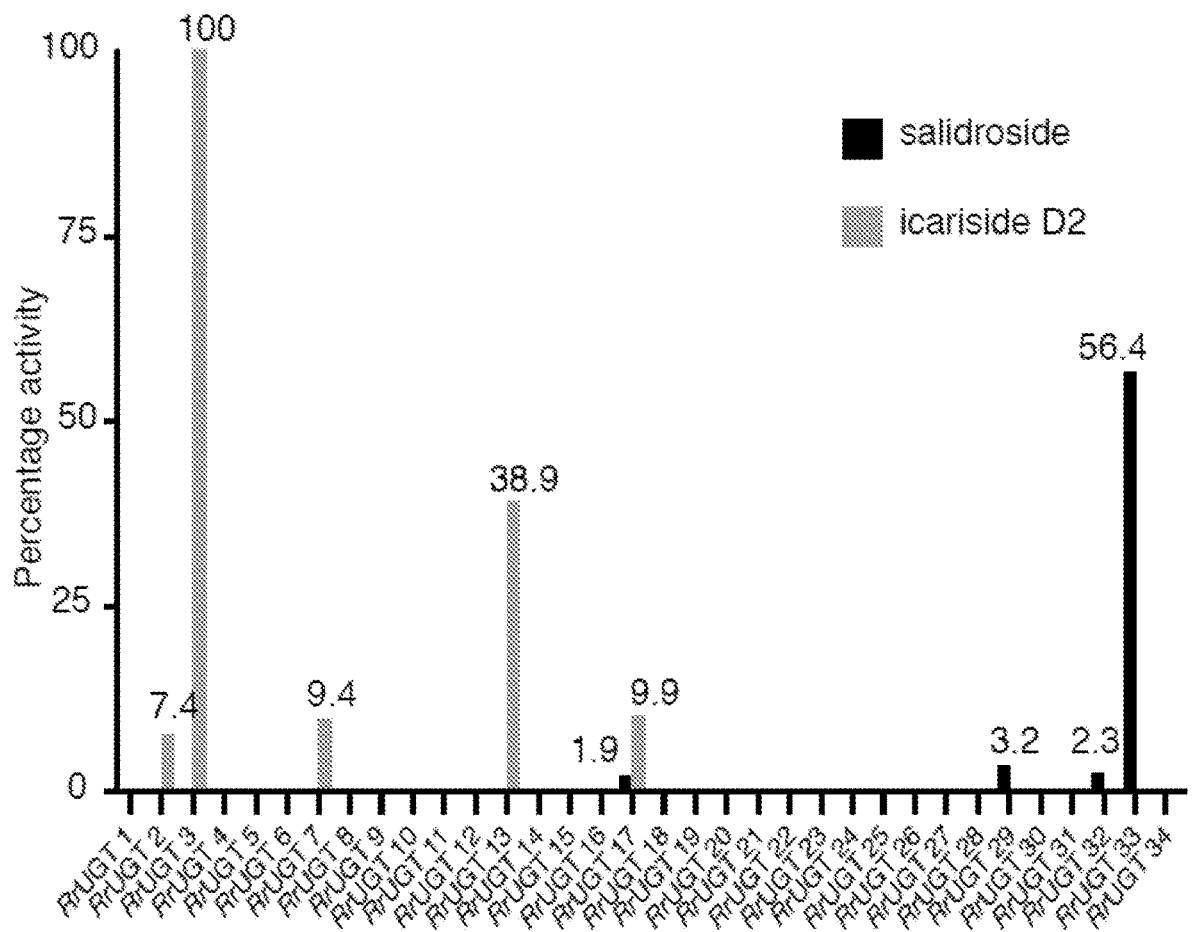
Figure 18:
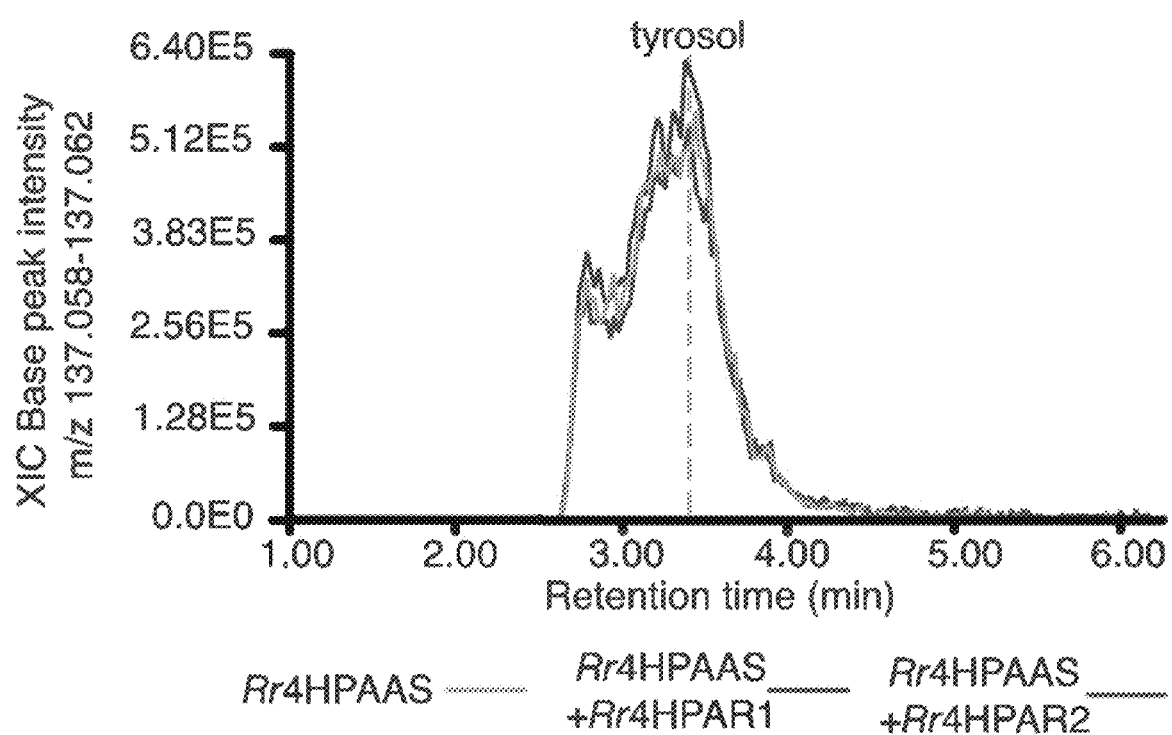
FIG. 18 is a chromatogram of the tyrosol [M−H]− ion generated in transgenic yeast expressing the Rr4HPAAS, the Rr4HPAAS+Rr4HPAR1 or Rr4HPAAS+Rr4HPAR2. The identity was verified by comparison to commercially purchased tyrosol.
Figure 19A:
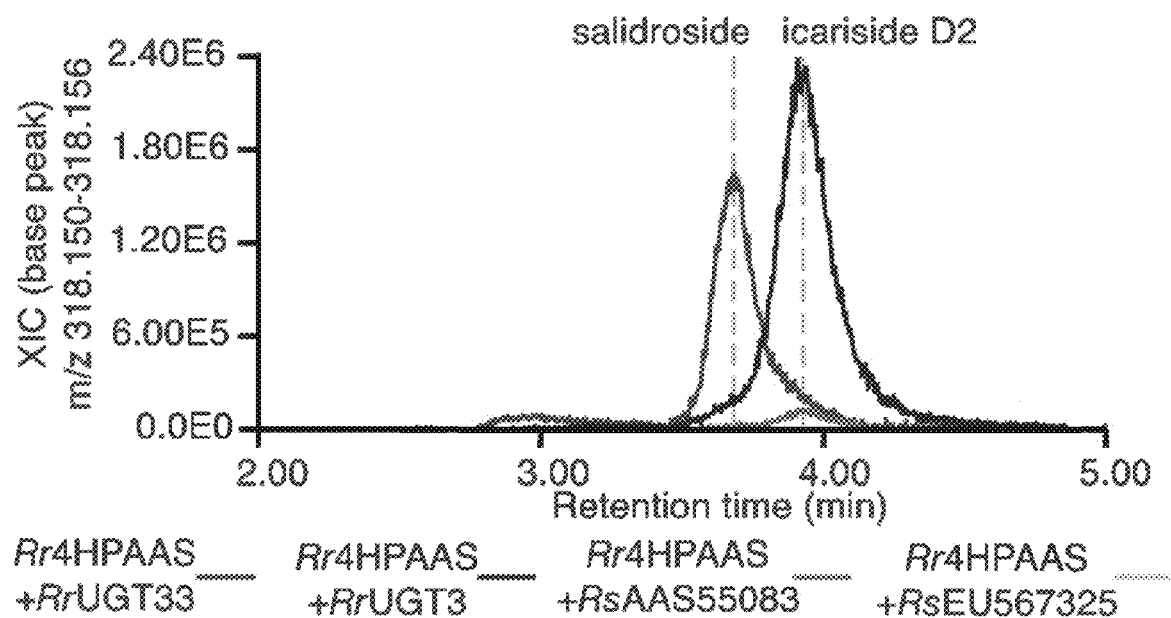
FIGS. 19A-B show R. rosea tyrosol UGTs as compared to previously characterized Rhodiola tyrosol UGTs.
Figure 19B:
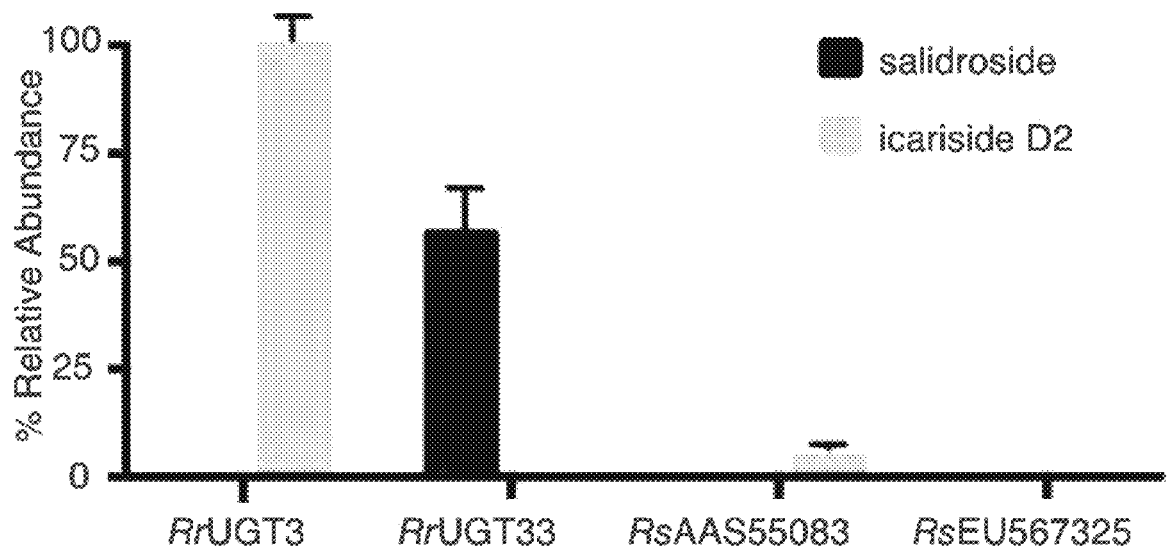
Figure 20:
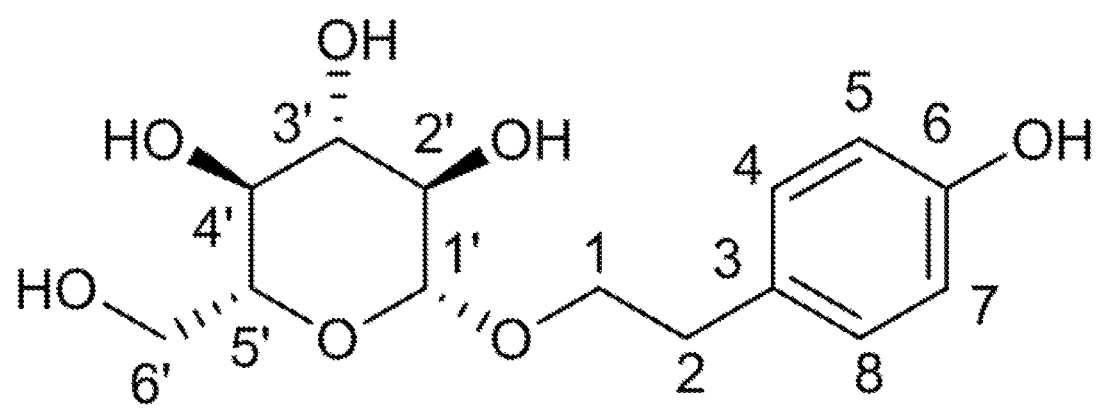
FIG. 20 is the structure of salidroside.
Figure 21:
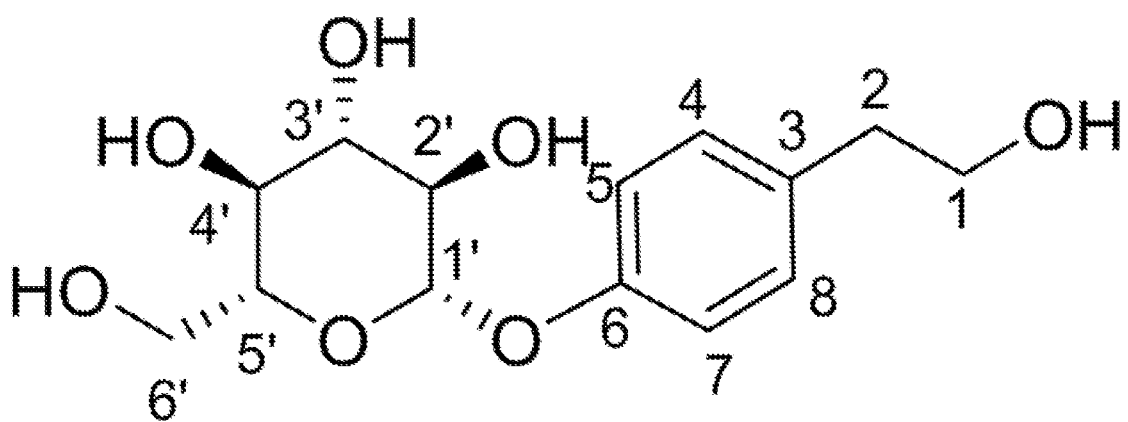
FIG. 21 is the structure of icariside D2.
Figure 22:
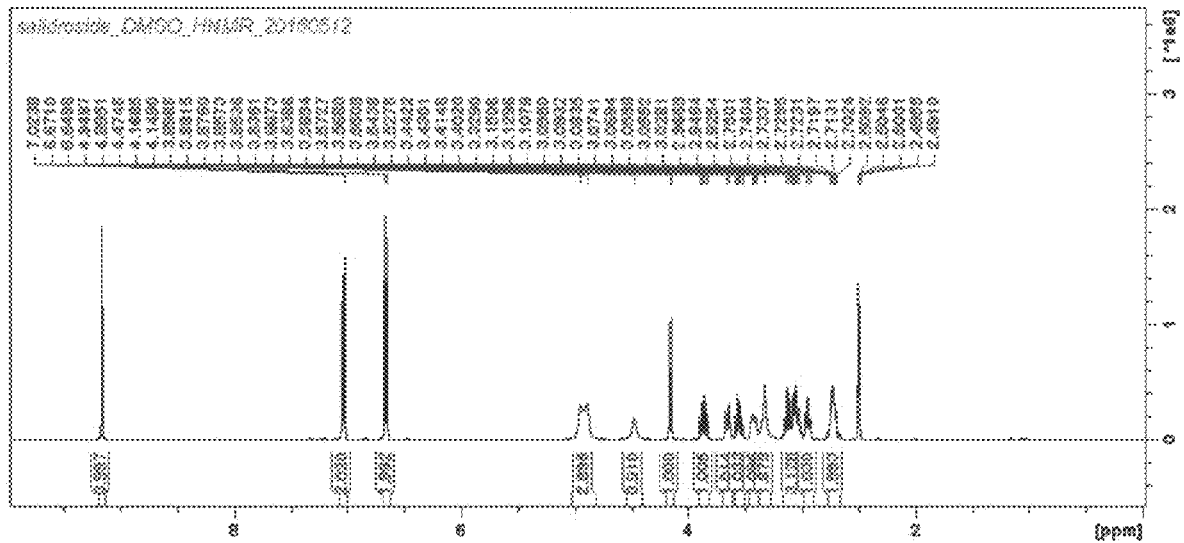
FIG. 22 is a $^1$H NMR spectrum (400 MHz, CDCl$_3$) of salidroside isolated from N. benthamiana leaves overexpressing R. rosea salidroside biosynthetic genes. δ: 9.16 (1H, s, OH), 7.03 (2H, d, J=8.4, 4-H, 8-H), 6.65 (2H, d, J=8.4, 5-H, 7-H), 4.92 (3H, m, Glu-OH), 4.47 (1H, s, Glu-OH), 4.16 (1H, d, J=7.6, 1'-H), 3.87 (1H, m, 1-H), 3.65 (1H, m, 6'-H), 3.56 (1H, m, 1-H), 3.42 (1H, m, 6'-H), 3.12 (1H, m, 3'-H), 3.07 (1H, m, 5'-H), 3.04 (1H, m, 4'-H), 2.95 (1H, m, 2'-H), 2.73 (2H, m, 2-H).
Figure 23:
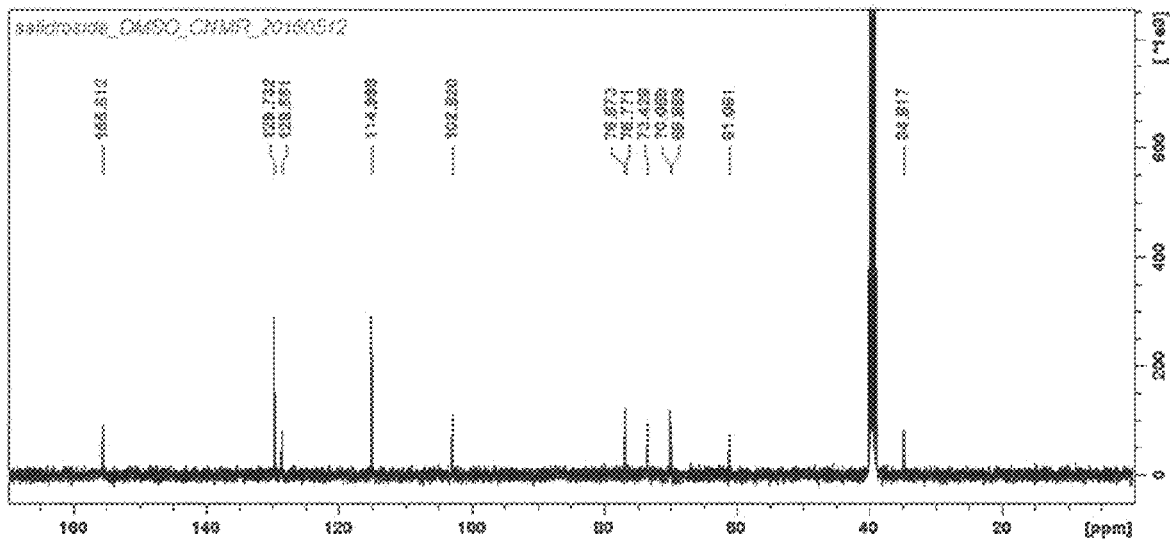
FIG. 23 is a $^{13}$C NMR spectrum (100 MHz, CDCl$_3$) of salidroside isolated from N. benthamiana leaves overexpressing R. rosea salidroside biosynthetic genes. δ: 155.6 (6-C), 129.7 (4, 8-C), 128.6 (3-C), 115.0 (5, 7-C), 102.8 (1'-C), 76.9 (3'-C), 76.8 (5'-C), 73.4 (2'-C), 70.1 (1-C), 69.9 (4'-C), 61.1 (6'-C), 34.8 (2-C).
Figure 24:
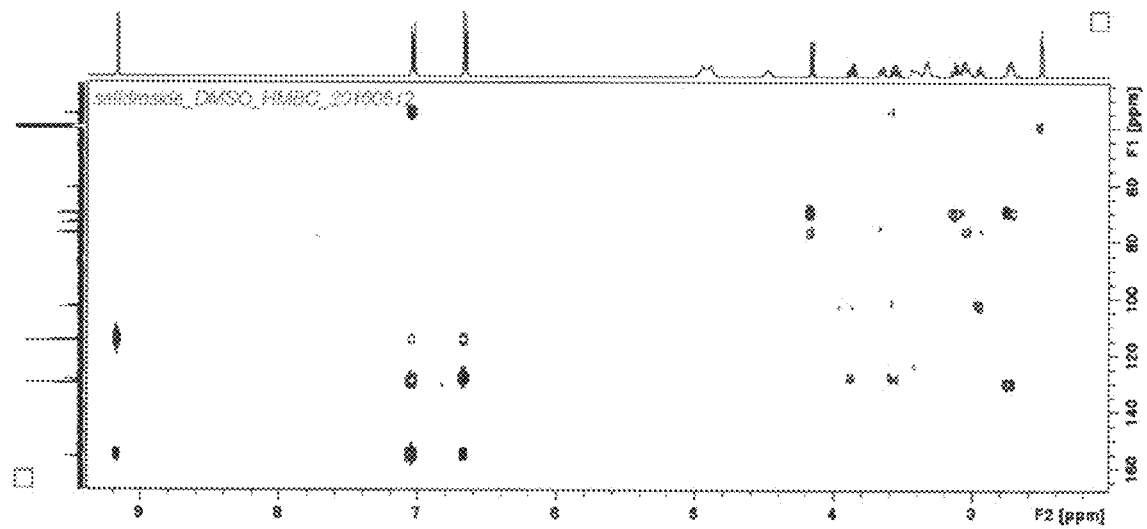
FIG. 24 is a heteronuclear multiple bond correlation (HMBC) spectrum of salidroside isolated from N. benthamiana leaves overexpressing R. rosea salidroside biosynthetic genes.
Figure 25:
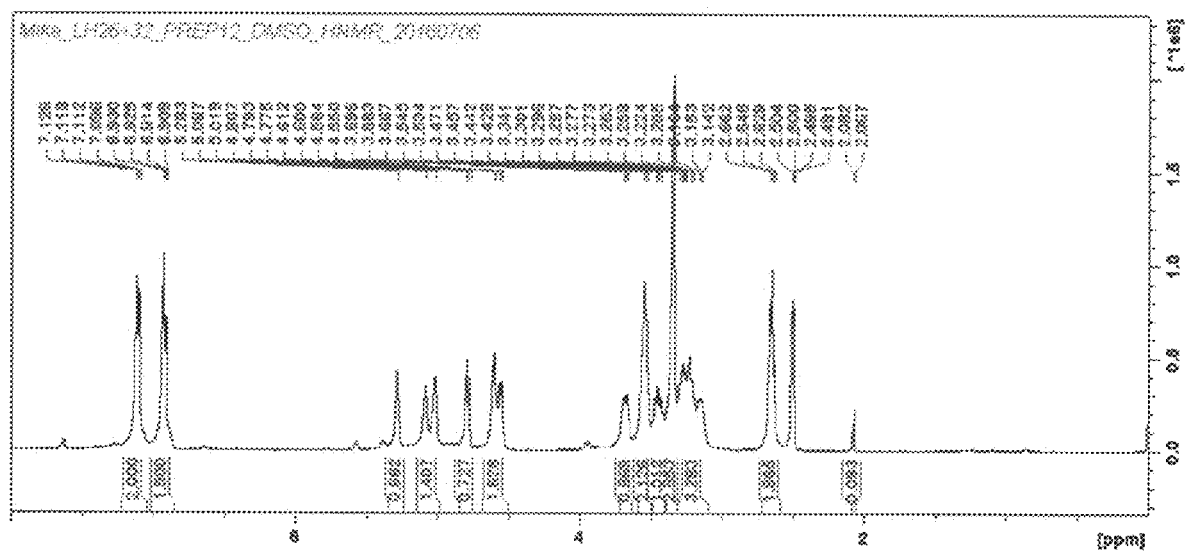
FIG. 25 is a $^1$H NMR spectrum (400 MHz, CDCl$_3$) of icariside D2 isolated from N. benthamiana leaves overexpressing R. rosea salidroside biosynthetic genes. δ: 7.11 (2H, d, J=8.8, 4-H, 8-H), 6.92 (2H, d, J=8.8, 5-H, 7-H), 5.28 (1H, s, Glu-OH), 5.09 (1H, s, Glu-OH), 5.02 (1H, s, Glu-OH), 4.78 (1H, d, J=7.2, 1'-H), 4.61 (1H, m, 1-H), 4.56 (1H, m, 1-H), 3.68 (1H, s, 6'-H), 3.55 (1H, m, OH), 3.45 (1H, s, 6'-H), 3.14-3.32 (4H, m, 2', 3', 4', 5'-H), 2.66 (2H, m, 2-H).
Figure 26:
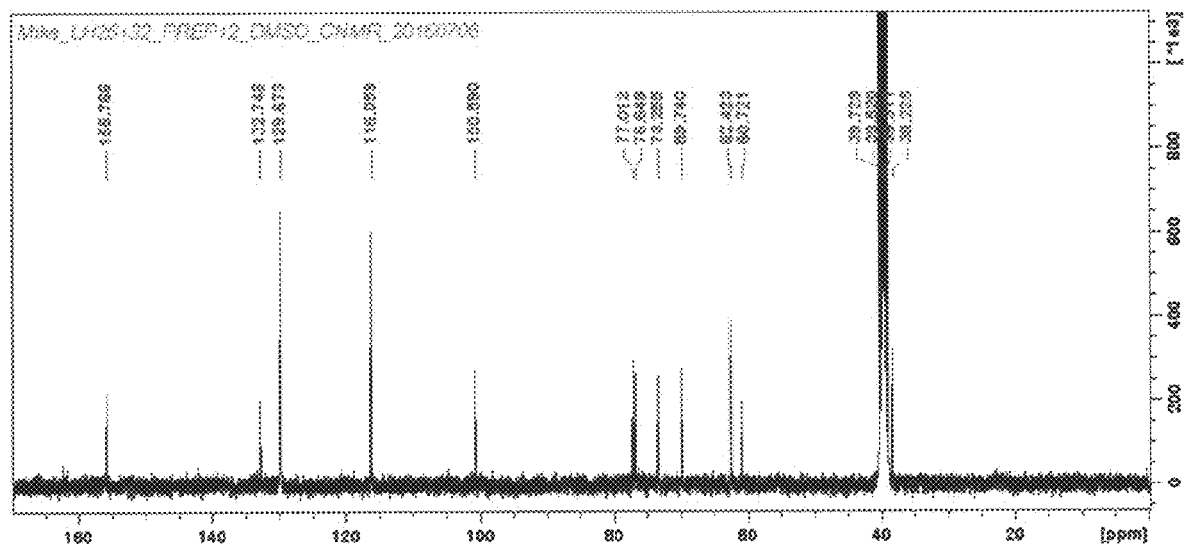
FIG. 26 is a $^{13}$C NMR spectrum (100 MHz, CDCl$_3$) of icariside D2 isolated from N. benthamiana leaves overexpressing R. rosea salidroside biosynthetic genes. δ: 155.8 (6-C), 132.7 (3-C), 129.7 (4, 8-C), 116.1 (5, 7-C), 100.6 (1'-C), 77.0 (3'-C), 76.6 (5'-C), 73.3 (2'-C), 69.7 (4'-C), 62.4 (1-C), 60.7 (6'-C), 38.2 (2-C).

To facilitate functional assessment of a large number of UGT candidates, an in vivo tyrosol glycosylation assay in the yeast S. cerevisiae was devised. Initial iterations of the tyrosol-producing yeast strains were generated by transforming wild type S. cerevisiae BY4743 with separate 2-micron TEF-promoter expression plasmids containing Rr4HPAAS and Rr4HPAR1, respectively. It was later observed that yeast contains endogenous ADH activity sufficient to reduce 4-hydroxyphenylacetaladehyde produced by Rr4HPAAS to tyrosol. Therefore, the Rr4HPAR1-containing plasmid was omitted in the final tyrosol-producing strain (FIG. 18). Each of the 34 R. rosea UGT candidate genes, carried on the yeast 2-micron TEF-promoter expression plasmids, was transformed into the background strain expressing Rr4HPAAS. After auxotrophic selection, colonies were cultured, harvested and subjected to metabolic profiling by LC-HRAM-MS. From this screen, we identified three UGTs (RrUGT 29, 32, and 33) with regio-specific T8GT activity, four UGTs (RrUGT 2, 3, 7, and 13) with regio-specific T4GT activity, and RrUGT17 with both T8GT and T4GT activities (FIG. 4B). Further phylogenetic analysis of the 34 cloned R. rosea UGTs against the 88 unique and complete A. thaliana UGTs suggests a correlation between the cladding of the UGTs and their respective biochemical activities (FIG. 4A) (Li et al., 2001). The UGTs that contain T4GT activity appear to be phylogenetically diverse with representative enzymes falling into the D, G, E and K groups, while all of identified T8GTs cluster within the G group (FIG. 4A). These results also show that RrUGT 3 and RrUGT33, the most active T4GT and T8GT, respectively, display significantly higher regio-specific tyrosol glycoside-producing activities than the two previously reported UGTs from R. sachalinensis (GenBank. AAS55083 and EU567325) (FIG. 19) (Ma et al., 2007; Yu et al., 2011).

Figure 4C:
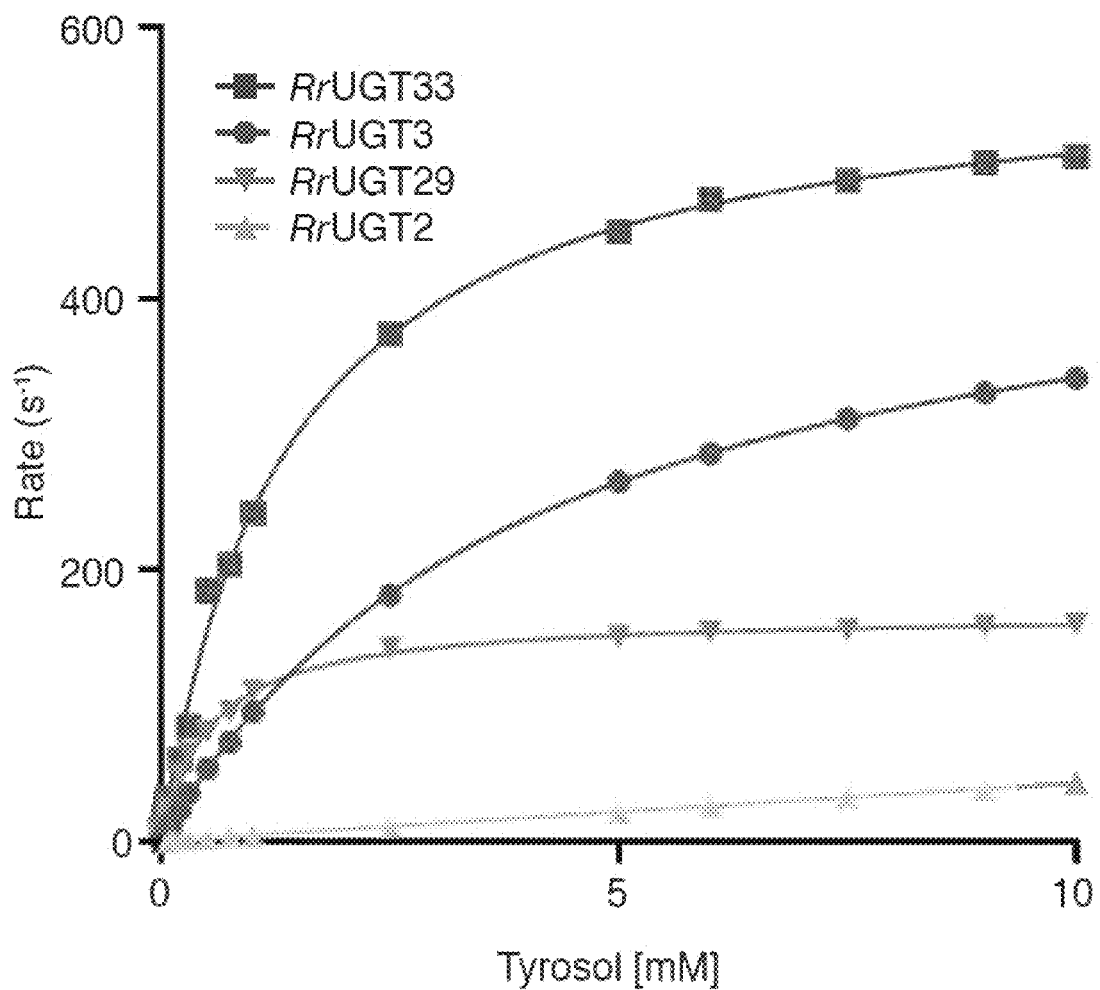

Using recombinant enzymes produced and purified from E. coli, the kinetic parameters for the salidroside-producing RrUGT29 and RrUGT33 and the icariside D2-producing RrUGT2 and RrUGT3 were measured (FIG. 4C and Table 1). RrUGT33 exhibits the highest T8GT catalytic efficiency with a $k_{cat}/K_m$ value of 420.6 s$^{-1}$ mM$^{-1}$ and was subsequently referred to as RrT8GT (Table 1). In contrast, RrUGT3 exhibits the greatest T4GT catalytic efficiency with a $k_{cat}/K_m$ value of 117.2 s$^{-1}$ mM$^{-1}$ and was subsequently referred to as RrT4GT (Table 1).

Heterologous Production of Salidroside and Icariside D2 in N. benthamiana

To further evaluate the biochemical function of R. rosea tyrosol glycoside biosynthetic genes in planta, these genes were expressed in N. benthamiana leaves using the Agrobacterium tumefaciens-mediated transient protein production technique (Sainsbury et al., 2009) followed by LC-HRAM-MS-based metabolic profiling. To first demonstrate the biochemical function of Rr4HPAAS in planta, Rr4HPAAS alone was transiently expressed in N. benthamiana leaves. PsTyDC and the previously reported Petrose-

Figure 5A:
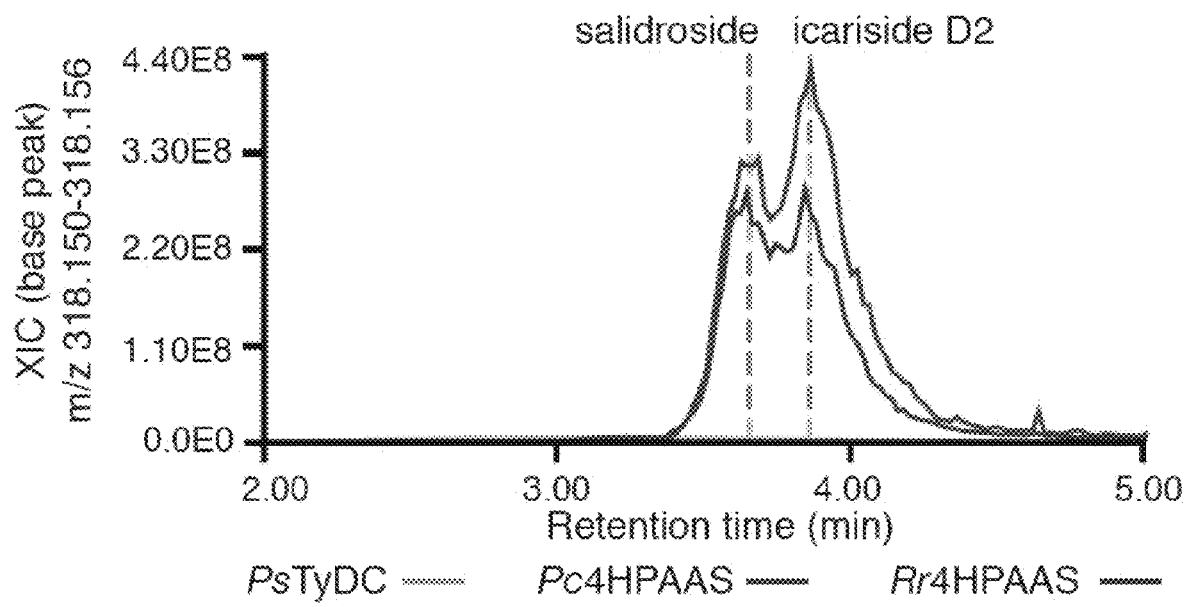
FIGS. 5A-C show heterologous production of tyrosine-derived metabolites in transgenic *N. benthamiana* as detected by LC-HRAM-MS.
Figure 5B:
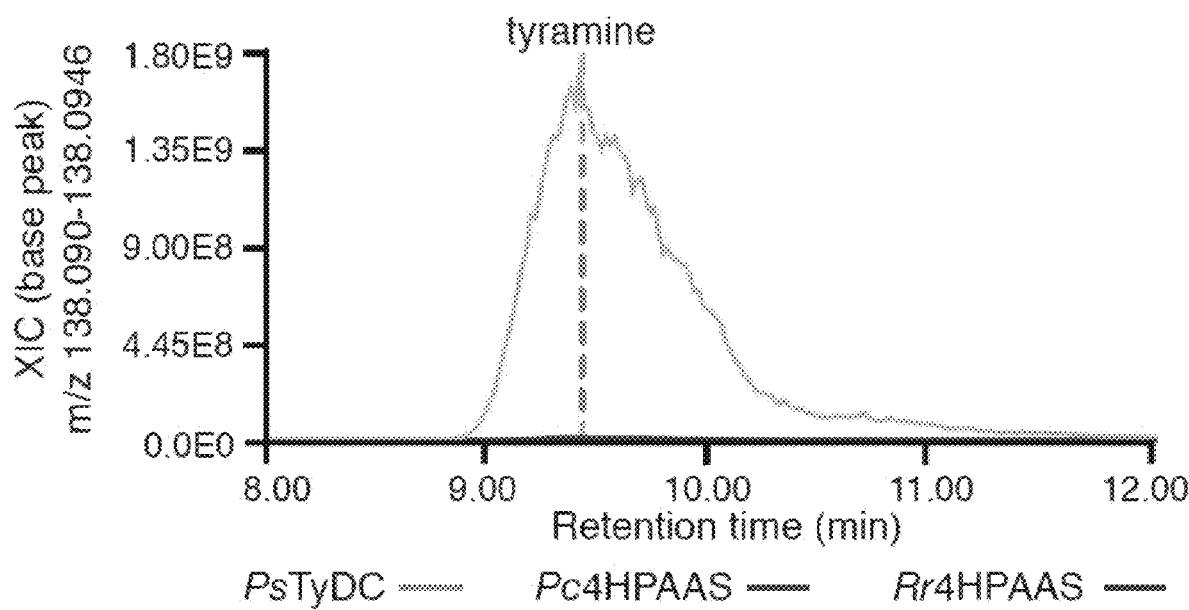
Figure 5C:
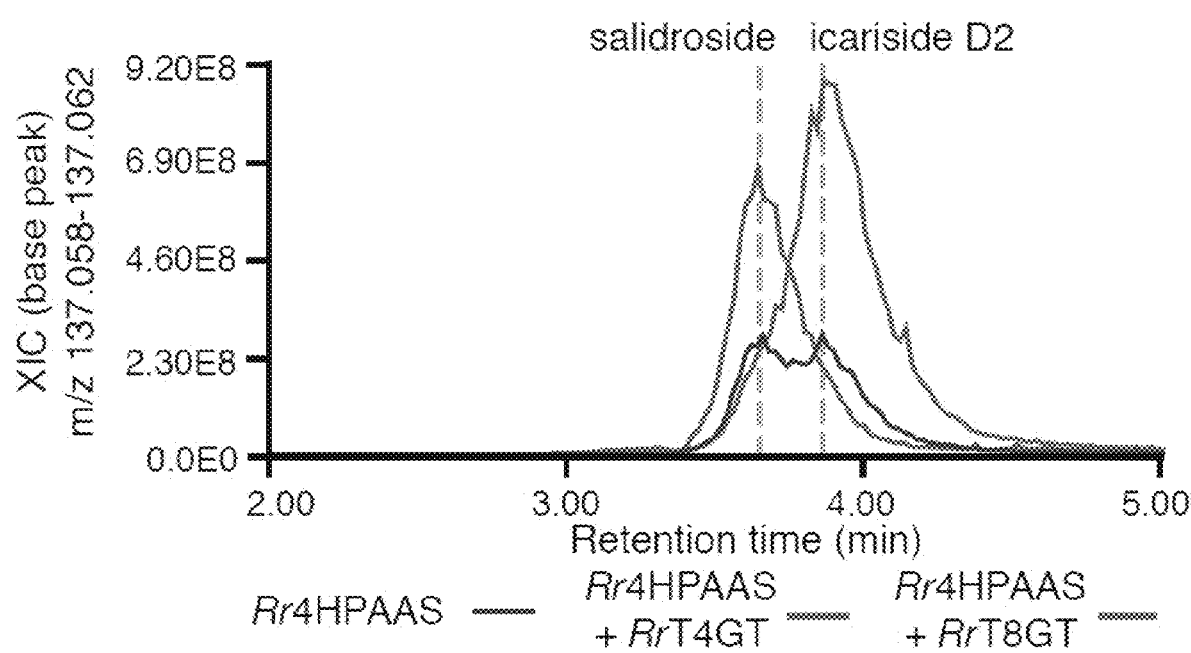
Figure 27:
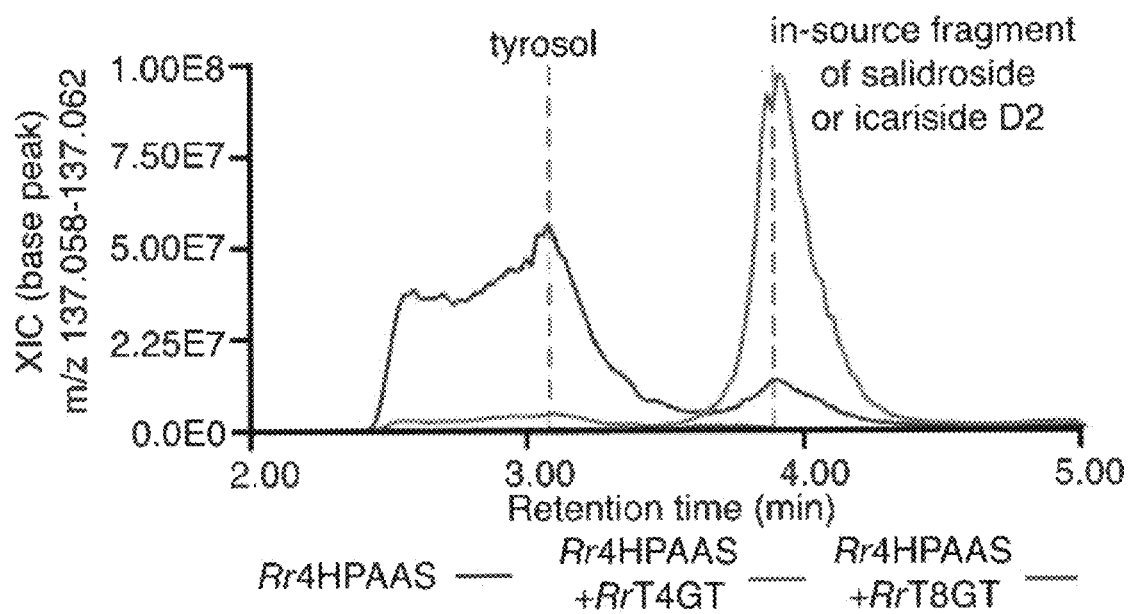
FIG. 27 is a chromatogram of the tyrosol [M−H]− ion generated in transgenic N. benthamiana expressing the Rr4HPAA. The addition of either the RrT4HGT or the RrT8HGT depletes the tyrosol substrate in the production of icariside D2 or salidroside. The identity of the ions was verified against authentic standards.

*linum crispum* 4HPAAS (Pc4HPAAS, GenBank. AAA33861) (*Torrens*-Spence et al., 2012) were also tested in parallel as controls. Interestingly, expression of Rr4HPAAS or Pc4HPAAS in *N. benthamiana* led to significant accumulation of both salidroside and icariside D2 in *N. benthamiana* leaves (FIG. 5A). The chemical identity of these compounds was confirmed by both LC-HRAM-MS and nuclear magnetic resonance (NMR) analyses (FIGS. 20-26). This result suggests that 4-HPAA produced by transgenic 4HPAAS can be readily metabolized by endogenous *N. benthamiana* reductase and glycosyltransferase enzymes to yield both salidroside and icariside D2. In contrast, the expression of PsTyDC yielded tyramine in high abundance in *N. benthamiana* leaves with no measurable production of tyrosol glycosides (FIG. 5B). Next, the in planta regio-specificity of RrT8GT and RrT4GT in tyrosol glycosylation was evaluated. Co-expression of either RrT8GT or RrT4GT with Rr4HPAAS led to regio-specific glycosylation of tyrosol and accumulation of salidroside or icariside D2, respectively (FIG. 5C). Meanwhile, the accumulation of free tyrosol was reduced in these plants compared to those with Rr4HPAAS expression alone (FIG. 27). Notably, the paired expression of Rr4HPAAS and one of the two regio-specific *R. rosea* tyrosol glycosyltransferases yielded up to 2% dry weight for salidroside or icariside D2 production in *N. benthamiana* leaves. This set of in planta experiments demonstrate that Rr4HPAAS and regio-specific RrT8GT are specialized metabolic enzymes underpinning salidroside biosynthesis in *Rhodiola*. Although icariside D2 does not naturally accumulate in *Rhodiola*, the identification of the regio-specific RrT4GT adds to the tool box for metabolic engineering of valuable tyrosol-derived glycosides.

Optimization of Salidroside Production in *S. cerevisiae*

Figure 28:
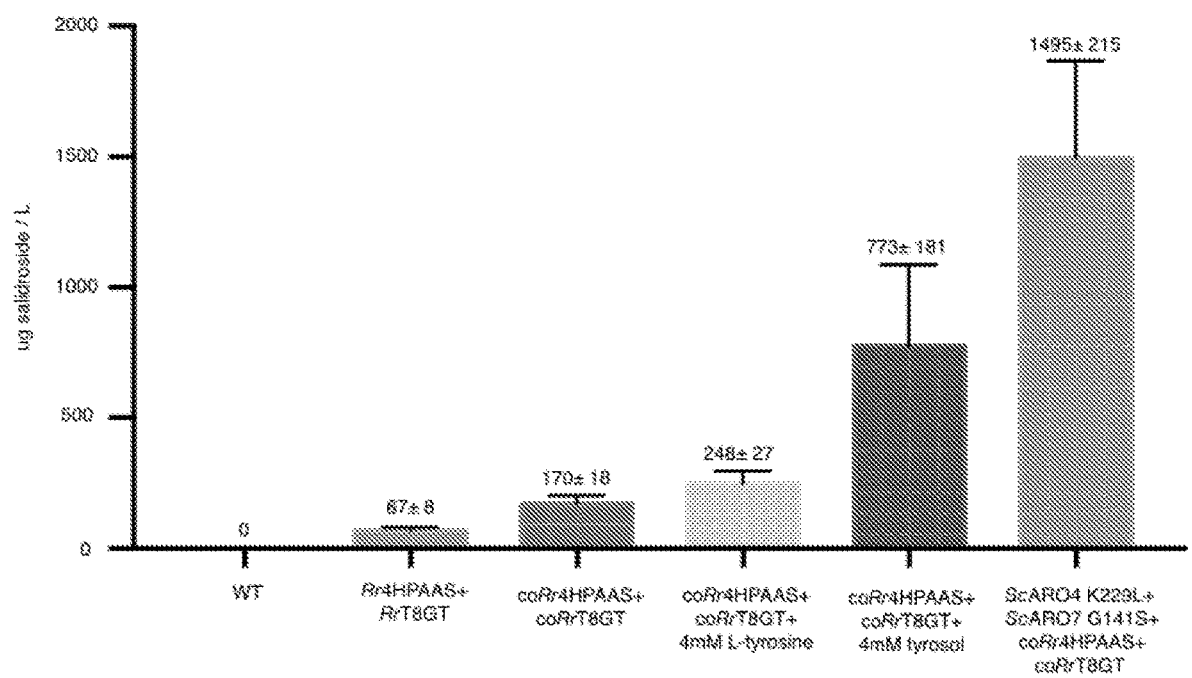
FIG. 28 is a chart showing titer of salidroside producing S. cerevisiae strains with and without substrate feeding. The first bar of the bar graph represents salidroside titer in wild type (WT) BY4743 yeast while the second bar demonstrates salidroside titer from the yeast strains expressing the native Rr4HPAAS and RrT8GT genes in separate pTEF 2µ plasmids. The third bar of the graph illustrates the salidroside titer from the S. cerevisiae strain transformed with a pTDH3 promoter 2µ multi gene plasmid containing coRr4HPAAS and coRrT8GT genes. The fourth and fifth bars show salidroside production from the aforementioned codon optimized multi gene plasmid with the addition of either 4 mM L-tyrosine or 4 mM tyrosol. The final bar shows the salidroside production from a strain containing the multi gene coRr4HPAAS and coRrT8GT plasmid additionally transformed with a second 2µ pTDH3 ARO4 K229L and ARO7 G141S multi gene plasmid.
Figure 29A:
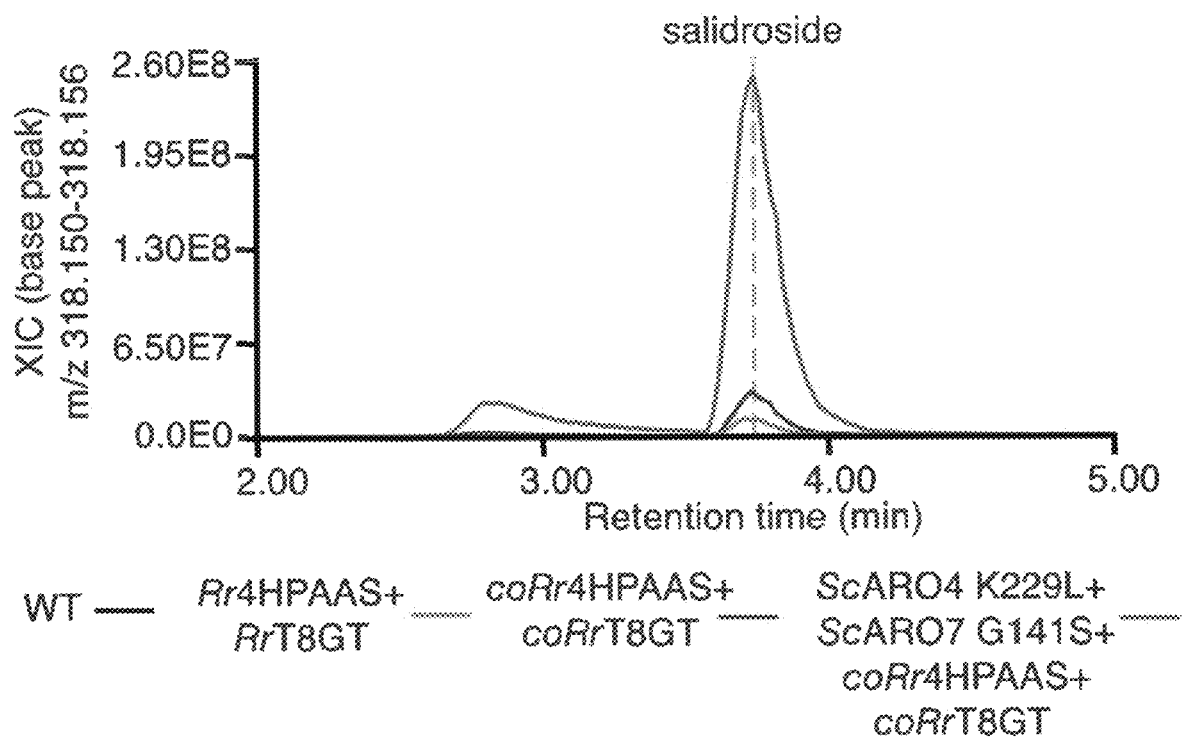
FIG. 29A-B are chromatograms of the salidroside [M+NH4]+ ion generated in transgenic S. cerevisiae.
Figure 29B:
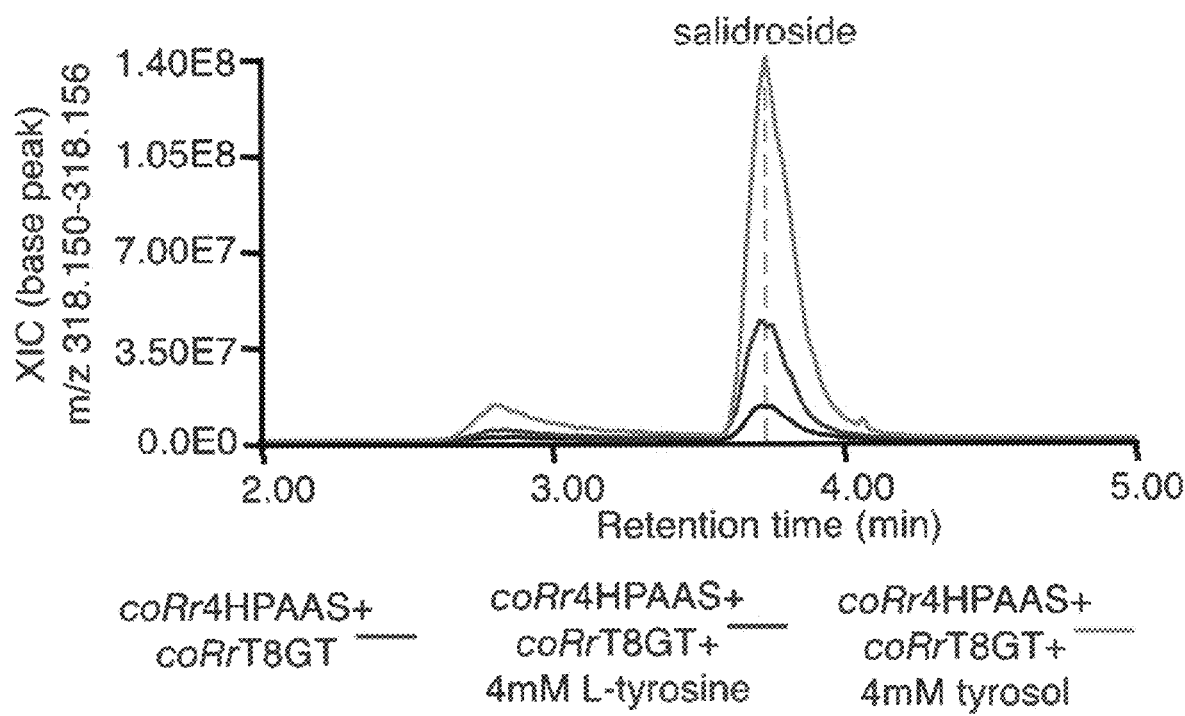
Figures 30, 31:
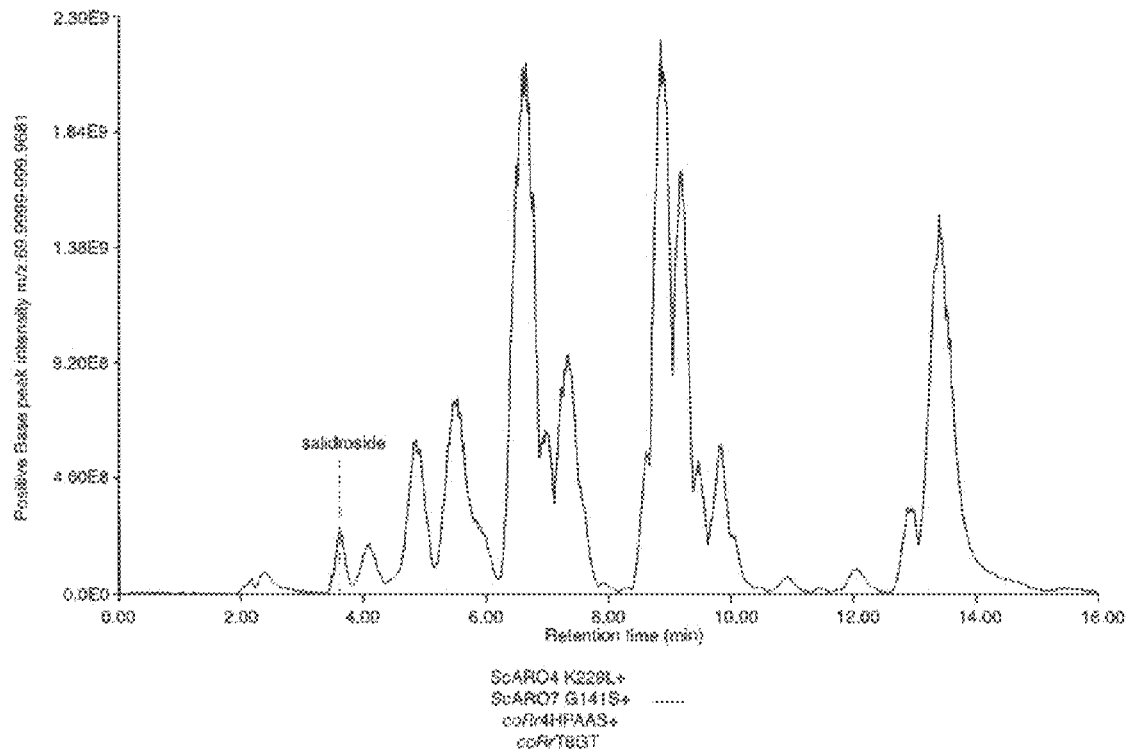
FIG. 30 is a graph showing total ion count of salidroside producing transgenic S. cerevisiae. Salidroside, labeled in the chromatogram, appears as one of the principle metabolites.
FIG. 31 is a multiple sequence alignment of key residues within biochemically characterized plant AAADs. The multiple sequence alignment of FIG. 31 shows portions of the full alignment of FIG. 32.

The complete elucidation of salidroside biosynthesis in *Rhodiola* provides new opportunities for bioengineering of sustainable salidroside production in heterologous hosts. Although *N. benthamiana* has been used for the commercial production of high value natural products and recombinant proteins, its scalability currently does not match to industrial yeast fermentation. To increase the salidroside titer in yeast, the Rr4HPAAS and RrT8GT genes were optimized according to *S. cerevisiae* codons, and assembled in a custom 2μ plasmid for constitutive expression driven by pTDH3 promoter in yeast (FIGS. 28 and 29A). The increased promoter strength and codon optimization of Rr4HPAAS (coRr4HPAAS) and RrT8GT (coRrT8GT) resulted in a 2.5-fold increase in salidroside titer as compared to the initial strain. To probe the potential bottlenecks in salidroside biosynthesis in yeast, we next fed the culture containing the codon optimized construct with either L-tyrosine or tyrosol. Both feeding experiments demonstrated significant increase in salidroside titer, suggesting that improved tyrosine flux may further improve salidroside titer (FIGS. 28 and 29B). Thus, a yeast strain was engineered to include the previously described feedback-insensitive mutants of the yeast L-tyrosine pathway enzymes ARO4 and ARO7 (Gold et al., 2015). Incorporation of both ARO4 K229L and ARO7 G141S into the prior best engineered yeast strain produced salidroside as one of the most abundant metabolites with a titer of 1.5 mg $L^{-1}$, when grown for 48 h in 4% glucose 2×yeast nitrogen base in shake flasks (FIGS. 28, 29A, and 30). In summary, this preliminary metabolic engineering exercise in yeast yielded a prototype salidroside-producing strain, which can be improved through additional rounds of targeted and untargeted genetic modifications to further increase titer.

Example #1: Discussion

As described herein, the *R. rosea* ortholog of the previously reported RcTyDC is a 4HPAAS, which catalyzes the direct conversion of tyrosine to 4-HPAA. This discovery therefore corrected a major long-standing misconception about the biosynthetic route towards tyrosol, an important precursor for many important phenolic natural products in plants (Chapple et al., 1986; Wyk, 2010).

Figure 6:
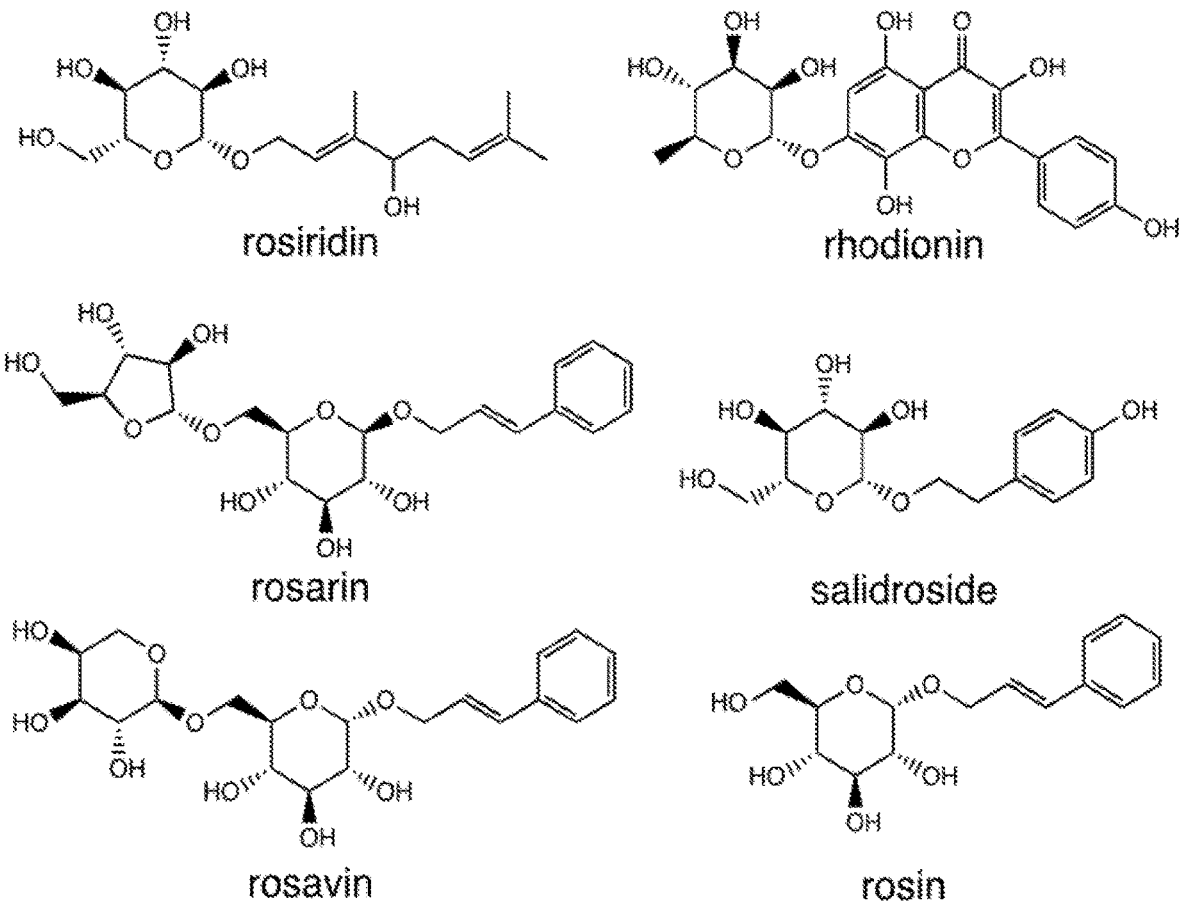
FIG. 6 shows the chemical structures of a number of *Rhodiola* glycosylated natural products.

UGTs play important roles in plant specialized metabolism as they alter the solubility, reactivity, bioactivity, intercellular and subcellular transport of a wide array of plant metabolites by glycosylation (Jones and Vogt, 2001). The resulting glycosides also have profound impact on human health with diverse pharmacological and nutraceutical indications (Jones and Vogt, 2001). Since natural product glycosides often contain distinct pharmacokinetic properties as compared to their aglycones, chemical derivatization via glycosylation has received considerable attention in pharmaceutical research (Gantt et al., 2011). Several *R. rosea* UGTs capable of producing salidroside and icariside D2 from the aglycone tyrosol in a regio-specific manner were identified. In this gene-mining process, a library was established containing phylogenetically diverse UGTs from *R. rosea*, which likely contain enzymes responsible for the biosynthesis of other phenolic glycosides from *Rhodiola*, such as rosiridin, rhodionin, rosarin, rosin, and rosavin (FIG. 6).

Unlike bacterial natural product biosynthetic pathways, which are encoded by operons ubiquitously present in bacterial genomes, enzyme-encoding genes of a given plant specialized metabolic pathway often scatter randomly across the plant genome, making metabolic pathway elucidation unattainable simply by genome mining. Plants, like many other multicellular eukaryotes, contain rich tissue types where specific natural products accumulate under developmental and environmental regulations. In recent years, this feature of plant specialized metabolism has been exploited for pathway and enzyme discovery in medicinal plants that lack classical genetic tools (Torrens-Spence et al., 2016). Through mining transcriptomics and metabolomics datasets generated separately from the root and crown tissues of *R. rosea*, candidate salidroside biosynthetic genes were prioritized based on correlation between transcript and metabolite abundances in these two tissues. Extended phylogenomics analyses of the involved enzyme families further provided additional information that facilitates salidroside biosynthetic gene discovery. The biochemical functions of the identified candidate enzymes were then examined in vitro using recombinantly expressed proteins, and in vivo through expression of the candidate enzymes in heterologous hosts, e.g. yeast and *N. benthamiana* in this case. Collectively, this work describes a rare de novo elucidation of the complete biosynthetic pathway of a given plant natural product. The workflow adopted in this study is generally applicable for future investigation of other largely unexplored specialized metabolic pathways in non-model plants, and will ultimately contribute to a capability of synthesizing structurally diverse plant natural products through the means of metabolic engineering.

Materials and Methods

Reagents

Salidroside, tyrosine, tyramine, tyrosol, phenylacetaldehyde, phenylethyl alcohol, sodium borohydride, NADPH, UDP-glucose, and PLP were purchased from Sigma-Aldrich. 4-HPAA was purchased from Santa Cruz Biotechnology, Inc.

Plant Materials

*R. rosea* seeds were purchased from Horizon Herbs. Seeds were stratified at 4° C. for three days, and germinated in potting soil. *R. rosea*, *P. crispum*, and *N. benthamiana* plants were grown under a 16-h-light/8-h-dark photoperiod at 23° C. in a local greenhouse.

RNA Isolation, Library Preparation, Transcriptome Assembly, cDNA Production and Molecular Cloning Tissue of seventy-day-old *R. rosea* plants were harvested for total RNA extraction using the Qiagen's RNeasy Mini Kit (Qiagen). RNA quality was assessed by Bioanalyzer (Agilent Technologies). For the RNAseq experiment, strand-specific mRNA libraries were prepared using total RNA prepared separately from the root and crown tissue using the TruSeq Stranded mRNA Library Prep Kit (Illumina), and sequenced on a HiSeq2000 sequencer (Illumina) in paired-end mode (PE100). Sequence FASTQ files were trimmed for sequencing adaptors using Trimmomatic (Bolger et al., 2014) and assembled into de novo transcriptomes using Trinity in strand-specific mode (Grabherr et al., 2011). Gene expression statistics (TPM values) were determined by RSEM (Li and Dewey, 2011). Completeness of the combined *R. rosea* root and crown transcriptome was evaluated using the BUSCO tool, with 'embryophyta_odb9' set as lineage and '*arabidopsis*' set as model species (Simao et al., 2015). Putative coding regions were predicted using Transdecoder (Haas et al., 2013). Transcripts and predicted protein sequences were annotated with TPM values and closest BLAST hits using in-house scripts. Transcriptome mining was performed on a local BLAST server (Anurag Priyam, 2015). First-strand cDNAs were synthesized by RT-PCR using total RNA sample as template and the Invitrogen SuperScript™ III kit (Invitrogen) with the oligo(dT)20 primer. The coding sequences (CDS) of candidate genes were amplified from cDNAs by PCR using gene-specific primers (Table 2). Select *R. rosea* and *R. sachalinensis* genes were also synthesized as gBlocks (IDT) with yeast codon optimization. Gibson assembly was used to ligate PCR amplicons or gBlocks into several base vectors. These include pHis8-4, a bacterial expression vector containing an N-terminal 8×His tag followed by a tobacco etch virus (TEV) cleavage site for recombinant protein production in *E. coli*; pEAQ-HT, a binary vector designed for transient expression of heterologous proteins in *N. benthamiana* (Peyret and Lomonossoff, 2013); p423TEF, p425TEF and p426TEF 2µ plasmids (Mumberg et al., 1995) with various auxotrophic growth markers for constitutive expression in *S. cerevisiae*; and a custom plasmid containing 2µ, pTDH3, tTDH1, HIS3 for constitutive multi gene expression in *S. cerevisiae* (Lee et al., 2015).

Sequence Alignment and Phylogenetic Analysis

The protein multiple sequence alignments were generated using ClustalW2 with default settings (Thompson et al., 2002). ESPript 3.0 (Gouet et al., 2003) was used to display the multiple sequence alignments. The phylogeny was inferred using the Maximum Likelihood method based on the Poisson correction model (L, 1965). The bootstrap consensus unrooted trees were inferred from 500 replicates to represent the phylogeny of the analyzed enzyme families (Sanderson and Wojciechowski, 2000). The phylogenetic analysis of the AAAD family includes 242 sequences from the Phytozome V12 embryophyte species with fully sequenced genome (*A. thaliana*, *G. raimondii*, *P. trichocarpa*, *M. domestica*, *M. truncatula*, *E. grandis*, *K. laxiflora*, *S. lycopersicum*, *A. coerulea*, *Z. mays*, *B. distachyon*, *O. sativa*, *Z. marina*, and *A. trichopoda*), the *R. rosea* transcriptome, and previously characterized AAAD proteins. The phylogenetic analysis of ADHs includes 346 PAR homologs from the Phytozome V12 embryophyte species and *R. rosea* transcriptome. The phylogenetic analysis of UGTs contains 113 non-redundant full-length UGT homologs from the *R. rosea* transcriptome. A second UGT tree was also generated using the 34 cloned *R. rosea* UGTs in addition to the 88 full length and unique UGTs from *Arabidopsis thaliana* (Li et al., 2001). Initial trees for the heuristic search were obtained automatically by applying Neighbor-Join and BioNJ algorithms to a matrix of pairwise distances estimated using a JTT model, and then selecting the topology with superior log likelihood value. All phylogenetic analyses were conducted in MEGA7 (Kumar et al., 2016).

*Agrobacterium*-Mediated Transient Expression of Heterologous Proteins in *N. benthamiana*

*A. tumefaciens* (LBA4404) containing the transgene construct was grown to optical density (OD) 600 of 1.6 in 50 mL of YM medium (0.4 g/L yeast extract, 10 g/L mannitol, 0.1 g/L NaCl, 0.2 g/L $MgSO_4 \cdot 7H_2O$, 0.5 g/L $K_2HPO_4 \cdot 3H_2O$), washed with washing buffer (10 mM MES (2-(N-morpholino)ethanesulfonic acid), pH 5.6), and resuspended in MMA buffer (10 mM MES, pH 5.6, 10 mM $MgCl_2$, 100 µM acetosyringone) to OD 600 of 0.8. For co-expressing multiple genes, individual *A. tumefaciens* cultures containing the unique transgene constructs were grown, pelleted, and washed separately. The cultures were then resuspended together at a higher optical density so that each individual culture was present at a concentration equivalent to OD 600 of 0.8. 1 mL of culture was used to infiltrate the underside of six-week-old *N. benthamiana* leaves.

Metabolomic Profiling by LC-HRAM-MS

Crown tissue and root tissue of a three-month-old *R. rosea* plant was harvested and stored at −80° C. before subsequent metabolomic analysis. Various transgene-carrying *S. cerevisiae* BY4743 strains and transiently transformed *N. benthamiana* plants were generated to test the activity of candidate genes involved in the tyrosol glycoside biosynthesis. 3 mL of saturated *S. cerevisiae* culture was used to inoculate 50 mL of synthetic minimal media (SD) in a shake flask. After 24 hours of shaking at 30° C., the culture was pelleted by centrifugation, washed with water, and stored at −80° C. before further processing. *N. benthamiana* leaf tissue was harvested 5 days after *Agrobacterium* infiltration and was stored at −80° C. before further processing. Frozen yeast or plant tissue was disrupted with a TissueLyser (Qiagen) using acid-washed metal beads in 50% methanol (500 µL per 100 mg fresh weight). The extracts were then analyzed by LC-HRAM-MS. Metabolite profiling was conducted on a QExactive benchtop orbitrap mass spectrometer equipped with an Ion Max source and a HESI II probe, which was coupled to a Dionex UltiMate 3000 UPLC system (Thermo Fisher Scientific). 2 µL of each sample was injected onto a 150×2.1 mm ZIC-pHILIC column (5 µm particle size, EMD Millipore). Solvent A was 20 mM ammonium carbonate, 0.1% ammonium hydroxide; solvent B was acetonitrile. The column oven and autosampler tray were held at 25° C. and 4° C., respectively. The chromatographic gradient was run at a flow rate of 0.15 mL/min as follows: 0-20 min, linear gradient from 80% to 20% solvent B; 20-20.5 min, linear gradient from 20% to 80% solvent B; 20.5-28 min, hold at 80% solvent B. The mass spectrometer was operated in full-scan, polarity-switching mode with the spray voltage set to 3.0 kV, the heated capillary held at 275°

C., and the HESI probe held at 350° C. The sheath gas flow was set to 40 units, the auxiliary gas flow was set to 15 units, and the sweep gas flow was set to 1 unit. The MS data acquisition was performed in a range of 70-1000 m/z, with the resolution set at 70,000, the AGC target at 10e6, and the maximum injection time at 20 msec. The raw data was converted to mzML format using MSConvert (Chambers et al., 2012), and analyzed using MetaboAnalyst (Xia and Wishart, 2016) and MZmine2 (Pluskal et al., 2010).

Small Molecule Isolation and NMR

For large-scale compound isolation from Agrobacterium-transformed N. benthamiana leaves, 15 g (dry weight) of N. benthamiana leaves (harvested 5 days post infection) were extracted with 70% EtOH. The solvent was evaporated from the extracts under reduced pressure using a rotary evaporator (Buchi). The residue was suspended in 100 mL of water, and extracted successively with hexane, chloroform and butanol. The water-soluble portion was separated by Sephadex LH20 using a $H_2O$/MeOH gradient of 0-100% MeOH. Fractions 26-32 and 36-44 were combined separately for further purification by a preparative HPLC (Shimadzu) equipped with a SPD-20A UV-VIS detector and a 150×21.2 mm 100 Å Kinetex 5µ $C_{18}$ column (Phenomenex). 7 mg of salidroside and 13 mg of icariside D2 were purified using water (solvent A) and a 60-minute gradient of 5-80% acetonitrile (solvent B) at a flow rate of 10 mL/min. The samples were dried by lyophilization and subjected to NMR analysis in DMSO-$d_6$. The solution NMR spectra were recorded on a Bruker AVANCE-400 NMR spectrometer with a Spectro Spin superconducting magnet.

Recombinant Protein Production and Purification

BL21(DE3) E. coli containing appropriate constructs were grown at 37° C. in terrific broth (TB) to OD 600 of 0.9, induced with 0.15 mM isopropyl-β-D-thiogalactoside (IPTG), and allowed to grow for an additional 20 h at 18° C. Cells were harvested by centrifugation, washed with phosphate buffered saline (PBS) (137 mM NaCl, 2.7 mM KCl, 10 mM $Na_2HPO_4$ and 1.8 mM $KH_2PO_4$), resuspended in 150 mL of lysis buffer (50 mM Tris pH 8.0, 0.5 M NaCl, 20 mM imidazole, and 0.5 mM dithiothreitol (DTT)), and lysed with five passes through a M-110L microfluidizer (Microfluidics). The resulting crude protein lysate was clarified by centrifugation prior to Qiagen Ni-NTA gravity flow chromatographic purification. After loading the clarified lysate, His-tagged recombinant protein-bound Ni-NTA resin was washed with 20 column volumes of lysis buffer, and eluted with 1 column volume of elution buffer (50 mM Tris pH 8.0, 0.5 M NaCl, 250 mM imidazole and 0.5 mM DTT). 1 mg of His-tagged TEV protease was added to the eluted protein, followed by dialysis at 4° C. for 16 h in dialysis buffer (50 mM Tris pH 8.0, 0.1 M NaCl, 20 mM imidazole and 2 mM DTT). After dialysis, protein solution was then passed through Ni-NTA resin to remove uncleaved protein and His-tagged TEV. The recombinant protein was further purified by gel filtration on a fast protein liquid chromatography (FPLC) system (GE Healthcare Life Sciences). The principle peaks were collected, verified for molecular weight by SDS-PAGE, and stored in storage buffer (20 mM Tris pH 8.0, 25 mM NaCl, and 0.5 mM DTT) at a protein concentration of 10 mg/mL. The purity of the recombinant protein was evaluated by ImageJ densitometric analysis using bovine serum albumin as the standard (Schneider et al., 2012). 200 µM PLP was added to all buffers during the purification of all AAAD family enzymes.

Enzyme Assays

The AAS enzyme assays were performed in 100 µL of reaction buffer (50 mM Tris, pH 8.0) containing 50 µg of recombinant enzyme, 200 µM PLP. Kinetic reactions were incubated with a range of amino acid substrate concentrations (1 µM-4 mM) at 30° C. for 30 minutes prior to quenching with 100 µL of 0.8 M formic acid. The reaction mixture was centrifuged, and the supernatant was analyzed by Pierce Quantitative Peroxide Assay Kit (Pierce) against a standard curve of hydrogen peroxide to demonstrate AAS activity or determine AAS kinetic parameters. Rr4HPAAS reactions were also analyzed by LC-MS-UV. 50 µL of reaction mixture was analyzed by an Ultimate 3000 liquid chromatography system (Dionex), equipped with a 150 mm C18 Column (Kinetex 2.6 µm silica core shell C18 100 Å pore, Phenomenex) and coupled to an UltiMate 3000 diode-array detector (DAD) in-line UV-Vis spectrophotometer (Dionex) and a TSQ Quantum Access MAX triple-quadrupole mass spectrometer (Thermo-Scientific). To resolve chromatographically L-tyrosine, tyrosol and 4-HPAAA, compounds were separated through the use of an isocratic mobile phase containing 50 mM monopotassium phosphate pH 4.6, 15% (v/v) acetonitrile and 0.5 mM octyl sulfate. Rr4HPAAS product formation was quantified using the UV absorbance at 280 nm and compared to analytical standards using the diode array detector wavelength at a wavelength range of 200-500 nm and chromatographic retention time. The reduction of aldehyde products was achieved by addition of saturated sodium borohydride in ethanol or by addition of 10 mM NADPH and 10 g of Rr4HPAR1 or Rr4HPAR2.

The phenylacetaldehyde reductase activity assays using Rr4HPAR1 and RrPAR2 were carried out in 200 µL reaction buffer (50 mM Tris, pH 8.0) at the presence of 2 mM phenylacetaldehyde, 5 mM NADPH and 5 µg of recombinant enzyme. The reactions were incubated at 30° C. for various time points, quenched with an equal volume of 0.8 M formic acid, and extracted by 100 µL of ethyl acetate. The organic phase was then analyzed by gas chromatography-mass spectrometry (GC-MS) using an 5% Phenyl Methyl Silox column (30 m×250 µm×0.25 µm, Agilent) with a temperature gradient as follows: 0-1 min 45° C., 4-13.33 min 45-185° C. The quadrupole MS was set to EI mode, electron energy at 70 eV, MS-source temperature at 230° C., MS-quad temperature at 150° C., scan mass range at 50-300 m/z and SIM for 120 m/z and 122 m/z. EI-MS spectra were compared against analytical standards. The 4-HPAA reductase activity assays were carried out in 100 µL of 50 mM Tris pH 8.0 with the addition of 5 mM 4-HPAA, 10 mM NADPH and 0.2 µg of Rr4HPAR1 or 15 µg of Rr4HPAR2. The reactions were incubated at 30° C. and then quenched at various time points with the addition of 100 µL methanol. The reaction mixture was then centrifuged and analyzed by LC-MS. Compounds were separated by reversed-phase chromatography with a ramp gradient of solvent A (0.1% formic acid in $H_2O$) and solvent B (0.1% formic acid in acetonitrile): 10% solvent B for 0.5 min, 5-40% solvent B over 8.5 min, 95% solvent B for 1.8 min followed by a final equilibration of 10% solvent B for 1 min with a flow rate at 0.7 mL/min. Product formation was measured using select ion monitoring in positive mode for a centroid center mass of 121.065 with a scan width of 0.002. The specific activity was determined at a five-minute reaction time point, and quantified against a standard curve of tyrosol.

Kinetic characterization of UGTs was conducted in 200 µL reaction buffer (50 mM Tris, pH 8.0) containing 10 mM UDP-glucose and various concentrations of tyrosol (0.01-5.0 mM). Reactions were started with addition of recombinant enzyme, incubated at 30° C. for 10 minutes, and quenched by addition of 200 µL of methanol. The reaction mixed was then analyzed by LC-HRAR-MS as described above. Compounds were separated by reversed-phase chromatography with a ramp gradient of solvent A (0.1% formic acid in H$_2$O) and solvent B (0.1% formic acid in acetonitrile): 5% solvent B for 0.5 min, 5-55% solvent B over 6 min, 55-5% solvent B over 1.0 min and a final equilibration of 5% solvent B for 1 min with a flow rate at 0.6 mL/min. Product formation was measured using select ion monitoring in positive mode for a centroid center mass of 318.15. Product mass was calculated by comparison to a standard curve of the NMR verified plant purified salidroside and icariside D2 samples.

Kinetic constants such as K$_m$ and V$_{max}$ were determined by fitting raw data to the Michaelis-Menten equation using the nonlinear regression function in Prism (version 7.0).

Accession Codes

The sequences of R. rosea genes reported in this article are deposited into NCBI GenBank under the following accession numbers: Rr4HPAAS (MF674522), RrAAS (MF674523), Rr4HPAR1-2 (MF674524-MF674525) and RrUDP1-34 (MF674526-MF674558, MG385659). Raw RNA-Seq reads have been submitted to NCBI SRA (SRR5936536 and SRR5936537). The de novo transcriptomes assembled from the raw reads have been submitted to NCBI TSA (GFVD00000000 for merged transcriptome, GFVE00000000 for crown transcriptome, and GFVF00000000 for root transcriptome). Raw and mzTab format feature called metabolomic data from the R. rosea crown and root have been uploaded to the EBI MetaboLights database (MTBLS566).

TABLE 1

Kinetic parameters of characterized enzymes.

| | Enzyme | | | | |
|---|---|---|---|---|---|
| | RrT4GT | RrT8GT | RrUGT29 | Rr4HPAAS | Rr4HPAAS |
| Substrate | tyrosol | tyrosol | tyrosol | L-tyrosine | L-DOPA |
| k$_{cat}$ (sec$^{-1}$) | 481.60 ± 3.91 | 576.20 ± 5.68 | 167.5 ± 0.82 | 4.92 ± 0.08 | 9.52 ± 0.37 |
| K$_m$ (mM) | 4.11 ± 0.08 | 1.37 ± 0.05 | 0.53 ± 0.01 | 0.42 ± 0.02 | 1.04 ± 0.10 |
| K$_{cat}$/K$_m$ (sec$^{-1}$ mM$^{-1}$) | 117.18 | 420.58 | 316.04 | 11.71 | 9.15 |

TABLE 2

Cloning primers.

| Gene | Vector/ direction | SEQ ID NO: | Sequence |
|---|---|---|---|
| Rr4HPAAS | pHis8-4 Forward | 97 | GAAAACTTGTACTTCCAGGCCCATGGCATGGGC AGCTTGCCTTCTCCTAATG |
| Rr4HPAAS | pHis8-4 Reverse | 98 | CTCGAATTCGGATCCGCCATGGCTAAGACACGA TGCTTTGAGCTGTTTCTTG |
| Rr4HPAAS | pEAQ-HT Forward | 99 | GTATATTCTGCCCAAATTCGCGACCGGTATGGGC AGCTTGCCTTCTCCTAATG |
| Rr4HPAAS | pEAQ-HT Reverse | 100 | GAAAATTTAATGAAACCAGAGTTAAAGGCCTCG AGCTAAGACACGATGCTTTGAGCTGTTTCTTG |
| Rr4HPAAS | p423 TEF Forward | 101 | GCATAGCAATCTAATCTAAGTTTTCTAGAACTAG TATGGGCAGCTTGCCTTCTCC |
| Rr4HPAAS | p423 TEF Reverse | 102 | CAGCCCGGGGGATCCACTAGTCTAAGACACGAT GCTTTGAGCTGTTTCTTG |
| RrAAS | pHis8-4 Forward | 103 | GAAAACTTGTACTTCCAGGCCCATGGCATGGAG GAGGAGTTGAAGCCG |
| RrAAS | pHis8-4 Reverse | 104 | CTCGAATTCGGATCCGCCATGGTCATGCATTTAT ATGCTTTTGTAGCAGTGAAGTG |
| RrPAR1 | pHis8-4 Forward | 105 | GAAAACTTGTACTTCCAGGCCCATGGCATGAGTT TAAGCGGAGCGGGG |
| RrPAR1 | pHis8-4 Reverse | 106 | CTCGAATTCGGATCCGCCATGGTCAGAGTTTGGC GAAACCCTTTTCC |
| RrPAR1 | p425 TEF Forward | 107 | GCATAGCAATCTAATCTAAGTTTTCTAGAACTAG TATGAGTTTAAGCGGAGCGGGG |
| RrPAR1 | p425 TEF Reverse | 108 | CAGCCCGGGGGATCCACTAGTTCAGAGTTTGGC GAAACCCTTTTCC |
| RrPAR2 | pHis8-4 Forward | 109 | GAAAACTTGTACTTCCAGGCCCATGGCATGGGTT TATCTGAAGAGAAGAAGTTAG |

TABLE 2-continued

Cloning primers.

| Gene | Vector/direction | SEQ ID NO: | Sequence |
|---|---|---|---|
| RrPAR2 | pHis8-4 Reverse | 110 | CTCGAATTCGGATCCGCCATGGTCATTTGTCTTTCAAACTTTCGACAGTGTCTC |
| RrUGT1 | p426TEF Forward | 111 | CAATCTAATCTAAGTTTTCTAGAACTAGTATGGTGACGAAAAAAACTCACATTCTTATCC |
| RrUGT1 | p426TEF Reverse | 112 | CAGCCCGGGGGATCCACTAGTTCAGGTAAGACCAGACACAAACTTGAC |
| RrUGT2 | p426TEF Forward | 113 | CAATCTAATCTAAGTTTTCTAGAACTAGTATGGGTTCTGATTCACGGCCTC |
| RrUGT2 | p426TEF Reverse | 114 | CAGCCCGGGGGATCCACTAGTCTAGGACAAAGTCTCTCTTCTCAACTTCAATTC |
| RrUGT2 | pHis8-4 Forward | 115 | GAAAACTTGTACTTCCAGGCCCATGGCATGGGTTCTGATTCACGGCCTC |
| RrUGT2 | pHis8-4 Reverse | 116 | CTCGAATTCGGATCCGCCATGGCTAGGACAAAGTCTCTCTTCTCAACTTCAATTC |
| RrUGT2 | pEAQ-HT Forward | 117 | GTATATTCTGCCCAAATTCGCGACCGGTATGGGTTCTGATTCACGGCCTC |
| RrUGT2 | pEAQ-HT Reverse | 118 | GAAAATTTAATGAAACCAGAGTTAAAGGCCTCGAGCTAGGACAAAGTCTCTCTTCTCAACTTC |
| RrUGT3 | p426TEF Forward | 119 | CAATCTAATCTAAGTTTTCTAGAACTAGTATGTCAGGCACACCACACATCG |
| RrUGT3 | p426TEF Reverse | 120 | CAGCCCGGGGGATCCACTAGTTCAATGCTTCATCGAACTCCGCC |
| RrUGT3 | pHis8-4 Forward | 121 | GAAAACTTGTACTTCCAGGCCCATGGCATGTCAGGCACACCACACATCG |
| RrUGT3 | pHis8-4 Reverse | 122 | CTCGAATTCGGATCCGCCATGGTCAATGCTTCATCGAACTCCGCC |
| RrUGT3 | pEAQ-HT Forward | 123 | GTATATTCTGCCCAAATTCGCGACCGGTATGTCAGGCACACCACACATCG |
| RrUGT3 | pEAQ-HT Reverse | 124 | GAAAATTTAATGAAACCAGAGTTAAAGGCCTCGAGTCAATGCTTCATCGAACTCCGCC |
| RrUGT4 | p426TEF Forward | 125 | CAATCTAATCTAAGTTTTCTAGAACTAGTATGGGTTCACAAGCCTCTCCAAAACC |
| RrUGT4 | p426TEF Reverse | 126 | CAGCCCGGGGGATCCACTAGTTCATTCCTTGAACTGGAGAATATCTTTCACAAGCC |
| RrUGT5 | p426TEF Forward | 127 | CAATCTAATCTAAGTTTTCTAGAACTAGTATGGAACCGAGACCTCACGCAG |
| RrUGT5 | p426TEF Reverse | 128 | CAGCCCGGGGGATCCACTAGTTTAATTAGTGTCACCAAGATGAGTTTTCTTTAGTAAG |
| RrUGT6 | p426TEF Forward | 129 | CAATCTAATCTAAGTTTTCTAGAACTAGTATGGAATCTGTACAAGGTGTTCAAGAAAAGC |
| RrUGT6 | p426TEF Reverse | 130 | CAGCCCGGGGGATCCACTAGTTCAGTTTGAATTCCTCGACAGGAGCAC |
| RrUGT7 | p426TEF Forward | 131 | CAATCTAATCTAAGTTTTCTAGAACTAGTATGGCTGAAAACACTCATGCTCATGC |
| RrUGT7 | p426TEF Reverse | 132 | CAGCCCGGGGGATCCACTAGTTCATTTCTTGAAGATTTGTAGGTCGTGGATG |
| RrUGT8 | p426TEF Forward | 133 | CAATCTAATCTAAGTTTTCTAGAACTAGTATGGCTTCCTCCTCTTTAGCTTGTGATTC |
| RrUGT8 | p426TEF Reverse | 134 | CAGCCCGGGGGATCCACTAGTTTATTTAACTGTTTCTTGTTTTTGCAGGACAGAATGAATG |

TABLE 2-continued

Cloning primers.

| Gene | Vector/direction | SEQ ID NO: | Sequence |
|---|---|---|---|
| RrUGT9 | p426TEF Forward | 135 | CAATCTAATCTAAGTTTTCTAGAACTAGTATGGGGTCTGAGCCACTAGTCC |
| RrUGT9 | p426TEF Reverse | 136 | CAGCCCGGGGGATCCACTAGTTTATGCTGAAATTGCATCCTTAGCAACTGG |
| RrUGT10 | p426TEF Forward | 137 | CAATCTAATCTAAGTTTTCTAGAACTAGTATGACGAGGCGCCACCAC |
| RrUGT10 | p426TEF Reverse | 138 | CAGCCCGGGGGATCCACTAGTTCATCCAAGGCCATTGACAAAACGAC |
| RrUGT11 | p426TEF Forward | 139 | CAATCTAATCTAAGTTTTCTAGAACTAGTATGGCAGGCGAGATTCTAATACTTCCG |
| RrUGT11 | p426TEF Reverse | 140 | CAGCCCGGGGGATCCACTAGTTCACTTGTGGGAGATAATGAAGTCCCTG |
| RrUGT12 | p426TEF Forward | 141 | CAATCTAATCTAAGTTTTCTAGAACTAGTATGGAGGAGGCGGCCAG |
| RrUGT12 | p426TEF Reverse | 142 | CAGCCCGGGGGATCCACTAGTTTAACACAGAGTCCAAATGTCCAGCAAC |
| RrUGT13 | p426TEF Forward | 143 | CAATCTAATCTAAGTTTTCTAGAACTAGTATGCTACCTCTCTTACATGTTACACTAAC |
| RrUGT13 | p426TEF Reverse | 144 | CAGCCCGGGGGATCCACTAGTTTACAAGCCAATGTTGGTCCTGAGATCAC |
| RrUGT14 | p426TEF Forward | 145 | CAATCTAATCTAAGTTTTCTAGAACTAGTATGGACACCACCGCCGC |
| RrUGT14 | p426TEF Reverse | 146 | CAGCCCGGGGGATCCACTAGTTTATCCCCTTCCAAGTTGAGTCAACGAC |
| RrUGT15 | p426TEF Forward | 147 | CAATCTAATCTAAGTTTTCTAGAACTAGTATGGCTGATGCTGCTCAACATGTC |
| RrUGT15 | p426TEF Reverse | 148 | CAGCCCGGGGGATCCACTAGTTTATTGAACTTTGTGAAATTGAAGATGACTCAAAAGG |
| RrUGT16 | p426TEF Forward | 149 | CAATCTAATCTAAGTTTTCTAGAACTAGTATGGCAGAGGAAAACAGAACCAGC |
| RrUGT16 | p426TEF Reverse | 150 | CAGCCCGGGGGATCCACTAGTTCATACAGCTGAAGATATTTGGATATGAATTGGTC |
| RrUGT17 | p426TEF Forward | 151 | CAATCTAATCTAAGTTTTCTAGAACTAGTATGGGCTCACTTCCTTCCAC |
| RrUGT17 | p426TEF Reverse | 152 | CAGCCCGGGGGATCCACTAGTTCAGACGCTAAACTGGACCACTTTTTCC |
| RrUGT18 | p426TEF Forward | 153 | CAATCTAATCTAAGTTTTCTAGAACTAGTATGGGCTCCCGAGGAAAGCCACATG |
| RrUGT18 | p426TEF Reverse | 154 | CAGCCCGGGGGATCCACTAGTTCATTTTGGGGAATTAGACAGCAGG |
| RrUGT19 | p426TEF Forward | 155 | CAATCTAATCTAAGTTTTCTAGAACTAGTATGACGTCATCAACACCTCCTCCTC |
| RrUGT19 | p426TEF Reverse | 156 | CAGCCCGGGGGATCCACTAGTCTAAAAAAATGCTTTAACATAGCTAGCGTCCG |
| RrUGT20 | p426TEF Forward | 157 | CAATCTAATCTAAGTTTTCTAGAACTAGTATGGGTTCACTCGACGTCGTC |
| RrUGT20 | p426TEF Reverse | 158 | CAGCCCGGGGGATCCACTAGTTCATTTCATAATAGCTTCATCAATCAACTCGG |
| RrUGT21 | p426TEF Forward | 159 | CAATCTAATCTAAGTTTTCTAGAACTAGTATGAAGTCCAACACTCATCTATTCCTC |

TABLE 2-continued

Cloning primers.

| Gene | Vector/direction | SEQ ID NO: | Sequence |
|---|---|---|---|
| RrUGT21 | p426TEF Reverse | 160 | CAGCCCGGGGGATCCACTAGTTCATACAACCGGCTCCAGTTGAC |
| RrUGT22 | p426TEF Forward | 161 | CAATCTAATCTAAGTTTTCTAGAACTAGTATGAAAACTCCTCAAAATCCACACGTAG |
| RrUGT22 | p426TEF Reverse | 162 | CAGCCCGGGGGATCCACTAGTTCATCCTGATAAATCTTTGAACTCATCTTGCTC |
| RrUGT23 | p426TEF Forward | 163 | CAATCTAATCTAAGTTTTCTAGAACTAGTATGGAAAGGCAGAGTGATCACCAAG |
| RrUGT23 | p426TEF Reverse | 164 | CAGCCCGGGGGATCCACTAGTTCATTTGGTGGATATCACATCTCTAACAAACTG |
| RrUGT24 | p426TEF Forward | 165 | CAATCTAATCTAAGTTTTCTAGAACTAGTATGAGCAACGCCGCCG |
| RrUGT24 | p426TEF Reverse | 166 | CAGCCCGGGGGATCCACTAGTTTAGTTTATGACTTCATTCACTTGCTCCAACAAC |
| RrUGT25 | p426TEF Forward | 167 | CAATCTAATCTAAGTTTTCTAGAACTAGTATGGCGCGCCACCACTTTG |
| RrUGT25 | p426TEF Reverse | 168 | CAGCCCGGGGGATCCACTAGTTTAGCAGGTAACAAGGTTATTAACCAAATCCTTGAG |
| RrUGT26 | p426TEF Forward | 169 | CAATCTAATCTAAGTTTTCTAGAACTAGTATGTCATCAGATTCCGGCCACATTATCC |
| RrUGT26 | p426TEF Reverse | 170 | CAGCCCGGGGGATCCACTAGTCTATATTATTTTTCTTAATGCCATGACTTGTCGGACC |
| RrUGT27 | p426TEF Forward | 171 | CAATCTAATCTAAGTTTTCTAGAACTAGTATGAGTTCAGTCAATGCTCAAAAGCC |
| RrUGT27 | p426TEF Reverse | 172 | CAGCCCGGGGGATCCACTAGTTCAAAAGTGCATTAGTAGTCCTTCCACAAATC |
| RrUGT28 | p426TEF Forward | 173 | CAATCTAATCTAAGTTTTCTAGAACTAGTATGGACTCGGTTGATCTGAACAAG |
| RrUGT28 | p426TEF Reverse | 174 | CAGCCCGGGGGATCCACTAGTCTAGTTGGCACTTGGCAACACAATCG |
| RrUGT29 | p426TEF Forward | 175 | CAATCTAATCTAAGTTTTCTAGAACTAGTATGGGATCTCTAGGAAAGAAGATTCAAC |
| RrUGT29 | p426TEF Reverse | 176 | CAGCCCGGGGGATCCACTAGTTTAGGTTGTAACTACAATTTTTTTTTGGAC |
| RrUGT29 | pHis8-4 Forward | 177 | GAAAACTTGTACTTCCAGGCCCATGGCATGGGATCTCTAGGAAAGAAGATTCAAC |
| RrUGT29 | pHis8-4 Reverse | 178 | CTCGAATTCGGATCCGCCATGGTTAGGTTGTAACTACAATTTTTTTTTGGAC |
| RrUGT29 | pEAQ-HT Forward | 179 | GTATATTCTGCCCAAATTCGCGACCGGTATGGGATCTCTAGGAAAGAAGATTCAAC |
| RrUGT29 | pEAQ-HT Reverse | 180 | GAAATTTAATGAAACCAGAGTTAAAGGCCTCGAGTTAGGTTGTAACTACAATTTTTTTTTGGAC |
| RrUGT30 | p426TEF Forward | 181 | CAATCTAATCTAAGTTTTCTAGAACTAGTATGGGCTCCCGAGGAAAGCCACATG |
| RrUGT30 | p426TEF Reverse | 182 | CAGCCCGGGGGATCCACTAGTTCATTTTGGGGAATTAGACAGCAGG |
| RrUGT31 | p426TEF Forward | 183 | CAATCTAATCTAAGTTTTCTAGAACTAGTATGGAATCTGTACAAGGTGTTCAAGAAAAG |
| RrUGT31 | p426TEF Reverse | 184 | CAGCCCGGGGGATCCACTAGTTCAGTTTGAATTCCTCGACAGGAGCAC |

TABLE 2-continued

Cloning primers.

| Gene | Vector/direction | SEQ ID NO: | Sequence |
|---|---|---|---|
| RrUGT32 | p426TEF Forward | 185 | CAATCTAATCTAAGTTTTCTAGAACTAGTATGGACTCGGTTGATCTGAACAAGAAACC |
| RrUGT32 | p426TEF Reverse | 186 | CAGCCCGGGGGATCCACTAGTCTACAATTTTTTTTTGGACAGAAGTACGTCATTTATAAGTC |
| RrUGT33 | p426TEF Forward | 187 | CAATCTAATCTAAGTTTTCTAGAACTAGTATGAGCTTAATTGAAAAACCACTCACG |
| RrUGT33 | p426TEF Reverse | 188 | CAGCCCGGGGGATCCACTAGTCTAACGGATATGTTTTGTTTTTGAGAGCAGGAC |
| RrUGT33 | pHis8-4 Forward | 189 | GAAAACTTGTACTTCCAGGCCCATGGCATGAGCTTAATTGAAAAACCACTCACG |
| RrUGT33 | pHis8-4 Reverse | 190 | CTCGAATTCGGATCCGCCATGGCTAACGGATATGTTTTGTTTTTGAGAGCAGGAC |
| RrUGT33 | pEAQ-HT Forward | 191 | GTATATTCTGCCCAAATTCGCGACCGGTATGAGCTTAATTGAAAAACCACTCACG |
| RrUGT33 | pEAQ-HT Reverse | 192 | GAAAATTTAATGAAACCAGAGTTAAAGGCCTCGAGCTAACGGATATGTTTTGTTTTTGAGAGCAGGAC |
| RrUGT34 | p426TEF Forward | 193 | GCATAGCAATCTAATCTAAGTTTTCTAGAACTAGTTGGACCCTGACGACAGCGTTTTG |
| RrUGT34 | p426TEF Reverse | 194 | CAGCCCGGGGGATCCACTAGTTTAGTTTTTGTTCTCGTACAAATAATGCACAAACTCATC |
| Pc4HPAAS | pHis8-4 Forward | 195 | GAAAACTTGTACTTCCAGGCCCATGGCATGGGCTCCATCGATAATC |
| Pc4HPAAS | pHis8-4 Reverse | 196 | CTCGAATTCGGATCCGCCATGGTTAGGATAAAATATTCACGATCTTCT |
| Pc4HPAAS | pEAQ-HT Forward | 197 | GTATATTCTGCCCAAATTCGCGACCGGTATGGGCTCCATCGATAATC |
| Pc4HPAAS | pEAQ-HT Reverse | 198 | GAAAATTTAATGAAACCAGAGTTAAAGGCCTCGAGTTAGGATAAAATATTCACGATCTTC |
| PsTyDC | pHis8-4 Forward | 199 | GAAAACTTGTACTTCCAGGCCCATGGCATGGGAAGCCTTCCGACTAATAACCTTG |
| PsTyDC | pHis8-4 Reverse | 200 | CTCGAATTCGGATCCGCCATGGCTAGGCACCAAGTATGGCATCTGTATG |
| PsTyDC | pEAQ-HT Forward | 201 | GTATATTCTGCCCAAATTCGCGACCGGTATGGGAAGCCTTCCGACTAATAACCTTG |
| PsTyDC | pEAQ-HT Reverse | 202 | GAAAATTTAATGAAACCAGAGTTAAAGGCCTCGAGCTAGGCACCAAGTATGGCATCTGTATG |
| AAS55083 | p426TEF Forward | 203 | CAATCTAATCTAAGTTTTCTAGAACTAGTATGGCAGGCAGTGGGACTG |
| AAS55083 | p426TEF Reverse | 204 | CAGCCCGGGGGATCCACTAGTTCAGTGTTTAACTGAGGATCTCCACTTTTTAGC |
| EU567325 | p426TEF Forward | 205 | GCATAGCAATCTAATCTAAGTTTTCTAGAACTAGTATGGGTTCTGAAACTCGGCCTTTG |
| EU567325 | p426TEF Reverse | 206 | CAGCCCGGGGGATCCACTAGTCTAGACTTTCTTTAACTTGAGTTCCTGAAGCAG |

Example #2: Results

Enzymes of the plant aromatic amino acid decarboxylases (AAAD) family that can be used in the production of one or more of tyrosol, salidroside, and icariside D2 were identified. These plant AAAD-family enzymes contain substitutions in one of two active site residues responsible for influencing aldehyde synthase chemistry. These activity-influencing residues are boxed in the multiple sequence alignment of biochemically characterized plant AAADs show in FIG. 26.

Figure 32:
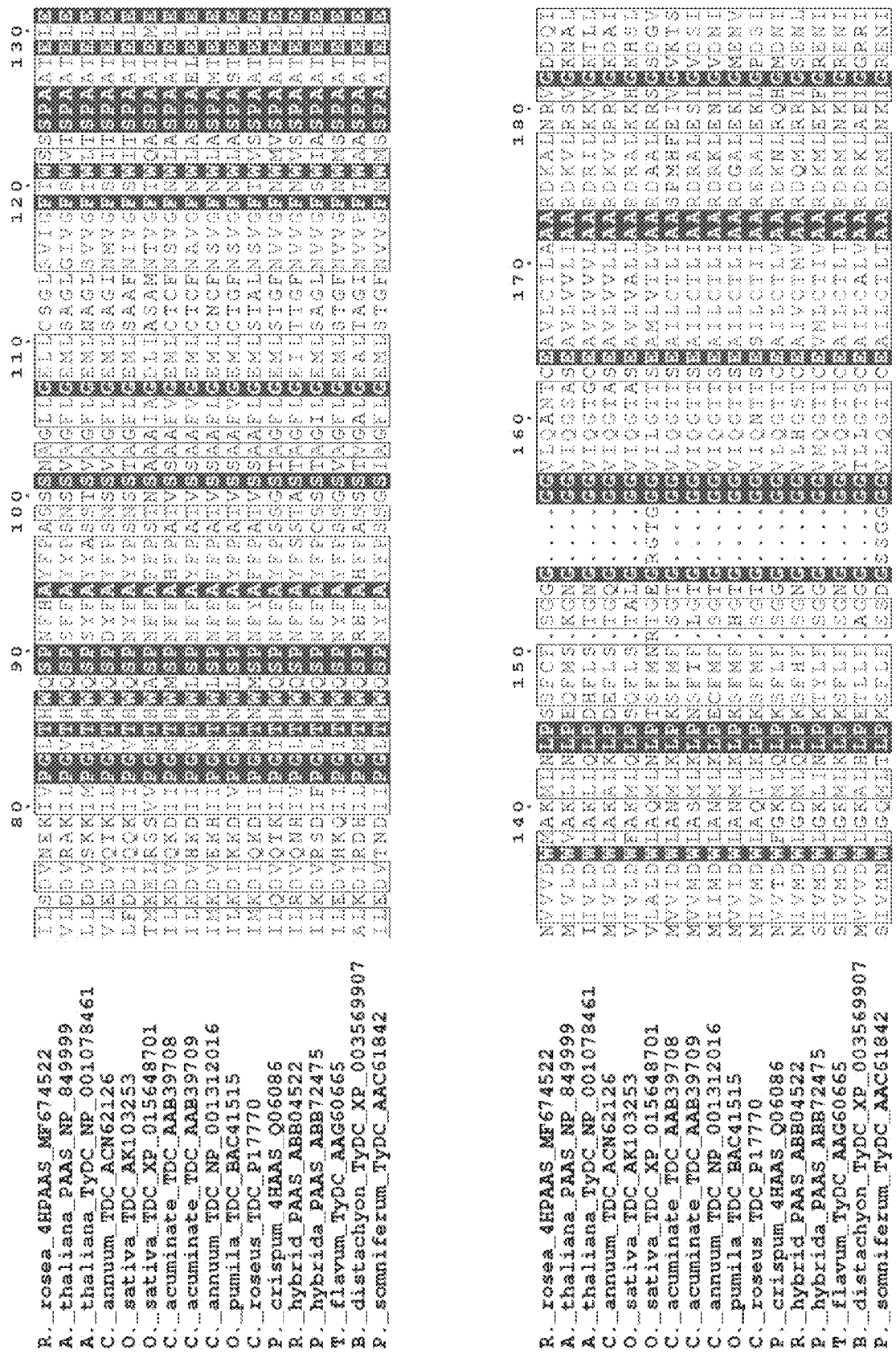
FIG. 32 is a multiple sequence alignment of key residues within biochemically characterized plant AAADs.

Plant AAAD enzymes that contain an active site histidine to asparagine or aspartic acid substitution have an aldehyde synthase activity. This active site substitution is represented by the Rr4HPAAS MF674522 histidine 198 in FIGS. 31 and 32.

Plant AAAD enzymes that contain an active site tyrosine to leucine, isoleucine, phenylalanine, methionine or valine substitution have an aldehyde synthase activity. This active site substitution is represented by the Rr4HPAAS MF674522 phenylalanine 343 in FIGS. 31 and 32.

Figure 33:
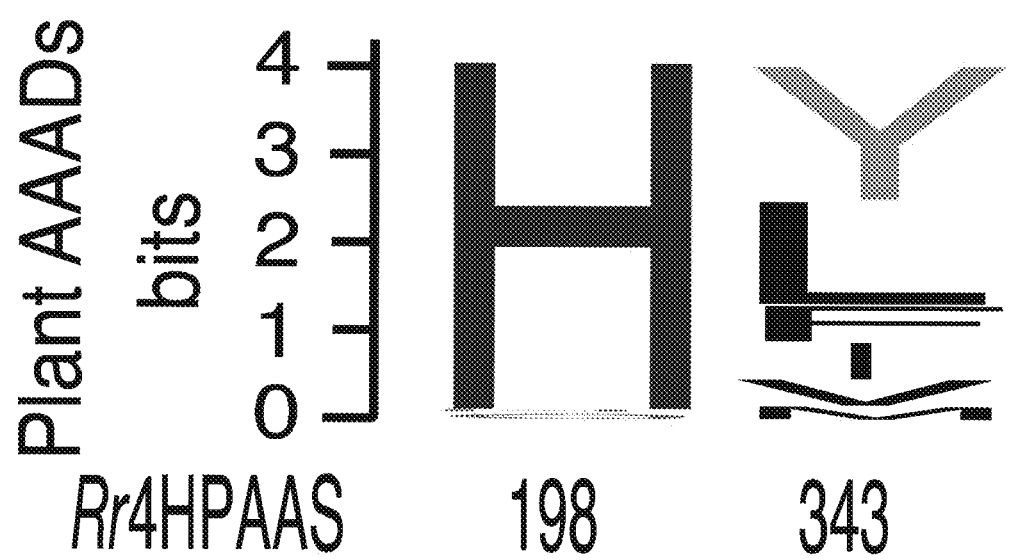
FIG. 33 is a chart showing sequence conservation for plant AAAD activity dictating residues. Multiple sequence alignments of the queried AAAD sequences evaluated for active site conservation using WebLogo. Polar amino acids are green, basic amino acids are blue, acidic amino acids are red and hydrophobic amino acids are black. The y-axis units (bits) display the maximum entropy for the given residue. The representative residues from the Rr4HPAAS MF674522 sequence are listed below with residue numbers.

These active site substitutions at positions 198 and 343 were selected from natural variation, shown in FIG. 33, found within all plant AAAD sequences available on Phytozome V12.1. We have curated 226 plant AAAD sequences from Phytozome 12. The list was queried for sequences containing substitution in one of the two activity dictating residues to make a list of 73 enzymes that likely have some 4HPAAS activity. These 73 AAS enzymes are identified as SEQ ID NOS: 21-93. In some embodiments, any of the enzymes of SEQ ID NOS: 21-93 can provide 4HPAAS activity in a host cell or method described herein.

Figure 34A:
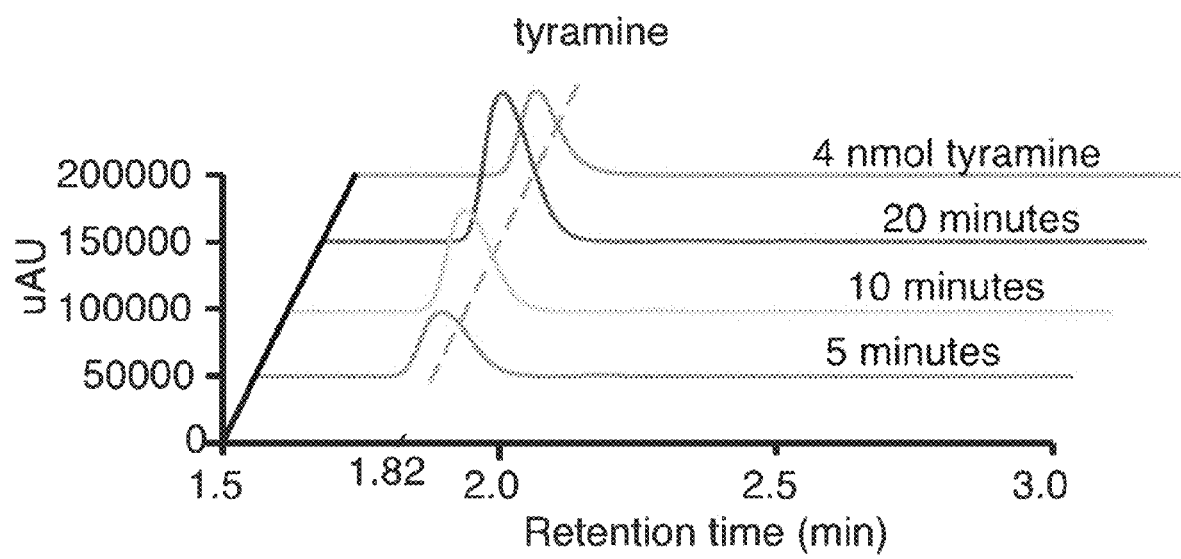
FIGS. 34A-C show product formation of PsTyDC and mutants.
Figure 34B:
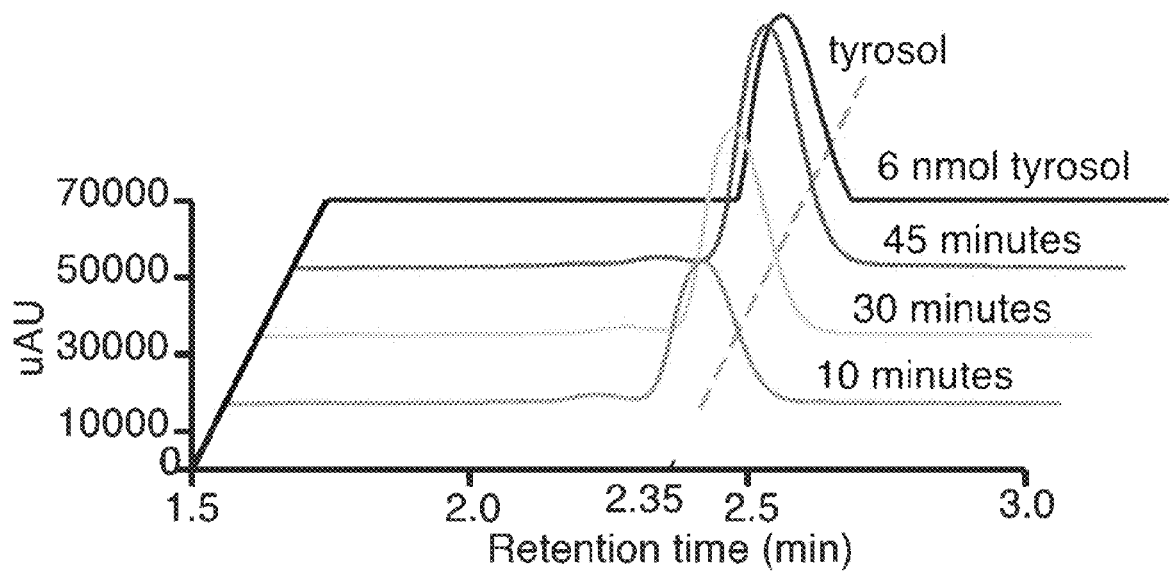
Figure 34C:
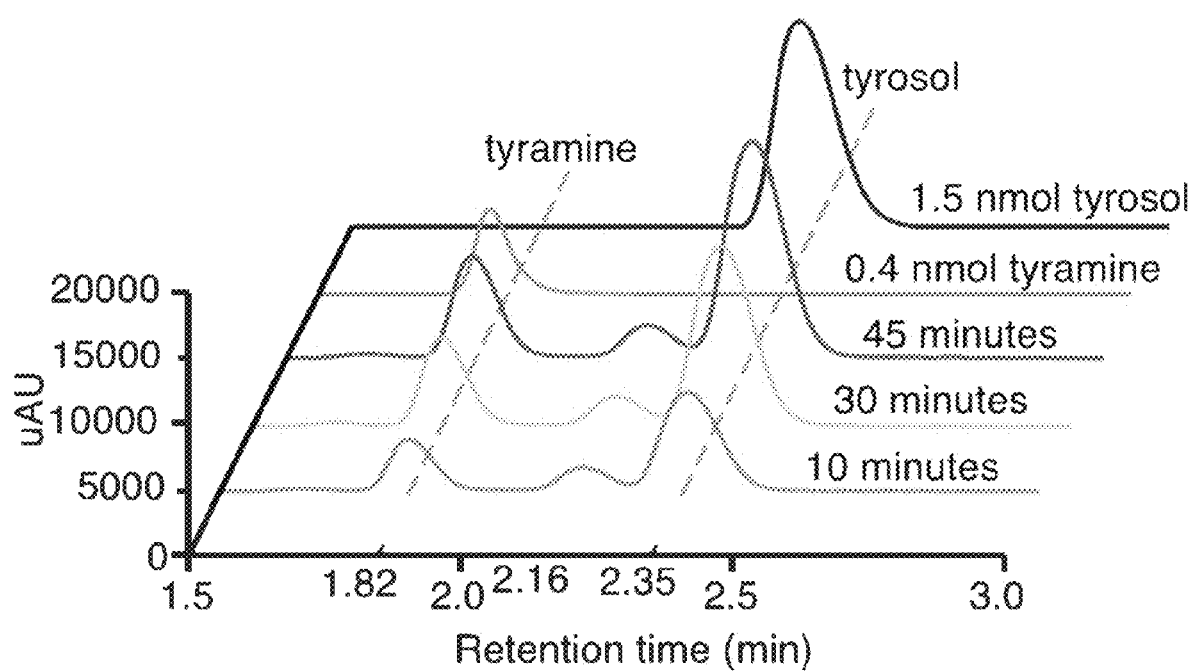

To demonstrate the roles of these residues in aldehyde synthase chemistry, the biochemical activity of wild type and mutant *Papaver somniferum* tyrosine decarboxylase (PsTyDC) enzymes were characterized. The substitution of the active site histidine (Rr4HPAAS MF674522 histidine 198) or the active site tyrosine (Rr4HPAAS MF674522 phenylalanine 343) within a *Papaver somniferum* tyrosine decarboxylase (PsTyDC) results in aldehyde synthase chemistry. FIGS. 34A-C are chromatograms showing product formation of PsTyDC and mutants.

Sequences

TABLE 2

Summary of Sequences.

| SEQ ID NO.: | Description |
| --- | --- |
| 1 | Rr4HPAAS DNA |
| 2 | Rr4HPAAS GenBank accession MF674522 |
| 3 | Rr4HPAR1 DNA |
| 4 | Rr4HPAR1 amino acid GenBank accession MF674524 |
| 5 | RrUGT2 DNA |
| 6 | RrUGT2 amino acid GenBank accession MF674527 |
| 7 | RrUGT3 DNA |
| 8 | RrUGT3 amino acid GenBank accession MF674528 |
| 9 | RrUGT7 DNA |
| 10 | RrUGT7 amino acid GenBank accession MF674532 |
| 11 | RrUGT13 DNA |
| 12 | RrUGT13 amino acid GenBank accession MF674538 |
| 13 | RrUGT17 DNA |
| 14 | RrUGT17 amino acid GenBank accession MF674542 |
| 15 | RrUGT29 DNA |
| 16 | RrUGT29 amino acid GenBank accession MF674554 |
| 17 | RrUGT32 DNA |
| 18 | RrUGT32 amino acid GenBank accession MF674557 |
| 19 | RrUGT33 DNA |
| 20 | RrUGT33 amino acid GenBank accession MF674558 |
| 21 | *Arabidopsis thaliana* AT2G20340.1 |

TABLE 2-continued

Summary of Sequences.

| SEQ ID NO.: | Description |
| --- | --- |
| 22 | *Brachypodium distachyon* 1g28960.3 |
| 23 | *Carica papaya* 16427710 |
| 24 | *Ricinus communis* 16804377 |
| 25 | *Cucumis sativus* 16963476 |
| 26 | *Vitis vinifera* 17835588 |
| 27 | *Citrus sinensis* 18113817 |
| 28 | *Capsella rubella* 20900667 |
| 29 | *Malus domestica* 22636618 |
| 30 | *Linum usitatissimum* 23178995 |
| 31 | *Eutrema salsugineum* 20200788 |
| 32 | *Populus trichocarpa* 27022899 |
| 33 | *Brachypodium stacei* 06G160800.1 |
| 34 | *Physcomitrella patens* Pp3c4_30790V3.1 |
| 35 | *Ananas comosus* 33033299 |
| 36 | *Zostera marina* 33182387 |
| 37 | *Daucus carota* subsp. *sativus* 36055203 |
| 38 | *Trifolium pratense* 35974269 |
| 39 | *Arabidopsis lyrata* 35943929 |
| 40 | *Sorghum bicolor* 002G120700.1 |
| 41 | *Sphagnum fallax* 0166s0011.1 |
| 42 | *Kalanchoe laxiflora* 1398s0003.1 |
| 43 | *Manihot esculenta* 12G038600.1 |
| 44 | *Prunus persica* 8G214500.1 |
| 45 | *Eucalyptus grandis* K01418.1 |
| 46 | *Amborella trichopoda* 31565185 |
| 47 | *Salix purpurea* 0252s0200.1 |
| 48 | *Medicago truncatula* 31080941 |
| 49 | *Brassica rapa* I01156.1 |
| 50 | *Brassica rapa* I04706.1 |
| 51 | *Brassica rapa* G00043.1 |
| 52 | *Glycine max* 03G167900.1 |
| 53 | *Fragaria vesca* 27261550 |
| 54 | *Kalanchoe fedtschenkoi* 0172s0035.1 |
| 55 | *Capsella grandiflora* 22666s0001.1 |
| 56 | *Selaginella moellendorffii* 15420188 |
| 57 | *Setaria italica* 3G188200.1 |
| 58 | *Kalanchoe fedtschenkoi* 0033s0078.1 |
| 59 | *Daucus carota* subsp. *sativus* 36068870 |
| 60 | *Daucus carota* subsp. *sativus* 36056758 |
| 61 | *Solanum tuberosum* 3DMP400026166 |
| 62 | *Solanum tuberosum* 3DMP400024738 |
| 63 | *Solanum lycopersicum* 36137005 |
| 64 | *Daucus carota* subsp. *sativus* 36065781 |
| 65 | *Oropetium thomaeum* 35995617 |
| 66 | *Oryza sativa* 33157740 |
| 67 | *Brachypodium stacei* 01G392300.1 |
| 68 | *Amaranthus hypochondriacus* 32828676 |
| 69 | *Brachypodium distachyon* 5g21770.1 |
| 70 | *Brachypodium distachyon* 2g02360.1 |
| 71 | *Sorghum bicolor* 009G192600.1 |
| 72 | *Kalanchoe laxiflora* 0994s0009.1 |
| 73 | *Kalanchoe laxiflora* 0003s0173.1 |
| 74 | *Panicum hallii* 32512198 |
| 75 | *Prunus persica* 6G202600.1 |
| 76 | *Prunus persica* 4G086700.1 |
| 77 | *Prunus persica* 4G087100.1 |
| 78 | *Medicago truncatula* 31073039 |
| 79 | *Zea mays* GRMZM2G009400 |
| 80 | *Glycine max* 07G059000.1 |
| 81 | *Panicum virgatum* Ca01381.1 |
| 82 | *Theobroma cacao* 27425420 |
| 83 | *Fragaria vesca* 27274768 |
| 84 | *Gossypium raimondii* 26786642 |
| 85 | *Populus trichocarpa* 26994989 |
| 86 | *Malus domestica* 22679008 |
| 87 | *Citrus clementina* 20801973 |
| 88 | *Citrus clementina* 20818150 |
| 89 | *Vitis vinifera* 17834108 |
| 90 | *Petunia hybrida* ABB72475.1 |
| 91 | *Carica papaya* 16421889 |
| 92 | *Sphagnum fallax* 0042s0024.1 |
| 93 | *Eucalyptus grandis* E01788.1 |
| 94 | pHis8-4 |
| 95 | pEAQ-HT |
| 96 | pJKW 1410 |

Rr4HPAAS DNA (SEQ ID NO: 1):
ATGGGCAGCTTGCCTTCTCCTAATGATCCATCAAACACCTTCAACCCCATGGACCTC

ACCGAGTTATCCACCGAGTCGAAACTCGTCGTAGATTTCATAACTCAGTACTACCAA

ACCCTAGAGACCCGACCCGTCCAGCCACGGGTCAAGCCAGGTTTCTTAACGGGCCA

GCTTCCAGATAAAGCACCCTTTCATGGTGAATCAATGGAAGTAATATTGTCTGATGT

AAATGAGAAGATTGTCCCTGGCCTCACTCATTGGCAAAGCCCTAATTTCCATGCATA

CTTTCCAGCCAGTTCCAGCAACGCAGGGCTGTTGGGAGAGTTACTATGCTCCGGACT

CAGTGTCATTGGGTTCACATGGAGCTCCTCCCCTGCCGCGACGGAGCTTGAGAATGT

CGTGGTTGACTGGATGGCCAAGATGCTTAACCTTCCATCCTCTTTCTGCTTCTCCGGC

GGAGGCGGTGGCGTTCTGCAAGCAAACACTTGCGAGGCTGTGTTGTGCACTTTAGCC

GCTGCGAGGGACAAGGCTCTTAACCGGGTGGGAGATGATCAGATCAATAAACTGGT

CCTCTACTGCTCCGACCAAACACATTTCACAATCCACAAGGGCGCAAAGTTGATAGG

AATCCGATCAAAGAACATAAAATCAATCACTACTAAGAAAGAGAACGAGTTTAAAC

TCTGTCCTAACGACCTACGCGACGCGATAAGGAGTGATCTGGAAGCAGGACTAGTT

CCGTTTTACGTATGCGGAACGATTGGAACGACCGCGTTAGGAGTTGTGGATCCGATT

AAAGAGCTGGGTAAGGTGGCAAGAGAGTTTGATTTGTGGTTACATGTTGATGGAGC

TTATGGTGGCAGTGCATGCATATGCCCTGAGTTTCAGCATTACCTTGATGGAGTTGA

CCTTGTTGACTCGATCAGCATGAATGCACATAAATGGCTTTTATCCAATCTAGATTG

CTGCTTCCTGTGGCTTCAATCTCCTAACGCCCTAATCGAATCCCTGGCCGCAGAAGC

TAACTTTCTGAAAGGTGGTAGTGAGATGGTGGATTACAAGGACTGGCAGATATCGTT

GAGTCGTCGATTTAGAGCGATCAAGATGTGGATGGTGATAAGGCGATACGGTGTGA

GTAATCTCATTGAGCATATTCGATCCGACGTGAGCATGGCGGTGAGATTCGAAGAG

ATGGTGGCGGCGGACGACCGGTTTGAAATCGTGTTTCCTAGAAAGTTTGCGCTTGTT

TGCTTCAAGCTTAGTAGCGAGAAGACACCACCGGGCCGCGACTCGGAGTTAACTCG

TGAGCTGATGGAGAGAGTCAACTCGAGTGGGAAGGCTTACTTGAGTGGAGTTCAAA

TGGGTCGGATCTTCTTCATCAGGTGTGTGATCGGGTCGAGTTTGACTGAGGAGAGAC

ACGTCGATAATCTGTGGAGGCTCATTCAAGAAACAGCTCAAAGCATCGTGTCTTAG

Rr4HPAAS GenBank accession M1F674522 (SEQ ID NO: 2):
MGSLPSPNDPSNTFNPMDLTELSTESKLVVDFITQYYQTLETRPVQPRVKPGFLTGQLPD

KAPFHGESMEVILSDVNEKIVPGLTHWQSPNFHAYFPASSSNAGLLGELLCSGLSVIGFT

WSSSPAATELENVVVDWMAKMLNLPSSFCFSGGGGGVLQANTCEAVLCTLAAARDKA

LNRVGDDQINKLVLYCSDQTHFTIHKGAKLIGIRSKNIKSITTKKENEFKLCPNDLRDAIR

SDLEAGLVPFYVCGTIGTTALGVVDPIKELGKVAREFDLWLHVDGAYGGSACICPEFQH

YLDGVDLVDSISMNAHKWLLSNLDCCFLWLQSPNALIESLAAEANFLKGGSEMVDYKD

WQISLSRRFRAIKMWMVIRRYGVSNLIEHIRSDVSMAVRFEEMVAADDRFEIVFPRKFA

LVCFKLSSEKTPPGRDSELTRELMERVNSSGKAYLSGVQMGRIFFIRCVIGSSLTEERHVD

NLWRLIQETAQSIVS

Rr4HPAR1 DNA (SEQ ID NO: 3):
ATGAGTTTAAGCGGAGCGGGGAAGGTGGTTTGCGTTACCGGCGCGTCTGGCTACAT

AGCGTCCTGGCTCGTCAAGCTTCTTCTCCAGCGCGGTTATACCGTCAAGGCCTCCGT

TCGCGATCCTAATGATCCGAAAAAGACTCAGCACTTGACGGCACTTGATGGAGCTA

AGGAGAGGCTGCAGTTGTACAAAGCCAATTTGCTTGAACAAGGCTCGTTTGATCCA

TAGTTGAAGGATGTGAAGGTGTTTTCCACACCGCGTCTCCCTTTTATCATGCAGTGG

ATGATCCGCAGGCCGAGTTAATTGACCCTGCTGTCAAGGGAACACTCAATGTTCTTT

CTTCATGTGCTAAAGTTGCGTCTCTTAAAAGAGTAGTCCTGACTTCTTCGATTGCTGC

TGTTGCATATAATGGGAAACCCCGTACTCCGGAGGTTGTAGTTGACGAGACTTGGTT

TTCTAACCCAGATGTTTGTAAGGAGATGAAGCTTTGGTATGTCATATCCAAGACACT

CGCTGAAGAAGCAGCATGGAAGTTTGTGAAAGAGAAAGGAATAGACATGGTTACCA

TAAATCCGGCCATGGTGATTGGTCCCCTTCTGCAACCAACACTCAATACCAGTGCTG

CTGCTATTCTGAACTTGATCAATGGATCGGAGACATACCCAAATGCTTCTTTTGGAT

GGGTCAATGTGAAAGATGTTGCAGAAGCACACGTTCTTGCATTTGAGGTTCCTTCAG

CTAATGGTAGATACTGCTTGGTGGAAAGAGTTGCCCACAGTTCTGAAGTGGTGAACA

TGCTCCATGAGCTCTACCCTGATATCAAACTTCCCGCCAAGTGTGCAGATGACAAAC

CATTTGTGCCAATTTATCAAGTTTCAAAAGAAAAGGCACATACTTTAGGGGTAAAAT

TCATTCCTTTAGAGGTAAGCCTCAAGGAAACAGTTGAAAGCTTGAAGGAAAAGGGT

TTCGCCAAACTCTGA

Rr4HPAR1 amino acid GenBank accession M1F674524 (SEQ ID NO: 4):
MSLSGAGKVVCVTGASGYIASWLVKLLLQRGYTVKASVRDPNDPKKTQHLTALDGAK

ERLQLYKANLLEQGSFDPIVEGCEGVFHTASPFYHAVDDPQAELIDPAVKGTLNVLSSC

AKVASLKRVVLTSSIAAVAYNGKPRTPEVVVDETWFSNPDVCKEMKLWYVISKTLAEE

AAWKFVKEKGIDMVTINPAMVIGPLLQPTLNTSAAAILNLINGSETYPNASFGWVNVKD

VAEAHVLAFEVPSANGRYCLVERVAHSSEVVNMLHELYPDIKLPAKCADDKPFVPIYQ

VSKEKAHTLGVKFIPLEVSLKETVESLKEKGFAKL

RrUGT2 DNA (SEQ ID NO: 5):
ATGGGTTCTGATTCACGGCCTCTACGCGTCTTCTTCTTTCCCTTCATGGCTCACGGCC

ATCTGATTCCGATGGTCGACATCGCCAGACTCTTCTCTTCTCAAGGAGTCCACTCCA

CCATCATCACCACCCCACTAAACGCCAATTACATCTCCAAAACGACGTCTCTATCCA

TCAAAACGATACCGTTTCCTGCTGCGGAAGTTGGGCTTCCGGACGGCTGCGAGAATA

TCGACATGCTTCCTTCGCCCGATCTCTTCTTCAAATTTTTCCAAGCCGCCAATTTACT

CCAAGCGCCGTTCGAGAACCTTCTAGAACTCGAAAGGCCCGATTGCTTAATCTCCGA

CATCTTCTTCCCCTGGTCAGTCGACTCCGCCGAGAAATTCAACATCCCGAGACTCGT

TTTCCACGGCACGAGCTTCTTCGCCATGTGCGCCATGGAGAGCTTGAAGACCCACAA

GCCCTATAAATCGGTAAGCACCGACTCTGAACCGTTCTTAATCCCGAATCTCCCTGA

TGAAATCAAAATGACTAAAAGTCAGTTCACGGTTGACGCTTGGGAAGACACCGAAA

AGGGCCTTGGGAAGCTGTTGGCTGATGCGAGAGCTTCAGGGCTGAGGAGCTTCGGC

ATGATCGTAAACAGCTTCCACGAGCTCGAACCGGCTTACGCGGATTATTACAAGAAT

GTGTTGAACATGAAAGCGTGGTGTGTCGGGCCTGTTTCGTTATATAACCGAAACGAT

GACGAGAAAATTGCAAGAGGGAAGAAATCAGCAATCGATGATCATGAGTGTTTAAA

ATGGCTGGAGGGAAAGCAGCCAGACTCCGTCGTGTACGTTTGTTTCGGGAGCAGCG

CGAGCTTCCCTGATGAGCAGTTGCGCGATATCGCATTGGGGCTGGAAGAATCTGGA

GTAAATTTCATCTGGGTGATCAGGAGAAGTTCCGAGTCAGGATCAGAAGATTACTTG

CCGGAGGGGTTTGAGGACCGGGTGAAGGACAGAGGGCTCGTGATCCGAGGTTGGGC

GCCACAGGTACTGATTTTGGACCATCCGTCGGTTGGGGGATTTGTGACTCACTGCGG

ATGGAATTCGGCATTGGAGGGGATTTCAGCTGGCTTGCCGATGGTGACTTGGCCACT

```
GTTCGCAGAGCAGTTTTTCAACCAGAAATTGATTACGGATGTGTTGAAAGTTGGGGT

TGAGGTTGGAGTGCAGAAATGGTCTCGGAACGGGGAGGATCGCGTGACGAAGGAG

AAGGTTGAGAAGGCGGTGAGGGCTGTTATGGTTGGGGAGGACGCTGAGGAGAGGC

GTGGCAGAGCTCGTCAGCTTGGGAAATTGGCAAAGAAAGCTGTGGCGAAAGATGGG

TCTTCGTACATTGATCTCCACAATTTGCTTGATGAATTGAAGTTGAGAAGAGAGACT

TTGTCCTAG

RrUGT2 amino acid GenBank accession MF674527 (SEQ ID NO: 6):
MGSDSRPLRVFFFPFMAHGHLIPMVDIARLFSSQGVHSTIITTPLNANYISKTTSLSIKTIPF

PAAEVGLPDGCENIDMLPSPDLFFKFFQAANLLQAPFENLLELERPDCLISDIFFPWSVDS

AEKFNIPRLVFHGTSFFAMCAMESLKTHKPYKSVSTDSEPFLIPNLPDEIKMTKSQFTVD

AWEDTEKGLGKLLADARASGLRSFGMIVNSFHELEPAYADYYKNVLNMKAWCVGPVS

LYNRNDDEKIARGKKSAIDDHECLKWLEGKQPDSVVYVCFGSSASFPDEQLRDIALGLE

ESGVNFIWVIRRSSESGSEDYLPEGFEDRVKDRGLVIRGWAPQVLILDHPSVGGFVTHCG

WNSALEGISAGLPMVTWPLFAEQFFNQKLITDVLKVGVEVGVQKWSRNGEDRVTKEK

VEKAVRAVMVGEDAEERRGRARQLGKLAKKAVAKDGSSYIDLHNLLDELKLRRETLS

RrUGT3 DNA (SEQ ID NO: 7):
ATGTCAGGCACACCACACATCGCCATCCTCCCCAGCCCCGGCATGGGCCACCTCATC

CCCATGGCCGAGTTCGCCAAGCGCCTAGTCCACCACCACAACTTCAGTATCACCTTC

GTCATCCCTACCGACGGCCCACCTTCCTCCGCCTACCAACAAGTCCTCACCTCCCTCC

CATCTTCCATAGATCACATCTTCCTTCCACAAGTCGACTTAACCGACGTCGTATCAC

AATCACCAGCTCATCCCAGAATCGAAACCCTAATCTCCCTCACCGTCGCTCGCTCCC

TCTCCTCCCTCCGCACCACCTTATCCTCTCTCCAATCGTCTAAAAACCTCGTCTCGCT

CGTCGTTGATCTTTTCGGCACTGATGCATTCGACCCGGCCATCGAGCTCGGCATCTC

GCCCTACATTTTCTTCCCTTCCACAGCCATGACGCTCTCGCTCTTCCTATACATGCCT

CAGCTTGACAAATCAGTCACGTGCGAATTTCGTCACATGACGGATTTGGTTCGAATT

CCTGGATGCGTTCCTGTCCGTGGATCGGATTTATTCGACCCGGTTCAAGACAGGACC

GACGAGGCTTATAAATGGGTCATACATCACTCCAACAGGTACCCTATGGCGGAGGG

TGTTATAGAGAATAGCTTCATGGAGTTGGAACATGGTGCGTTAAAGTATTTGCAAAC

GGTTCAATCGGGTAAGCCGCCTGTCTACGCGGTCGGACCGTTGATTAAAATGGATTA

TGATGTTGACGATTCCGGGTCGAAGATAATCGAGTGGCTCGATGATCAACCGGTTGG

TTCGGTTTTATTTGTTTCGTTTGGAAGCGGCGGAACGCTCTCGTATGAGCAAATGAC

CGAGCTGGCTCACGGTTTGGAATCGAGCCAGCAACGGTTCTTATGGGTGGTTCGGAG

TCCGAATCAAATCCCCAACAGCACGTATTTCAGTGTACAAAGCCAAAAAGACCCGT

TGGCTTACTTGCCAGAAGGATTTTTAAACCGAACCGAGGGTAGGGGTCTGGTCGTAT

CGAATTGGGCCCCACAGGCTCAAATTTTGAGTCACGGTTCGACCGGTGGGTTCATGA

GCCACTGTGGTTGGAATTCGATTTTGGAGAGTGTGGTGCACGGCGTGCCGATCATAG

CGTGGCCGTTGTACGCCGAGCAGAAGATGAATTCGATAATCGTGGTGGAGGACGTT

AAGGTGGCGCTGAGGCCGGCGGGGGTAGGGGAGAGGGTGGTGGAGAGGTCGGAGA

TAACCGCAGTGGTGAAGGCGTTGATGGAGGGTGAGGAGGGGAAGAAGGTAAGGAA

TAGGATGAAGGAACTCAAGGAAGCGGCGGCACGTGCGGTTAGTGATGACGGTGCGT

CGACCATAGCGATTGCGGACTTGGCGCAAAAATGGCGGAGTTCGATGAAGCATTGA
```

-continued

RrUGT3 amino acid GenBank accession MF674528 (SEQ ID NO: 8):
MSGTPHIAILPSPGMGHLIPMAEFAKRLVHHHNFSITFVIPTDGPPSSAYQQVLTSLPSSID

HIFLPQVDLTDVVSQSPAHPRIETLISLTVARSLSSLRTTLSSLQSSKNLVSLVVDLFGTDA

FDPAIELGISPYIFFPSTAMTLSLFLYMPQLDKSVTCEFRHMTDLVRIPGCVPVRGSDLFD

PVQDRTDEAYKWVIHEISNRYPMAEGVIENSFMELEHGALKYLQTVQSGKPPVYAVGPL

IKMDYDVDDSGSKIIEWLDDQPVGSVLFVSFGSGGTLSYEQMTELAHGLESSQQRFLWV

VRSPNQIPNSTYFSVQSQKDPLAYLPEGFLNRTEGRGLVVSNWAPQAQILSHGSTGGFM

SHCGWNSILESVVHGVPIIAWPLYAEQKMNSIIVVEDVKVALRPAGVGERVVERSEITAV

VKALMEGEEGKKVRNRMKELKEAAARAVSDDGASTIAIADLAQKWRSSMKH-

RrUGT7 DNA (SEQ ID NO: 9):
ATGGCTGAAAACACTCATGCTCATGCCATAGTGGTACCATTTCCAGTTCAAGGACAC

ATAAAGCCCTCGCTGAATCTAGCCCTCAAGCTAGCATCTCAAGGCTTCACCATCACT

TTTGTCACCACTCATTTCACCCACCAGCAAATCTCCCAAGCTCACAAAAACAGTACA

AATACAAACCATGACATGTTTTTCCAGGCACGAAACTCCAGTCTCGATATCCGCCAT

GTAACGGTGACAGACACTTTTCCTTTGGGATTCGATCGCGCAGGGAATCAGGATCAG

TTTTGGGAGGGCATGCTTCACGTATTCCCTGCACATGTTGATGAACTGGTGGATCAG

TTAATGAATTCTTCGAAGCCGAGACCAACTTGTTTGATTCTGGATACATTTTATAACT

GGGGTTCCAAAATTGCTAACAAGTTTAATTTAGTGCATATTTCATTTTGGACTCAGTC

TGCTCTTTCTTTCACTTTGTTTTACCATTGGGAACTTTTAAAGAAAAATGGTCACTTT

GGCTCTCCAGATAATCGCACGGATGTCATCGATTATATTCCCGGTGTGCAAGAGATC

AAGCCCGCAGACTTAATATCCTACCTTCAGATGAGTGATACAACTACTGTGGCTCAC

AGGACTTGTTTCACAGCATTTGAAGATGTCAGGAAGGCAGATTTCATCCTGGCTAAT

ACAATCCAAGAATTTGAAACTGATACAATTTCTTCTATCCGATTTCACCAGCCATTTT

TCTACCCAATTGGACCTGTTTTTTTAACAAAGTCTGAACAACAAGCTAGCTCAGCTTT

GTGGTCTGAGTCAGACTGTGAGCAGTGGCTAAGTACAAAACCAAAAGGGTCTGTTC

TCTATGCCTCATTTGGGAGCTATGCTCGTGTAACTAGGCATGATATCGCAGAGATAG

CCTACGGATTGATGCAAAGTGAGGTGAATTTTATTTGGGTGATTCGCGACGATATTG

TGGGTGCACACGAGACTGATTTTTTACCAACAGAATTCATAAATGGAATCAAACTCA

AAGATCAGGGACTACTAGTTTCCTGGTGCTCTCAAACTGAAGTTTTGTCCAATGCGG

CGATTGGAGGATTTCTGACTCATTGTGGATGGAACTCGATACTCGAAAGCGTATGGT

GTGAAGTTCCATTATTGTGTTTTCCAATAATGACTGATCAGCCTAGTAACAGGAAAC

TGGTGGTGGATGACTGGAGGATCGGCGTCAACCTATCTGCGGCGGAGGAGGTCAGT

AGAGAAGAAGTGTCAATGAAGGTCAGGAACTTGATTTCTGGAGAATTGGGGAATGA

GTTGAGAGTGCAGATTCAAAAGTACAAAAAGTTGATGGAGAATGGTATAATGGAAG

GTGGATCATCACATTCCAATTGGAACAAGTTCATCCACGACCTACAAATCTTCAAGA

AATGA

RrUGT7 amino acid GenBank accession MF674532 (SEQ ID NO: 10):
MAENTHAHAIVVPFPVQGHIKPSLNLALKLASQGFTITFVTTHFTHQQISQAHKNSTNTN

HDMFFQARNSSLDIRHVTVTDTFPLGFDRAGNQDQFWEGMLHVFPAHVDELVDQLMN

SSKPRPTCLILDTFYNWGSKIANKFNLVHISFWTQSALSFTLFYHWELLKKNGHFGSPDN

RTDVIDYIPGVQEIKPADLISYLQMSDTTTVAHRTCFTAFEDVRKADFILANTIQEFETDTI

SSIRFHQPFFYPIGPVFLTKSEQQASSALWSESDCEQWLSTKPKGSVLYASFGSYARVTR

HDIAEIAYGLMQSEVNFIWVIRDDIVGAHETDFLPTEFINGIKLKDQGLLVSWCSQTEVLS

NAAIGGFLTHCGWNSILESVWCEVPLLCFPIIVITDQPSNRKLVVDDWRIGVNLSAAEEVS

REEVSMKVRNLISGELGNELRVQIQKYKKLMENGIMEGGSSHSNWNKFIHDLQIFKK-

RrUGT13 DNA (SEQ ID NO: 11):
ATGGCAGAAATAAGTCTCATCTTCATCCCTTTTCCCGTAATCAGCCATCTCACTCCCA

CAATCGAAATCGCCAAAATCCTCCTCAGCAGAGACCACCGCCTTTCCATCACCTTCC

TCGTCATCGACATCCCCCAACGAGACGCCTCACTCGCCTCCCTCACCACCTCCATCA

TCTCCGATCGCCTCCACTTCCTCGATGTCGTACTTCCTCCCAACCAACACTCCCAATC

ATCCAAGCCATCAGGCATCGCGGCTATCGAGTCCGCCAAACCCGCAGTCAAGAAAA

CGATCAGCGATCTTGTTGTACGATCTCAGTCCGCCGCATCTGGTCCGCGGATAGCTG

GCTTCGTGCTGGACATGTTCTGCACGGCCATGATCGACATCGCAACTGAGTTTAACC

TTCCTTCGTATATTTACTACACTTGCGGCTCTTCGTTTCTTTCAATCGTGCTCCACGTC

CAGAAGCTCTGCGATGACGACGCTCTCGATATCGCCGATTTCAAAAACTCGAGTGTG

GAGTTTTCGTTACCTGAGTTTTCAAACTTGATTCCGGCTAGGCTGCTTCCATCCATGG

CGCTCGATAAGGACTTCTCGGCTTCATTCGTCGGCAAAGCTAGAGCGTTCAGGAAGA

CGAAGGGCATTTTGGTCAACTCGCTTGTAGAGTTGGAGCCTCACGCAATCGAGTCGA

TGAAATTAGACCGGTCTGTTCCTCCGATTTACTCGGTCGGACCAGTGCTCAACATGA

ATAGCAACACTGCATTTATCAGACAGGAGCAGGAGAAGGAGATCATGGAGTGGCTG

GACCAACAGCCTCCAGCATCTGTAGTTTTCTTGTGTTTTGGCAGCAGGGGAGCGTTC

AAGCCGGACCAGGTGAAGGAAATCGCACGGGGGTTGGAGTCGAGCGGCTGCCGGTT

CCTCTGGGCGCTTCGGCAGCCTTCATCAAGCAATGTGAGGTTTTCACCTCCTACAGA

TTATGAAGATTTCTCTGAGGTTCTGCCTGAAGGGTTTTTGCAGCGGACATATGGTGTT

GGGAAAGTGATTGGTTGGGCACCCCAGACAGCTGTTTTAGACCACCCTTCGGTGGGT

GGATTCGTATCGCATTGCGGTTGGAACTCGATACTGGAATCTCTTTGGTTTGGTGTGC

CGATTGCGACTTGGCCTCTGTATGCTGAGCAGCAGATGAATGCGTTTGAGGTTGTGA

AGGAGATGAAGATTGGAGTGGAGATAAGTTTGGATTATCGGCTTGAAATGGGCGGT

AAACAAGCAGAAGGTTCTGGGATTATAAGTGGTGAACAGATTGAGAGAGGGATTAG

AGATGTGATGCAGGAGGATAGTGAAGTGAGGAAGAAGGTGAAGCTGATGATGGAA

AAGAGTAGAGAGGCAGTTGTGGAGGGAGGCTCCTCTTATAATTATATCCAAAACTTC

ATCAGTGATCTCAGGACCAACATTGGCTTGTAA

RrUGT13 amino acid GenBank accession MF674538 (SEQ ID NO: 12):
MAEISLIFIPFPVISHLTPTIEIAKILLSRDHRLSITFLVIDIPQRDASLASLTTSIISDRLHFLD

VVLPPNQHSQSSKPSGIAAIESAKPAVKKTISDLVVRSQSAASGPRIAGFVLDMFCTAMID

IATEFNLPSYIYYTCGSSFLSIVLHVQKLCDDDALDIADFKNSSVEFSLPEFSNLIPARLLPS

MALDKDFSASFVGKARAFRKTKGILVNSLVELEPHAIESMKLDRSVPPIYSVGPVLNMN

SNTAFIRQEQEKEIMEWLDQQPPASVVFLCFGSRGAFKPDQVKEIARGLESSGCRFLWAL

RQPSSSNVRFSPPTDYEDFSEVLPEGFLQRTYGVGKVIGWAPQTAVLDHPSVGGFVSHC

GWNSILESLWFGVPIATWPLYAEQQMNAFEVVKEMKIGVEISLDYRLEMGGKQAEGSGI

ISGEQIERGIRDVMQEDSEVRKKVKLMMEKSREAVVEGGSSYNYIQNFISDLRTNIGL-

RrUGT17 DNA (SEQ ID NO: 13):
ATGGGCTCACTTCCTTCCACAAAATCCCATGCAGTCCTCGTCCCATACCCTGCCCAA

GGCCACATCAACCCTTTCATGCAACTTGCCAAGCTCCTACACTCAAAAGGTTTCCAC

-continued

```
ATAACCTTCGTCAACAATGACCACAACCATCGCCGTTTGCTCAGAACAAAAGGGCA

TGATTTTGTTCAAGGGTTGGAAGGTTTAAGGTTTGAAGCTGTGCCGGATGGCCTACC

TCCATCTGACCGTGATGCCACTCAGGATGTCCCTAAGCTGACTGAATCTATTTACAA

TAAGAGCATGAACCAACCGTTCAGTGATCTGCTTCAGAGGCTAAACTCAACGCCCG

GTTCCCCTCCGGTCACTTGTGTCATATCCGATGTTGCCATGTTTTTTGCTTGGGACGT

GGCGGATGAGCTTGGCATCCCTAATGTTCAGTTTTGGACAGCTTCAGCTTGTGGCCT

TTTGGGATACTTACAGTATGATGAGCTCCTAAGAAGAGCCATAGTCCCATTCAAAGA

TGAAAATTTCATGACGGATGGTTCGTTGGAGGCTTTGATTGACTGGATTCCTGGCAT

GCCTAACATGAGGCTGAAGGACTTGCCAAGCTTCATGCGGACCACAAGCCCTGACG

ACGTGTTGTTCAATTACTTGCGTACAATAACCACGAAAGCTCTAAAATCCTCGGCCT

TGTTGCTGAACACATTTGATGATTTTGAACATGAAGTAGTTGAAGAGATGAAGAAA

ATGCAACCAAACATATTCCTAGGAGGTCCACTCAACATGCTTCTCAGGCACACATCA

AAAACTGAAATCACATCCTTAACAACAAGTTTATGGAAAGAGGACACTCATTGTTTA

GAATGGCTGGACAAGCAAGAACCGGAGTCAGTGGTATACATCAATTACGGATCGGT

GACGATAATGTCTGATCACCATTTAAATGAGTTTGCTTGGGGTTTGGCTAACAGCAA

GCACCCTTTTTTGTGGATCGTGAGGCCGGATGTTGTGAGGGGCGAGTCGGGGACTTT

GCCCAAGGAGTTTTATGATGAGATCAAGGACAGGGGATTGATAACGAGCTGGTGTC

CGCAACCAGAGGTGCTTAAACATCCATCCGTAGGTGTATACTTGACGCATTGTGGTT

GGAACTCTATCACGGAGAGTGTGGCCGGAGGAGTGCCATTGATGTGCTGGCCGTTTT

TCGCTGAGCAACAGACGAATAGCCGATTCGCGTGTACGGTGTGGGCACTGGAGTG

GAGGTGAATGCGGATGTGAAGAGGGAGGAGCTAGCGGAACAAGTGATGGAGATGT

TGGAAGGAAAGAGGGGGCAAGAGTTGAGGAAAAATGCTAAGGAGTGGAGGAGGAA

GGCGGAGGAGGCGACGGACATTGGCGGTTCTGCCTATGCTGATTTCGATAGGTTTAT

GGAAAAAGTGGTCCAGTTTAGCGTCTGA
```

RrUGT17 amino acid GenBank accession MF674542 (SEQ ID NO: 14):
MGSLPSTKSHAVLVPYPAQGHINPFMQLAKLLHSKGFHITFVNNDHNHRRLLRTKGHDF

VQGLEGLRFEAVPDGLPPSDRDATQDVPKLTESIYNKSMNQPFSDLLQRLNSTPGSPPVT

CVISDVAMFFAWDVADELGIPNVQFWTASACGLLGYLQYDELLRRAIVPFKDENFMTD

GSLEALIDWIPGMPNMRLKDLPSFMRTTSPDDVLFNYLRTITTKALKSSALLLNTFDDFE

HEVVEEMKKMQPNIFLGGPLNMLLRHTSKTEITSLTTSLWKEDTHCLEWLDKQEPESVV

YINYGSVTIMSDHHLNEFAWGLANSKHPFLWIVRPDVVRGESGTLPKEFYDEIKDRGLIT

SWCPQPEVLKHPSVGVYLTHCGWNSITESVAGGVPLMCWPFFAEQQTNSRFACTVWGT

GVEVNADVKREELAEQVMEMLEGKRGQELRKNAKEWRRKAEEATDIGGSAYADFDRF

MEKVVQFSV-

RrUGT29 DNA (SEQ ID NO: 15):
```
ATGGGATCTCTAGGAAAGAAGATTCAACAAAAGCCACATGCAATATGCACCCCATA

CCCAGCACAAGGCCATATTAATCCCATGCTTAAACTAGCCAAGCTCCTACACCACTC

AGGCTTCTACATAACCTTTGTTCACACAACCTACAACTACAATCGCCTTCTCAAGAC

CCACGGGTCTGATTCCTTAAGTGGTCTACCAGATTTCCAATTTGAGACCATCCCTGAT

GGACTACCACCATCAGATGCAGCTGATGTCACACAAGACATCCCTGCCTTGTGTAAA

TCAACCACCGAAACCTGCTTAGTCCCATTCAAAGAGCTCCTGGCTAAGCTGCATAAC

AAGTCAATGGCGTCACCGGAGGAAGTTCCTCCAGTGACATGCATAGTTTCTGATGGT
```

-continued

```
TGCATGTCATTTACTGTGGATGCTGCAGAAGAGGCAGGGGTTCCTAATGTGCTTCTT

TGGACTACCAGTGCATGCGGATTTTTAGGATATGCTAATTACCCGAAACTTATTGAC

AGAGGCATAATTCCACTCAAAGATGAGAGCTACTTTACGAATGGGTACCTAGACAA

GACAGTAGATGGAATACCTGGAATGAAAGGCATACGGCTACGAGACTTCCCAAACT

TTGTATGCACCACAAACCCAGATGAGTTTATGGTGAAATATGCAATTCAAGAGATCA

CTAGAGCTGCCAGAGCAGATGCTGTTATTTTGAACACCTTTGACGCTTTGGAACATG

ATTTCTTAGATGGCCTATCAAACATATACCCAAAGGTCCTCCCTATTGGCCCGCTCC

AGCTTCCGCTCAACCAAATCCCAGAGAGCTCACCTCTACATTCAATCTGTTCTAGTC

TCTGGAAAGATGAACCACAGTGCATTACCTGGTTAAACTCCCAAAAACCAAAATCA

GTCGTTTATGTTAACTACGGAAGTATCACAGTTATGACTCCGCAACAAATGGTGGAG

TTCGCATGGGGACTGGCTAATACAAAATACCCTTTTCTGTGGATTATTAGACCTGAT

TTGGTTGCTGGTGAGACAGCTGTCCTACCTCCAGATTTTTTGGAAGTGACAAAAGGA

AGGAGCTGCTTGGCTAGTTGGTGCCCACAGGAACAAGTTCTTAGTCACACATCCATA

GGAGGGTTCTTAACCCATTGTGGGTGGAACTCAATGCTAGAAAGCGTGGTCGAAGG

AGTTCCAATGGTATGCTGGCCGTTTTTTGCTGAGCAACAGACTAATTGCTGGGCTGC

TCGGACAAAATGGGGTATAGGTATGGAAATTGACAATGATGTTAAGAGGGATAAGG

TTCAGAAAATGGTGACAGAGCTTATGGAGGGCGAAAAGGGAAAGGAGATGAAGAG

GAAGGGCGGAGAATGGAAGAAGCTTGGGGCAGAAGCTGCCGGTCCTAATGGCTCAG

CTACCTTAAACTTCAGCAGACTTATAAATGACGTACTTCTGTCCAAAAAAAAAATTG

TAGTTACAACCTAA
```

RrUGT29 amino acid GenBank accession MF674554 (SEQ ID NO: 16):
MGSLGKKIQQKPHAICTPYPAQGHINPMLKLAKLLHHSGFYITFVHTTYNYNRLLKTHG

SDSLSGLPDFQFETIPDGLPPSDAADVTQDIPALCKSTTETCLVPFKELLAKLHNKSMASP

EEVPPVTCIVSDGCMSFTVDAAEEEAGVPNVLLWTTSACGFLGYANYPKLIDRGIIPLKDE

SYFTNGYLDKTVDGIPGMKGIRLRDFPNFVCTTNPDEFMVKYAIQEITRAARADAVILNT

FDALEHDFLDGLSNIYPKVLPIGPLQLPLNQIPESSPLHSICSSLWKDEPQCITWLNSQKPK

SVVYVNYGSITVMTPQQMVEFAWGLANTKYPFLWIIRPDLVAGETAVLPPDFLEVTKGR

SCLASWCPQEQVLSHTSIGGFLTHCGWNSMLESVVEGVPMVCWPFFAEQQTNCWAAR

TKWGIGMEIDNDVKRDKVQKMVTELMEGEKGKEMKRKGGEWKKLGAEAAGPNGSAT

LNFSRLINDVLLSKKKIVVTT

RrUGT32 DNA (SEQ ID NO: 17):
```
ATGGGATCTCTAGGAAAGAAGATTCAACAAAAGCCACATGCAATATGCACCCCATA

CCCAGCACAAGGCCATATTAATCCCATGCTTAAACTAGCCAAGCTCCTACACCACTC

AGGCTTCTACATAACCTTTGTTCACACAACCTACAACTACAATCGCCTTCTCAAGAC

CCACGGGTCTGATTCCTTAAGTGGTCTACCAGATTTCCAATTTGAGACCATCCCTGAT

GGACTACCACCATCAGATGCAGCTGATGTCACACAAGACATCCCTGCCTTGTGTAAA

TCAACCACCGAAACCTGCTTAGTCCCATTCAAAGAGCTCCTGGCTAAGCTGCATAAC

AAGTCAATGGCGTCACCGGAGGAAGTTCCTCCAGTGACATGCATAGTTTCTGATGGT

TGCATGTCATTTACTGTGGATGCTGCAGAAGAGGCAGGGGTTCCTAATGTGCTTCTT

TGGACTACCAGTGCATGCGGATTTTTAGGATATGCTAATTACCCGAAACTTATTGAC

AGAGGCATAATTCCACTCAAAGATGAGAGCTACTTTACGAATGGGTACCTAGACAA
```

-continued

```
GACAGTAGATGGAATACCTGGAATGAAAGGCATACGGCTACGAGACTTCCCAAACT

TTGTATGCACCACAAACCCAGATGAGTTTATGGTGAAATATGCAATTCAAGAGATCA

CTAGAGCTGCCAGAGCAGATGCTGTTATTTTGAACACCTTTGACGCTTTGGAACATG

ATTTCTTAGATGGCCTATCAAACATATACCCAAAGGTCCTCCCTATTGGCCCGCTCC

AGCTTCCGCTCAACCAAATCCCAGAGAGCTCACCTCTACATTCAATCTGTTCTAGTC

TCTGGAAAGATGAACCACAGTGCATTACCTGGTTAAACTCCCAAAAACCAAAATCA

GTCGTTTATGTTAACTACGGAAGTATCACAGTTATGACTCCGCAACAAATGGTGGAG

TTCGCATGGGGACTGGCTAATACAAAATACCCTTTTCTGTGGATTATTAGACCTGAT

TTGGTTGCTGGTGAGACAGCTGTCCTACCTCCAGATTTTTTGGAAGTGACAAAAGGA

AGGAGCTGCTTGGCTAGTTGGTGCCCACAGGAACAAGTTCTTAGTCACACATCCATA

GGAGGGTTCTTAACCCATTGTGGGTGGAACTCAATGCTAGAAAGCGTGGTCGAAGG

AGTTCCAATGGTATGCTGGCCGTTTTTTGCTGAGCAACAGACTAATTGCTGGGCTGC

TCGGACAAAATGGGGTATAGGTATGGAAATTGACAATGATGTTAAGAGGGATAAGG

TTCAGAAAATGGTGACAGAGCTTATGGAGGGCGAAAAGGGAAAGGAGATGAAGAG

GAAGGGCGGAGAATGGAAGAAGCTTGGGGCAGAAGCTGCCGGTCCTAATGGCTCAG

CTACCTTAAACTTCAGCAGACTTATAAATGACGTACTTCTGTCCAAAAAAAAATTGT

AG
```

RrUGT32 amino acid GenBank accession MF674557 (SEQ ID NO: 18):
```
MGSLGKKIQQKPHAICTPYPAQGHINPMLKLAKLLHHSGFYITFVHTTYNYNRLLKTHG

SDSLSGLPDFQFETIPDGLPPSDAADVTQDIPALCKSTTETCLVPFKELLAKLHNKSMASP

EEVPPVTCIVSDGCMSFTVDAAEEAGVPNVLLWTTSACGFLGYANYPKLIDRGIIPLKDE

SYFTNGYLDKTVDGIPGMKGIRLRDFPNFVCTTNPDEFMVKYAIQEITRAARADAVILNT

FDALEHDFLDGLSNIYPKVLPIGPLQLPLNQIPESSPLHSICSSLWKDEPQCITWLNSQKPK

SVVYVNYGSITVMTPQQMVEFAWGLANTKYPFLWIIRPDLVAGETAVLPPDFLEVTKGR

SCLASWCPQEQVLSHTSIGGFLTHCGWNSMLESVVEGVPMVCWPFFAEQQTNCWAAR

TKWGIGMEIDNDVKRDKVQKMVTELMEGEKGKEMKRKGGEWKKLGAEAAGPNGSAT

LNFSRLINDVLLSKKKL-
```

RrUGT33 DNA (SEQ ID NO: 19):
```
ATGAGCTTAATTGAAAAACCACTCACGGCCATAGAGACTCGTGAAAAACCACACGC

TGTGTGCATCCCATACCCAGCTCAAGGCCATATCAATCCCATGATGCAACTTGCAAA

GCTCCTCCACCACTCTGGTTTCCACATAACGTTTGTCCACACTGAGTATAATTATGAC

CGTCTAGTGAAGTCTCAAGGTTCAGCTTGTGTGGCTGGTTTACCGGATTTCCGCTTTG

AAGCCATCCCAGATGGCTTGCCCTCGACGAATGGTGATGTTACTCAAGACATTCCTC

TGTTGAGTAGCTCTACTTCTAAAACCTGCTTGAAGCCGTTTAAGGAGTTATTGAAGA

GGTTGCAGGACAAATGCAAAGAGTTACCTGATGATGTTCCGCCTCTGTCGTGCATCG

TGTCTGATGCAGCCATGTCGTTTACGATCGATGCATCTGAGGAGTTTGGAGTGCCCA

TAGCGCTTCTTTGGACTGCAAGTGCCTGCGGGTTCTTGGGTTACACGCATTACCCAT

ATCTAATTGACAGAGGTGTCATCCCATTGAAAGATGAGAGCCAATTAACAAACGGA

TACCTAGATATGAGCATAGATGGCATACCTTGTATGGAAGGTATCCGCTTACGAGAC

CTCCCAAGCTTTCTACGCACAACTGATTTAGATGATATGATGTTTAGTTATATACTGC

ACGAAATAAAACAAGTTTCAAGAGGCAGTGCTATCATTCTGAACACCTTTGAAGCTT

TGGACCATGATGTCTTGGATAGTCTCTCCAAAATTTACCAAAATGTCATCCTGCCAG
```

-continued

TTGGCCCTCTACATGTCTCGCTCAACAAGATCCCAAAACACTACCCACTTCAATCTTT

AAGCTCGAATTTATGGAAAGATGACACAGACTGCATTCCCTGGCTGAGCTCTAAGGC

TTCAAAATCAGTTATATACGTTAACTTTGGGAGCATCACGACGGTATCACCAAAACA

AATTGTGGAGTTTGCGTGGGGATTGGCTAACAGCAAACACCCTTTCCTTTGGATAAT

CAGACCGGACTTGGTGGCAGGTGAGGCATCCATCATTCCGCAGGACTTCATGGATG

AAACAAAAGGAAGAGGTTTGTTGGCTGGTTGGTGTGACCAAGAGCTTGTTCTCAACC

ATCCATCCATTGGAGGGTTTCTTACGCACTGTGGCTGGAACTCAATTATTGAAAGCA

TTAGCGCAGGAGTCCCTACGGTCTGCTGGCCATTTTTTGCTGAGCAGCAAACAAATT

GTTGGTTTGCTTGCAAAAAATGGTGCATTGGGATGGAGATGCATACTGATGTAAAGA

GGGATGAGGTTGACAAGCTGTTGAGAGAGCTAATGGAAGGTGACAAAGGGGAGGA

GTTGAAGAGGAAGGCAACCAACTGGAAGAGGCTGGCAGAAGAAGCTGTTTCCTCCA

CTGGCTTATCAACCTTAAACTTCAGGACGTTAGTGAATCAAGTCCTGCTCTCAAAAA

CAAAACATATCCGTTAG

RrUGT33 amino acid GenBank accession MF674558 (SEQ ID NO: 20):
MSLIEKPLTAIETREKPHAVCIPYPAQGHINPMMQLAKLLHHSGFHITFVHTEYNYDRLV

KSQGSACVAGLPDFRFEAIPDGLPSTNGDVTQDIPLLSSSTSKTCLKPFKELLKRLQDKCK

ELPDDVPPLSCIVSDAAMSFTIDASEEFGVPIALLWTASACGFLGYTHYPYLIDRGVIPLK

DESQLTNGYLDMSIDGIPCMEGIRLRDLPSFLRTTDLDDMMFSYILHEIKQVSRGSAIILN

TFEALDHDVLDSLSKIYQNVILPVGPLHVSLNKIPKHYPLQSLSSNLWKDDTDCIPWLSS

KASKSVIYVNFGSITTVSPKQIVEFAWGLANSKHPFLWIIRPDLVAGEASIIPQDFMDETK

GRGLLAGWCDQELVLNHPSIGGFLTHCGWNSIIESISAGVPTVCWPFFAEQQTNCWFAC

KKWCIGMEMHTDVKRDEVDKLLRELMEGDKGEELKRKATNWKRLAEEAVSSTGLSTL

NFRTLVNQVLLSKTKHIR

Arabidopsis thaliana AT2G20340.1 (SEQ ID NO: 21):
MENGSGKVLKPMDSEQLREYGHLMVDFIADYYKTIEDFPVLSQVQPGYLHKLLPDSAP

DHPETLDQVLDDVRAKILPGVTHWQSPSFFAYYPSNSSVAGFLGEMLSAGLGIVGFSWV

TSPAATELEMIVLDWVAKLLNLPEQFMSKGNGGGVIQGSASEAVLVVLIAARDKVLRSV

GKNALEKLVVYSSDQTHSALQKACQIAGIHPENCRVLTTDSSTNYALRPESLQEAVSRD

LEAGLIPFFLCANVGTTSSTAVDPLAALGKIANSNGIWFHVDAAYAGSACICPEYRQYID

GVETADSFNMNAHKWFLTNFDCSLLWVKDQDSLTLALSTNPEFLKNKASQANLVVDY

KDWQIPLGRRFRSLKLWMVLRLYGSETLKSYIRNHIKLAKEFEQLVSQDPNFEIVTPRIF

ALVCFRLVPVKDEEKKCNNRNRELLDAVNSSGKLFMSHTALSGKIVLRCAIGAPLTEEK

HVKEAWKIIQEEASYLLHK

Brachypodium distachyon 1g28960.3 (SEQ ID NO: 22):
MDGSTTSNGGGWMRPMDEEQLRECGHRMVDFIADYYKSIETYPVLSQVQPGYLKEL
LPDSAPNQPDTLDALFDDIREKIVPGVTHWQSPNYFAYYPSNSSTAGFLGEMLSAAFNIV
GFSWITSPAATELEVIVLDWVAKMLKLPSEFLSAALGGGVIQGTASEAILVVLLSARDRT
LRKHGKKSLEKIVVYASDQTHSALKKACQIAGIFPENIRIVKADCSMNYAVTPGAVSEAI
SIDLSAGLIPFFICATVGTTSSSAVDPLHELGQIAQAHDMWFHIDAAYAGSACICPEYRKY
LNGVEEADSFNMNAHKWFLTNFDCSLLWVKDRNYLIQALSTNPEFLKNKASQENSVID
FKDWQIPLGRRFRSLKLWMVLRLYGVENLQSYIRKHIQLAQHFEQLVISDPRFEVVTPR
NFSLVCFCLVPPTCEVDNGHKLNYDLMDSANSSGKIFISHTVLSGKFVLRFVVGAPLTEE
QHVDAAWKLLQDEATKLLGNVVQ

*Carica papaya* 16427710 (SEQ ID NO: 23):
MDAEQLRENGHKMVDFIADYYKTIENFPVLSQVEPGYLRDLIPDSAPNSPESFQQLLDD

VRTKILPGVTHWQSPNYFAYYPSNSSVAGFLGEMLSAGLNIVGFSWITSPAATELEMIVL

DWLAKLLKLPEDFHSTGNGGGVIQGTASEAILVVLLAARDKVLKRVGKNALEKLVVYT

SDQTHSAFQKACQIGGIHPENCRVLKTDSSTNYALSPDLLKEAISCDVAAGLIPFFFCATV

GTTSSTAVDPLMALGKIATSNEIWFHVDAAYAGSACICPEYRPYIDGVEEADSFNMNAH

KWFLTNFDCSVLWVKDKYSLIQSLSTNPEFLKNKASQADMVVDYKDWQIPLGRRFRSL

KLWMVLRLYGVENLKSYIRNHIKLAKHFEELVTQDPRFEVVTPRIFSLVCFRLLPPGNDE

NHGNKLNQDLLETVNSTGKLFISHTVLSGKYILRFAVGAPLTEERHVNEAWKILQDEAS

TLLENP

*Ricinus communis* 16804377 (SEQ ID NO: 24):
MFREGELRPMDAEQLREHGHKMVDFIADYYKTIENFPVLSQVEPGYLRKLLPDSAPNQP

ESLQNVLDDVQAKILPGVTHWQSPNYFAYYPSNSSVAGFLGEMLSAGINMVGFSWITSP

AATELEMIVLDWLGKMLKLPEEFLSTGQGGGVIQGTASEAVLVALVAARDKVLRRVGK

DALRKLVVYGSDQTHSALQKACQIGGIHPVNCRLLETDSSTNYALAPDLLSRAISEDISL

GLIPFFLCATVGTTSSTAVDPLLALGKIAKSNGMWFHVDAAYAGSACVCPEYRCYMDG

VEEADSFNMNAHKWFLTNFDCSALWVKDRNALIQSLSTSPEFLQNKPSQTNTVVDYKD

WQIPLGRRFRSLKLWMVLRLYGVEKLQCYIRNHINLAKYFEGLIAEDTRFEVVSPPIFAL

VCFRLLPPDNNVDHGNKLSHDLLDAVNSTGKIFISHTVLSGKYILRFAVGAPLTEERHVT

AAWKVLQDEACALLETSRIS

*Cucumis sativus* 16963476 (SEQ ID NO: 25):
MDNELKPMDAEQLREHAHKMVDFIADYYKNIEDFPVLSQVEPGYLQNLLPESAPLNPES

LQSVLDDVQKKIFPGVTHWQSPNYFAYYPSNSSIAGFLGEMLSAAFNVIGFSWVTSPAA

TELEMIVLDWLAKLLKLPDDFLSSGNGGGVIQGTASEAVLVVLLAARDRALRRFGKDY

LKKLVVYASDQTHSALQKACQIGGIHPENCRWLKADISTNYALSPDVLSEELSRDTARG

LIPFFLCATVGTTSSTAVDPLPELGTIAKRHEMWFHVDAAYAGSACVCPEYRQYIDGVE

EADSFNMNLHKWFLTNFDCSALWIKDRHALIRSLSTNPEFLKNKASEAELVVDYKDWQI

PLGRRFRSLKVWMVLRLYGTENLQKYIRNHISLAERFEALVREDPRFEIVTPRIFSLVCFR

LLPSRKNEDGGNRLNQSLLDAVNASGNIFISHTVLSGKYILRFAVGAPLTEEKHINSAWK

LLQDVASTLLAI

*Vitis vinifera* 17835588 (SEQ ID NO: 26):
MDAEQLRENGHKMVDFIADYYKSIENFPVLSQVEPGYLRELLPDSAPNQPESLQQVFDD

LQAKILPGVTHWQSPNFFAYYPSNSSTAGFLGEMLSAGLNIVGFSWITSPAATELEMIVL

DWLAKLLNLPDDFLSAGNGGGVIQGTASEAVLVVLLAARDRVLRTVGKTALEKLVVY

GSDQTHSALQKACQIGGIHPENCKLLKADSSTGYALSPDLLSEAVSHDITNGLIPFFLCAN

VGTTSSTAVDPLLELGKVTKSNGIWFHVDAAYAGSACVCPEYRHYIDGVEEADSFNMN

AHKWFLTNFDCSVLWVKDRNALVQALSTNPVFLKNKASDANIVIVVDYKDWQVPLGRR

FRSLKLWMVLRLYGVENLQRYIRNHIKLAKQFEELVAQDPRFEIVAPRKFALVCFRLLPP

HRNEDFSNKLNHNLLDTVNSTGKVYISHTALSGKYTLRLAVGAPLTEERHVNAAWKVI

QEKASVLLSEFGMNGLFDNINLKFILNHQIDISILLNYN

*Citrus sinensis* 18113817 (SEQ ID NO: 27):
MDAEQLRENAHKMVDFIADYYKSIENFPVLSQVQPGYLHNLIPDSAPHHPESLQNVLDG

YIDIQEKILPGVTHWQSPNYFAYYPSNSSVAGFLGEMLSAGLNIVGFSWITSPAATELEMI

-continued

VLDWLAKLLKLPEDFLSSGQGGGVIQGTASEAVLVVLLAARDKALKRVGKNSLEKLVV

YASDQTHSALQKACQIGGIHPQNFRVLKTDSSTNYSLSPDSLAEAISRDLTIGLIPFFLCAT

VGTTSSTAVDPLLALGNIAKSNGMWFHVDAAYAGSACICPEYRQYIDGVEEADSFNMN

AHKWFLTNFDCSALWVKDRNTLIQSLSTNPEFLKNKASQANMVVDYKDWQIPLGRRFR

SLKLWMVLRLYGLENLQGYIRNHIQLAKHFEGLVAQDLRFEVVTPRIFSLVCFRLLPPHN

DEDHGNKLNHKLLDDINSTGKIFISHTVLSGKYILRFAVGAPLTEWRHVNAAWEVMQD

KASALLARLSIE

*Capsella rubella* 20900667 (SEQ ID NO: 28):
MGFCQIELLRHINKHNMQNGSGKNVLKPMDSEQLREYGHRMVDFIADYYKTIEDFPVL

SQVQPGYLHQLLPDSAPDHPETLDQVLDDVRAKILPGVTHWQSPGFFAYYPSNSSVAGF

LGEMLSAGLGIVGFSWVTSPAATELEMIVLDWLAKLLNLPKEFLSKGNGGGVIQGSASE

AVLVVLIAARDKVLRSAGKNALGKLVVYSSDQTHSALQKACQIAGIHPENCRVLETDAS

TNYALRPELLQEAVSKDLKAGLIPFFLCANVGTTSSTAVDPLAALGKIANSNEIWFHVDA

AYAGSACICPEYRKYIDGVETADSFNMNAHKWFLTNFDCSLLWVKEQDSLTEALSTNP

EFLKNKASQANLVVDYKDWQIPLGRRFRSLKLWMVLRLYGAETLKSYIRNHIKLAKYF

EKLVSQDPNFEIVTPRIFSLVCFRLVPKNDDEKKCNNQNRKLLEAANSSGKLFMSHTALS

GKIVLRCAIGAPLTEEKHMKEAWKVIQDEASFLLHK

*Malta domestica* 22636618 (SEQ ID NO: 29):
MSGLKPMDAEQLRENAHKMVDFIADYYKTIEDFPVLSQVQPGYLRDLLPDSAPTHPESL

QQVFDDIQAKILPGVTHWQSPNFFGYYPSNSSVAGFLGEMLSAGLNIVGFSWITSPAATE

LEMIVLDWFAKMLKLPEEFLSAGQGGGVIQGTASEAVLVVLLAARDRILRAEGKKALE

KLVVYASDQTHSALQKACQIGGIHPENCRVLSTDSSTNYALSPNVLNEAISNDIASGLVP

FFLCATVGTTSSTAVDPLLELGKITKSNGMWFHVDAAYAGSACICPEYRHHIDGVEEAD

SFNMNAHKWFLTNFDCSLLWIKDRNALVQALSTNPEFLKNKASQANLVVDYKDWQIPL

GRRFRSLKLWMVLRLYGLENLQSYIRNHIDLAKCFEDLVAQDSRFEIVTPRIFSLVCFRL

LPPHNDETYATKLNHDLLDTVNSTGKIFVSHTVLSGKYVLRFAVGAPLTEERHVLAAW

KLLQEEASALLAPL

*Linum usitatissimum* 23178995 (SEQ ID NO: 30):
MGGYRSLNLIFIFISFVADIRDLGYNTKEGDDGGGALKPMDAEQLRQNAHQMVDFIADY

YKNIETYPVLSQVEPGYLRELLPDSAPNRPESLQSVLDDVQSKIMPGVTHWQSPNYFAY

YPSNSSVAGFLGEMLSAGINMVGFSWITSPAATELEMIVLDWLGKLLKLPEEFLSSGHG

GGVIQGTASEAILVVLLAARDKMLRKFGKSALEKLVVYASDQTHSALQKACQIGGIYPE

NCRLLKTDSSVNYSLTPELVSEAVSQDISAGLIPFFLCGTVGTTSSATVDPLGTLGKIAKN

NDMWFHVDAAYAGSACICPEYRQYLDGVEEADSFNMNAHKWFLTNFDCSTLWVKDK

SALIQALSTNPEFLKNKASQANLVVDYKDWQIPLGRRFRSLKLWMVLRLYGVENLQQY

LRNHIELARHFEECVNHDPRFEALSGKYTLRVAIGAPLTEKRHVAAALKVLQDEATSLL

VATSPLLENGNSS

*Eutrema salsugineum* 20200788 (SEQ ID NO: 31):
MENGNKNVLKPMDSEQLREYGHRMVDFIADYYKTIEDFPVLSQVQPGYLHNLLPDSAP

DQPETLEEVLDDVKGKILPGVTHWQSPSFFAYYPSNSSVAGFLGEMLSAGLGIVGFSWIT

SPAATELEMIVLDWLAKLLNLPEQFLSRGNGGGVIQGSASEAELVVLIAARDKVLRSVG

KKALEKLVVYSSDQTHSALQKACQIAGIHPENCRVLKADYSTNYALRPETLQEAVSKDL

-continued

EAGLIPFFLCANVGTTSSTAVDPLAALGEIAKSNEMWFHVDAAYAGSACICPEYRQYID

GVETADSFNMNAHKWFLTNFDCSLLWVKDQYALTEARSTNPEFLKNKASQANLVVDY

KDWQIPLGRRFRSLKLWMVLRLYGSENLKSYIRNHIKLAKDFEQLVSEDPNFEIVTPRIFS

LVCFRIVPAENDEKKCNNQNRNLLDAVNSSGKLFLSHTALSGKIVLRCAIGAPLTEEKHV

KEAWKVIQEEASYLLRK

*Populus trichocarpa* 27022899 (SEQ ID NO: 32):
MESKGLQPMDSEQLRENAHKMVDFIADYYKSIENFPVLSQVEPGYLRELLPDSAPNQPE

TLQNVLDDVQAKILPGVTHWQSPSYFAYYPSNSSVAGFLGEMLSAGINMVGFSWITSPA

ATELEMIVLDWLGKLLKLPEDFLSTGQGGGVIQGTASEAVLVVLLAARDRVLRKLGKN

ALEKLVVYASDQTHSALQKACQIGGIHPENCKLLKTGSSTNYALSPDLLGKAISDDISTG

LVPFFLCATVGTTSSTAVDPLLSLGKIAKNNGIWFHVDAAYAGSACICPEYRCYIDGVEE

ADSFNMNAHKWFLTNFDCSALWVKDRNALIQSLSTNPEFLKNKASQANMVVDYKDW

QIPLGRRFRSLKLWMVLRLYGLENLQCYIRNHINLAKYFEGLVAADSRFEVVTPRIFSLV

CFRLLPPNNNEDHGNNLNHDLLDAVNSTGKIFISHTVLSGKYILRFAVGAPLTEERHVTA

AWKVLQDEASALLGSL

*Brachypodium stacei* 06G160800.1 (SEQ ID NO: 33):
MDGSTTSNGDGGGWIVIRPMDEEQLRECGHRMVDFIADYYKSIETYPVLSQVQPGYLK

ELLPDSAPNQPDTLDALFDDIQEKIVPGVTHWQSPNYFAYYPSNSSTAGFLGEMLSAAFN

IVGFSWITSPAATELEVIVLDWVAKMLKLPSQFLSAGLGGGVIQGTASEAILVVLLSARD

RTLRKHGKKSLEKLVVYASDQTHSALQKACQIAGIFSDNIRIVKADCSMNYAVTPGSVS

EAISIDLSSGLIPFFICATLGTTSSSAVDPLHELGQIAQAHDMWFHIDAAYAGSACICPEYQ

QYLNGVEEADSFNMNAHKWFLTNFDCSLLWVKDRNYLIQALSTNPEFLKNKASQENSV

IDFKDWQIPLGRRFRSLKLWMVLRLYGVENLQSYIRKHIQLAQRFEQLVISDSRFEVVTP

RNFSLVCFCLVPPTSEVDNGHKLNYDLMDSVNSSGKIFISHTVLSGKFVLRFAVGAPLTE

EQHVNAAWKLLQDEATKLLGSVVV

*Physcomitrella patens* Pp3c4_30790V3.1 (SEQ ID NO: 34):
MGSEAGSRSSLTKPFDPEEFRKHAHRMVDFIADYHRDIENFPVQSQVEPGYLQKLLPEN

APDEPESLDDILADVQSKIVPGVTHWQSPNFYGYYPSNGSTAGFLGEMLSGGFNIIGFSW

ITSPAATELEIIVMDWLGKLLKLPNEFLSSGKGGGVIQGTASEAVLVVMLAARKRAVEK

LTKEQGISEFEALAKLVAYTSDQAHSCVNKASQIAGISIENLRLIPTDVSTNYAMSSKVLA

NTLANDVKAGLVPFFLCGVIGSTSSAAVDPLSELGDLAQEYGMWFHVDGAYAGNACIC

PEFRPYLNGVEKADSFDMNPHKWLLTNFDCSTLWVKNPSLLVDALSTNPVFLRNKQSD

NNLVVDYKDWQIPLGRRFRSLKLWMVLRMYGSNGLRSYITNHCNLAKHFEELLRTDSR

FEVVAPRVFSLVCFRLKSPANDADNSCSLSAKLVDALNSDGNILITNTVLGGRYTIRFTV

GASRTELRHVDAAWKVIQQLASKLLKECSS

*Ananas comosus* 33033299 (SEQ ID NO: 35):
MESELKPMDSEQLREYAHKMVDFIADYYKMIESFPVLSQVKPGYLKELLPDSAPCKPEN

LEDVFDDIRQKIIPGITHWQSPDYFAYYPSNSSTAGFLGEMLSAGFNIIGFSWIASPAATEL

EMIVLDWFAKMLKLPEQFLSTGQGGGVIQGTASEAVLVVLLAARDKILLKAGRKSLEKL

VVYCSDQTHSAMQKACQIAGIFPENFRVLKTDSSSNYALLPEVLSEATSKDLSFGLIPFFL

CATVGTTSSAAVDPLLKLGNISKVHDMWFHVDAAHAGSACICPEYRHHIDGVEEADSF

CMNAHKWFLTNFDCSLLWVKDRSALIQSLSTNPEFLKNKASQENSVVDFKDWQIPLGR

-continued

RFRSLKLWMVLRLYGLENLQSYIREHIKLAEQFEQLISSDSRFEIVAPRTFSLVCFRLLPPL

YDQDDGYKLNYNLLDAVNRSGKIFMSHTVLSGKFVLRFAIGAPLTEERHVVAAWKVLQ

DEATILLRGS

Zostera marina 33182387 (SEQ ID NO: 36):
MLNGNMGENEPFKPMDSEQLREYGHKMVDFIADYYKSIEKFPVLSQVQPYYLKDLLPD

AAPDQPEKFQDVLDDITKKIIPGVTHWQSPNFFGYYPGNSSIAGFLGEMICSGLNVIGFS

WITSPASTELEVIVLDWLAKLLNLPDQFLSSGHGGGVIQGTASEAILVVLLAARDKILGRI

GRNSLDKLVVYSSDQVHAAFKKACQIAGIYTENFRVLKTDASSGYGIDPKKFDQAIHDD

MEAGLIPFFLCSTVGTTSSASVDPLVEIGQITEENDMWFHVDAAYAGSACICPEYRHYLD

GVEYADSFCMNAHKWLLTNFDCSALWVKDSSALVNSLSTNPEFLKNKMSEQKKVVDF

KDWQIPLGRRFRSLKLWMVLRLYGAENLREYIRNHIKLANLFEQLVRSDSRFEIVCPTLF

SLVCFRFLPSNDDNDGYELNSMLLDAVNSTGQLFFTHTIISDKYILRFAVGAALTEERHV

RESWKVIQNQATIISRQHILSKTNMKSKCEGMIANE

Daucus carota subsp. sativus 36055203 (SEQ ID NO: 37):
MDGVLKPMDAEQLRENAHKMVDFIADYYKNIETFPVLSQVEPGYLRDLLPHSAPDQPE

SLQNILDDIQAKILPGVTHWQSPNYFAYFPSNSSVAGFLGEMLSAGINMVGFSWITSPAA

TELEMIVLDWLAKLLKLPDHFLSTGQGGGVIQGTASEAVLVVLLAARDKVLRITGKDAL

GKLVVYCSDQTHSALQKACQIAGIHPGNCRVLKTESCNDYSLSPETFEQAISTDVASGLI

PLLLCATVGTTSSTAVDPLLELGKITKMKGIWLHVDAAYAGSACVCPEFRHYIDGVEEA

DSFNMNAHKWFLTNFDCSALWVKDRSALIHSLSTNPEFLKNKASQENLVVDYKDWQIP

LGRRFRSLKLWMVLRLYGLENLQSYIRNHIQLAATFESFVTEDPRFEVVAPRKFALVCFR

LLPPSHKDEDCSNQLNRDLLDAVNATGKAFVSHTALSGRYVVRFAIGAPLTEESHIIEAW

KIFQEVATVLLKSLKMNHTRPLN

Trifolium pratense 35974269 (SEQ ID NO: 38):
MVDFIADYYKTIENFPVLSQVEPGYLGKLLPDSAPTYPTTLEHVLNDVQHKILPGVTHW

QSPNYFAYFPSNSSIAGFLGEMLSAGINIVGFSWITSPAATELESIVLDWLAKALFLPQDF

LSNGKGGGVIQGTASEAVLVVLLAARDKILRTVGRSALPKLVTYASDHVHSSLLKACQI

GGLDPELCRLLKTDSSTNFALSPDVLSEATSNDIASGLIPFFLCANVGTTSSTAVDPLPALA

KVTKTNNIWLHVDAAYAGSACICPEYRHFIDGVEEADSFNMNAHKWFLTNFDCSLLWV

KDRSALIQSLSTNPEFLKNKASEGNMVIDYKDWQIPLGRRFRSLKLWMVLRLYGLEGLR

SHIRNHIALAASFEELVVQDARFKVVTPRTFSLVCFRLLPPPNSEDNGNKLNHDLLDLVN

STGSVFITHTVLSGEYILRLAVGAPLTEVRHVNAAWQILQEKATALLENL

Arabidopsis lyrata 35943929 (SEQ ID NO: 39):
MDSEQLREYGHRMVDFIADYYKTIEDFPVLSQVQPGYLHKLLPDSAPDHPETLDQVLDD

VRAKILPGVTHWQSPSFFAYYPSNSSVAGFLGEMLSAGLGIVGFSWVTSPAATELEMIVL

DWLAKLLNLPEQFMSKGNGGGVIQGSASEAVLVVLIAARDKVLRSVGKNALQKLVVYS

SDQTHSALQKACQIAGIHPENCRVLKTDSSTNYALRPELLQEAVSQDLDAGLIPFFLCAN

VGTTSSTAVDPLAALGKIANRNEMWFHVDAAYAGSACICPEYRQYIDGVETADSFNMN

AHKWFLTNFDCSLLWVKDQDSLTLALSTNPEFLKNKASQANLVVDYKDWQIPLGRRFR

SLKLWMVLRLYGSETLKSYIRNHIKLAKEFEQLVSQDPNFEIVTPRIFSLVCFRLVPVKNE

EKKCNNRNRELLDAVNSSGKLFISHTVSDFSSFFLLFFLLDNVLNLRGNRLCRGKSYCVA

Q

-continued

Sorghum bicolor 002G120700.1 (SEQ ID NO: 40):
MDGSGSSGGTNGGSGGDGAGWLRPMDAEQLRECGHRMVDFVADYYKSIETFPVLSQV

QPGYLKELLPDTAPNKPDTLEALFDDIREKIVPGVTHWQSPNYFAYYPSNSSTAGFLGE

MLSAAFNIVGFSWITSPAATELEVIVLDWFAKMLRLPSQFLSTALGGGVIQGTASEAVLV

VLLAARDRTLRKHGKTSLEKLVVYASDQTHSALQKACQIAGIFPENVRLVKADCNRNY

AVAPLAISDAIATDLSSGLIPFFICATVGTTSSSAVDPLPELGQIAKANDMWLHIDAAYAG

SACICPEYREIFILNGVEEADSFNMNAHKWFLTNFDCSLLWVKDRSYLIQSLSTNPEFLKN

KASEANSVFDFKDWQIPLGRRFRSLKLWMVLRLYGVENLQSYIRKHIELAKEFEQLVIS

DSRFEVVTPRTFSLVCFRLVPLASDQDNGRKLNYDLMDAANSSGKIFISHTVLSGKFVLR

FAVGAPLTEGQHIFSAWKILQDLATKQLLESS

Sphagnum fallax 0166s0011.1 (SEQ ID NO: 41):
MGSEAGEGSRLSKPLDVEEFRKHAHQMVDFVADYHRDIESFPVRSQVKPGYLRPLLPDS

APAEPETVEDVFADLWSKILPGLTHWQSPKFFGYYPCNVSTAGMLGEMLCGGLNVNGF

SWITSPAATELETIVLDWLGKLLHLPEEFLSTSGKGGGVIQGTASEAVLVVMLAARKRA

LKQVSSAAQGMSEAEALSKLVVYSSDQTHSCVIKACQVASIATENFRPLPTDASTNFALS

PAVVRKAIATDVEAGLIPFFLCGTLGTTSSAAVDPLEELGDIAKEYGMWYHIDAAYAGN

ACICPEFRHYLNGVEKADSYNMNPHKWLLTNFDCSTLWMKDSEFLLAALSNKPVFLRN

EATDNNLVVDYKDWQIPLGRRFRALKLWMVMRLYGTSGLQSFIRSHVSSAKHFESLVR

ADSRFEVMAPMTFSLVCFRLRTLPGSQDNSNSLNSKLVDALNRKGNILVTHTELSGIYTV

RFAVGATHTELQHVQAAWEVIQAEASHLLNGKQ

Kalanchoe laxiflora 1398s0003.1 (SEQ ID NO: 42):
MILSIHPFPFTLSARFSGAAAANILSKASCWLRCLRSMEGELKPMDAEQLREYGHRMVD

FVADYYKTIEDHPVLSQVEPGYLRKLLPDSAPDKPESFENVLSDVKTKIIPGVTHWQSPN

YFAYFPSNSSTAGFLGEMLSACFNIVGFSWITSPAATELEMIVLDWFAKMLKLPDFFLST

GQGGGVIQGTASEAVLVVLLAARDIFLRKLGKGFLEKLVVYASDQTHSALQKACQIAGI

HPENVRALKTDSSTNYGLSPDLLSKEICHDIANGLVPFFACASVGTTSSTAVDPILELANV

TKSYNIWLHVDSAYAGSACVCPEYRHHIDGVEEVDSFNMNAHKWFLTNFDCSLLWVK

DRNALIQSLSTNPEFLKNKASQSNSVLDYKDWQIPLGRRFRSLKLWLVLRLYGVENLQA

YIRNHIELALNFEELVSQDMRFEIVAPRTFALVCFRLLLPCGFEDHTNDVNSDLLQAVNS

TGKIFISHTVLSGTYVLRFAVGAPLTEERHIDAAWKLIQDQASSLLEKL

Manihot esculenta 12G038600.1 (SEQ ID NO: 43):
MEGELRPMDAEQLREYGHQMVDFIADYYKTIENFPVLSQVEPGYLHKLLPDSAPNQPE

ALQNVLDDVRVKILPGVTHWQSPNYFAYYPSNSSVAGFLGEMLSAGINMIGFSWITSPA

ATELEMIVLDWLGKMLKLPEEFLSSGQGGGVIQGTASEAVLVVLLAARDKVLTRVGKD

SLKKLVVYGSDQTHSALQKACQIAGVHLDNCRLLKTDSSKNYALSPDILCDAISQDMSN

GLIPFFLCATVGTTSSATVDPLLALGKIAKKYGMWFHVDAAYAGSACICPEYRCYIDGV

EEADSFNMNAHKWFLTNFDCSALWVKDRNALIQSLSTNPEFLKNKASQANMVVDYKD

WQIPLGRRFRSLKLWMVLRLYGVANLQSYIRNHINLAKYFEGLVAGDSRFEVVAPRLFS

LVCFRLLPPDNDENHGNKLNHDLLDAANSTGKIFISHTVLSGKYILRFAVGAPLTEERHV

TAAWKVLQDEASALLGSL

Prunus persica 8G214500.1 (SEQ ID NO: 44):
MESGLKPMDAEQLRENAHKMVDFIADYYKTIENFPVLSQVQPGYLRELLPDSAPTHPEP

LQHIFDDIQAKILPGVTHWQSPNFFGYYPSNSSIAGFLGEMMSAGLNIVGFSWITSPAATE

-continued

LEMIVLDWFGKMLKLPEEFLSAGKGGGVIQGTASEAVLVVLLAARDKILRRVGKNSLE

KLVVYASDQTHSALQKACQIGGIHPENCRLLRTDSSTNYALSPNVLNEAISNDVTSGLIP

FFLCATVGTTSSTAVDPLLELGKIAKSNDMWFHVDAAYAGSACICPEYRHYIDGVEEAD

SFNTNAHKWFLTNFDCSVLWIKDRNALIQALSTNPEFLKNKASQANLVVDYKDWQIPL

GRRFRSLKLWMVLRLYGLENLQSYIRNHINLAKHFKELVAQDPRFEIVTPRLFSLVCFRL

LPPHNDETCATKLNHGLLDAVNATGKIFISHTVLSGKYLLRLAVGAPLTEERHVNAAWK

LLQDEASALLATL

*Eucalyptus grandis* K01418.1 (SEQ ID NO: 45):
MEERLKPMDAEQLRESAHRMVDFIADYYKSIESFPVLSQVEPGYLRKLLPDSAPDHPESL

QQVLEDVQAKILPGVTHWQSPNYFAYYPSNSSIAGFMGEMLSAGLNIVGFSWITSPAAT

ELEIIVLDWLAKLLNLPDDFLSTGPGGGVIQGTASEAVLVVLLAARDKFLSRIGKSSLDK

LVVYSSDQTHSALQKACQIGGIYPENCRVLKTDASTNYALSPDLLNEVISQDISTGLVPFL

LCATVGTTSSTAVDPLPALATVAKRNGMWFHIDAAYAGSACICPEYRPYIDGVEEADSF

NMNAHKWFLTNFDCSALWIKDRKALIQALSTNPEFLKNKASQANIVIVVDYRDWQIPLG

RRFRSLKLWMVLRLYGVQNLQQYIRNHIELARQFEDLVIQDPRFEVVTPRIFSLVCFRLL

SPDNDGDKGNKLNRDLLDTVNSTGKIFISHTVLSGTYILRFAVGAPLTEERHVNEAWKV

LQDEASKLLATIQNN

*Amborella trichopoda* 31565185 (SEQ ID NO: 46):
MDAEELREHGHRMVDFISDYYKEIESYPVRSQVQPGYLRNLIPDSAPDMPESFESILEDIR

HKIIPGVTHWQSPKYFAYYPSNSSTAGFLGEMLSAGFNIVGFSWVTSPAATELEVIVLDW

LAKVLKLPEQFLSTGKGGGVIQGTASEAMLVALLAARDKALRRVGQNLLENLVVYGSD

QTHSALIKACKIAGINPMNCRLLQATFMTNYALSPEVASESISNDIAAGLLPIFLCATVGT

TSSTAVDPLAALGRLAKANDMWFHIDAAYAGSACICPEYRHYIDGVEEADSFNMNPHK

WLLTNFDCSTLWVKDSSNLIQSLSTNPEFLRNKASEEDLVVDYKDWQIPLGRRFRSLKL

WMVLRMYGVANLQNHIRTHINLAKHFEELIATDTRFEIIVPRVFALVCFALKPMPNGQD

DASKLNLKLLEAVNNSGAMFLTHTVLSGRFVLRFVVGAPLTEERHVNTAWKVLQDHA

NLILGTV

*Salix purpurea* 0252s0200.1 (SEQ ID NO: 47):
MESKGLKPMDSEQLRENAHKMVDFIADYYKSIENFPVLSQVEPGYLRELLPDSAPNQPE

TLQNVLDDVQAKILPGVTHWQSPSYFAYYPSNSSVAGFLGEMLSAGINMVGFSWITSPA

ATELEMIVLEWLGKLLKLPEDFLSTGQGGGVIQGTASESVLVVLLAARDRVLTKLGKNA

LEKLVVYASDQTHSALQKACKIGGIHPENCKLLKTDSSTNYALSPDLLSKAISDDISTGLI

PFFLCATVGTTSSTAVDPLHALGKIAKNNGIWFHVDAAYAGSACICPEYRCYIDGVEEA

DSFNMNAHKWLLTNFDCSALWVKDRNALIQALSTNPEFLKNKASQANIVIVVDYKDWQI

PLGRRFRSLKLWMVLRLYGLENLQCYIRNHINLAKYFEGLVAADSRFEVVTPRIFSLVCF

RLLPPSNNEDHGNNLNRDLLDAVNSSGKIFISHTVLSGKYILRFAVGAPLTEERHVIAAW

KVLQDESTSLLGSL

*Medicago truncatula* 31080941 (SEQ ID NO: 48):
MVLQIWCLTHDSDKKLGGGYLLFPVIKVAYTVHTLTEWCCVTEEGGGSELKAMDAEQ

LREQGHMMVDFIADYYKTIENFPVLSQVQPGYLGKLLPDSAPTHPESLQHVLNDVQEKI

LPGVTHWQSPNYFAYFPSNSSIAGFLGEMLSAGLSIVGFSWISSPAATELETIVLDWLAK

ALLLPHDFFSTGQGGGVIQGTASEAVLVVLVAARDKILRTVGRSALPKLVTYASDQTHS

SLQKACQIAGLNPELCRLLKTDSSTNFALSPDVLSEAISNDIASGLTPFFLCATVGTTSSTA

-continued

VDPLPALAKVTKPNNIWLHVDAAYAGSACICPEYRHFIDGVEEADSFNMNAHKWFLTN

FDCSVLWVKDRSALIQSLSTNPEFLKNKASQENTVIDYKDWQIPLGRRFRSLKLWMVM

RLYGLEGLRTHIRSHIALAVYFEELVVQDTRFKVVAPRTFSLVCFRLLPPQNSEDNGNKL

NHDLLDAVNSTGDVFITHTVLSGEYILRLAVGAPLTEVRHVHAAWQILQEKATALLESL

*Brassica rapa* 101156.1 (SEQ ID NO: 49):
MQIRAKIPVFGRENGSRHVLKPMDSEQLREYGHRMVDFIADYYKTIESFPVLSQVQPGY

LHNLLPDSAPDHPETVEQVLDDVKTKILPGVTHWQSPNFFAYYPSNSSVAGFLGEMLSA

GVGIVGFSWVTSPAATELEMIVLDWLAKLLNLPEHFLSKGNGGGVIQGSASEAILVVMI

AARDKVLRSAGKNALGKLVVYSSDQTHSALQKACQIAGIHPENCRVLKADSSTNYALR

PELLQEAVSRDLEAGLIPFFLCGNVGTTSSAAVDPLAALGKIAKSNEIWFHVDAAYAGS

ACICPEYRQYIDGVETADSFNMNAHKWFLTNFDCSLLWVKDQHALTEALSTNPEFLKN

KASQANLVVDYKDWQIPLGRRFRSLKLWMVLRLYGAEALKNYIRNHIKLAKDLEQLVS

QDPNFEVITPRIFSLVCFRIVPTDNDEKKCNSRNLELLEAVNSSGKLFISHTALSGKIVLRC

AIGAPLTEEKHVKETWKVIQEKVSYLLRK

*Brassica rapa* 104706.1 (SEQ ID NO: 50):
MDSEQLREYGHRMVDFIADYYKTIETFPVLSQVQPGYLHNLLPDSAPDQPETVEQVLDD

VKTKILPGITHWQSPTFYAYYPSNSSVAGFLGEMLSAGLGIVGFSWVTSPAATELEMIVL

DWLAKLLNLPEQFLSKGNGGGVIQGSASEAILVVMIGAREKVLRRVGKNALGKLVVYS

SDQTHSALQKACQIAGIHPENCRVLKADSSTNYALRPELLQEAVSKDIEAGLIPFFLCGN

VGTTSSTAVDPLAALGKIAKSNEIWFHVDAAYAGSACICPEYRQYIDGVETADSFNMNA

HKWFLTNFDCSLLWVKDQYVLTEALSTNPEFLKNKASQANLVVDYKDWQIPLGRRFRS

LKLWMVLRLYGAETLKSYIRNHIKLAKDLEQLVSQDPNFEVVTPRIFSLVCFRILPVDND

EKECNNRNRNLLDAVNSSGKLFLSHTALSGKIVLRCAIGAPLTEERHVKETWKVIQEEAS

RLLGK

*Brassica rapa* G00043.1 (SEQ ID NO: 51):
MDSEQLREYGHRMVDFIADYYKTIETFPVLSQVQPGYLHNLLPDSAPDQPETLEQVLDD

VKEKILPGVTHWQSPSFFAYYPANSSVAGFLGEMLSAALNIVGFSWVSSPAATELEMIVL

DWFAKLLNLPEQFLSRGNGGGVIQGTASEAILVVMIAARDKVLRSLGKKALEKLVVYSS

DQTHSSLLKACQIAGIHLENCRMLKTDSSTNYALRPESLQEAVSGDLEAGLIPFFLCGTV

GTTSSTAVDPLAELGKIAKSNEMWFHVDAAYAGSACICPEYRQYIDGVETADSFNMNA

HKWFLTNFDCSLLWVKDRYALTEALSTNPEFLKNKASQANLVVDYKDWQIPLGRRFRS

LKLWMVLRLYGAETLKSYIKNHIKLAKDLEQLVSQDPNFEVVTPRIFSLVCFRIVPVDND

EKTCNNLNRSLLDAVNSSGKLFISHTTLSGKFVLRLAIGAPLTEEKHVMDAWKVIQEEAS

FLLASQVK

*Glycine max* 03G167900.1 (SEQ ID NO: 52):
MEEESALRPMDAEQLREQAHKMVDFIADYYKTIEDFPVLSQVQPGYLGKLLPDSAPDSP

ESLQNVLDDVQEKILPGVTHWQSPNYFAYFPSNSSIAGFLGEMLSAGLNIVGFSWITSPA

ATELETIVLDWLAKAFQLPDYFYSSGKGGGVIQGTASEAVLVVLLAARDKILRRVGRNA

LPKLVMYASDQTHSALLKACQIAGINPELCRLLKTDSSTNYALSPDVLSEAISNDIAGGL

VPFFLCATVGTTSSTAVDPLPALGKIAKTNKLWFHVDAAYAGSACVCPEYRHCIDGVEE

ADSFNMNAHKWFLTNFDCSLLWVKDRSSLIQSLSTNPEFLKNKASQGNMVIDYKDWQI

PLGRRFRSLKLWMVLRLYGLDGLRSHIRNHIELAANFEELVRQDTRFKVVAPRTFSLVC

-continued

FRLLPHPNSADHGNKLNSDLLDSVNSTGNAFITHTVLSGEYILRFAVGAPLTERRHVNM

AWQILQDKATALLESL

*Fragaria vesca* 27261550 (SEQ ID NO: 53):
MDAEQLRENAHKMVDFIADYYKTIEDFPVLSQVQPGYLRELLPDSAPTQPESLQHIFDDI

QAKILPGVTHWQSPNFFAYYPSNSSIAGFLGEMLSAGLNIVGFSWVTSPAATELEMIVLD

WLAKLIKLPDEFLSAGQGGGVIQGTASEAILVVMLAARDKILRRVGKNALEKLVVYASD

QTHSALQKACQIAGIHPENCRILSTNSTTNYALSPSVGTTSSTAVDPLGELGKIAKNNEM

WFHVDAAYAGSACICPEYRHYIDGVEKADSFNMNAHKWFLTNFDCSVLWIKDRNALV

QSLSTNPEFLKNKASQANIVIVVDYKDWQVPLGRRFRSLKLWMVLRLYGLENLQSYIRT

HINLAKHFEELVAQDPRFEIVTPRLYSLVCFRLLPPHGNEACASKLNHDLLDAVNSTGKI

YISHTVLSGAYILRFAVGAPLTEEKHVTAAWKKLKSVIRDVLALANSFVSITFSHMYREA

NFLTDALASVGHSLSSSMCWFDGIPPQAQMALLMDSSCIGHLRGSSL

*Kalanchoe fedtschenkoi* 0172s0035.1 (SEQ ID NO: 54):
MEGELKPMDAEQLREYGHRMVDFVADYYKTIEDHPVLSQVEPGYLRKLLPDSAPDKPE

SFENVLSDVKTKIIPGVTHWQSPNYFAYFPSNSSTAGFLGEMLSACFNIVGFSWITSPAAT

ELEMIVLDWFAKMLKLPDFFLSTGQGGGVIQGTASEAVLVVLLAARDIFLRKLGKGFLE

KLVVYASDQTHSALQKACQIAGIHPENVKALKTDSSTNYGLSPDLLSKEICHDIANGLVP

FFACASVGTTSSTAIDPILELANVTKSYNIWLHVDSAYAGSACVCPEYRHHIDGVEEVDS

FNMNAHKWFLTNFDCSLLWVKDRNALIQSLSTNPEFLKNKASQKSVLDYKDWQIPLG

RRFRSLKLWLVLRLYGVENLQAYIRNHIELAIHFEELVSQDMRFEIVAPRTFALVCFRLL

LPCGFEDRTNDVNGDLLQAVNSTGKIFISHTVLSGTYVMRFAVGAPLTEERHIDAAWKL

IQDQASSLLEKL

*Capsella grandiflora* 22666s0001.1 (SEQ ID NO: 55):
MDSEQLREYGHRMVDFIADYYKTIEDFPVLSQVQPGYLHKLLPDSAPDQPETLDQVLDD

VRAKILPGVTHWQSPGFFAYYPSNSSVAGFLGEMLSAGLGIVGFSWVTSPAATELEMIV

LDWLAKLLNLPKEFLSKGNGGGVIQGSASEAVLVVLIAARDKVLRSAGKNALGKLVVY

SSDQTHSALQKACQIAGIHPENCRVLETDASTNYALRPELLQEAVSKDLKAGLIPFFLCA

NVGTTSSTAVDPLAALGKIANSNEIWFHVDAAYAGSACICPEYRKYIDGVETADSFNMN

AHKWFLTNFDCSLLWVKEQDSLTEALSTNPEFLKNKASQANLVVDYKDWQIPLGRRFR

SLKLWMVLRLYGAETLKSYIRNHIKLAKYYEKLVSQDPNFEIVTPRIFSLVCFRLVPKNE

DEKKCNNQNRKLLEAANSSGKLFMSHTALSGKIVLRCAIGAPLTEEKHMKEAWKVIQD

EASFLLHK

*Selaginella moellendorffii* 15420188 (SEQ ID NO: 56):
MGEANIGPKPIDAEEFRKHAHEMVDFIADYYRDIESFPVRSQVSQPGYLKTLLPPAAPED

PEALEEVFADIQSKIIPGVTHWQSPNFFGYYPSNSSTAGLLGEMLSAGLNIVGFSWITSPA

ATELEIIVLDWLAKLLKLPDEFLFGGNGGGVIQGTASEAVSVVLLAARTRAISENKRKGL

SEAEILSKLAVYTSDQTHSCLQKGCAIAGIPLENLVIVPTDSSTNYAVSPAAMRQALEDG

VKQGLLPFFLCGTVGTTSSSAVDPLSALGDIAKDFGMWFHVDAAYAGSACICPEFRHHL

DGVEKADSFNMNAHKWLLTNFDCSALWVKESSHLVSALSTTPEFLRNKASDLNQVVD

YKDWQIPLGRRFRSLKLWFVMRIVINGASGLRSYIRNHVRLAKRFEGFVREDPRFQLLVP

RTFGLICFRLKPESDDPDNGRTLNSTLLEAVNSSGRMFITHTVLSGVYTLRMAIGGPLTQ

DKHVDAAWKLIQEEATTLLVKGPSHILANNLRLSPILANNLRLSPILANNRI

-continued

*Setaria italica* 3G188200.1 (SEQ ID NO: 57):
MDILNHADTTTANGTSPAAAAAAAVVAPATPSSLVTPPLDADEFRRQGRLVVDFIADYY
TRINEYPVRPAVAPGFLARQLPETAPARPERDALAAALRDVRDLILPGVTHWQSPRHFA
HFAATASNVGALGEALAAGLNINPFTWAASPAATELEVVVTDWLGKALHLPERLLFSG
GGGGTLLGTSCEAMLCTIVAARDRKLAEIGEERIGDLVVYFSDQTHFSFQKAARIAGIRR
GNCREIPTSRESGFTLSPKALRAAVRADEASGRVPLFLCATVGTTPTAAIDPLRELCAAV
SGHGVWVHVDAAYAGAACVCPEFRHAIAGAEAVDSFSTNPHKWLLANMDCCALWVT
RPAALVAALGTDHDVILKDPSAAAQDGHDVVVDYKDWQVALSRRFRALKLWLVLRC
HGVEGLRGFVRAHVRMAAAFEAMVRADTRFEVPVPRQFALVCFRLRPASAGEKRTRG
GEVVEPNELNRRLLEAVNATGRAYISSAVVGGVYVLRCAIGNSLTEERHVREAWSVVQ
EQANVVLAAATATCPDERAVHRARCVETDAADAPASVPPVQMRFPSAQS

*Kalanchoe fedtschenkoi* 0033s0078.1 (SEQ ID NO: 58):
MGSLPSPHDPSNAFNPMDVAELSWSRLVMDFITQYYQTLETRPVQPRVKPGFLTGQLPE
KAPFHAESMEEILSDVSEKIVPGLTHWQSPNFHAYFPASSSNAGLLGEMLCSGLSVIGFT
WNSSPAATELENVVVDWLADMLNLPPSFRFSGGGGGGVLQSNTCEAVLCTLAAARD
KVLERIGDDKINKLVAYCSDQTHFTLHKGAKLIGIRRANIKSIGTRRENGFGLCPNDLRN
AITGDLEAGLVPFYLCGTIGTTALGAVDPIKELGKVAREFDLWFHIDAAYGGSACICPEF
RHYLDGVELVDSISMNAHKWLLSNLDCCFLWLQNPKCLIQCLAAEAEFLKGSGEMVDY
KDWQISLSRRFRAIKMWMVFRRYGVSNLMEHIRSDVSMAARFEEMVSADDRFEIVFPR
KFALVCFKLNTKGSVQHGEDDGEDGLDGDSVLTRELMGRVNSSGKAYLSGVEMGRIFF
IRCVIGSSLTEERHVDNLWNLIQEKTQSIMPCRA

*Daucus carota* subsp. *sativus* 36068870 (SEQ ID NO: 59):
MGSLSTQKFNPLNLDFFSSESNKVIEFITAYYKNVEKYPVRSQVEPGFLLNMYPKKAPSQ
PVSLDTILQELEADIIPGMTHWQSPNFYAYFRTTTSNAAFQGEMLCNALNVAGFNWICSP
AATELEMIVMDWLGKMLSLPQSFLFAGNGGGVLQGSTSEALICVLSAARDRALKQYGE
DSITKLVVYASDQTHFVVKKAAKLVGIPTKNFRVIPTSIATCFALKPNDIKMAIERDLESG
LVPLFVCATVGATPSGSVDPVEGLGLLAKNYGLWLHIEAAYAGSAFICPELTHYLRGIEH
AHSISINLHKWLLTNMDCSCLWVKSPDVLLESLSMTDEILRNEASESKKVVDFMDWQIA
TSKLFRALKLWFVLRRYGVDNLMAHIRSDIELAKHFEALVNSDKRFEVVVPVNFSLVCF
RLKPNEEGEESLKVLMNWNLMEAVNSSGRAYMTHAVLGDIFVIRCAIGTSLTEERHVNE
LWKLILEKTEVILKRDQ

*Daucus carota* subsp. *sativus* 36056758 (SEQ ID NO: 60):
MNTFDTEDFRKQAHLIIDFLADYYQNIEKFPVRSQVSPGYLGEILPDSAPHDPEPIEKILED
VRSNIIPGITHWQSPNFFAYFPSCGSTAGFLGEMLANGFNVVGFNWISSPAATELETIVM
DWLGKMLQLPEAFLFSGGGGGVLQGTTCEAMLCTLVAARDRTLREQGMENFDKLLCP
VQLELEILSDVQNGLIPLFLCVTIGTTPSTAVDPLATLSEVAKKYKLWVHVDAAYAGSA
CICPEFRHFLDGLENVNSFSMNAHKWFLTTLDCCCLWVNDPSALIKSLSTYPEFLRNHAS
ESNKVVDYKDWQIMLSRRFRALKLWFVLRSYGVEKLREFIRVHVEMAKYFEGLVAMD
QRFEVVVPRLFAMVCFRVVCCGENDVNEINEKLLESVNQSGRIYVSHAVLDGVYVIRFA
IGATLTDYSHVSAAWEVVQEHADALLA

*Solanum tuberosum* 3DMP400026166 (SEQ ID NO: 61):
MGTLNINHELDDQIFNTINPLDPEEFRRQGHKIVNFLADYYQNIEQYPVCSQVNPGYLQK
IVPNSAPNNSESLEKILKDVERDIIPGLTHWQSPNFFAYFPSSGSTAGFLGEMLSVGFNVV -continued

GFNWISSPAATELESIVMDWFGKMLNLPNCFLFASGGGGVLQGTTCEAMLCTIVAARD

QMLRKISRENFGKLVVYASDQTHFSLKKAAHIAGIDPGNFRVIPTIKANEYTLCPKSLRL

AILNDLKEGNVPLFLCATIGTTATTSVDPLRLLCEIAKEFGIWVHVDAAYAGSACICPEFQ

VFLDGVENANSFSLNAHKWFFSTLDCCCLWVKDPSALTNALSTNPECLRNKATELNQVI

DYKDWQIALSKRFRALKLWLVLRSYGVTNLRNLIRSHVNMAKHFEGLVATDKRFEIFV

PRKFAMVCFRISPLVLSQVSTKFDDEKEVNMFNTKLVESINSCGKLYLTHGVVGGTYIIR

FAIGASLTHYRHVDVAWKVIQDHANALLNQGYV

*Solanum tuberosum* 3DMP400024738 (SEQ ID NO: 62):
MGTMKINPEHEFDGQFSINTSSSRLLDPEEFRRQGHMMVDFLADYFQNIEKYPVRSQVE

PGYLKKLLPDSAPYKPEPIAKILEDVERDIFPGLTHWQSPNFFAYFPCTSSTAGILGEMLS

AGLNVVGFSLIASPAATELESIVMDWLGKMISLPKTYLFSGGHGGGGVIQGTTCEAMLC

TIVAAREQMLEKVGREKVDKLVVYASDQTHFSFEKAVKISGIKLENFRVIPTTKDTEFAL

DPKSLSRTIEQDIKSGFIPLFMCATIGTTSTTVVDPLKLLCEITKDYGIWVHVDAAYAGGA

CICPEFQHFLDGIENANSFSFNAHKWLFSNLDCCCLWVKDPSALTNALSTRPECLRNKAT

DTKQVVDYKDWQLSLSRRFRALKLWLVLRSYGIDNLRNFIRSHVKMAKHFEQLVSMD

ERFEIVAPRNFSMVCFRVSPLALGNKQVNKFNMELLESINSCGNIHMTHALVGGVYMIR

FAIAAPLTEYKHIDMAWEVICNHANAMLDVN

*Solanum lycopersicum* 36137005 (SEQ ID NO: 63):
MGTLNINHELDDQIFNTINPLDPEEFRRQGHKIVNFLADYYQNIEQYPVCSQVNPGYLQN

IVPNSAPNNPESLDKILKDVQNDIIPGLTHWQSPNFFAYFPSSGSTVGFVGEMLSVGFNV

VGFNWISSPAATELESIVMDWFGKMLNLPNCFLFASGGGGVLQGTTCEAILCTIVAARD

QMLRKISRENFGKLVVYASGQTHFSLKKSAHIAGIDPGNFRVIPTIKAKEYTLCPKSLRLA

ILNDLKEGNVPLFLCATIGTTSTTSVDPLRLLCDISKEFGIWVHVDAAYVGSACICPEFQV

FLDGVENANSFSLNDPSALTNALSTNLEFLRNKATELNQVIDYKDWQIALSRRFRALKL

WLVLRSYGVTNLRNLIRSHVNMTKHFEGLIAMDKRFEIFVPRKFAMVCFRISPLVLSQVS

IKFDDEKEVNMFNTKLLESINSCSKLYLTHGIVGGTYIIRFAIGASLTHYRHVDIA

*Daucus carota* subsp. *sativus* 36065781 (SEQ ID NO: 64):
MCKPKSSPASHINWQSPNFFAYFPSSGSTAGFLGEMLSTGFNVVGFHWMASPAATELEN

VVTDWFGKMLQLPKSFLFSGGGGVLQGTTCEAMLCTLVAARDKNLRQHGMENIGKL

VVYCSDQTHSAMQKAAKIAGIDPKNFRTVETSRASNFQLCPRRLESAILTDIQNGLIPLYL

CATVGTTSSTAVDPLPALTEVAKKYDLWVHVDAAYAGSACICPELRQYLNGVENADSF

SLNAHKWFLTTLDCCCLWVKNPSALIKSLSTYPEFLRNNASETNKVVDYKDWQIMLSR

RFRALKLWFVLRSYGVGQLREFIRGHVDMAKYFEGLVGKDKRFEVVVPRLFSMVCIRV

RPSAMTGKSCGNDVNELNRKLLESLNESGRIYVSHTVLDGIYIIRFAIGATLTDINHVSAA

WKVVQDHATALLDDTNFLAKKVADIILS

*Oropetium thomaeum* 35995617 (SEQ ID NO: 65):
MAILNHADDASPANDDNPATAPAMAPATNPRPLDADEFRRQGRLVVDFIADYYARVEE

YPVRPSVTPGFLSRKLPETAPEQPEPGHGDAFASALRDVRDLILPGITHWQSPNHFAHFA

ATASNVGALGEALAAGLNINPFTWAASSAATELEVVVTDWLGKALHLPQELLFSGGGG

GTLLGTSCEAMLCTVVAARDRKLGEIGEHRIGDLVVYCSDQTHFSFRKAARVAGIRRAN

CREIPTSLESDFALSPSALLAAVRADEAAGLVPLYLCVTVGTTPTAAVDPVRELCAAVA

GRGVWVHVDAAYAGAARVCPELLRHAGAIVDGVDSFSTNPHKWLLANMDCCALWVQ

-continued

QPDALVAALGTDHDVILKDPAAAAAGDVVVDYKDWQVALSRRFRALKLWLLLRCHG

VEGLRAHVRDGLRMAEAFEAMVRADARFEVPVRRQLSLVCFRLRPTAVIREKQQQQRG

RRRDHDDDTAAANELNRRLLEAVNATGRTYMSCAVVGGVYMLRCAIGNSLTEDRHVE

EAWNVVQEQASAILDAAMVVRADECTVCTAAHCVQMGMVDDILAASFPTGNEVTIR

*Oryza sativa* 33157740 (SEQ ID NO: 66):
MAILNHSDAAFPVAATTPLLGRRPLDAGEFRRQGRQVVDFIADYYAGINDYPVRPAVAP

GFLAGKLPATAPSTPEPDALTAGLRDVRELMLPGLTHWQSPRHFAHFSATASNVGALGE

ALAAGLNVNPFTWEASPAATELEVVVTDWLGKALHLPERLLFAGGGGGTLLGTSCEAM

LCTIVAARDEKLAEIGEERIGDLVVYCSDQTHFSFQKAARIAGIRRGNCREIPTCRESGFV

LTATALQAAVAADEAAGRVPLFLCATVGTTPTAAVDPLRELCAAVEGRGVWVHVDAA

YAGAACVCPEFRHAIAGAEAVDSFSTNPHKWLLANMDCCALWVARPAALVAALGTDD

DVILKDAAAAARPARGDHRHHAAVDYKDWQVALSRRFRALKLWLVLRCHGVDGLRA

VVRSHVRMAAALERIVIVRADARFEVPVPRQFALVCFRLRGGGAAAQLVGGDELTASNE

LNRRLLEAVNATGRAYMSSAVVGGMYVLRCAVGNSLTEEHEIVREAWSVVQGQAAAV

LATAGAAADTARTKDHAAGDDHGADQPHAMTTTTTMGCRSGPWEL

*Brachypodium stacei* 01G392300.1 (SEQ ID NO: 67):
MAPASSTRQVITDHKTQKENSSCTVINHLLDADEFRRQGHKVIDFIADYYSGIADYPVHP

SVTPGFLLNQLPADPPEDPDTFASALQDVRDLILPGMTHWQSPRHLAHFPASSSVTGALG

EALAAGINAVPFMWSASPAATELEMVAVDWLGKALHLPKTLLFSGAGGGTLLGTSYRK

LAETGAGRIGDLVVYGSDQTHFALRKAARIAGIRHGRCRELRTCIADMFALSPAALSAA

MDADAGAGLVPLFLCATVGTTQTKAVDPIGALCAEAAPHGVWVHVDAAYGGSALVCP

ELARDAIDGVEAVDSFSMNAHKWLLVNTDCCALWVKRPALLVSALGTQDEDEVILRD

AAAQGHDVVDYKDWAVTLTRRFRALKLWLVLRCYGVEGLREHIRGHVRMAALFEGM

VNADPRFEVVTERRFALVCFRLRPDQLPDEGNKKKTMAAANELNRRLLQEVNAAALGP

YMSAANVGGIYVLRCAVGSTLTEKRHVRQAWEVVQEKATSILRA

*Amaranthus hypochondriacus* 32828676 (SEQ ID NO: 68):
SLHDETLQGIKYVTQYYKNVEKYPVVSKVKWGYLRQILPENAPSLPESIDQILEDVDTKI

VPGLTHWQSPNFFAYFPATASNAAMLGDIVCSGLNVVGFSWISSPAATELEAIVMDWM

AKLLMLPPTFLFSGGGGGVIHGSTCEAIVCTQAAARDVALNIHGEEKITKLVVYASDQT

HISFQKAAKLIGIPPRNFRVLPTSSATDFALSPTTLRASIEVDLSQGLVPFYICATIGATPSG

AVDPIDGLGQIARDYGAWLHVDAAFAGNACICPEYRHYLDGVELADSISMNPHKWLLT

NMECSCLWLKNPKLMVDSLSTKPEILNNKATQSGDVIDYKDWQIALSRRFRALKLWIVI

RRYGSTYLMNHVRSDIELAKYFESLIKQDERFELVVPRKFSLVCFRMKLVGREDVETLT

NQKLLEDVNSSGKAYMTHAVIGGKFVIRCAIGGTLTEKRHIDSLWKLIIEKVPLTTCEL

*Brachypodium distachyon* 5g21770.1 (SEQ ID NO: 69):
MSSNSCPAAAATFTTPPGAHPLPLDADAFRRQGRQVADFIADYYDRIEDYPVRPNVSP

GFLAAQLPDAAPSWPEEPDALASALRDVRDLILPGLTHWQSPRHFAHFAATASNAGAL

GEFLAAGLNVNPFTWAASPAAAELEVVVTDWLGQALGLPEKLLFRGGSGGGGTLLGTS

CEAMLCTIVAARDQKLLKIGEDRIGDLVVYCSDQTHFSFKKAARVAGIRRGNCRVIPTRF

EDGFALSPAALAAAVRDDVARGKVPLFLCATVGTTATGAVDPVRELCAAVGAGHGSG

VWVHVDAAYAGGACVCPEFRHVAAGAEEADSFSTNPHKWLLANMDCCALWIRRPGL

LVAALGAGEDEDAILNKAPPAARGMQADLMVDYKDWQVPLSRRFRALKLWLVLRCH

GVEGLRGVVRGHVRMAAAFEAMVRADPRFEVPVPPAFALVCFRLRPLAAHPGSSSGID

-continued

EVNGRLLEAVNGTGRAYMSGAVVGGAYVLRCAVGNSLTEDRHVREAWSVVQEQADA

ILAPSDDEDRCCTDQIQTEMELQRRPLGAAADVFA

*Brachypodium distachyon* 2g02360.1 (SEQ ID NO: 70):
MAPASSKLHAITDDKTQQQNSSCPAASNGAIEPSNAKCAASSNHLLDADEFRRQGHKVI

DFIADYYAGIADYPVHPSVTPGFLLNQLPADPPSRPEDHPDGAFGPALQDVRDVILPGMT

HWQSPRHFAHFPASSSVAGVLGEALAAGINAVPFTWAASPAAAELEMVAVDWLGKAL

HLPESLLFSGAGGGTLLGTSCEAILCALVAARDRKLADIGTDRIGDLVVYGSDQTHFALR

KAARIAGIRHDRCRELQTCLADMFALSPAALSAAMDADAGAGLVPLFLCATVGTTQTT

AVDQVGALCAAAAPHGVWVHVDAAYAGSALVCPELARDAIDGIEVVDSFSMNAHKW

LLANTDCCALWVKQPKLLVVSLGTQNEELILRDAAAEGHDVVDYKDWAITLTRRFRAL

KLWLVFRCYGVEGLREHIRAHVRMAALFEGLVKDDPRFEVVTERRFALVCFRLRAPDQ

LMDEGNEKKKTTAAANELNRRLLREVNGVALGPYMSAAVVGGIYILRCAVGSTLTEER

HVRQAWEVVQERATSILRG

*Sorghum bicolor* 009G192600.1 (SEQ ID NO: 71):
MGVAVTAEVVHARSCKGTPPVGAAASVMVWDGAGQGYSCQPVGTTTANGGTTPAAP

VAIAMPSLPHPLLDADEFRRQGRLVVDFIADYYARIDEYPVRPAVAPGFLARQLPETAPA

RPEPDALAAALRDVRDLILPGVTHWQSPRHFAHFAATASNVGALGEALAAGLNINPFT

WAASPAATELEVVVTDWLGKALHLPESLLFSGGGGGTLLGTSCEAMLCTIVAARDRKL

AEVGEERMGDLVVYCSDQTHFSFQKAARIAGIRRGNCREIPTSMEAGFTLSPKALAAAV

RADEAAGRVPLFLCATVGTTPTAAVDPVRELCAAVAGRGVWVHVDAAYAGAASVCPE

LRHAVAGVERVDSFSTNPHKWLLANMDCCALWVRRPAALTAALGTDHDVILKDPSAQ

AAQEGGAVVDYKDWQVALSRRFRALKLWLVLRCHGVEGLRGLVRAHVRMAAAFEA

MVRTDARFEVPVPRQFALVCFRLRAAAVLVVGEKRARDGDDEVVTAGNELNRRLLEA

VNATGRVYMSSAVVGGTYILRCAIGNSLTEERHVREAWSVVQEQATAILAAARRPTAR

TNRRTVRRAHAAL

*Kalanchoe laxiflora* 0994s0009.1 (SEQ ID NO: 72):
MGSLQSPHDPNAFNPMDVAELSIESRLVMDFITQYYQTLETRPVQPRVKPGFLTGQLPE

KPPFHAESMEEILSDVSEKIVPGLTHWQSPNFHAYFPASSSNAGLLGEMLCSGLSVIGFT

WNSSPAATELENVVVDWLADMLNLPPSFRFSGGGGGVLQSNTCEAVLCTLAAARDKV

LERIGDDKINKLVVYCSDQTHFTLHKGAKLIGIRRANIKSISTRRENGFGLCPNDLRNAIK

SDLEAGLVPFYLCGTIGTTALGAVDPIKELGKVAREFDLWFHIDAAYGGSACICPEFRHY

LDGVELVDSISMNAHKWLLSNLDCCFLWLQNPKCLIQCLAAEGEFLKGSGEMVDYKD

WQISLSRRFRAIKMWMVFRRYGVSNLMEHIRSDVSMAARFEEMVAADDRFEIVFPRKF

ALVCFKLNTKGSVQHGEVDGEDGLDGDSVLTRELMGRVNSSGKAYLSGVEMGRIFFIR

CVIGSSLTEERHVDNLWNLIQEKTQSIMPRRA

*Kalanchoe laxiflora* 0003s0173.1 (SEQ ID NO: 73):
MGSLSSPRDLTKPFNPLDPTELAVESSLVTDFIAEYYRTVEQRPVQPHVTPGFLTSQLPSA

APFASESVESILQDVYDKILPGLVQWQSPNFHAYYPATCSNAGLLGEMLCSGLNVVGFT

WSASPAAAELEQVVVDWMGKMMGLPQSFLFSGGGGGVLQGSTCEAVVCTLAAARDR

ALERVGDDMFNKLVVYCSDQTHFTLKKGSKLVGIRPANVKAIKTTKNNEYGLCPTDLR

NLVASDVKAGFIPIYLCGTIGTTAFGAVDPIRELGKVAREFNMWFHVDAAYAGSAFICPE

FRHYMDGVELADSFSTNPHKWLLSNMDCCVLWLKFPKRVIKSLAAEGVFLEGGSETMV

```
DYKDWQIALSRRFRAIKLWMVIKRYGLKNLISHIRSDVSMAKRFEELLLSDRRFEVVFPR

KFSLVCFKLDVMKNVPEVVDEDDGELSHDSKLTRELMASVNVTGKAFLTGVRLGRIFFI

RCAIGSTLTEDRHIQDLWKLIQEKAHKICANHDLKFRV

Panicum hallii 32512198 (SEQ ID NO: 74):
MAILNHGDTTTANGSSPADAAAVAPAMPSLVQPPLDADEFRRQGRLVVDFIADYYTRID

EHPVRPAVAPGFLARQLPDTAPARPEPGDDALAAALRDVRDLILPGVTHWQSPRHFAHF

AATASNVGALGEALTAGLNINPFTWAASPAATELEVVVTDWLGKALHLPESLLFSGGG

GATLLGTSCEAMLCTLVAARDRKLAEIGEERIGDLVVYCSDQTHFSFQKAARIAGIRRG

NYREIPTSRESGFTLSPKVLRAAVRADEAAGRVPLFLCATVGTTPTAAVDPLRELCATVA

GHGVWVHVDAAYAGAACVCPEFRHAIAGAEAVDSFSTNPHKWLLANMDCCALWVRR

PEALTAALGTDHDVILKDPSSERDCGRGVVDYKDWQVALSRRFRALKLWLVLRCHGV

EGLRGFVRAHVRMAAAFEDMVRADARFEVPVPRQFALVCFRLRSAAAGEKRARDGDD

AEPNELNRRLLEAVNATGRAYMSSAVVGGIYVLRCAIGNSLTEERHVREAWCVVQEQA

TVVLAAAACTEERAVHSARCADAPAAVPPVQNEGYGEPTSIAAKIFGTSIARCSIKSEAS

TYHSWSTLWRTLMFKLLTWIISRL

Prunus persica 6G202600.1 (SEQ ID NO: 75):
MTSALDPVEFRRQGHMMVDFIADYYQNIDKYPVLSQVDPGYLRKRLPESAPDNPEPIETI

LQDVQEHIVPGLTHWQSPSFFAYFASNVSIAGFLGEMLSTGFNVVGFNWVSSPAATELE

SIVMDWLGNLLSLPKSFLFSGNGGGVIHGSTCEAIVCTMAASRDQMLSRIGGDNIGKLV

VYGSDQTHSALQKASQIVGINPKNFRAIEATRSTTFALSPESLKLAISSDIEAGLVPLFLCA

TVGTTATTAVDPLGPLCDVAKHHGMWVHVDAAYAGSACICPEFRHFIDGIEGVDSFSFN

AHKWFFTGLDCCCLWVKNPGALISSLSANPEFLRNKPTDSKQVVDYKDWQIALSRRFR

AMKLWLVLRSYGVVNLRNFLRSHVKMAKLFEGLVAMDQRFEIVVPRNFSMVPPTTPTS

NSFHQNGIEINVEKCTNEVNCKLLEAINASGRVFMTHAMVGGMYVIRCAVGVTQTEEK

HIAMAWKVVQEHADVILKNNGDDGDANLKLPLLDKIA

Prunus persica 4G086700.1 (SEQ ID NO: 76):
MGSLNFDHPQENNSAHMSGPLDLVELRRQGHMIIDFITDYYQNIEKHPVLSQVQPGYLK

QRLPESAPYNPEPIETILRDVQDHIVPGLTHWQSPNHFAYFPATISTAGFLGEMLTTCFNV

VGFNWMASPAATELETIVMDWLGDMLKLPNSFLFSGTGGGVLHGSTHESVVCTMAAA

RDQILSRIGEENIGKLVVYGSDQTHSVIQKVSQIVGIPSKNFRAIETTISSSFTLSPETLRLT

VCSDMEAGLVPFYLCATVGTTATTAVDPLGPLCDVAKDYGMWVHVDAAYAGSACICP

EFRQYIDGIEGANSFSFNAQKWFFTALDCCCLWVKNPSALTKSMSTDLEVLRNKASESK

RVVDFKDWQIALTRRFRAIKLWLVLRSYGVANLRNFLRSHVKMAKRFEGLVRTDERFE

VVVPRIFALVCFRISPSAISKANPTPSDEKCVNEVNCKLLEAINGSGWVYMTHAVVGGM

YVLRCAIGASLTKEKHVAMAWKVVQEHVDAILPLTMY

Prunus persica 4G087100.1 (SEQ ID NO: 77):
MMGSVEFEHPQENNSAHMTTSPLDPEEFRRQGHMVIDFIADYYKTIEKYPVLSQVQPGY

LKKRLPESAPYDPEPIETILQDVQDHLVPGLTHWLSPNHFGYFPAAISTAAFLGEMLTTG

FNVVGFNWMASPAATELENIVMDWLGDMLKLPKSFLFSGNGGGVLQGTTCEAIVCTM

AAARDQMLRQIGRENIGKLVVYGSDQTHSALQKASQIVGIHPKNFRAIETTTSTSFALSP

EVLKSTICSDIEAGLVPLFLCATVGTTAITAVDPLGPLCEVAKEHDMWVHVDAAYAGSA

FICPEFQYFIDGVEGADSFSLNAHKWFFTTLDCCCLWVKNPSALVSSLSTNPEFLRNKAT

DSKQVVDYKDWQIALSRRFKAIKLWLVLRSYGVGNLRNFLRSHVKMAKIFEGLVGMD
```

KRFEIVAPRHFSLVCFRVSPSAISKANPSLSDHDNGKLKAHNYELLNGVKCVVNEVNSK

LLEAINGSGLVYMSHAVVGGMYVLRCAIGASLTEEKHVAMAWKVVQEHADAILGTKII

VDQT

*Medicago truncatula* 31073039 (SEQ ID NO: 78):
MNTSSSNPPQSDPQKTMNPLDLEEFKRQGYMMIDFLTDYYKNIENYPVLSKVEPGYLAK

ILPSSAPFQPESIESILEDVQQHIIPGITHWMSPNYYAYFPSSGSIAGFIGEMLSTGFNVVGF

NWLSSPAATELETIVMNWLGKLLNLPKSFIFSSNIKGGGEIKKLSQIGKDNIGKLVVYCSD

QTHSALQKATQIVGIHSENFRVIKTKGSNLFALSPDSLLSTILLDVDNGLIPYFLCATIGTT

STNAVDPIKLLCNVTKEYDIWVHVDAAYAGSVCICPEFRHCIDGIEELNSFSFNAHKWFL

TNLACCCLWVKDHNALTTSLSTNPEFLRNKKSDSKEVIDYKDWQIPLSRKFNALKLWIV

LRSYGVENLKNFLRNHVEMAKIFEGLVRKDERFEIVVPSKFSLVCFRISPFAISIANDSEG

YYVGKMMNDAYLVNEMNHKLLDLINSSGKAYMSHGEVEGSFVIRCAIGATLTEEHHVT

MTWKLVQQIASFLLGTPLN

*Zea mays* GRMZM2G009400 (SEQ ID NO: 79):
MAILNRADTSHTTTASNGSATPAAPVAIAMPSLPHPPLDADEFRRQGRLVVDFIADYYA

RIDGYPVRPAVAPGFLIRQLPEAAPARPEPDALAAALRDVRDLILPGVTHWQSPRHFAHF

AATASNVGALGEALAAGLNVNPFTWAASPAATELEVVVTDWLGKALHLPESLLFSGGG

GGTLLGTSCEAMLCTIVAARDRKLAEVGEERIGDLVVYCSDQTHFSFQKAARIAGIRRG

NCREIPTSRESGFTLSPKALAAAVRADEAAGRVPLFLCATVGTTPTAAVDPLRELCAAV

AGHDVWVHVDAAYAGAACVCPEFSHVVAGVEAAESFSTNPHKWLLANMDCCALWV

RRPAALTAALGTDHDVILKDPAAAQAQAQQQQCSDGGVVDYKDWQVALSRRFRALKL

WLVLRCHGVEGLRGLVRAHVRMAAAFEAMVRGDARFEVHVPRQFALVCFRLRAVAV

AVAGEKRAGDYDGVAAGNELNRRLLEAVNATGRVYMSSAVVGGAYILRCAIGNSLTE

ERHVREAWSVVQEQATAILSAATATARTNGLTVRRARCDAEADVSDVPTPQQPLPLG

*Glycine max* 07G059000.1 (SEQ ID NO: 80):
MEMKNTMNRNPQSDAPIIKPLDPEEFKRQGYMMVDFLADYIRNVSHYPVLSKVEPGYL

KQRLPTSAPCGPEPIESILKDVQDHIIPGLTHWQSPNFYGYFPSSGSIAGFMGEMLSAGLN

VVGFNWVSSPSATELESIVMDWLGQVLNLPKSFLFCGDHGGGVVLGTTCEAILCTLVAA

REKKLSQVGKENIGKLVVYGSDQTHSALQKAAQIAGIHPANFRVIKTKRSNSFALSPDSL

LSTILLDVERGLIPCFLCATVGTTAIATIDPIGPLCNVAKDYGIWVHVDAAYAGSACICPE

FRHCIDGVEEVNSFSLNAHKWFLTNLTCCCLWVKDHIALTKSLTVNPQFLRNKASESKR

VIDYKDWQIPLSRKFNALKLWLVLRSYGVENIRNFLRNHVQMAKTFEGLVRLDKRFEIV

VPPKFSLVCFRIAPSAIIANGLSKGVEACYNGKLVNDEYMVNEVNRKLLDSVNSSGDAF

MTHGEVEGAFMIRCAIGGTLTEEHHVIMAWKLVQEHANSLLGL

*Panicum virgatum* Ca01381.1 (SEQ ID NO: 81):
MAILNHGDTTAASGTSPAAAAVNVAPPMHSLVQPVLDADEFRRQGRLVVDFIADYYTR

IDEYPVRPAVAPGFLARQLPEAAPARPEPGGDALAAALRDVRDLILPGVTHWQSPRHFA

HFATTGSNVGALGEALAAGLNINPFTWAASPAATELEVVVTDWLGKALHLPERLLFSG

GGGGTLLGTSCEAMLCTLVAARDRKLAEIGEERMGDLVVYCSDQTHFSFRKAARIAGIR

RGNCREIPTSRESGFALQPRTLLAAVRADEAAGRVPMFLCATVGTTPTAAVDPLRELCA

AVAGRGVWVHVDAAYAGAACVCPEFRGATAGAEAVDSFSTNPHKWLLANMDCCAL

WVRRPEALTAALGTDHDVILKDPSSERGGGVVDYKDWQVALSRRFRALKLWLVLRCH

```
GVEGLRGLVRADARFEVPVPRQFALVCFRLRAAAAAAVGEKRGRDRDNDAEPNELNR

RLLEAVNATGRAYMSSAVVGGIYVLRCAIGNSLTEERHVREAWRVVQEQATAVLAAA

ACTEERAVRSAR

Theobroma cacao 27425420 (SEQ ID NO: 82):
MSSASRKTFLPLEPTSFTNESKAVIDFIADYYKNIEEYPVQSGVEPGYLSAKLPDSAPYCP

ESLEDILKDVNDCIIPGLTHWQSPNFFAYFQANASTAGFLGEMLCSGFNVVGFNWISSPA

ATELESIVLDWMGKLLKLPSSFLFSGTGGGVLHGSTCEAAVCTLAAARDKALKELGGW

ENITKLMVYASDQTHFTFQKAAKLVGIPPSNFRFIETSLSTGFSMSSDQVRLAIEHDIKSG

LVPLFLCATIGTTACGAIDPIAELGQVAREYKLWLHIDAAYAGSACICPELRHFLDGVEL

ANSVSMNPHKWFLTNMDCCCLWITEPRLLVDSLSTDPEILRNKASEFKAVLDYKDWQV

ALSRRFRALKLWIVIRRHGLANLVYHIRSDISMAERFEAFVAKDDRFDIVVPRKFALVCF

RLKPKQELEGLELNSRLLEAINSSGRAFMTHAVVGGIYVIRCAIGTTMTEERHVDALWK

LIQEKAQGLLME

Fragaria vesca 27274768 (SEQ ID NO: 83):
MGSLDFHHVPEKTNSDPPMANPMDPEEFRRQGHIMIDFIADYYKNIEKYPVLSQVQPGY

LKKLLPESAPYNPEPIETILQDVQDHIVPGITHWQSPSYFAYFPSSGSIAGFLGEMLSTGFN

VVGFNWMSSPAATELERTTCEAIVCTMAAARDQMLSRIGKDNIGKLVVYGSDQTHSAL

KKASQIVGIHPNNFRAIKTTKSTEFALSPELLRSTICSDIDKGLVPLFLCATMGTTATTSVD

PLRGLCDVAKDYDLWVHVDAAYAGSICICPEFRHFIEGVDGANSFSFNAHKWFFTTLDC

CCLWVKNPTALINSLSTNPEFLRNKASDSKQVVDYKDWQVALSRRFRALKLWLVLRSY

GVANLRSFLRSHVKMAEVFEKLVRENKWFEVVVPRNFAMVCFRISPSAIRKAPTDDDGI

DVVINEVNSKLLEAMNTSGSVYMTHAVVGGMYVLRCAIGATMTEEKHVLMAWKCGS

ALERKDVAANETLSFNFQRRFDRRARQRRGHVGFRLAITMLDLKTSERDGARRWSIGA

YANQITTISQANSSVAWTMEFHSCFIFFCGSIKLDTQVPNDDFVLSARWPPSFPVSGWSTI

NFHETIKIYVGSLDSLDSWTMEFHSCFTFFCGS

Gossypium raimondii 26786642 (SEQ ID NO: 84):
MVSASRKTFLPLDPVTFSNESKAVIDFIADYYENVEKYPVQSTVEPGYLSAMLPESAPYC

PEPLQDILEDVSNCIIPGLTHWQSPNFFAYFHANASTAGFFGEMLCSGFNVVGFNWISSP

AATELESIVLDWMGKMLKLPSSFLFSGTGGGVLHGSSCEAAVCVLAAARDKALKELGG

WENITKLVVYASDQAHFTFQKAAKLVGIPPSNFRLIETSFSTGFSLSPENLRFVIEDNIRSG

LVPLFLCATIGTTPSGAVDPIAELGKVAMEFKLWLHIDAAYAGSGCICPELRHYLDGVEL

ANSISMNPHKWFLTNMDCCCLWIKEPKLLVDSLSTDPEILRNNASKSKAVVDCKDWQI

ALSRRFRALKLWVVIRRHGLANLMCHIRSDIAMAKRFEALVGEDERFEIVVPRKFALVC

FRLKPKVEEEDLNCKLVEAINSSGRAFMSHAVLSGIYVIRCAIGTTLTQQHHVDALWKLI

QDKAQSLLM

Populus trichocarpa 26994989 (SEQ ID NO: 85):
MGSLSTNTFSPLDPNGFTNDSKMVIDFIADYYKNIENNPVQSQVKPGYLLTQLPDTAPYC

EESLEDVLKDVTDSIIPGLTHWQSPNFFAYFQANASTAGFVGEMLCTGLNVVGFNWIAS

PAATELESIVMDWMGKMLKLPSTFLFSGNGGGVLHGSTCEAIVCTLVAARDETLRMIGA

ENITKLVVYASDQTHSTLLKGVKLVGIPSSNFRCLSTSFSSEFSLSPQALEDAIENDIKAGL

VPLFLCATVGTTACGAVDPVMDLGEIARKYNLWFHIDAAYAGSACICPEFRHYLDGVEL

ADSLSMNPHKWLLTNMDCCCLWVKQPRLLTESLSSDAEFLRNNASESSDVVDYKDWQI

ALSRRFRALKLWIVIRRHGLANLMCHIRSDVNLAKRFESLVAKDSRFEVVVRRRFSLVC
```

-continued

FRLKHNDECQGLELNRKLLAAVNESGRAFMTHAVVGGLFIIRCAIGSTLTEERHVDDLW

KLIQEKAADLLSKKQVLLDN

*Malus domestica* 22679008 (SEQ ID NO: 86):
MSLLAFYSNSGERSKRVHLSASTYGNSTPNSYISLPYALFSSATQLINIHSNSSNFQMGSLI

SQENNSPNVPTNPLDPEEFRRQGHLVIDFIADYYKSIEKHPVLSQVQPGYLKKRLPDTAP

YNPEPLETILQDVQDHIVPGITHWQSPNYFAYFPSSGSVAGFLGEMLSSGFNVVGFNWM

SSPAATELESTVRDWFGNMLKLPKSFLFSGNGGDVIQGTTCEALVCAMVAARDQKLSK

FGRHNIGKLVVYGSDQTHSALQKASQIVGIHPENFRSTETTRSTSFALSPESLKVIIYSDIEA

GLVPLFLCATVGTTAIATVDPLGPLCGVAGDYGMWVHVDAAYAGSACICPSFDISLMA

SRVQIHSVSTRTNGSSPLSTVVAFGLRIPTRWNKATELKQVVDYKDWQIALSRRFRSMK

LWLVLRSYGVANLRNFLRSHVKMAKIFEGLVAMDKRFEIVAPRNFSLVCFRVSPSSISN

KASSDQNGKTDYCCDANGDENSVIINEVNRKLLESINVSGHVYMTHGVVGGLYMLRFA

VGATLTEEHHIALAWKVVQEHADQILTKY

*Citrus clementina* 20801973 (SEQ ID NO: 87):
MRAGEASIIKMGSFGLSANNITHGSSFSADLEPKSFSDESKAVIDFIADYYKNIEKYPVQS

KVEPGYLSARLPDTAPHSPESLDDILKDVTDCILPGLTHWQSPNFFGYFQANASTAGFLG

EMLCSGFNVVGFNWLASPVATELESIVMDWMGKMLKLPSSFLFSGTGGGVLHGSTCES

LVCTLAAARDKALEKLGGGFDNITKLAVYASDQTHFALQKSAKLIGIPPANFRPLRTSFS

TEFSLSPDTVRAAIEDDIKSGHVPLYLCATVGTTGAGAVDPIEELGKIANEYKLWLHIDA

AYAGSACICPEYRHYLNGVELADSISLNPHKWFLTNMDCCCLWVKHPSFLVDSLSTESD

IMRNRSPASNTSTNAAPVIDYKDWQIALSRRFKALKLWTVIRKHGYSGLMYHIRSDVSM

AKRFAAMVAKDERFEIVVPRKFALVCFRLKPKRESEGSELNRELVDALNGSGRAFLTQA

MLGGVYVIRCSIGTTLTQDRHVDDLWKLIQEKADRLLSLQEPEHASR

*Citrus clementina* 20818150 (SEQ ID NO: 88):
MGSLNSDHELKTNSASFNNPMDSEEFRRQGHMIIDFIADYYRDVEKYPVLSQVEPGYLQ

KRLPESAPYNPEPIETILQDVQQHIVPGITHWQSPYYFAYFPSSGSIAGFLGEMLSSGFNV

VGFNWMSSPAATELENIVMDWLGEMLKLPKSFLFSGTGGGVIQGTTCEAILCTLAAARD

QILNEIGRENISRLVVYGSDQTHSALQKAAQIAGIDPKNFRAIKTTKSSSFTLTPESLQAAI

DLDIQSGLIPLFLCATVGTTAITTVDPLGPLCDIAKRYSIWIHVDAAYAGSACICPEFRHFI

DGIESADSFSLNAHKWFFTTLDCCCMWVKNPNALIKALSTNPEFLRNKASDSKQVVDY

KDWQISLSRRFRALKLWLVLRSFGVANLRNFLRSHVGMAQLFQELVGGDNRFEIVAPR

NFAVVCFRVLPSASGLGNGKANEGANELNRKLLESINASGQLYVSHGMVAGIYFIRFAV

GATLTEDRHVIAAWKVVQEKLDGILATS

*Vitis vinifera* 17834108 (SEQ ID NO: 89):
MGSLSFNTFSPLDPQSFSEESKMVVDFIADYYKNVEKYPVQSQVDPGYLMHHCPDTAPY

CPEPLETILKDVSDGIIPGLTHWQSPNFFGYFQANASTAGFLGEMLCTGLNVVGFNWIAS

PAATELESIAIICSLAAARDKVLKKLGHHKITKLVVYGSDQTHSTLQKASKLVGIPASNFR

SLPTSFSNYFALCPDDVRTAMEEDIGAGLVPLFLCATVGTTSSGAVDPLEALGHVAKDF

KVHHLNGVELAHSISMNPHKWLLTNMDCCCLWIKEPKLFVDSLSTAPEFLRNNASESK

KVIDYKDWQIALSRRFRAIKVWAVVPRRFALVCFRLRPREEGESTELNSRLLMAVNGSG

AAFMTHAVVGGIYIIRCAIGSTLTETRHVDSLWKLIQEKAQLVLQEPGLALEEDYIDPCIG

VSATSLHAVVRWYCNYSSEINAHLVFIAFFVVVCKENRENYVLGVNGPPN

*Petunia hybrida* ABB72475.1 (SEQ ID NO: 90):
MDTIKINPEFDGQFCKTTSLLDPEEFRRNGHMMVDFLADYFHNIEKYPVRSQVEPGYLE
RLLPDSAPIQPEPIEKILKDVRSDIFPGLTHWQSPNFFAYFPCSSSTAGILGEMLSAGLNVV
GFSWIASPAATELESIVMDWLGKLINLPKTYLFSGGGGGVMQGTTCEVMLCTIVAARDK
MLEKFGRENIDKLVVYASDQTHFSFQKAVKISGIKPENFRAIPTTKATEFSLNPESLRRAI
QEDKKAGLIPLFLCTSIGTTSTTAVDPLKPLCEIAEEYGIWVHVDAAYAGSACICPEFQHF
LDGVEHANSFSFNAHKWLFTTLDCCCLWLKDPSSLTKALSTNPEVLRNDATDSEQVVD
YKDWQITLSRRFRSLKLWLVLKSYGVANLRNFIRSHIEMAKHFEELVAMDERFEIMAPR
NFSLVCFRVSLLALEKKFNFVDETQVNEFNAKLLESITSSGNVYMTHTVVEGVYMIRFAV
GAPLTDYPHIDMAWNVVRNHATMMLNA

*Carica papaya* 16421889 (SEQ ID NO: 91):
MSSLSRDLNASPLEPENFRVESKRVIDFIADYYKNIETYPVQSRVKPGYLAGRLPSSAPFS
PESLETILQDIAENISPGLTHWQSPNFFGYFQANASTAGFHGEMLCSGLNVVGFNWISSP
AATELESLVMDWMGNMLKLPSSFLFSGSGGGVLHGSTCEAVVCTLAAARDKTLNQLG
GNYQNITKFVVYASDQTHFTLQKAAKLIGIPPSNFRSLTTSFPSGFSLSPEKLQSAIKDDIK
SGYVPLYVCATVGTTAAGAVDPILELGKVAQEYNLWFHIDAAYAGSACICTEFRHYLN
GVELADSISTNPHKWLLTNMECSCLWVKSPSSLVDSLSTKSEIIVIRNAATDSNQVIDYKD
WQIALSRRFRALKLWIVIRRHGLSGLTSHIHKDIKMAELFESLVAKDKRFEIVVPRKFAL
VCFRFKPEKENQDLSELNSKLLNAVNSSGCAFMTHAVLEGVYTIRCAIGTTLTEEHHVV
NLWKLIQEKAQSLIINEY

*Sphagnum fallax* 0042s0024.1 (SEQ ID NO: 92):
MSSKVAPWSRLSKPLDVEEFRTHAHRMVDFIADYHHNIQSFPVHSQLKPGYLRPLLPDT
APTEPEVVEDVFADVWNKILPGITHWQSPKFFGYYPFNVSTAGILGEILSGGVNVTGFSW
ITSPVVTELEIIVLDWLGKLLHLPEEFLSSGKGGGVIQGTSSEAVVCTSQHMSEAEALTKL
VVYTSDQAQSCVLRACQIAGIATANFRPLPTDASSHFSLSPAVLIKAAATDVAAGLFPFF
LCGKVGTTSSSAVDPLLELGDIAKRYGMWYHIDAAYAGSACICPEFRHYLNGVEKADS
YNMNPHDWMLTNFDCSTLWVKNSELLVAALSNKPVYLQNEATDNNLVDCSHIRNHISI
AKHFESLVRADFRFEMIVPTNFSLVCFRLRTPAGSKDNSRTLNSKLVEALNRKGDILVTH
TELSGRYTLRFAVGGTHMELHHVQAAWNLRLQRQVF

*Eucalyptus grandis* E01788.1 (SEQ ID NO: 93):
MNPLDPGEFRRQGHMVVDFLAKYYENIEKYPVLSQVEPGYLSKRLPSSAPQDEEPMEAI
LDDVHQHIFPGLTHWQSPNFFAYYQTNTSTAAILGEMLCAGFNVAGFNWVSSPAATELE
SLVMDWLGKMLDLPRPFLPFGNGGGVIEGNTSEAIICTLTAARDRVLRKLGHNSIAKLV
VYGSDQTNCSFQKAARVVGIDPRNFRALKMTRSTLFGLSPDSLEKAIRLDINAGLIPLYL
CATVGTTSCAAVDPLEPLCKVASKFSMWIHVDAAYAGASCICPEYRKFINGVEFADSFS
FNAHKWLLTPLDCCCLWVKDPNALVKSLSTDPEYLKNEATESKQVIDYADWQLSLSRR
FRALKLWLVLRSHGVQNLRSHIKNHCRLAKLFEELVEEDPQFEVVFPRNFALVCFRIHPS
GVAGMLNAQLLHAINASGRVFMSHTTVGGVYVLRFAVGATLVTEKHVIMAWKVVQE
HANSLLSMPASEQHSA pHis8-4 (SEQ ID NO: 94):
TGGCGAATGGGACGCGCCCTGTAGCGGCGCATTAAGCGCGGCGGGTGTGGTGGTTA
CGCGCAGCGTGACCGCTACACTTGCCAGCGCCCTAGCGCCCGCTCCTTTCGCTTTCTT
CCCTTCCTTTCTCGCCACGTTCGCCGGCTTTCCCCGTCAAGCTCTAAATCGGGGGCTC -continued

```
CCTTTAGGGTTCCGATTTAGTGCTTTACGGCACCTCGACCCCAAAAAACTTGATTAG
GGTGATGGTTCACGTAGTGGGCCATCGCCCTGATAGACGGTTTTTCGCCCTTTGACG
TTGGAGTCCACGTTCTTTAATAGTGGACTCTTGTTCCAAACTGGAACAACACTCAAC
CCTATCTCGGTCTATTCTTTTGATTTATAAGGGATTTTGCCGATTTCGGCCTATTGGTT
AAAAAATGAGCTGATTTAACAAAAATTTAACGCGAATTTTAACAAAATATTAACGTT
TACAATTTCAGGTGGCACTTTTCGGGGAAATGTGCGCGGAACCCCTATTTGTTTATTT
TTCTAAATACATTCAAATATGTATCCGCTCATGAATTAATTCTTAGAAAAACTCATC
GAGCATCAAATGAAACTGCAATTTATTCATATCAGGATTATCAATACCATATTTTTG
AAAAAGCCGTTTCTGTAATGAAGGAGAAAACTCACCGAGGCAGTTCCATAGGATGG
CAAGATCCTGGTATCGGTCTGCGATTCCGACTCGTCCAACATCAATACAACCTATTA
ATTTCCCCTCGTCAAAAATAAGGTTATCAAGTGAGAAATCACCATGAGTGACGACTG
AATCCGGTGAGAATGGCAAAAGTTTATGCATTTCTTTCCAGACTTGTTCAACAGGCC
AGCCATTACGCTCGTCATCAAAATCACTCGCATCAACCAAACCGTTATTCATTCGTG
ATTGCGCCTGAGCGAGACGAAATACGCGATCGCTGTTAAAAGGACAATTACAAACA
GGAATCGAATGCAACCGGCGCAGGAACACTGCCAGCGCATCAACAATATTTTCACC
TGAATCAGGATATTCTTCTAATACCTGGAATGCTGTTTTCCCGGGGATCGCAGTGGT
GAGTAACCATGCATCATCAGGAGTACGGATAAAATGCTTGATGGTCGGAAGAGGCA
TAAATTCCGTCAGCCAGTTTAGTCTGACCATCTCATCTGTAACATCATTGGCAACGCT
ACCTTTGCCATGTTTCAGAAACAACTCTGGCGCATCGGGCTTCCCATACAATCGATA
GATTGTCGCACCTGATTGCCCGACATTATCGCGAGCCCATTTATACCCATATAAATC
AGCATCCATGTTGGAATTTAATCGCGGCCTAGAGCAAGACGTTTCCCGTTGAATATG
GCTCATAACACCCCTTGTATTACTGTTTATGTAAGCAGACAGTTTTATTGTTCATGAC
CAAAATCCCTTAACGTGAGTTTTCGTTCCACTGAGCGTCAGACCCCGTAGAAAAGAT
CAAAGGATCTTCTTGAGATCCTTTTTTTCTGCGCGTAATCTGCTGCTTGCAAACAAA
AAACCACCGCTACCAGCGGTGGTTTGTTTGCCGGATCAAGAGCTACCAACTCTTTTT
CCGAAGGTAACTGGCTTCAGCAGAGCGCAGATACCAAATACTGTCCTTCTAGTGTAG
CCGTAGTTAGGCCACCACTTCAAGAACTCTGTAGCACCGCCTACATACCTCGCTCTG
CTAATCCTGTTACCAGTGGCTGCTGCCAGTGGCGATAAGTCGTGTCTTACCGGGTTG
GACTCAAGACGATAGTTACCGGATAAGGCGCAGCGGTCGGGCTGAACGGGGGGTTC
GTGCACACAGCCCAGCTTGGAGCGAACGACCTACACCGAACTGAGATACCTACAGC
GTGAGCTATGAGAAAGCGCCACGCTTCCCGAAGGGAGAAAGGCGGACAGGTATCCG
GTAAGCGGCAGGGTCGGAACAGGAGAGCGCACGAGGGAGCTTCCAGGGGGAAACG
CCTGGTATCTTTATAGTCCTGTCGGGTTTCGCCACCTCTGACTTGAGCGTCGATTTTT
GTGATGCTCGTCAGGGGGCGGAGCCTATGGAAAAACGCCAGCAACGCGGCCTTTT
TACGGTTCCTGGCCTTTTGCTGGCCTTTTGCTCACATGTTCTTTCCTGCGTTATCCCCT
GATTCTGTGGATAACCGTATTACCGCCTTTGAGTGAGCTGATACCGCTCGCCGCAGC
CGAACGACCGAGCGCAGCGAGTCAGTGAGCGAGGAAGCGGAAGAGCGCCTGATGC
GGTATTTTCTCCTTACGCATCTGTGCGGTATTTCACACCGCATATATGGTGCACTCTC
AGTACAATCTGCTCTGATGCCGCATAGTTAAGCCAGTATACACTCCGCTATCGCTAC
GTGACTGGGTCATGGCTGCGCCCCGACACCCGCCAACACCCGCTGACGCGCCCTGA
CGGGCTTGTCTGCTCCCGGCATCCGCTTACAGACAAGCTGTGACCGTCTCCGGGAGC
```

-continued

```
TGCATGTGTCAGAGGTTTTCACCGTCATCACCGAAACGCGCGAGGCAGCTGCGGTAA
AGCTCATCAGCGTGGTCGTGAAGCGATTCACAGATGTCTGCCTGTTCATCCGCGTCC
AGCTCGTTGAGTTTCTCCAGAAGCGTTAATGTCTGGCTTCTGATAAAGCGGGCCATG
TTAAGGGCGGTTTTTTCCTGTTTGGTCACTGATGCCTCCGTGTAAGGGGGATTTCTGT
TCATGGGGTAATGATACCGATGAAACGAGAGAGGATGCTCACGATACGGGTTACT
GATGATGAACATGCCCGGTTACTGGAACGTTGTGAGGGTAAACAACTGGCGGTATG
GATGCGGCGGGACCAGAGAAAAATCACTCAGGGTCAATGCCAGCGCTTCGTTAATA
CAGATGTAGGTGTTCCACAGGGTAGCCAGCAGCATCCTGCGATGCAGATCCGGAAC
ATAATGGTGCAGGGCGCTGACTTCCGCGTTTCCAGACTTTACGAAACACGGAAACCG
AAGACCATTCATGTTGTTGCTCAGGTCGCAGACGTTTTGCAGCAGCAGTCGCTTCAC
GTTCGCTCGCGTATCGGTGATTCATTCTGCTAACCAGTAAGGCAACCCCGCCAGCCT
AGCCGGGTCCTCAACGACAGGAGCACGATCATGCGCACCCGTGGGGCCGCCATGCC
GGCGATAATGGCCTGCTTCTCGCCGAAACGTTTGGTGGCGGGACCAGTGACGAAGG
CTTGAGCGAGGGCGTGCAAGATTCCGAATACCGCAAGCGACAGGCCGATCATCGTC
GCGCTCCAGCGAAAGCGGTCCTCGCCGAAAATGACCCAGAGCGCTGCCGGCACCTG
TCCTACGAGTTGCATGATAAAGAAGACAGTCATAAGTGCGGCGACGATAGTCATGC
CCCGCGCCCACCGGAAGGAGCTGACTGGGTTGAAGGCTCTCAAGGGCATCGGTCGA
GATCCCGGTGCCTAATGAGTGAGCTAACTTACATTAATTGCGTTGCGCTCACTGCCC
GCTTTCCAGTCGGGAAACCTGTCGTGCCAGCTGCATTAATGAATCGGCCAACGCGCG
GGGAGAGGCGGTTTGCGTATTGGGCGCCAGGGTGGTTTTTCTTTTCACCAGTGAGAC
GGGCAACAGCTGATTGCCCTTCACCGCCTGGCCCTGAGAGAGTTGCAGCAAGCGGT
CCACGCTGGTTTGCCCCAGCAGGCGAAAATCCTGTTTGATGGTGGTTAACGGCGGGA
TATAACATGAGCTGTCTTCGGTATCGTCGTATCCCACTACCGAGATATCCGCACCAA
CGCGCAGCCCGGACTCGGTAATGGCGCGCATTGCGCCCAGCGCCATCTGATCGTTGG
CAACCAGCATCGCAGTGGGAACGATGCCCTCATTCAGCATTTGCATGGTTTGTTGAA
AACCGGACATGGCACTCCAGTCGCCTTCCCGTTCCGCTATCGGCTGAATTTGATTGC
GAGTGAGATATTTATGCCAGCCAGCCAGACGCAGACGCGCCGAGACAGAACTTAAT
GGGCCCGCTAACAGCGCGATTTGCTGGTGACCCAATGCGACCAGATGCTCCACGCC
CAGTCGCGTACCGTCTTCATGGGAGAAAATAATACTGTTGATGGGTGTCTGGTCAGA
GACATCAAGAAATAACGCCGGAACATTAGTGCAGGCAGCTTCCACAGCAATGGCAT
CCTGGTCATCCAGCGGATAGTTAATGATCAGCCCACTGACGCGTTGCGCGAGAAGAT
TGTGCACCGCCGCTTTACAGGCTTCGACGCCGCTTCGTTCTACCATCGACACCACCA
CGCTGGCACCCAGTTGATCGGCGCGAGATTTAATCGCCGCGACAATTTGCGACGGC
GCGTGCAGGGCCAGACTGGAGGTGGCAACGCCAATCAGCAACGACTGTTTGCCCGC
CAGTTGTTGTGCCACGCGGTTGGGAATGTAATTCAGCTCCGCCATCGCCGCTTCCAC
TTTTTCCCGCGTTTTCGCAGAAACGTGGCTGGCCTGGTTCACCACGCGGGAAACGGT
CTGATAAGAGACACCGGCATACTCTGCGACATCGTATAACGTTACTGGTTTCACATT
CACCACCCTGAATTGACTCTCTTCCGGGCGCTATCATGCCATACCGCGAAAGGTTTT
GCGCCATTCGATGGTGTCCGGGATCTCGACGCTCTCCCTTATGCGACTCCTGCATTA
GGAAGCAGCCCAGTAGTAGGTTGAGGCCGTTGAGCACCGCCGCCGCAAGGAATGGT
```

-continued

GCATGCAAGGAGATGGCGCCCAACAGTCCCCCGGCCACGGGGCCTGCCACCATACC

CACGCCGAAACAAGCGCTCATGAGCCCGAAGTGGCGAGCCCGATCTTCCCCATCGG

TGATGTCGGCGATATAGGCGCCAGCAACCGCACCTGTGGCGCCGGTGATGCCGGCC

ACGATGCGTCCGGCGTAGAGGATCGAGATCTCGATCCCGCGAAATTAATACGACTC

ACTATAGGGGAATTGTGAGCGGATAACAATTCCCCTCTAGAAATAATTTTGTTTAAC

TTTAAGAAGGAGATATACCATGAAACACCACCACCACCACCACCACGGTGGTG

AAAACTTGTACTTCCAGGCCCATGGCGGATCCGAATTCGAGCTCCGTCGACAAGCTT

GCGGCCGCACTCGAGCACCACCACCACCACCACTGAGATCCGGCTGCTAACAAAGC

CCGAAAGGAAGCTGAGTTGGCTGCTGCCACCGCTGAGCAATAACTAGCATAACCCC

TTGGGGCCTCTAAACGGGTCTTGAGGGGTTTTTTGCTGAAAGGAGGAACTATATCCG

GAT pEAQ-HT (SEQ ID NO: 95):
CCTGTGGTTGGCATGCACATACAAATGGACGAACGGATAAACCTTTTCACGCCCTTT

TAAATATCCGATTATTCTAATAAACGCTCTTTTCTCTTAGGTTTACCCGCCAATATAT

CCTGTCAAACACTGATAGTTTGTGAACCATCACCCAAATCAAGTTTTTTGGGGTCGA

GGTGCCGTAAAGCACTAAATCGGAACCCTAAAGGGAGCCCCCGATTTAGAGCTTGA

CGGGGAAAGCCGGCGAACGTGGCGAGAAAGGAAGGGAAGAAAGCGAAAGGAGCG

GCGCCATTCAGGCTGCGCAACTGTTGGGAAGGGCGATCGGTGCGGGCCTCTTCGCT

ATTACGCCAGCTGGCGAAAGGGGGATGTGCTGCAAGGCGATTAAGTTGGGTAACGC

CAGGGTTTTCCCAGTCACGACGTTGTAAAACGACGGCCAGTGAATTGTTAATTAAGA

ATTCGAGCTCCACCGCGGAAACCTCCTCGGATTCCATTGCCCAGCTATCTGTCACTTT

ATTGAGAAGATAGTGGAAAAGGAAGGTGGCTCCTACAAATGCCATCATTGCGATAA

AGGAAAGGCCATCGTTGAAGATGCCTCTGCCGACAGTGGTCCCAAAGATGGACCCC

CACCCACGAGGAGCATCGTGGAAAAAGAAGACGTTCCAACCACGTCTTCAAAGCAA

GTGGATTGATGTGATATCTCCACTGACGTAAGGGATGACGCACAATCCCACTATCCT

TCGCAAGACCCTTCCTCTATATAAGGAAGTTCATTTCATTTGGAGAGGTATTAAAAT

CTTAATAGGTTTTGATAAAAGCGAACGTGGGGAAACCCGAACCAAACCTTCTTCTAA

ACTCTCTCTCATCTCTCTTAAAGCAAACTTCTCTCTTGTCTTTCTTGCGTGAGCGATCT

TCAACGTTGTCAGATCGTGCTTCGGCACCAGTACAACGTTTTCTTTCACTGAAGCGA

AATCAAAGATCTCTTTGTGGACACGTAGTGCGGCGCCATTAAATAACGTGTACTTGT

CCTATTCTTGTCGGTGTGGTCTTGGGAAAAGAAAGCTTGCTGGAGGCTGCTGTTCAG

CCCCATACATTACTTGTTACGATTCTGCTGACTTTCGGCGGGTGCAATATCTCTACTT

CTGCTTGACGAGGTATTGTTGCCTGTACTTCTTTCTTCTTCTTCTTGCTGATTGGTTCT

ATAAGAAATCTAGTATTTTCTTTGAAACAGAGTTTTCCCGTGGTTTTCGAACTTGGAG

AAAGATTGTTAAGCTTCTGTATATTCTGCCCAAATTCGCGACCGGTATGCATCACCA

TCACCATCATCCCGGGCATCACCATCACCATCACTAGCTCGAGGCCTTTAACTCTGG

TTTCATTAAATTTTCTTTAGTTTGAATTTACTGTTATTCGGTGTGCATTTCTATGTTTG

GTGAGCGGTTTTCTGTGCTCAGAGTGTGTTTATTTTATGTAATTTAATTTCTTTGTGA

GCTCCTGTTTAGCAGGTCGTCCCTTCAGCAAGGACACAAAAAGATTTTAATTTTATT

AAAAAAAAAAAAAAAAAGACCGGGAATTCGATATCAAGCTTATCGACCTGCAGAT

CGTTCAAACATTTGGCAATAAAGTTTCTTAAGATTGAATCCTGTTGCCGGTCTTGCG

-continued

```
ATGATTATCATATAATTTCTGTTGAATTACGTTAAGCATGTAATAATTAACATGTAAT
GCATGACGTTATTTATGAGATGGGTTTTTATGATTAGAGTCCCGCAATTATACATTTA
ATACGCGATAGAAAACAAAATATAGCGCGCAAACTAGGATAAATTATCGCGCGCGG
TGTCATCTATGTTACTAGATCTCTAGAGTCTCAAGCTTGGCGCGCCAGCTTGGCGTA
ATCATGGTCATAGCTGTTGCGATTAAGAATTCGAGCTCGGTACCCCCCTACTCCAAA
AATGTCAAAGATACAGTCTCAGAAGACCAAAGGGCTATTGAGACTTTTCAACAAAG
GGTAATTTCGGGAAACCTCCTCGGATTCCATTGCCCAGCTATCTGTCACTTCATCGA
AAGGACAGTAGAAAAGGAAGGTGGCTCCTACAAATGCCATCATTGCGATAAAGGAA
AGGCTATCATTCAAGATGCCTCTGCCGACAGTGGTCCCAAAGATGGACCCCCACCCA
CGAGGAGCATCGTGGAAAAAGAAGACGTTCCAACCACGTCTTCAAAGCAAGTGGAT
TGATGTGACATCTCCACTGACGTAAGGGATGACGCACAATCCCACTATCCTTCGCAA
GACCCTTCCTCTATATAAGGAAGTTCATTTCATTTGGAGAGGACAGCCCAAGCTTCG
ACTCTAGAGGATCCCCTTAAATCGATATGGAACGAGCTATACAAGGAAACGACGCT
AGGGAACAAGCTAACAGTGAACGTTGGGATGGAGGATCAGGAGGTACCACTTCTCC
CTTCAAACTTCCTGACGAAAGTCCGAGTTGGACTGAGTGGCGGCTACATAACGATGA
GACGAATTCGAATCAAGATAATCCCCTTGGTTTCAAGGAAAGCTGGGGTTTCGGGA
AAGTTGTATTTAAGAGATATCTCAGATACGACAGGACGGAAGCTTCACTGCACAGA
GTCCTTGGATCTTGGACGGGAGATTCGGTTAACTATGCAGCATCTCGATTTTTCGGTT
TCGACCAGATCGGATGTACCTATAGTATTCGGTTTCGAGGAGTTAGTATCACCGTTT
CTGGAGGGTCTCGAACTCTTCAGCATCTCTGTGAGATGGCAATTCGGTCTAAGCAAG
AACTGCTACAGCTTGCCCCAATCGAAGTGGAAAGTAATGTATCAAGAGGATGCCCT
GAAGGTACTGAGACCTTCGAAAAAGAAAGCGAGTAAGGGGAGCTCGAATTCGCTGA
AATCACCAGTCTCTCTCTACAAATCTATCTCTCTATTTTCTCCATAAATAATGTGT
GAGTAGTTTCCCGATAAGGGAAATTAGGGTTCTTATAGGGTTTCGCTCATGTGTTGA
GCATATAAGAAACCCTTAGTATGTATTTGTATTTGTAAAATACTTCTATCAATAAAA
TTTCTAATTCCTAAAACCAAAATCCAGTACTAAAATCCAGATCTCCTAAAGTCCCTA
TAGATCTTTGTCGTGAATATAAACCAGACACGAGACGACTAAACCTGGAGCCCAGA
CGCCGTTCGAAGCTAGAAGTACCGCTTAGGCAGGAGGCCGTTAGGGAAAGATGCT
AAGGCAGGGTTGGTTACGTTGACTCCCCCGTAGGTTTGGTTTAAATATGATGAAGTG
GACGGAAGGAAGGAGGAAGACAAGGAAGGATAAGGTTGCAGGCCCTGTGCAAGGT
AAGAAGATGGAAATTTGATAGAGGTACGCTACTATACTTATACTATACGCTAAGGG
AATGCTTGTATTTATACCCTATACCCCCTAATAACCCCTTATCAATTTAAGAAATAAT
CCGCATAAGCCCCCGCTTAAAAATTGGTATCAGAGCCATGAATAGGTCTATGACCAA
AACTCAAGAGGATAAAACCTCACCAAAATACGAAAGAGTTCTTAACTCTAAAGATA
AAAGATGGCGCGTGGCCGGCCTACAGTATGAGCGGAGAATTAAGGGAGTCACGTTA
TGACCCCCGCCGATGACGCGGGACAAGCCGTTTTACGTTTGGAACTGACAGAACCG
CAACGTTGAAGGAGCCACTCAGCCGCGGGTTTCTGGAGTTTAATGAGCTAAGCACAT
ACGTCAGAAACCATTATTGCGCGTTCAAAAGTCGCCTAAGGTCACTATCAGCTAGCA
AATATTTCTTGTCAAAAATGCTCCACTGACGTTCCATAAATTCCCCTCGGTATCCAAT
TAGAGTCTCATATTCACTCTCAATCCAAATAATCTGCACCGGATCTGGATCGTTTCGC
ATGATTGAACAAGATGGATTGCACGCAGGTTCTCCGGCCGCTTGGGTGGAGAGGCT
```

```
ATTCGGCTATGACTGGGCACAACAGACAATCGGCTGCTCTGATGCCGCCGTGTTCCG

GCTGTCAGCGCAGGGGCGCCCGGTTCTTTTTGTCAAGACCGACCTGTCCGGTGCCCT

GAATGAACTGCAGGACGAGGCAGCGCGGCTATCGTGGCTGGCCACGACGGGCGTTC

CTTGCGCAGCTGTGCTCGACGTTGTCACTGAAGCGGGAAGGGACTGGCTGCTATTGG

GCGAAGTGCCGGGGCAGGATCTCCTGTCATCTCACCTTGCTCCTGCCGAGAAAGTAT

CCATCATGGCTGATGCAATGCGGCGGCTGCATACGCTTGATCCGGCTACCTGCCCAT

TCGACCACCAAGCGAAACATCGCATCGAGCGAGCACGTACTCGGATGGAAGCCGGT

CTTGTCGATCAGGATGATCTGGACGAAGAGCATCAGGGGCTCGCGCCAGCCGAACT

GTTCGCCAGGCTCAAGGCGCGCATGCCCGACGGCGATGATCTCGTCGTGACCCATG

GCGATGCCTGCTTGCCGAATATCATGGTGGAAAATGGCCGCTTTTCTGGATTCATCG

ACTGTGGCCGGCTGGGTGTGGCGGACCGCTATCAGGACATAGCGTTGGCTACCCGTG

ATATTGCTGAAGAGCTTGGCGGCGAATGGGCTGACCGCTTCCTCGTGCTTTACGGTA

TCGCCGCTCCCGATTCGCAGCGCATCGCCTTCTATCGCCTTCTTGACGAGTTCTTCTG

AGCGGGACTCTGGGGTTCGAAATGACCGACCAAGCGACGCCCAACCTGCCATCACG

AGATTTCGATTCCACCGCCGCCTTCTATGAAAGGTTGGGCTTCGGAATCGTTTTCCG

GGACGCCGGCTGGATGATCCTCCAGCGCGGGGATCTCATGCTGGAGTTCTTCGCCCA

CGGGATCTCTGCGGAACAGGCGGTCGAAGGTGCCGATATCATTACGACAGCAACGG

CCGACAAGCACAACGCCACGATCCTGAGCGACAATATGATCGCGGCGTCCACATCA

ACGGCGTCGGCGGCGACTGCCCAGGCAAGACCGAGATGCACCGCGATATCTTGCTG

CGTTCGGATATTTTCGTGGAGTTCCCGCCACAGACCCGGATGATCCCCGATCGTTCA

AACATTTGGCAATAAAGTTTCTTAAGATTGAATCCTGTTGCCGGTCTTGCGATGATT

ATCATATAATTTCTGTTGAATTACGTTAAGCATGTAATAATTAACATGTAATGCATG

ACGTTATTTATGAGATGGGTTTTTATGATTAGAGTCCCGCAATTATACATTTAATACG

CGATAGAAAACAAAATATAGCGCGCAAACTAGGATAAATTATCGCGCGCGGTGTCA

TCTATGTTACTAGATCGGGACTGTAGGCCGGCCCTCACTGGTGAAAAGAAAAACCA

CCCCAGTACATTAAAAACGTCCGCAATGTGTTATTAAGTTGTCTAAGCGTCAATTTG

TTTACACCACAATATATCCTGCCACCAGCCAGCCAACAGCTCCCCGACCGGCAGCTC

GGCACAAAATCACCACTCGATACAGGCAGCCCATCAGTCCGGGACGGCGTCAGCGG

GAGAGCCGTTGTAAGGCGGCAGACTTTGCTCATGTTACCGATGCTATTCGGAAGAAC

GGCAACTAAGCTGCCGGGTTTGAAACACGGATGATCTCGCGGAGGGTAGCATGTTG

ATTGTAACGATGACAGAGCGTTGCTGCCTGTGATCAAATATCATCTCCCTCGCAGAG

ATCCGAATTATCAGCCTTCTTATTCATTTCTCGCTTAACCGTGACAGAGTAGACAGG

CTGTCTCGCGGCCGAGGGGCGCAGCCCCTGGGGGGATGGGAGGCCCGCGTTAGCG

GGCCGGGAGGGTTCGAGAAGGGGGGGCACCCCCCTTCGGCGTGCGCGGTCACGCGC

ACAGGGCGCAGCCCTGGTTAAAAACAAGGTTTATAAATATTGGTTTAAAAGCAGGT

TAAAAGACAGGTTAGCGGTGGCCGAAAAACGGGCGGAAACCCTTGCAAATGCTGGA

TTTTCTGCCTGTGGACAGCCCCTCAAATGTCAATAGGTGCGCCCCTCATCTGTCAGC

ACTCTGCCCCTCAAGTGTCAAGGATCGCGCCCCTCATCTGTCAGTAGTCGCGCCCCT

CAAGTGTCAATACCGCAGGGCACTTATCCCCAGGCTTGTCCACATCATCTGTGGGAA

ACTCGCGTAAAATCAGGCGTTTTCGCCGATTTGCGAGGCTGGCCAGCTCCACGTCGC
```

-continued

```
CGGCCGAAATCGAGCCTGCCCCTCATCTGTCAACGCCGCGCCGGGTGAGTCGGCCCC
TCAAGTGTCAACGTCCGCCCCTCATCTGTCAGTGAGGGCCAAGTTTTCCGCGAGGTA
TCCACAACGCCGGCGGCCGCGGTGTCTCGCACACGGCTTCGACGGCGTTTCTGGCGC
GTTTGCAGGGCCATAGACGGCCGCCAGCCCAGCGGCGAGGGCAACCAGCCCGGTGA
GCGTCGGAAAGGCGCTCGGTCTTGCCTTGCTCGTCGGTGATGTACACTAGTCGCTGG
CTGCTGAACCCCAGCCGGAACTGACCCCACAAGGCCCTAGCGTTTGCAATGCACC
AGGTCATCATTGACCCAGGCGTGTTCCACCAGGCCGCTGCCTCGCAACTCTTCGCAG
GCTTCGCCGACCTGCTCGCGCCACTTCTTCACGCGGGTGGAATCCGATCCGCACATG
AGGCGGAAGGTTTCCAGCTTGAGCGGGTACGGCTCCCGGTGCGAGCTGAAATAGTC
GAACATCCGTCGGGCCGTCGGCGACAGCTTGCGGTACTTCTCCCATATGAATTTCGT
GTAGTGGTCGCCAGCAAACAGCACGACGATTTCCTCGTCGATCAGGACCTGGCAAC
GGGACGTTTTCTTGCCACGGTCCAGGACGCGGAAGCGGTGCAGCAGCGACACCGAT
TCCAGGTGCCCAACGCGGTCGGACGTGAAGCCCATCGCCGTCGCCTGTAGGCGCGA
CAGGCATTCCTCGGCCTTCGTGTAATACCGGCCATTGATCGACCAGCCCAGGTCCTG
GCAAAGCTCGTAGAACGTGAAGGTGATCGGCTCGCCGATAGGGGTGCGCTTCGCGT
ACTCCAACACCTGCTGCCACACCAGTTCGTCATCGTCGGCCCGCAGCTCGACGCCGG
TGTAGGTGATCTTCACGTCCTTGTTGACGTGGAAAATGACCTTGTTTTGCAGCGCCTC
GCGCGGGATTTTCTTGTTGCGCGTGGTGAACAGGGCAGAGCGGGCCGTGTCGTTTGG
CATCGCTCGCATCGTGTCCGGCCACGGCGCAATATCGAACAAGGAAAGCTGCATTTC
CTTGATCTGCTGCTTCGTGTGTTTCAGCAACGCGGCCTGCTTGGCCTCGCTGACCTGT
TTTGCCAGGTCCTCGCCGGCGGTTTTTCGCTTCTTGGTCGTCATAGTTCCTCGCGTGT
CGATGGTCATCGACTTCGCCAAACCTGCCGCCTCCTGTTCGAGACGACGCGAACGCT
CCACGGCGGCCGATGGCGCGGGCAGGGCAGGGGGAGCCAGTTGCACGCTGTCGCGC
TCGATCTTGGCCGTAGCTTGCTGGACCATCGAGCCGACGGACTGGAAGGTTTCGCGG
GGCGCACGCATGACGGTGCGGCTTGCGATGGTTTCGGCATCCTCGGCGGAAAACCC
CGCGTCGATCAGTTCTTGCCTGTATGCCTTCCGGTCAAACGTCCGATTCATTCACCCT
CCTTGCGGGATTGCCCCGACTCACGCCGGGGCAATGTGCCCTTATTCCTGATTTGAC
CCGCCTGGTGCCTTGGTGTCCAGATAATCCACCTTATCGGCAATGAAGTCGGTCCCG
TAGACCGTCTGGCCGTCCTTCTCGTACTTGGTATTCCGAATCTTGCCCTGCACGAATA
CCAGCGACCCCTTGCCCAAATACTTGCCGTGGGCCTCGGCCTGAGAGCCAAAACACT
TGATGCGGAAGAAGTCGGTGCGCTCCTGCTTGTCGCCGGCATCGTTGCGCCACATCT
AGGTACTAAAACAATTCATCCAGTAAAATATAATATTTTATTTTCTCCCAATCAGGC
TTGATCCCCAGTAAGTCAAAAAATAGCTCGACATACTGTTCTTCCCCGATATCCTCC
CTGATCGACCGGACGCAGAAGGCAATGTCATACCACTTGTCCGCCCTGCCGCTTCTC
CCAAGATCAATAAAGCCACTTACTTTGCCATCTTTCACAAAGATGTTGCTGTCTCCC
AGGTCGCCGTGGGAAAAGACAAGTTCCTCTTCGGGCTTTTCCGTCTTTAAAAAATCA
TACAGCTCGCGCGGATCTTTAAATGGAGTGTCTTCTTCCCAGTTTTCGCAATCCACAT
CGGCCAGATCGTTATTCAGTAAGTAATCCAATTCGGCTAAGCGGCTGTCTAAGCTAT
TCGTATAGGGACAATCCGATATGTCGATGGAGTGAAAGAGCCTGATGCACTCCGCA
TACAGCTCGATAATCTTTTCAGGGCTTTGTTCATCTTCATACTCTTCCGAGCAAGGA
CGCCATCGGCCTCACTCATGAGCAGATTGCTCCAGCCATCATGCCGTTCAAAGTGCA
```

-continued

```
GGACCTTTGGAACAGGCAGCTTTCCTTCCAGCCATAGCATCATGTCCTTTTCCCGTTC

CACATCATAGGTGGTCCCTTTATACCGGCTGTCCGTCATTTTTAAATATAGGTTTTCA

TTTTCTCCCACCAGCTTATATACCTTAGCAGGAGACATTCCTTCCGTATCTTTTACGC

AGCGGTATTTTTCGATCAGTTTTTTCAATTCCGGTGATATTCTCATTTTAGCCATTTAT

TATTTCCTTCCTCTTTTCTACAGTATTTAAAGATACCCCAAGAAGCTAATTATAACAA

GACGAACTCCAATTCACTGTTCCTTGCATTCTAAAACCTTAAATACCAGAAAACAGC

TTTTTCAAAGTTGTTTTCAAAGTTGGCGTATAACATAGTATCGACGGAGCCGATTTTG

AAACCACAATTATGGGTGATGCTGCCAACTTACTGATTTAGTGTATGATGGTGTTTTT

GAGGTGCTCCAGTGGCTTCTGTTTCTATCAGCTGTCCCTCCTGTTCAGCTACTGACGG

GGTGGTGCGTAACGGCAAAAGCACCGCCGGACATCAGCGCTATCTCTGCTCTCACTG

CCGTAAAACATGGCAACTGCAGTTCACTTACACCGCTTCTCAACCCGGTACGCACCA

GAAAATCATTGATATGGCCATGAATGGCGTTGGATGCCGGGCAACAGCCCGCATTA

TGGGCGTTGGCCTCAACACGATTTTACGTCACTTAAAAAACTCAGGCCGCAGTCGGT

AACTATGCGGTGTGAAATACCGCACAGATGCGTAAGGAGAAAATACCGCATCAGGC

GCTCTTCCGCTTCCTCGCTCACTGACTCGCTGCGCTCGGTCGTTCGGCTGCGGCGAGC

GGTATCAGCTCACTCAAAGGCGGTAATACGGTTATCCACAGAATCAGGGGATAACG

CAGGAAAGAACATGTGAGCAAAAGGCCAGCAAAAGGCCAGGAACCGTAAAAAGGC

CGCGTTGCTGGCGTTTTTCCATAGGCTCCGCCCCCCTGACGAGCATCACAAAAATCG

ACGCTCAAGTCAGAGGTGGCGAAACCCGACAGGACTATAAAGATACCAGGCGTTTC

CCCCTGGAAGCTCCCTCGTGCGCTCTCCTGTTCCGACCCTGCCGCTTACCGGATACCT

GTCCGCCTTTCTCCCTTCGGGAAGCGTGGCGCTTTCTCATAGCTCACGCTGTAGGTAT

CTCAGTTCGGTGTAGGTCGTTCGCTCCAAGCTGGGCTGTGTGCACGAACCCCCCGTT

CAGCCCGACCGCTGCGCCTTATCCGGTAACTATCGTCTTGAGTCCAACCCGGTAAGA

CACGACTTATCGCCACTGGCAGCAGGTAACCTCGCGCATACAGCCGGGCAGTGACG

TCATCGTCTGCGCGGAAATGGACGGGCCCCGGCGCCAGATCTGGGGAAC
``` pJKW 1410 (SEQ ID NO: 96):
```
CCCTGAATTCGCATCTAGACTGATGAGACGTGGTAGAGCCACAAACAGCCGGTACA

AGCAACGATCTCCAGGACCATCTGAATCATGCGCGGATGACACGAACTCACGACGG

CGATCACAGACATTAACCCACAGTACAGACACTGCGACAACGTGGCAATTCGTCGC

AATACAACGTGAGACCGAAAGTGAAACGTGATTTCATGCGTCATTTTGAACATTTTG

TAAATCTTATTTAATAATGTGTGCGGCAATTCACATTTAATTTATGAATGTTTTCTTA

ACATCGCGGCAACTCAAGAAACGGCAGGTTCGGATCTTAGCTACTAGAGAAAGAGG

AGAAATACTAGATGCGTAAAGGCGAAGAGCTGTTCACTGGTGTCGTCCCTATTCTGG

TGGAACTGGATGGTGATGTCAACGGTCATAAGTTTTCCGTGCGTGGCGAGGGTGAA

GGTGACGCAACTAATGGTAAACTGACGCTGAAGTTCATCTGTACTACTGGTAAACTG

CCGGTTCCTTGGCCGACTCTGGTAACGACGCTGACTTATGGTGTTCAGTGCTTTGCTC

GTTATCCGGACCATATGAAGCAGCATGACTTCTTCAAGTCCGCCATGCCGGAAGGCT

ATGTGCAGGAACGCACGATTTCCTTTAAGGATGACGGCACGTACAAAACGCGTGCG

GAAGTGAAATTTGAAGGCGATACCCTGGTAAACCGCATTGAGCTGAAAGGCATTGA

CTTTAAAGAGGACGGCAATATCCTGGGCCATAAGCTGGAATACAATTTTAACAGCC

ACAATGTTTACATCACCGCCGATAAACAAAAAAATGGCATTAAAGCGAATTTTAAA
```

-continued

```
ATTCGCCACAACGTGGAGGATGGCAGCGTGCAGCTGGCTGATCACTACCAGCAAAA

CACTCCAATCGGTGATGGTCCTGTTCTGCTGCCAGACAATCACTATCTGAGCACGCA

AAGCGTTCTGTCTAAAGATCCGAACGAGAAACGCGATCATATGGTTCTGCTGGAGTT

CGTAACCGCAGCGGGCATCACGCATGGTATGGATGAACTGTACAAATGACCAGGCA

TCAAATAAAACGAAAGGCTCAGTCGAAAGACTGGGCCTTTCGTTTTATCTGTTGTTT

GTCGGTGAACGCTCTCTACTAGAGTCACACTGGCTCACCTTCGGGTGGGCCTTTCTG

CGTTTATAGGTCTCAGCTGGAAATCTGCTCGTCAGTGGTGCTCACACTGACGAATCA

TGTACAGATCATACCGATGACTGCCTGGCGACTCACAACTAAGCAAGACAGCCGGA

ACCAGCGCCGGCGAACACCACTGCATATATGGCATATCACAACAGTCCACGTCTCA

AGCAGTTACAGAGATGTTACGAACCACTAGTGCACTGCAGTACAAACACAGTCCTTT

CCCGCAATTTTCTTTTTCTATTACTCTTGGCCTCCTCTAGTACACTCTATATTTTTTA

TGCCTCGGTAATGATTTTCATTTTTTTTTTCCACCTAGCGGATGACTCTTTTTTTTTC

TTAGCGATTGGCATTATCACATAATGAATTATACATTATATAAAGTAATGTGATTTCT

TCGAAGAATATACTAAAAAATGAGCAGGCAAGATAAACGAAGGCAAAGATGACAG

AGCAGAAAGCCCTAGTAAAGCGTATTACAAATGAAACCAAGATTCAGATTGCGATC

TCTTTAAAGGGTGGTCCCCTAGCGATAGAGCACTCGATCTTCCCAGAAAAAGAGGC

AGAAGCAGTAGCAGAACAGGCCACACAATCGCAAGTGATTAACGTCCACACAGGTA

TAGGGTTTCTGGACCATATGATACATGCTCTGGCCAAGCATTCCGGCTGGTCGCTAA

TCGTTGAGTGCATTGGTGACTTACACATAGACGACCATCACACCACTGAGGACTGCG

GGATTGCTCTCGGTCAAGCTTTTAAAGAGGCCCTAGGGGCCGTGCGTGGAGTAAAA

AGGTTTGGATCAGGATTTGCGCCTTTGGATGAGGCACTTTCCAGAGCGGTGGTTGAT

CTTTCGAACAGGCCGTACGCAGTTGTCGAACTTGGTTTGCAAAGGGAGAAAGTAGG

TGATCTCTCTTGCGAGATGATCCCGCATTTTCTTGAAAGCTTTGCAGAGGCTAGCAG

AATTACCCTCCACGTTGATTGTCTGCGAGGCAAGAATGATCATCACCGTAGTGAGAG

TGCGTTCAAGGCTCTTGCGGTTGCCATAAGAGAAGCCACCTCGCCCAATGGTACCAA

CGATGTTCCCTCCACCAAAGGTGTTCTTATGTAGTGACACCGATTATTTAAAGCTGCT

GCATACGATATATATACATGTGTATATATGTATACCTATGAATGTCAGTAAGTATGT

ATACGAACAGTATGATACTGAAGATGACAAGGTAATGCATCATTCTATACGTGTCAT

TCTGAACGAGGCGCGCTTTCCTTTTTCTTTTGCTTTTCTTTTTTTTCTCTTGAACT

CGACGGATCATAGAGTAACGAAGCATCTGTGCTTCATTTTGTAGAACAAAAATGCA

ACGCGAGAGCGCTAATTTTTCAAACAAAGAATCTGAGCTGCATTTTTACAGAACAGA

AATGCAACGCGAAAGCGCTATTTTACCAACGAAGAATCTGTGCTTCATTTTTGTAAA

ACAAAAATGCAACGCGAGAGCGCTAATTTTTCAAACAAAGAATCTGAGCTGCATTTT

TACAGAACAGAAATGCAACGCGAGAGCGCTATTTTACCAACAAAGAATCTATACTT

CTTTTTTGTTCTACAAAAATGCATCCCGAGAGCGCTATTTTTCTAACAAAGCATCTTA

GATTACTTTTTTTCTCCTTTGTGCGCTCTATAATGCAGTCTCTTGATAACTTTTTGCAC

TGTAGGTCCGTTAAGGTTAGAAGAAGGCTACTTTGGTGTCTATTTTCTCTTCCATAAA

AAAAGCCTGACTCCACTTCCCGCGTTTACTGATTACTAGCGAAGCTGCGGGTGCATT

TTTTCAAGATAAAGGCATCCCCGATTATATTCTATACCGATGTGGATTGCGCATACTT

TGTGAACAGAAAGTGATAGCGTTGATGATTCTTCATTGGTCAGAAAATTATGAACGG
```

-continued

```
TTTCTTCTATTTTGTCTCTATATACTACGTATAGGAAATGTTTACATTTTCGTATTGTT

TTCGATTCACTCTATGAATAGTTCTTACTACAATTTTTTTGTCTAAAGAGTAATACTA

GAGATAAACATAAAAAATGTAGAGGTCGAGTTTAGATGCAAGTTCAAGGAGCGAAA

GGTGGATGGGTAGGTTATATAGGGATATAGCACAGAGATATATAGCAAAGAGATAC

TTTTGAGCAATGTTTGTGGAAGCGGTATTCGCAATATTTTAGTAGCTCGTTACAGTCC

GGTGCGTTTTTGGTTTTTTGAAAGTGCGTCATCAGAGCGCTTTTGGTTTTCAAAAGCG

CTCTGAAGTTCCTATACTTTCTAGCTAGAGAATAGGAACTTCCCGAGCGGCCGCGTG

TTACAACCAATTAACCAATTCTGATTAGAAAAACTCATCGAGCATCAAATGAAACTG

CAATTTATTCATATCAGGATTATCAATACCATATTTTTGAAAAGCCGTTTCTGTAAT

GAAGGAGAAAACTCACCGAGGCAGTTCCATAGGATGGCAAGATCCTGGTATCGGTC

TGCGATTCCGACTCGTCCAACATCAATACAACCTATTAATTTCCCCTCGTCAAAAT

AAGGTTATCAAGTGAGAAATCACCATGAGTGACGACTGAATCCGGTGAGAATGGCA

AAAGCTTATGCATTTCTTTCCAGACTTGTTCAACAGGCCAGCCATTACGCTCGTCATC

AAAATCACTCGCATCAACCAAACCGTTATTCATTCGTGATTGCGCCTGAGCGAGGCG

AAATACGCGATCGCTGTTAAAAGGACAATTACAAACAGGAATCGAATGCAACCGGC

GCAGGAACACTGCCAGCGCATCAACAATATTTTCACCTGAATCAGGATATTCTTCTA

ATACCTGGAATGCTGTTTTCCCGGGGATCGCAGTGGTGAGTAACCATGCATCATCAG

GAGTACGGATAAAATGCTTGATGGTCGGAAGAGGCATAAATTCCGTCAGCCAGTTT

AGTCTGACCATCTCATCTGTAACATCATTGGCAACGCTACCTTTGCCATGTTTCAGAA

ACAACTCTGGCGCATCGGGCTTCCCATACAATCGATAGATTGTCGCACCTGATTGCC

CGACATTATCGCGAGCCCATTTATACCCATATAAATCAGCATCCATGTTGGAATTTA

ATCGCGGCCTGGAGCAAGACGTTTCCCGTTGAATATGGCTCATAACACCCCTTGTAT

TACTGTTTATGTAAGCAGACAGTTTTATTGTTCATGATGATATATTTTTATCTTGTGC

AATGTAACATCAGAGATTTTGAGACACAACGTGGCTTTGTTGAATAAATCGAACTTT

TGCTGAGTTGAAGGATCAGTCATGACCAAAATCCCTTAACGTGAGTTTTCGTTCCAC

TGAGCGTCAGACCCCGTAGAAAAGATCAAAGGATCTTCTTGAGATCCTTTTTTTCTG

CGCGTAATCTGCTGCTTGCAAACAAAAAAACCACCGCTACCAGCGGTGGTTTGTTTG

CCGGATCAAGAGCTACCAACTCTTTTTCCGAAGGTAACTGGCTTCAGCAGAGCGCAG

ATACCAAATACTGTTCTTCTAGTGTAGCCGTAGTTAGGCCACCACTTCAAGAACTCT

GTAGCACCGCCTACATACCTCGCTCTGCTAATCCTGTTACCAGTGGCTGCTGCCAGT

GGCGATAAGTCGTGTCTTACCGGGTTGGACTCAAGACGATAGTTACCGGATAAGGC

GCAGCGGTCGGGCTGAACGGGGGGTTCGTGCACACAGCCCAGCTTGGAGCGAACGA

CCTACACCGAACTGAGATACCTACAGCGTGAGCTATGAGAAAGCGCCACGCTTCCC

GAAGGGAGAAAGGCGGACAGGTATCCGGTAAGCGGCAGGGTCGGAACAGGAGAGC

GCACGAGGGAGCTTCCAGGGGGAAACGCCTGGTATCTTTATAGTCCTGTCGGGTTTC

GCCACCTCTGACTTGAGCGTCGATTTTTGTGATGCTCGTCAGGGGGGCGGAGCCTAT

GGAAAAACGCCAGCAACGCGGCCTTTTTACGGTTCCTGGCCTTTTGCTGGCCTTTTG

CTCACATGTTCTTTCCTGCGTTATCCCCTGATTCTGTGGATAACCGTGCGGCCGC
```

REFERENCES

Altschul, S., Gish, W., Miller, W., Myers, E., and Lipman, D. (1990). Basic local alignment search tool. Journal of Molecular Biology. 215 (3): 403-4.

Anurag Priyam, B. J. W., Vivek Rai, Alekhya Munagala, Ismail Moghul, Filip Ter, Mark Anthony Gibbins, Hong-Kee Moon, Guy Leonard, Wolfgang Rumpf, View ORCID ProfileYannick Wurm. (2015). Sequence server: a modern graphical user interface for custom BLAST databases. bioRxiv 033142.

Bai, Y. F., Bi, H. P., Zhuang, Y. B., Liu, C., Cai, T., Liu, X. N., Zhang, X. L., Liu, T., and Ma, Y. H. (2014). Production of salidroside in metabolically engineered *Escherichia coli*. Sci Rep-Uk 4.

Bolger, A. M., Lohse, M., and Usadel, B. (2014). Trimmomatic: a flexible trimmer for Illumina sequence data. Bioinformatics 30, 2114-2120.

Booker, A., Zhai, L., Gkouva, C., Li, S., and Heinrich, M. (2016). From Traditional Resource to Global Commodities:—A Comparison of *Rhodiola* Species Using NMR Spectroscopy-Metabolomics and HPTLC. Frontiers in pharmacology 7, 254.

Burkhard, P., Dominici, P., Borri-Voltattorni, C., Jansonius, J. N., and Malashkevich, V. N. (2001). Structural insight into Parkinson's disease treatment from drug-inhibited DOPA decarboxylase. Nature structural biology 8, 963-967.

Chambers, M. C., Maclean, B., Burke, R., Amodei, D., Ruderman, D. L., Neumann, S., Gatto, L., Fischer, B., Pratt, B., Egertson, J., et al. (2012). A cross-platform toolkit for mass spectrometry and proteomics. Nat Biotechnol 30, 918-920.

Chapple, C. C., Walker, M. A., and Ellis, B. E. (1986). Plant tyrosine decarboxylase can be strongly inhibited by L-alpha-aminooxy-beta-phenylpropionate. Planta 167, 101-105.

Chung, D., Kim, S. Y., and Ahn, J. H. (2017). Production of three phenylethanoids, tyrosol, hydroxytyrosol, and salidroside, using plant genes expressing in *Escherichia coli*. Sci Rep 7, 2578.

Cifani, C., Micioni Di, B. M., Vitale, G., Ruggieri, V., Ciccocioppo, R., and Massi, M. (2010). Effect of salidroside, active principle of *Rhodiola rosea* extract, on binge eating. Physiology & behavior 101, 555-562.

De Luca, V., Marineau, C., and Brisson, N. (1989). Molecular cloning and analysis of cDNA encoding a plant tryptophan decarboxylase: comparison with animal dopa decarboxylases. Proc Natl Acad Sci USA 86, 2582-2586.

Dorji, L.a.K. (2016). Ecological status of high altitude medicinal plants and their sustainability: Lingshi, Bhutan. BMC Ecology.

Du, M., and Xie, J. M. (1995). Flavonol Glycosides from *Rhodiola-Crenulata*. Phytochemistry 38, 809-810.

Ehrlich, F. (1907). Ober die Bedingungen der Fuselolbildung und uber ihren Zusammenhang mit dem Eiweissaufbau der Hefe. European journal of inorganic chemistry 40, 1027-1047.

Facchini, P. J., Huber-Allanach, K. L., and Tari, L. W. (2000). Plant aromatic L-amino acid decarboxylases: evolution, biochemistry, regulation, and metabolic engineering applications. Phytochemistry 54, 121-138.

Fan, B., Chen, T., Zhang, S., Wu, B., and He, B. (2017). Mining of efficient microbial UDP-glycosyltransferases by motif evolution cross plant kingdom for application in biosynthesis of salidroside. Scientific Reports 7:463, 1-9.

Fu, K. J., Ohba, H., Gilbert, M. G. (2009). *Rhodiola*. Flora China 8.

Gachon, C. M., Langlois-Meurinne, M. & Saindrenan, P. (2005) Plant secondary metabolism glycosyltransferases: the emerging functional analysis. Trends in plant science 10, 542-549.

Gantt, R. W., Peltier-Pain, P., and Thorson, J. S. (2011). Enzymatic methods for glyco(diversification/randomization) of drugs and small molecules. Natural product reports 28, 1811-1853.

Gauger, K. J., Rodriguez-Cortes, A., Hartwich, M., and Schneider, S. S. (2010). *Rhodiola crenulata* inhibits the tumorigenic properties of invasive mammary epithelial cells with stem cell characteristics. J Med Plants Res 4, 446-454.

Gold, N. D., Gowen, C. M., Lussier, F. X., Cautha, S. C., Mahadevan, R., and Martin, V. J. J. (2015). Metabolic engineering of a tyrosine-overproducing yeast platform using targeted metabolomics. Microb Cell Fact 14.

Gouet, P., Robert, X., and Courcelle, E. (2003). ESPript/ENDscript: Extracting and rendering sequence and 3D information from atomic structures of proteins. Nucleic acids research 31, 3320-3323.

Grabherr, M. G., Haas, B. J., Yassour, M., Levin, J. Z., Thompson, D. A., Amit, I., Adiconis, X., Fan, L., Raychowdhury, R., Zeng, Q. D., et al. (2011). Full-length transcriptome assembly from RNA-Seq data without a reference genome. Nat. Biotechnol. 29, 644-U130.

Guan, S., Xiong, Y., Song, B., Song, Y., Wang, D., Chu, X., Chen, N., Huo, M., Deng, X., and Lu, J. (2012). Protective effects of salidroside from *Rhodiola rosea* on LPS-induced acute lung injury in mice. Immunopharmacology and immunotoxicology 34, 667-672.

Gutensohn, M., Klempien, A., Kaminaga, Y., Nagegowda, D. A., Negre-Zakharov, F., Huh, J. H., Luo, H., Weizbauer, R., Mengiste, T., Tholl, D., et al. (2011). Role of aromatic aldehyde synthase in wounding/herbivory response and flower scent production in different *Arabidopsis* ecotypes. The Plant journal: for cell and molecular biology 66, 591-602.

Haas, B. J., Papanicolaou, A., Yassour, M., Grabherr, M., Blood, P. D., Bowden, J., Couger, M. B., Eccles, D., Li, B., Lieber, M., et al. (2013). De novo transcript sequence reconstruction from RNA-seq using the Trinity platform for reference generation and analysis. Nat Protoc 8, 1494-1512.

Hagel, J. M., and Facchini, P. J. (2013). Benzylisoquinoline alkaloid metabolism: a century of discovery and a brave new world. Plant & cell physiology 54, 647-672.

Han, Q., Ding, H., Robinson, H., Christensen, B. M., and Li, J. (2010). Crystal structure and substrate specificity of *Drosophila* 3,4-dihydroxyphenylalanine decarboxylase. PloS one 5, e8826.

Jones, P., and Vogt, T. (2001). Glycosyltransferases in secondary plant metabolism: tranquilizers and stimulant controllers. Planta 213, 164-174.

Kaminaga, Y., Schnepp, J., Peel, G., Kish, C. M., Ben-Nissan, G., Weiss, D., Orlova, I., Lavie, O., Rhodes, D., Wood, K., et al. (2006). Plant phenylacetaldehyde synthase is a bifunctional homotetrameric enzyme that catalyzes phenylalanine decarboxylation and oxidation. The Journal of biological chemistry 281, 23357-23366.

Kawalleck, P., Keller, H., Hahlbrock, K., Scheel, D., and Somssich, I. E. (1993). A pathogen-responsive gene of parsley encodes tyrosine decarboxylase. J. Biol. Chem. 268, 2189-2194.

Khanum, F., Bawa, A. S., and Singh, B. (2005). *Rhodiola rosea*: A versatile adaptogen. Compr Rev Food Sci F 4, 55-62.

Kumar, S., Stecher, G., and Tamura, K. (2016). MEGA7: Molecular Evolutionary Genetics Analysis Version 7.0 for Bigger Datasets. Mol Biol Evol 33, 1870-1874.

L, Z. E.a.P. (1965). Evolutionary divergence and convergence in proteins. Evolving Genes and Proteins.

Lan, X., Chang, K., Zeng, L., Liu, X., Qiu, F., Zheng, W., Quan, H., Liao, Z., Chen, M., Huang, W., et al. (2013). Engineering salidroside biosynthetic pathway in hairy root cultures of *Rhodiola crenulata* based on metabolic characterization of tyrosine decarboxylase. PloS one 8, e75459.

Landtag, J., Baumert, A., Degenkolb, T., Schmidt, J., Wray, V., Scheel, D., Strack, D., and Rosahl, S. (2002). Accumulation of tyrosol glucoside in transgenic potato plants expressing a parsley tyrosine decarboxylase. Phytochemistry 60, 683-689.

Lee, M. E., DeLoache, W. C., Cervantes, B., and Dueber, J. E. (2015). A Highly Characterized Yeast Toolkit for Modular, Multipart Assembly. ACS synthetic biology 4, 975-986.

Lei, Y. D., Gao, H., Tsering, T., Shi, S. H., and Zhong, Y. (2006). Determination of genetic variation in *Rhodiola crenulata* from the Hengduan Mountains Region, China using inter-simple sequence repeats. Genet Mol Biol 29, 339-344.

Li, B., and Dewey, C. N. (2011). RSEM: accurate transcript quantification from RNA-Seq data with or without a reference genome. Bmc Bioinformatics 12.

Li, B., Ruotti, V., Stewart, R. M., Thomson, J. A., and Dewey, C. N. (2010). RNA-Seq gene expression estimation with read mapping uncertainty. Bioinformatics 26, 493-500.

Li, Y., Baldauf, S., Lim, E. K., and Bowles, D. J. (2001). Phylogenetic analysis of the UDP-glycosyltransferase multigene family of *Arabidopsis thaliana*. J. Biol. Chem. 276, 4338-4343.

Ma, L. Q., Liu, B. Y., Gao, D. Y., Pang, X. B., Lu, S. Y., Yu, H. S., Wang, H., Yan, F., Li, Z. Q., Li, Y. F., et al. (2007). Molecular cloning and overexpression of a novel UDP-glucosyltransferase elevating salidroside levels in *Rhodiola sachalinensis*. Plant cell reports 26, 989-999.

Mumberg, D., Muller, R., and Funk, M. (1995). Yeast Vectors for the Controlled Expression of Heterologous Proteins in Different Genetic Backgrounds. Gene 156, 119-122.

Nelissen, H., Clarke, J. H., De Block, M., De Block, S., Vanderhaeghen, R., Zielinski, R. E., Dyer, T., Lusta, S., Inze, D., and Van Lijsebettens, M. (2003). DRL1, a homolog of the yeast TOT4/KT112 protein, has a function in meristem activity and organ growth in plants. The Plant cell 15, 639-654.

O'Connor, S. E. (2015). Engineering of Secondary Metabolism. Annual review of genetics 49, 71-94.

Panossian, A., Hamm, R., Wikman, G., and Efferth, T. (2014). Mechanism of action of *Rhodiola*, salidroside, tyrosol and triandrin in isolated neuroglial cells: an interactive pathway analysis of the downstream effects using RNA microarray data. Phytomedicine: international journal of phytotherapy and phytopharmacology 21, 1325-1348.

Peyret, H., and Lomonossoff, G. P. (2013). The pEAQ vector series: the easy and quick way to produce recombinant proteins in plants. Plant Mol. Biol. 83, 51-58.

Pluskal, T., Castillo, S., Villar-Briones, A., and Oresic, M. (2010). MZmine 2: Modular framework for processing, visualizing, and analyzing mass spectrometry-based molecular profile data. Bmc Bioinformatics 11.

Rohloff, J. (2002). Volatiles from rhizomes of *Rhodiola rosea* L. Phytochemistry 59, 655-661.

Ross, J., Li, Y., Lim, E., and Bowles, D. J. (2001). Higher plant glycosyltransferases. Genome Biol 2, REVIEWS3004.

Sainsbury, F., Thuenemann, E. C., and Lomonossoff, G. P. (2009). pEAQ: versatile expression vectors for easy and quick transient expression of heterologous proteins in plants. Plant Biotechnol J 7, 682-693.

Samanani, N., Liscombe, D. K., and Facchini, P. J. (2004). Molecular cloning and characterization of norcoclaurine synthase, an enzyme catalyzing the first committed step in benzylisoquinoline alkaloid biosynthesis. The Plant journal: for cell and molecular biology 40, 302-313.

Sanderson, M. J., and Wojciechowski, M. F. (2000). Improved bootstrap confidence limits in large-scale phylogenies, with an example from Neo-*Astragalus* (Leguminosae). Systematic biology 49, 671-685.

Schneider, C. A., Rasband, W. S., and Eliceiri, K. W. (2012). NIH Image to ImageJ: 25 years of image analysis. Nat Methods 9, 671-675.

Simao, F. A., Waterhouse, R. M., Ioannidis, P., Kriventseva, E. V., and Zdobnov, E. M. (2015). BUSCO: assessing genome assembly and annotation completeness with single-copy orthologs. Bioinformatics 31, 3210-3212.

Skopinska-Rozewska, E., Malinowski, M., Wasiutynski, A., Sommer, E., Furmanowa, M., Mazurkiewicz, M., and Siwicki, A. K. (2008). The influence of *Rhodiola* quadrifida 50% hydro-alcoholic extract and salidroside on tumor-induced angiogenesis in mice. Pol J Vet Sci 11, 97-104.

Strommer, J. (2011). The plant ADH gene family. Plant Journal 66, 128-142.

Thompson, J. D., Gibson, T. J., and Higgins, D. G. (2002). Multiple sequence alignment using ClustalW and ClustalX. Current protocols in bioinformatics Chapter 2, Unit 2 3.

Tieman, D. M., Loucas, H. M., Kim, J. Y., Clark, D. G., and Klee, H. J. (2007). Tomato phenylacetaldehyde reductases catalyze the last step in the synthesis of the aroma volatile 2-phenylethanol. Phytochemistry 68, 2660-2669.

Torrens-Spence, M. P., Fallon, T. R., and Weng, J. K. (2016). A Workflow for Studying Specialized Metabolism in Nonmodel Eukaryotic Organisms. Methods Enzymol. 576, 69-97.

Torrens-Spence, M. P., Gillaspy, G., Zhao, B., Harich, K., White, R. H., and Li, J. (2012). Biochemical evaluation of a parsley tyrosine decarboxylase results in a novel 4-hydroxyphenylacetaldehyde synthase enzyme. Biochemical and biophysical research communications 418, 211-216.

Torrens-Spence, M. P., Lazear, M., von Guggenberg, R., Ding, H., and Li, J. (2014). Investigation of a substrate-specifying residue within *Papaver somniferum* and *Catharanthus roseus* aromatic amino acid decarboxylases. Phytochemistry 106, 37-43.

Torrens-Spence, M. P., Liu, P., Ding, H., Harich, K., Gillaspy, G., and Li, J. (2013). Biochemical evaluation of the decarboxylation and decarboxylation-deamination activities of plant aromatic amino acid decarboxylases. The Journal of biological chemistry 288, 2376-2387.

Tu, Y., Roberts, L., Shetty, K., and Schneider, S. S. (2008). Rhodiola crenulata induces death and inhibits growth of breast cancer cell lines. Journal of medicinal food 11, 413-423.

Wang, H., Fan, W., Li, H., Yang, J., Huang, J., and Zhang, P. (2013). Functional characterization of Dihydroflavonol-4-reductase in anthocyanin biosynthesis of purple sweet potato underlies the direct evidence of anthocyanins function against abiotic stresses. PloS one 8, e78484.

Wang, M., and Maeda, H. A. (2017). Aromatic amino acid aminotransferases in plants. Phytochemistry Reviews.

Weng, J. K., Ye, M., Li, B., and Noel, J. P. (2016). Co-evolution of Hormone Metabolism and Signaling Networks Expands Plant Adaptive Plasticity. Cell 166, 881-893.

Wyk, H.S.L.A.l.o.t.a.w.P.M.T.A.l.o.t.a.w.B.-E.V. (2010). The ethnobotany and pharmacognosy of Olea europaea subsp. africana (Oleaceae). South African Journal of Botany 76, 324-331.

Xia, J., and Wishart, D. S. (2016). Using MetaboAnalyst 3.0 for Comprehensive Metabolomics Data Analysis. Current protocols in bioinformatics 55, 14 10 11-14 10 91.

Xie, D. Y., Sharma, S. B., Paiva, N. L., Ferreira, D., and Dixon, R. A. (2003). Role of anthocyanidin reductase, encoded by BANYULS in plant flavonoid biosynthesis. Science 299, 396-399.

Yang, Y. N., Liu, Z. Z., Feng, Z. M., Jiang, J. S., and Zhang, P. C. (2012). Lignans from the Root of Rhodiola crenulata. J Agr Food Chem 60, 964-972.

Yousef, G. G., Grace, M. H., Cheng, D. M., Belolipov, I. V., Raskin, I., and Lila, M. A. (2006). Comparative phytochemical characterization of three Rhodiola species. Phytochemistry 67, 2380-2391.

Yu, H. S., Ma, L. Q., Zhang, J. X., Shi, G. L., Hu, Y. H., and Wang, Y. N. (2011). Characterization of glycosyltransferases responsible for salidroside biosynthesis in Rhodiola sachalinensis. Phytochemistry 72, 862-870.

Yuan, T., Fujioka, S., Takatsuto, S., Matsumoto, S., Gou, X., He, K., Russell, S. D., and Li, J. (2007). BEN1, a gene encoding a dihydroflavonol 4-reductase (DFR)-like protein, regulates the levels of brassinosteroids in Arabidopsis thaliana. The Plant journal: for cell and molecular biology 51, 220-233.

Zhang, L., Yu, H. X., Sun, Y., Lin, X. F., Chen, B., Tan, C., Cao, G. X., and Wang, Z. W. (2007). Protective effects of salidroside on hydrogen peroxide-induced apoptosis in SH-SY5Y human neuroblastoma cells. Eur J Pharmacol 564, 18-25.

INCORPORATION BY REFERENCE AND EQUIVALENTS

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A host cell comprising a transgene encoding a heterologous 4-hydroxyphenylacetaldehyde synthase (4HPAAS) operably linked to a promoter, wherein the heterologous 4HPAAS comprises an amino acid sequence having at least 95% amino acid sequence identity to SEQ ID NO: 2, and wherein the amino acid sequence of the heterologous 4HPAAS comprises:
   a) an amino acid residue selected from the group consisting of L, I, M and V at a position corresponding to the F residue at position 343 in SEQ ID NO: 2;
   b) an amino acid residue selected from the group consisting of N and D at a position corresponding to the H residue at position 198 in SEQ ID NO: 2; or
   c) a combination thereof.

2. The host cell of claim 1, wherein the amino acid sequence of the heterologous 4HPAAS comprises an amino acid residue selected from the group consisting of L, I, M and V at a position corresponding to the F residue at position 343 in SEQ ID NO: 2.

3. The host cell of claim 1, wherein the amino acid sequence of the heterologous 4HPAAS comprises an amino acid residue selected from the group consisting of N and D at a position corresponding to the H residue at position 198 in SEQ ID NO: 2.

4. A host cell comprising a transgene encoding a heterologous 4-hydroxyphenylacetaldehyde synthase (4HPAAS) operably linked to a promoter, wherein the heterologous 4HPAAS comprises an amino acid sequence having at least 95% amino acid sequence identity to SEQ ID NO: 2, and wherein the amino acid sequence of the heterologous 4HPAAS comprises an amino acid residue selected from the group consisting of F, L, I, M and V at a position corresponding to the F residue at position 343 in SEQ ID NO: 2, and an amino acid residue selected from the group consisting of N and D at a position corresponding to the H residue at position 198 in SEQ ID NO: 2.

5. The host cell of claim 1, wherein the host cell further comprises a transgene encoding a heterologous tyrosol: UDP-glucose 8-O-glucosyltransferase (T8GT) operably linked to a promoter, wherein the T8GT comprises an amino acid sequence having at least 95% identity to one or more of SEQ ID NO: 14, SEQ ID NO: 16, SEQ ID NO: 18, and SEQ ID NO: 20.

6. A method of making 4-hydroxyphenylacetaldehyde (4-HPAA) in a host cell, the method comprising expressing in the host cell a transgene that encodes a heterologous 4-hydroxyphenylacetaldehyde synthase (4HPAAS) operably linked to a promoter, wherein the heterologous 4HPAAS comprises an amino acid sequence having at least 95% amino acid sequence identity to SEQ ID NO: 2, and wherein the amino acid sequence of the heterologous 4HPAAS comprises:
   a) an amino acid residue selected from the group consisting of L, I, M and V at a position corresponding to the F residue at position 343 in SEQ ID NO: 2;
   b) an amino acid residue selected from the group consisting of N and D at a position corresponding to the H residue at position 198 in SEQ ID NO: 2; or
   c) a combination thereof.

7. The method of claim 6, wherein the amino acid sequence of the heterologous 4HPAAS comprises an amino acid residue selected from the group consisting of L, I, M and V at a position corresponding to the F residue at position 343 in SEQ ID NO: 2.

8. The method of claim 6, wherein the amino acid sequence of the heterologous 4HPAAS comprises an amino acid residue selected from the group consisting of N and D at a position corresponding to the H residue at position 198 in SEQ ID NO: 2.

9. A method of making 4-hydroxyphenylacetaldehyde (4-HPAA) in a host cell, the method comprising expressing in the host cell a transgene that encodes a heterologous 4-hydroxyphenylacetaldehyde synthase (4HPAAS) operably linked to a promoter, wherein the heterologous 4HPAAS comprises an amino acid sequence having at least 95% amino acid sequence identity to SEQ ID NO: 2, and wherein the amino acid sequence of the heterologous 4HPAAS comprises an amino acid residue selected from the group consisting of F, L, I, M and V at a position corresponding to the F residue at position 343 in SEQ ID NO: 2, and an amino acid residue selected from the group consisting of N and D at a position corresponding to the H residue at position 198 in SEQ ID NO: 2.

10. The method of claim 6, wherein the amino acid sequence of the heterologous 4HPAAS comprises SEQ ID NO: 2.

11. The method of claim 6, further comprising making tyrosol in the host cell, wherein the host cell further expresses a transgene encoding a heterologous 4-hydroxyphenylacetaldehyde reductase (4HPAR), wherein the heterologous 4HPAR comprises an amino acid sequence having SEQ ID NO: 4.

12. The method of claim 11, further comprising making salidroside in the host cell, wherein the host cell further comprises one or more enzymes that catalyze conversion of tyrosol to tyrosol 8-O-glucoside (salidroside).

13. The method of claim 11, further comprising making icariside D2 in the host cell, wherein the host cell further comprises one or more enzymes that catalyze conversion of tyrosol to icariside D2.

14. The host cell of claim 1, wherein the host cell is a fungal cell or a bacterial cell.

15. The host cell of claim 14, wherein the host cell is a fungal cell.

16. The host cell of claim 15, wherein the fungal cell is a yeast cell.

17. The host cell of claim 16, wherein the yeast cell is a *Saccharomyces cerevisiae* cell.

18. The host cell of claim 14, wherein the host cell is a bacterial cell.

19. The host cell of claim 18, wherein the bacterial cell is an *Escherichia coli* cell.

20. The host cell of claim 18, wherein the bacterial cell is an *Agrobacterium tumefaciens* cell.

* * * * *